United States Patent
Arnold et al.

(10) Patent No.: US 8,735,405 B2
(45) Date of Patent: May 27, 2014

(54) 6,6-BICYCLIC RING SUBSTITUTED HETEROBICYCLIC PROTEIN KINASE INHIBITORS

(75) Inventors: Lee D. Arnold, Mt. Sinai, NY (US);
Cara Cesario, Mishawaka, IN (US);
Heather Coate, San Diego, CA (US);
Andrew P. Crew, N. Babylon, NY (US);
Hanqing Dong, Syosset, NY (US);
Kenneth Foreman, Syosset, NY (US);
Ayako Honda, Quincy, MA (US);
Radoslaw Laufer, Ontario, CA (US);
An-Hu Li, Commack, NY (US); Kristen Michelle Mulvihill, Dix Hills, NY (US);
Mark J. Mulvihill, Dix Hills, NY (US);
Anthony I. Nigro, Westwood, NJ (US);
Bijoy Panicker, Holbrook, NY (US);
Arno G. Steinig, E. Northport, NY (US);
Yingchuan Sun, Arlington, MA (US);
Quinghua Weng, Hicksville, NY (US);
Douglas S. Werner, Holtsville, NY (US); Michael J. Wyle, Hempstead, NY (US); Tao Zhang, Waltham, MA (US)

(73) Assignee: OSI Pharmaceuticals, LLC, Farmingdale, NY (US)

(*) Notice: Subject to any disclaimer, the term of this patent is extended or adjusted under 35 U.S.C. 154(b) by 0 days.

(21) Appl. No.: 13/446,629

(22) Filed: Apr. 13, 2012

(65) Prior Publication Data
US 2012/0196847 A1    Aug. 2, 2012

Related U.S. Application Data

(60) Division of application No. 13/308,694, filed on Dec. 1, 2011, now Pat. No. 8,367,826, which is a division of application No. 12/540,047, filed on Aug. 12, 2009, now Pat. No. 8,101,613, which is a division of application No. 12/244,947, filed on Oct. 3, 2008, now Pat. No. 7,820,662, which is a continuation of application No. 11/095,162, filed on Mar. 31, 2005, now Pat. No. 7,534,797.

(60) Provisional application No. 60/559,250, filed on Apr. 2, 2004.

(51) Int. Cl.
A01N 43/90     (2006.01)
A61K 31/519    (2006.01)
C07D 487/00    (2006.01)

(52) U.S. Cl.
USPC .............. 514/262.1; 514/265.1; 544/262; 544/280

(58) Field of Classification Search
None
See application file for complete search history.

(56) References Cited

U.S. PATENT DOCUMENTS

| | | |
|---|---|---|
| 3,840,537 A | 10/1974 | Garside |
| 5,217,999 A | 6/1993 | Levitzki |
| 5,302,606 A | 4/1994 | Spada |
| 5,326,905 A | 7/1994 | Dow |
| 5,397,787 A | 3/1995 | Buzzetti |
| 5,556,874 A | 9/1996 | Dobrusin |
| 6,194,439 B1 | 2/2001 | Dow |
| 6,265,411 B1 | 7/2001 | Thomas |
| 6,337,338 B1 | 1/2002 | Kozlowski |
| 6,362,336 B1 | 3/2002 | Lohmann |
| 6,486,179 B2 | 11/2002 | Jirousek |
| 6,713,474 B2 | 3/2004 | Hirst |
| 6,939,874 B2 | 9/2005 | Harmange |
| 7,087,602 B2 | 8/2006 | Thomas |
| 7,087,613 B2 | 8/2006 | Norris |
| 7,115,617 B2 | 10/2006 | Buchanan |
| 7,202,243 B2 | 4/2007 | Hendrix |
| 7,232,911 B2 | 6/2007 | Vangelisti |
| 7,244,733 B2 | 7/2007 | Hunt |
| 7,271,262 B2 | 9/2007 | La Greca |
| 7,326,699 B2 | 2/2008 | Capraro |
| 7,332,497 B2 | 2/2008 | Hirst |
| 7,345,038 B2 | 3/2008 | Bright |
| 7,348,358 B2 | 3/2008 | Larsson |
| 7,459,554 B2 | 12/2008 | Dong |

(Continued)

FOREIGN PATENT DOCUMENTS

| | | |
|---|---|---|
| JP | 05/089352 A | 4/2005 |
| WO | 97/28161 A1 | 8/1997 |

(Continued)

OTHER PUBLICATIONS

EP Search Report Application No. 09156987.1-2117 dated Feb. 26, 2010.
EP Search Report Application No. EP11155270.9 date of completion of report Jan. 18, 2012.

(Continued)

*Primary Examiner* — Jeffrey H Murray
(74) *Attorney, Agent, or Firm* — Guyan Liang; Astellas US LLC

(57) ABSTRACT

Compounds of the formula

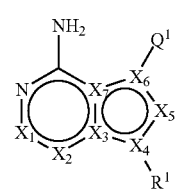

I and pharmaceutically acceptable salts thereof, wherein $X_1$, $X_2$, $X_3$, $X_4$, $X_5$, $X_6$, $X_7$, $R^1$, and $Q^1$ are defined herein, inhibit the IGF-1R enzyme and are useful for the treatment and/or prevention of hyperproliferative diseases such as cancer, inflammation, psoriasis, allergy/asthma, disease and conditions of the immune system, disease and conditions of the central nervous system.

17 Claims, No Drawings

(56) References Cited

U.S. PATENT DOCUMENTS

| | | |
|---|---|---|
| 7,534,797 B2 | 5/2009 | Arnold |
| 7,648,987 B2 | 1/2010 | Crew |
| 7,820,662 B2 | 10/2010 | Arnold |
| 7,915,256 B2 | 3/2011 | Andrews |
| 2002/0076408 A1 | 6/2002 | Buchsbaum |
| 2003/0108545 A1 | 6/2003 | Rockwell |
| 2003/0114467 A1 | 6/2003 | Shakespeare |
| 2003/0144252 A1 | 7/2003 | Furr |
| 2003/0153752 A1 | 8/2003 | Hirst |
| 2003/0157104 A1 | 8/2003 | Waksal |
| 2003/0175763 A1 | 9/2003 | Degenhardt |
| 2004/0014774 A1 | 1/2004 | Myers |
| 2004/0052785 A1 | 3/2004 | Goodman |
| 2004/0057950 A1 | 3/2004 | Waksal |
| 2004/0092546 A1 | 5/2004 | Wei |
| 2004/0102655 A1 | 5/2004 | Liang et al. |
| 2004/0106605 A1 | 6/2004 | Carboni |
| 2004/0180911 A1 | 9/2004 | Capraro |
| 2004/0209930 A1 | 10/2004 | Carboni |
| 2004/0220189 A1 | 11/2004 | Sun |
| 2005/0009832 A1 | 1/2005 | Sun |
| 2005/0032759 A1 | 2/2005 | Massimini |
| 2005/0037999 A1 | 2/2005 | La Greca |
| 2005/0054638 A1 | 3/2005 | Barlaam |
| 2005/0136063 A1 | 6/2005 | Wang |
| 2005/0153966 A1 | 7/2005 | Gangloff |
| 2005/0215530 A1 | 9/2005 | Ryan |
| 2005/0215564 A1 | 9/2005 | Stiles |
| 2005/0271747 A1 | 12/2005 | Higgins |
| 2006/0019957 A1 | 1/2006 | Crew |
| 2006/0046977 A1 | 3/2006 | Nunes |
| 2006/0069084 A1 | 3/2006 | Burns |
| 2006/0084654 A1 | 4/2006 | Beck |
| 2006/0154982 A1 | 7/2006 | Larsson |
| 2006/0166992 A1 | 7/2006 | Hendrix |
| 2006/0235031 A1 | 10/2006 | Arnold |
| 2007/0087613 A1 | 4/2007 | Schumacher |
| 2007/0112005 A1 | 5/2007 | Chen |
| 2007/0149521 A1 | 6/2007 | Crew |
| 2007/0202101 A1 | 8/2007 | Rosen |
| 2007/0203143 A1 | 8/2007 | Sheppard |
| 2007/0238734 A1 | 10/2007 | Nemecek |
| 2007/0254883 A1 | 11/2007 | Crew |
| 2007/0280928 A1 | 12/2007 | Buck |
| 2008/0014200 A1 | 1/2008 | Arnold |
| 2008/0139582 A1 | 6/2008 | Honigberg |
| 2008/0254040 A1 | 10/2008 | Stefanic |
| 2008/0267957 A1 | 10/2008 | Arnold |
| 2009/0093488 A1 | 4/2009 | Buck |
| 2009/0181940 A1 | 7/2009 | Beck |
| 2009/0263397 A1 | 10/2009 | Buck |
| 2009/0286768 A1 | 11/2009 | Crew |
| 2009/0325928 A1 | 12/2009 | Arnold |
| 2010/0286155 A1 | 11/2010 | Buck |
| 2011/0046144 A1 | 2/2011 | Mulvihill |

FOREIGN PATENT DOCUMENTS

| | | |
|---|---|---|
| WO | 00/17203 A1 | 3/2000 |
| WO | 01/12227 A1 | 2/2001 |
| WO | 01/72751 A1 | 10/2001 |
| WO | 02/060492 | 8/2002 |
| WO | 02/079192 A1 | 10/2002 |
| WO | 02/092599 A1 | 11/2002 |
| WO | 03/000187 A2 | 1/2003 |
| WO | 03/024967 A2 | 3/2003 |
| WO | 03/080064 A1 | 10/2003 |
| WO | 2004/056830 A1 | 7/2004 |
| WO | 2005/037836 A2 | 4/2005 |
| WO | 2005/061519 A1 | 7/2005 |
| WO | 2005/097800 A1 | 10/2005 |
| WO | 2006/004703 A2 | 1/2006 |
| WO | 2007/075554 A2 | 7/2007 |
| WO | 2007/079164 A2 | 7/2007 |
| WO | 2007/131991 A | 11/2007 |
| WO | 2008/076143 A1 | 6/2008 |
| WO | 2008/106168 A1 | 9/2008 |
| WO | 2009/073139 A2 | 6/2009 |
| WO | 2010/107968 A1 | 9/2010 |
| WO | 2011/060112 A1 | 5/2011 |
| WO | 2011/112666 A1 | 9/2011 |
| WO | 2011/163430 A1 | 12/2011 |

OTHER PUBLICATIONS

International Preliminary Report on Patentability and Written Opinion in PCT/US2010/031547date of issuance of report Oct. 25, 2011.
International Preliminary Report on Patentability and Written Opinion in PCT/US2010/056290 issued May 15, 2012.
ISR and WOSA for PCT/US2011/041547 date of mailing Sep. 21, 2011.
ISR and WOSA date of mailing Jun. 27, 2012 PCT/US2012/029598.
Search Report ROC (Taiwan) Patent Application No. 100123371 (English Translation) date of completion of search Feb. 2, 2012.
Abushanab et al. Journal of Organic Chemistry, 1975 vol. 40, No. 23, pp. 3376-3378.
Almeida, et al. M. Q., et al., (2008) J. Clin. Enocrinol Metab 93, pp. 3524-3531.
Balak, M.N., et al., (2006) Clinical Cancer Res 12(21) pp. 6494-6501.
Bhattacharya, B.K. et al. Journal of Heterocyclic Chemistry 1993 pp. 1341-1349.
Brown Eric, et al. (2009) Proceedings of the Annual Meeting of the American Association for Cancer Research; 100th Annual Meeting of the American Assoc. for Cancer Research Denver, CA, USA; Apr. 18-22, 2009 vol. 50 p. 419.
Clinicaltrials.gov, US National Institute of Health: "Study of Erlotinib (Tarceva®) in Combination With OSI-906 in Patients With Advanced Non-small Cell Lung Carcinoma (NSCLC) With Activating Mutations of the Epidermal Growth Factor Receptor (EGFR) Gene," OSI Pharmaceuticals XP002677837, retrieved from the Internet: URL:http://clinicaltrials.gov/archive/NCTO 1221077/ 2011-02-22.
Goodman and Gilman, (Tenth Edition 2001) Goodman and Gilman's The Pharmacological Basis of Therapeutics Chapter 1, pp. 3-29.
Guillory J K Ed-Brittan H G: "Generation of Polymorphs, Hydrates, Solvates, and Amorphous Solids ," Polymorphism in Pharmaceutical Solids, XX,XX 1999 pp. 183-226, XP002376368 Chapters, I, II and III.
Heim-Riether, A. et al. Journal of Organic Chemistry, 2005 vol. 70, No. 18, pp. 7331-7337.
Ji, Qun-sheng, et al., (2007) Mol Cancer Ther 6 (8) pp. 2158-2167.
Knutsen, L., et al., Journal of the Chemcial Society 1984 vol. 2, pp. 229-238.
Knutsen, L., et al., Journal of the Chemcial Society 1985 pp. 621-630.
Mitchell, W.L. et al. J. Heterocyclic Chem., 1984 vol. 21, No. 3, pp. 697-699.
Pao, W. et al. 2010 Nature Reviews Cancer 10(11) pp. 760-774.
Park, J.O. et al., (2003) Japanese Journal of Clinical Oncology 33 (10) pp. 533-537.
Sharma, S.V., et al., 2007 Nature Reviews|Cancer Vol .7, pp. 169-181.
Thomson, S., et al., 2005 Cancer Res 65 (20) pp. 9455-9462.
Yuen, J. SP, et al. (2008) Expert Opinion in Therapeutic Targets 12(5) pp. 589-603.
Dorwald, F.A. Side Reactions in Organic Synthesis, 2005, Wiley: VCH, Weinheim p. IX of Preface p. 1-15, 41, 279-308.
International Search Report in PCT/EP97/00350 date of mailing May 21, 1997.
International Search Report in PCT/US2006/046226 date of mailing May 21, 2007.
International Search Report in PCT/US2004/034219-date of mailing May 6, 2005.
International Search Report in PCT/US2005/010606-date of mailing Aug. 29, 2005.
International Search Report in PCT/US2009/031177 date of mailing Aug. 4, 2009.

(56) References Cited

OTHER PUBLICATIONS

International Preliminary Report on Patentability and Written Opinion of the International Searching Authority in PCT/US2009/031177 date of issuance Jul. 20, 2010.
IPRP in PCT/US2004/034219-date of completion of report Dec. 9, 2005.
IPRP in PCT/US2005/010606-date of completion of report Jul. 6, 2006.
ISR/WOSA in PCT/US2005/010606-date of mailing Aug. 29, 2005.
ISR/WOSA in PCT/US2006/048222 date of mailing Apr. 7, 2007.
ISR/WOSA in PCT/US2007/009178 date of mailing Apr. 21, 2008.
ISR/WOSA in PCT/US2008/002593 date of mailing Jul. 28, 2008.
ISR and WOSA for PCT/US2009/044325 date of mailing Sep. 18, 2009.
ISR and WOSA dated Jul. 30, 2010 received from the European Patent Office in PCT/US2010/033825.
ISR and WOSA dated Nov. 7, 2011 PCT/US2011/045807.
WOSA in PCT/US2004/034219-date of mailing Jun. 5, 2005.
WOSA in PCT/US2005/010606 date of mailing Aug. 29, 2005.
Written Opinion of the International Search Authority in PCT/US2009/031177 date of mailing Aug. 4, 2009.
Written Opinion of the International Search Authority in PCT/US2006/046226 dated May 21, 2009.
Austrian Search and Written Opinion in Singapore 200606863-9 Report Dec. 23, 2008.
Database WPI Week 200529, Derwent Publications Ltd., London, GB; (Apr. 7, 2005) AN 2005-277172.
Adachi, Y. et al. (2004) CAS Accession #2005:366557, corresponding to Novartis Foundation Symposium 262 (biology of IGF-1), 177-192.
Akio, M.et al. (1995) English Language Abstract of JP 07133280.
Albert, A. et al. (1970) Journal of the Chemical Society, vol. 11, pp. 1540-1547.
Albert, A. et al. (1969) Chem. Biol. Pterdines.Proc.Int.Symp., 4th, 4:1-5.
Arteaga, C.L. and Johnson, D.H. (2001) Current Opinion Oncol. 13:491-498.
Baserga, R. (1999) Exp.Cell.Res, vol. 253, pp. 1-6.
Bertino, J. R. et al. (2000), "Part XIV;Oncology, The Principles of Cancer Therapy" Cecil Textbook of Medicine, Goldman, L. et al., 21st Edition, W.B. Saunders Co., Philadelphia, PA, pp. 1060-1070.
Bevacizumab and Gemcitabine Combined with either Cetuximab or Erlotinib in Treating Patients with Advanced Pancreatic Cancer Internet Citation, [Online] Sep. 7, 2004, XP002410261. Retrieved from the Internet: URL:http://www.clinicaltrials.gov/ct/.
Blair, J. B. et al., Thieno[3,2-b]- and Thieno[2,3-b]pyrrole Bioisoteric Analogues of the Hallucinogen and Serotonin Agonist N,N-Dimethyltryptamine. J. Chem. Med. 1999, 42, 1106-1111.
Breault, G.A., et al., Cyclin-Dependent Kinase 4 Inhibitors as a Treatment for Cancer. Part 2: Identification and Optimisation of Substitiuted 2,4-Bis Anilino Pyrimidines. Bioorganic & Medicinial Chemistry Letters 13 (2003) 2961-2966.
Bulgaru, A.M. et al. (2003) Expert Rev. Anticancer Ther.3:269-279.
Camirand, A. et al. (2005) Breast Cancer Research 2005, 7:R570-R570.
Chakravarti, A. et al.(2002) Cancer Research 62: 200-207.
Ciardiello, F. et al. (2000) Clin. Cancer Res. 6:2053-2063.
Ciardiello, F. et al. (2000) Clin. Cancer Res. 6:3739-3747.
Ciardiello, F. et al. (2003) Clin. Cancer Res. 9:1546-1556.
Contessa, J. N. et al. (1999) Clin. Cancer Res. 5:405-411.
Dancey, J. and Sausville, E.A. (2003) Nature Rev. Drug Discovery 2:296-313.
De Bono, J.S. and Rowinsky, E.K. (2002) Trends in Mol. Medicine 8:S19-S26.
Dineen, et al. "Efficient Transamidation of Primary Carboxamides by in Situ Activation with N, N-Dialkylformamide Dimethyl Acetals" Journal of the American Chemical Society, 2006, 128, 16406-16409.

Dohle, W. et al. "Mild Synthesis of Polyfunctional Benzimidazoles and Indoles by the Reduction of Functionalized Nitroarenes with Phenylmagnesium Chloride" Chemistry a European Journal 2003, 9, 5323-5331.
Expert Opinion Ther. Pat., (1998) vol. 8, pp. 475-478.
Galisteo, M.L. et al. (2006) PNAS 103 (26): 9796-9801.
Grunwald, V. and Hidalgo, M. (2003) J. Nat. Cancer Inst. 95:851-867.
Gundisch, D. et al., Synthesis and Evaluation of Pyridazine and Pyrimidine Containing Bioisoteres of (+)-Pyrido[3.4-b]homotropane and Pyrido-]3.4-b]tropane as Novel nAChR Ligands. Bioorganic & Medicinal Chemistry 10 (2002) 1-9.
Gupta, R.A. and Dubois, R.N. (2000) Nature Med. 6:974-975.
Gura, et al. (1997) Science 278:1041-1042.
Hartz, R. A. et al. (2002) Bioorganic & Medicinal Chemistry Letters, vol. 12, pp. 291-294.
Herbst, R.S. et al. (2001) Expert Opin. Biol. Ther. 1:719-732.
Holbro, T. and Hynes, N. E. (2004) Annu Rev Pharmacol Toxicol 44:195-217.
Huang, S. et al. (1999) Cancer Res. 59:1935-1940.
Hurbin, A. et al. (2003) Ann. N. Y. Acad. Sci 1010:354-357.
Jiang, R. et al. "3,5-Disubstituted quinolines as novel c-Jun N-terminal kinase inhibitors." Bioorganic & Medicinal Chemistry Letters 2007, 17, 6378-6382.
Johnson, J.I.et al. (2001) British Journal of Cancer 84:1424-1431.
Jones, H.E. et al. (2004) Endocr Relat Cancer 11:793-814.
Khalil, M.Y. et al. (2003) Expert Rev. Anticancer Ther. 3:367-380.
Kim, E.S. et al. (2001) Current Opinion Oncol. 13:506-513.
Knowlden, J. M. (2005) Endocrinology 146(11):4609-4618.
Kopecky, D. J. et al: "Identification and optimization of N <3>, N<6>-diaryl-1H-pyrazolo [3,4-d] pyrimidine-3, 6-diamines as a novel class of ACK1 inhibitors" Bioorganic & Medicinal Chemistry Letters, Pergamon, Elsevier Science, vol. 18, No. 24. Dec. 15, 2008.
Krishnan, S. et al. (2003) Frontiers in Bioscience 8, e1-13.
Kurmasheva, R. T. and Houghton, P. J. (2006) Biochim Biophys Acta 1766:1-22.
Levitzki, A. (2003) Lung Cancer 41 Suppl 1, S9-14.
Li, M. et al. (2002) Clin.Cancer Res. 8:3570-3578.
Liu, B. (2001) Oncogene 20:1913-1922.
Liu, M. et. al. "Synthesis and SAR of 1,9-dihydro-9-hydroxypyraxolo[3,4-b]quinolin-4-ones as novel, selective c-Jun N-terminal kinase inhibitors" Bioorganic & Medicinal Chemistry Letters 2006, 16, 2590-2594.
Lu, D. et al. (2004) J. Biol. Chem. Jan 23; 279(4): 2856-65.
Lu, Y. et al. (2001) Journal of the National Cancer Institute 93: 1852-1857.
Magne, N. et al. (2002) British Journal of Cancer 86:819-827.
Magne, N. et al. (2003) Clin. Can. Res. 9:4735:4732.
Mahajan, N.P.(2005) Cancer Research 65 (22):10514-10523.
Mahajan, N.P.(2007) PNAS 104 (20): 8438-8443.
Manser, E. et al. (1993) Nature 363 (6427):364-367.
McCarty, M. F. (2004) Integrative Cancer Therapies 3(4): 349-380.
Michelotti, E.L. et. al. "Two classes of p38a MAP kinase inhibitors having a common diphenylether core but exhibiting divergent binding modes" Bioorganic & Medicinal Chemistry Letters 2005, 15, 5274-5279.
Miyazaki,Y. et al. "Design and effective synthesis of novel templates, 3,7-diphenyl-4-amino-thieno and furo-[3,2-c] pyridines as protein kinase inhibitors and in vitro evaluation targeting angiogenetic kinases" Bioorganic & Medicinal Chemistry Letters 2007, 17, 250-254.
Morgillo, F. et al. (2006) Cancer Res 66(20):10100-10111.
Mulvihill, M.J. et al: "Novel 2-phenylquinolin-7-yl-derived imidazo[1,5-a]pyrazines as potent insulin-like growth factor-I receptor (IGF-IR) inhibitors" Bioorganic & Medicinal Chemistry, Elsevier Science Ltd. vol. 16, No. 3, Oct. 23, 2007, pp. 1359-1375.
Nahta, R. (2005) Cancer Research 65:11118-111128.
National Library of Medicine-Medical Subject Headings definition of Sarcoma (http://www.nlm.nih.gov/mesh/2008/MBrowser.html, then type "sarcoma").

(56) References Cited

OTHER PUBLICATIONS

Parrizas, M. et al. (1997) Endocrinology, vol. 138, pp. 1427-1433.
Pink, C.J. et al. (2008) "Organic Solvent Nanofiltration and Absorbents; A Hybrid Approach to Achieve Ultra Low Palladium Contamination of Post Coupling Reaction Products," Organic Process Research & Development, vol. 12, No. 4, pp. 589-595.
Raben, D. et al. (2002) Semin. Oncol. vol. 29, No. 1, suppl 4 (February): pp. 37-46.
Robertson, D. et al., Imidazole-Pyridine Bioisosterism: Comparison of the Intropis Activities of Pyridine- and Imidazole-Substituted 6-Phenyldihydropyridazinone Cardiotonics. J. Med. Chem. 1988, vol. 31, pp. 461-465.
Roskoski, R., Jr. (2004) Biochem Biophys Res Commun 319:1-11.
Smalley Jr., T. L. et al., Synthesis and evaluation of a novel heterocyclic inhibitors of GSK-3. Bioorganic & Medicinal Letters 16 (2006) 2091-2094.
Seymour, L. (2003) Current Opin. Investig. Drugs 4(6):658-666.
Snow, R.J. et al. "Hit-to-lead studies on benzimidazole inhibitors of ITK: Discovery of a novel class of kinase inhibitors" Bioorganic & Medicinal Chemistry Letters 2007 17 3660-3665.
Solomon, B. et al (2003) Int. J. Radiat. Oncol. Biol. Phys. 55:713-723.
Krontiris, T.G., (1994) Internal Medicine 4th Edition, Chapters 71 and 72, pp. 699-729 (Editor is Stein, J.H.).
Steinbach, J. P. et al.(2004) Biochem Biophys Res Commun. Aug. 27;321 (3): 524-30.
Thomas, et al. (1998) Expert Opinion Ther. Pat., vol. 8, pp. 475-478.
Torrance, C.J. et al. (2000) Nature Med. 6:1024-1028.
Tortora, G. et al. (2003) Clin. Cancer Res. 9:1566-1572.
Valeriote, F. et al. (1975) Cancer Chemotherapy Reports (5):895-900.
Van Der Horst, E.T. et al. (2005) PNAS 102 (44):15901-15906.
Yang, W. et al. (1999) The Journal of Biological Chemistry 274 (13): 8524-8530.
Communication Pursuant to Article 94(3) EPC Application No. 08 726 171.5-2123 dated May 3, 2012.
Communication Pursuant to Article 94(3) EPC Application No. 09 156 987-2117 dated Feb. 24, 2012.

6,6-BICYCLIC RING SUBSTITUTED HETEROBICYCLIC PROTEIN KINASE INHIBITORS

This application claims the benefit of U.S. Application No. 60/559,250 filed Apr. 2, 2004.

BACKGROUND OF THE INVENTION

The present invention is directed to novel heterobicyclic compounds, their salts, and compositions comprising them. In particular, the present invention is directed to novel heterobicyclic compounds that inhibit the activity of tyrosine kinase enzymes in animals, including humans, for the treatment and/or prevention of various diseases and conditions such as cancer.

Protein tyrosine kinases (PTKs) are enzymes that catalyse the phosphorylation of specific tyrosine residues in various cellular proteins involved in regulation of cell proliferation, activation, or differentiation (Schlessinger and Ulrich, 1992, *Neuron* 9:383-391). Aberrant, excessive, or uncontrolled PTK activity has been shown to result in uncontrolled cell growth and has been observed in diseases such as benign and malignant proliferative disorders, as well as having been observed in diseases resulting from an inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular). The Receptor Tyrosine Kinases (RTKs) comprise a large family of transmembrane receptors with at least nineteen distinct RTK subfamilies having diverse biological activities. The RTK family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently results in a variety of cellular responses (Ullrich & Schlessinger, 1990, *Cell* 61:203-212). Thus, RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate a corresponding cellular response such as cell division, differentiation, metabolic effects, and changes in the extracellular microenvironment (Schlessinger and Ullrich, 1992, *Neuron* 9:1-20).

Malignant cells are associated with the loss of control over one or more cell cycle elements. These elements range from cell surface receptors to the regulators of transcription and translation, including the insulin-like growth factors, insulin growth factor-1 (IGF-1) and insulin growth factor-2 (IGF-2) (M. J. Ellis, "The Insulin-Like Growth Factor Network and Breast Cancer", Breast Cancer, Molecular Genetics, Pathogenesis and Therapeutics, Humana Press 1999). The insulin growth factor system consists of families of ligands, insulin growth factor binding proteins, and receptors.

A major physiological role of the IGF-1 system is the promotion of normal growth and regeneration. Overexpressed IGF-1R (type 1 insulin-like growth factor receptor can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines.

Apoptosis is a ubiquitous physiological process used to eliminate damaged or unwanted cells in multicellular organisms. Misregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

Inappropriately high protein kinase activity has been implicated in many diseases resulting from abnormal cellular function. This might arise either directly or indirectly by a failure of the proper control mechanisms for the kinase, related to mutation, over-expression or inappropriate activation of the enzyme; or by an over- or underproduction of cytokines or growth factors participating in the transduction of signals upstream or downstream of the kinase. In all of these instances, selective inhibition of the action of the kinase might be expected to have a beneficial effect.

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth.

The IGF-1 pathway in human tumor development has an important role: 1) IGF-1R overexpression is frequently found in various tumors (breast, colon, lung, sarcoma) and is often associated with an aggressive phenotype. 2) High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.*, 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

Many of the tyrosine kinases, whether an RTK or non-receptor tyrosine kinase, have been found to be involved in cellular signaling pathways involved in numerous disorders, including cancer, psoriasis, fibrosis, atherosclerosis, restenosis, auto-immune disease, allergy, asthma, transplantation rejection, inflammation, thrombosis, nervous system diseases, and other hyperproliferative disorders or hyper-immune responses. It is desirable to provide novel inhibitors of kinases involved in mediating or maintaining disease states to treat such diseases.

The identification of effective small compounds that specifically inhibit signal transduction and cellular proliferation, by modulating the activity of receptor and non-receptor tyrosine and serine/threonine kinases, to regulate and modulate abnormal or inappropriate cell proliferation, differentiation, or metabolism is therefore desirable. In particular, the identification of methods and compounds that specifically inhibit the function of a tyrosine kinase essential for angiogenic processes or for the formation of vascular hyperpermeability leading to edema, ascites, effusions, exudates, macromolecular extravasation, matrix deposition, and their associated disorders would be beneficial.

It has been recognized that inhibitors of protein-tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. This compound, in addition to inhibiting BCR-ABL kinase, also inhibits KIT kinase and PDGF receptor kinase, although it is not effective against all mutant isoforms of KIT kinase. In recent clinical studies on the use of Gleevec™ to treat patients with GIST, a disease in which KIT kinase is involved in transformation of the cells, many of the patients showed marked clinical improvement. Other kinase inhibitors show even greater selectively. For example, the 4-anilinoquinazoline compound Tarceva™ inhibits only EGF receptor kinase with high potency, although it can inhibit the signal transduction of other receptor kinases, probably because such receptors heterodimerize with the EGF receptor.

In view of the importance of PTKs to the control, regulation, and modulation of cell proliferation and the diseases and disorders associated with abnormal cell proliferation, many attempts have been made to identify small molecule tyrosine kinase inhibitors. Bis-, mono-cyclic, bicyclic or heterocyclic aryl compounds (International Patent Publication No. WO 92/20642) and vinylene-azaindole derivatives (International Patent Publication No. WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0566266 A1; *Expert Opin. Ther. Pat.* (1998), 8(4): 475-478), selenoindoles and selenides (International Patent Publication No. WO 94/03427), tricyclic polyhydroxylic compounds (International Patent Publication No. WO 92/21660) and benzylphosphonic acid compounds (International Patent Publication No. WO 91/15495) have been described as compounds for use as tyrosine kinase inhibitors for use in the treatment of cancer. Anilinocinnolines (PCT WO97/34876) and quinazoline derivative compounds (International Patent Publication No. WO 97/22596; International Patent Publication No. WO97/42187) have been described as inhibitors of angiogenesis and vascular permeability. Bis(indolylmaleimide) compounds have been described as inhibiting particular PKC serine/threonine kinase isoforms whose signal transducing function is associated with altered vascular permeability in VEGF-related diseases (International Patent Publication Nos. WO 97/40830 and WO 97/40831).

International Patent Publication Nos. WO 03/018021 and WO 03/018022 describe pyrimidines for treating IGF-1R related disorders, International Patent Publication Nos. WO 02/102804 and WO 02/102805 describe cyclolignans and cyclolignans as IGF-1R inhibitors, International Patent Publication No. WO 02/092599 describes pyrrolopyrimidines for the treatment of a disease which responds to an inhibition of the IGF-1R tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo[2,3-d]pyrimidines and their use as tyrosine kinase inhibitors.

Parrizas, et al. describes tyrphostins with in vitro and in vivo IGF-1R inhibitory activity (Endocrinology, 138:1427-1433 (1997)), and International Patent Publication No. WO 00/35455 describes heteroaryl-aryl ureas as IGF-1R inhibitors. International Patent Publication No. WO 03/048133 describes pyrimidine derivatives as modulators of IGF-1R. International Patent Publication No. WO 03/024967 describes chemical compounds with inhibitory effects towards kinase proteins. International Patent Publication No. WO 03/068265 describes methods and compositions for treating hyperproliferative conditions. International Patent Publication No. WO 00/17203 describes pyrrolopyrimidines as protein kinase inhibitors. Japanese Patent Publication No. JP 07/133,280 describes a cephem compound, its production and antimicrobial composition. A. Albert et al., *Journal of the Chemical Society*, 11: 1540-1547 (1970) describes pteridine studies and pteridines unsubstituted in the 4-position, a synthesis from pyrazines via 3,4-dhydropteridines. A. Albert et al., *Chem. Biol. Pteridines Proc. Int. Symp.*, 4th, 4: 1-5 (1969) describes a synthesis of pteridines (unsubstituted in the 4-position) from pyrazines, via 3-4-dihydropteridines.

IGF-1R performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells.

Although the anticancer compounds described above have made a significant contribution to the art, there is a continuing need in this field of art to improve anticancer pharmaceuticals with better selectivity or potency, reduced toxicity, or fewer side effects.

SUMMARY OF THE INVENTION

The present invention relates to compounds of Formula I:

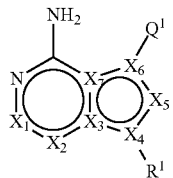

or a pharmaceutically acceptable salt thereof. The compounds of Formula I inhibit the IGF-1R enzyme and are useful for the treatment and/or prevention of hyperproliferative diseases such as cancer, inflammation, psoriasis, allergy/asthma, disease and conditions of the immune system, disease and conditions of the central nervous system.

DETAILED DESCRIPTION OF THE INVENTION

The present invention relates to a compound of Formula I:

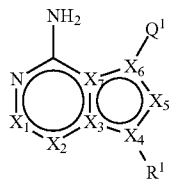

or a pharmaceutically acceptable salt thereof, wherein:
$X_1$, and $X_2$ are each independently N or C-$(E^1)_{aa}$;
$X_5$ is N, C-$(E^1)_{aa}$, or N-$(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;
$Q^1$ is

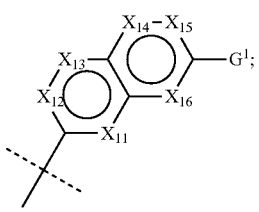

$X_{11}$, $X_{12}$, $X_{13}$, $X_{14}$, $X_{15}$, and $X_{16}$ are each independently N, C-$(E^{11})_{bb}$, or $N^+$—$O^-$;
wherein at least one of $X_{11}$, $X_{12}$, $X_{13}$, $X_{14}$, $X_{15}$, and $X_{16}$ is N or $N^+$—$O^-$;
$R^1$ is absent, $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents;
$E^1$, $E^{11}$, $G^1$, and $G^{41}$ are each independently halo, —$CF_3$, —$OCF_3$, —$OR^2$, —$NR^3R^3(R^{2a})_{j1}$, —$C(=O)R^2$, —$CO_2R^2$, —$CONR^2R^3$, —$NO_2$, —$CN$, —$S(O)_{j1}R^2$, —$SO_2NR^2R^3$, —$NR^2C(=O)R^3$, —$NR^2C(=O)OR^3$, —$NR^2C(=O)NR^3R^{2a}$, —$NR^2S(O)_{j1}R^3$, —$C(=S)OR^2$, —$C(=O)SR^2$, —$NR^2C(=NR^3)NR^{2a}R^{3a}$, —$NR^2C(=NR^3)OR^{2a}$, —$NR^2C(=NR^3)SR^{2a}$, —$C(=O)OR^2$, —$OC(=O)NR^2R^3$, —$OC(=O)SR^2$, —$SC(=O)OR^2$, —$SC(=O)NR^2R^3$, $C_{0-10}$alkyl, $C_{2-10}$alkenyl, $C_{2-10}$alkenyl, $C_{1-10}$alkoxy$C_{1-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$cycloalkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, oxo, —$CF_3$, —$OCF_3$, $OR^{222}$, $NR^{222}R^{333}$ $(R^{222a})_{j1a}$, —$C(=O)R^{222}$, —$CO_2R^{222}$, —$C(=O)NR^{222}R^{333}$, —$NO_2$, —$CN$, —$S(=O)_{j1a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j1a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, —$OC(=O)SR^{222}$, —$SC(=O)OR^{222}$, or —$SC(=O)NR^{222}R^{333}$ substituents;
or $E^1$, $E^{11}$, or $G^1$ optionally is —$(W^1)_n$—$(Y^1)_m$—$R^4$;
or $E^1$, $E^{11}$, $G^1$, or $G^{41}$ optionally independently is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{222}$, —$NR^{222}R^{333}$ $(R^{222a})_{j2a}$, —$C(O)R^{222}$, —$CO_2R^{222}$, —$C(=O)NR^{222}R^{333}$, —$NO_2$, —$CN$, —$S(O)_{j2a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, —$OC(=O)SR^{222}$, —$SC(=O)OR^{222}$, or —$SC(=O)NR^{222}R^{333}$ substituents;

$G^{11}$ is halo, oxo, —$CF_3$, —$OCF_3$, —$OR^{21}$, —$NR^{21}R^{31}$ $(R^{2a1})_{j4}$, —$C(O)R^{21}$, —$CO_2R^{21}$, —$C(=O)NR^{21}R^{31}$, $NO_2$, —$CN$, —$S(O)_{j4}R^{21}$, —$SO_2NR^{21}R^{31}$, $NR^{21}C(=O)R^{31}$, —$NR^{32}C(=O)OR^{31}$, $NR^{21}C(=NR^{31})OR^{2a1}$, —$NR^{21}CS(O)_{j4}R^{31}$, —$C(=S)OR^{21}$, —$C(=O)SR^{21}$, —$NR^{21}C(=NR^{31})NR^{2a1}R^{3a1}$, —$NR^{21}C(=NR^{31})OR^{2a1}$, —$NR^{21}C(=NR^{31})SR^{2a1}$, —$OC(=O)OR^{21}$, —$OC(=O)NR^{21}R^{31}$, —$OC(=O)SR^{21}$, —$SC(=O)OR^{21}$, —$SC(=O)NR^{21}R^{31}$, —$P(O)OR^{21}OR^{31}$, $C_{1-10}$alkylidene, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl $C_{2-10}$alkenyl, cyclo$C_{3-8}$ alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, oxo, —$CF_3$, —$OCF_3$, —$OR^{2221}$, —$NR^{2221}R^{3331}$ $(R^{222a1})_{j4a}$, —$C(O)R^{2221}$, —$CO_2R^{2221}$, —$C(=O)NR^{2221}R^{3331}$, $NO_2$, —$CN$, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents;

or $G^{11}$ is aryl-$C_{0-10}$alkyl, aryl-$C_{2-10}$alkenyl, aryl-$C_{2-10}$alkynyl, hetaryl-$C_{2-10}$alkenyl, or hetaryl-$C_{2-10}$alkynyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —CN, —$S(O)_{j5a}R^{2221}$, —$SO_2NR^{2221}R^{3331}$, —$NR^{2221}C(=O)R^{3331}$, —$NR^{2221}C(=O)R^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents;

or $G^{11}$ is C, taken together with the carbon to which it is attached forms a double bond which is substituted with $R^5$ and $G^{111}$;

$R^2$, $R^{2a}$, $R^3$, $R^{3a}$, $R^{222}$, $R^{222a}$, $R^{333}$, $R^{333a}$, $R^{21}$, $R^{2a1}$, $R^{31}$, $R^{3a1}$, $R^{2221}$, $R^{222a1}$, $R^{3331}$, and $R^{333a1}$ are each independently $C_{1-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, or aryl-$C_{2-10}$alkynyl, hetaryl-$C_{1-10}$alkyl, hetaryl-$C_{2-10}$alkenyl, or hetaryl-$C_{2-10}$alkynyl, any of which is optionally substituted by one or more independent $G^{111}$ substituents;

or in the case of $NR^2R^3(R^{2a})_{j1}$ or —$NR^{222}R^{333}(R^{222a})_{j1a}$ or —$NR^{222}R^{333}(R^{222a})_{j2a}$ or —$NR^{21}R^{31}(R^{2a1})_{j4}$ or —$NR^{2221}R^{3331}(R^{222a1})_{j4}$ or —$NR^{2221}R^{3331}(R^{222a1})_{j5a}$, then $R^2$ and $R^3$, or $R^{222}$ and $R^{333}$, or $R^{2221}$ and $R^{3331}$, respectfully, are optionally taken together with the nitrogen atom to which they are attached to form a 3-10 membered saturated or unsaturated ring, wherein said ring is optionally substituted by one or more independent $G^{11}$ substituents and wherein said ring optionally includes one or more heteroatoms other than the nitrogen to which $R^2$ and $R^3$, or $R^{222}$ and $R^{333}$, or $R^{2221}$ and $R^{3331}$ are attached;

$W^1$ and $Y^1$ are each independently —O—, —$NR^7$—, —$S(O)_{j7}$—, —$CR^5R^6$—, —$N(C(O)OR^7)$—, —$N(C(O)R^7)$—, —$N(SO_2R^7)$—, —$CH_2O$—, —$CH_2S$—, —$CH_2N(R^7)$—, —$CH(NR^7)$—, —$CH_2N(C(O)R^7)$—, —$CH_2N(C(O)OR^7)$—, —$CH_2N(SO_2R^7)$—, —$CH(NHR^7)$—, —$CH(NHC(O)R^7)$—, —$CH(NHSO_2R^7)$—, —$CH(NHC(O)OR^7)$—, —$CH(OC(O)R^7)$—, —$CH(OC(O)NHR^7)$—, —CH=CH—, —C≡C—, —$C(=NOR^7)$—, —C(O)—, —CH(OR^7)—, —$C(O)N(R^7)$—, —$N(R^7)C(O)$—, —$N(R^7)S(O)$—, —$N(R^7)S(O)_2$—, —$OC(O)N(R^7)$—, —$N(R^7)C(O)N(R^8)$—, —$NR^7C(O)O$—, —$S(O)N(R^7)$—, —$S(O)_2N(R^7)$—, —$N(C(O)R^7)S(O)$—, —$N(C(O)R^7)S(O)_2$—, —$N(R^7)S(O)N(R^8)$—, —$N(R^7)S(O)_2N(R^8)$—, —$C(O)N(R^7)C(O)$—, —$S(O)N(R^7)C(O)$—, —$S(O)_2N(R^7)C(O)$—, —$OS(O)N(R^7)$—, —$OS(O)_2N(R^7)$—, —$N(R^7)S(O)O$—, —$N(R^7)S(O)_2O$—, —$N(R^7)S(O)C(O)$—, —$N(R^7)S(O)_2C(O)$—, —$SON(C(O)R^7)$—, —$SO_2N(C(O)R^7)$—, —$N(R^7)SON(R^8)$—, —$N(R^7)SO_2N(R^8)$—, —C(O)O—, —$N(R^7)P(OR^8)O$—, —$N(R^7)P(OR^8)$—, —$N(R^7)P(O)(OR^8)O$—, —$N(R^7)P(O)(OR^8)$—, —$N(C(O)R^7)P(OR^8)O$—, —$N(C(O)R^7)P(OR^8)$—, —$N(C(O)R^7)P(O)(OR^8)O$—, —$N(C(O)R^7)P(OR^8)$—, —$CH(R^7)S(O)$—, —$CH(R^7)S(O)_2$—, —$CH(R^7)N(C(O)OR^8)$—, —$CH(R^7)N(C(O)R^8)$—, —$CH(R^7)N(SO_2R^8)$—, —$CH(R^7)O$—, —$CH(R^7)S$—, —$CH(R^7)N(R^8)$—, —$CH(R^7)N(C(O)R^8)$—, —$CH(R^7)N(C(O)OR^8)$—, —$CH(R^7)N(SO_2R^8)$—, —$CH(R^7)C(=NOR^8)$—, —$CH(R^7)C(O)$—, —$CH(R^7)CH(OR^8)$—, —$CH(R^7)C(O)N(R^8)$—, —$CH(R^7)N(R^8)C(O)$—, —$CH(R^7)N(R^8)S(O)$—, —$CH(R^7)N(R^8)S(O)_2$—, —$CH(R^7)OC(O)N(R^8)$—, —$CH(R^7)N(R^8)C(O)N(R^{7a})$—, —$CH(R^7)NR^8C(O)O$—, —$CH(R^7)S(O)N(R^8)$—, —$CH(R^7)S(O)_2N(R^8)$—, —$CH(R^7)N(C(O)R^8)S(O)$—, —$CH(R^7)N(C(O)R^8)S(O)$—, —$CH(R^7)N(R^8)S(O)N(R^{7a})$—, —$CH(R^7)N(R^8)S(O)_2N(R^{7a})$—, —$CH(R^7)C(O)N(R^8)C(O)$—, —$CH(R^7)S(O)N(R^8)C(O)$—, —$CH(R^7)S(O)_2N(R^8)C(O)$—, —$CH(R^7)OS(O)N(R^8)$—, —$CH(R^7)OS(O)_2N(R^8)$—, —$CH(R^7)N(R^8)S(O)O$—, —$CH(R^7)N(R^8)S(O)_2O$—, —$CH(R^7)N(R^8)S(O)C(O)$—, —$CH(R^7)N(R^8)S(O)_2C(O)$—, —$CH(R^7)SON(C(O)R^8)$—, —$CH(R^7)SO_2N(C(O)R^8)$—, —$CH(R^7)N(R^8)SON(R^{7a})$—, —$CH(R^7)N(R^8)SO_2N(R^{7a})$—, —$CH(R^7)C(O)O$—, —$CH(R^7)N(R^8)P(OR^{7a})O$—, —$CH(R^7)N(R^8)P(OR^{7a})$—, —$CH(R^7)N(R^8)P(O)(OR^{7a})O$—, —$CH(R^7)N(R^8)P(O)(OR^{7a})$—, —$CH(R^7)N(C(O)R^8)P(OR^{7a})O$—, —$CH(R^7)N(C(O)R^8)P(OR^{7a})$—, —$CH(R^7)N(C(O)R^8)P(O)(OR^{7a})O$—, or —$CH(R^7)N(C(O)R^8)P(OR^{7a})$—;

$R^5$, $R^6$, $G^{11}$, and $G^{1111}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —CN, —$S(O)_{j5a}R^{77}$, —$SO_2NR^{77}R^{87}$, —$NR^{77}C(=O)R^{87}$, —$NR^{77}C(=O)OR^{87}$, —$NR^{77}C(=O)NR^{78}R^{87}$, —$NR^{77}S(O)_{j5a}R^{87}$, —$C(=S)OR^{77}$, —$C(=O)SR^{77}$, —$NR^{77}C(=NR^{87})NR^{78}R^{88}$, —$NR^{77}C(=NR^{87})OR^{78}$, —$NR^{77}C(=NR^{87})SR^{78}$, —$OC(=O)OR^{77}$, —$OC(=O)NR^{77}R^{87}$, —$OC(=O)SR^{77}$, —$SC(=O)OR^{77}$, —$P(O)OR^{77}OR^{87}$, or —$SC(=O)NR^{77}R^{87}$ substituents;

or $R^5$ with $R^6$ are optionally taken together with the carbon atom to which they are attached to form a 3-10 membered saturated or unsaturated ring, wherein said ring is optionally substituted with one or more independent $R^{69}$ substituents and wherein said ring optionally includes one or more heteroatoms;

$R^7$, $R^{7a}$, and $R^8$ are each independently acyl, $C_{0-10}$alkyl, $C_{2-10}$alkenyl, aryl, heteroaryl, heterocyclyl or cyclo$C_{3-10}$alkyl, any of which is optionally substituted by one or more independent $G^{111}$ substituents;

$R^4$ is $C_{0-10}$alkyl, $C_{2-10}$alkenyl, $C_{2-10}$alkynyl, aryl, heteroaryl, cyclo$C_{3-10}$alkyl, heterocyclyl, cyclo$C_{3-8}$alkenyl, or heterocycloalkenyl, any of which is optionally substituted by one or more independent $G^{41}$ substituents;

$R^{69}$ is halo, —$OR^{78}$, —SH, —$NR^{78}R^{88}$, —$CO_2R^{78}$, —$C(=O)NR^{78}R^{88}$, —$NO_2$, —CN, —$S(O)_{j8}R^{78}$, —$SO_2NR^{78}R^{88}$, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, cyclo$C_{1-10}$alkylthio$C_{2-10}$alkynyl, cyclo$C_{3-8}$alkyl, cyclo$C_{3-8}$alkenyl, cyclo$C_{3-8}$alkenyl$C_{1-10}$alkyl, cyclo$C_{3-8}$alkenyl$C_{1-10}$alkyl, cyclo$C_{3-8}$alkenyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —OR$^{778}$, —SO$_2$NR$^{778}$R$^{888}$, or —NR$^{778}$R$^{888}$ substituents;

or R$^{69}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, hetaryl-C$_{2-10}$alkynyl, mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —N(C$_{1-6}$alkyl)-C$_{1-6}$alkyl-aryl, any of which is optionally substituted with one or more independent halo, cyano, nitro, —OR$^{778}$, C$_{1-10}$alkyl, C$_{2-10}$alkenyl, C$_{2-10}$alkynyl, haloC$_{1-10}$alkyl, haloC$_{2-10}$alkenyl, haloC$_{2-10}$ alkynyl, —COOH, C$_{1-4}$alkoxycarbonyl, —C(=O)NR$^{778}$R$^{888}$, —SO$_2$NR$^{778}$R$^{888}$, or —NR$^{778}$R$^{888}$ substituents;

or in the case of —NR$^{78}$R$^{88}$, R$^{78}$ and R$^{88}$ are optionally taken together with the nitrogen atom to which they are attached to form a 3-10 membered saturated or unsaturated ring, wherein said ring is optionally substituted with one or more independent halo, cyano, hydroxy, nitro, C$_{1-10}$alkoxy, —SO$_2$NR$^{778}$R$^{888}$, or —NR$^{778}$R$^{888}$ substituents, and wherein said ring optionally includes one or more heteroatoms other than the nitrogen to which R$^{78}$ and R$^{88}$ are attached;

R$^{77}$, R$^{78}$, R$^{87}$, R$^{88}$, R$^{778}$, and R$^{888}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, C$_{1-10}$alkylcarbonyl, C$_{2-10}$alkenylcarbonyl, C$_{2-10}$alkynylcarbonyl, C$_{1-10}$alkoxycarbonyl, C$_{1-10}$alkoxycarbonylC$_{1-10}$alkyl, monoC$_{1-6}$alkylaminocarbonyl, diC$_{1-6}$alkylaminocarbonyl, mono(aryl)aminocarbonyl, di(aryl)aminocarbonyl, or C$_{1-10}$alkyl(aryl)aminocarbonyl, any of which is optionally substituted with one or more independent halo, cyano, hydroxy, nitro, C$_{1-10}$alkoxy, —SO$_2$N(C$_{0-4}$alkyl)(C$_{0-4}$alkyl), or —N(C$_{0-4}$alkyl)(C$_{0-4}$alkyl) substituents;

or R$^{77}$, R$^{78}$, R$^{87}$, R$^{88}$, R$^{778}$, and R$^{888}$ are each independently aryl-C$_{1-10}$alkyl, aryl-C$_{2-10}$alkenyl, aryl-C$_{2-10}$alkynyl, hetaryl-C$_{1-10}$alkyl, hetaryl-C$_{2-10}$alkenyl, hetaryl-C$_{2-10}$alkynyl, mono(C$_{1-6}$ alkyl)aminoC$_{1-6}$alkyl, di(C$_{1-6}$alkyl)aminoC$_{1-6}$ alkyl, mono(aryl)aminoC$_{1-6}$ alkyl, di(aryl)aminoC$_{1-6}$ alkyl, or —N(C$_{1-6}$alkyl)-C$_{1-6}$alkyl-aryl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, halo C$_{2-10}$alkynyl, —COOH, C$_{1-4}$alkoxycarbonyl, —CON(C$_{0-4}$alkyl)(C$_{0-10}$alkyl), —SO$_2$N(C$_{0-4}$alkyl)(C$_{0-4}$alkyl), or —N(C$_{0-4}$alkyl)(C$_{0-4}$ alkyl) substituents;

n, m, j1, j1a, j2a, j4, j4a, j5a, j7, and j8 are each independently 0, 1, or 2; and aa and bb are each independently 0 or 1.

In an aspect of the present invention, a compound is represented by Formula I, or a pharmaceutically acceptable salt thereof, wherein X$_3$ is N; X$_1$, X$_2$, and X$_5$ are C-(E$^1$)$_{aa}$; X$_4$, X$_6$, and X$_7$ are C; and the other variables are described as above for Formula I.

In a second aspect of the present invention, a compound is represented by Formula I, or a pharmaceutically acceptable salt thereof, wherein X$_4$ is N; X$_1$, X$_2$, and X$_5$ are C-(E$^1$)$_{aa}$; and X$_3$, X$_6$, and X$_7$ are C; and the other variables are described as above for Formula I.

In a third aspect of the present invention, a compound is represented by Formula I, or a salt thereof, wherein X$_5$ is N-(E$^1$)$_{aa}$; X$_1$ and X$_2$ are C-(E$^1$)$_{aa}$; X$_3$, X$_4$, X$_6$, and X$_7$ are C; and the other variables are described as above for Formula I.

In a fourth aspect of the present invention, a compound is represented by Formula I, or a salt thereof, wherein X$_6$ is N; X$_1$, X$_2$, and X$_5$ are C-(E$^1$)$_{aa}$; X$_3$, X$_4$, and X$_7$ are C; and the other variables are described as above for Formula I.

In a fifth aspect of the present invention, a compound is represented by Formula I, or a salt thereof, wherein X$_7$ is N; X$_1$, X$_2$, and X$_5$ are C-(E$^1$)$_{aa}$; X$_3$, X$_4$, and X$_6$ are C; and the other variables are described as above for Formula I.

In a sixth aspect of the present invention, a compound is represented by Formula I, or a salt thereof, wherein X$_1$ and X$_3$ are N; X$_2$ and X$_5$ are C-(E$^1$)$_{aa}$; X$_4$, X$_6$, and X$_7$ are C; and the other variables are described as above for Formula I.

In a seventh aspect of the present invention, a compound is represented by Formula I, or a salt thereof, wherein X$_1$ and X$_4$ are N; X$_2$ and X$_5$ are C-(E$^1$)$_{aa}$; X$_3$, X$_6$, and X$_7$ are C; and the other variables are described as above for Formula I.

In an eighth aspect of the present invention, a compound is represented by Formula I, or a salt thereof, wherein X$_1$ is N; X$_5$ is N-(E$^1$)$_{aa}$; X$_2$ is C-(E$^1$)$_{aa}$; X$_3$, X$_4$, X$_6$, and X$_7$ are C; and the other variables are described as above for Formula I.

In a ninth aspect of the present invention, a compound is represented by Formula I, or a salt thereof, wherein X$_1$ and X$_6$ are N; X$_2$ and X$_5$ are C-(E$^1$)$_{aa}$; X$_3$, X$_4$, and X$_7$ are C; and the other variables are described as above for Formula I.

In a tenth aspect of the present invention, a compound is represented by Formula I, or a salt thereof, wherein X$_1$ and X$_7$ are N; X$_2$ and X$_5$ are C-(E$^1$)$_{aa}$; X$_3$, X$_4$, and X$_6$ are C; and the other variables are described as above for Formula I.

In a eleventh aspect of the present invention, a compound is represented by Formula I, or a salt thereof, wherein X$_2$ and X$_3$ are N; X$_1$ and X$_5$ are C-(E$^1$)$_{aa}$; X$_4$, X$_6$, and X$_7$ are C; and the other variables are described as above for Formula I.

In a twelfth aspect of the present invention, a compound is represented by Formula I, or a salt thereof, wherein X$_2$ and X$_4$ are N; X$_1$ and X$_5$ are C-(E$^1$)$_{aa}$; X$_3$, X$_6$, and X$_7$ are C; and the other variables are described as above for Formula I.

In a thirteenth aspect of the present invention, a compound is represented by Formula I, or a salt thereof, wherein X$_2$ is N; X$_5$ is N-(E$^1$)$_{aa}$; X$_1$ is C-(E$^1$)$_{aa}$; X$_3$, X$_4$, X$_6$, and X$_7$ are C; and the other variables are described as above for Formula I.

In a fourteenth aspect of the present invention, a compound is represented by Formula I, or a salt thereof, wherein X$_2$ and X$_6$ are N; X$_1$ and X$_5$ are C-(E$^1$)$_{aa}$; X$_3$, X$_4$, and X$_7$ are C; and the other variables are described as above for Formula I.

In a fifteenth aspect of the present invention, a compound is represented by Formula I, or a salt thereof, wherein X$_2$ and X$_7$ are N; X$_1$ and X$_5$ are C-(E$^1$)$_{aa}$; X$_3$, X$_4$, and X$_6$ are C; and the other variables are described as above for Formula I.

In a sixteenth aspect of the present invention, a compound is represented by Formula I, or a salt thereof, wherein X$_3$ and X$_4$ are N; X$_1$, X$_2$, and X$_5$ are C-(E$^1$)$_{aa}$; X$_6$ and X$_7$ are C; R$^1$ is absent; and the other variables are described as above for Formula I.

In a seventeenth aspect of the present invention, a compound is represented by Formula I, or a salt thereof, wherein X$_3$ and X$_5$ are N; X$_1$ and X$_2$ are C-(E$^1$)$_{aa}$; X$_4$, X$_6$, and X$_7$ are C; and the other variables are described as above for Formula I.

In an eighteenth aspect of the present invention, a compound is represented by Formula I, or a salt thereof, wherein X$_4$ and X$_5$ are N; X$_1$ and X$_2$ are C-(E$^1$)$_{aa}$; X$_3$, X$_6$ and X$_7$ are C; and the other variables are described as above for Formula I.

In a nineteenth aspect of the present invention, a compound is represented by Formula I, or a salt thereof, wherein X$_4$ and X$_6$ are N; X$_1$, X$_2$, and X$_5$ are C-(E$^1$)$_{aa}$; X$_3$ and X$_7$ are C; R$^1$ is absent; and the other variables are described as above for Formula I.

In a twentieth aspect of the present invention, a compound is represented by Formula I, or a salt thereof, wherein $X_4$ and $X_7$ are N; $X_1$, $X_2$, and $X_5$ are C-$(E^1)_{aa}$; $X_3$ and $X_6$ are C; $R^1$ is absent; and the other variables are described as above for Formula I.

In a twenty-first aspect of the present invention, a compound is represented by Formula I, or a salt thereof, wherein $X_5$ and $X_6$ are N; $X_1$ and $X_2$ are C-$(E^1)_{aa}$, $X_3$, $X_4$, and $X_7$ are C; and the other variables are described as above for Formula I.

In a twenty-second aspect of the present invention, a compound is represented by Formula I, or a salt thereof, wherein $X_5$ and $X_7$ are N; $X_1$ and $X_2$ are C-$(E^1)_{aa}$; $X_3$, $X_4$, and $X_6$ are C; and the other variables are described as above for Formula I.

In a twenty-third aspect of the present invention, a compound is represented by Formula I, or a salt thereof, wherein $X_2$, $X_3$, and $X_4$ are N; $X_1$ and $X_5$ are C-$(E^1)_{aa}$; $X_6$ and $X_7$ are C; $R^1$ is absent; and the other variables are described as above for Formula I.

In a twenty-fourth aspect of the present invention, a compound is represented by Formula I, or a salt thereof, wherein $X_2$, $X_3$, and $X_5$ are N; $X_1$ is C-$(E^1)_{aa}$; $X_4$, $X_6$ and $X_7$ are C; and the other variables are described as above for Formula I.

In a twenty-fifth aspect of the present invention, a compound is represented by Formula I, or a salt thereof, wherein $X_3$, $X_4$, and $X_5$ are N; $X_1$ and $X_2$ are C-$(E^1)_{aa}$; $X_6$ and $X_7$ are C; $R^1$ is absent; and the other variables are described as above for Formula I.

In a twenty-sixth aspect of the present invention, a compound is represented by Formula I, or a salt thereof, wherein $X_1$, $X_3$, and $X_4$ are N; $X_2$ and $X_5$ are C-$(E^1)_{aa}$; $X_6$ and $X_7$ are C; $R^1$ is absent; and the other variables are described as above for Formula I.

In a twenty-seventh aspect of the present invention, a compound is represented by Formula I, or a salt thereof, wherein $X_1$, $X_4$, and $X_5$ are N; $X_2$ is C-$(E^1)_{aa}$; $X_3$, $X_6$ and $X_7$ are C; and the other variables are described as above for Formula I.

In a twenty-eighth aspect of the present invention, a compound is represented by Formula I, or a salt thereof, wherein $X_2$, $X_4$, and $X_5$ are N; $X_1$ is C-$(E^1)_{aa}$; $X_3$, $X_6$ and $X_7$ are C; and the other variables are described as above for Formula I.

In a twenty-ninth aspect of the present invention, a compound is represented by Formula I, or a salt thereof, wherein $X_1$, $X_5$, and $X_6$ are N; $X_2$ is C-$(E^1)_{aa}$; $X_3$, $X_4$, and $X_7$ are C; and the other variables are described as above for Formula I.

In a thirtieth aspect of the present invention, a compound is represented by Formula I, or a salt thereof, wherein $X_2$, $X_5$, and $X_6$ are N; $X_1$ is C-$(E^1)_{aa}$; $X_3$, $X_4$, and $X_7$ are C; and the other variables are described as above for Formula I.

In a thirty-first aspect of the present invention, a compound is represented by Formula I, or a salt thereof, wherein $X_4$, $X_5$, and $X_6$ are N; $X_1$ and $X_2$ are C-$(E^1)_{aa}$; $X_3$ and $X_7$ are C; $R^1$ is absent; and the other variables are described as above for Formula I.

In a thirty-second aspect of the present invention, a compound is represented by Formula I, or a salt thereof, wherein $X_1$, $X_3$, and $X_5$ are N; $X_2$ is C-$(E)_{aa}$; $X_4$, $X_6$ and $X_7$ are C; and the other variables are described as above for Formula I.

In a thirty-third aspect of the present invention, a compound is represented by Formula I, or a salt thereof, wherein $X_1$, $X_4$, and $X_6$ are N; $X_2$ and $X_5$ are C-$(E^1)_{aa}$; $X_3$ and $X_7$ are C; $R^1$ is absent; and the other variables are described as above for Formula I.

In a thirty-fourth aspect of the present invention, a compound is represented by Formula I, or a salt thereof, wherein $X_1$, $X_5$, and $X_7$ are N; $X_2$ is C-$(E^1)_{aa}$; $X_3$, $X_4$, and $X_6$ are C; and the other variables are described as above for Formula I.

In a thirty-fifth aspect of the present invention, a compound is represented by Formula I, or a salt thereof, wherein $X_1$, $X_4$, and $X_7$ are N; $X_2$ and $X_5$ are C-$(E^1)_{aa}$; $X_3$ and $X_6$ are C; $R^1$ is absent; and the other variables are described as above for Formula I.

In a thirty-sixth aspect of the present invention, a compound is represented by Formula I, or a salt thereof, wherein $X_2$, $X_4$, and $X_6$ are N; $X_1$ and $X_5$ are C-$(E^1)_{aa}$; $X_3$ and $X_7$ are C; $R^1$ is absent; and the other variables are described as above for Formula I.

In a thirty-seventh aspect of the present invention, a compound is represented by Formula I, or a salt thereof, wherein $X_2$, $X_4$, and $X_7$ are N; $X_1$ and $X_5$ are C-$(E^1)_{aa}$; $X_3$ and $X_6$ are C; $R^1$ is absent; and the other variables are described as above for Formula I.

In a thirty-eighth aspect of the present invention, a compound is represented by Formula I, or a salt thereof, wherein $X_2$, $X_5$, and $X_7$ are N; $X_1$ is C-$(E^1)_{aa}$; $X_3$, $X_4$, and $X_6$ are C; and the other variables are described as above for Formula I.

In a thirty-ninth aspect of the present invention, a compound is represented by Formula I, or a salt thereof, wherein $X_1$, $X_4$, $X_5$, and $X_6$ are N; $X_2$ is C-$(E^1)_{aa}$; $X_3$ and $X_7$ are C; $R^1$ is absent; and the other variables are described as above for Formula I.

In a fortieth aspect of the present invention, a compound is represented by Formula I, or a salt thereof, wherein $X_2$, $X_4$, $X_5$, and $X_6$ are N; $X_1$ is C-$(E^1)_{aa}$; $X_3$ and $X_7$ are C; $R^1$ is absent; and the other variables are described as above for Formula I.

In a forty-first aspect of the present invention, a compound is represented by Formula I, or a salt thereof, wherein $X_1$, $X_3$, $X_4$, and $X_5$ are N; $X_2$ is C-$(E^1)_{aa}$; $X_6$ and $X_7$ are C; $R^1$ is absent; and the other variables are described as above for Formula I.

In a forty-second aspect of the present invention, a compound is represented by Formula I, or a salt thereof, wherein $X_2$, $X_3$, $X_4$, and $X_5$ are N; $X_1$ is C-$(E^1)_{aa}$; $X_6$ and $X_7$ are C; $R^1$ is absent; and the other variables are described as above for Formula I.

The following embodiments refer to all of the forty-two aspects above:

In an embodiment of each of the above aspects, a compound is represented by Formula I, or a pharmaceutically acceptable salt thereof, wherein $X_{11}$, $X_{12}$, and $X_{13}$ are N; $X_{14}$, $X_{15}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{11}$, $X_{12}$, and $X_{14}$ are N; $X_{13}$, $X_{15}$, and $X_{16}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{11}$, $X_{12}$, and $X_{15}$ are N; $X_{13}$, $X_{14}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{11}$, $X_{12}$, and $X_{16}$ are N; $X_{13}$, $X_{14}$, and $X_{15}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{11}$, $X_{13}$, and $X_{14}$ are N; $X_{12}$, $X_{15}$, and $X_{16}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{11}$, $X_{13}$, and $X_{15}$ are N; $X_{12}$, $X_{14}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{11}$, $X_{13}$, and $X_{16}$ are N; $X_{12}$, $X_{14}$, and $X_{15}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{11}$, $X_{14}$, and $X_{15}$ are N; $X_{12}$, $X_{13}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{11}$, $X_{14}$, and $X_{16}$ are N; $X_{12}$, $X_{13}$, and $X_{15}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{11}$, $X_{15}$, and $X_{16}$ are N; $X_{12}$, $X_{13}$, and $X_{14}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{12}$, $X_{13}$, and $X_{14}$ are N; $X_{11}$, $X_{15}$, and $X_{16}$ are C-$(E^{11})_{bb}$; and the other variables are as described in each of the above aspects.

In still yet another embodiment of each of the above aspects, a compound is represented by Formula I, or a pharmaceutically acceptable salt thereof, wherein $X_{12}$, $X_{13}$, and $X_{15}$ are N; $X_{11}$, $X_{14}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{12}$, $X_{13}$, and $X_{16}$ are N; $X_{11}$, $X_{14}$, and $X_{15}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{12}$, $X_{14}$, and $X_{15}$ are N; $X_{11}$, $X_{13}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{12}$, $X_{14}$, and $X_{16}$ are N; $X_{11}$, $X_{13}$, and $X_{15}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{12}$, $X_{15}$, and $X_{16}$ are N; $X_{11}$, $X_{13}$, and $X_{14}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{13}$, $X_{14}$, and $X_{15}$ are N; $X_{11}$, $X_{12}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{13}$, $X_{14}$, and $X_{16}$ are N; $X_{11}$, $X_{12}$, and $X_{15}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{14}$, $X_{15}$, and $X_{16}$ are N; $X_{11}$, $X_{12}$, and $X_{13}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{13}$, $X_{15}$, and $X_{16}$ are N; $X_{11}$, $X_{12}$, and $X_{14}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{11}$ and $X_{12}$ are N; $X_{13}$, $X_{14}$, $X_{15}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{11}$ and $X_{13}$ are N; $X_{12}$, $X_{14}$, $X_{15}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{11}$ and $X_{14}$ are N; $X_{12}$, $X_{13}$, $X_{15}$, and $X_{16}$ are C-$(E^{11})_{bb}$; and the other variables are as described in each of the above aspects.

In still yet another embodiment of each of the above aspects, a compound is represented by Formula I, or a pharmaceutically acceptable salt thereof, wherein $X_{11}$ and $X_{15}$ are N; $X_{12}$, $X_{13}$, $X_{14}$, and $X_{16}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{11}$ and $X_{16}$ are N; $X_{12}$, $X_{13}$, $X_{14}$, and $X_{15}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{12}$ and $X_{13}$ are N; $X_{11}$, $X_{14}$, $X_{15}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{12}$ and $X_{14}$ are N; $X_{11}$, $X_{13}$, $X_{15}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{12}$ and $X_{15}$ are N; $X_{11}$, $X_{13}$, $X_{14}$, and $X_{16}$ are C-$(E^{11})_{bb}$; and the other variables are as described in each of the above aspects.

In still yet another embodiment of each of the above aspects, a compound is represented by Formula I, or a pharmaceutically acceptable salt thereof, wherein $X_{12}$ and $X_{16}$ are N; $X_{11}$, $X_{13}$, $X_{14}$, and $X_{15}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{13}$ and $X_{14}$ are N; $X_{11}$, $X_{12}$, $X_{15}$, and $X_{16}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{13}$ and $X_{15}$ are N; $X_{11}$, $X_{12}$, $X_{14}$, and $X_{16}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{13}$ and $X_{16}$ are N; $X_{11}$, $X_{12}$, $X_{14}$, and $X_{15}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{14}$ and $X_{15}$ are N; $X_{11}$, $X_{12}$, $X_{13}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{14}$ and $X_{16}$ are N; $X_{11}$, $X_{12}$, $X_{13}$, and $X_{15}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{15}$ and $X_{16}$ are N; $X_{11}$, $X_{12}$, $X_{13}$, and $X_{14}$ are C-$(E^{11})_{bb}$; and the other variables are as described in each of the above aspects.

In another embodiment of each of the above aspects, a compound is represented by Formula I, or a pharmaceutically acceptable salt thereof, wherein $X_{11}$ is N; $X_{12}$, $X_{13}$, $X_{14}$, $X_{15}$, and $X_{16}$ are C-$(E^{11})_{bb}$; and the other variables are as described in each of the above aspects.

In yet another embodiment of each of the above aspects, a compound is represented by Formula I, or a pharmaceutically acceptable salt thereof, wherein $X_{12}$ is N; $X_{11}$, $X_{13}$, $X_{14}$, $X_{15}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{13}$ is N; $X_{11}$, $X_{12}$, $X_{14}$, $X_{15}$, and $X_{16}$ are C-$(E^{11})_{bb}$; and the other variables are as described in each of the above aspects.

In yet still another embodiment of each of the above aspects, a compound is represented by Formula I, or a pharmaceutically acceptable salt thereof, wherein $X_{14}$ is N; $X_{11}$, $X_{12}$, $X_{13}$, $X_{15}$, and $X_{16}$ are C-$(E''')_{bb}$; and the other variables are as described in each of the above aspects.

In still another embodiment of each of the above aspects, a compound is represented by Formula I, or a pharmaceutically acceptable salt thereof, wherein $X_{15}$ is N; $X_{11}$, $X_{12}$, $X_{13}$, $X_{14}$, and $X_{16}$ are C-$(E^{11})_{bb}$; and the other variables are as described in each of the above aspects.

In still another embodiment of each of the above aspects, a compound is represented by Formula I, or a pharmaceutically acceptable salt thereof, wherein $X_{16}$ is N; $X_{11}$, $X_{12}$, $X_{13}$, $X_{14}$, and $X_{15}$ are C-$(E^{11})_{bb}$; and the other variables are as described in each of the above aspects.

Advantageous embodiments of the above aspects include:

An embodiment of each of the above aspects, wherein a compound is represented by Formula I, or a pharmaceutically acceptable salt thereof, wherein $X_{11}$ and $X_{16}$ are N; $X_{12}$, $X_{13}$, $X_{14}$, and $X_{15}$ are C-$(E^{11})_{bb}$; and the other variables are as described in each of the above aspects.

An embodiment of each of the above aspects, wherein a compound is represented by Formula I, or a pharmaceutically acceptable salt thereof, wherein $X_{14}$ and $X_{16}$ are N; $X_{11}$, $X_{12}$, $X_{13}$, and $X_{15}$ are C-$(E^{11})_{bb}$; and the other variables are as described in each of the above aspects.

An embodiment of each of the above aspects, wherein a compound is represented by Formula I, or a pharmaceutically acceptable salt thereof, wherein $X_{15}$ and $X_{16}$ are N; $X_{11}$, $X_{12}$, $X_{13}$, and $X_{14}$ are C-$(E^{11})_{bb}$ and the other variables are as described in each of the above aspects.

An embodiment of each of the above aspects, wherein a compound is represented by Formula I, or a pharmaceutically acceptable salt thereof, wherein $X_{11}$ is N; $X_{12}$, $X_{13}$, $X_{14}$, $X_{15}$, and $X_{16}$ are C-$(E^{11})_{bb}$; and the other variables are as described in each of the above aspects.

An embodiment of each of the above aspects, wherein a compound is represented by Formula I, or a pharmaceutically acceptable salt thereof, wherein $X_{16}$ is N; $X_{11}$, $X_{12}$, $X_{13}$, $X_{14}$, and $X_{15}$ are C-$(E^{11})_{bb}$; and the other variables are as described in each of the above aspects.

The compounds of the present invention include compounds represented by Formula I above, or a pharmaceutically acceptable salt thereof, and wherein $X_3$ is N; $X_1$, $X_2$, and $X_5$ are C-$(E^1)_{aa}$; and $X_4$, $X_6$, and $X_7$ are C; or wherein $X_4$ is N; $X_1$, $X_2$, and $X_5$ are C-$(E^1)_{aa}$; and $X_3$, $X_6$, and $X_7$ are C; or wherein $X_5$ is N-$(E^1)_{aa}$; $X_1$ and $X_2$ are C-$(E^1)_{aa}$; and $X_3$, $X_4$, $X_6$, and $X_7$ are C; or wherein $X_6$ is N; $X_1$, $X_2$, and $X_5$ are C-$(E^1)_{aa}$; and $X_3$, $X_4$, and $X_7$ are C; or wherein $X_7$ is N; $X_1$, $X_2$, and $X_5$ are C-$(E^1)_{aa}$; and $X_3$, $X_4$, and $X_6$ are C; or wherein $X_1$ and $X_3$ are N; $X_2$ and $X_5$ are C-$(E^1)_{aa}$; and $X_4$, $X_6$, and $X_7$ are C; or wherein $X_1$ and $X_4$ are N; $X_2$ and $X_5$ are C-$(E^1)_{aa}$; and $X_3$, $X_6$, and $X_7$ are C; or wherein $X_1$ is N; $X_5$ is N-$(E^1)_{aa}$; $X_2$ is C-$(E^{11})_{aa}$; and $X_3$, $X_4$, $X_6$, and $X_7$ are C; or wherein $X_1$ and $X_6$ are N; $X_2$ and $X_5$ are C-$(E^1)_{aa}$; and $X_3$, $X_4$, and $X_7$ are C; or wherein $X_1$ and $X_7$ are N; $X_2$ and $X_5$ are C-$(E^{11})_{aa}$; and $X_3$, $X_4$, and $X_6$ are C; or wherein $X_2$ and $X_3$ are N; $X_1$ and $X_5$ are C-$(E^1)_{aa}$; and $X_4$, $X_6$, and $X_7$ are C; or wherein $X_2$ and $X_4$ are N; $X_1$ and $X_5$ are C-$(E^1)_{aa}$; and $X_3$, $X_6$, and $X_7$ are C; or wherein $X_2$ is N; $X_5$ is N-$(E^1)_{aa}$, $X_1$ is C-$(E^1)_{aa}$; and $X_3$, $X_4$, $X_6$, and $X_7$ are C; or wherein $X_2$ and $X_6$ are N; $X_1$ and $X_5$ are C-$(E^1)_{aa}$; and $X_3$, $X_4$, and $X_7$ are C; or wherein $X_2$ and $X_7$ are N; $X_1$ and $X_5$ are C-$(E^1)_{aa}$; and $X_3$, $X_4$, and $X_6$ are C; or wherein $X_3$ and $X_4$ are N; $X_1$, $X_2$, and $X_5$ are C-$(E^1)_{aa}$; $X_6$ and $X_7$ are C; and $R^1$ is absent; or wherein $X_3$ and $X_5$ are N; $X_1$ and $X_2$ are C-$(E^1)_{aa}$; and $X_4$, $X_6$, and $X_7$ are C; or wherein $X_4$ and $X_5$ are N; $X_1$ and $X_2$ are C-$(E^1)_{aa}$; and $X_3$, $X_6$, and $X_7$ are C; or wherein $X_4$ and $X_6$ are N; $X_1$, $X_2$, and $X_5$ are C-$(E^1)_{aa}$; $X_3$ and $X_7$ are C; and $R^1$ is absent; or wherein $X_4$ and $X_7$ are N; $X_1$, $X_2$, and $X_5$ are C-$(E^1)_{aa}$; $X_3$ and $X_6$ are C; and $R^1$ is absent; or wherein $X_5$ and $X_6$ are N; $X_1$ and $X_2$ are C-$(E^1)_{aa}$; and $X_3$, $X_4$, and $X_7$ are C; or wherein $X_5$ and $X_7$ are N; $X_1$ and $X_2$ are C-$(E^1)_{aa}$; and $X_3$, $X_4$, and $X_6$ are C; or wherein $X_2$, $X_3$, and $X_4$ are N; $X_1$ and $X_5$ are C-$(E^1)_{aa}$; $X_6$ and $X_7$ are C; and $R^1$ is absent; or wherein $X_2$, $X_3$, and $X_5$ are N; $X_1$ is C-$(E^1)_{aa}$; and $X_4$, $X_6$ and $X_7$ are C; or wherein $X_3$, $X_4$, and $X_5$ are N; $X_1$ and $X_2$ are C-$(E^1)_{aa}$; $X_6$ and $X_7$ are C; and $R^1$ is absent; or wherein $X_1$, $X_3$, and $X_4$ are N; $X_2$ and $X_5$ are C-$(E^1)_{aa}$; $X_6$ and $X_7$ are C; and $R^1$ is absent; or wherein $X_1$, $X_4$, and $X_5$ are N; $X_2$ is C-$(E^1)_{aa}$; and $X_3$, $X_6$, and $X_7$ are C; or wherein $X_2$, $X_4$, and $X_5$ are N; $X_1$ is C-$(E^1)_{aa}$; and $X_3$, $X_6$, and $X_7$ are C; or wherein $X_1$, $X_5$, and $X_6$ are N; $X_2$ is C-$(E^1)_{aa}$; and $X_3$, $X_4$, and $X_7$ are C; or wherein $X_2$, $X_5$, and $X_6$ are N; $X_1$ is C-$(E^1)_{aa}$; and $X_3$, $X_4$, and $X_7$ are C; or wherein $X_4$, $X_5$, and $X_6$ are N; $X_1$ and $X_2$ are C-$(E^1)_{aa}$; $X_3$ and $X_7$ are C; and $R^1$ is absent; or wherein $X_1$, $X_3$, and $X_5$ are N; $X_2$ is C-$(E^1)_{aa}$; and $X_4$, $X_6$, and $X_7$ are C; or wherein $X_1$, $X_4$, and $X_6$ are N; $X_2$ and $X_5$ are C-$(E^1)_{aa}$; $X_3$ and $X_7$ are C; and $R^1$ is absent; or wherein $X_1$, $X_5$, and $X_7$ are N; $X_2$ is C-$(E^1)_{aa}$; and $X_3$, $X_4$, and $X_6$ are C; or wherein $X_1$, $X_4$, and $X_7$ are N; $X_2$ and $X_5$ are C-$(E^1)_{aa}$; $X_3$ and $X_6$ are C; and $R^1$ is absent; or wherein $X_2$, $X_4$, and $X_6$ are N; $X_1$ and $X_5$ are C-$(E^1)_{aa}$; $X_3$ and $X_7$ are C; and $R^1$ is absent; or wherein $X_2$, $X_4$, and $X_7$ are N; $X_1$ and $X_5$ are C-$(E^1)_{aa}$; $X_3$ and $X_6$ are C; and $R^1$ is absent; or wherein $X_2$, $X_5$, and $X_7$ are N; $X_1$ is C-$(E^1)_{aa}$; and $X_3$, $X_4$, and $X_6$ are C; or wherein $X_1$, $X_4$, $X_5$, and $X_6$ are N; $X_2$ is C-$(E^1)_{aa}$; $X_3$ and $X_7$ are C; and $R^1$ is absent; or wherein $X_2$, $X_4$, $X_5$, and $X_6$ are N; $X_1$ is C-$(E^{11})_{aa}$; $X_3$ and $X_7$ are C; and $R^1$ is absent; or wherein $X_1$, $X_3$, $X_4$, and $X_5$ are N; $X_2$ is C-$(E^1)_{aa}$; $X_6$ and $X_7$ are C; and $R^1$ is absent; or wherein $X_2$, $X_3$, $X_4$, and $X_5$ are N; $X_1$ is C-$(E^1)_{aa}$; $X_6$ and $X_7$ are C; and $R^1$ is absent; or wherein any one of $X_{11-16}$ is N; or wherein any two of $X_{11-16}$ is N; or wherein any three of $X_{11-16}$ is N; or wherein any one of $X_{11}$, $X_{14}$, $X_{15}$, or $X_{16}$ is N; or wherein any two of $X_{11}$, $X_{14}$, $X_{15}$, or $X_{16}$ is N; or wherein any two of $X_{14}$, $X_{15}$, or $X_{16}$ is N; or wherein $X_{16}$ is N; or wherein $X_{14}$ and $X_{16}$ are N; or wherein $X_{15}$ and $X_{16}$ are N; or wherein $X_{11}$ and $X_{16}$ are N; or wherein $X_{11}$ is N; or wherein $G^1$ is $-OR^2$, $-NR^2R^3(R^{2a})_{j1}$, $-S(O)_{j1}R^2$, $C_{0-10}$alkyl, cyclo$C_{3-8}$alkyl, heterocyclyl-$C_{0-10}$alkyl, any of which is optionally substituted with one or more independent halo, oxo, $-CF_3$, $-OCF_3$, $-OR^{222}$, $-NR^{222}R^{333}$ $(R^{222a})_{j1a}$, $-C(=O)R^{222}$, $-CO_2R^{222}$, $-C(=O)NR^{222}R^{333}$, $-NO_2$, $-CN$, $-S(=O)_{j1a}R^{222}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(=O)_{j1a}R^{333}$, $-C(=S)OR^{222}$, $-SC(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $-C(=O)SR^{222}$, $-SC(=O)OR^{222}$, or $-SC(=O)NR^{222}R^{333}$ substituents; or $G^1$ is aryl-$C_{0-10}$alkyl or hetaryl-$C_{0-10}$alkyl, any of which is optionally substituted with one or more independent halo, $-CF_3$, $-OCF_3$, $-OR^{222}$, $NR^{222}R^{333}(R^{222a})_{j2a}$, $-C(O)R^{222}$, $-CO_2R^{222}$, $C(=O)NR^{222}R^{333}$, $-NO_2$, $-CN$, $-S(O)_{j2a}R^{222}$, $-SO_2NR^{222}R^{333}$, $-NR^{222}C(=O))R^{333}$, $-NR^{222}C(=O)OR^{333}$, $-NR^{222}C(=O)NR^{333}R^{222a}$, $-NR^{222}S(O)_{j2a}R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $OC(=O)SR^{222}$, $-SC(=O)OR^{222}$, or $-SC(=O)NR^{222}R^{333}$ substituents; or wherein $G^1$ is $C_{0-10}$alkyl, cyclo$C_{3-8}$alkyl, or heterocyclyl-$C_{0-10}$alkyl, any of which is optionally substituted with one or more independent halo, oxo, $-CF_3$, $-OCF_3$, $OR^{222}$, $NR^{222}R^{333}(R^{222a})_{j1a}$, $-C(=O)R^{222}$, $-CO_2R^{222}$, $-C(=O)NR^{222}R^{333}$, $-NO_2$, $-CN$, $-S(=O)_{j1a}R^{222}$, $-SO_2NR^{222}R^{333}$, $-NR^{222}C(=O)R^{333}$, $-NR^{222}C(=O)OR^{333}$, $-NR^{222}C(=O)NR^{333}R^{222a}$, $-NR^{222}S(O)_{j1a}R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $-OC(=O)SR^{222}$, $-SC(=O)OR^{222}$, or $-SC(=O)NR^{222}R^{333}$ substituents; or $G^1$ is aryl-$C_{0-10}$alkyl or hetaryl-$C_{0-10}$alkyl, any of which is optionally substituted with one or more independent halo, $-CF_3$, $-OCF_3$, $-OR^{222}$, $NR^{222}R^{333}(R^{222a})_{j2a}$, $-C(O)R^{222}$, $-CO_2R^{222}$, $C(=O)NR^{222}R^{333}$, $-NO_2$, $-CN$, $-S(O)_{j2a}R^{222}$, $-SO_2NR^{222}R^{333}$, $-NR^{222}C(=O))R^{333}$, $-NR^{222}C(=O)OR^{333}$, $-NR^{222}C(=O)NR^{333}R^{222a}$, $-NR^{222}S(O)_{j2a}R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $OC(=O)SR^{222}$, $-SC(=O)OR^{222}$, or $-SC(=O)NR^{222}R^{333}$ substituents; or wherein $G^1$ is aryl-$C_{0-10}$alkyl or hetaryl-$C_{0-10}$alkyl, any of which is optionally substituted with one or more independent halo, $-CF_3$, $-OCF_3$, $-OR^{222}$, $NR^{222}R^{333}(R^{222a})_{j2a}$, $-C(O)R^{222}$, $-CO_2R^{222}$, $C(=O)NR^{222}R^{333}$, $-NO_2$, $-CN$, $-S(O)_{j2a}R^{222}$, $-SO_2NR^{222}R^{333}$, $-NR^{222}C(=O))R^{333}$, $-NR^{222}C(=O)OR^{333}$, $-NR^{222}C(=O)NR^{333}R^{222a}$, $-NR^{222}S(O)_{j2a}R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222a}$, $-NR^{222}C(=NR^{333})SR^{222a}$, $-OC(=O)OR^{222}$, $-OC(=O)NR^{222}R^{333}$, $OC(=O)SR^{222}$, $-SC(=O)OR^{222}$, or $-SC(=O)NR^{222}R^{333}$ substituents; or wherein $X_{14}$ and $X_{16}$ are N; or wherein $X_{16}$ is N; or wherein $X_{15}$ and $X_{16}$ are N; or wherein $X_{11}$ and $X_{16}$ are N; or wherein $X_{11}$ is N; or wherein $R^1$ is cyclo$C_{3-10}$alkyl, bicyclo$C_{5-10}$alkyl, aryl, heteroaralkyl, heterocyclyl, heterobicyclo$C_{5-10}$alkyl, spiroalkyl, or heterospiroalkyl any of which is optionally substituted by one or more independent $G^{11}$ substituents; or wherein $R^1$ is $C_{0-10}$alkyl, heteroaralkyl, or aralkyl, any of which is optionally substituted by one or more independent $G^{11}$ substituents; or wherein $R^1$ is cyclo$C_{3-10}$alkyl, bicyclo$C_{5-10}$alkyl, spiroalkyl, or heterospiroalkyl any of which is optionally substituted by one or more independent $G^1$ substituents; or wherein $R^1$ is heterocyclyl or heterobicyclo$C_{5-10}$alkyl, of which is optionally substituted by one or more independent $G^{11}$ substituents; or wherein $R^1$ is aryl or heteroaryl, any of which is optionally substituted by one or more independent $G^{11}$ substituents; or wherein $R^1$ is $C_{1-10}$alkyl, cyclo$C_{3-10}$alkyl, bicyclo$C_{5-10}$alkyl, aralkyl, heteroaralkyl, heterocyclyl, heterobicyclo $C_{5-10}$alkyl, spiroalkyl, or heterospiroalkyl any of which is optionally substituted by one or more independent $G^{11}$ substituents; or wherein $X_{16}$ is N; or wherein $X_{14}$ and $X_{16}$ are N; or wherein $X_{15}$ and $X_{16}$ are N; or wherein $X_{11}$ and $X_{16}$ are N; or wherein $X_{11}$ is N; or wherein $G^{11}$ is oxo, $-OCF_3$, $-OR^{21}$, $-NR^{21}R^{31}(R^{2a1})_{j4}$, $-C(O)R^{21}$, $-CO_2R^{21}$, $-C(=O)NR^{21}R^{31}$, $-CN$, $-SO_2NR^{21}R^{31}$, $-NR^{21}C(=O)R^{31}$, $-NR^{32}C(=O)OR^{31}$, $-NR^{21}C(=O)NR^{31}R^{2a1}$, $-NR^{21}S(O)_{j4}R^{31}$, $-OC(=O)NR^{21}R^{31}$, $C_{0-10}$alkyl, $C_{1-10}$alkoxy$C_{1-10}$alkyl, cyclo$C_{3-8}$alkyl$C_{1-10}$alkyl, heterocyclyl-$C_{0-10}$alkyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)NR$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein G$^{11}$ is oxo, —OCF$_3$, —OR$^{21}$, —NR$^{21}$R$^{31}$(R$^{2a1}$)$_{j4}$, —CO$_2$R$^{21}$, —C(=O))NR$^{21}$R$^{31}$, —NR$^{21}$(C=O)R$^{31}$, —NR$^{21}$C(=O)OR$^{31}$, —NR$^{21}$C(=O)NR$^{31}$R$^{2a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl cycloC$_{3-8}$alkylC$_{1-10}$alkyl, heterocyclyl-C$_{0-10}$alkyl, any of which is optionally substituted with one or more independent halo, oxo, —OR$^{2221}$, or —NR$^{2221}$R$^{3331}$(R$^{222a1}$)$_{j4a}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is oxo, —OR$^{21}$, —NR$^{21}$R$^{31}$(R$^{2a1}$)$_{j4}$, —CO$_2$R$^{21}$, —C(=O)NR$^{21}$R$^{31}$, C$_{0-10}$alkyl, heterocyclyl-C$_{0-10}$alkyl, and of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)NR$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, —NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(=O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, NR$^{222}$C(=NR$^{333}$)SR$^{222a}$, —OC(=O)OR$^{222}$, —OC(=O)NR$^{222}$R$^{333}$, —C(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein any one of $X_{11-16}$ is N; or
wherein any two of $X_{11-16}$ is N; or
wherein any three of $X_{11-16}$ is N; or
wherein any one of $X_{11}$, $X_{14}$, $X_{15}$, or $X_{16}$ is N; or
wherein any two of $X_{11}$, $X_{14}$, $X_{15}$, or $X_{16}$ is N; or
wherein any two of $X_{14}$, $X_{15}$, or $X_{16}$ is N; or
wherein $X_{16}$ is N; or
wherein $X_{14}$ and $X_{16}$ are N; or
wherein $X_{15}$ and $X_{16}$ are N; or
wherein $X_{11}$ and $X_{16}$ are N; or
wherein $X_{11}$ is N; or
wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, —NR$^{222}$R$^{333}$ (R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(=O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —C(=O)SR$^{222}$, —C(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein G$^1$ is C$_{0-10}$alkyl, cycloC$_{3-8}$alkyl, or heterocyclyl-C$_{0-10}$alkyl, any of which is optionally substituted with one or more independent halo, oxo, —CF$_3$, —OCF$_3$, OR$^{222}$, NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C=O) NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein $X_{14}$ and $X_{16}$ are N; or
wherein $X_{16}$ is N; or
wherein $X_{15}$ and $X_{16}$ are N; or
wherein $X_{11}$ and $X_{16}$ are N; or
wherein $X_{11}$ is N; or
wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein R$^1$ is C$_{0-10}$alkyl, heteroaralkyl, or aralkyl, any of which is optionally substituted by one or more independent G$^{11}$ substituents; or wherein R$^1$ is cycloC$_{3-10}$alkyl, bicycloC$_{5-10}$alkyl, spiroalkyl, or heterospiroalkyl any of which is optionally substituted by one or more independent G$^{11}$ substituents; or wherein R$^1$ is heterocyclyl or heterobicycloC$_{5-10}$alkyl, of which is optionally substituted by one or more independent G$^{11}$ substituents; or wherein R$^1$ is aryl or heteroaryl, any of which is optionally substituted by one or more independent G$^{11}$ substituents; or wherein R$^1$ is C$_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl any of which is optionally substituted by one or more independent G$^{11}$ substituents; or wherein $X_{16}$ is N; or
wherein $X_{14}$ and $X_{16}$ are N; or
wherein $X_{15}$ and $X_{16}$ are N; or
wherein $X_{11}$ and $X_{16}$ are N; or
wherein $X_{11}$ is N; or G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, NO$_2$, —CN, —S(O)$_{j4}$R$^{21}$, —SO$_2$NR$^{21}$R$^{31}$, NR$^{21}$(C=O)R$^{31}$, —NR$^{32}$C(=O)OR$^{31}$, —NR$^{21}$C(=O)NR$^{31}$R$^{2a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl, cycloC$_{3-8}$ alkylC$_{1-10}$alkyl, heterocyclyl-C$_{0-10}$alkyl, any of which is optionally substituted with one or more independent halo, oxo, —CF$_3$, —OCF$_3$, —OR$^{2221}$, —NR$^{2221}$R$^{3331}$ (R$^{222a1}$)$_{j4a}$, —C(O)R$^{2221}$, —CO$_2$R$^{2221}$, —C(=O)NR$^{2221}$R$^{3331}$, NO$_2$, —CN, —S(O)$_{j4a}$R$^{2221}$, —SO$_2$NR$^{2221}$R$^{3331}$, —NR$^{2221}$C(=O)NR$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —CN, —SO$_2$NR$^{21}$R$^{31}$, NR$^{21}$(C=O)R$^{31}$, —NR$^{32}$C(=O)OR$^{31}$, —NR$^{21}$C(=O)NR$^{31}$R$^{2a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl, cycloC$_{3-8}$alkylC$_{1-10}$alkyl, heterocyclyl-C$_{0-10}$alkyl, any of which is optionally substituted with one or more independent halo, oxo, —OR$^{2221}$, or —NR$^{2221}$R$^{3331}$(R$^{222a1}$)$_{j4a}$ substituents, or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or wherein G$^{11}$ is oxo, —OR$^{21}$, —NR$^{21}$R$^{31}$(R$^{2a1}$)$_{j4}$, —CO$_2$R$^{21}$, —C(=O)NR$^{21}$R$^{31}$, C$_{0-10}$alkyl, heterocyclyl-C$_{0-10}$alkyl, and of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or wherein G$^{11}$ is oxo, —OR$^{21}$, —NR$^{21}$R$^{31}$(R$^{2a1}$)$_{j4}$, —CO$_2$R$^{21}$, —C(=O)NR$^{21}$R$^{31}$, C$_{0-10}$alkyl, heterocyclyl-C$_{0-10}$alkyl, any of which is optionally substituted with one or more independent halo, oxo, —OR$^{2221}$, or —NR$^{2221}$R$^{3331}$(R$^{222a1}$)$_{j4a}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

wherein G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —CN, —SO$_2$NR$^{21}$R$^{31}$, —NR$^{21}$(C=O)R$^{31}$, —NR$^{32}$C(=O)OR$^{31}$, —NR$^{21}$C(=O)NR$^{31}$R$^{2a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl, cycloC$_{3-8}$alkylC$_{1-10}$alkyl, heterocyclyl-C$_{0-10}$alkyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, NO$_2$, —CN, —S(O)$_{j4a}$R$^{2221}$, —SO$_2$NR$^{2221}$R$^{3331}$, —NR$^{2221}$C(=O)NR$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)$^{333}$, —NR$^{222}$C(=O)OR$^{333}$, —NR$^{222}$C(=O)NR$^{333}$R$^{2222}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein any one of X$_{11-16}$ is N; or
wherein any two of X$_{11-16}$ is N; or
wherein any three of X$_{11-16}$ is N; or
wherein any one of X$_{11}$, X$_{14}$, X$_{15}$, or X$_{16}$ is N; or
wherein any two of X$_{11}$, X$_{14}$, X$_{15}$, or X$_{16}$ is N; or
wherein any two of X$_{14}$, X$_{15}$, or X$_{16}$ is N; or
wherein X$_{16}$ is N; or wherein $X_{14}$ and $X_{16}$ are N; or
wherein $X_{15}$ and $X_{16}$ are N; or
wherein $X_{11}$ and $X_{16}$ are N; or
wherein $X_{11}$ is N; or
wherein $G^1$ is —$OR^2$, —$NR^2R^3(R^{2a})_{j1}$, —$S(O)_{j1}R^2$, $C_{0-10}$alkyl, cyclo$C_{3-8}$alkyl, heterocyclyl-$C_{0-10}$alkyl, any of which is optionally substituted with one or more independent halo, oxo, —$CF_3$, —$OCF_3$, —$OR^{222}$, —$NR^{222}R^{333}$ $(R^{222a})_{j1a}$, —$C(=O)R^{222}$, —$CO_2R^{222}$, —$C(=O)NR^{222}R^{333}$, —$NO_2$, —$CN$, —$S(=O)_{j1a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(=O)_{j1a}R^{333}$, —$C(=S)OR^{222}$, —$SC(=O)SR^{222}$, —$NR^{222}C(=NR^{333})NR^{222a}R^{333a}$, —$NR^{222}C(=NR^{333})OR^{222a}$, $NR^{222}C(=NR^{333})SR^{222a}$, —$OC(=O)OR^{222}$, —$OC(=O)NR^{222}R^{333}$, —$C(=O)SR^{222}$, —$SC(=O)OR^{222}$, or —$SC(=O)NR^{222}R^{333}$ substituents; or $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —$CN$, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$SC(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein $G^1$ is $C_{1-10}$alkyl, cyclo$C_{3-8}$alkyl, or heterocyclyl-$C_{0-10}$alkyl, any of which is optionally substituted with one or more independent halo, oxo, —$CF_3$, —$OCF_3$, —$OR^{222}$, —$NR^{222}R^{333}(R^{222a})_{j1a}$, —$C(=O)R^{222}$, —$CO_2R^{222}$, —$C(=O)NR^{222}R^{333}$, —$NO_2$, —$CN$, —$S(=O)_{j1a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(=O)_{j1a}R^{333}$, —$C(=S)OR^{222}$, —$SC(=O)SR^{222}$, —$NR^{222}C(=NR^{333})NR^{222a}R^{333a}$, —$NR^{222}C(=NR^{333})OR^{222a}$, $NR^{222}C(=NR^{333})SR^{222a}$, —$OC(=O)OR^{222}$, —$OC(=O)NR^{222}R^{333}$, —$C(=O)SR^{222}$, —$SC(=O)OR^{222}$, or —$SC(=O)NR^{222}R^{333}$ substituents; or $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —$CN$, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —$CN$, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein $X_{14}$ and $X_{16}$ are N; or
wherein $X_{16}$ is N; or
wherein $X_{15}$ and $X_{16}$ are N; or
wherein $X_{11}$ and $X_{16}$ are N; or
wherein $X_{11}$ is N; or wherein $R^1$ is cyclo$C_{3-10}$alkyl, bicyclo$C_{5-10}$alkyl, aryl, heteroaralkyl, heterocyclyl, heterobicyclo$C_{5-10}$alkyl, spiroalkyl, or heterospiroalkyl any of which is optionally substituted by one or more independent $G^{11}$ substituents; or wherein $R^1$ is $C_{0-10}$alkyl, heteroaralkyl, or aralkyl, any of which is optionally substituted by one or more independent $G^{11}$ substituents; or wherein $R^1$ is cyclo$C_{3-10}$alkyl, bicyclo$C_{5-10}$alkyl, spiroalkyl, or heterospiroalkyl any of which is optionally substituted by one or more independent $G^{11}$ substituents; or wherein $R^1$ is heterocyclyl or heterobicyclo$C_{5-10}$alkyl, of which is optionally substituted by one or more independent $G^{11}$ substituents; or wherein $R^1$ is aryl or heteroaryl, any of which is optionally substituted by one or more independent $G^{11}$ substituents; or wherein $R^1$ is $C_{0-10}$alkyl, cyclo$C_{3-10}$alkyl, bicyclo$C_{5-10}$alkyl, aralkyl, heteroaralkyl, heterocyclyl, heterobicyclo $C_{5-10}$alkyl, spiroalkyl, or heterospiroalkyl any of which is optionally substituted by one or more independent $G^{11}$ substituents; or wherein $X_{16}$ is N; or
wherein $X_{14}$ and $X_{16}$ are N; or
wherein $X_{15}$ and $X_{16}$ are N; or
wherein $X_{11}$ and $X_{16}$ are N; or
wherein $X_{11}$ is N; or wherein $G^{11}$ is oxo, —$OCF_3$, —$OR^{21}$, —$NR^{21}R^{31}(R^{2a1})_{j4}$, —$C(O)R^{21}$, —$CO_2R^{21}$, —$C(=O)NR^{21}R^{31}$, —$CN$, —$SO_2NR^{21}R^{31}$, —$NR^{21}(C=O)R^{31}$, —$NR^{32}C(=O)OR^{31}$, —$NR^{21}C(=O)NR^{31}R^{2a1}$, —$NR^{21}S(O)_{j4}R^{31}$, —$OC(=O)NR^{21}R^{31}$, $C_{0-10}$alkyl, $C_{1-10}$alkoxy$C_{1-10}$alkyl, cyclo$C_{3-8}$alkyl$C_{1-10}$alkyl, heterocyclyl-$C_{0-10}$alkyl, any of which is optionally substituted with one or more independent halo, oxo, —$CF_3$, —$OCF_3$, —$OR^{2221}$, —$NR^{2221}R^{3331}(R^{222a1})_{j4a}$, —$C(O)R^{2221}$, —$CO_2R^{2221}$, —$C(=O)NR^{2221}R^{3331}$, $NO_2$, —$CN$, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —$CN$, —$S(O)_{j5a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is C, taken together with the carbon to which it is attached forms a C=C double bond which is substituted with $R^5$ and $G^{111}$; or wherein $G^{11}$ is oxo, —$OCF_3$, —$OR^{21}$, —$NR^{21}R^{31}(R^{2a1})_{j4}$, —$C(O)R^{21}$, —$CO_2R^{21}$, —$C(=O)NR^{21}R^{31}$, —$CN$, —$SO_2NR^{21}R^{31}$, —$NR^{21}(C=O)R^{31}$, —$NR^{32}C(=O)OR^{31}$, —$NR^{21}C(=O)NR^{31}R^{2a1}$, —$NR^{21}S(O)_{j4}R^{31}$, —$OC(=O)NR^{21}R^{31}$, $C_{0-10}$alkyl, $C_{1-10}$alkoxy$C_{1-10}$alkyl, cyclo$C_{3-8}$alkyl$C_{1-10}$alkyl, heterocyclyl-$C_{0-10}$alkyl, any of which is optionally substituted with one or more independent halo, oxo, —$OR^{2221}$, $NR^{2221}R^{3331}(R^{222a1})_{j4a}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, $NO_2$, —CN, —$S(O)_{j4a}R^{2221}$, —$SO_2NR^{2221}R^{3331}$, —$NR^{2221}C(=O)NR^{3331}$, —$NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents;

wherein $G^{11}$ is oxo, —$OR^{21}$, —$NR^{21}R^{31}(R^{2a1})_{j4}$, —$CO_2R^{21}$, —$C(=O)NR^{21}R^{31}$, $C_{0-10}$alkyl, heterocyclyl-$C_{0-10}$alkyl, and of which is optionally substituted with one or more independent halo, oxo, —$CF_3$, —$OCF_3$, —$OR^{2221}$, —$NR^{2221}R^{3331}(R^{222a1})_{j4a}$, —$C(O)R^{2221}$, —$CO_2R^{2221}$, —$C(=O)NR^{2221}R^{3331}$, —$NO_2$, —CN, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —CN, —$S(O)_{j5a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or wherein $G^{11}$ is oxo, —$OR^{21}$, —$NR^{21}R^{31}(R^{2a1})_{j4}$, —$CO_2R^{21}$, —$C(=O)NR^{21}R^{31}$, $C_{0-10}$alkyl, heterocyclyl-$C_{0-10}$alkyl, and of which is optionally substituted with one or more independent halo, oxo, —$OR^{2221}$, or —$NR^{2221}R^{3331}(R^{2221})_{j4a}$ substituents; or $G^{11}$ is hetaryl-$C_{0-10}$alkyl, any of which is optionally substituted with one or more independent halo, —$CF_2$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —CN, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents;

wherein $G^{11}$ is oxo, —$OCF_3$, —$OR^{21}$, —$NR^{21}R^{31}(R^{2a1})_{j4}$, —$C(O)R^{21}$, —$CO_2R^{21}$, —$C(=O)NR^{21}R^{31}$, —CN, —$SO_2NR^{21}R^{31}$, —$NR^{21}C(=O)R^{31}$, —$NR^{32}C(=O)OR^{31}$, —$NR^{21}C(=O)NR^{31}R^{2a1}$, —$NR^{21}S(O)_{j4}R^{31}$, —$OC(=O)NR^{21}R^{31}$, $C_{0-10}$alkyl, $C_{1-10}$alkoxy$C_{1-10}$alkyl, cyclo$C_{3-8}$alkyl$C_{1-10}$alkyl, heterocyclyl-$C_{0-10}$alkyl, any of which is optionally substituted with one or more independent halo, oxo, —$CF_3$, —$OCF_3$, —$OR^{2221}$, —$NR^{2221}R^{3331}(R^{222a1})_{j4a}$, —$C(O)R^{2221}$, —$CO_2R^{2221}$, —$C(=O)NR^{2221}R^{3331}$, $NO_2$, —CN, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —CN, —$S(O)_{j5a}R^{2221}$, —$SO_2NR^{2221}R^{3331}$, —$NR^{2221}C(=O)R^{3331}$, —$NR^{2221}C(=O)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is C, taken together with the carbon to which it is attached forms a C=C double bond which is substituted with $R^5$ and $G^{111}$; or wherein $R^1$ is cyclo$C_{3-10}$alkyl, bicyclo$C_{5-10}$alkyl, aryl, heteroaralkyl, heterocyclyl, heterobicyclo$C_{5-10}$alkyl, spiroalkyl, or heterospiroalkyl any of which is optionally substituted by one or more independent $G^{11}$ substituents; or wherein $G^1$ is —$OR^2$, —$NR^2R^3(R^{2a})_{j1}$, —$S(O)_{j1}R^2$, $C_{0-10}$alkyl, cyclo$C_{3-8}$alkyl, heterocyclyl-$C_{0-10}$alkyl, any of which is optionally substituted with one or more independent halo, oxo, —$CF_3$, —$OCF_3$, —$OR^{222}$, —$NR^{222}R^{333}j(R^{222a})_{j1a}$, —$C(=O)R^{222}$, —$CO_2R^{222}$, —$C(=O)NR^{222}R^{333}$, —$NO_2$, —CN, —$S(O)_{j1a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(=O)_{j1a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, —$C(=O)SR^{222}$, —$SC(=O)OR^{222}$, or —$SC(=O)NR^{222}R^{333}$ substituents; or $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —CN, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein any one of $X_{11-16}$ is N; or
wherein any two of $X_{11-16}$ is N; or
wherein any three of $X_{11-16}$ is N; or
wherein any one of $X_{11}$, $X_{14}$, $X_{15}$, or $X_{16}$ is N; or
wherein any two of $X_{11}$, $X_{14}$, $X_{15}$, or $X_{16}$ is N; or
wherein any two of $X_{14}$, $X_{15}$, or $X_{16}$ is N; or
wherein $X_{16}$ is N; or
wherein $X_{14}$ and $X_{16}$ are N; or
wherein $X_{15}$ and $X_{16}$ are N; or
wherein $X_{11}$ and $X_{16}$ are N; or
wherein $X_{11}$ is N; or
wherein $G^1$ is —$OR^2$, —$NR^2R^3(R^{2a})_{j1}$, —$S(O)_{j1}R^2$, $C_{0-10}$alkyl, cyclo$C_{3-8}$alkyl, heterocyclyl-$C_{0-10}$alkyl, any of which is optionally substituted with one or more independent halo, oxo, —$CF_3$, —$OCF_3$, —$OR^{222}$, —$NR^{222}R^{333}(R^{222a})_{j1a}$, —$C(=O)R^{222}$, —$CO_2R^{222}$, —$C(=O)NR^{222}R^{333}$, —$NO_2$, —CN, —$S(=O)_{j1a}R^{222}$, —$SO_2NR^{222}R^{333}$, —$NR^{222}C(=O)R^{333}$, —$NR^{222}C(=O)OR^{333}$, —$NR^{222}C(=O)NR^{333}R^{222a}$, —$NR^{222}S(=O)_{j1a}R^{333}$, —$C(=S)OR^{222}$, —$SC(=O)SR^{222}$, —$NR^{222}C(=NR^{333})NR^{222a}R^{333a}$, —$NR^{222}C(=NR^{333})OR^{222a}$, $NR^{222}C(=NR^{333})SR^{222a}$, —$OC(=O)OR^{222}$, —$OC(=O)NR^{222}R^{333}$, —$C(=O)SR^{222}$, —$SC(=O)OR^{222}$, or —$SC(=O)NR^{222}R^{333}$ substituents; or $G^1$ is aryl-$C_{0-10}$alkyl or hetaryl-$C_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein G$^1$ is C$_{0-10}$alkyl, cycloC$_{3-8}$alkyl, or heterocyclyl-C$_{0-10}$alkyl, any of which is optionally substituted with one or more independent halo, oxo, —CF$_3$, —OCF$_3$, —OR$^{222}$, NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C)=O) NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein X$_{14}$ and X$_{16}$ are N; or
wherein X$_{16}$ is N; or
wherein X$_{15}$ and X$_{16}$ are N; or
wherein X$_{11}$ and X$_{16}$ are N; or
wherein X$_{11}$ is N; or wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein R$^1$ is C$_{0-10}$alkyl, heteroarylkyl, or aralkyl, any of which is optionally substituted by one or more independent G$^{11}$ substituents; or wherein R$^1$ is cycloC$_{3-10}$alkyl, bicycloC$_{5-10}$alkyl, spiroalkyl, or heterospiroalkyl any of which is optionally substituted by one or more independent G$^{11}$ substituents; or wherein R$^1$ is heterocyclyl or heterobicycloC$_{5-10}$alkyl, of which is optionally substituted by one or more independent G$^{11}$ substituents; or wherein R$^1$ is aryl or heteroaryl, any of which is optionally substituted by one or more independent G$^{11}$ substituents; or wherein R$^1$ is C$_{0-10}$alkyl, cycloC$_{3-10}$alkyl, bicyclo C$_{5-10}$alkyl, aralkyl, heteroaralkyl, heterocyclyl, heterobicycloC$_{5-10}$alkyl, spiroalkyl, or heterospiroalkyl any of which is optionally substituted by one or more independent G$^{11}$ substituents; or wherein X$_{16}$ is N; or
wherein X$_{14}$ and X$_{16}$ are N; or
wherein X$_{15}$ and X$_{16}$ are N; or
wherein X$_{11}$ and X$_{16}$ are N; or
wherein X$_{11}$ is N; or wherein G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —CN, —SO$_2$NR$^{21}$R$^{31}$, —NR$^{21}$(C=O)R$^{31}$, —NR$^{32}$C(=O)OR$^{31}$, —NR$^{21}$C(=O)NR$^{31}$R$^{a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl, cycloC$_{3-8}$alkylC$_{1-10}$alkyl, heterocyclyl-C$_{0-10}$alkyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, NO$_2$, —CN, —S(O)$_{j4a}$R$^{2221}$, —SO$_2$NR$^{2221}$R$^{3331}$, —NR$^{2221}$C(=O)NR$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein G$^{11}$ is oxo, —OCF$_3$, —OR$^{21}$, —NR$^{21}$R$^{31}$(R$^{2a1}$)$_{j4}$, —CO$_2$R$^{21}$, —C(=O))NR$^{21}$R$^{31}$, —NR$^{21}$(C=O)R$^{31}$, —NR$^{21}$C(=O)OR$^{31}$, —NR$^{21}$C(=O)NR$^{31}$R$^{a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl cycloC$_{3-8}$alkylC$_{1-10}$alkyl, heterocyclyl-C$_{0-10}$alkyl, any of which is optionally substituted with one or more independent halo, oxo, —OR$^{2221}$, or —NR$^{2221}$R$^{3331}$(R$^{222a1}$)$_{j4a}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or wherein G$^{11}$ is oxo, —OR$^{21}$, —NR$^{21}$R$^{31}$(R$^{2a1}$)$_{j4}$, —CO$_2$R$^{21}$, —C(=O)NR$^{21}$R$^{31}$, C$_{0-10}$alkyl, heterocyclyl-C$_{0-10}$alkyl, and of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or wherein G$^{11}$ is oxo, —OR$^{21}$, —NR$^{21}$R$^{31}$(R$^{2a1}$)$_{j4}$, —CO$_2$R$^{21}$, —C(=O)NR$^{21}$R$^{31}$, C$_{0-10}$alkyl, heterocyclyl-C$_{0-10}$alkyl, and of which is optionally substituted with one or more independent halo, oxo, —OR$^{2221}$, or —NR$^{2221}$R$^{3331}$(R$^{222a1}$)$_{j4a}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or wherein G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —CN, —SO$_2$NR$^{21}$R$^{31}$, —NR$^{21}$(C=O)R$^{31}$, —NR$^{32}$C(=O)OR$^{31}$, —NR$^{21}$C(=O)NR$^{31}$R$^{2a1}$, —NR$^{21}$S(O)$_{j4}$R$^{31}$, —OC(=O)NR$^{21}$R$^{31}$, C$_{0-10}$alkyl, C$_{1-10}$alkoxyC$_{1-10}$alkyl, cycloC$_{3-8}$alkylC$_{1-10}$alkyl, heterocyclyl-C$_{0-10}$alkyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, NO$_2$, —CN, —S(O)$_{j4a}$R$^{2221}$, —SO$_2$NR$^{2221}$R$^{3331}$, —NR$^{2221}$C(=O)NR$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents; or G$^{11}$ is C, taken together with the carbon to which it is attached forms a C=C double bond which is substituted with R$^5$ and G$^{111}$; or wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, —NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(=O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —C(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein any one of X$_{11-16}$ is N; or wherein any two of X$_{11-16}$ is N; or wherein any three of X$_{11-16}$ is N; or wherein any one of X$_{11}$, X$_{14}$, X$_{15}$, or X$_{16}$ is N; or wherein any two of X$_{11}$, X$_{14}$, X$_{15}$, or X$_{16}$ is N; or wherein any two of X$_{14}$, X$_{15}$, or X$_{16}$ is N; or wherein X$_{16}$ is N; or wherein X$_{14}$ and X$_{16}$ are N; or wherein X$_{15}$ and X$_{16}$ are N; or wherein X$_{11}$ and X$_{16}$ are N; or wherein X$_{11}$ is N; or wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, —NR$^{222}$R$^{333}$ (R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(=O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —C(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, OC(=O)SR$^{222}$, —SC(=O)OR$^{222}$, or —SC(=O)NR$^{222}$R$^{333}$ substituents; or wherein G$^1$ is C$_{0-10}$alkyl, cycloC$_{3-8}$alkyl, or heterocyclyl-C$_{0-10}$alkyl, any of which is optionally substituted with one or more independent halo, oxo, —CF$_3$, —OCF$_3$, —OR$^{222}$, NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C)=O) NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)

$NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, —$OC(=O)SR^{222}$, —$SC(=O)OR^{222}$, or —$SC(=O)NR^{222}R^{333}$ substituents; or $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —$CN$, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein $G^1$ is aryl-$C_{0-10}$alkyl or hetaryl-$C_{0-10}$alkyl, any of which is optionally substituted with one or more independent halo, —$CF_3$, —$OCF_3$, —$OR^{222}$, $NR^{222}R^{333}(R^{222a})_{j2a}$, —$C(O)R^{222}$, —$CO_2R^{222}$, $C(=O)NR^{222}R^{333}$, —$NO_2$, —$CN$, —$S(O)_{j2a}R^{222}$, —$SO_2NR^{222}R^{333}$, —$NR^{222}C(=O))R^{333}$, —$NR^{222}C(=O)OR^{333}$, —$NR^{222}C(=O)NR^{333}R^{222a}$, —$NR^{222}S(O)_{j2a}R^{333}$, —$C(=S)OR^{222}$, —$C(=O)SR^{222}$, —$NR^{222}C(=NR^{333})NR^{222a}R^{333a}$, —$NR^{222}C(=NR^{333})OR^{222a}$, —$NR^{222}C(=NR^{333})SR^{222a}$, —$OC(=O)OR^{222}$, —$OC(=O)NR^{222}R^{333}$, $OC(=O)SR^{222}$, —$SC(=O)OR^{222}$, or —$SC(=O)NR^{222}R^{333}$ substituents; or wherein $X_{14}$ and $X_{16}$ are N; or wherein $X_{16}$ is N; or wherein $X_{15}$ and $X_{16}$ are N; or wherein $X_{11}$ and $X_{16}$ are N; or wherein $X_{11}$ is N; or wherein $R^1$ is cyclo$C_{3-10}$alkyl, bicyclo$C_{5-10}$alkyl, aryl, heteroaralkyl, heterocyclyl, heterobicyclo$C_{5-10}$alkyl, spiroalkyl, or heterospiroalkyl any of which is optionally substituted by one or more independent $G^{11}$ substituents; or wherein $R^1$ is $C_{0-10}$alkyl, heteroarakyl, or aralkyl, any of which is optionally substituted by one or more independent $G^{11}$ substituents; or wherein $R^1$ is cyclo$C_{3-10}$alkyl, bicyclo$C_{5-10}$alkyl, spiroalkyl, or heterospiroalkyl any of which is optionally substituted by one or more independent $G^{11}$ substituents; or wherein $R^1$ is heterocyclyl or heterobicyclo$C_{5-10}$alkyl, of which is optionally substituted by one or more independent $G^{11}$ substituents; or wherein $R^1$ is aryl or heteroaryl, any of which is optionally substituted by one or more independent $G^1$ substituents; or wherein $R^1$ is $C_{0-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl any of which is optionally substituted by one or more independent $G^{11}$ substituents; or wherein $X_{16}$ is N; or wherein $X_{14}$ and $X_{16}$ are N; or wherein $X_{15}$ and $X_{16}$ are N; or wherein $X_{11}$ and $X_{16}$ are N; or wherein $X_{11}$ is N; or wherein $G^{11}$ is oxo, —$OCF_3$, —$OR^{21}$, —$NR^{21}R^{31}(R^{2a1})_{j4}$, —$C(O)R^{21}$, —$CO_2R^{21}$, —$C(=O)NR^{21}R^{31}$, —$CN$, —$SO_2NR^{21}R^{31}$, —$NR^{21}(C=O)R^{31}$, —$NR^{32}C(=O)OR^{31}$, —$NR^{21}C(=O)NR^{31}R^{2a1}$, —$NR^{21}S(O)_{j4}R^{31}$, —$OC(=O)NR^{21}R^{31}$, $C_{0-10}$alkyl, $C_{1-10}$alkoxy$C_{1-10}$alkyl, cyclo$C_{3-8}$alkyl$C_{1-10}$alkyl, heterocyclyl-$C_{0-10}$alkyl, any of which is optionally substituted with one or more independent halo, oxo, —$CF_3$, —$OCF_3$, —$OR^{2221}$, —$NR^{2221}R^{3331}(R^{222a1})_{j4a}$, —$C(O)R^{2221}$, —$CO_2R^{2221}$, —$C(=O)NR^{2221}R^{3331}$, —$NO_2$, —$CN$, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)$ $NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —$CN$, —$S(O)_{j5a}R^{2221}$, —$SO_2NR^{2221}R^{3331}$, —$NR^{2221}C(=O)R^{3331}$, —$NR^{2221}C(=)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is C, taken together with the carbon to which it is attached forms a C=C double bond which is substituted with $R^5$ and $G^{111}$; or wherein $G^{11}$ is oxo, —$OCF_3$, —$OR^{21}$, —$NR^{21}R^{31}(R^{2a1})_{j4}$, —$CO_2R^{21}$, —$C(=O))NR^{21}R^{31}$, —$NR^{21}(C=O)R^{31}$, —$NR^{21}C(=O)OR^{31}$, —$NR^{21}C(=O)NR^{31}R^{2a1}$, —$NR^{21}S(O)_{j4}R^{31}$, —$OC(=O)NR^{21}R^{31}$, $C_{0-10}$alkyl, $C_{1-10}$alkoxy $C_{1-10}$alkyl cyclo$C_{3-8}$alkyl$C_{1-10}$alkyl, heterocyclyl-$C_{0-10}$alkyl, any of which is optionally substituted with one or more independent halo, oxo, —$OR^{2221}$, or —$NR^{2221}R^{3331}(R^{222a1})_{j4a}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —$CN$, —$S(O)_{j5a}R^{2221}$, —$SO_2NR^{2221}R^{3331}$, —$NR^{2221}C(=O)R^{3331}$, $NR^{2221}C(=O)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or wherein $G^{11}$ is oxo, —$OR^{21}$, —$NR^{21}R^{31}(R^{2a1})_{j4}$, —$CO_2R^{21}$, —$C(=O)NR^{21}R^{31}$, $C_{0-10}$alkyl, heterocyclyl-$C_{0-10}$alkyl, and of which is optionally substituted with one or more independent halo, oxo, —$CF_3$, —$OCF_3$, —$OR^{2221}$, —$NR^{2221}R^{3331}(R^{222a1})_{j4a}$, —$C(O)R^{2221}$, —$CO_2R^{2221}$, —$C(=O)NR^{2221}R^{3331}$, —$NO_2$, —$CN$, —$S(O)_{j4a}R^{2221}$, —$SO_2NR^{2221}R^{3331}$, —$NR^{2221}C(=O)NR^{3331}$, $NR^{2221}C(=O)OR^{3331}$, —$NR^{2221}C(=O)NR^{3331}R^{222a1}$, —$NR^{2221}S(O)_{j4a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or $G^{11}$ is hetaryl-$C_{0-10}$alkyl, any of which is optionally substituted with one or more independent halo, —$CF_3$, —$OCF_3$, —$OR^{2221}$, —$NR^{2221}R^{3331}(R^{222a1})_{j5a}$, —$C(O)R^{2221}$, —$CO_2R^{2221}$, —$C(=O)NR^{2221}R^{3331}$, —$NO_2$, —$CN$, —$S(O)_{j5a}R^{2221}$, —$SO_2NR^{2221}R^{3331}$, —$NR^{2221}C(=O)R^{3331}$, —$NR^{2221}C(=)OR^{3331}$, —$NR^{2221}C(=O)NR^{3331}R^{222a1}$, —$NR^{2221}S(O)_{j5a}R^{3331}$, —$C(=S)OR^{2221}$, —$C(=O)SR^{2221}$, —$NR^{2221}C(=NR^{3331})NR^{222a1}R^{333a1}$, —$NR^{2221}C(=NR^{3331})OR^{222a1}$, —$NR^{2221}C(=NR^{3331})SR^{222a1}$, —$OC(=O)OR^{2221}$, —$OC(=O)NR^{2221}R^{3331}$, —$OC(=O)SR^{2221}$, —$SC(=O)OR^{2221}$, —$P(O)OR^{2221}OR^{3331}$, or —$SC(=O)NR^{2221}R^{3331}$ substituents; or wherein $G^{11}$ is oxo, —$OR^{21}$, —$NR^{21}R^{31}(R^{2a1})_{j4}$, —$CO_2R^{21}$, —$C(=O)NR^{21}R^{31}$, $C_{0-10}$alkyl, heterocyclyl-$C_{0-10}$alkyl, and of which is optionally substituted with one or more independent halo, oxo, —OR$^{2221}$, or —NR$^{2221}$R$^{3331}$ (R$^{222a1}$)$_{j4a}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C (=O)R$^{3331}$, —NR$^{2221}$C(=O)OR$^{3331}$, —NR$^{2221}$C(=O) NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$) SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O) OR$^{2221}$OR$^{3331}$, or —SC(=O)NR$^{2221}$R$^{3331}$ substituents; or wherein G$^{11}$ is oxo, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —CN, —SO$_2$NR$^{21}$R$^{31}$, NR$^{21}$(C=O)R$^{31}$, —NR$^{32}$C(=O)OR$^{31}$, —NR$^{21}$C(=O)NR$^{31}$R$^{2a1}$, —NR$^{21}$S(O)$_{j4}$R$^{31}$, —OC(=O) NR$^{21}$R$^{31}$, C$_{0-10}$alkyl, C$_{1-10}$alkoxyC$_{1-10}$alkyl, cycloC$_{3-8}$alkylC$_{1-10}$alkyl, heterocyclyl-C$_{0-10}$alkyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C (=O)NR$^{3331}$, NR$^{2221}$C(=O)OR$^{3331}$, —NR$^{2221}$C(=O) NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(NR$^{3331}$) SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O) OR$^{2221}$OR$^{3331}$, or —SC(=O)NR$^{2221}$R$^{3331}$ substituents; or G$^{11}$ is hetaryl-C$_{0-10}$alkyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —C(=O)NR$^{2221}$R$^{3331}$, —NO$_2$, —CN, —S (O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C (=NR$^{3331}$)OR$^{222a1}$, —NR$^{2221}$C(=NR$^{3331}$)SR$^{222a1}$, —OC (=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O) NR$^{2221}$R$^{3331}$ substituents; or G$^{11}$ is C, taken together with the carbon to which it is attached forms a C=C double bond which is substituted with R$^5$ and G$^{111}$; or wherein R$^1$ is cycloC$_{3-10}$alkyl, bicycloC$_{5-10}$alkyl, aryl, heteroaralkyl, heterocyclyl, heterobicycloC$_{5-10}$alkyl, spiroalkyl, or heterospiroalkyl any of which is optionally substituted by one or more independent G$^{11}$ substituents; or wherein G$^1$ is —OR$^2$, —NR$^2$R$^3$(R$^{2a}$)$_{j1}$, —S(O)$_{j1}$R$^2$, C$_{0-10}$alkyl, cycloC$_{3-8}$alkyl, heterocyclyl-C$_{0-10}$alkyl, any of which is optionally substituted with one or more independent halo, oxo, —CF$_3$, —OCF$_3$, —OR$^{222}$, —NR$^{222}$R$^{333}$ (R$^{222a}$)$_{j1a}$, —C(=O)R$^{222}$, —CO$_2$R$^{222}$, —C(=O) NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O) OR$^{333}$, —NR$^{222}$C(=O)NR$^{333}$R$^{222a}$, —NR$^{222}$S (=O)$_{j1a}$R$^{333}$, —C(=S)OR$^{222}$, —C(=O)SR$^{222}$, —NR$^{222}$C (=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC (=O)NR$^{222}$R$^{333}$, —C(=O)SR$^{222}$, —SC(=O)OR$^{222}$, or —SC(=O)NR$^{222}$R$^{333}$ substituents; or G$^1$ is aryl-C$_{0-10}$alkyl or hetaryl-C$_{0-10}$alkyl, any of which is optionally substituted with one or more independent halo, —CF$_3$, —OCF$_3$, —OR$^{222}$, NR$^{222}$R$^{333}$(R$^{222a}$)$_{j2a}$, —C(O)R$^{222}$, —CO$_2$R$^{222}$, C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O))R$^{333}$, —NR$^{222}$C(=O) OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$) NR$^{222a}$R$^{333a}$, —NR$^{222}$C(=NR$^{333}$)OR$^{222a}$, —NR$^{222}$C (=NR$^{333}$)SR$^{222a}$, —OC(=O)OR$^{222}$, —OC(=O) NR$^{222}$R$^{333}$, OC(=O)SR$^{222}$, —SC(=O)OR$^{222}$, or —SC (=O)NR$^{222}$R$^{333}$ substituents; or wherein, in each case, the other variables are as defined above for Formula I.

The compounds of the present invention include any one of,

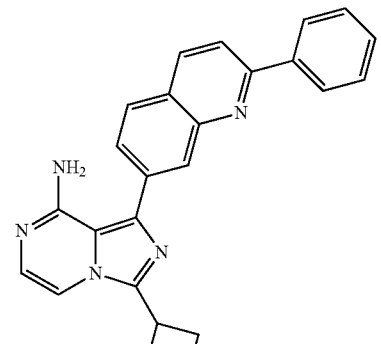

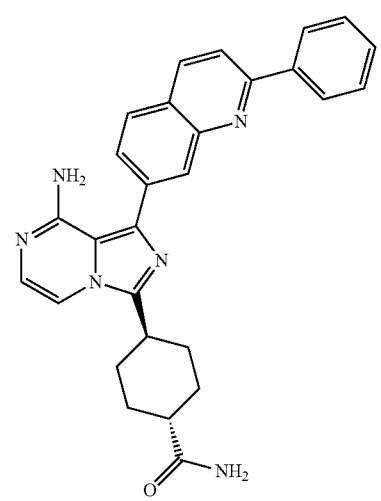

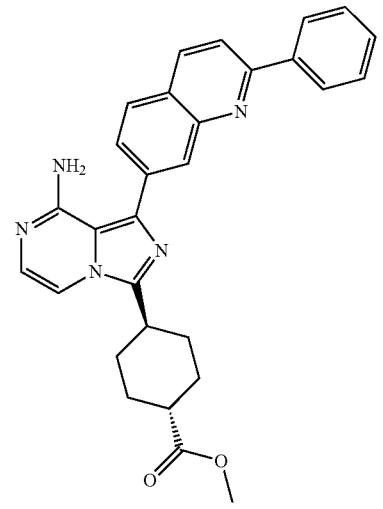

37
38
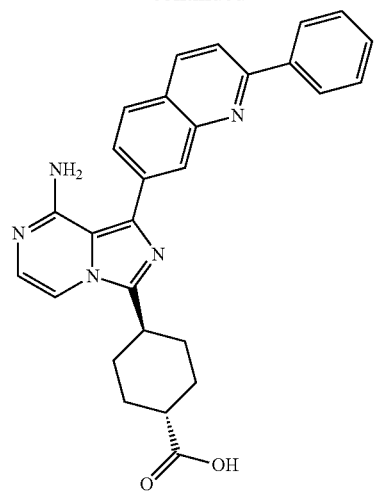
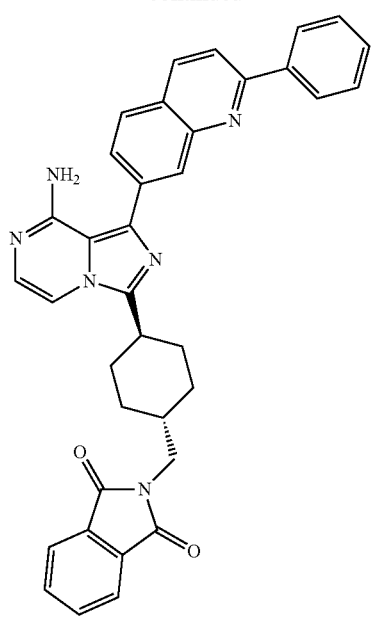
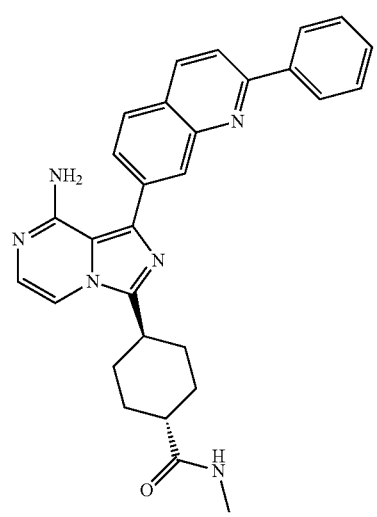
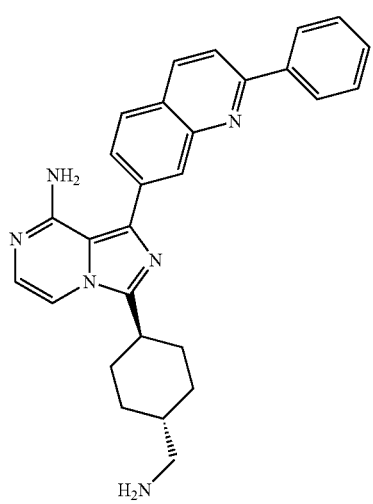
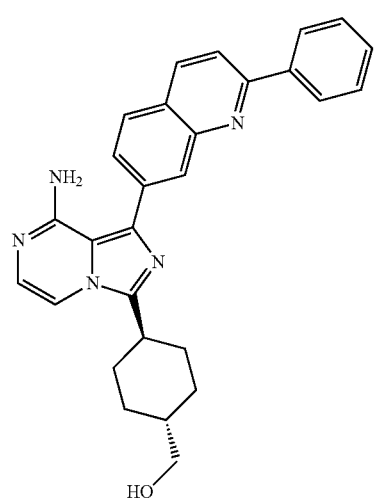
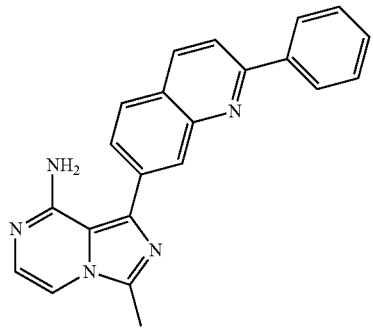

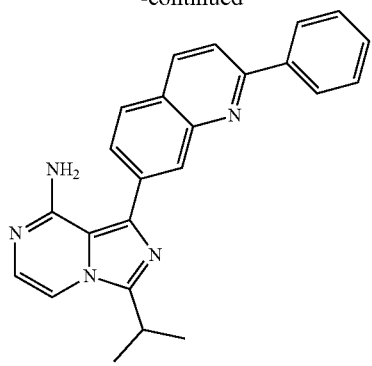
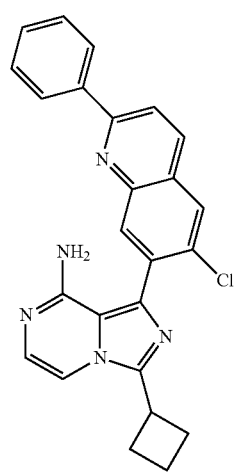
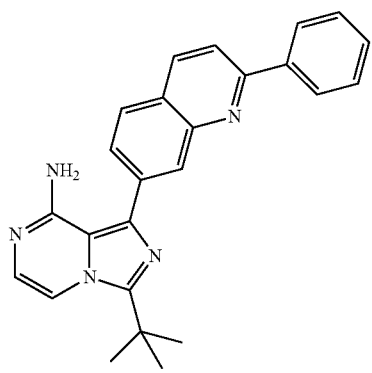
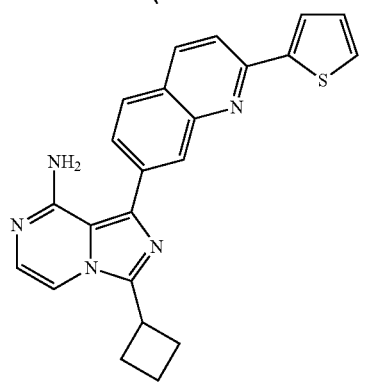
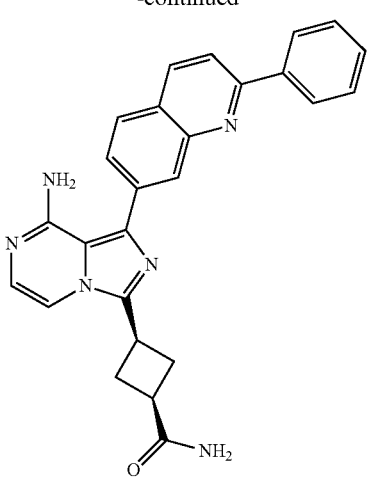
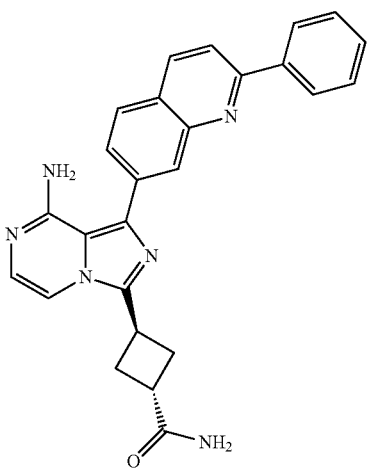
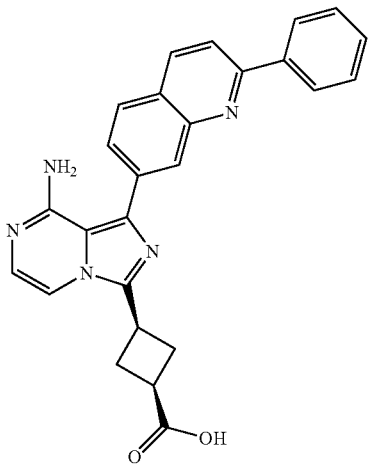

-continued
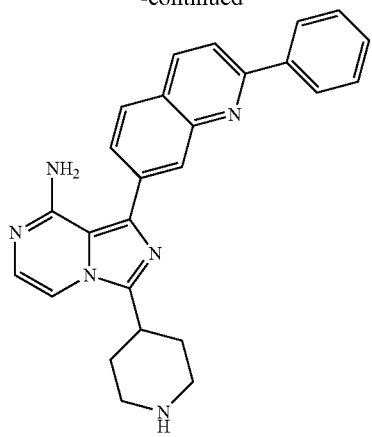
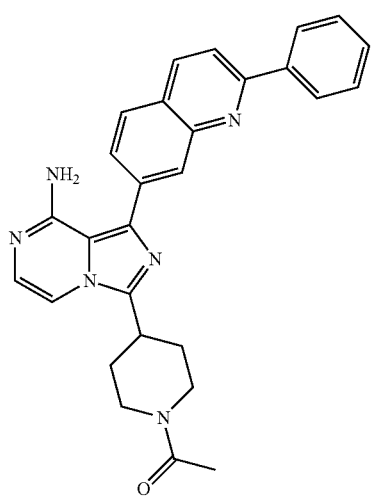
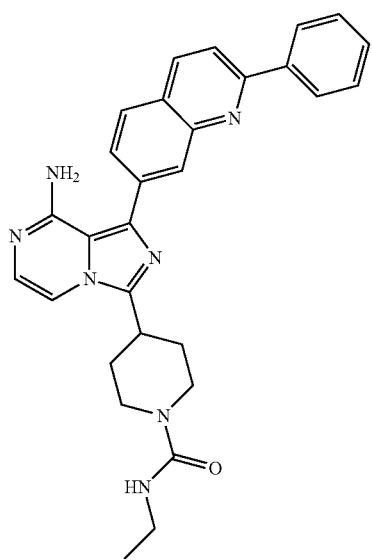
-continued
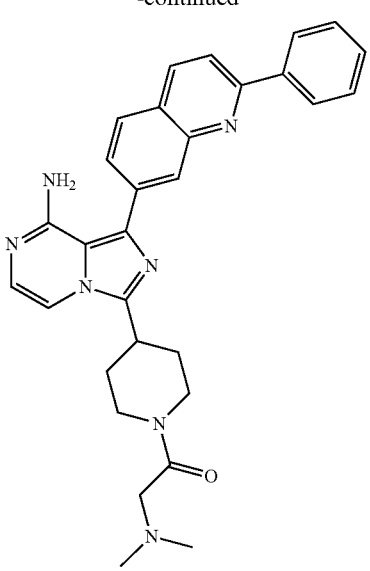
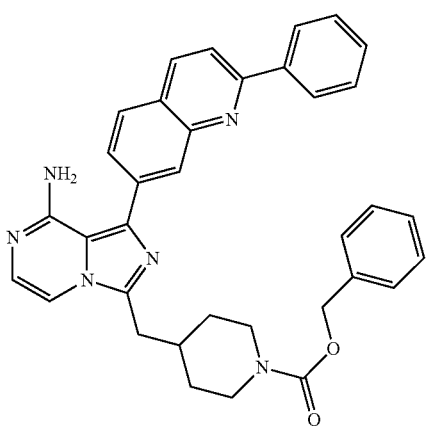
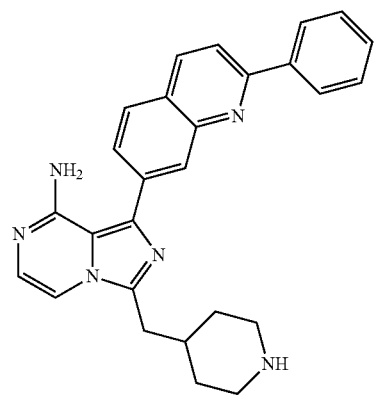

43
-continued
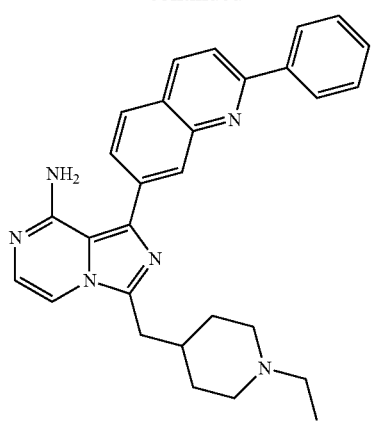
44
-continued
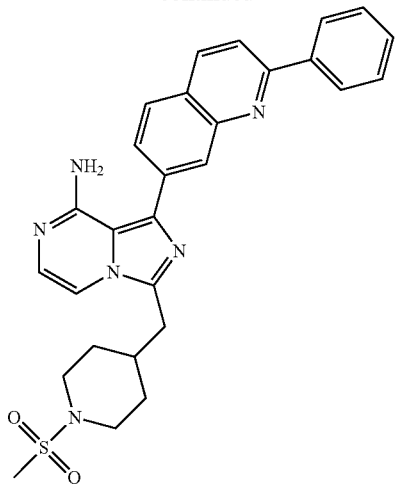
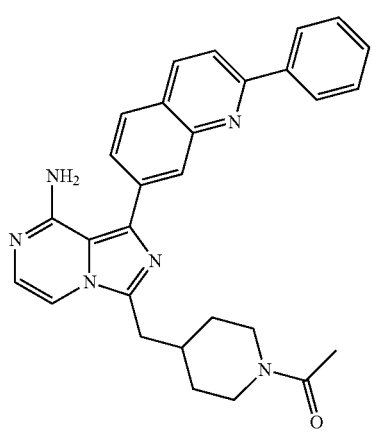
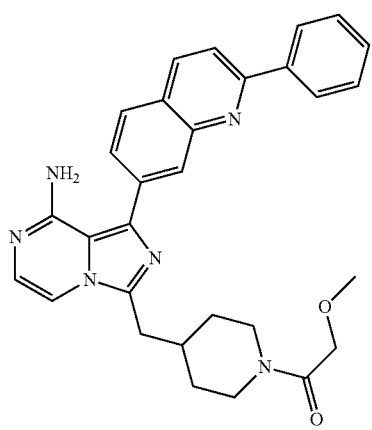
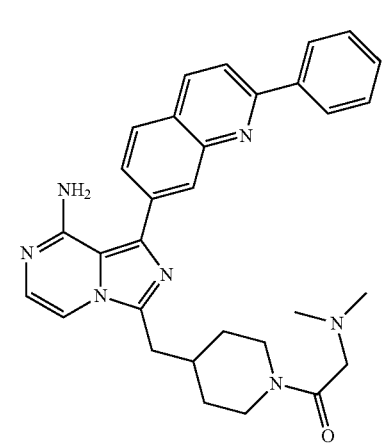

45
-continued
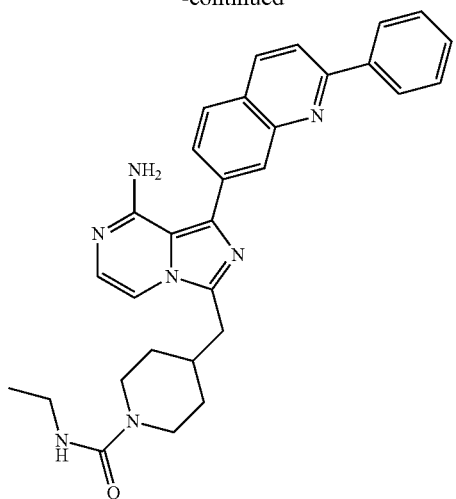
46
-continued
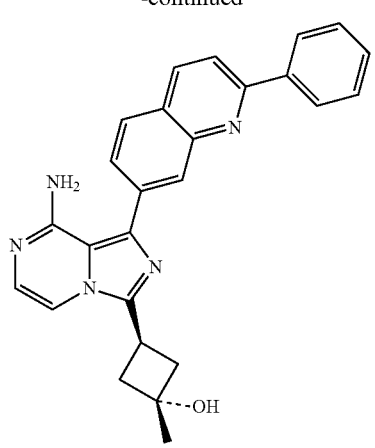
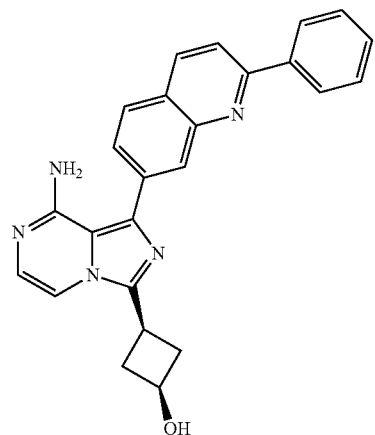
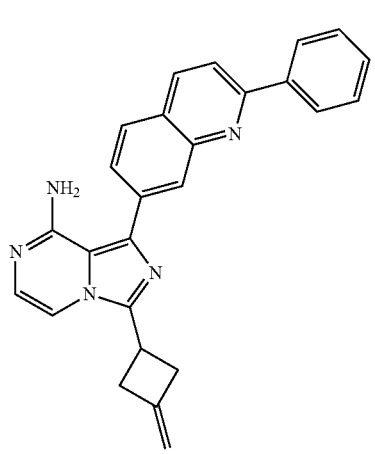
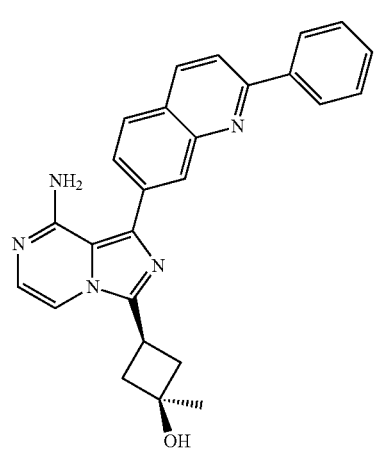
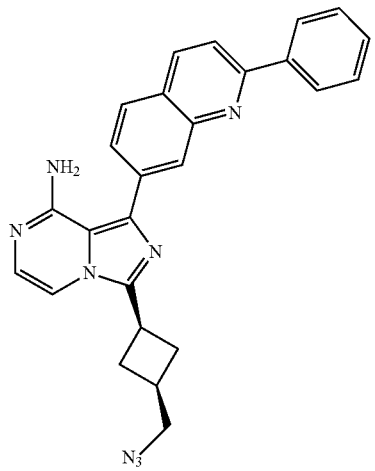

47
-continued
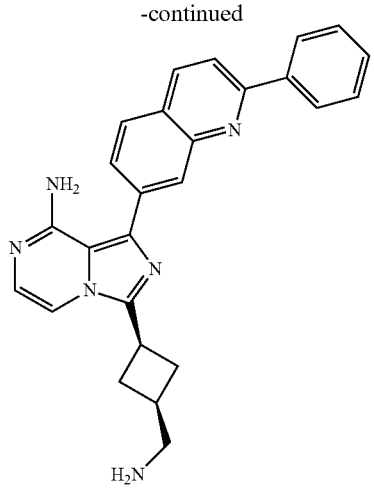
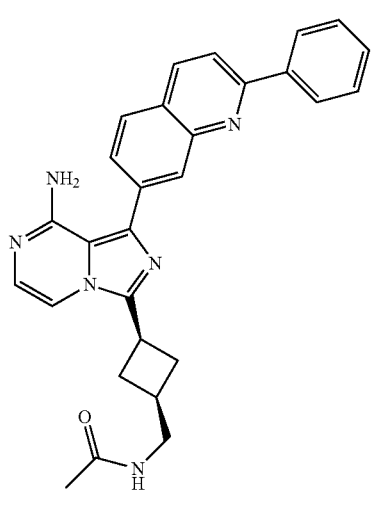
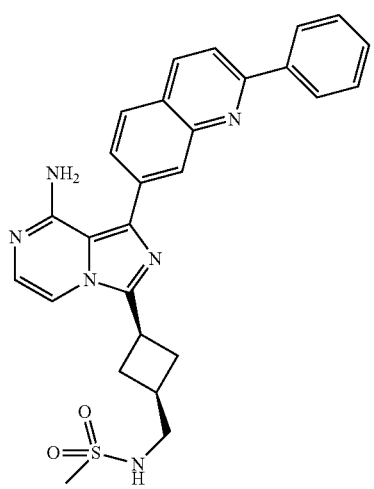
48
-continued
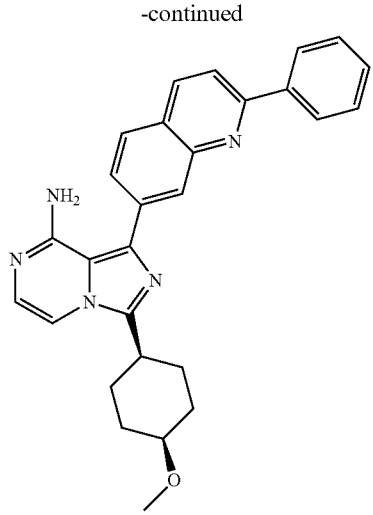
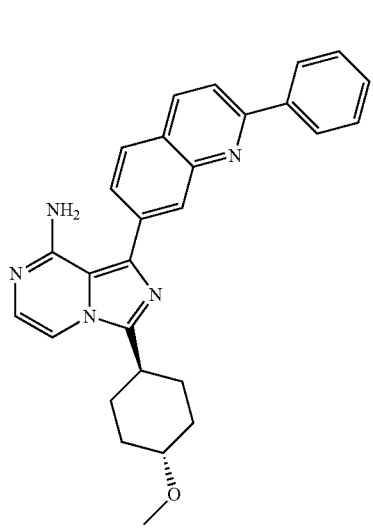
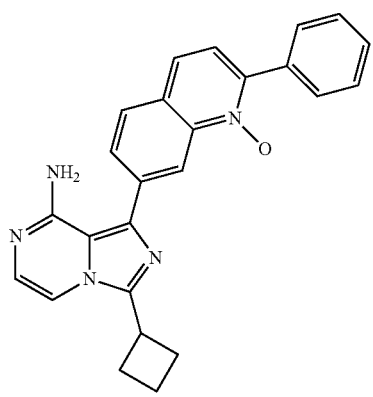

49
-continued
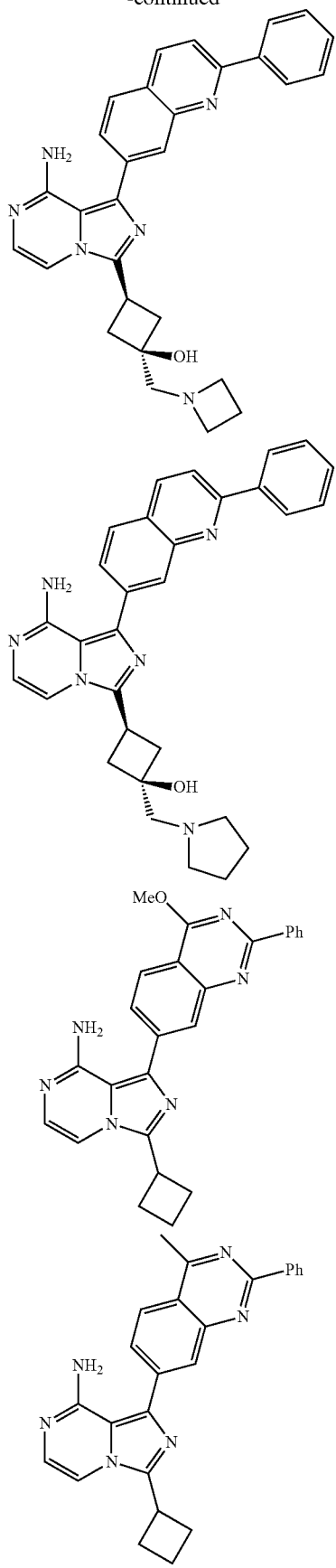
50
-continued
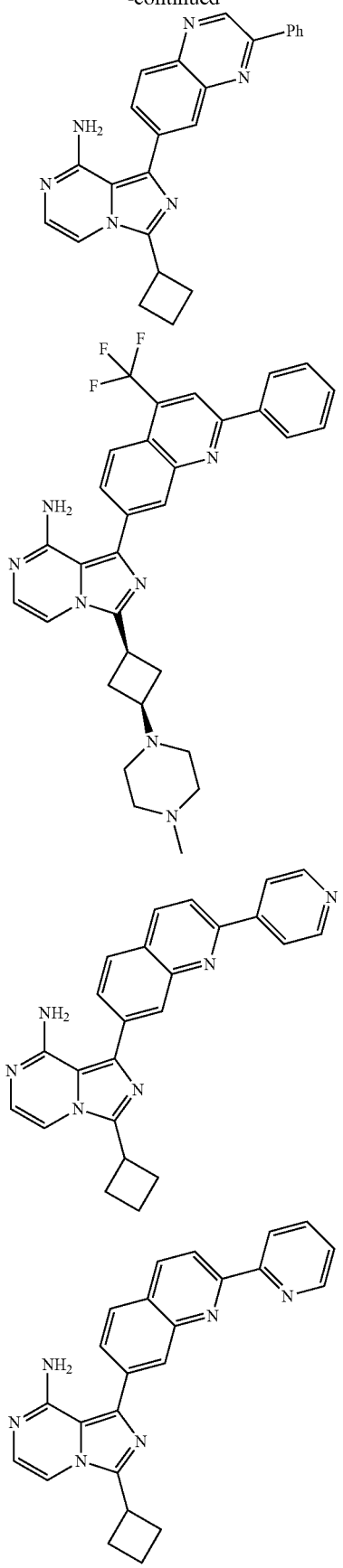

51
-continued
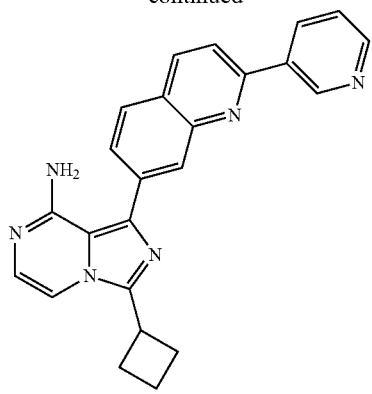
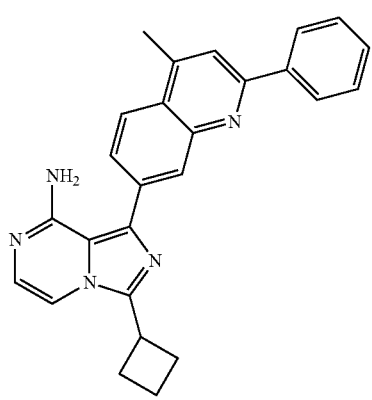
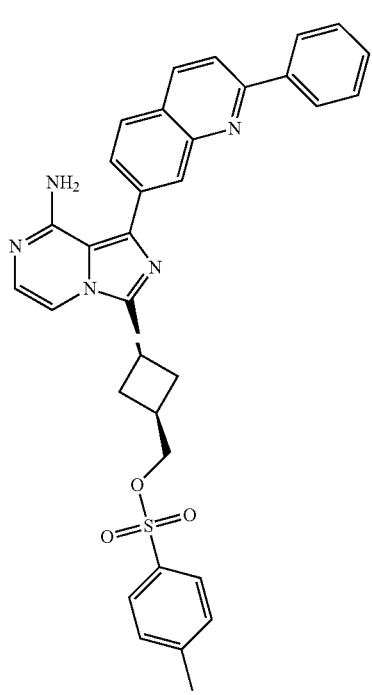
52
-continued
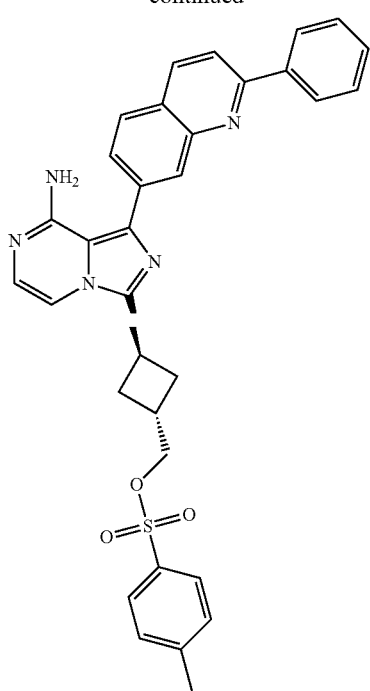
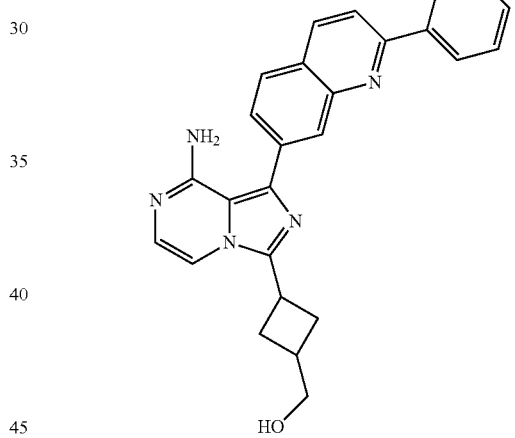
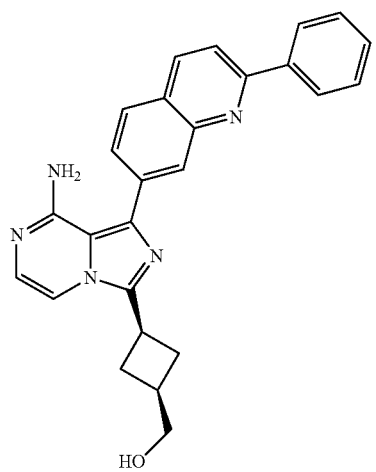

53
-continued
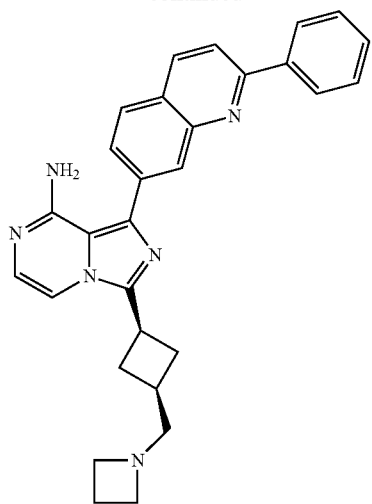
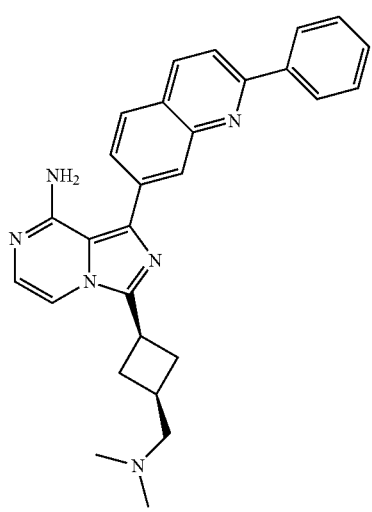
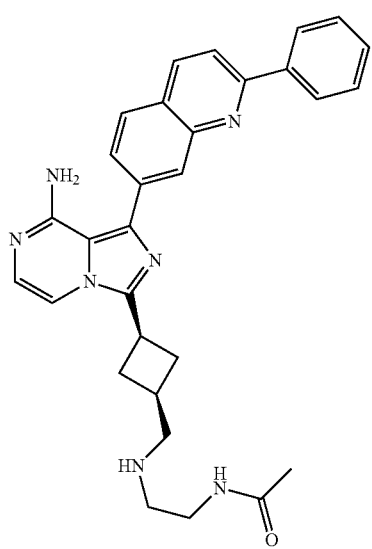
54
-continued
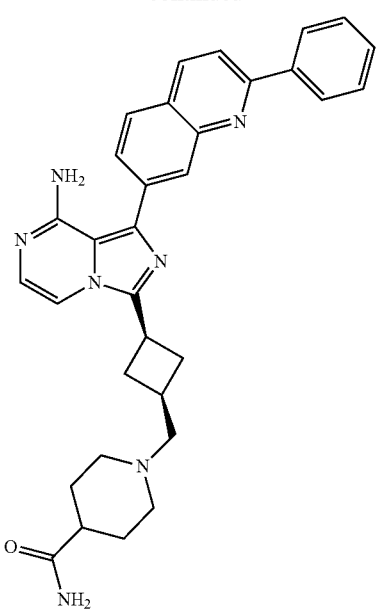
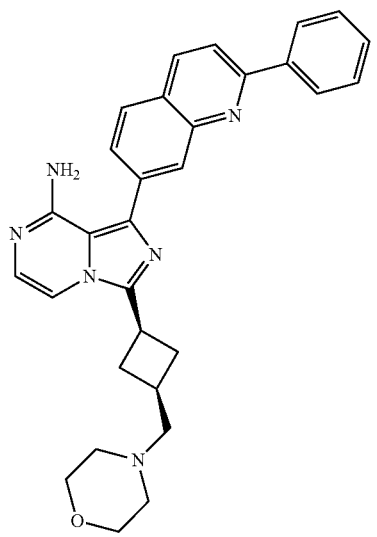
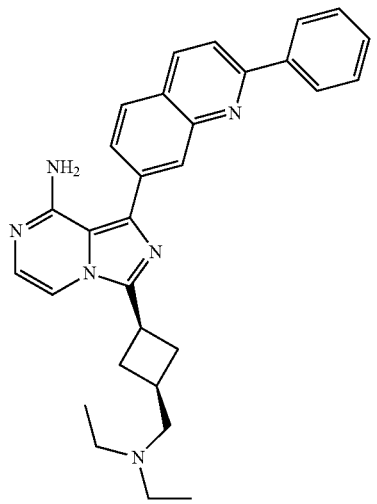

55
-continued
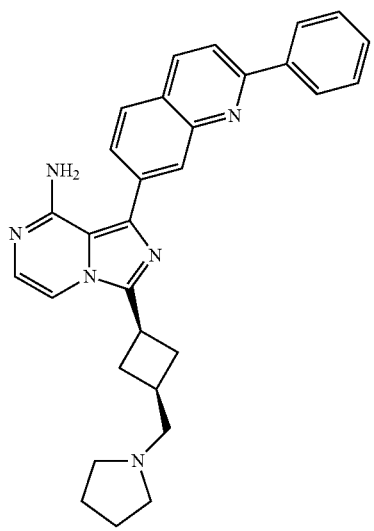
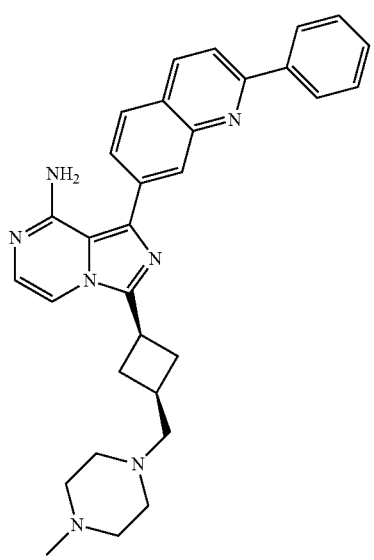
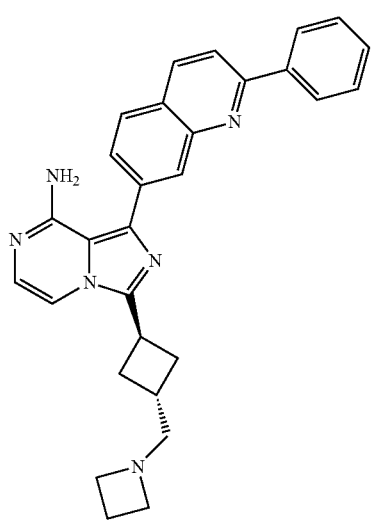
56
-continued
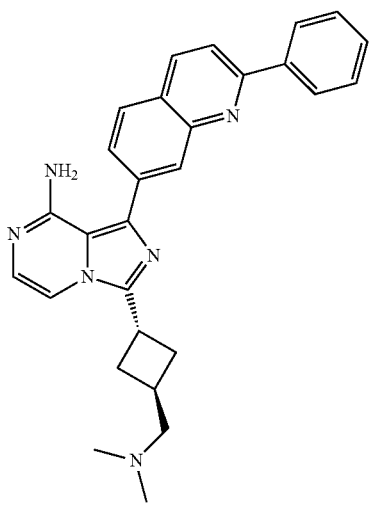
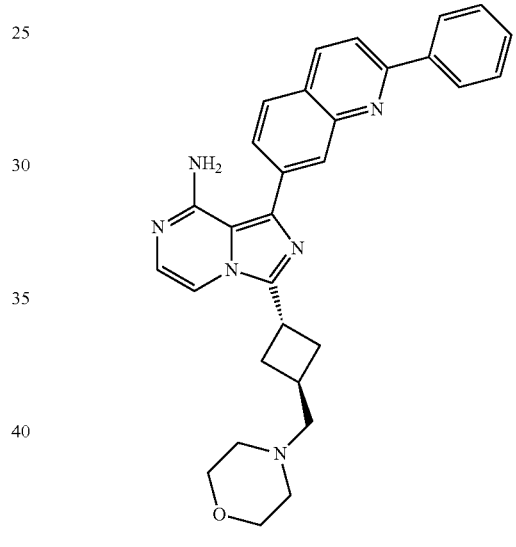
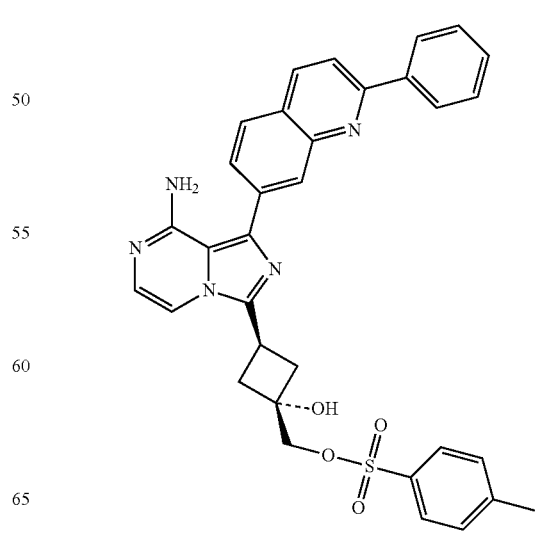

57
-continued
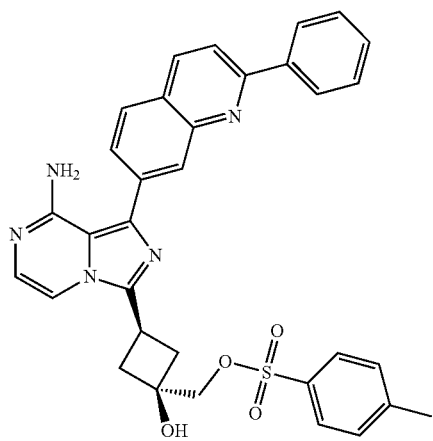
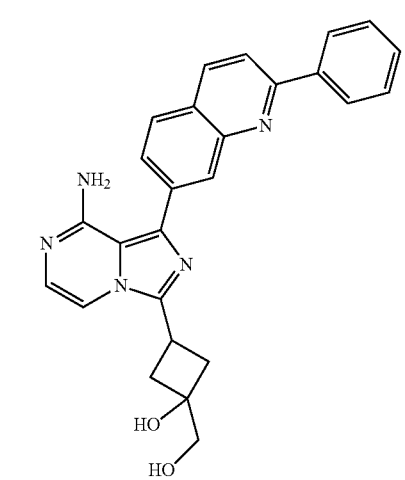
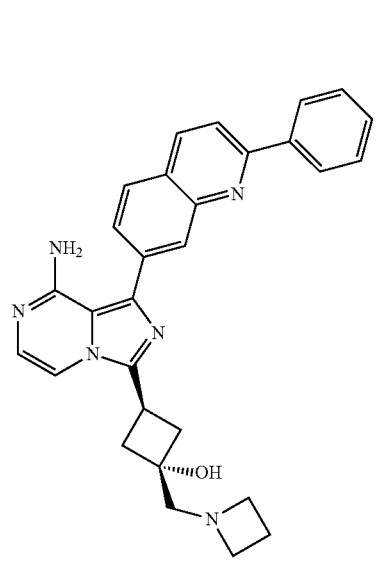
58
-continued
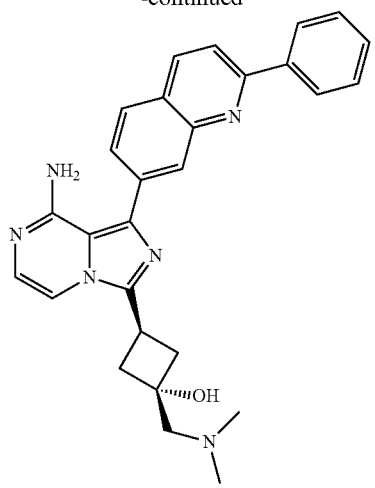
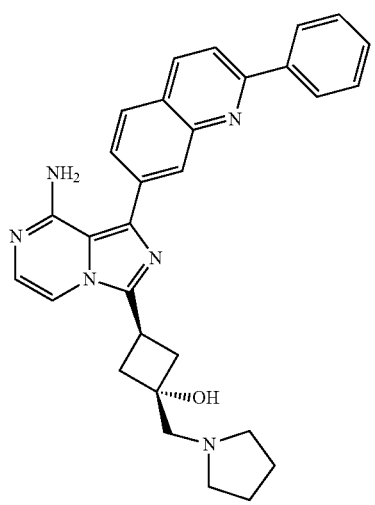
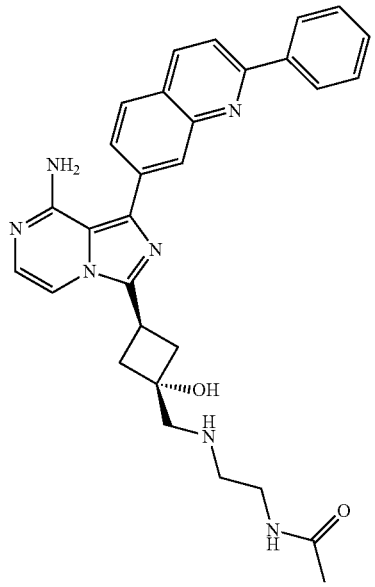

59
-continued
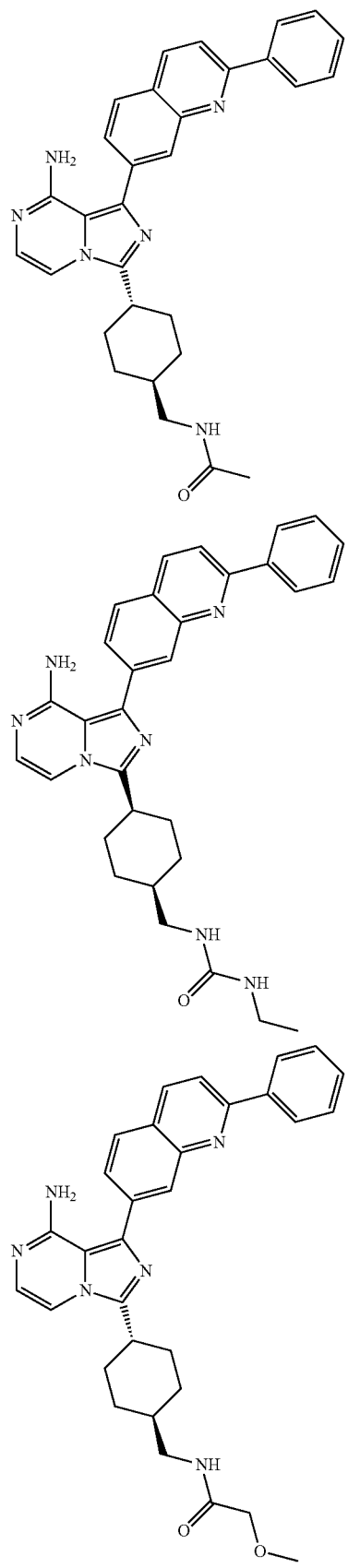
60
-continued
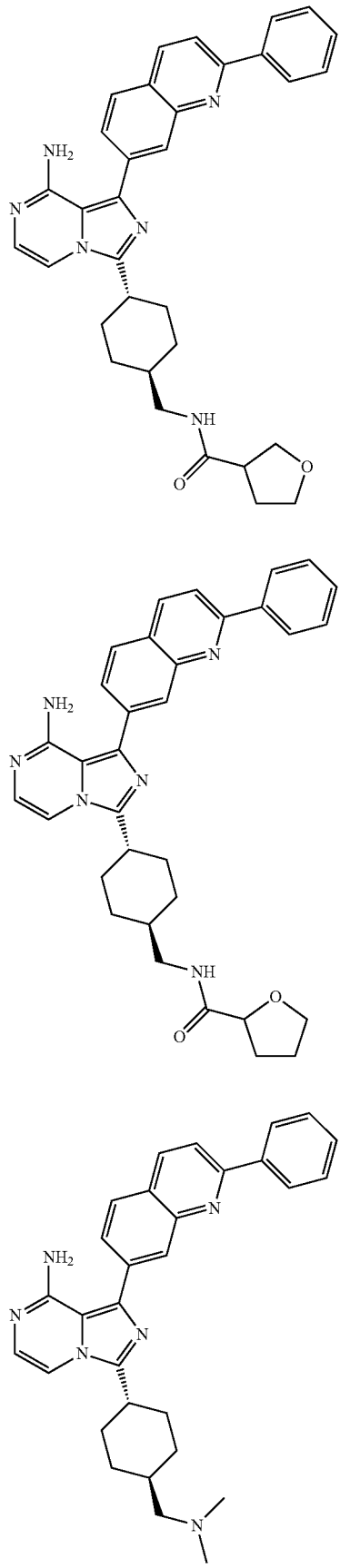

61
-continued
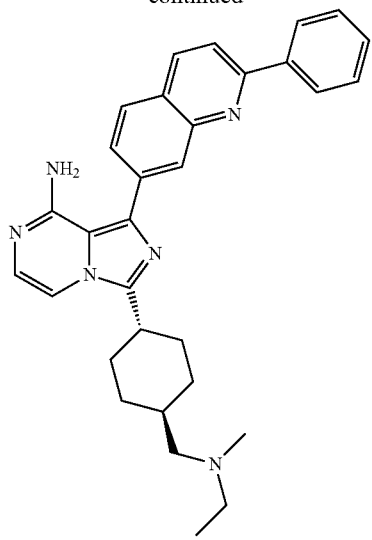
62
-continued
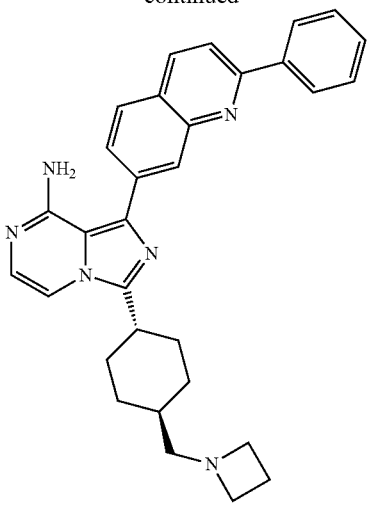
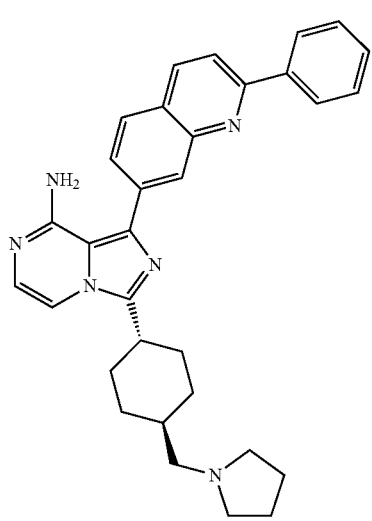
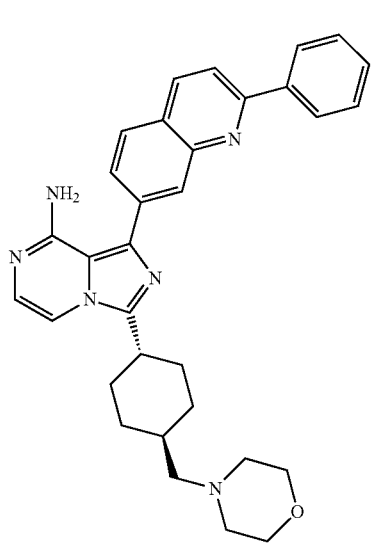
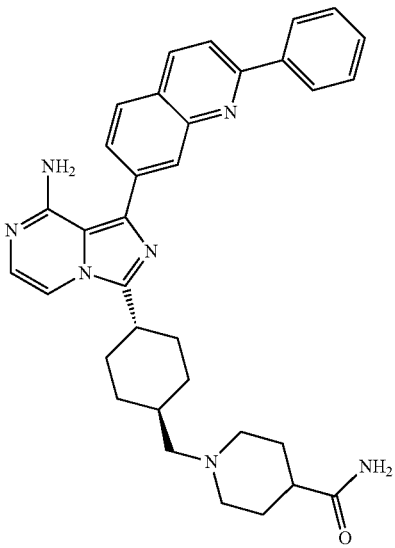

63
-continued
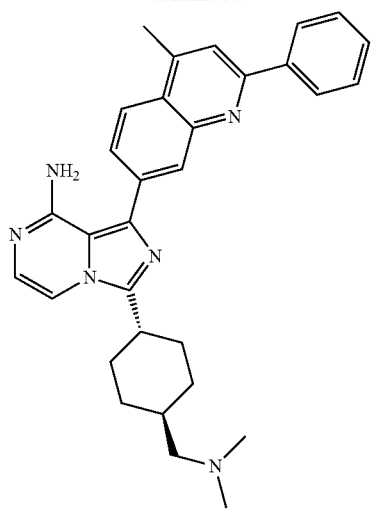
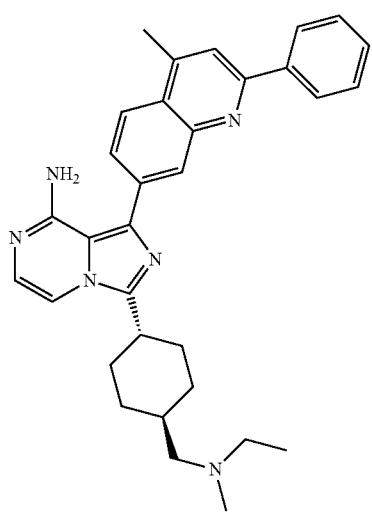
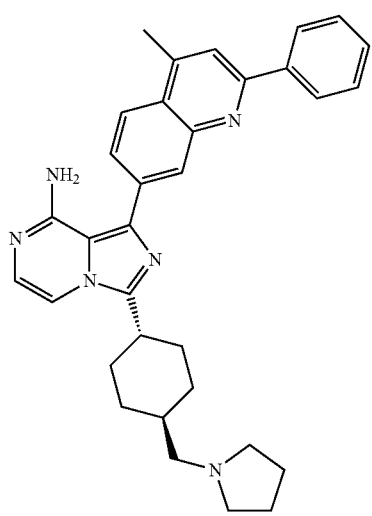
64
-continued
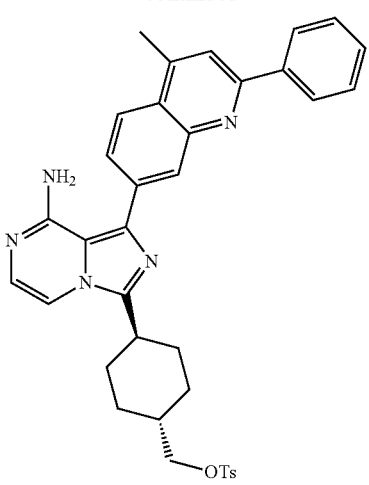
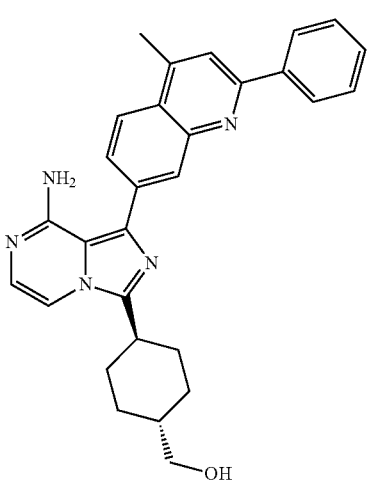
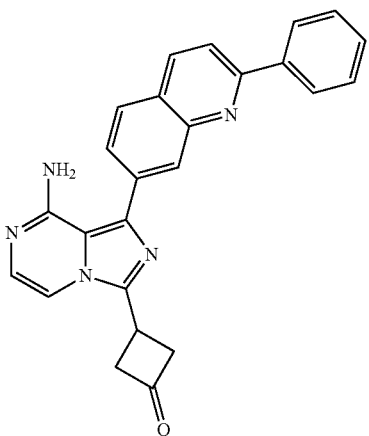

65
-continued
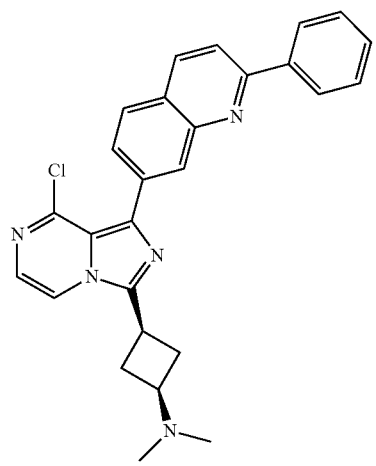
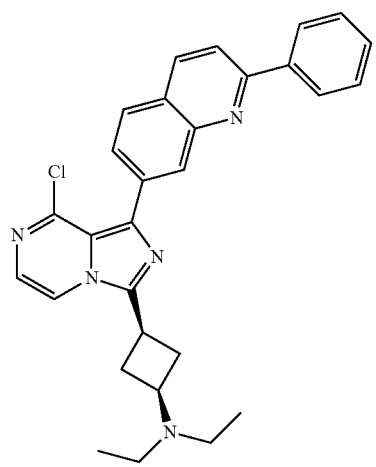
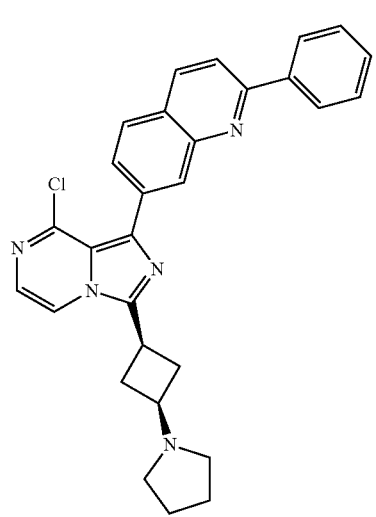
66
-continued
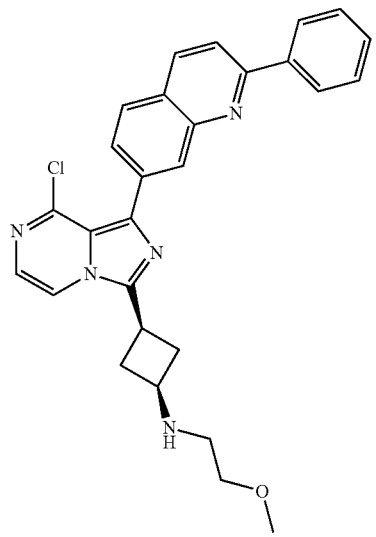
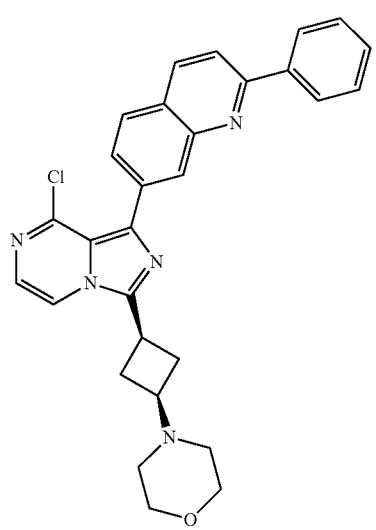

67
-continued
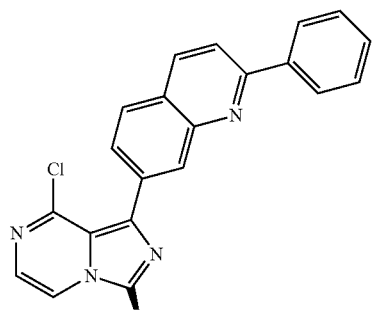
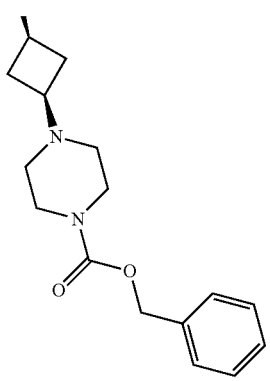
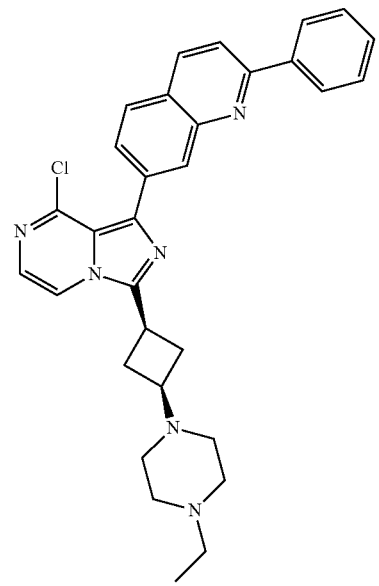
68
-continued
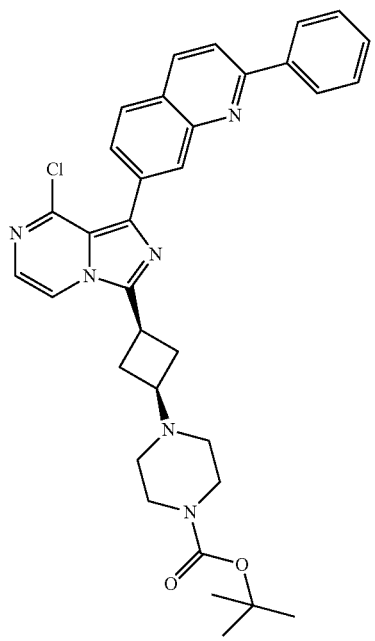
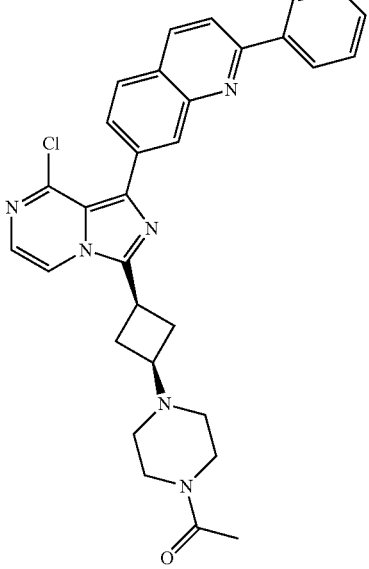

69
-continued
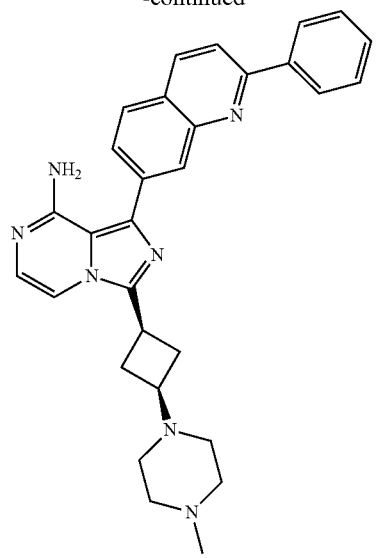
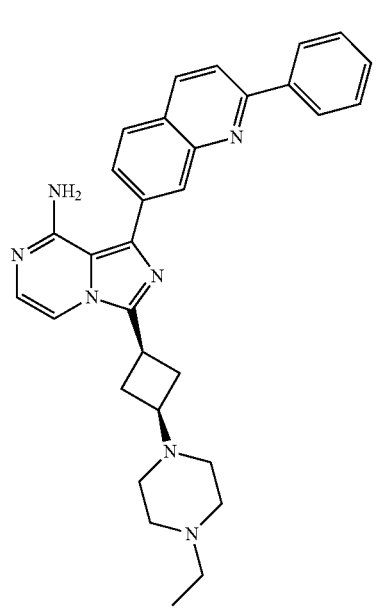
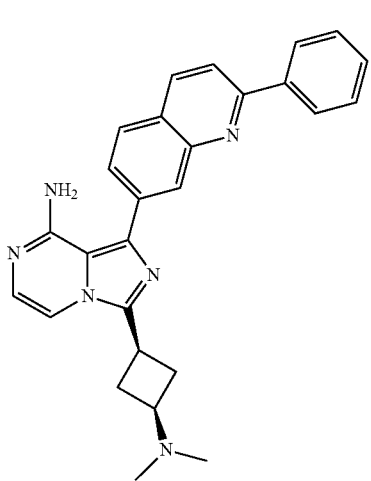
70
-continued
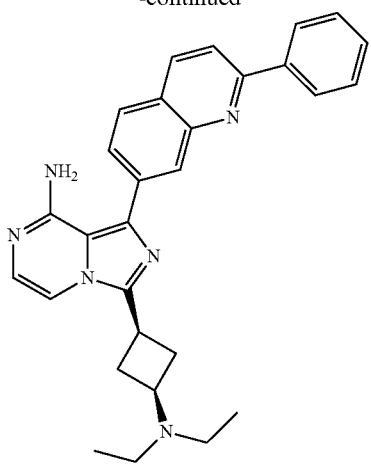
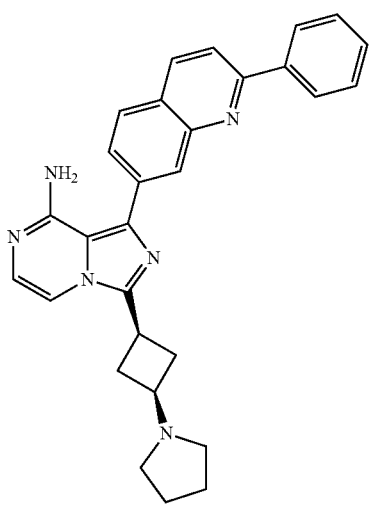
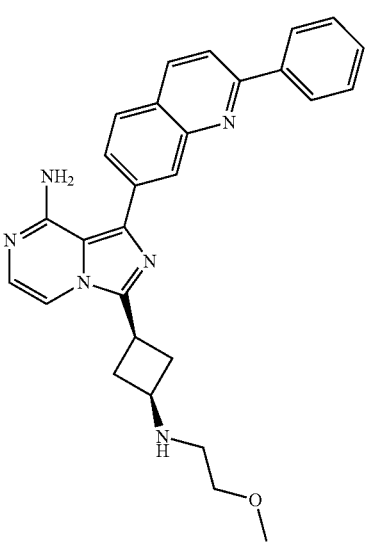

71
-continued
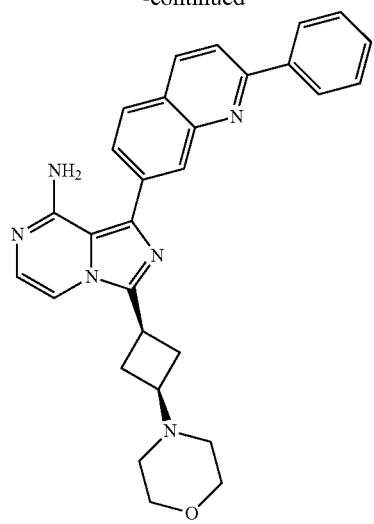
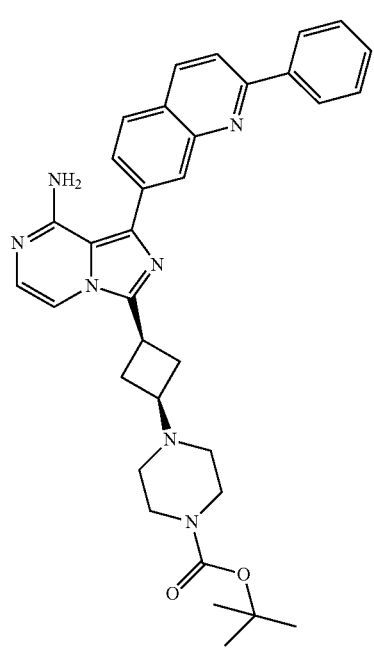
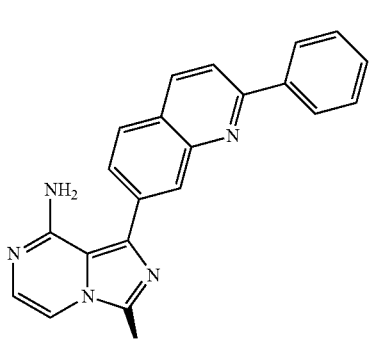
72
-continued
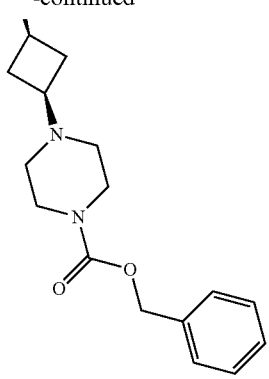
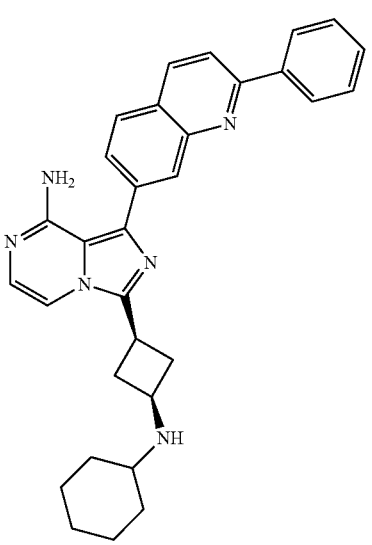
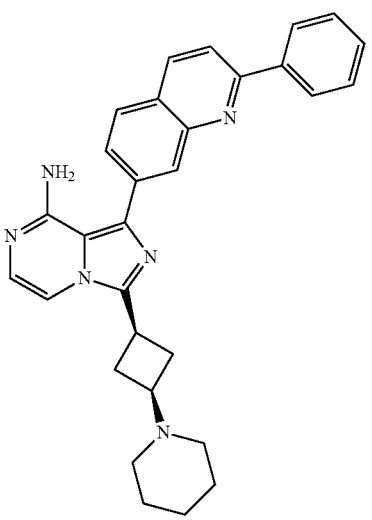

73
-continued
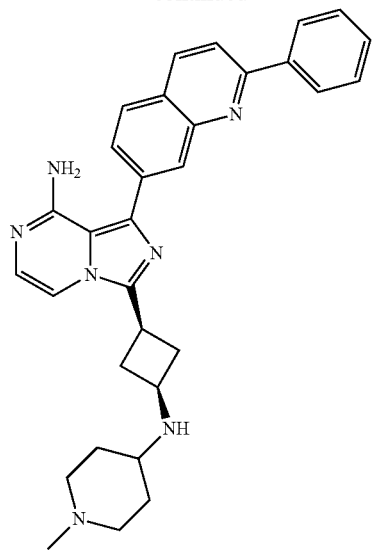
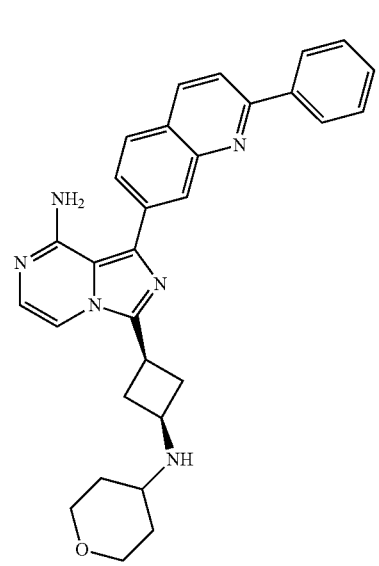
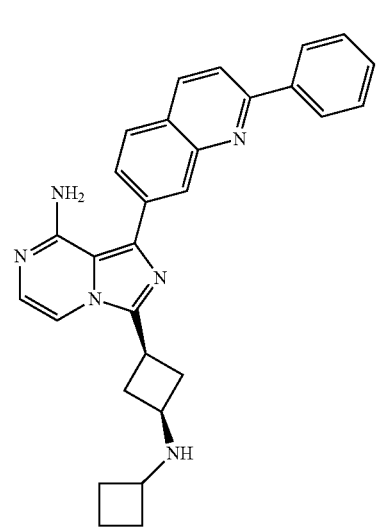
74
-continued
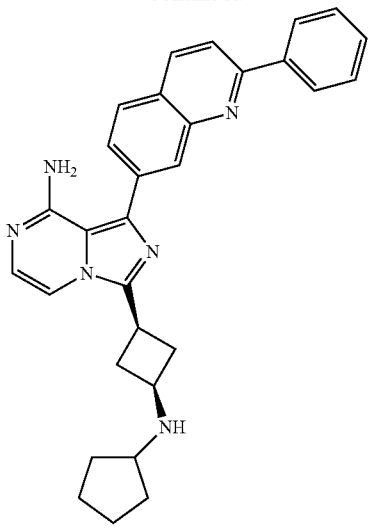
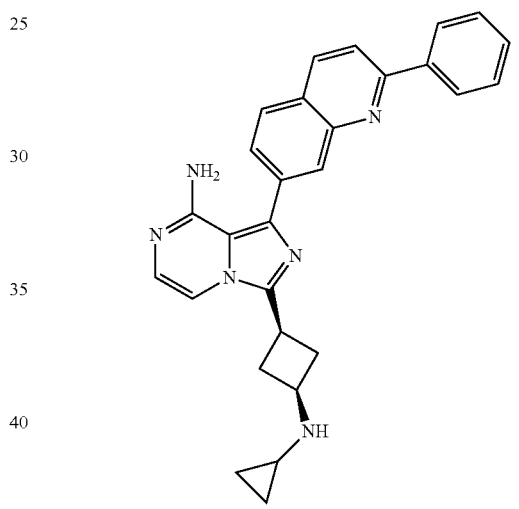
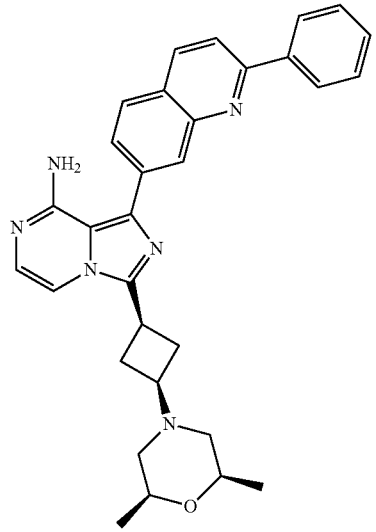

75
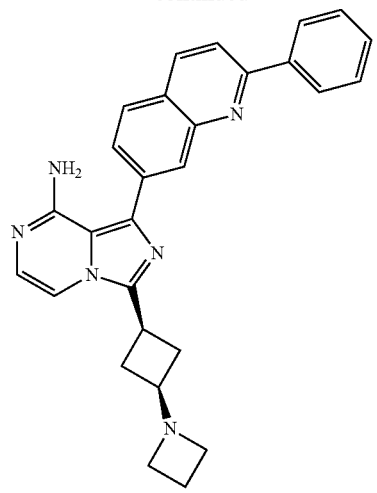
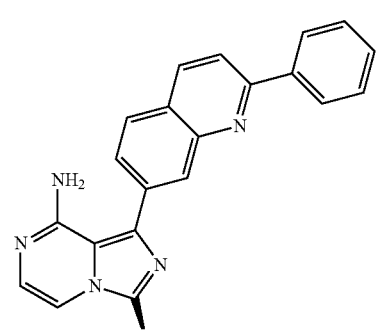
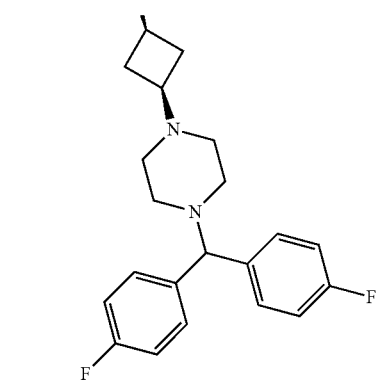
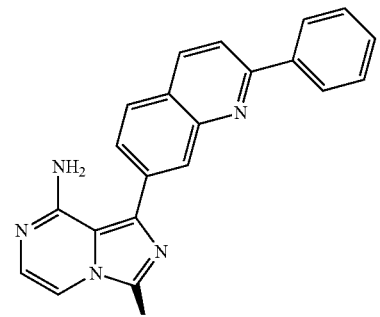
76
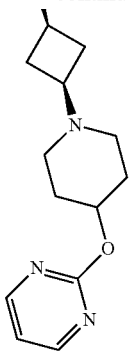
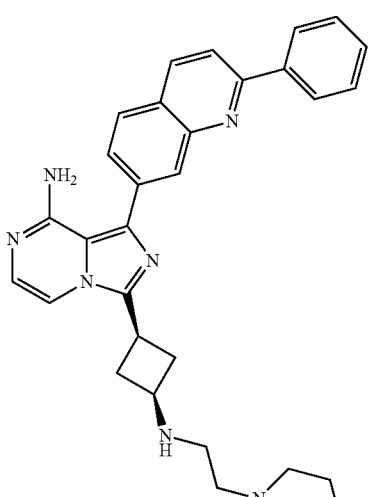
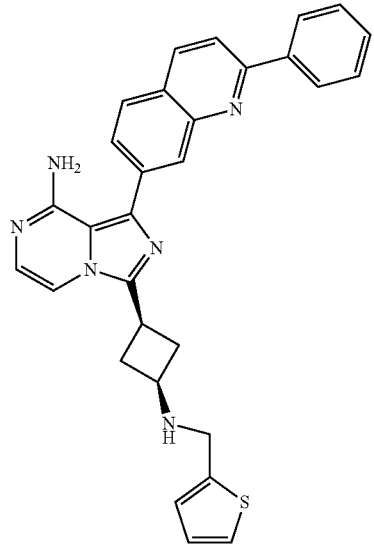

77
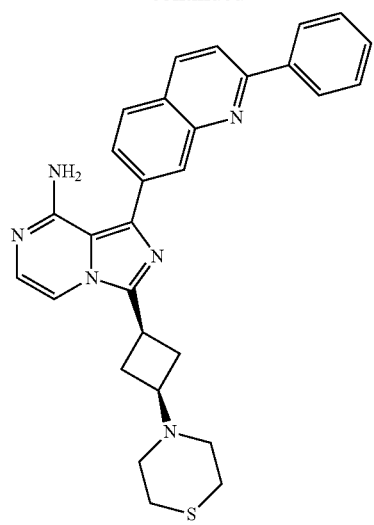
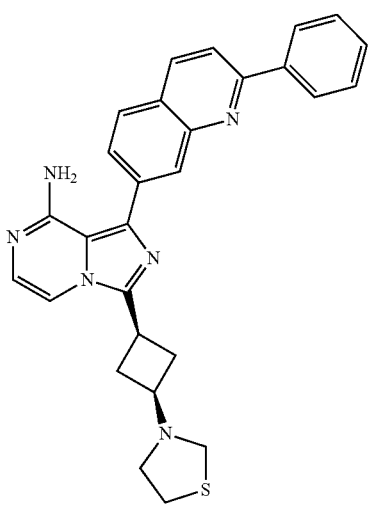
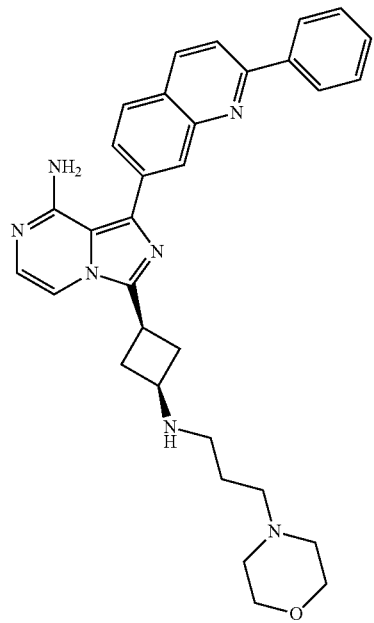
78
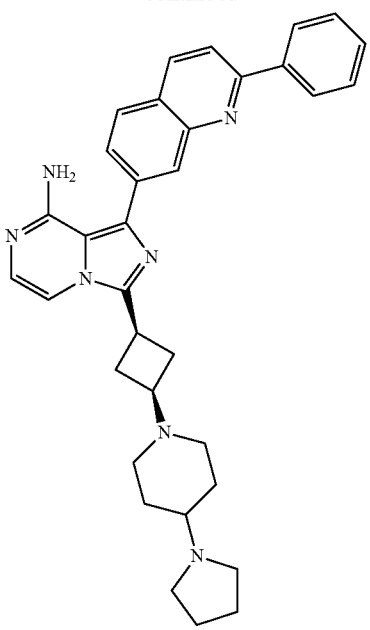
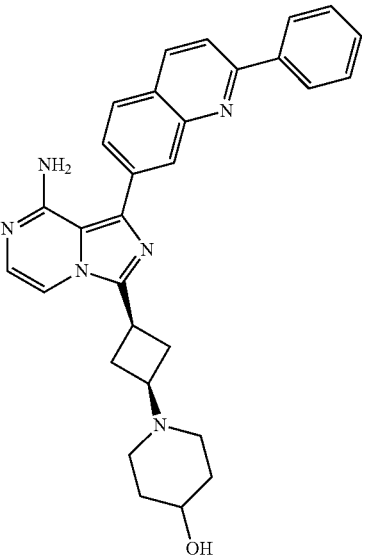

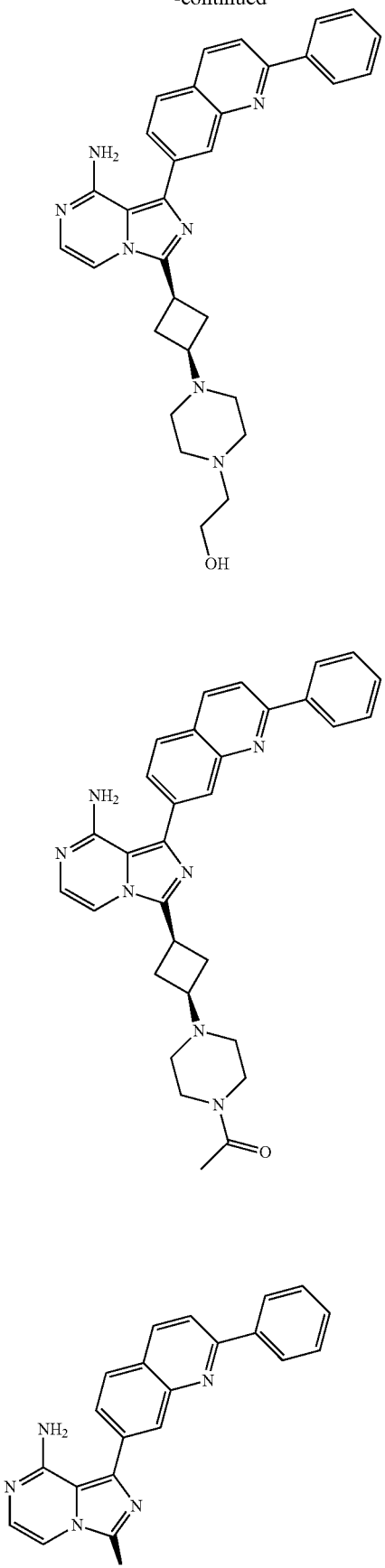

81
-continued
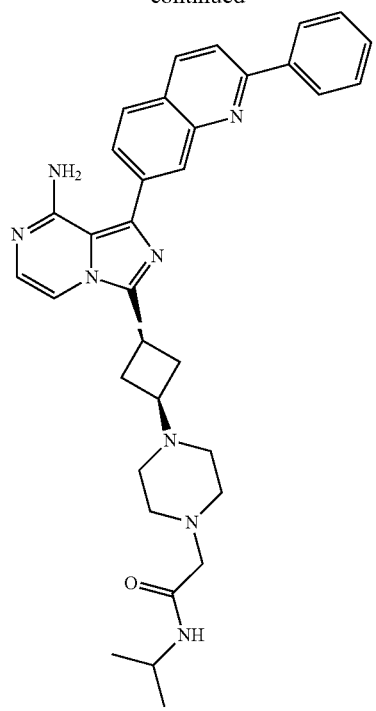
82
-continued
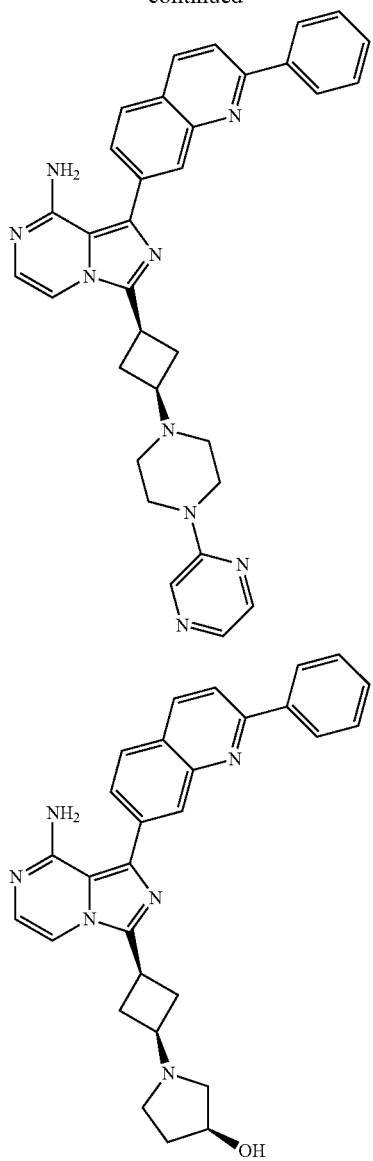
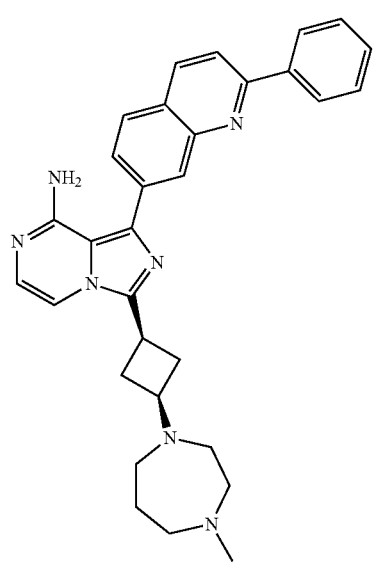
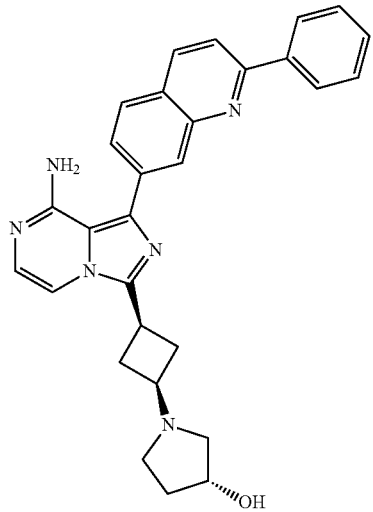

83
-continued
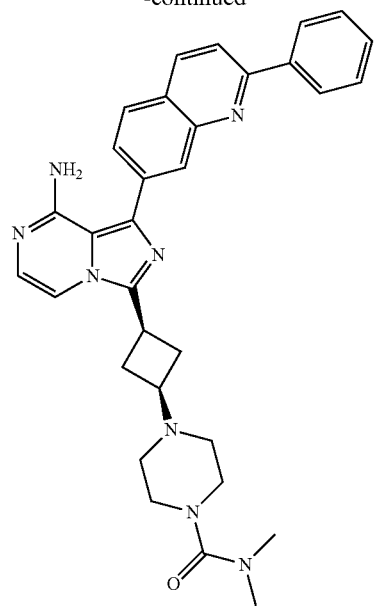
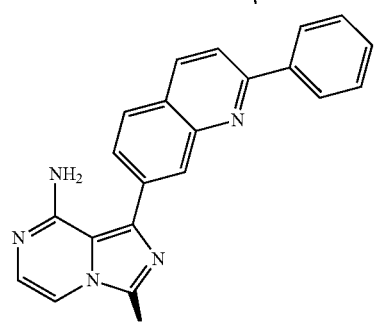
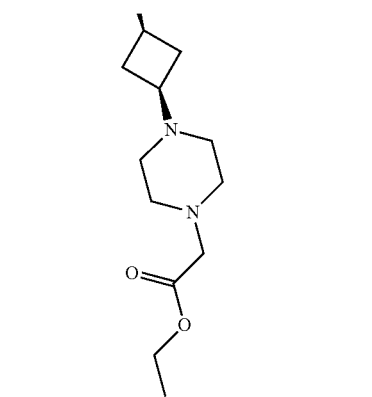
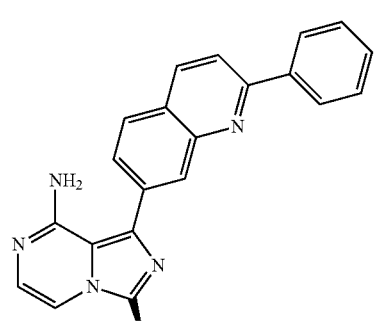
84
-continued
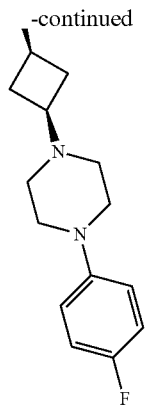
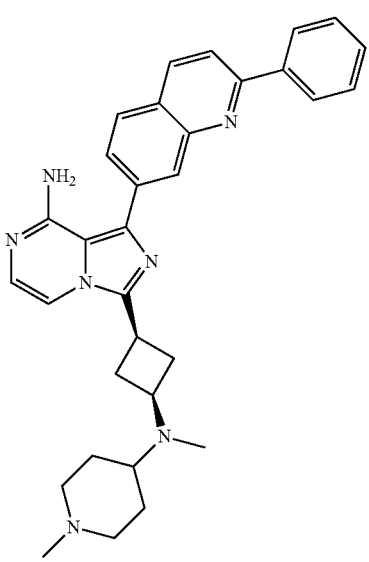
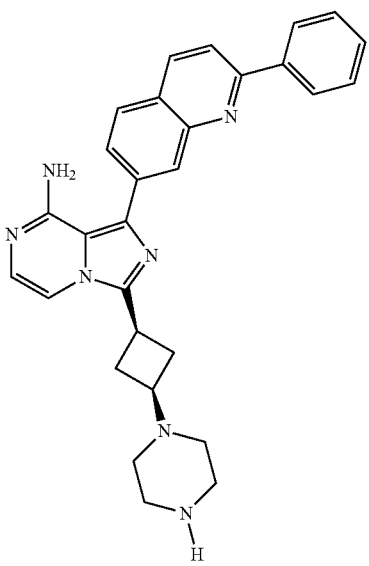

85
-continued
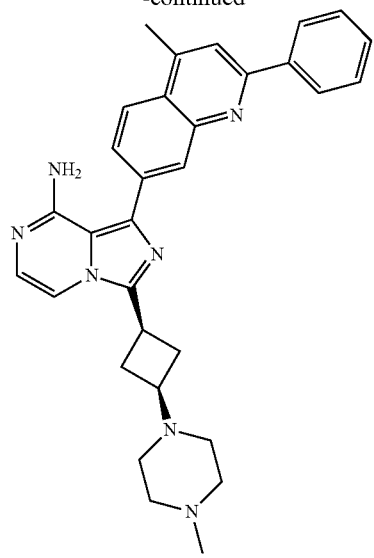
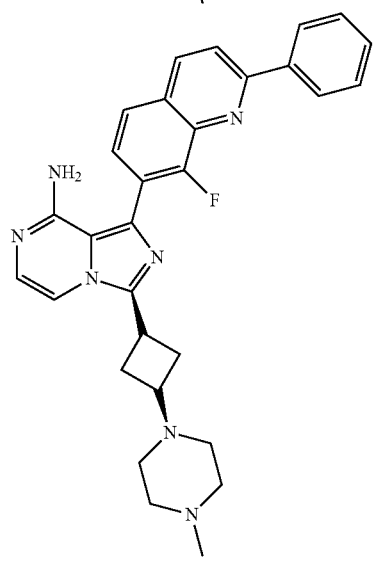
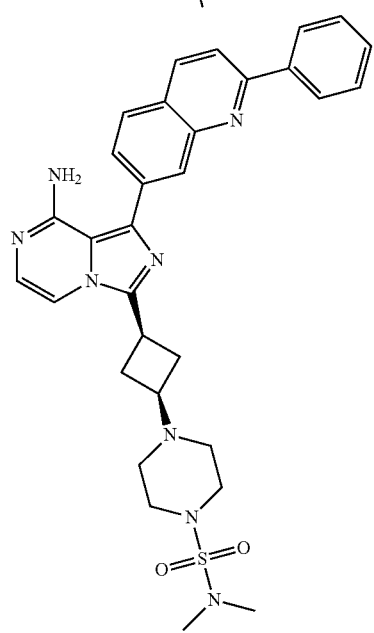
86
-continued
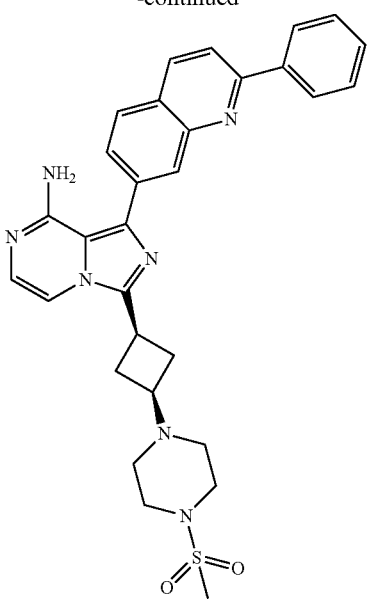
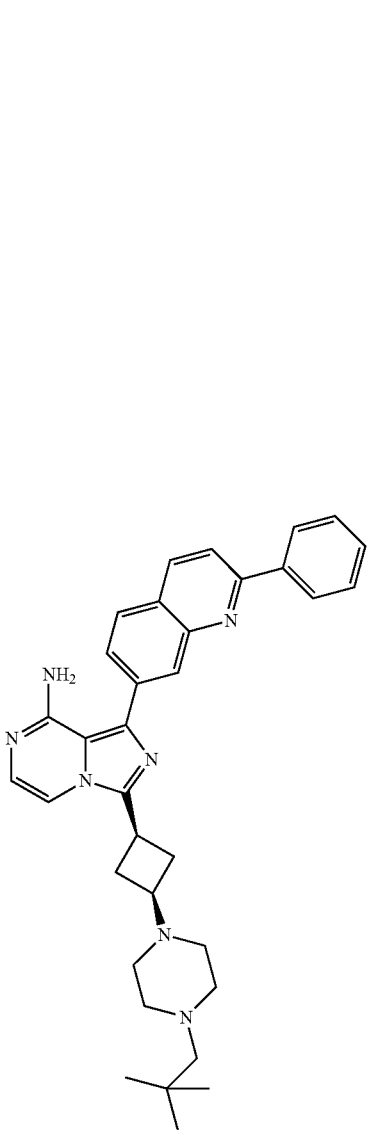

87
-continued
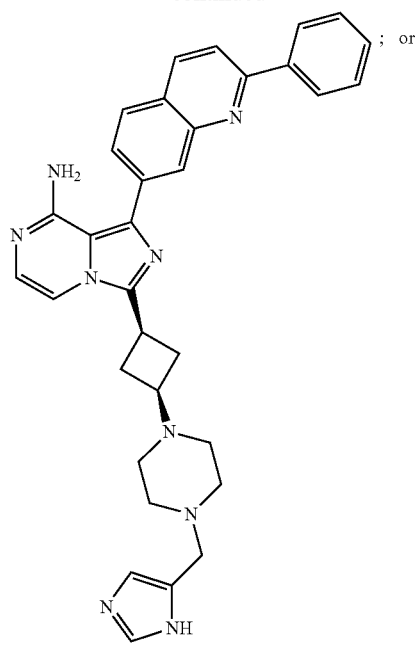
; or
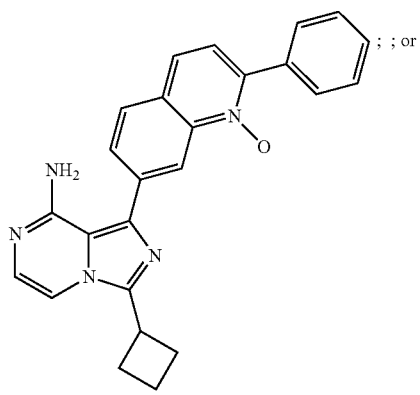
; ; or
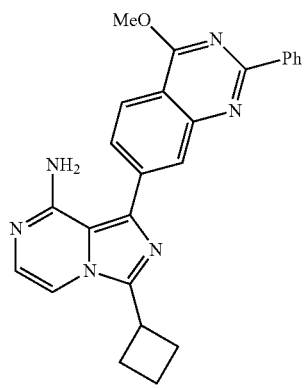
88
-continued
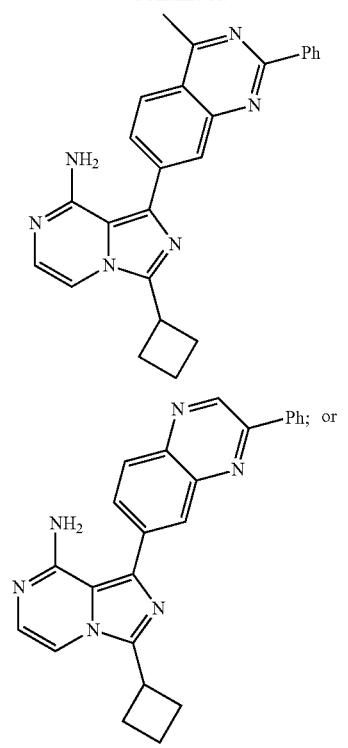
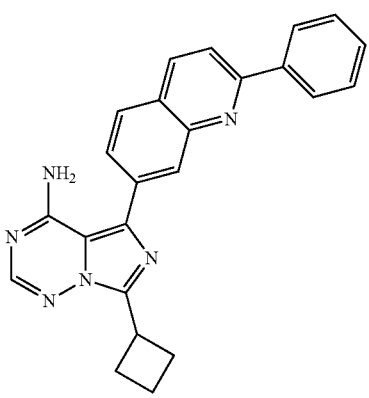
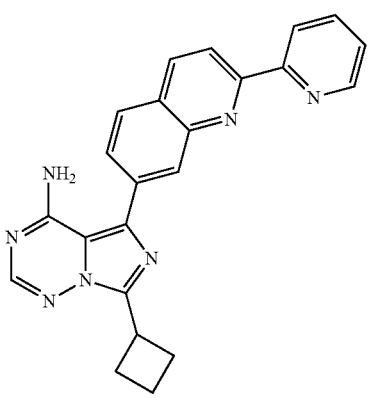

89
-continued
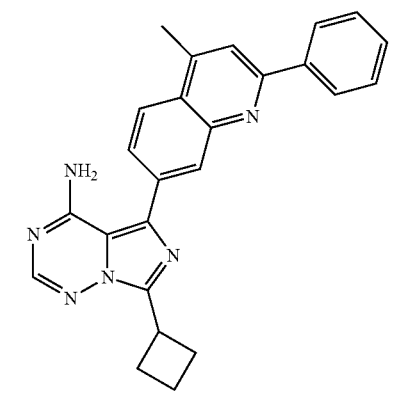
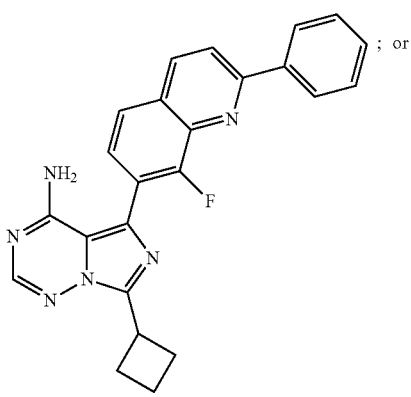
; or
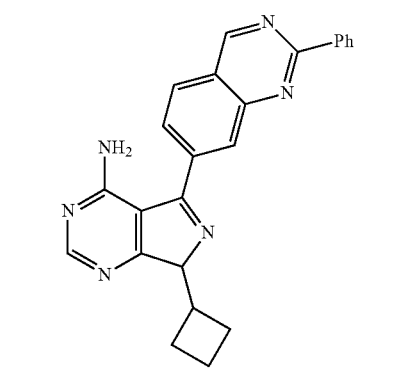
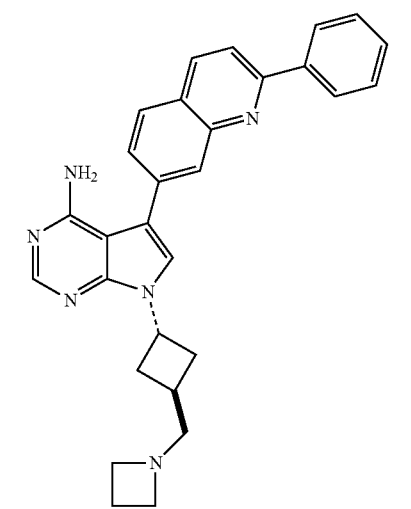
90
-continued
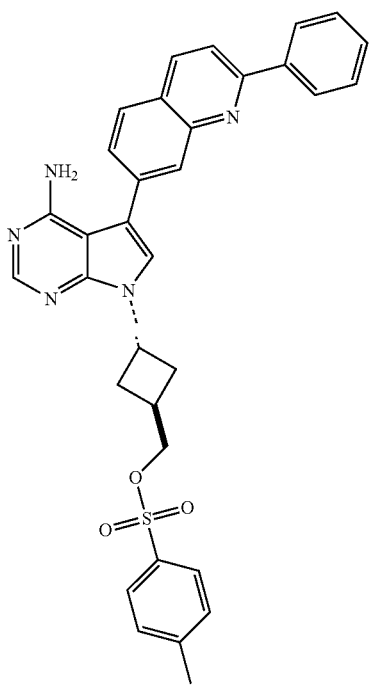
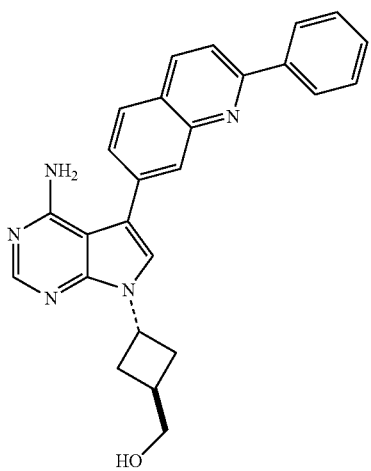
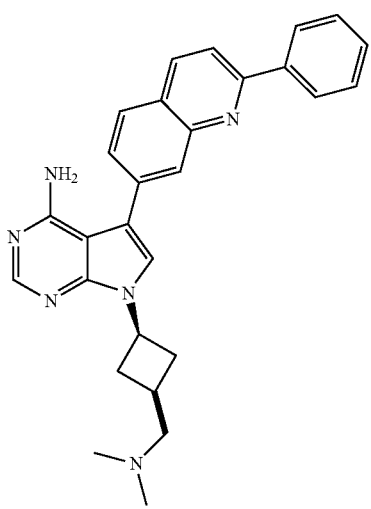

91
-continued
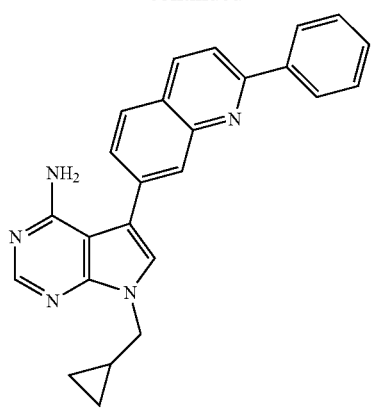
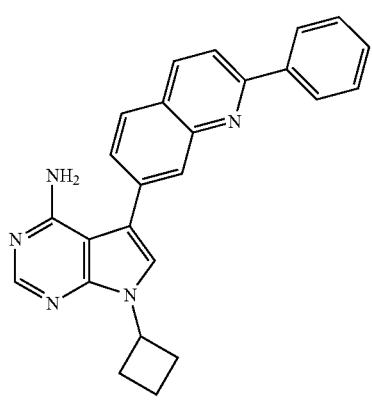
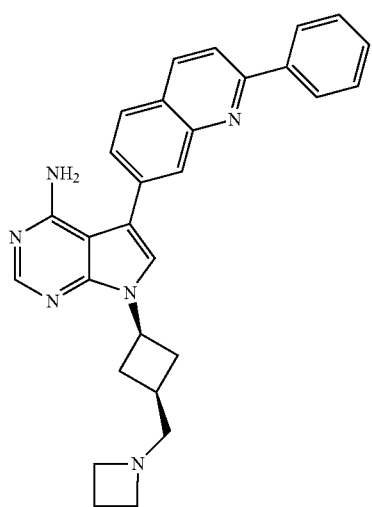
92
-continued
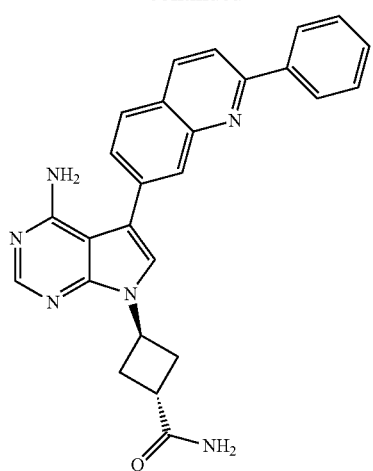
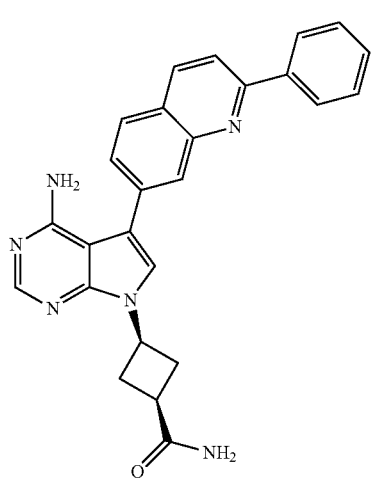
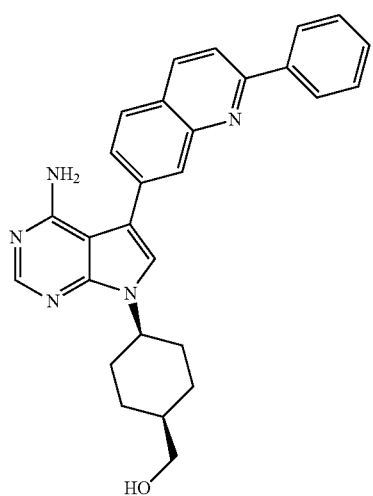

-continued
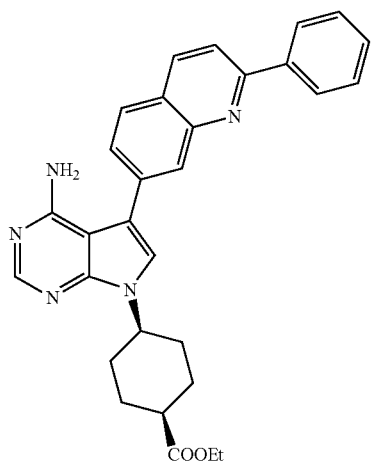
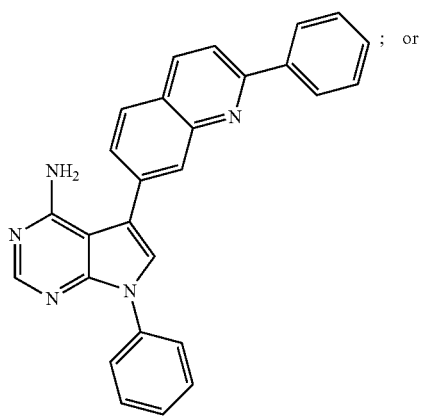; or
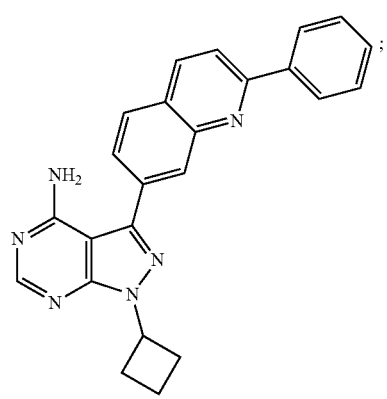;
or a pharmaceutically acceptable salt thereof.
The compounds of the present invention include any one of,
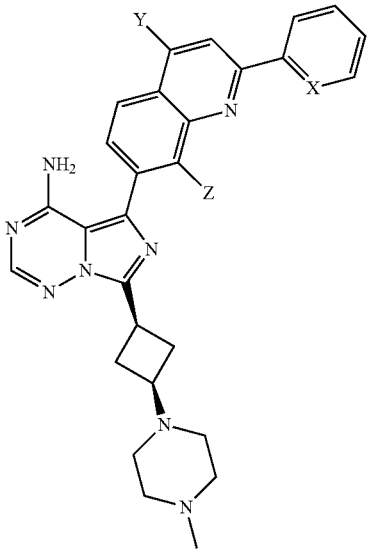
wherein
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |
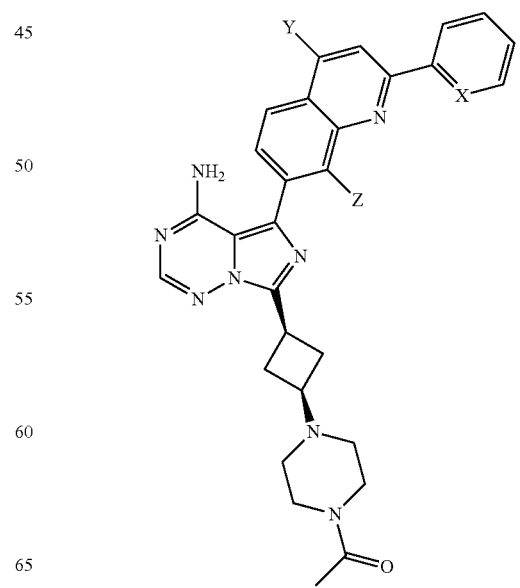

95
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
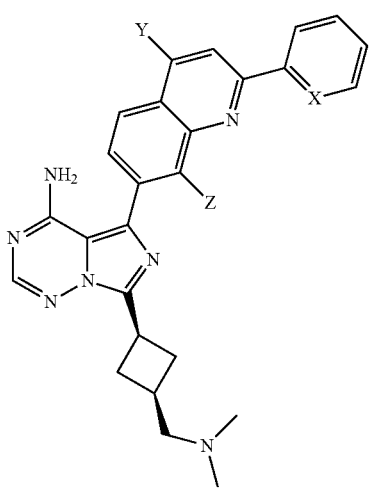
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
96
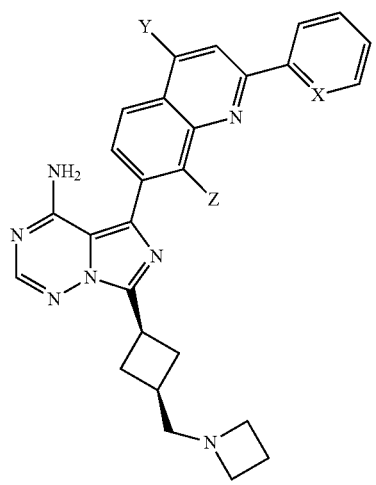
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
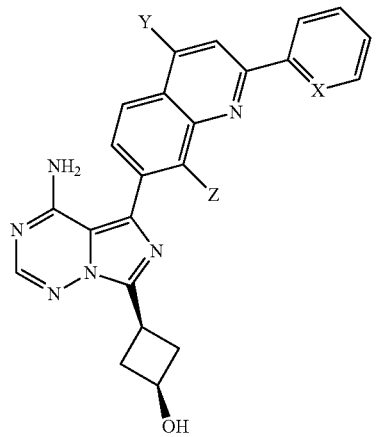
or wherein
| X | Y | Z |
|---|---|---|
| CH | H | H |
| CH | CH₃ | H |
| CH | H | F |
| CH | CH₃ | F |
| N | H | H |

-continued
| X | Y | Z |
|---|---|---|
| N | CH₃ | H |
| N | H | F |
| N | CH₃ | F |
| CF | H | H |
| CF | CH₃ | H |
| CF | H | F |
| CF | CH₃ | F; |
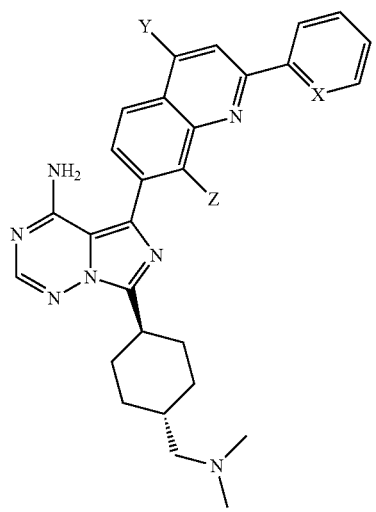
wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
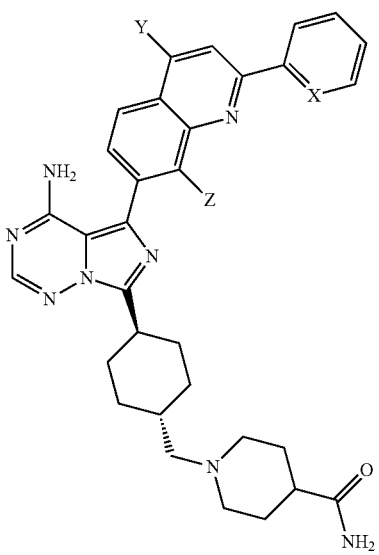

99
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
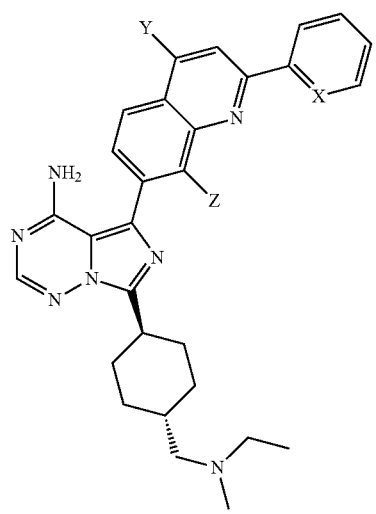
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
100
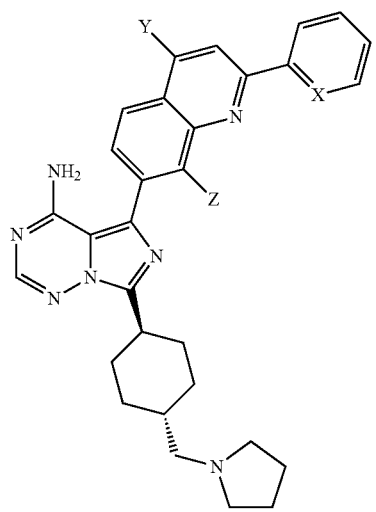
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
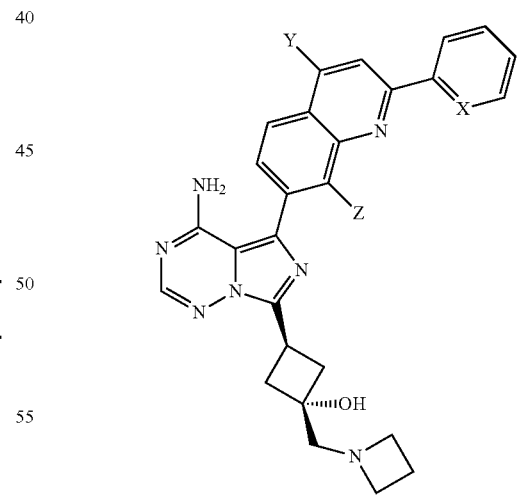
or wherein
| X | Y | Z |
|---|---|---|
| CH | H | H |
| CH | CH₃ | H |

101
-continued
| X | Y | Z |
|---|---|---|
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
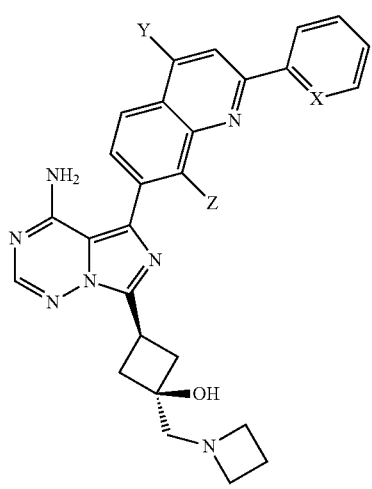
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
102
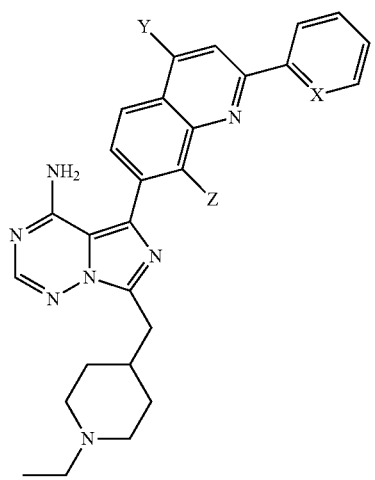
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
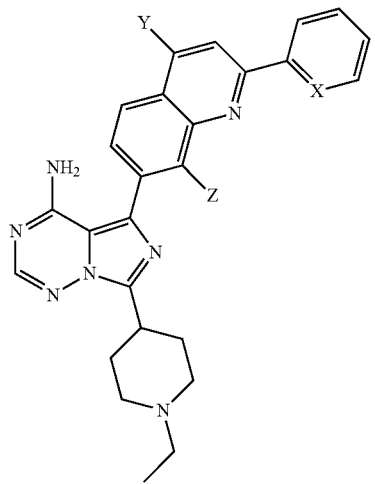
or wherein
| X | Y | Z |
|---|---|---|
| CH | H | H |
| CH | CH₃ | H |
| CH | H | F |

103
-continued
| X  | Y   | Z |
|----|-----|---|
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F; |
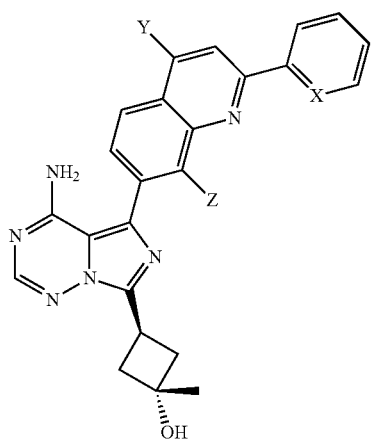
or wherein
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F; |
104
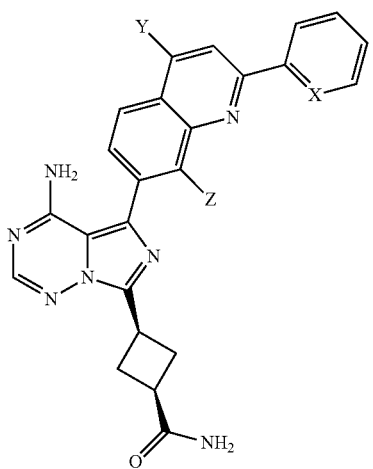
or wherein
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F; |
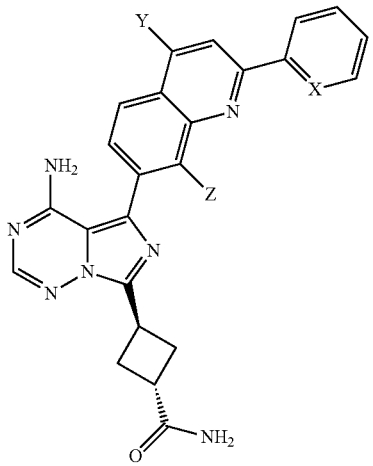
or wherein
| X  | Y   | Z |
|----|-----|---|
| CH | H   | H |
| CH | CH₃ | H |
| CH | H   | F |
| CH | CH₃ | F |

-continued
| X | Y | Z |
|---|---|---|
| N | H | H |
| N | CH₃ | H |
| N | H | F |
| N | CH₃ | F |
| CF | H | H |
| CF | CH₃ | H |
| CF | H | F |
| CF | CH₃ | F; |
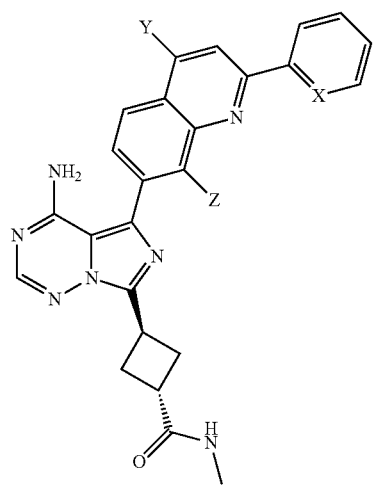
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
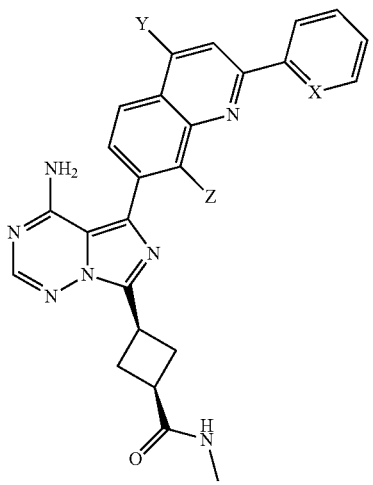
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
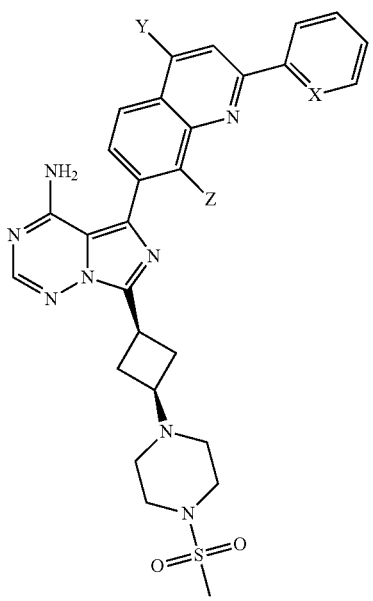

or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
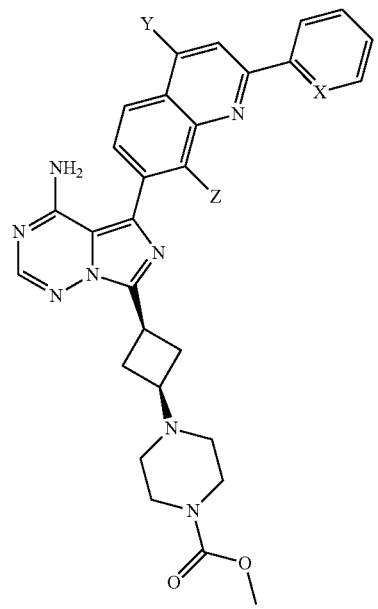
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
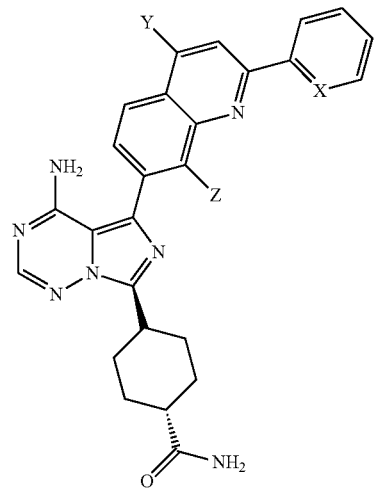

or wherein

| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |

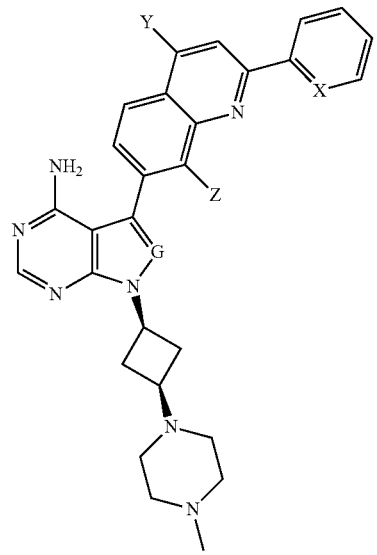

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

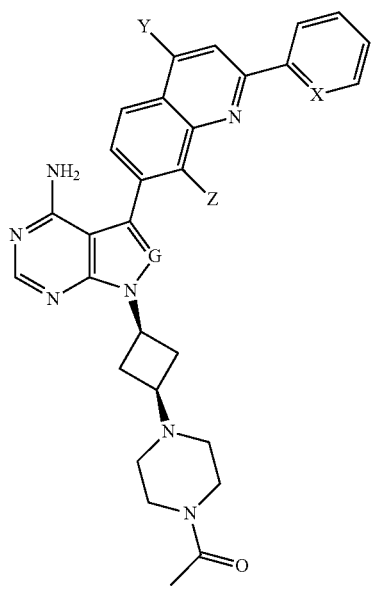

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |

-continued

| X | Y | Z | G |
|---|---|---|---|
| CF | CH₃ | H | N |
| CF | H | F | N |
| CF | CH₃ | F | N; |

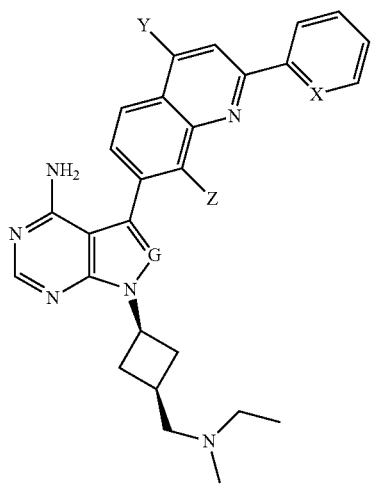

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

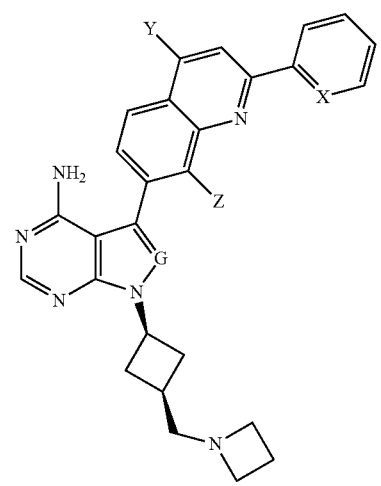

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

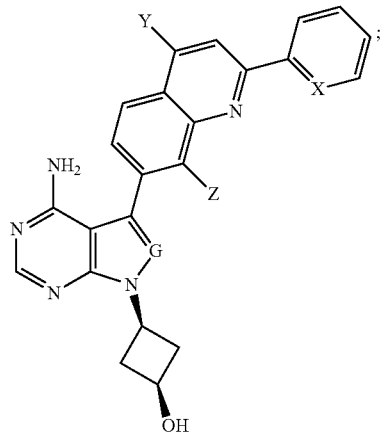

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

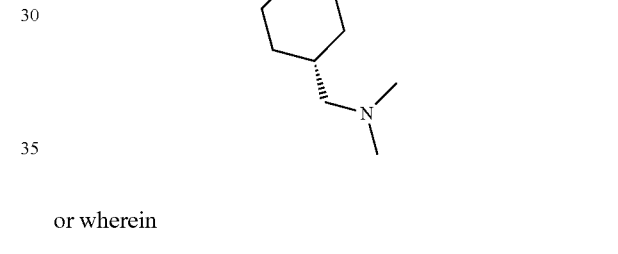

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

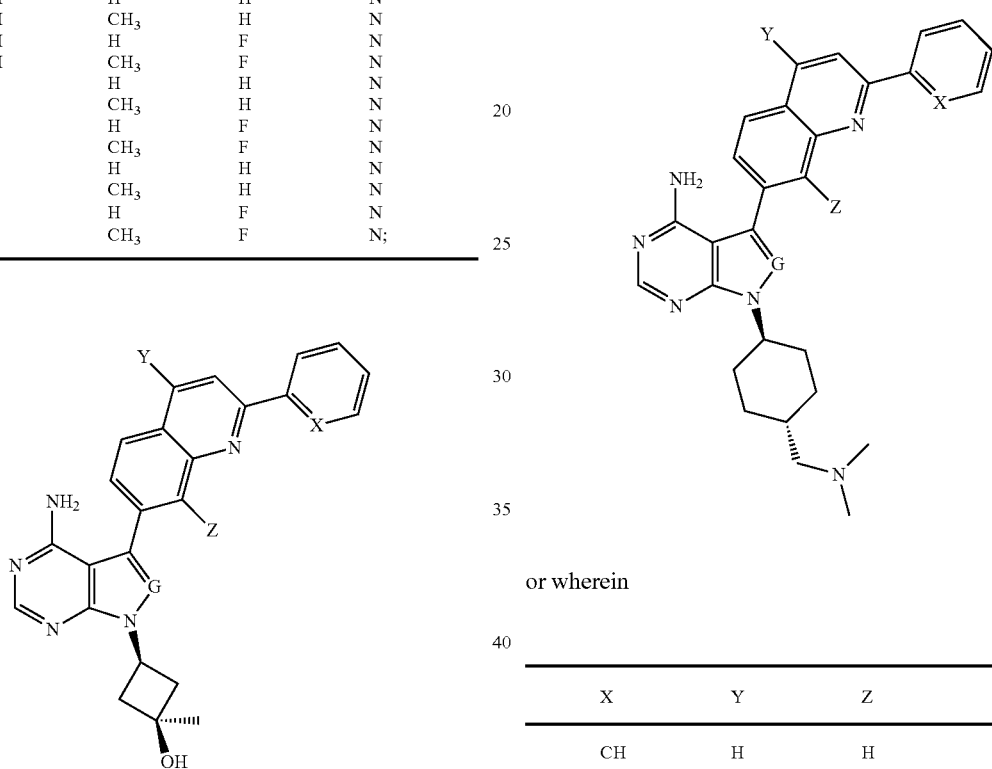

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |

115

-continued

| X  | Y   | Z | G  |
|----|-----|---|----|
| CF | H   | H | N  |
| CF | CH3 | H | N  |
| CF | H   | F | N  |
| CF | CH3 | F | N; |

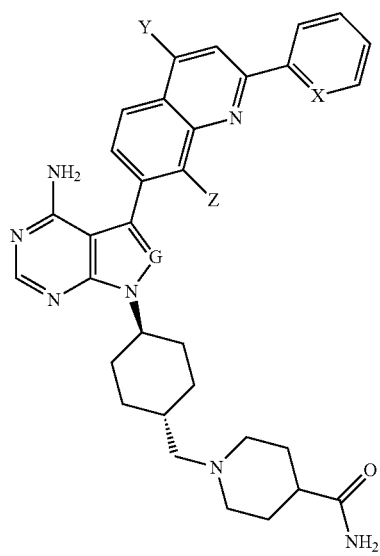

or wherein

| X  | Y   | Z | G  |
|----|-----|---|----|
| CH | H   | H | CH |
| CH | CH3 | H | CH |
| CH | H   | F | CH |
| CH | CH3 | F | CH |
| N  | H   | H | CH |
| N  | CH3 | H | CH |
| N  | H   | F | CH |
| N  | CH3 | F | CH |
| CF | H   | H | CH |
| CF | CH3 | H | CH |
| CF | H   | F | CH |
| CF | CH3 | F | CH |
| CH | H   | H | N  |
| CH | CH3 | H | N  |
| CH | H   | F | N  |
| CH | CH3 | F | N  |
| N  | H   | H | N  |
| N  | CH3 | H | N  |
| N  | H   | F | N  |
| N  | CH3 | F | N  |
| CF | H   | H | N  |

116

-continued

| X  | Y   | Z | G  |
|----|-----|---|----|
| CF | CH3 | H | N  |
| CF | H   | F | N  |
| CF | CH3 | F | N; |

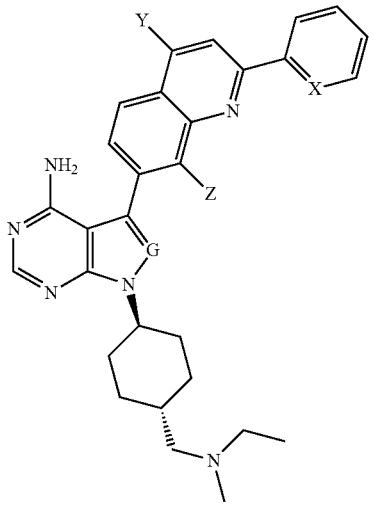

or wherein

| X  | Y   | Z | G  |
|----|-----|---|----|
| CH | H   | H | CH |
| CH | CH3 | H | CH |
| CH | H   | F | CH |
| CH | CH3 | F | CH |
| N  | H   | H | CH |
| N  | CH3 | H | CH |
| N  | H   | F | CH |
| N  | CH3 | F | CH |
| CF | H   | H | CH |
| CF | CH3 | H | CH |
| CF | H   | F | CH |
| CF | CH3 | F | CH |
| CH | H   | H | N  |
| CH | CH3 | H | N  |
| CH | H   | F | N  |
| CH | CH3 | F | N  |
| N  | H   | H | N  |
| N  | CH3 | H | N  |
| N  | H   | F | N  |
| N  | CH3 | F | N  |
| CF | H   | H | N  |
| CF | CH3 | H | N  |

117
-continued

| X | Y | Z | G |
|---|---|---|---|
| CF | H | F | N |
| CF | CH₃ | F | N; |

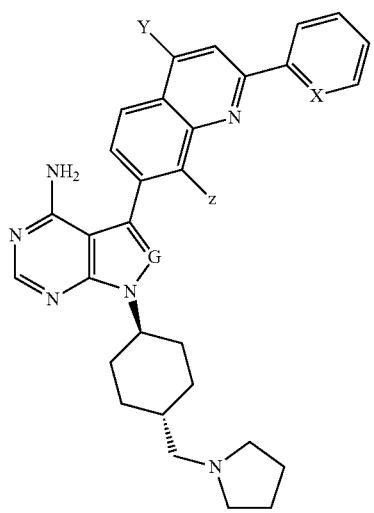

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |

118
-continued

| X | Y | Z | G |
|---|---|---|---|
| CF | H | F | N |
| CF | CH₃ | F | N; |

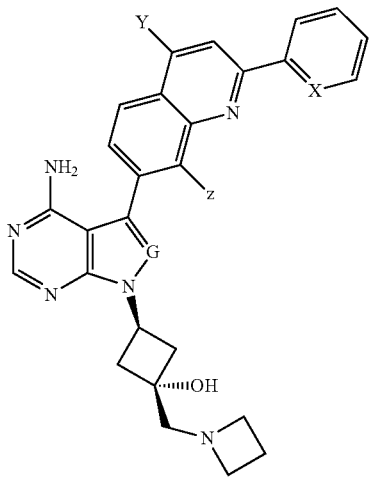

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |

119

-continued

| X | Y | Z | G |
|---|---|---|---|
| CF | H | F | N |
| CF | CH₃ | F | N; |

120

-continued

| X | Y | Z | G |
|---|---|---|---|
| CF | H | F | N |
| CF | CH₃ | F | N; | or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N | or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

121

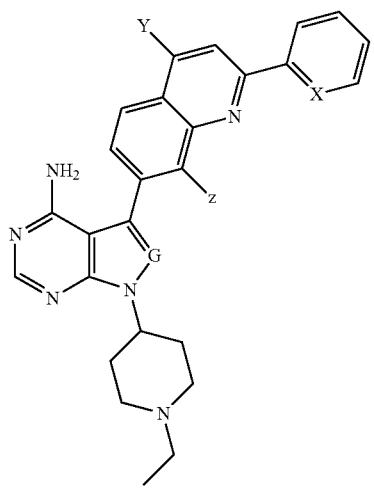

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

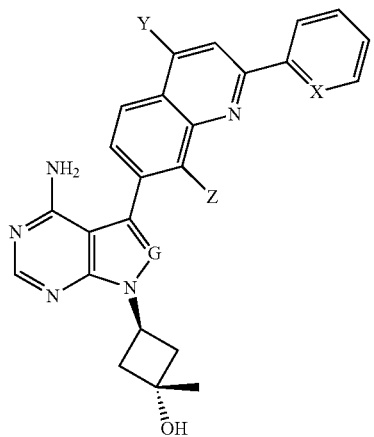

122 or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

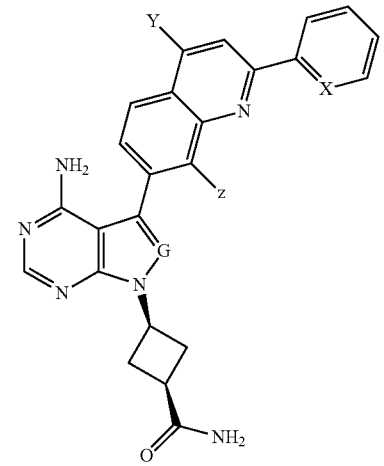

or wherein

| X | Y | Z | G |
|---|---|---|---|
| CH | H | H | C—CH₃ |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |

123
-continued

| X | Y | Z | G |
|---|---|---|---|
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

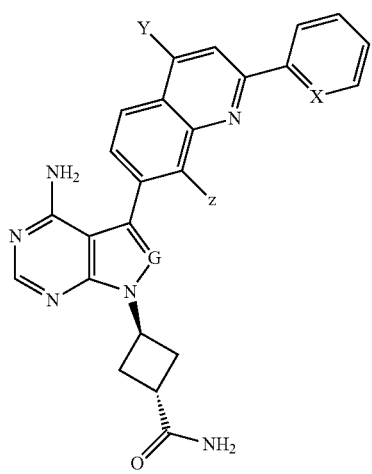

or wherein

| X | Y | Z | G |
|---|---|---|---|
| CH | H | H | C—CH₃ |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |

124
-continued

| X | Y | Z | G |
|---|---|---|---|
| CF | H | F | N |
| CF | CH₃ | F | N; |

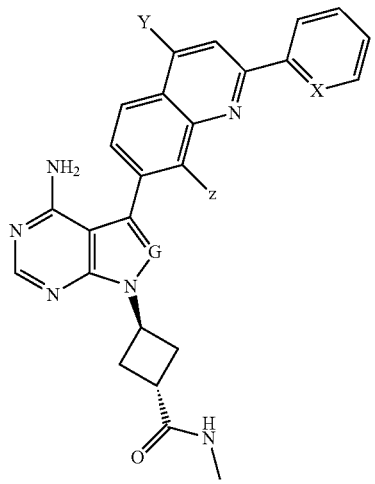

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |

125

-continued

| X | Y | Z | G |
|---|---|---|---|
| CF | H | F | N |
| CF | CH₃ | F | N; |

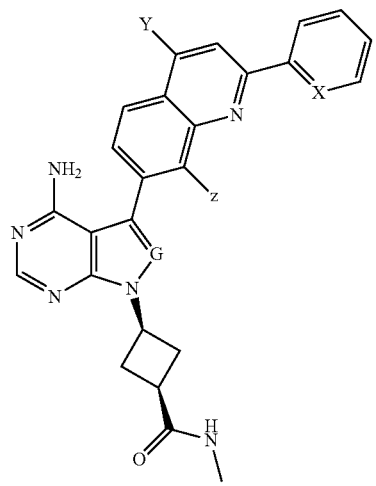

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

126

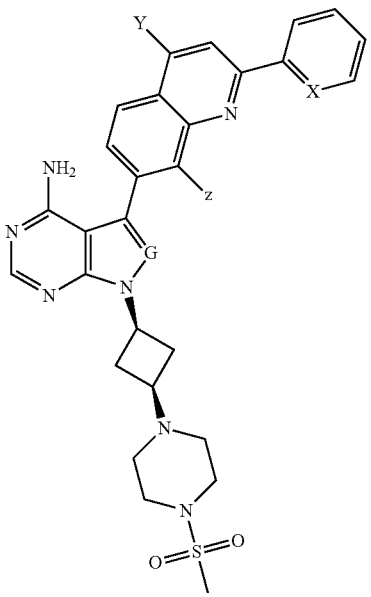

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

127

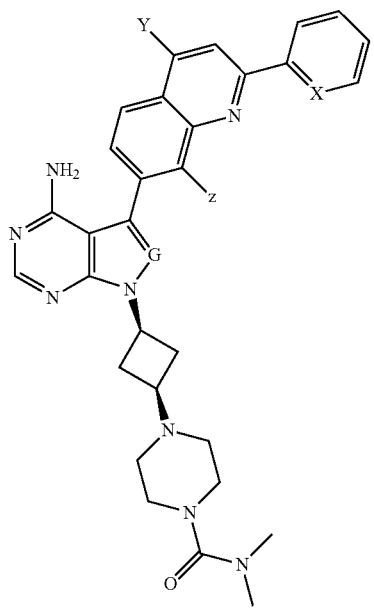

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

128

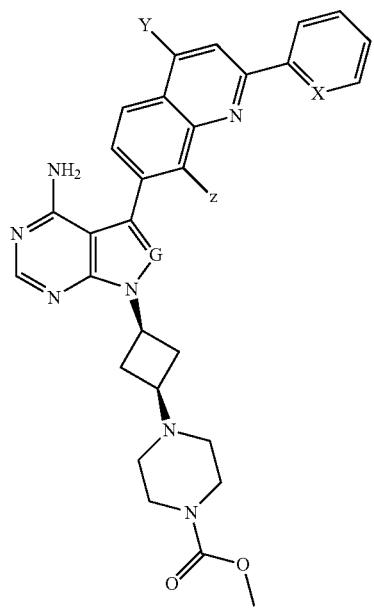

or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

129

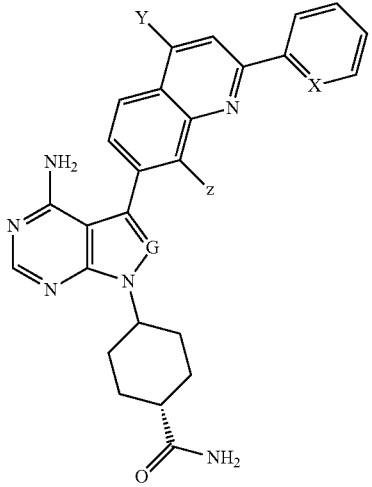

130

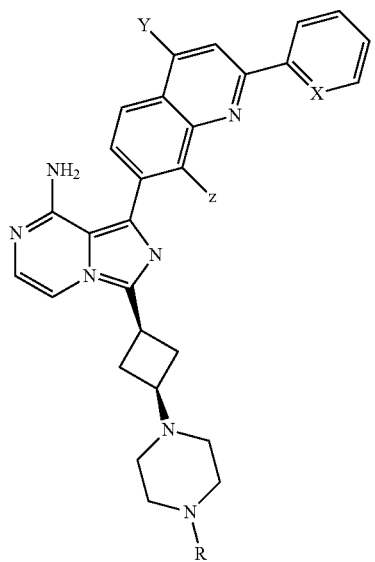

or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | Ac |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) | or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N; |

-continued

| X | Y | Z | R |
|---|---|---|---|
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NMe₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |

-continued

| X | Y | Z | R |
|---|---|---|---|
| N | CH₃ | F | Et |
| CF | H | H | Et |
| CF | CH₃ | H | Et |
| CF | H | F | Et |
| CF | CH₃ | F | Et; |

or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | Ac |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |

-continued

| X | Y | Z | R |
|---|---|---|---|
| N | H | F | CO(CH$_2$CH$_3$) |
| N | CH$_3$ | F | CO(CH$_2$CH$_3$) |
| CF | H | H | CO(CH$_2$CH$_3$) |
| CF | CH$_3$ | H | CO(CH$_2$CH$_3$) |
| CF | H | F | CO(CH$_2$CH$_3$) |
| CF | CH$_3$ | F | CO(CH$_2$CH$_3$) |
| CH | H | H | CO(NMe$_2$) |
| CH | CH$_3$ | H | CO(NMe$_2$) |
| CH | H | F | CO(NMe$_2$) |
| CH | CH$_3$ | F | CO(NMe$_2$) |
| N | H | H | CO(NMe$_2$) |
| N | CH$_3$ | H | CO(NMe$_2$) |
| N | H | F | CO(NMe$_2$) |
| N | CH$_3$ | F | CO(NMe$_2$) |
| CF | H | H | CO(NMe$_2$) |
| CF | CH$_3$ | H | CO(NMe$_2$) |
| CF | H | F | CO(NMe$_2$) |
| CF | CH$_3$ | F | CO(NMe$_2$) |
| CH | H | H | CO(iPr) |
| CH | CH$_3$ | H | CO(iPr) |
| CH | H | F | CO(iPr) |
| CH | CH$_3$ | F | CO(iPr) |
| N | H | H | CO(iPr) |
| N | CH$_3$ | H | CO(iPr) |
| N | H | F | CO(iPr) |
| N | CH$_3$ | F | CO(iPr) |
| CF | H | H | CO(iPr) |
| CF | CH$_3$ | H | CO(iPr) |
| CF | H | F | CO(iPr) |
| CF | CH$_3$ | F | CO(iPr) |
| CH | H | H | CO(CH$_2$OCH$_3$) |
| CH | CH$_3$ | H | CO(CH$_2$OCH$_3$) |
| CH | H | F | CO(CH$_2$OCH$_3$) |
| CH | CH$_3$ | F | CO(CH$_2$OCH$_3$) |
| N | H | H | CO(CH$_2$OCH$_3$) |
| N | CH$_3$ | H | CO(CH$_2$OCH$_3$) |
| N | H | F | CO(CH$_2$OCH$_3$) |
| N | CH$_3$ | F | CO(CH$_2$OCH$_3$) |
| CF | H | H | CO(CH$_2$OCH$_3$) |
| CF | CH$_3$ | H | CO(CH$_2$OCH$_3$) |
| CF | H | F | CO(CH$_2$OCH$_3$) |
| CF | CH$_3$ | F | CO(CH$_2$OCH$_3$) |
| CH | H | H | CO(CH$_2$NMe$_2$) |
| CH | CH$_3$ | H | CO(CH$_2$NMe$_2$) |
| CH | H | F | CO(CH$_2$NMe$_2$) |
| CH | CH$_3$ | F | CO(CH$_2$NMe$_2$) |
| N | H | H | CO(CH$_2$NMe$_2$) |
| N | CH$_3$ | H | CO(CH$_2$NMe$_2$) |
| N | H | F | CO(CH$_2$NMe$_2$) |
| N | CH$_3$ | F | CO(CH$_2$NMe$_2$) |
| CF | H | H | CO(CH$_2$NMe$_2$) |
| CF | CH$_3$ | H | CO(CH$_2$NMe$_2$) |
| CF | H | F | CO(CH$_2$NMe$_2$) |
| CF | CH$_3$ | F | CO(CH$_2$NMe$_2$) |
| CH | H | H | CO$_2$CH$_3$ |
| CH | CH$_3$ | H | CO$_2$CH$_3$ |
| CH | H | F | CO$_2$CH$_3$ |
| CH | CH$_3$ | F | CO$_2$CH$_3$ |
| N | H | H | CO$_2$CH$_3$ |
| N | CH$_3$ | H | CO$_2$CH$_3$ |
| N | H | F | CO$_2$CH$_3$ |
| N | CH$_3$ | F | CO$_2$CH$_3$ |
| CF | H | H | CO$_2$CH$_3$ |
| CF | CH$_3$ | H | CO$_2$CH$_3$ |
| CF | H | F | CO$_2$CH$_3$ |
| CF | CH$_3$ | F | CO$_2$CH$_3$ |
| CH | H | H | CO$_2$CH$_2$CH$_3$ |
| CH | CH$_3$ | H | CO$_2$CH$_2$CH$_3$ |
| CH | H | F | CO$_2$CH$_2$CH$_3$ |
| CH | CH$_3$ | F | CO$_2$CH$_2$CH$_3$ |
| N | H | H | CO$_2$CH$_2$CH$_3$ |
| N | CH$_3$ | H | CO$_2$CH$_2$CH$_3$ |
| N | H | F | CO$_2$CH$_2$CH$_3$ |
| N | CH$_3$ | F | CO$_2$CH$_2$CH$_3$ |
| CF | H | H | CO$_2$CH$_2$CH$_3$ |
| CF | CH$_3$ | H | CO$_2$CH$_2$CH$_3$ |
| CF | H | F | CO$_2$CH$_2$CH$_3$ |
| CF | CH$_3$ | F | CO$_2$CH$_2$CH$_3$ |

-continued

| X | Y | Z | R |
|---|---|---|---|
| CH | H | H | Et |
| CH | CH$_3$ | H | Et |
| CH | H | F | Et |
| CH | CH$_3$ | F | Et |
| N | H | H | Et |
| N | CH$_3$ | H | Et |
| N | H | F | Et |
| N | CH$_3$ | F | Et |
| CF | H | H | Et |
| CF | CH$_3$ | H | Et |
| CF | H | F | Et |
| CF | CH$_3$ | F | Et; |

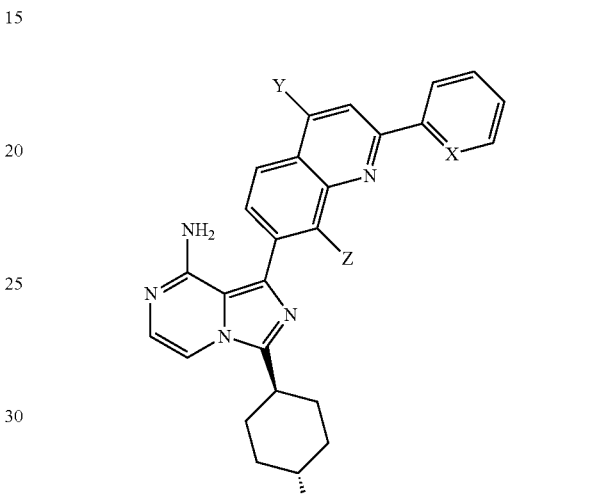

or wherein

| X | Y | Z | R |
|---|---|---|---|
| CH | CH$_3$ | F | CH$_3$ |
| CH | H | F | CH$_3$ |
| N | H | H | CH$_3$ |
| N | CH$_3$ | H | CH$_3$ |
| N | H | F | CH$_3$ |
| N | CH$_3$ | F | CH$_3$ |
| CF | H | H | CH$_3$ |
| CF | CH$_3$ | H | CH$_3$ |
| CF | H | F | CH$_3$ |
| CF | CH$_3$ | F | CH$_3$ |
| CH | H | H | Ac |
| CH | CH$_3$ | H | Ac |
| CH | H | F | Ac |
| CH | CH$_3$ | F | Ac |
| N | H | H | Ac |
| N | CH$_3$ | H | Ac |
| N | H | F | Ac |
| N | CH$_3$ | F | Ac |
| CF | H | H | Ac |
| CF | CH$_3$ | H | Ac |
| CF | H | F | Ac |
| CF | CH$_3$ | F | Ac |
| CH | H | H | CO(CF$_3$) |
| CH | CH$_3$ | H | CO(CF$_3$) |
| CH | H | F | CO(CF$_3$) |
| CH | CH$_3$ | F | CO(CF$_3$) |
| N | H | H | CO(CF$_3$) |
| N | CH$_3$ | H | CO(CF$_3$) |
| N | H | F | CO(CF$_3$) |
| N | CH$_3$ | F | CO(CF$_3$) |
| CF | H | H | CO(CF$_3$) |

-continued

| X | Y | Z | R |
|---|---|---|---|
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NMe₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et; |

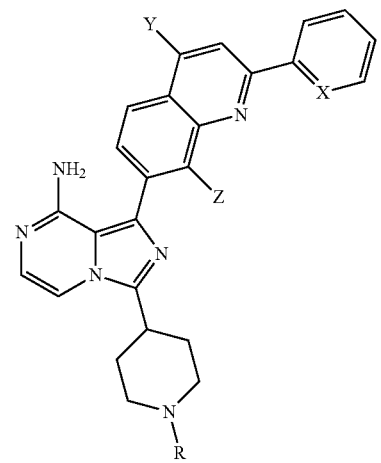

or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | iPr |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |

| X | Y | Z | R |
|---|---|---|---|
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NEt₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et; |

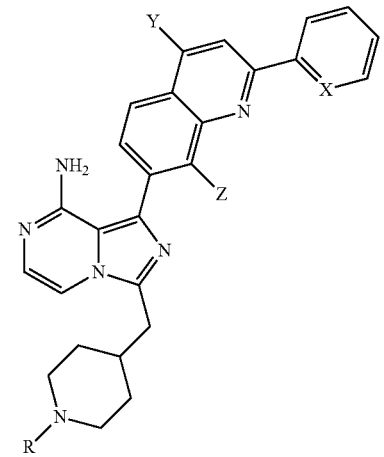

or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | iPr |
| CH | CH₃ | H | Ac |
| CH | H | F | Ac |
| CH | CH₃ | F | Ac |
| N | H | H | Ac |
| N | CH₃ | H | Ac |
| N | H | F | Ac |

139
-continued

| X | Y | Z | R |
|---|---|---|---|
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OEt) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NEt₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |

140
-continued

| X | Y | Z | R |
|---|---|---|---|
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | CH₂CH₂OCH₃ |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et; |

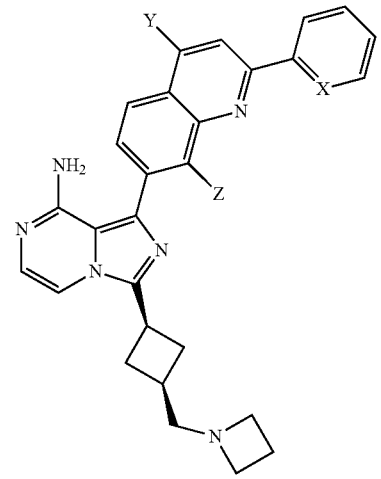

or wherein

| X | Y | Z |
|---|---|---|
| CH | Et | H |
| CH | CH₃ | H |
| CH | H | F |
| CH | CH₃ | F |

141
-continued
| X | Y | Z |
|---|---|---|
| N | H | H |
| N | CH₃ | H |
| N | H | F |
| N | CH₃ | F |
| CF | H | H |
| CF | CH₃ | H |
| CF | H | F |
| CF | CH₃ | F; |
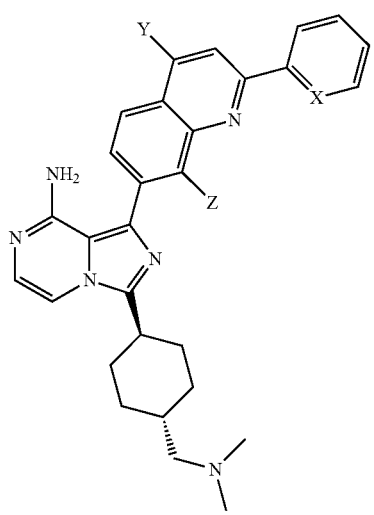
or wherein
| X | Y | Z |
|---|---|---|
| CH | Et | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
142
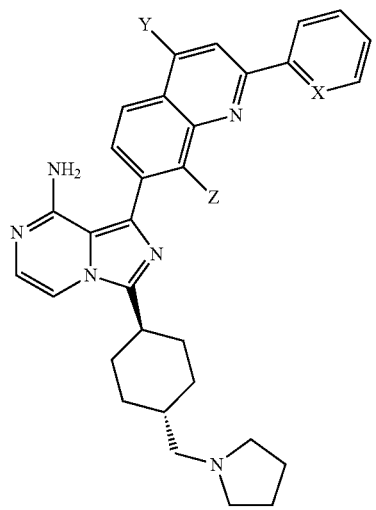
or wherein
| X | Y | Z |
|---|---|---|
| CH | Et | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
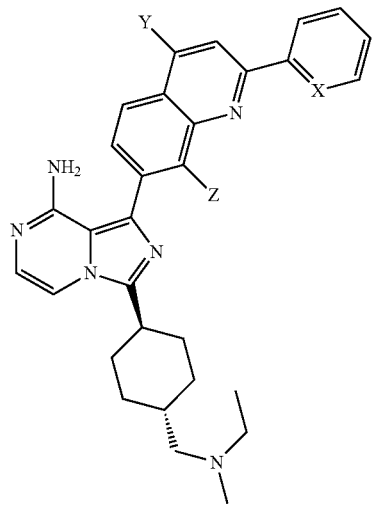
or wherein
| X | Y | Z |
|---|---|---|
| CH | Et | H |
| CH | H | F |

143
-continued
| X | Y | Z |
|---|---|---|
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
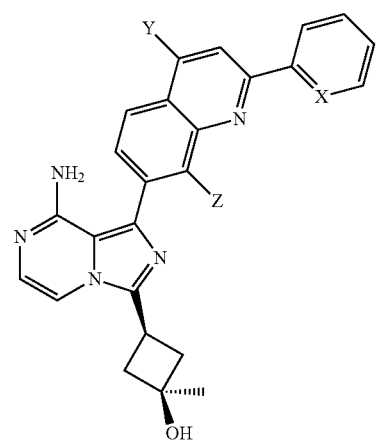
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
144
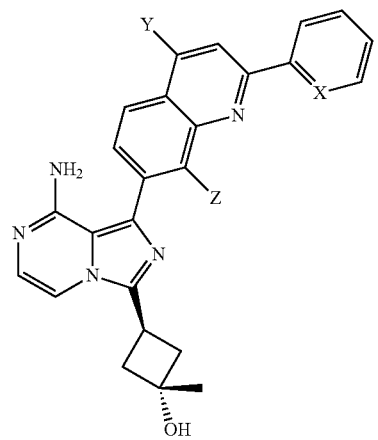
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
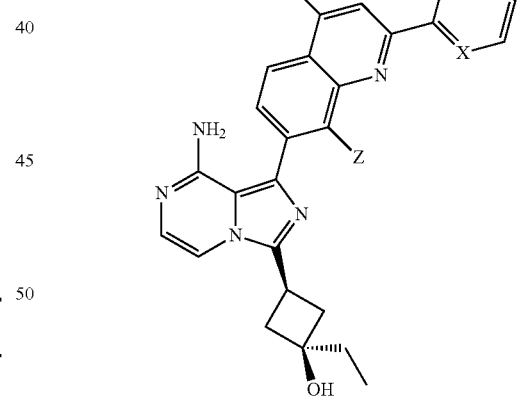
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |

-continued
| X | Y | Z |
|---|---|---|
| N | CH₃ | F |
| CF | H | H |
| CF | CH₃ | H |
| CF | H | F |
| CF | CH₃ | F; |
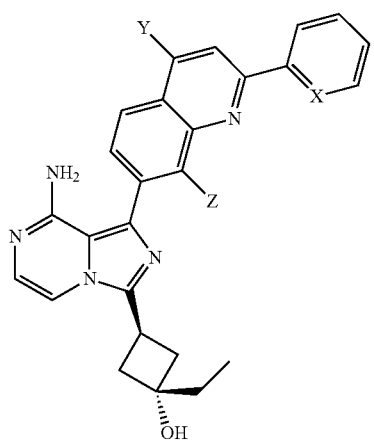
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
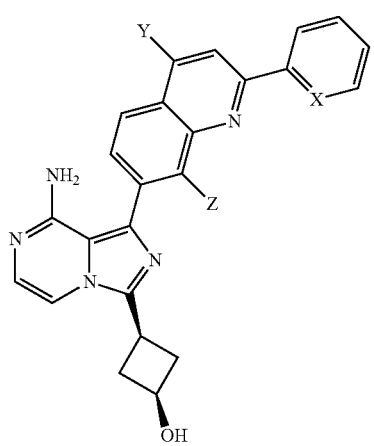
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |
or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F; |

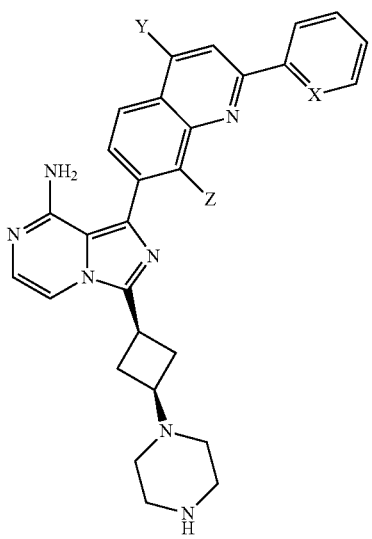

or wherein

| X | Y | Z |
|---|---|---|
| CH | Et | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
| CF | CH$_3$ | H |
| CF | H | F |
| CF | CH$_3$ | F; | or a pharmaceutically acceptable salt thereof.

The present invention includes a method of inhibiting protein kinase activity according to the present invention comprises administering a compound of Formula I, or a pharmaceutically acceptable salt thereof. The method includes wherein the protein kinase is IGF-IR. The method includes wherein the activity of the protein kinase affects hyperproliferative disorders. The method includes wherein the activity of the protein kinase influences angiogenesis, vascular permeability, immune response, cellular apoptosis, tumor growth, or inflammation.

A method of the present invention of treating a patient having a condition which is mediated by protein kinase activity, comprises administering to the patient a therapeutically effective amount of a compound of Formula I, or a pharmaceutically acceptable salt thereof. The method includes wherein the protein kinase is IGF-IR. The method includes wherein the condition mediated by protein kinase activity is a hyperproliferative disorder. The method includes wherein the activity of the protein kinase influences angiogenesis, vascular permeability, immune response, cellular apoptosis, tumor growth, or inflammation. The method includes wherein the protein kinase is a protein serine/threonine kinase or a protein tyrosine kinase. The method includes wherein the condition mediated by protein kinase activity is one or more ulcers. The method includes wherein the ulcer or ulcers are caused by a bacterial or fungal infection; or the ulcer or ulcers are Mooren ulcers; or the ulcer or ulcers are a symptom of ulcerative colitis. The method includes wherein the condition mediated by protein kinase activity is Lyme disease, sepsis or infection by Herpes simplex, Herpes Zoster, human immunodeficiency virus, parapoxvirus, protozoa, or toxoplasmosis. The method includes wherein the condition mediated by protein kinase activity is von Hippel Lindau disease, pemphigoid, psoriasis, Paget's disease, or polycystic kidney disease. The method includes wherein the condition mediated by protein kinase activity is fibrosis, sarcoidosis, cirrhosis, thyroiditis, hyperviscosity syndrome, Osler-Weber-Rendu disease, chronic occlusive pulmonary disease, asthma, exudtaes, ascites, pleural effusions, pulmonary edema, cerebral edema or edema following burns, trauma, radiation, stroke, hypoxia, or ischemia. The method includes wherein the condition mediated by protein kinase activity is ovarian hyperstimulation syndrome, preeclampsia, menometrorrhagia, or endometriosis. The method includes wherein the condition mediated by protein kinase-activity is chronic inflammation, systemic lupus, glomerulonephritis, synovitis, inflammatory bowel disease, Crohn's disease, glomerulonephritis, rheumatoid arthritis and osteoarthritis, multiple sclerosis, or graft rejection. The method includes wherein the condition mediated by protein kinase activity is sickle cell anaemia. The method includes wherein the condition mediated by protein kinase activity is an ocular condition. The method includes wherein the ocular condition is ocular or macular edema, ocular neovascular disease, seleritis, radial keratotomy, uveitis, vitritis, myopia, optic pits, chronic retinal detachment, post-laser treatment complications, conjunctivitis, Stargardt's disease, Eales disease, retinopathy, or macular degeneration. The method includes wherein the condition mediated by protein kinase activity is a cardiovascular condition. The method includes wherein the condition mediated by protein kinase activity is atherosclerosis, restenosis, ischemia/reperfusion injury, vascular occlusion, venous malformation, or carotid obstructive disease. The method includes wherein the condition mediated by protein kinase activity is cancer. The method includes wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites. The method includes wherein the cancer is Kaposi's sarcoma, Hodgkin's disease, lymphoma, myeloma, or leukemia. Further, the method includes wherein the condition mediated by protein kinase activity is Crow-Fukase (POEMS) syndrome or a diabetic condition. The method includes wherein the diabetic condition is insulin-dependent diabetes mellitus glaucoma, diabetic retinopathy, or microangiopathy. The method also includes wherein the protein kinase activity is involved in T cell activation, B cell activation, mast cell degranulation, monocyte activation, signal transduction, apoptosis, the potentiation of an inflammatory response or a combination thereof.

The present invention includes the use of a compound of Formula I, or a pharmaceutically acceptable salt thereof, for the preparation of a pharmaceutical composition for the treatment of a disease which responds to an inhibition of the IGF-IR-dependent cell proliferation.

The present invention includes the use of a compound of Formula I, or a pharmaceutically acceptable salt thereof, for the preparation of a pharmaceutical composition for the treatment of a disease which responds to an inhibition of the IGF-IR tyrosine kinase.

The present invention includes a pharmaceutical composition comprising a therapeutically effective amount of a compound of Formula I, or a pharmaceutically acceptable salt thereof, and a pharmaceutically acceptable carrier. The invention includes a method of inhibiting protein kinase activity that comprises administering such pharmaceutical composition. The invention includes a method of treating a patient having a condition which is mediated by protein kinase activity by administering to the patient a therapeutically effective amount of such pharmaceutical composition.

The following include core structures of the present invention wherein at least one of $X_3$-$X_7$ is optionally substituted N and the core structure can have $Q^1$ and $R^1$ substituents as defined above (the substituent is hydrogen where hydrogen is specified):

| Structure | Name of unsubstituted core with NH$_2$ group |
|---|---|
| | 1H-Pyrrolo[3,2-c]pyridin-4-ylamine |
| | 1H-Pyrrolo[2,3-c]pyridin-7-ylamine |
| | 2H-Pyrrolo[3,4-c]pyridin-4-ylamine |
| | Pyrrolo[1,2-a]pyrazin-1-ylamine |
| | Pyrrolo[1,2-c]pyrimidin-1-ylamine |
| | 7H-Pyrrolo[2,3-d]pyrimidin-4-ylamine |
| | 5H-Pyrrolo[3,2-d]pyrimidin-4-ylamine |
| | 6H-Pyrrolo[3,4-d]pyrimidin-4-ylamine |
| | Pyrrolo[2,1-f][1,2,4]triazin-4-ylamine |
| | Pyrrolo[1,2-a][1,3,5]triazin-4-ylamine |
| | 1H-Pyrrolo[2,3-d]pyridazin-4-ylamine |
| | 1H-Pyrrolo[2,3-d]pyridazin-7-ylamine |
| | 1-Methyl-6H-pyrrolo[3,4-d]pyridazine |
| | Pyrrolo[1,2-d][1,2,4]triazin-1-ylamine |
| | Pyrrolo[1,2-d][1,2,4]triazin-4-ylamine |
| | 1H-Pyrazolo[4,3-c]pyridin-4-ylamine |

| Structure | Name of unsubstituted core with NH₂ group |
| --- | --- |
| | 1H-Pyrazolo[3,4-c]pyridin-7-ylamine |
| | 1H-Pyrazolo[4,3-d]pyrimidin-7-ylamine |
| | 1H-Pyrazolo[3,4-d]pyrimidin-4-ylamine |
| | 1H-Pyrazolo[3,4-d]pyridazin-7-ylamine |
| | 1H-Pyrazolo[3,4-d]pyridazin-4-ylamine |
| | Imidazo[1,5-c]pyrimidin-5-ylamine |
| | Imidazo[1,5-d][1,2,4]triazin-4-ylamine |
| | Imidazo[1,5-a][1,3,5]triazin-4-ylamine |
| | Imidazo[1,5-a]pyrazin-8-ylamine |
| | Imidazo[1,5-d][1,2,4]triazin-1-ylamine |
| | Imidazo[5,1-f][1,2,4]triazin-4-ylamine |

The following include core structures of the present invention wherein $R^1$ is absent, at least one of $X_3$-$X_7$ is optionally substituted N and the core structure can have $Q^1$ substituent as defined above (the substituent is hydrogen where hydrogen is specified):

| Structure | Name of unsubstituted core with NH₂ group |
| --- | --- |
| | Pyrazolo[1,5-a]pyrazin-4-ylamine |
| | Pyrazolo[1,5-d][1,2,4]triazin-4-ylamine |
| | 1,5,7,7a-Tetraaza-inden-4-ylamine |
| | 3H-Imidazo[4,5-c]pyridin-4-ylamine |
| | 3H-Imidazo[4,5-d]pyridazin-4-ylamine |
| | 7H-Purin-6-ylamine |

| Structure | Name of unsubstituted core with NH₂ group |
|---|---|
| 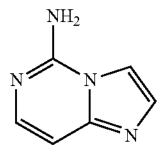 | Imidazo[1,2-c]-pyrimidin-5-ylamine |
| 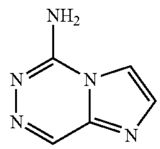 | Imidazo[1,2-d]-[1,2,4]triazin-5-ylamine |
| 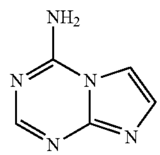 | Imidazo[1,2-a]-[1,3,5]triazin-4-ylamine |
| 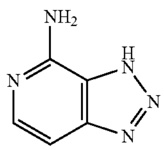 | 3H-[1,2,3]-Triazolo[4,5-c]-pyridin-4-ylamine |
| 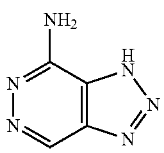 | 3H-[1,2,3]-Triazolo[4,5-d]-pyridazin-4-ylamine |
| 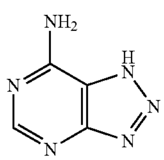 | 1H-[1,2,3]-Triazolo[4,5-d]-pyrimidin-7-ylamine |
| 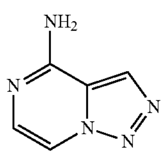 | [1,2,3]Triazolo[1,5-a]pyrazin-4-ylamine |
| 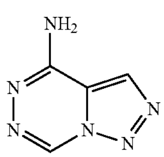 | 1,2,5,6,7a-Pentaazainden-4-ylamine |
| 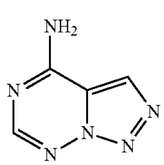 | 1,2,5,7,7a-Pentaazainden-4-ylamine |

The compounds of the present invention include:
3-Cyclobutyl-1-(2-pyridin-2-ylquinolin-7-yl)-imidazo[1,5-a]pyrazin-8-ylamine;
3-Cyclobutyl-1-(2-thiophen-2-ylquinolin-7-yl)-imidazo[1,5-a]pyrazin-8-ylamine;
3-Cyclobutyl-1-(2-phenoxyquinolin-7-yl)-imidazo[1,5-a]pyrazin-8-ylamine;
[7-(8-Amino-3-cyclobutylimidazo[1,5-a]pyrazin-1-yl)-quinolin-2-yl]-phenylamine;
1-(6-Chloro-2-phenylquinolin-7-yl)-3-cyclobutylimidazo[1,5-a]pyrazin-8-ylamine;
1-(6-Chloro-2-pyridin-2-ylquinolin-7-yl)-3-cyclobutylimidazo[1,5-a]pyrazin-8-ylamine;
1-(6-Chloro-2-thiophen-2-ylquinolin-7-yl)-3-cyclobutyl-imidazo[1,5-a]pyrazin-8-ylamine;
1-(6-Chloro-2-phenoxyquinolin-7-yl)-3-cyclobutylimidazo[1,5-a]pyrazin-8-ylamine;
[7-(8-Amino-3-cyclobutyl imidazo[1,5-a]pyrazin-1-yl)-6-chloroquinolin-2-yl]-phenyl-amine;
3-Cyclobutyl-1-(8-fluoro-2-phenylquinolin-7-yl)-imidazo[1,5-a]pyrazin-8-ylamine;
3-Cyclobutyl-1-(8-fluoro-2-pyridin-2-ylquinolin-7-yl)-imidazo[1,5-a]pyrazin-8-ylamine;
3-Cyclobutyl-1-(8-fluoro-2-thiophen-2-ylquinolin-7-yl)-imidazo[1,5-a]pyrazin-8-ylamine;
3-Cyclobutyl-1-(8-fluoro-2-phenoxyquinolin-7-yl)-imidazo[1,5-a]pyrazin-8-ylamine;
[7-(8-Amino-3-cyclobutylimidazo[1,5-a]pyrazin-1-yl)-8-fluoroquinolin-2-yl]-phenyl-amine;
3-Cyclobutyl-1-(4-methyl-2-phenylquinolin-7-yl)-imidazo[1,5-a]pyrazin-8-ylamine;
3-Cyclobutyl-1-(4-methyl-2-pyridin-2-ylquinolin-7-yl)-imidazo[1,5-a]pyrazin-8-ylamine;
3-Cyclobutyl-1-(4-methyl-2-thiophen-2-ylquinolin-7-yl)-imidazo[1,5-a]pyrazin-8-ylamine;
[7-(8-Amino-3-cyclobutylimidazo[1,5-a]pyrazin-1-yl)-4-methylquinolin-2-yl]-phenyl amine;
3'-Cyclobutyl-1-(4-methyl-2-phenoxyquinolin-7-yl)-imidazo[1,5-a]pyrazin-8-ylamine;
[7-(8-Amino-3-cyclobutylimidazo[1,5-a]pyrazin-1-yl)-2-phenylquinolin-4-yl]-methyl amine;
[7-(8-Amino-3-cyclobutylimidazo[1,5-a]pyrazin-1-yl)-2-pyridin-2-ylquinolin-4-yl]-methylamine;
[7-(8-Amino-3-cyclobutylimidazo[1,5-a]pyrazin-1-yl)-2-thiophen-2-ylquinolin-4-yl]-methylamine;
[7-(8-Amino-3-cyclobutylimidazo[1,5-a]pyrazin-1-yl)-2-phenoxyquinolin-4-yl]-methylamine;
7-(8-Amino-3-cyclobutylimidazo[1,5-a]pyrazin-1-yl)-$N^4$-methyl-$N^2$-phenylquinoline-2,4-diamine;
3-[8-Amino-1-(2-phenylquinolin-7-yl)-imidazo[1,5-a]pyrazin-3-yl]-cyclobutanol;
3-[8-Amino-1-(2-pyridin-2-ylquinolin-7-yl)-imidazo[1,5-a]pyrazin-3-yl]-cyclobutanol;
3-[8-Amino-1-(2-thiophen-2-ylquinolin-7-yl)-imidazo[1,5-a]pyrazin-3-yl]-cyclobutanol;
3-[8-Amino-1-(2-phenoxyquinolin-7-yl)-imidazo[1,5-a]pyrazin-3-yl]-cyclobutanol;
3-[8-Amino-1-(2-phenylaminoquinolin-7-yl)-imidazo[1,5-a]pyrazin-3-yl]-cyclobutanol;
3-[8-Amino-1-(6-chloro-2-phenylquinolin-7-yl)-imidazo[1,5-a]pyrazin-3-yl]-cyclobutanol;
3-[8-Amino-1-(6-chloro-2-pyridin-2-ylquinolin-7-yl)-imidazo[1,5-a]pyrazin-3-yl]-cyclobutanol;
3-[8-Amino-1-(6-chloro-2-thiophen-2-ylquinolin-7-yl)-imidazo[1,5-a]pyrazin-3-yl]-cyclobutanol;
3-[8-Amino-1-(6-chloro-2-phenylaminoquinolin-7-yl)-imidazo[1,5-a]pyrazin-3-yl]-cyclobutanol;
3-[8-Amino-1-(6-chloro-2-phenoxyquinolin-7-yl)-imidazo[1,5-a]pyrazin-3-yl]-cyclobutanol;

3-[8-Amino-1-(8-fluoro-2-pyridin-2-ylquinolin-7-yl)-imidazo[1,5-a]pyrazin-3-yl]-cyclobutanol;
3-[8-Amino-1-(8-fluoro-2-thiophen-2-ylquinolin-7-yl)-imidazo[1,5-a]pyrazin-3-yl]-cyclobutanol;
3-[8-Amino-1-(8-fluoro-2-phenoxyquinolin-7-yl)-imidazo[1,5-a]pyrazin-3-yl]-cyclobutanol;
3-[8-Amino-1-(8-fluoro-2-phenylaminoquinolin-7-yl)-imidazo[1,5-a]pyrazin-3-yl]-cyclobutanol;
3-[8-Amino-1-(8-fluoro-2-phenylquinolin-7-yl)-imidazo[1,5-a]pyrazin-3-yl]-cyclobutanol;
3-[8-Amino-1-(8-fluoro-4-methyl-2-phenylquinolin-7-yl)-imidazo[1,5-a]pyrazin-3-yl]-cyclobutanol;
3-[8-Amino-1-(8-fluoro-4-methyl-2-thiophen-2-yl-quinolin-7-yl)-imidazo[1,5-a]pyrazin-3-yl]-cyclobutanol;
3-[8-Amino-1-(8-fluoro-4-methyl-2-pyridin-2-ylquinolin-7-yl)-imidazo[1,5-a]pyrazin-3-yl]-cyclobutanol;
3-[8-Amino-1-(8-fluoro-4-methyl-2-phenylaminoquinolin-7-yl)-imidazo[1,5-a]pyrazin-3-yl]-cyclobutanol;
3-[8-Amino-1-(8-fluoro-4-methyl-2-phenoxyquinolin-7-yl)-imidazo[1,5-a]pyrazin-3-yl]-cyclobutanol;
3-(3-Azetidin-1-ylmethylcyclobutyl)-1-(2-pyridin-2-ylquinolin-7-yl)-imidazo[1,5-a]pyrazin-8-ylamine;
3-(3-Azetidin-1-ylmethylcyclobutyl)-1-(2-thiophen-2-ylquinolin-7-yl)-imidazo[1,5-a]pyrazin-8-ylamine;
3-(3-Azetidin-1-ylmethylcyclobutyl)-1-(2-phenoxyquinolin-7-yl)-imidazo[1,5-a]pyrazin-8-ylamine;
{7-[8-Amino-3-(3-azetidin-1-ylmethylcyclobutyl)-imidazo[1,5-a]pyrazin-1-yl]-quinolin-2-yl}-phenylamine;
3-(3-Azetidin-1-ylmethylcyclobutyl)-1-(6-chloro-2-phenylquinolin-7-yl)-imidazo[1,5-a]pyrazin-8-ylamine;
3-(3-Azetidin-1-ylmethylcyclobutyl)-1-(6-chloro-2-pyridin-2-yl-quinolin-7-yl)-imidazo[1,5-a]pyrazin-8-ylamine;
3-(3-Azetidin-1-ylmethylcyclobutyl)-1-(6-chloro-2-thiophen-2-yl-quinolin-7-yl)-imidazo[1,5-a]pyrazin-8-ylamine;
{7-[8-Amino-3-(3-azetidin-1-ylmethylcyclobutyl)-imidazo[1,5-a]pyrazin-1-yl]-6-chloro-quinolin-2-yl}-phenylamine;
3-(3-Azetidin-1-ylmethylcyclobutyl)-1-(6-chloro-2-phenoxyquinolin-7-yl)-imidazo[1,5-a]pyrazin-8-ylamine;
3-(3-Azetidin-1-ylmethylcyclobutyl)-1-(4-methyl-2-phenylquinolin-7-yl)-imidazo[1,5-a]pyrazin-8-ylamine;
3-(3-Azetidin-1-ylmethylcyclobutyl)-1-(4-methyl-2-pyridin-2-ylquinolin-7-yl)-imidazo[1,5-a]pyrazin-8-ylamine;
3-(3-Azetidin-1-ylmethylcyclobutyl)-1-(4-methyl-2-thiophen-2-ylquinolin-7-yl)-imidazo[1,5-a]pyrazin-8-ylamine;
3-(3-Azetidin-1-ylmethylcyclobutyl)-1-(4-methyl-2-phenoxyquinolin-7-yl)-imidazo[1,5-a]pyrazin-8-ylamine;
{7-[8-Amino-3-(3-azetidin-1-ylmethylcyclobutyl)-imidazo[1,5-a]pyrazin-1-yl]-4-methyl-quinolin-2-yl}-phenylamine;
3-(3-Dimethylaminomethylcyclobutyl)-1-(2-phenylquinolin-7-yl)-imidazo[1,5-a]pyrazin-8-ylamine;
3-(3-Dimethylaminomethylcyclobutyl)-1-(2-pyridin-2-ylquinolin-7-yl)-imidazo[1,5-a]pyrazin-8-ylamine;
3-(3-Dimethylaminomethylcyclobutyl)-1-(2-thiophen-2-ylquinolin-7-yl)-imidazo[1,5-a]pyrazin-8-ylamine;
{7-[8-Amino-3-(3-dimethylaminomethylcyclobutyl)-imidazo[1,5-a]pyrazin-1-yl-]quinolin-2-yl}-phenylamine;
3-(3-Dimethylaminomethylcyclobutyl)-1-(2-phenoxyquinolin-7-yl)-imidazo[1,5-a]pyrazin-8-ylamine;
1-(6-Chloro-2-phenylquinolin-7-yl)-3-(3-dimethylaminomethylcyclobutyl)-imidazo[1,5-a]pyrazin-8-ylamine;
1-(6-Chloro-2-pyridin-2-ylquinolin-7-yl)-3-(3-dimethylaminomethylcyclobutyl)-imidazo[1,5-a]pyrazin-8-ylamine;
1-(6-Chloro-2-thiophen-2-ylquinolin-7-yl)-3-(3-dimethylaminomethylcyclobutyl)-imidazo[1,5-a]pyrazin-8-ylamine;
1-(6-Chloro-2-phenoxyquinolin-7-yl)-3-(3-dimethylaminomethylcyclobutyl)-imidazo[1,5-a]pyrazin-8-ylamine;
{7-[8-Amino-3-(3-dimethylaminomethylcyclobutyl)-imidazo[1,5-a]pyrazin-1-yl]-6-chloroquinolin-2-yl}-phenylamine;
3-(3-Dimethylaminomethylcyclobutyl)-1-(4-methyl-2-phenylquinolin-7-yl)-imidazo[1,5-a]pyrazin-8-ylamine;
3-(3-Dimethylaminomethylcyclobutyl)-1-(4-methyl-2-pyridin-2-ylquinolin-7-yl)-imidazo[1,5-a]pyrazin-8-ylamine;
3-(3-Dimethylaminomethylcyclobutyl)-1-(4-methyl-2-thiophen-2-ylquinolin-7-yl)-imidazo[1,5-a]pyrazin-8-ylamine;
{7-[8-Amino-3-(3-dimethylaminomethylcyclobutyl)-imidazo[1,5-a]pyrazin-1-yl]-4-methylquinolin-2-yl}-phenylamine;
3-(3-Dimethylaminomethylcyclobutyl)-1-(4-methyl-2-phenoxyquinolin-7-yl)-imidazo[1,5-a]pyrazin-8-ylamine;
4-[8-Amino-1-(2-pyridin-2-ylquinolin-7-yl)-imidazo[1,5-a]pyrazin-3-yl]-cyclohexanecarboxylic acid amide;
4-[8-Amino-1-(2-thiophen-2-ylquinolin-7-yl)-imidazo[1,5-a]pyrazin-3-yl]-cyclohexanecarboxylic acid amide;
4-[8-Amino-1-(2-phenoxyquinolin-7-yl)-imidazo[1,5-a]pyrazin-3-yl]-cyclohexanecarboxylic acid amide;
4-[8-Amino-1-(2-phenylaminoquinolin-7-yl)-imidazo[1,5-a]pyrazin-3-yl]-cyclohexanecarboxylic acid amide;
4-[8-Amino-1-(6-chloro-2-phenylquinolin-7-yl)-imidazo[1,5-a]pyrazin-3-yl]-cyclohexanecarboxylic acid amide;
4-[8-Amino-1-(6-chloro-2-pyridin-2-ylquinolin-7-yl)-imidazo[1,5-a]pyrazin-3-yl]-cyclohexanecarboxylic acid amide;
4-[8-Amino-1-(6-chloro-2-thiophen-2-ylquinolin-7-yl)-imidazo[1,5-a]pyrazin-3-yl]-cyclohexanecarboxylic acid amide;
4-[8-Amino-1-(6-chloro-2-phenylaminoquinolin-7-yl)-imidazo[1,5-a]pyrazin-3-yl]-cyclohexanecarboxylic acid amide;
4-[8-Amino-1-(6-chloro-2-phenoxyquinolin-7-yl)-imidazo[1,5-a]pyrazin-3-yl]-cyclohexanecarboxylic acid amide;
4-[8-Amino-1-(4-methyl-2-phenylquinolin-7-yl)-imidazo[1,5-a]pyrazin-3-yl]-cyclohexanecarboxylic acid amide;
4-[8-Amino-1-(4-methyl-2-pyridin-2-ylquinolin-7-yl)-imidazo[1,5-a]pyrazin-3-yl]-cyclohexanecarboxylic acid amide;
4-[8-Amino-1-(4-methyl-2-thiophen-2-ylquinolin-7-yl)-imidazo[1,5-a]pyrazin-3-yl]-cyclohexanecarboxylic acid amide;
4-[8-Amino-1-(4-methyl-2-phenoxyquinolin-7-yl)-imidazo[1,5-a]pyrazin-3-yl]-cyclohexanecarboxylic acid amide;
4-[8-Amino-1-(4-methyl-2-phenylaminoquinolin-7-yl)-imidazo[1,5-a]pyrazin-3-yl]-cyclohexanecarboxylic acid amide;
4-[8-Amino-1-(2-pyridin-2-ylquinolin-7-yl)-imidazo[1,5-a]pyrazin-3-yl]-cyclohexanecarboxylic acid methylamide;
4-[8-Amino-1-(2-thiophen-2-ylquinolin-7-yl)-imidazo[1,5-a]pyrazin-3-yl]-cyclohexanecarboxylic acid methylamide;
4-[8-Amino-1-(2-phenylaminoquinolin-7-yl)-imidazo[1,5-a]pyrazin-3-yl]-cyclohexanecarboxylic acid methylamide;
4-[8-Amino-1-(2-phenoxyquinolin-7-yl)-imidazo[1,5-a]pyrazin-3-yl]-cyclohexanecarboxylic acid methylamide;
3-(4-Aminomethylcyclohexyl)-1-(2-pyridin-2-ylquinolin-7-yl)-imidazo[1,5-a]pyrazin-8-ylamine;

3-(4-Aminomethylcyclohexyl)-1-(2-thiophen-2-ylquinolin-7-yl)-imidazo[1,5-a]pyrazin-8-ylamine;
3-(4-Aminomethylcyclohexyl)-1-(2-phenoxyquinolin-7-yl)-imidazo[1,5-a]pyrazin-8-ylamine;
{7-[8-Amino-3-(4-aminomethylcyclohexyl)-imidazo[1,5-a]pyrazin-1-yl]-quinolin-2-yl}-phenylamine;
7-Cyclobutyl-5-(2-phenylquinolin-7-yl)-7H-pyrrolo[2,3-d]pyrimidin-4-ylamine;
7-Cyclobutyl-5-(2-pyridin-2-ylquinolin-7-yl)-7H-pyrrolo[2,3-d]pyrimidin-4-ylamine;
7-Cyclobutyl-5-(2-thiophen-2-ylquinolin-7-yl)-7H-pyrrolo[2,3-d]pyrimidin-4-ylamine;
[7-(4-Amino-7-cyclobutyl-7H-pyrrolo[2,3-d]pyrimidin-5-yl)-quinolin-2-yl]-phenylamine;
7-Cyclobutyl-5-(2-phenoxyquinolin-7-yl)-7H-pyrrolo[2,3-d]pyrimidin-4-ylamine;
5-(6-Chloro-2-phenylquinolin-7-yl)-7-cyclobutyl-7H-pyrrolo[2,3-d]pyrimidin-4-ylamine;
5-(6-Chloro-2-pyridin-2-ylquinolin-7-yl)-7-cyclobutyl-7H-pyrrolo[2,3-d]pyrimidin-4-ylamine;
5-(6-Chloro-2-thiophen-2-ylquinolin-7-yl)-7-cyclobutyl-7H-pyrrolo[2,3-d]pyrimidin-4-ylamine;
5-(6-Chloro-2-phenoxyquinolin-7-yl)-7-cyclobutyl-7H-pyrrolo[2,3-d]pyrimidin-4-ylamine;
[7-(4-Amino-7-cyclobutyl-7H-pyrrolo[2,3-d]pyrimidin-5-yl)-6-chloroquinolin-2-yl]-phenylamine;
3-[4-Amino-5-(2-phenylquinolin-7-yl)-pyrrolo[2,3-d]pyrimidin-7-yl]-cyclobutanol;
3-[4-Amino-5-(2-thiophen-2-ylquinolin-7-yl)-pyrrolo[2,3-d]pyrimidin-7-yl]-cyclobutanol;
3-[4-Amino-5-(2-pyridin-2-ylquinolin-7-yl)-pyrrolo[2,3-d]pyrimidin-7-yl]-cyclobutanol;
3-[4-Amino-5-(2-phenylaminoquinolin-7-yl)-pyrrolo[2,3-d]pyrimidin-7-yl]-cyclobutanol;
3-[4-Amino-5-(2-phenoxyquinolin-7-yl)-pyrrolo[2,3-d]pyrimidin-7-yl]-cyclobutanol;
3-[4-Amino-5-(6-chloro-2-pyridin-2-ylquinolin-7-yl)-pyrrolo[2,3-d]pyrimidin-7-yl]-cyclobutanol;
3-[4-Amino-5-(6-chloro-2-phenylquinolin-7-yl)-pyrrolo[2,3-d]pyrimidin-7-yl]-cyclobutanol;
3-[4-Amino-5-(6-chloro-2-thiophen-2-ylquinolin-7-yl)-pyrrolo[2,3-d]pyrimidin-7-yl]-cyclobutanol;
3-[4-Amino-5-(6-chloro-2-phenoxyquinolin-7-yl)-pyrrolo[2,3-d]pyrimidin-7-yl]-cyclobutanol;
3-[4-Amino-5-(6-chloro-2-phenylaminoquinolin-7-yl)-pyrrolo[2,3-d]pyrimidin-7-yl]-cyclobutanol;
3-[4-Amino-5-(8-fluoro-2-phenylquinolin-7-yl)-pyrrolo[2,3-d]pyrimidin-7-yl]-cyclobutanol;
3-[4-Amino-5-(8-fluoro-2-thiophen-2-ylquinolin-7-yl)-pyrrolo[2,3-d]pyrimidin-7-yl]-cyclobutanol;
3-[4-Amino-5-(8-fluoro-2-pyridin-2-ylquinolin-7-yl)-pyrrolo[2,3-d]pyrimidin-7-yl]-cyclobutanol;
3-[4-Amino-5-(8-fluoro-2-phenylaminoquinolin-7-yl)-pyrrolo[2,3-d]pyrimidin-7-yl]-cyclobutanol;
3-[4-Amino-5-(8-fluoro-2-phenoxyquinolin-7-yl)-pyrrolo[2,3-d]pyrimidin-7-yl]-cyclobutanol;
7-Cyclobutyl-5-(8-fluoro-2-phenylquinolin-7-yl)-7H-pyrrolo[2,3-d]pyrimidin-4-ylamine;
7-Cyclobutyl-5-(8-fluoro-2-pyridin-2-ylquinolin-7-yl)-7H-pyrrolo[2,3-d]pyrimidin-4-ylamine;
7-Cyclobutyl-5-(8-fluoro-2-thiophen-2-yl-quinolin-7-yl)-7H-pyrrolo[2,3-d]pyrimidin-4-ylamine;
7-Cyclobutyl-5-(8-fluoro-2-phenoxyquinolin-7-yl)-7H-pyrrolo[2,3-d]pyrimidin-4-ylamine;
[7-(4-Amino-7-cyclobutyl-7H-pyrrolo[2,3-d]pyrimidin-5-yl)-8-fluoroquinolin-2-yl]-phenylamine;
7-(3-Azetidin-1-ylmethylcyclobutyl)-5-(2-phenylquinolin-7-yl)-7H-pyrrolo[2,3-d]pyrimidin-4-ylamine;
7-(3-Azetidin-1-ylmethylcyclobutyl)-5-(2-pyridin-2-ylquinolin-7-yl)-7H-pyrrolo[2,3-d]pyrimidin-4-ylamine;
7-(3-Azetidin-1-ylmethylcyclobutyl)-5-(2-thiophen-2-yl-quinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-quinolin-2-yl}-phenylamine;
7-(3-Azetidin-1-ylmethylcyclobutyl)-5-(2-phenoxyquinolin-7-yl)-7H-pyrrolo[2,3-d]pyrimidin-4-ylamine;
7-(3-Azetidin-1-ylmethylcyclobutyl)-5-(6-chloro-2-pyridin-2-ylquinolin-7-yl)-7H-pyrrolo[2,3-d]pyrimidin-4-ylamine;
7-(3-Azetidin-1-ylmethylcyclobutyl)-5-(6-chloro-2-phenylquinolin-7-yl)-7H-pyrrolo[2,3-d]pyrimidin-4-ylamine;
7-(3-Azetidin-1-ylmethylcyclobutyl)-5-(6-chloro-2-thiophen-2-ylquinolin-7-yl)-7H-pyrrolo[2,3-d]pyrimidin-4-ylamine;
7-(3-Azetidin-1-ylmethylcyclobutyl)-5-(6-chloro-2-phenoxyquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-6-chloroquinolin-2-yl}-phenylamine;
7-(3-Azetidin-1-ylmethylcyclobutyl)-5-(8-fluoro-2-phenylquinolin-7-yl)-7H-pyrrolo[2,3-d]pyrimidin-4-ylamine;
7-(3-Azetidin-1-ylmethylcyclobutyl)-5-(8-fluoro-2-pyridin-2-ylquinolin-7-yl)-7H-pyrrolo[2,3-d]pyrimidin-4-ylamine;
7-(3-Azetidin-1-ylmethylcyclobutyl)-5-(8-fluoro-2-thiophen-2-ylquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-8-fluoroquinolin-2-yl}-phenyl-amine;
7-(3-Azetidin-1-ylmethylcyclobutyl)-5-(8-fluoro-2-phenoxyquinolin-7-yl)-7H-pyrrolo[2,3-d]pyrimidin-4-ylamine;
7-(3-Azetidin-1-ylmethylcyclobutyl)-5-(4-methyl-2-pyridin-2-ylquinolin-7-yl)-7H-pyrrolo[2,3-d]pyrimidin-4-ylamine;
7-(3-Azetidin-1-ylmethylcyclobutyl)-5-(4-methyl-2-phenylquinolin-7-yl)-7H-pyrrolo[2,3-d]pyrimidin-4-ylamine;
7-(3-Azetidin-1-ylmethylcyclobutyl)-5-(4-methyl-2-thiophen-2-ylquinolin-7-yl)-7H-pyrrolo[2,3-d]pyrimidin-4-ylamine;
7-(3-Azetidin-1-ylmethylcyclobutyl)-5-(4-methyl-2-phenoxyquinolin-7-yl)-7H-pyrrolo[2,3-d]pyrimidin-4-ylamine;
{7-[4-Amino-7-(3-azetidin-1-ylmethyl cyclobutyl)-7H-pyrrolo[2,3-d]pyrimidin-5-yl]-4-methylquinolin-2-yl}-phenylamine;
{7-[4-Amino-7-(3-azetidin-1-ylmethylcyclobutyl)-7H-pyrrolo[2,3-d]pyrimidin-5-yl]-2-phenylquinolin-4-yl}-methylamine;
{7-[4-Amino-7-(3-azetidin-1-ylmethyl cyclobutyl)-7H-pyrrolo[2,3-d]pyrimidin-5-yl]-2-pyridin-2-ylquinolin-4-yl}-methylamine;
{7-[4-Amino-7-(3-azetidin-1-ylmethylcyclobutyl)-7H-pyrrolo[2,3-d]pyrimidin-5-yl]-2-thiophen-2-ylquinolin-4-yl}-methylamine;
7-[4-Amino-7-(3-azetidin-1-ylmethylcyclobutyl)-7H-pyrrolo[2,3-d]pyrimidin-5-yl]-$N^4$-methyl-$N^2$-phenylquinoline-2,4-diamine;

{7-[4-Amino-7-(3-azetidin-1-ylmethylcyclobutyl)-7H-pyrrolo[2,3-d]pyrimidin-5-yl]-2-phenoxyquinolin-4-yl}-methylamine;
7-(3-Dimethylaminomethylcyclobutyl)-5-(2-phenylquinolin-7-yl)-7H-pyrrolo[2,3-d]pyrimidin-4-ylamine;
7-(3-Dimethylaminomethylcyclobutyl)-5-(2-pyridin-2-ylquinolin-7-yl)-7H-pyrrolo[2,3-d]pyrimidin-4-ylamine;
7-(3-Dimethylaminomethylcyclobutyl)-5-(2-thiophen-2-ylquinolin-7-yl)-7H-pyrrolo[2,3-d]pyrimidin-4-ylamine;
7-(3-Dimethylaminomethylcyclobutyl)-5-(2-phenoxyquinolin-7-yl)-7H-pyrrolo[2,3-d]pyrimidin-4-ylamine;
{7-[4-Amino-7-(3-dimethylaminomethylcyclobutyl)-7H-pyrrolo[2,3-d]pyrimidin-5-yl]-quinolin-2-yl}-phenylamine;
5-(6-Chloro-2-phenylquinolin-7-yl)-7-(3-dimethylaminomethylcyclobutyl)-7H-pyrrolo[2,3-d]pyrimidin-4-ylamine;
5-(6-Chloro-2-pyridin-2-ylquinolin-7-yl)-7-(3-dimethylaminomethylcyclobutyl)-7H-pyrrolo[2,3-d]pyrimidin-4-ylamine;
5-(6-Chloro-2-thiophen-2-ylquinolin-7-yl)-7-(3-dimethylaminomethylcyclobutyl)-7H-pyrrolo[2,3-d]pyrimidin-4-ylamine;
{7-[4-Amino-7-(3-dimethylaminomethylcyclobutyl)-7H-pyrrolo[2,3-d]pyrimidin-5-yl]-6-chloroquinolin-2-yl}-phenylamine;
5-(6-Chloro-2-phenoxyquinolin-7-yl)-7-(3-dimethylaminomethylcyclobutyl)-7H-pyrrolo[2,3-d]pyrimidin-4-ylamine;
7-(3-Dimethylaminomethylcyclobutyl)-5-(8-fluoro-2-pyridin-2-ylquinolin-7-yl)-7H-pyrrolo[2,3-d]pyrimidin-4-ylamine;
7-(3-Dimethylaminomethylcyclobutyl)-5-(8-fluoro-2-phenylquinolin-7-yl)-7H-pyrrolo[2,3-d]pyrimidin-4-ylamine;
7-(3-Dimethylaminomethylcyclobutyl)-5-(8-fluoro-2-thiophen-2-ylquinolin-7-yl)-7H-pyrrolo[2,3-d]pyrimidin-4-ylamine;
7-(3-Dimethylaminomethylcyclobutyl)-5-(8-fluoro-2-phenoxyquinolin-7-yl)-7H-pyrrolo[2,3-d]pyrimidin-4-ylamine;
7-(3-Dimethylaminomethylcyclobutyl)-5-(4-methyl-2-phenylquinolin-7-yl)-7H-pyrrolo[2,3-d]pyrimidin-4-ylamine;
7-(3-Dimethylaminomethylcyclobutyl)-5-(4-methyl-2-pyridin-2-ylquinolin-7-yl)-7H-pyrrolo[2,3-d]pyrimidin-4-ylamine;
7-(3-Dimethylaminomethylcyclobutyl)-5-(4-methyl-2-thiophen-2-ylquinolin-7-yl)-7H-pyrrolo[2,3-d]pyrimidin-4-ylamine;
7-(3-Dimethylaminomethylcyclobutyl)-5-(4-methyl-2-phenoxyquinolin-7-yl)-7H-pyrrolo[2,3-d]pyrimidin-4-ylamine;
4-[4-Amino-5-(2-phenylquinolin-7-yl)-pyrrolo[2,3-d]pyrimidin-7-yl]-cyclohexanecarboxylic acid amide;
4-[4-Amino-5-(2-pyridin-2-ylquinolin-7-yl)-pyrrolo[2,3-d]pyrimidin-7-yl]-cyclohexanecarboxylic acid amide;
4-[4-Amino-5-(2-thiophen-2-ylquinolin-7-yl)-pyrrolo[2,3-d]pyrimidin-7-yl]-cyclohexanecarboxylic acid amide;
4-[4-Amino-5-(2-phenoxyquinolin-7-yl)-pyrrolo[2,3-d]pyrimidin-7-yl]-cyclohexanecarboxylic acid amide;
4-[4-Amino-5-(2-phenylquinolin-7-yl)-pyrrolo[2,3-d]pyrimidin-7-yl]-cyclohexanecarboxylic acid methylamide;
4-[4-Amino-5-(2-thiophen-2-ylquinolin-7-yl)-pyrrolo[2,3-d]pyrimidin-7-yl]-cyclohexanecarboxylic acid methylamide;
4-[4-Amino-5-(2-phenoxyquinolin-7-yl)-pyrrolo[2,3-d]pyrimidin-7-yl]-cyclohexanecarboxylic acid methylamide;
4-[4-Amino-5-(2-pyridin-2-ylquinolin-7-yl)-pyrrolo[2,3-d]pyrimidin-7-yl]-cyclohexanecarboxylic acid methylamide;
4-[4-Amino-5-(6-chloro-2-pyridin-2-ylquinolin-7-yl)-pyrrolo[2,3-d]pyrimidin-7-yl]-cyclohexanecarboxylic acid methylamide;
4-[4-Amino-5-(6-chloro-2-phenylquinolin-7-yl)-pyrrolo[2,3-d]pyrimidin-7-yl]-cyclohexanecarboxylic acid methylamide;
4-[4-Amino-5-(6-chloro-2-thiophen-2-ylquinolin-7-yl)-pyrrolo[2,3-d]pyrimidin-7-yl]-cyclohexanecarboxylic acid methylamide;
4-[4-Amino-5-(6-chloro-2-phenoxyquinolin-7-yl)-pyrrolo[2,3-d]pyrimidin-7-yl]-cyclohexanecarboxylic acid methylamide;
4-[4-Amino-5-(6-chloro-2-pyridin-2-ylquinolin-7-yl)-pyrrolo[2,3-d]pyrimidin-7-yl]-cyclohexanecarboxylic acid amide;
4-[4-Amino-5-(6-chloro-2-phenylquinolin-7-yl)-pyrrolo[2,3-d]pyrimidin-7-yl]-cyclohexanecarboxylic acid amide;
4-[4-Amino-5-(6-chloro-2-thiophen-2-ylquinolin-7-yl)-pyrrolo[2,3-d]pyrimidin-7-yl]-cyclohexanecarboxylic acid amide;
4-[4-Amino-5-(6-chloro-2-phenoxyquinolin-7-yl)-pyrrolo[2,3-d]pyrimidin-7-yl]-cyclohexanecarboxylic acid amide;
7-(4-Aminomethylcyclohexyl)-5-(2-thiophen-2-ylquinolin-7-yl)-7H-pyrrolo[2,3-d]pyrimidin-4-ylamine;
7-(4-Aminomethylcyclohexyl)-5-(2-phenylquinolin-7-yl)-7H-pyrrolo[2,3-d]pyrimidin-4-ylamine;
7-(4-Aminomethylcyclohexyl)-5-(2-phenoxyquinolin-7-yl)-7H-pyrrolo[2,3-d]pyrimidin-4-ylamine;
7-(4-Aminomethylcyclohexyl)-5-(2-pyridin-2-ylquinolin-7-yl)-7H-pyrrolo[2,3-d]pyrimidin-4-ylamine;
7-(4-Aminomethylcyclohexyl)-5-(6-chloro-2-thiophen-2-ylquinolin-7-yl)-7H-pyrrolo[2,3-d]pyrimidin-4-ylamine;
7-(4-Aminomethylcyclohexyl)-5-(6-chloro-2-pyridin-2-ylquinolin-7-yl)-7H-pyrrolo[2,3-d]pyrimidin-4-ylamine;
7-(4-Aminomethylcyclohexyl)-5-(6-chloro-2-phenoxyquinolin-7-yl)-7H-pyrrolo[2,3-d]pyrimidin-4-ylamine;
7-(4-Aminomethylcyclohexyl)-5-(6-chloro-2-phenylquinolin-7-yl)-7H-pyrrolo[2,3-d]pyrimidin-4-ylamine;
7-(4-Aminomethylcyclohexyl)-5-(4-methyl-2-phenylquinolin-7-yl)-7H-pyrrolo[2,3-d]pyrimidin-4-ylamine;
7-(4-Aminomethylcyclohexyl)-5-(4-methyl-2-thiophen-2-ylquinolin-7-yl)-7H-pyrrolo[2,3-d]pyrimidin-4-ylamine;
7-(4-Aminomethylcyclohexyl)-5-(4-methyl-2-phenoxyquinolin-7-yl)-7H-pyrrolo[2,3-d]pyrimidin-4-ylamine;
7-(4-Aminomethylcyclohexyl)-5-(4-methyl-2-pyridin-2-ylquinolin-7-yl)-7H-pyrrolo[2,3-d]pyrimidin-4-ylamine;
1-(4-Aminomethylcyclohexyl)-3-(2-thiophen-2-ylquinolin-7-yl)-1H-pyrazolo[3,4-d]pyrimidin-4-ylamine;
1-(4-Aminomethylcyclohexyl)-3-(2-pyridin-2-yl-quinolin-7-yl)-1H-pyrazolo[3,4-d]pyrimidin-4-ylamine;
1-(4-Aminomethylcyclohexyl)-3-(2-phenoxyquinolin-7-yl)-1H-pyrazolo[3,4-d]pyrimidin-4-ylamine;
1-(4-Aminomethylcyclohexyl)-3-(2-phenylquinolin-7-yl)-1H-pyrazolo[3,4-d]pyrimidin-4-ylamine;
1-(4-Aminomethylcyclohexyl)-3-(6-chloro-2-phenylquinolin-7-yl)-1H-pyrazolo[3,4-d]pyrimidin-4-ylamine;
1-(4-Aminomethylcyclohexyl)-3-(6-chloro-2-pyridin-2-ylquinolin-7-yl)-1H-pyrazolo[3,4-d]pyrimidin-4-ylamine;
1-(4-Aminomethylcyclohexyl)-3-(6-chloro-2-thiophen-2-ylquinolin-7-yl)-1H-pyrazolo[3,4-d]pyrimidin-4-ylamine;

1-(4-Aminomethylcyclohexyl)-3-(6-chloro-2-phenoxyquinolin-7-yl)-1H-pyrazolo[3,4-d]pyrimidin-4-ylamine;
1-(4-Aminomethylcyclohexyl)-3-(4-methyl-2-thiophen-2-ylquinolin-7-yl)-1H-pyrazolo[3,4-d]pyrimidin-4-ylamine;
1-(4-Aminomethylcyclohexyl)-3-(4-methyl-2-pyridin-2-ylquinolin-7-yl)-1H-pyrazolo[3,4-d]pyrimidin-4-ylamine;
1-(4-Aminomethylcyclohexyl)-3-(4-methyl-2-phenoxyquinolin-7-yl)-1H-pyrazolo[3,4-d]pyrimidin-4-ylamine;
1-(4-Aminomethylcyclohexyl)-3-(4-methyl-2-phenylquinolin-7-yl)-1H-pyrazolo[3,4-d]pyrimidin-4-ylamine;
1-(4-Aminomethylcyclohexyl)-3-(8-fluoro-2-thiophen-2-ylquinolin-7-yl)-1H-pyrazolo[3,4-d]pyrimidin-4-ylamine;
1-(4-Aminomethylcyclohexyl)-3-(8-fluoro-2-phenylquinolin-7-yl)-1H-pyrazolo[3,4-d]pyrimidin-4-ylamine;
1-(4-Aminomethylcyclohexyl)-3-(8-fluoro-2-phenoxyquinolin-7-yl)-1H-pyrazolo[3,4-d]pyrimidin-4-ylamine;
1-(4-Aminomethylcyclohexyl)-3-(8-fluoro-2-pyridin-2-ylquinolin-7-yl)-1H-pyrazolo[3,4-d]pyrimidin-4-ylamine;
4-[4-Amino-3-(2-pyridin-2-ylquinolin-7-yl)-pyrazolo[3,4-d]pyrimidin-1-yl]-cyclohexanecarboxylic acid amide;
4-[4-Amino-3-(2-phenylquinolin-7-yl)-pyrazolo[3,4-d]pyrimidin-1-yl]-cyclohexanecarboxylic acid amide;
4-[4-Amino-3-(2-thiophen-2-ylquinolin-7-yl)-pyrazolo[3,4-d]pyrimidin-1-yl]-cyclohexanecarboxylic acid amide;
4-[4-Amino-3-(2-phenoxyquinolin-7-yl)-pyrazolo[3,4-d]pyrimidin-1-yl]-cyclohexanecarboxylic acid amide;
4-[4-Amino-3-(6-chloro-2-phenylquinolin-7-yl)-pyrazolo[3,4-d]pyrimidin-1-yl]-cyclohexanecarboxylic acid amide;
4-[4-Amino-3-(6-chloro-2-pyridin-2-ylquinolin-7-yl)-pyrazolo[3,4-d]pyrimidin-1-yl]-cyclohexanecarboxylic acid amide;
4-[4-Amino-3-(6-chloro-2-thiophen-2-ylquinolin-7-yl)-pyrazolo[3,4-d]pyrimidin-1-yl]-cyclohexanecarboxylic acid amide;
4-[4-Amino-3-(6-chloro-2-phenoxyquinolin-7-yl)-pyrazolo[3,4-d]pyrimidin-1-yl]-cyclohexanecarboxylic acid amide;
4-[4-Amino-3-(8-fluoro-2-phenylquinolin-7-yl)-pyrazolo[3,4-d]pyrimidin-1-yl]-cyclohexanecarboxylic acid amide;
4-[4-Amino-3-(6-chloro-2-thiophen-2-ylquinolin-7-yl)-pyrazolo[3,4-d]pyrimidin-1-yl]-cyclohexanecarboxylic acid amide;
4-[4-Amino-3-(8-fluoro-2-pyridin-2-ylquinolin-7-yl)-pyrazolo[3,4-d]pyrimidin-1-yl]-cyclohexanecarboxylic acid amide;
4-[4-Amino-3-(8-fluoro-2-phenoxyquinolin-7-yl)-pyrazolo[3,4-d]pyrimidin-1-yl]-cyclohexanecarboxylic acid amide;
4-[4-Amino-3-(4-methyl-2-phenylquinolin-7-yl)-pyrazolo[3,4-d]pyrimidin-1-yl]-cyclohexanecarboxylic acid amide;
4-[4-Amino-3-(4-methyl-2-thiophen-2-ylquinolin-7-yl)-pyrazolo[3,4-d]pyrimidin-1-yl]-cyclohexanecarboxylic acid amide;
4-[4-Amino-3-(4-methyl-2-pyridin-2-ylquinolin-7-yl)-pyrazolo[3,4-d]pyrimidin-1-yl]-cyclohexanecarboxylic acid amide;
4-[4-Amino-3-(4-methyl-2-phenoxyquinolin-7-yl)-pyrazolo[3,4-d]pyrimidin-1-yl]-cyclohexanecarboxylic acid amide;
4-[4-Amino-3-(2-pyridin-2-ylquinolin-7-yl)-pyrazolo[3,4-d]pyrimidin-1-yl]-cyclohexanecarboxylic acid methylamide;
4-[4-Amino-3-(2-phenylquinolin-7-yl)-pyrazolo[3,4-d]pyrimidin-1-yl]-cyclohexanecarboxylic acid methylamide;
4-[4-Amino-3-(2-thiophen-2-ylquinolin-7-yl)-pyrazolo[3,4-d]pyrimidin-1-yl]-cyclohexanecarboxylic acid methylamide;
4-[4-Amino-3-(2-phenoxyquinolin-7-yl)-pyrazolo[3,4-d]pyrimidin-1-yl]-cyclohexanecarboxylic acid methylamide;
4-[4-Amino-3-(6-chloro-2-phenylquinolin-7-yl)-pyrazolo[3,4-d]pyrimidin-1-yl]-cyclohexanecarboxylic acid methylamide;
4-[4-Amino-3-(6-chloro-2-pyridin-2-ylquinolin-7-yl)-pyrazolo[3,4-d]pyrimidin-1-yl]-cyclohexanecarboxylic acid methylamide;
4-[4-Amino-3-(6-chloro-2-thiophen-2-ylquinolin-7-yl)-pyrazolo[3,4-d]pyrimidin-1-yl]-cyclohexanecarboxylic acid methylamide;
4-[4-Amino-3-(6-chloro-2-phenoxyquinolin-7-yl)-pyrazolo[3,4-d]pyrimidin-1-yl]-cyclohexanecarboxylic acid methylamide;
4-[4-Amino-3-(8-fluoro-2-phenylquinolin-7-yl)-pyrazolo[3,4-d]pyrimidin-1-yl]-cyclohexanecarboxylic acid methylamide;
4-[4-Amino-3-(6-chloro-2-thiophen-2-ylquinolin-7-yl)-pyrazolo[3,4-d]pyrimidin-1-yl]-cyclohexanecarboxylic acid methylamide;
4-[4-Amino-3-(8-fluoro-2-pyridin-2-ylquinolin-7-yl)-pyrazolo[3,4-d]pyrimidin-1-yl]-cyclohexanecarboxylic acid methylamide;
4-[4-Amino-3-(8-fluoro-2-phenoxyquinolin-7-yl)-pyrazolo[3,4-d]pyrimidin-1-yl]-cyclohexanecarboxylic acid methylamide;
4-[4-Amino-3-(4-methyl-2-phenylquinolin-7-yl)-pyrazolo[3,4-d]pyrimidin-1-yl]-cyclohexanecarboxylic acid methylamide;
4-[4-Amino-3-(4-methyl-2-thiophen-2-ylquinolin-7-yl)-pyrazolo[3,4-d]pyrimidin-1-yl]-cyclohexanecarboxylic acid methylamide;
4-[4-Amino-3-(4-methyl-2-pyridin-2-ylquinolin-7-yl)-pyrazolo[3,4-d]pyrimidin-1-yl]-cyclohexanecarboxylic acid methylamide;
4-[4-Amino-3-(4-methyl-2-phenoxyquinolin-7-yl)-pyrazolo[3,4-d]pyrimidin-1-yl]-cyclohexanecarboxylic acid methylamide;
1-Cyclobutyl-3-(2-thiophen-2-ylquinolin-7-yl)-1H-pyrazolo[3,4-d]pyrimidin-4-ylamine;
1-Cyclobutyl-3-(2-phenylquinolin-7-yl)-1H-pyrazolo[3,4-d]pyrimidin-4-ylamine;
1-Cyclobutyl-3-(2-phenoxyquinolin-7-yl)-1H-pyrazolo[3,4-d]pyrimidin-4-ylamine;
1-Cyclobutyl-3-(2-pyridin-2-ylquinolin-7-yl)-1H-pyrazolo[3,4-d]pyrimidin-4-ylamine;
3-(6-Chloro-2-phenylquinolin-7-yl)-1-cyclobutyl-1H-pyrazolo[3,4-d]pyrimidin-4-ylamine;
3-(6-Chloro-2-pyridin-2-ylquinolin-7-yl)-1-cyclobutyl-1H-pyrazolo[3,4-d]pyrimidin-4-ylamine;
3-(6-Chloro-2-thiophen-2-ylquinolin-7-yl)-1-cyclobutyl-1H-pyrazolo[3,4-d]pyrimidin-4-ylamine;
3-(6-Chloro-2-phenoxyquinolin-7-yl)-1-cyclobutyl-1H-pyrazolo[3,4-d]pyrimidin-4-ylamine;
1-Cyclobutyl-3-(4-methyl-2-thiophen-2-ylquinolin-7-yl)-1H-pyrazolo[3,4-d]pyrimidin-4-ylamine;
1-Cyclobutyl-3-(4-methyl-2-pyridin-2-ylquinolin-7-yl)-1H-pyrazolo[3,4-d]pyrimidin-4-ylamine;
1-Cyclobutyl-3-(4-methyl-2-phenylquinolin-7-yl)-1H-pyrazolo[3,4-d]pyrimidin-4-ylamine;

1-Cyclobutyl-3-(4-methyl-2-phenoxyquinolin-7-yl)-1H-pyrazolo[3,4-d]pyrimidin-4-ylamine;
3-[4-Amino-3-(2-phenylquinolin-7-yl)-pyrazolo[3,4-d]pyrimidin-1-yl]-cyclobutanol;
3-[4-Amino-3-(2-pyridin-2-ylquinolin-7-yl)-pyrazolo[3,4-d]pyrimidin-1-yl]-cyclobutanol;
3-[4-Amino-3-(2-thiophen-2-ylquinolin-7-yl)-pyrazolo[3,4-d]pyrimidin-1-yl]-cyclobutanol;
3-[4-Amino-3-(2-phenoxyquinolin-7-yl)-pyrazolo[3,4-d]pyrimidin-1-yl]-cyclobutanol;
3-[4-Amino-3-(6-chloro-2-thiophen-2-ylquinolin-7-yl)-pyrazolo[3,4-d]pyrimidin-1-yl]-cyclobutanol;
3-[4-Amino-3-(6-chloro-2-pyridin-2-ylquinolin-7-yl)-pyrazolo[3,4-d]pyrimidin-1-yl]-cyclobutanol;
3-[4-Amino-3-(6-chloro-2-phenylquinolin-7-yl)-pyrazolo[3,4-d]pyrimidin-1-yl]-cyclobutanol;
3-[4-Amino-3-(6-chloro-2-phenoxyquinolin-7-yl)-pyrazolo[3,4-d]pyrimidin-1-yl]-cyclobutanol;
3-[4-Amino-3-(4-methyl-2-phenylquinolin-7-yl)-pyrazolo[3,4-d]pyrimidin-1-yl]-cyclobutanol;
3-[4-Amino-3-(4-methyl-2-pyridin-2-ylquinolin-7-yl)-pyrazolo[3,4-d]pyrimidin-1-yl]-cyclobutanol;
3-[4-Amino-3-(4-methyl-2-thiophen-2-ylquinolin-7-yl)-pyrazolo[3,4-d]pyrimidin-1-yl]-cyclobutanol;
3-[4-Amino-3-(4-methyl-2-phenoxyquinolin-7-yl)-pyrazolo[3,4-d]pyrimidin-1-yl]-cyclobutanol;
1-(3-Azetidin-1-ylmethylcyclobutyl)-3-(2-pyridin-2-ylquinolin-7-yl)-1H-pyrazolo[3,4-d]pyrimidin-4-ylamine;
1-(3-Azetidin-1-ylmethylcyclobutyl)-3-(2-phenylquinolin-7-yl)-1H-pyrazolo[3,4-d]pyrimidin-4-ylamine;
1-(3-Azetidin-1-ylmethylcyclobutyl)-3-(2-thiophen-2-ylquinolin-7-yl)-1H-pyrazolo[3,4-d]pyrimidin-4-ylamine;
1-(3-Azetidin-1-ylmethylcyclobutyl)-3-(2-phenoxyquinolin-7-yl)-1H-pyrazolo[3,4-d]pyrimidin-4-ylamine;
1-(3-Azetidin-1-ylmethylcyclobutyl)-3-(6-chloro-2-thiophen-2-ylquinolin-7-yl)-1H-pyrazolo[3,4-d]pyrimidin-4-ylamine;
1-(3-Azetidin-1-ylmethylcyclobutyl)-3-(6-chloro-2-phenylquinolin-7-yl)-1H-pyrazolo[3,4-d]pyrimidin-4-ylamine;
1-(3-Azetidin-1-ylmethylcyclobutyl)-3-(6-chloro-2-phenoxyquinolin-7-yl)-1H-pyrazolo[3,4-d]pyrimidin-4-ylamine;
1-(3-Azetidin-1-ylmethylcyclobutyl)-3-(6-chloro-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-phenylquinolin-7-yl)-1H-pyrazolo[3,4-d]pyrimidin-4-ylamine;
1-(3-Azetidin-1-ylmethylcyclobutyl)-3-(4-methyl-2-thiophen-2-ylquinolin-7-yl)-1H-pyrazolo[3,4-d]pyrimidin-4-ylamine;
1-(3-Azetidin-1-ylmethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(2-phenylquinolin-7-yl)-1H-pyrazolo[3,4-d]pyrimidin-4-ylamine;
1-(3-Dimethylaminomethylcyclobutyl)-3-(2-thiophen-2-ylquinolin-7-yl)-1H-pyrazolo[3,4-d]pyrimidin-4-ylamine;
1-(3-Dimethylaminomethylcyclobutyl)-3-(2-pyridin-2-ylquinolin-7-yl)-1H-pyrazolo[3,4-d]pyrimidin-4-ylamine;
1-(3-Dimethylaminomethylcyclobutyl)-3-(2-phenoxyquinolin-7-yl)-1H-pyrazolo[3,4-d]pyrimidin-4-ylamine;
3-(6-Chloro-2-phenylquinolin-7-yl)-1-(3-dimethylaminomethylcyclobutyl)-1H-pyrazolo[3,4-d]pyrimidin-4-ylamine;
3-(6-Chloro-2-thiophen-2-ylquinolin-7-yl)-1-(3-dimethylaminomethylcyclobutyl)-1H-pyrazolo[3,4-d]pyrimidin-4-ylamine;
3-(6-Chloro-2-phenoxyquinolin-7-yl)-1-(3-dimethylaminomethylcyclobutyl)-1H-pyrazolo[3,4-d]pyrimidin-4-ylamine;
3-(6-Chloro-2-pyridin-2-ylquinolin-7-yl)-1-(3-dimethylaminomethylcyclobutyl)-1H-pyrazolo[3,4-d]pyrimidin-4-ylamine;
1-(3-Dimethylaminomethylcyclobutyl)-3-(4-methyl-2-pyridin-2-ylquinolin-7-yl)-1H-pyrazolo[3,4-d]pyrimidin-4-ylamine;
1-(3-Dimethylaminomethylcyclobutyl)-3-(4-methyl-2-phenylquinolin-7-yl)-1H-pyrazolo[3,4-d]pyrimidin-4-ylamine;
1-(3-Dimethylaminomethylcyclobutyl)-3-(4-methyl-2-thiophen-2-ylquinolin-7-yl)-1H-pyrazolo[3,4-d]pyrimidin-4-ylamine;
1-(3-Dimethylaminomethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(8-fluoro-2-phenylquinolin-7-yl)-1H-pyrazolo[3,4-d]pyrimidin-4-ylamine;
1-(3-Dimethylaminomethylcyclobutyl)-3-(8-fluoro-2-pyridin-2-ylquinolin-7-yl)-1H-pyrazolo[3,4-d]pyrimidin-4-ylamine;
1-(3-Dimethylaminomethylcyclobutyl)-3-(8-fluoro-2-thiophen-2-ylquinolin-7-yl)-1H-pyrazolo[3,4-d]pyrimidin-4-ylamine;
1-(3-Dimethylaminomethylcyclobutyl)-3-(8-fluoro-2-phenoxyquinolin-7-yl)-1H-pyrazolo[3,4-d]pyrimidin-4-ylamine;
3-Cyclobutyl-1-(3-phenylquinoxalin-6-yl)-imidazo[1,5-a]pyrazin-8-ylamine;
3-[8-Amino-1-(3-phenylquinoxalin-6-yl)-imidazo[1,5-a]pyrazin-3-yl]-cyclobutanol;
3-(3-Azetidin-1-ylmethylcyclobutyl)-1-(3-phenylquinoxalin-6-yl)-imidazo[1,5-a]pyrazin-8-ylamine;
4-[8-Amino-1-(3-phenylquinoxalin-6-yl)-imidazo[1,5-a]pyrazin-3-yl]-cyclohexanecarboxylic acid amide;
4-[8-Amino-1-(3-phenylquinoxalin-6-yl)-imidazo[1,5-a]pyrazin-3-yl]₇ cyclohexanecarboxylic acid methylamide;
4-[8-Amino-1-(2-phenylquinazolin-7-yl)-imidazo[1,5-a]pyrazin-3-yl]-cyclohexanecarboxylic acid amide;
4-[8-Amino-1-(2-phenylquinazolin-7-yl)-imidazo[1,5-a]pyrazin-3-yl]-cyclohexanecarboxylic acid methylamide;
3-Cyclobutyl-1-(2-phenylquinazolin-7-yl)-imidazo[1,5-a]pyrazin-8-ylamine;
3-[8-Amino-1-(2-phenylquinazolin-7-yl)-imidazo[1,5-a]pyrazin-3-yl]-cyclobutanol;
3-(3-Azetidin-1-ylmethylcyclobutyl)-1-(2-phenylquinazolin-7-yl)-imidazo[1,5-a]pyrazin-8-ylamine;
3-[3-(2-Methoxyethoxy)-cyclobutyl]-1-(2-phenylquinolin-7-yl)-imidazo[1,5-d]pyrazin-8-ylamine;
1-(6-Chloro-2-phenylquinolin-7-yl)-3-[3-(2-methoxyethoxy)-cyclobutyl]-imidazo[1,5-a]pyrazin-8-ylamine;
3-[3-(2-Methoxyethoxy)-cyclobutyl]-1-(4-methyl-2-phenylquinolin-7-yl)-imidazo[1,5-a]pyrazin-8-ylamine;

3-(1-Methyl-1,2,3,6-tetrahydropyridin-4-yl)-1-(2-phenylquinolin-7-yl)-imidazo[1,5-a]pyrazin-8-ylamine;
1-{4-[8-Amino-1-(2-phenylquinolin-7-yl)-imidazo[1,5-a]pyrazin-3-yl]-3,6-dihydro-2H-pyridin-1-yl}-ethanone;
3-Bicyclo[3.1.0]hex-6-yl-1-(2-phenylquinolin-7-yl)-imidazo[1,5-a]pyrazin-8-ylamine;
6-[8-Amino-1-(2-phenylquinolin-7-yl)-imidazo[1,5-a]pyrazin-3-yl]-bicyclo[3.1.0]hexan-3-ol;
7-Cyclobutyl-5-(2-phenylquinolin-7-yl)-imidazo[5,1-f][1,2,4]triazin-4-ylamine;
7-Cyclobutyl-5-(2-thiophen-2-ylquinolin-7-yl)-imidazo[5,1-f][1,2,4]triazin-4-ylamine;
7-Cyclobutyl-5-(2-phenoxyquinolin-7-yl)-imidazo[5,1-f][1,2,4]triazin-4-ylamine;
7-Cyclobutyl-5-(2-pyridin-2-ylquinolin-7-yl)-imidazo[5,1-f][1,2,4]triazin-4-ylamine;
3-[4-Amino-5-(2-phenylquinolin-7-yl)-imidazo[5,1-f][1,2,4]triazin-7-yl]-cyclobutanol;
3-[4-Amino-5-(2-thiophen-2-ylquinolin-7-yl)-imidazo[5,1-f][1,2,4]triazin-7-yl]-cyclobutanol;
3-[4-Amino-5-(2-phenoxyquinolin-7-yl)-imidazo[5,1-f][1,2,4]triazin-7-yl]-cyclobutanol;
3-[4-Amino-5-(2-pyridin-2-ylquinolin-7-yl)-imidazo[5,1-f][1,2,4]triazin-7-yl]-cyclobutanol;
7-(3-Azetidin-1-ylmethylcyclobutyl)-5-(2-phenylquinolin-7-yl)-imidazo[5,1-f][1,2,4]triazin-4-ylamine;
7-(3-Azetidin-1-ylmethylcyclobutyl)-5-(2-thiophen-2-ylquinolin-7-yl)-imidazo[5,1-f][1,2,4]triazin-4-ylamine;
7-(3-Azetidin-1-ylmethylcyclobutyl)-5-(2-phenoxyquinolin-7-yl)-imidazo[5,1-f][1,2,4]triazin-4-ylamine;
7-(3-Azetidin-1-ylmethylcyclobutyl)-5-(2-pyridin-2-ylquinolin-7-yl)-imidazo[5,1-f][1,2,4]triazin-4-ylamine;
7-(3-Dimethylaminomethylcyclobutyl)-5-(2-pyridin-2-ylquinolin-7-yl)-imidazo[5,1-f][1,2,4]triazin-4-ylamine;
7-(3-Dimethylaminomethylcyclobutyl)-5-(2-thiophen-2-ylquinolin-7-yl)-imidazo[5,1-f][1,2,4]triazin-4-ylamine;
7-(3-Dimethylaminomethylcyclobutyl)-5-(2-phenylquinolin-7-yl)-imidazo[5,1-f][1,2,4]triazin-4-ylamine;
7-(3-Dimethylaminomethylcyclobutyl)-5-(2-phenoxyquinolin-7-yl)-imidazo[5,1-f][1,2,4]triazin-4-ylamine;
4-[4-Amino-5-(2-phenylquinolin-7-yl)-imidazo[5,1-f][1,2,4]triazin-7-yl]-cyclohexanecarboxylic acid amide;
4-[4-Amino-5-(2-thiophen-2-ylquinolin-7-yl)-imidazo[5,1-f][1,2,4]triazin-7-yl]-cyclohexanecarboxylic acid amide;
4-[4-Amino-5-(2-phenoxyquinolin-7-yl)-imidazo[5,1-f][1,2,4]triazin-7-yl]-cyclohexanecarboxylic acid amide;
4-[4-Amino-5-(2-phenylquinolin-7-yl)-imidazo[5,1-f][1,2,4]triazin-7-yl]-cyclohexanecarboxylic acid methylamide;
4-[4-Amino-5-(2-thiophen-2-ylquinolin-7-yl)-imidazo[5,1-f][1,2,4]triazin-7-yl]-cyclohexanecarboxylic acid methylamide;
4-[4-Amino-5-(2-phenoxyquinolin-7-yl)-imidazo[5,1-f][1,2,4]triazin-7-yl]-cyclohexanecarboxylic acid methylamide;
7-(4-Aminomethylcyclohexyl)-5-(2-phenylquinolin-7-yl)-imidazo[5,1-f][1,2,4]triazin-4-ylamine;
7-(4-Aminomethylcyclohexyl)-5-(2-thiophen-2-ylquinolin-7-yl)-imidazo[5,1-f][1,2,4]triazin-4-ylamine;
7-(4-Aminomethylcyclohexyl)-5-(2-phenoxyquinolin-7-yl)-imidazo[5,1-f][1,2,4]triazin-4-ylamine;
7-(4-Aminomethylcyclohexyl)-5-(6-chloro-2-phenylquinolin-7-yl)-imidazo[5,1-f][1,2,4]triazin-4-ylamine;
4-[4-Amino-5-(6-chloro-2-phenylquinolin-7-yl)-imidazo[5,1-f][1,2,4]triazin-7-yl]-cyclohexanecarboxylic acid amide;
4-[4-Amino-5-(6-chloro-2-phenylquinolin-7-yl)-imidazo[5,1-f][1,2,4]triazin-7-yl]-cyclohexanecarboxylic acid methylamide;
5-(6-Chloro-2-phenylquinolin-7-yl)-7-cyclobutylimidazo[5,1-f][1,2,4]triazin-4-ylamine;
3-[4-Amino-5-(6-chloro-2-phenylquinolin-7-yl)-imidazo[5,1-f][1,2,4]triazin-7-yl]-cyclobutanol;
7-(3-Azetidin-1-ylmethylcyclobutyl)-5-(6-chloro-2-phenylquinolin-7-yl)-imidazo[5,1-f][1,2,4]triazin-4-ylamine;
7-(3-Azetidin-1-ylmethylcyclobutyl)-5-(2-phenylquinolin-7-yl)-5H-pyrrolo[3,2-d]pyrimidin-4-ylamine;
3-[4-Amino-5-(2-phenylquinolin-7-yl)-5H-pyrrolo[3,2-d]pyrimidin-7-yl]-cyclobutanol;
7-Cyclobutyl-5-(2-phenylquinolin-7-yl)-5H-pyrrolo[3,2-d]pyrimidin-4-ylamine;
7-Phenyl-5-(2-phenylquinolin-7-yl)-7H-pyrrolo[2,3-d]pyrimidin-4-ylamine;
3-Isopropyl-1-(2-phenylquinolin-7-yl)-imidazo[1,5-a]pyrazin-8-ylamine;
3-tert-Butyl-1-(2-phenylquinolin-7-yl)-imidazo[1,5-a]pyrazin-8-ylamine;
5-[8-Amino-1-(2-phenylquinolin-7-yl)-imidazo[1,5-a]pyrazin-3-yl]-pyrrolidin-3-ol;
3-Cyclobutyl-1-(2-phenylquinolin-7-yl)-2H-imidazo[1,5-a]pyrazin-8-ylamine;
trans-4-[8-Amino-1-(2-phenylquinolin-7-yl)-imidazo[1,5-a]pyrazin-3-yl]-cyclohexanecarboxylic acid amide;
trans-4-[8-Amino-1-(2-phenylquinolin-7-yl)-imidazo[1,5-a]pyrazin-3-yl]-cyclohexanecarboxylic acid methyl ester;
trans-4-[8-Amino-1-(2-phenylquinolin-7-yl)-imidazo[1,5-a]pyrazin-3-yl]-cyclohexanecarboxylic acid;
trans-4-[8-Amino-1-(2-phenylquinolin-7-yl)-imidazo[1,5-a]pyrazin-3-yl]-cyclohexanecarboxylic acid methylamide;
trans-{4-[8-Amino-1-(2-phenylquinolin-7-yl)-imidazo[1,5-a]pyrazin-3-yl]-cyclohexyl}-methanol;
trans-2-{4-[8-Amino-1-(2-phenylquinolin-7-yl)-imidazo[1,5-a]pyrazin-3-yl]-cyclohexylmethyl}-isoindole-1,3-dione;
trans-3-(4-Aminomethylcyclohexyl)-1-(2-phenylquinolin-7-yl)-imidazo[1,5-a]pyrazin-8-ylamine;
3-(3-Azetidin-1-ylmethylcyclobutyl)-1-(2-phenylquinolin-7-yl)-imidazo[1,5-a]pyrazin-8-ylamine; and
{3-[8-Amino-1-(2-phenylquinolin-7-yl)-imidazo[1,5-a]pyrazin-3-yl]-cyclobutyl}-methanol.

Unless otherwise stated, the connections of compound name moieties are at the rightmost recited moiety. That is, the substituent name starts with a terminal moiety, continues with any bridging moieties, and ends with the connecting moiety. For example, hetarylthioC$_{1-4}$alkyl has a heteroaryl group connected through a thio sulfur to a C$_{1-4}$alkyl that connects to the chemical species bearing the substituent.

As used herein, for example, "C$_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group. Further, C$_0$alkyl includes being a substituted bond—that is, for example, —X—Y—Z is —C(O)—C$_{2-4}$alkyl when X is C$_0$alkyl, Y is C$_0$alkyl, and Z is —C(O)—C$_{2-4}$alkyl.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(=O)—R, in which R is a general substituent variable such as, for example $R^1$ described above. Examples include, but are not limited to, (bi)(cyclo)alkylketo, (cyclo)alkenylketo, alkynylketo, arylketo, hetarylketo, heterocyclylketo, heterobicycloalkylketo, spiroalkylketo.

Unless otherwise specified, the term "cycloalkyl" refers to a 3-8 carbon cyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "bicycloalkyl" refers to a structure consisting of two cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkylcarbonyloxyalkyl" refers to an ester moiety, for example acetoxymethyl, n-butyryloxyethyl, and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl, and the like.

The term "alkylsulfonylalkyl" refers to an alkyl group substituted with an alkylsulfonyl, moiety, for example mesylmethyl, isopropylsulfonylethyl, and the like.

The term "alkylsulfonyl" refers to a sulfonyl moiety substituted with an alkyl group, for example mesyl, n-propylsulfonyl, and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, and the like.

The term "haloalkenyl" refers to an alkenyl group substituted with one or more halo groups.

Unless otherwise specified, the term "cycloalkenyl" refers to a cyclic aliphatic 3 to 8 ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term, "haloalkynyl" refers to an alkynyl group substituted with one or more independent halo groups.

The term "alkylcarbonyl" refers to an alkylketo functionality, for example acetyl, n-butyryl, and the like.

The term "alkenylcarbonyl" refers to an alkenylketo functionality, for example, propenoyl and the like.

The term "aryl" refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" or "hetaryl" or "heteroar-" or "hetar-" refer to a substituted or unsubstituted 5- or 6-membered unsaturated ring containing one, two, three, or four independently selected heteroatoms, preferably one or two heteroatoms independently selected from oxygen, nitrogen, and sulfur or to a bicyclic unsaturated ring system containing up to 10 atoms including at least one heteroatom selected from oxygen, nitrogen, and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with one or more substituents.

The terms "aryl-alkyl" or "arylalkyl" or "aralkyl" are used to describe a group wherein the alkyl chain can be branched or straight chain forming a bridging portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 342-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl.

The terms "aryl-cycloalkyl" or "arylcycloalkyl" are used to describe a group wherein the terminal aryl group is attached to a cycloalkyl group, for example phenylcyclopentyl and the like.

The terms "aryl-alkenyl" or "arylalkenyl" or "aralkenyl" are used to describe a group wherein the alkenyl chain can be branched or straight chain forming a bridging portion of the aralkenyl moiety with the terminal aryl portion, as defined above, for example styryl (2-phenylvinyl), phenpropenyl, and the like.

The terms "aryl-alkynyl" or "arylalkynyl" or "aralkynyl" are used to describe a group wherein the alkynyl chain can be branched or straight chain forming a bridging portion of the aryl-alkynyl moiety with the terminal aryl portion, as defined above, for example 3-phenyl-1-propynyl, and the like.

The terms "aryl-oxy" or "aryloxy" or "aroxy" are used to describe a terminal aryl group attached to a bridging oxygen atom. Typical aryl-oxy groups include phenoxy, 3,4-dichlorophenoxy, and the like.

The terms "aryl-oxyalkyl" or "aryloxyalkyl" or "aroxyalkyl" are used to describe a group wherein an alkyl group is substituted with a terminal aryl-oxy group, for example pentafluorophenoxymethyl and the like.

The term "heterocycloalkenyl" refers to a cycloalkenyl structure in which at least one carbon atom is replaced with a heteroatom selected from oxygen, nitrogen, and sulfur.

The terms "hetaryl-oxy" or "heteroaryl-oxy" or "hetaryloxy" or "heteroaryloxy" or "hetaroxy" or "heteroaroxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetarylalkyl" or "heteroaryl-alkyl" or "hetaralkyl" or "heteroaralkyl" are used to describe a group wherein the alkyl chain can be branched or straight chain forming a bridging portion of the heteroaralkyl moiety with the terminal heteroaryl portion, as defined above, for example 3-furylmethyl, thenyl, furfuryl, and the like.

The terms "hetarylalkenyl" or "heteroarylalkenyl" or "hetaryl-alkenyl" or "heteroaryl-alkenyl" or "hetaralkenyl" or "heteroaralkenyl" are used to describe a group wherein the alkenyl chain can be branched or straight chain forming a bridging portion of the heteroaralkenyl moiety with the terminal heteroaryl portion, as defined above, for example 3-(4-pyridyl)-1-propenyl.

The terms "hetarylalkynyl" or "heteroarylalkynyl" or "hetaryl-alkynyl" or "heteroaryl-alkynyl" or "hetaralkynyl" or "heteroaralkynyl" are used to describe a group wherein the alkynyl chain can be branched or straight chain forming a bridging portion of the heteroaralkynyl moiety with the heteroaryl portion, as defined above, for example 4-(2-thienyl)-1-butynyl.

The term "heterocyclyl" or "hetcyclyl" refers to a substituted or unsubstituted 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl.

The terms "heterocyclylalkyl" or "heterocyclyl-alkyl" or "hetcyclylalkyl" or "hetcyclyl-alkyl" are used to describe a group wherein the alkyl chain can be branched or straight chain forming a bridging portion of the heterocyclylalkyl moiety with the terminal heterocyclyl portion, as defined above, for example 3-piperidinylmethyl and the like.

The terms "heterocyclylalkenyl" or "heterocyclyl-alkenyl" or "hetcyclylalkenyl" or "hetcyclyl-alkenyl" are used to describe a group wherein the alkenyl chain can be branched or straight chain forming a bridging portion of the heterocyclylalkenyl moiety with the terminal heterocyclyl portion, as defined above, for example 2-morpholinyl-1-propenyl and the like.

The terms "heterocyclylalkynyl" or "heterocyclyl-alkynyl" or "hetcyclylalkynyl" or "hetcyclyl-alkynyl" are used to describe a group wherein the alkynyl chain can be branched or straight chain forming a bridging portion of the heterocyclylalkynyl moiety with the terminal heterocyclyl portion, as defined above, for example 2-pyrrolidinyl-1-butynyl and the like.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" or "cycloalkyl-alkyl" refer to a terminal cycloalkyl group as defined above attached to an alkyl group, for example cyclopropylmethyl, cyclohexylethyl, and the like.

The terms "cycloalkylalkenyl" or "cycloalkyl-alkenyl" refer to a terminal cycloalkyl group as defined above attached to an alkenyl group, for example cyclohexylvinyl, cycloheptylalkyl, and the like.

The terms "cycloalkylalkynyl" or "cycloalkyl-alkynyl" refer to a terminal cycloalkyl group as defined above attached to an alkynyl group, for example cyclopropylpropargyl, 4-cyclopentyl-2-butynyl, and the like.

The terms "cycloalkenylalkyl" or "cycloalkenyl-alkyl" refer to a terminal cycloalkenyl group as defined above attached to an alkyl group, for example 2-(cyclopenten-1-yl)ethyl and the like.

The terms "cycloalkenylalkenyl" or "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" or "cycloalkenyl-alkynyl" refer to terminal a cycloalkenyl group as defined above attached to an alkynyl group, for example 1-(cyclohexen-3-yl)propargyl and the like.

The term "carboxylcycloalkylalkyl" refers to a terminal carboxyl (—COOH) group attached to the cycloalkyl ring portion of a cycloalkylalkyl group as defined above.

The term "carboxylcycloalkylalkenyl" refers to a terminal carboxyl (—COOH) group attached to the cycloalkyl ring portion of a cycloalkylalkenyl group as defined above.

The term "carboxylcycloalkylalkynyl" refers to a terminal carboxyl (—COOH) group attached to the cycloalkyl ring portion of a cycloalkylalkynyl group as defined above.

The term "carboxylcycloalkenylalkyl" refers to a terminal carboxyl (—COOH) group attached to the cycloalkenyl ring portion of a cycloalkenylalkyl group as defined above.

The term "carboxylcycloalkenylalkenyl" refers to a terminal carboxyl (—COOH) group attached to the cycloalkenyl ring portion of a cycloalkenylalkenyl group as defined above.

The term "carboxylcycloalkenylalkynyl" refers to a terminal carboxyl (—COOH) group attached to the cycloalkenyl ring portion of a cycloalkenylalkynyl group as defined above.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like.

The term "alkylthio" includes both branched and straight chain alkyl groups attached to a bridging sulfur atom, for example methylthio and the like.

The term "haloalkylthio" refers to an alkylthio group substituted with one or more halo groups, for example trifluoromethylthio and the like.

The term "alkoxyalkyl" refers to an alkyl group substituted with an alkoxy group, for example isopropoxymethyl and the like.

The term "alkoxyalkenyl" refers to an alkenyl group substituted with an alkoxy group, for example 3-methoxyallyl and the like.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined above substituted with an alkoxycarbonyl, for example 4-(ethoxycarbonyl)-2-butenyl and the like.

The term "alkoxycarbonylalkynyl" refers to a straight chain or branched alkynyl as defined above substituted with an alkoxycarbonyl, for example 4-(ethoxycarbonyl)-2-butynyl and the like.

The term "haloalkoxyalkyl" refers to a straight chain or branched alkyl as defined above substituted with a haloalkoxy, for example 2-chloroethoxymethyl, trifluoromethoxymethyl and the like.

The term "haloalkoxyalkenyl" refers to a straight chain or branched alkenyl as defined above substituted with a haloalkoxy, for example 4-(chloromethoxy)-2-butenyl and the like.

The term "haloalkoxyalkynyl" refers to a straight chain or branched alkynyl as defined above substituted with a haloalkoxy, for example 4-(2-fluoroethoxy)-2-butynyl and the like.

The term "alkylthioalkyl" refers to a straight chain or branched alkyl as defined above substituted with an alkylthio group, for example methylthiomethyl, 3-(isobutylthio)heptyl, and the like.

The term "alkylthioalkenyl" refers to a straight chain or branched alkenyl as defined above substituted with an alkylthio group, for example 4-(methylthio)-2-butenyl and the like.

The term "alkylthioalkynyl" refers to a straight chain or branched alkynyl as defined above substituted with an alkylthio group, for example 4-(ethylthio)-2-butynyl and the like.

The term "haloalkylthioalkyl" refers to a straight chain or branched alkyl as defined above substituted with an haloalkylthio group, for example 2-chloroethylthiomethyl, trifluoromethylthiomethyl and the like.

The term "haloalkylthioalkenyl" refers to a straight chain or branched alkenyl as defined above substituted with an haloalkylthio group, for example 4-(chloromethylthio)-2-butenyl and the like.

The term "haloalkylthioalkynyl" refers to a straight chain or branched alkynyl as defined above substituted with a haloalkylthio group, for example 4-(2-fluoroethylthio)-2-butynyl and the like.

The term "dialkoxyphosphorylalkyl" refers to two straight chain or branched alkoxy groups as defined above attached to a pentavalent phosphorous atom, containing an oxo substituent, which is in turn attached to an alkyl, for example diethoxyphosphorylmethyl and the like.

One in the art understands that an "oxo" requires a second bond from the atom to which the oxo is attached. Accordingly, it is understood that oxo cannot be substituted onto an aryl or heteroaryl ring.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above (or a pharmaceutically acceptable salt thereof).

Moreover, within this preferred embodiment, the invention encompasses a pharmaceutical composition for the treatment of disease by inhibiting kinases, comprising a pharmaceutically acceptable carrier and a non-toxic therapeutically effective amount of compound of Formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biological Assays

The efficacy of the Examples of the invention, compounds of Formula I, as inhibitors of insulin-like growth factor-1 receptor (IGF-1R) were demonstrated and confirmed by a number of pharmacological in vitro assays. The following assays and their respective methods can be carried out with the compounds according to the invention. Activity possessed by compounds of Formula I may be demonstrated in vivo.

In Vitro Tyrosine Kinase Assay

The IGF-1R inhibitory of a compound of Formula I can be shown in a tyrosine kinase assay using purified GST fusion protein containing the cytoplasmic kinase domain of human IGF-1R expressed in Sf9 cells. This assay is carried out in a final volume of 90 µL containing 1-100 nM (depending on the specific activity) in an Immulon-4 96-well plate (Thermo Labsystems) pre-coated with 1 µg/well of substrate poly-glu-tyr (4:1 ratio) in kinase buffer (50 mM Hepes, pH 7.4, 125 mM NaCl, 24 mM $MgCl_2$, 1 mM $MnCl_2$, 1% glycerol, 200 µM $Na_3VO_4$, and 2 mM DTT). The enzymatic reaction was initiated by addition of ATP at a final concentration of 100 µM. After incubation at rt for 30 min, the plates were washed with 2 mM imidazole buffered saline with 0.02% Tween-20. Then the plate was incubated with anti-phosphotyrosine mouse monoclonal antibody pY-20 conjugated with horseradish peroxidase (HRP) (Calbiochem) at 167 ng/mL diluted in phosphate buffered saline (PBS) containing 3% bovine serum albumin (BSA), 0.5% Tween-20 and 200 µM $Na_3VO_4$ for 2 h at rt. Following 3×2504 washes, the bound anti-phosphotyrosine antibody was detected by incubation with 100 µL/well ABTS (Kirkegaard & Perry Labs, Inc.) for 30 min at rt. The reaction was stopped by the addition of 100 µL/well 1% SDS, and the phosphotyrosine dependent signal was measured by a plate reader at 405/490 nm.

All EXAMPLES showed inhibition of IGF-1R. The following EXAMPLES showed efficacy and activity by inhibiting IGF-1 R in the biochemical assay with $IC_{50}$ values less than 50 µM to less than 50 nM. Preferably the $IC_{50}$ value is less than 5 µM. Advantageously, the $IC_{50}$ value is less than 1 µM. More advantageously, the $IC_{50}$ value is less than 200 nM. Even more advantageously, the $IC_{50}$ value is less than 100 nM. Still more advantageously, the $IC_{50}$ value is less than 50 nM.

The most preferred EXAMPLES are selective towards IGF-1R.

Cell-Based Autophosphotyrosine Assay

NIH 3T3 cells stably expressing full-length human IGF-1R were seeded at $1\times10^4$ cells/well in 0.1 mL Dulbecco's minimal essential medium (DMEM) supplemented with 10% fetal calf serum (FCS) per well in 96-well plates. On Day 2, the medium is replaced with starvation medium (DMEM containing 0.5% FCS) for 2 h and a compound was diluted in 100% dimethyl sulfoxide (DMSO), added to the cells at six final concentrations in duplicates (20, 6.6, 2.2, 0.74, 0.25 and 0.082 µM), and incubated at 37° C. for additional 2 h. Following addition of recombinant human IGF-1 (100 ng/mL) at 37° C. for 15 min, the media was then removed and the cells were washed once with PBS (phosphate-buffered saline), then lysed with cold TGH buffer (1% Triton-100, 10% glycerol, 50 mM HEPES [pH 7.4]) supplemented with 150 mM NaCl, 1.5 mM MgCl, 1 mM EDTA and fresh protease and phosphatase inhibitors [10 µg/mL leupeptin, 25 µg/mL aprotinin, 1 mM phenyl methyl sulphonyl fluoride (PMSF), and 200 µM $Na_3VO_4$]. Cell lysates were transferred to a 96-well microlite2 plate (Corning CoStar #3922) coated with 10 ng/well of IGF-1R antibody (Calbiochem, Cat#GR31L) and incubated at 4° C. overnight. Following washing with TGH buffer, the plate was incubated with anti-phosphotyrosine mouse monoclonal antibody pY-20 conjugated with horseradish peroxidase (HRP) for 2 h at rt. The autophosphotyrosine was then detected by addition of Super Signal ELISA Femto Maximum Sensitivity Substrate (Pierce) and chemiluminescence was read on a Wallac Victor$^2$ 1420 Multilabel Counter. The $IC_{50}$ curves of the compounds were plotted using an ExcelFit program.

The preferred EXAMPLES showed inhibition of IGF-1R in the cell-based assay. The following EXAMPLES showed efficacy and activity by inhibiting IGF-1R with $IC_{50}$ values less than 50 µM, with selectivity over insulin receptor expected to be, but not limited to, in a range from 1-30 fold. Preferably the $IC_{50}$ value is less than 5 µM. More advantageously, the $IC_{50}$ value is less than 1 µM. Even more advantageously, the $IC_{50}$ value is less than 200 nM. Insulin receptor autophosphotyrosine assays are performed essentially as described above for IGF-1R cell-based assays, but use insulin (10 nM) as activating ligand and an insulin receptor antibody as capture antibody with HepG2 cells expressing endogenous human insulin receptor.

Compound of Formula I-AA is equal to compound of Formula I wherein $X_1$ and $X_2$=CH, $X_3$ and $X_5$=N, and $X_4$, $X_6$, and $X_7$=C:

177

I-AA

EXPERIMENTAL

In Scheme 1-Scheme 43 and the examples and intermediates to follow serve to demonstrate how to synthesize compounds of this invention, but in no way limit the invention. Additionally, the following abbreviations are used: Me for methyl, Et for ethyl, $^i$Pr or $^i$Pr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-CH$_3$O)Ph for p-methoxyphenyl, (p-NO$_2$)Ph for p-nitrophenyl, 4Br-Ph or (4Br)Ph for 4-bromophenyl, 2-CF$_3$-Ph or (2CF$_3$)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, TMP for tetramethylpiperidine, n-BuLi for n-butyllithium, CDI for 1,1'-carbonyldiimidazole, DEAD for diethlyl azodicarboxylate, PS-PPh$_3$ for polystyrene triphenylphosphine, DIEA for diisopropylethylamine, DIAD for diisopropyl azodicarboxylate, DBAD for di-tert-butyl azodicarboxylate, HPFC for high performance flash chromatography, rt or RT for room temperature, min for minute, h for hour, Bn for benzyl, and LAH for lithium aluminum hydride.

Accordingly, the following are compounds which are useful as intermediates in the formation of IGF-1R inhibiting EXAMPLES.

The compounds of Formula I of this invention and the intermediates used in the synthesis of the compounds of this invention were prepared according to the following methods. Method A was used when preparing compounds of Formula I-AA as shown below in Scheme 1:
Method A:

Scheme 1

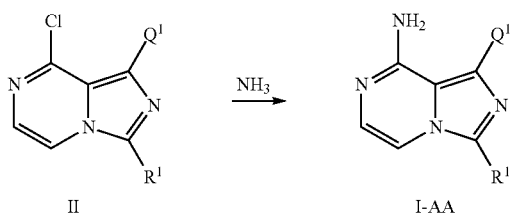

where Q$^1$ and R$^1$ are as defined previously for compound of Formula I.

In a typical preparation of compounds of Formula I-AA, compound of Formula II was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II of Scheme 1 were prepared as shown below in Scheme 2.

Scheme 2

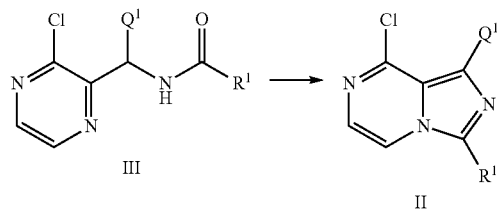

where Q$^1$ and R$^1$ are as defined previously for compound of Formula I.

In a typical preparation of a compound of Formula II, an intermediate of Formula III was treated with POCl$_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride (CH$_2$Cl$_2$) or chloroform (CHCl$_3$). If desired, mixtures of these solvents were used or no solvent was used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III of Scheme 2 were prepared as shown below in Scheme 3:

Scheme 3

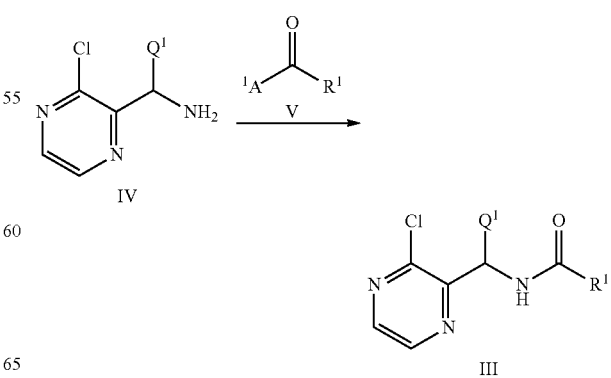

where $Q^1$ and $R^1$ are as defined previously for compound of Formula I and $A^1$=OH, alkoxy, or a leaving group such as chloro or imidazole.

In a typical preparation, of a compound of Formula III, a compound of Formula IV and compound of Formula V were reacted under suitable amide coupling conditions. Suitable conditions include but are not limited to treating compounds of Formula IV and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvents were methylene chloride and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially, equimolar amounts of reactants were preferably used although higher or lower amounts were used if desired. Alternatively, compounds of Formula IV and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about -20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula IV and V (where $A^1$=F, Cl, Br, I) and base and substoichiometric amounts of DMAP were preferably used although higher or lower amounts were used if desired. Additionally, other suitable reaction conditions for the conversion of a compound of Formula IV to a compound of Formula III can be found in Larock, R. C. *Comprehensive Organic Transformations*, $2^{nd}$ ed.; Wiley and Sons: New York, 1999, pp 1941-1949.

The compounds of Formula IV of Scheme 3 were prepared as shown below in Scheme 4:

Scheme 4

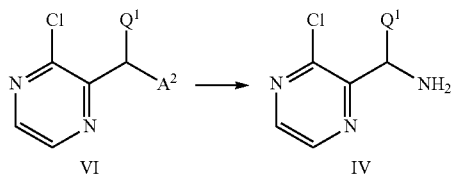

where $Q^1$ is as defined previously for compound of Formula I and $A^2$ phthalimido or $N^3$.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. In the transformation of compound of Formula VI to IV, if $A^2$=$N_3$, then one skilled in the art would recognize that typical azide reduction conditions could be employed, including but not limited to $PPh_3$ and water or hydrogenation in the presence of a metal catalyst such as palladium.

The compounds of Formula VI of Scheme 4 were prepared as shown below in Scheme 5:

Scheme 5

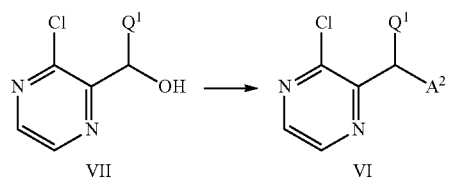

where $Q^1$ is as defined previously for compound of Formula I and $A^2$=phthalimido or $N^3$.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS-$PPh_3$), and DIAD. The above process may be carried out at temperatures between about -78° C. and about 100° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent or a slight excess, 1.1 equivalents, of triphenylphosphine, DIAD and phthalimide was used per equivalent of compound of Formula VII. Additionally, compound of Formula VII can be reacted with $Ts_2O$, $Ms_2O$, $Tf_2O$, TsCl, MsCl, or $SOCl_2$ in which the hydroxy group is converted to a leaving group such as its respective tosylate, mesylate, triflate, or halogen such as chloro and subsequently reacted with an amine equivalent such as $NH(Boc)_2$, phthalimide, potassium phthalimide, or sodium azide. Conversion of the amine equivalents by known methods such as by treating under acidic conditions ($NH(Boc)_2$), with hydrazine (phthalimide) as shown in Scheme 4, or with triphenylphosphine/water (azide) will afford the desired amine as shown in Scheme 4.

The compounds of Formula VII of Scheme 5 were prepared from aldehydes $Q^1$-CHO and a 2-chloropyrazine VIII as shown below in Scheme 6:

Scheme 6

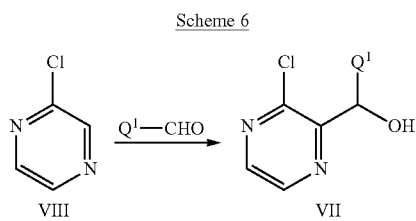

VIII        VII where $Q^1$ is as defined previously for compound of Formula I.

In a typical preparation, of a compound of Formula VII, a compound of Formula VIII was reacted under suitable reaction conditions in a suitable solvent with a compound of Formula $Q^1$-CHO. Suitable conditions included but were not limited to treating compounds of Formula VIII with a base such as lithium tetramethylpiperidide (Li-TMP) followed by treating with compounds of Formula $Q^1$-CHO. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I of this invention and the intermediates used in the synthesis of the compounds of this invention were prepared according to the following methods. Method AA was used when preparing compounds of Formula I-AA from compound of Formula I-AAA as shown below in Scheme 7:

Method AA:

Scheme 7

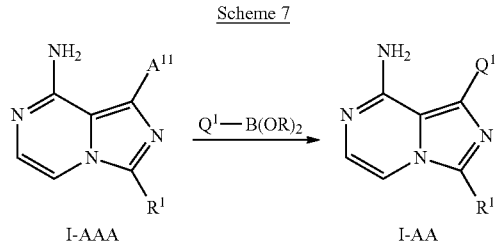

I-AAA        I-AA where $Q^1$ and $R^1$ are as defined previously for compound of Formula I, $A^{11}$=halogen such as Cl, Br, or I and $B(OR)_2$=suitable boronic acid/ester.

In a typical preparation of compounds of Formula I-AA, compound of Formula I-AAA was reacted with a suitable boronic acid/ester ($Q^1$-$B(OR)_2$) in a suitable solvent via typical Suzuki coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AA from I-AAA. For example, compound of Formula I-AAA could be reacted with a suitable organotin reagent $Q^1$-$SnBu_3$ or the like in a suitable solvent via typical Stille coupling procedures.

The compounds of Formula I-AAA of Scheme 7 were prepared as shown below in Scheme 8.

Scheme 8

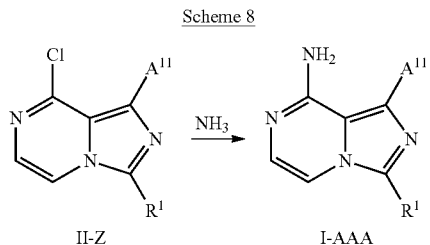

II-Z        I-AAA where $R^1$ is as defined previously for compound of Formula I and $A^{11}$=halogen such as Cl, Br, or I.

In a typical preparation of compounds of Formula I-AAA, compound of Formula II-Z was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-Z of Scheme 8 were prepared as shown below in Scheme 9.

Scheme 9

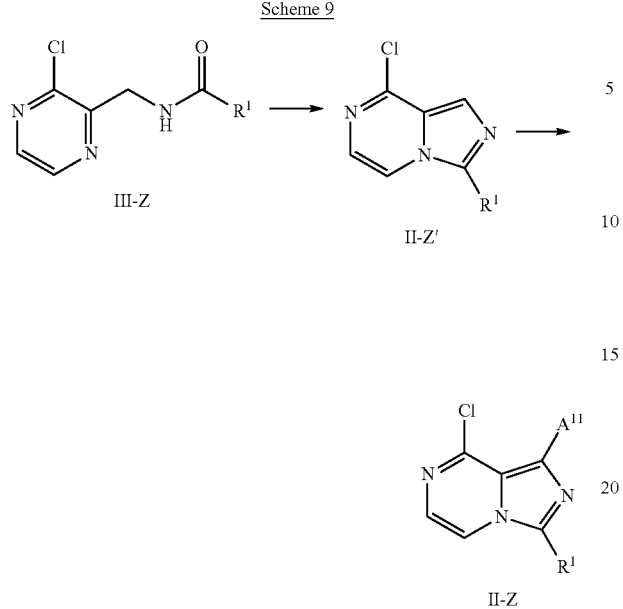

where $R^1$ is as defined previously for compound of Formula I and $A^{11}$=halogen such as Cl, Br, or I.

In a typical preparation of a compound of Formula II-Z, intermediate III-Z was converted to compound of Formula II-Z'. Intermediate of Formula III-Z was treated with POCl$_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride (CH$_2$Cl$_2$) or chloroform (CHCl$_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired. In the conversion of compound of Formula III-Z to II-Z', suitable halogenating agent were used, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III-Z of Scheme 9 were prepared as shown below in Scheme 10:

Scheme 10

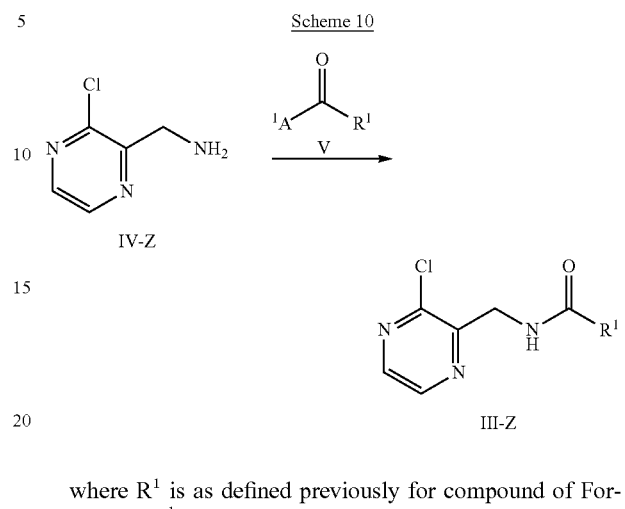

where $R^1$ is as defined previously for compound of Formula I and $A^1$=OH, alkoxy, or a leaving group such as chloro or imidazole.

In a typical preparation, of a compound of Formula III-Z, a compound of Formula IV-Z and compound of Formula V were reacted under suitable amide coupling conditions. Suitable conditions include but are not limited to treating compounds of Formula IV-Z and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, if compound of Formula IV-Z was a salt or bis-salt, a suitable base was required and included, but was not limited to, diisopropylethylamine or triethylamine. Alternatively, compounds of Formula IV-Z and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula IV-Z and V (where $A^1$=F, Cl, Br, I) and base and substoichiometric amounts of DMAP were preferably used although higher or lower amounts were used if desired. Additionally, other suitable reaction conditions for the conversion of an amine (compound of Formula IV-Z) to an amide (compound of Formula III-Z) can be found in Larock, R. C. *Comprehensive Organic Transformations*, 2$^{nd}$ ed.; Wiley and Sons: New York, 1999, pp 1941-1949.

The compounds of Formula IV-Z of Scheme 10 were prepared as shown below in Scheme 11:

Scheme 11

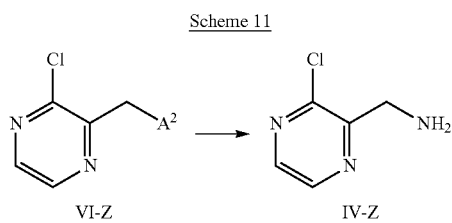

where A$^2$ is phthalimido or N$^3$.

In a typical preparation, of a compound of Formula IV-Z, a compound of Formula VI-Z is reacted under suitable reaction conditions in a suitable solvent. When A$^2$=phthalimido, suitable conditions include treatment of compound of Formula VI-Z with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VI-Z of Scheme 11 were prepared as shown below in Scheme 12:

Scheme 12

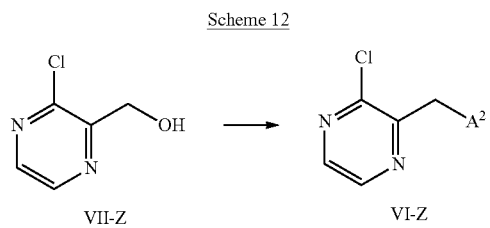

where A$^2$=phthalimido or N$^3$.

In a typical preparation of a compound of Formula VI-Z (when A$^2$=phthalimido), a compound of Formula VII-Z was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS-PPh$_3$) and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, 1.0 or 1.1 equivalents of triphenylphosphine, DIAD and phthalimide was used per equivalent of compound of Formula VII-Z. Additionally, compound of Formula VII-Z can be reacted with Ts$_2$O, Ms$_2$O, Tf$_2$O, TsCl, MsCl, or SOCl$_2$ in which the hydroxy group is converted to a leaving group such as its respective tosylate, mesylate, triflate, or halogen such as chloro and subsequently reacted with an amine equivalent such as NH(Boc)$_2$, phthalimide, potassium phthalimide or sodium azide. Conversion of the amine equivalents by known methods such as by treating under acidic conditions (NH(Boc)$_2$), with hydrazine (phthalimide) as shown in Scheme 4, or with triphenylphosphine/water (azide) will afford the desired amine as shown in Scheme 4.

The compounds of Formula VII-Z of Scheme 12 were prepared from 2-chloropyrazine VIII as shown below in Scheme 13:

Scheme 13

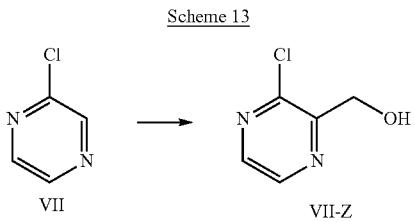

In a typical preparation, of a compound of Formula VII-Z, a compound of Formula VIII was reacted under suitable reaction conditions in a suitable solvent. Suitable reaction conditions included, but were not limited to, treating compounds of Formula VIII with a base such as lithium tetramethylpiperidide (Li-TMP) followed by treatment with a reagent containing a carbonyl equivalent followed by treatment with a suitable reducing agent. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. Suitable carbonyl equivalent reagents include, but are not limited to, formamides such as DMF or suitable chloroformate such as methyl or ethyl chloroformate. After addition of the suitable carbonyl equivalent reagent, the reaction if charged with a polar protic solvent such as, but not limited to, methanol or ethanol followed by treatment with a suitable reducing agent such as sodium borohydride. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula X-Z ($Q^1$-CHO) of Scheme 6 were prepared as shown below in Scheme 14:

Scheme 14

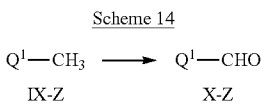

where $Q^1$ is as defined previously for compound of Formula I.

In a typical preparation, of a compound of Formula X-Z ($Q^1$-CHO), a compound of Formula IX-Z ($Q^1$-CH$_3$) was reacted with a suitable oxidizing agent under suitable reaction conditions. Suitable oxidizing agents included, but were not limited to, selenium dioxide. Suitable reaction conditions for use in the above process included, but were not limited to, heating a mixture of selenium dioxide and compounds of Formula IX-Z ($Q^1$-CH$_3$) neat or in a suitable solvent such as, but not limited to, chlorobenzene or sulpholane. The above process may be carried out at temperatures between about 120° C. and about 180° C. Preferably, the reaction was carried out at 150° C. to 165° C. The above process to produce compounds of the present invention was preferably carried out at about atmospheric pressure although higher or lower pressures were used if desired. Preferably, 1-1.5 equivalents of selenium dioxide were used although higher or lower amounts were used if desired. Alternatively, a compound of Formula IX-Z ($Q^1$-CH$_3$) was reacted first with a halogenating agent and a radical initiator under suitable reaction conditions in a suitable solvent to give a compound of Formula $Q^1$-CH$_2$-Hal (wherein Hal=Cl or Br) that was then further reacted with DMSO and a base under suitable reaction conditions to give a compound of Formula X-Z ($Q^1$-CHO). Suitable halogenating agents included, but were not limited to, bromine, N-bromosuccinimide, and chlorine. Preferably, N-bromosuccinimide was used. Suitable radical initiators included, but were not limited to, 2,2'-azobisisobutyronitrile (AIBN) and UV light. Preferably, AIBN was used. Preferably, carbon tetrachloride was used as solvent for the halogenation step, although other halogenated solvents may be added. The halogenation may be carried out at temperatures between about 60° C. and about 100° C. Preferably, the reaction was carried out at about 80° C. Suitable bases included, but were not limited to, sodium hydrogencarbonate, sodium dihydrogenphosphate, disodium hydrogenphosphate, and collidine. Preferably, sodium hydrogencarbonate was used. DMSO was preferably used as solvent although other solvents may be added. The second step may be carried out at temperatures between about 40° C. and about 140° C. Preferably, the reaction was carried out at about 90° C. Additionally, other suitable reaction conditions for the conversion of $Q^1$-CH$_3$ to $Q^1$-CHO can be found in Larock, R. C. *Comprehensive Organic Transformations*, 2$^{nd}$ ed.; Wiley and Sons: New York, 1999, pp 1205-1207 and 1222-1224.

The compounds of Formula IX-ZA (compound of Formula IX-Z wherein $X_{16}$=N, $X_{14}$ and $X_{15}$=C-E$^{11}$, and $X_{11}$-$X_{13}$=N or C-E$^{11}$) of Scheme 14 were prepared as shown below in Scheme 15:

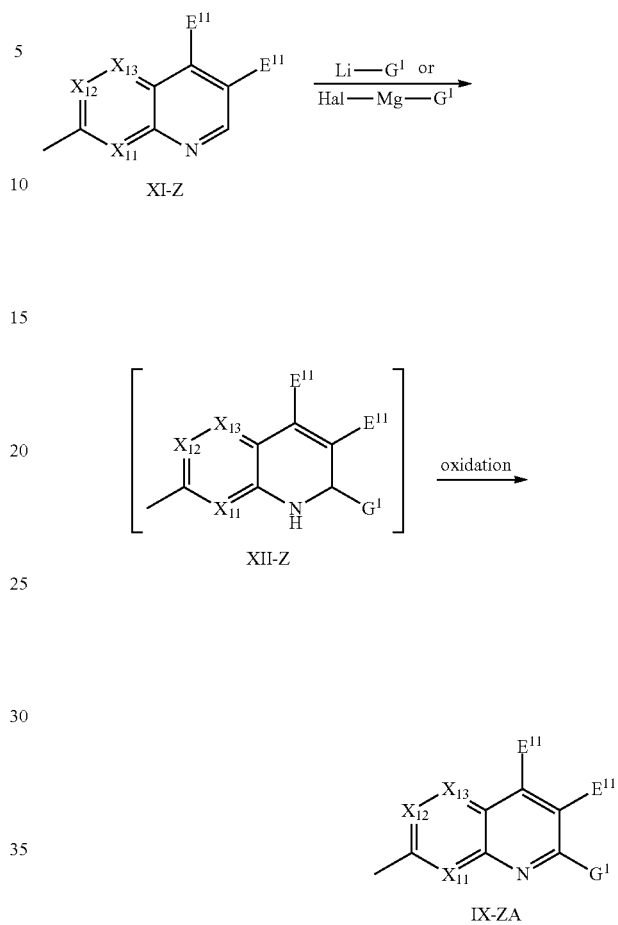

where Hal=Cl, Br, or I; and $E^{11}$ and $G^1$ are as defined previously for compound of Formula I.

In a typical preparation, of a compound of Formula IX-ZA, a compound of Formula XI-Z was reacted first with an organolithium reagent Li-$G^1$ or a Grignard reagent Hal-Mg-$G^1$ in a suitable solvent to give a compound of Formula XII-Z that was then further reacted with an oxidizing agent in a suitable solvent. Suitable solvents for use in the first step of above process included, but were not limited to, ethers such as tetrahydrofuran (THF), glyme, and the like. If desired, mixtures of these solvents were used, however, the preferred solvent was THF. The above process may be carried out at temperatures between about −60° C. and about 66° C. Preferably, the reaction was carried out at about 0° C. to about 25° C. Suitable oxidizing agents included, but were not limited to, air, sulfur, and 2,3-dichloro-5,6-dicyano-1,4-benzoquinone (DDQ). Preferred oxidizing agents were air and DDQ. Suitable solvents for this process included, but were not limited to, esters such as ethyl acetate, ethers such as THF, aromatic solvents such as toluene. This process may be carried out at temperatures between about 0° C. and the reflux temperature of the solvent used. Preferably, the reaction was carried out at about 20° C. to about 25° C. Alternatively, a compound of Formula XII-Z or a mixture of compounds of Formula XII-Z and IX-ZA were subjected directly to the process described in Scheme 14 to obtain compounds of Formula X-Z ($Q^1$-CHO).

The compounds of Formula XIV-Z ($Q^1$-B(OR)$_2$) of Scheme 7 were prepared as shown below in Scheme 16:

Scheme 16

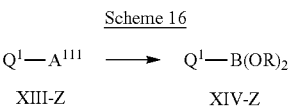

$Q^1$—$A^{111}$   →   $Q^1$—B(OR)$_2$

XIII-Z                 XIV-Z where $Q^1$ is as defined previously for compound of Formula I, $A^{111}$=OTf or halogen such as Cl, Br, or I and B(OR)$_2$=suitable boronic acid/ester.

In a typical preparation, of a compound of Formula XIV-Z ($Q^1$-B(OR)$_2$), a compound of Formula XIII-Z ($Q^1$-$A^{111}$) was reacted with a suitable metal catalyst and a suitable boronating agent under suitable reaction conditions. Suitable metal catalyst agents included, but were not limited to, Pd(OAc)$_2$ in the presence of 1,3-bis(2,6-diisopropylphenyl)imidazolium chloride. Suitable boronating agents included, but were not limited to, bis(pinacolato)diboron. Suitable reaction conditions for use in the above process included, but were not limited to, heating a mixture of Pd(OAc)$_2$, 1,3-bis(2,6-diisopropylphenypimidazolium chloride, KOAc, and bis(pinacol) borane in a suitable solvent such as, but not limited to, THF. The above process may be carried out at temperatures between about 20° C. and about 100° C. Preferably, the reaction was carried out at 60° C. to 80° C. The above process to produce compounds of the present invention was preferably carried out at about atmospheric pressure although higher or lower pressures were used if desired. Preferably, 2-3 equivalents of KOAc, 1-1.5 equivalents of bis(pinacol)borane, 0.03-1 equivalent of Pd(OAc)$_2$, and 0.09-3 equivalents of 1,3-bis(2,6-diisopropylphenyl)imidazolium chloride were used although higher or lower amounts were used if desired. Additionally, other suitable reaction conditions for the conversion of $Q^1$-$A^{111}$ to $Q^1$-B(OR)$_2$ can be found in the literature which involve a variety of $Q^1$-$A^{111}$ or aryl/heteroarylhalides and a variety of conditions (Bioorganic & Medicinal Chemistry Letters, 2003, 12(22), 4001; Bioorganic & Medicinal Chemistry Letters, 2003, 13(18), 3059; Chemical Communications (Cambridge, UK), 2003, 23, 2924; Synthesis, 2002, 17, 2503; Angewandte Chemie, International Ed., 2002, 41(16), 3056; Journal of the American Chemical Society, 2002, 124(3), 390; Organic Letters, 2002, 4(4), 541; Tetrahedron, 2001, 57(49), 9813; Journal of Organic Chemistry, 2000, 65(1), 164; Journal of Organic Chemistry, 1997, 62(19), 6458; Journal of Organometallic Chemistry, 1983, 259(3), 269). In some cases, compounds of Formula XIII-Z ($Q^1$-$A^{111}$) and XIV-Z ($Q^1$-B(OR)$_2$) are commercially available or synthesized according to literature procedures. In cases where neither are available, compounds of Formula XIII-Z ($Q^1$-$A^{111}$) and XIV-Z ($Q^1$-B(OR)$_2$) were synthesized via procedures described in the experimental section herein.

Both $R^1$ and $Q^1$ in the compounds described herein in some instances contain functional groups which can be further manipulated. It would be appreciated by those skilled in the art that such manipulation of functional groups can be accomplished with key intermediates or with late stage compounds. Such functional group transformations are exemplified in the following Schemes 17-27 as well as in the experimental section but are in no way meant to limit the scope of such transformations. Additionally, the chemistry shown in Schemes 17-27 can also be applied to compounds of I-AAA, and II-Z'.

The compounds of Formula I-A (compounds of Formula I-AA where $R^1$=Z—CONR$^2$R$^3$) were prepared as shown below in Scheme 17:

Scheme 17

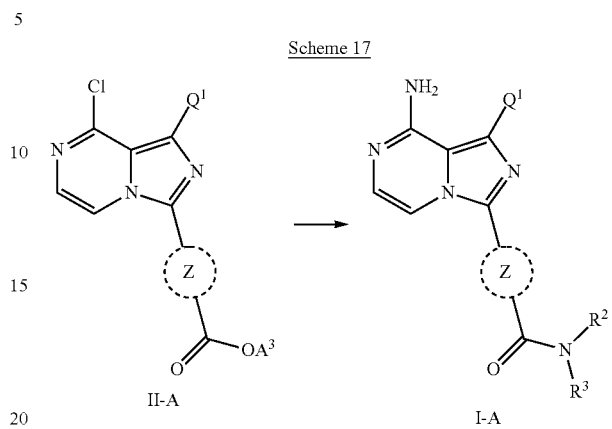

II-A             I-A where $Q^1$, $R^2$, and $R^3$ are as defined previously for compound of Formula I and $A^3$=hydrogen or alkyl such as methyl or ethyl.

In a typical preparation of compound of Formula I-A, when $A^3$=alkyl and $R^2$ and $R^3$ were both equal to H, reaction of compound of Formula II-A (compounds of Formula II where $R^1$=Z—CO$_2$A$^3$) with ammonia in a suitable solvent, afforded compound of Formula I-A. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvents were isopropanol and a mixture of isopropanol/THF. The above process was carried out at temperatures between about –78° C. and about 120° C. Preferably, the reaction was carried out between 80° C. and about 120° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, in a typical preparation of compound of Formula I-A, compound of Formula II-A (when $A^3$=H) was reacted with HNR$^2$R$^3$ followed by ammonia in a suitable solvent. When $A^3$=H, typical coupling procedures as described in Scheme 3 (conversion of CO$_2$H to COCl via treatment with SOCl$_2$ or oxalyl chloride followed by reaction with HNR$^2$R$^3$ or treatment of CO$_2$H and HNR$^2$R$^3$ with EDC or DCC in conjunction with DMAP, HOBT, or HOAt and the like) were employed to afford the transformation of a carboxylic acid to an amide. When $A^3$=alkyl such as methyl or ethyl, treatment of the ester with Al(NR$^2$R$^3$) afforded conversion of CO$_2$A$^3$ to CO(NR$^2$R$^3$). Subsequent treatment with ammonia afforded compounds of Formula I-A.

The compounds of Formula I-A' (compounds of Formula I-AA where $R^1$=Z—CO$_2$A$^3$) and I-A" (compounds of Formula I-AA where $R^1$=Z—CO$_2$H) were prepared as shown below in Scheme 18:

Scheme 18

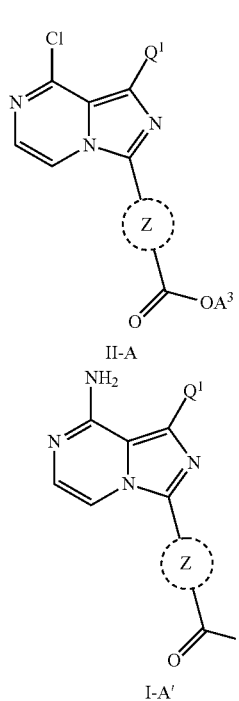

where Q¹ is as defined previously for compounds of Formula I and A³=alkyl such as methyl or ethyl.

In a typical preparation of compound of Formula I-A', compound of Formula II-A was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 100° C. and about 120° C. The above process to produce compounds of the present invention was preferably carried out at about atmospheric pressure although higher or lower pressures were used if desired. In most cases, the reactions were run in a sealed tube. Substantially, equimolar amounts of reactants were preferably used although higher or lower amounts were used if desired. Typically, an excess of ammonia was used and the reaction was monitored in order to ensure that additional of ammonia to the ester moiety did not occur to an appreciable extent. Additionally, in a typical preparation of compound of Formula I-A", compound of Formula I-A' was reacted under typical saponification conditions such as NaOH in THF/$H_2O$/ MeOH. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was a mixture of THF/$H_2O$/MeOH. The above process was carried out at temperatures between about −78° C. and about 120° C. Preferably, the reaction was carried out between rt and about 60° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II-B (compounds of Formula II where R¹=Z—$CH_2OH$) and I-B (compounds of Formula I-AA where R¹=Z—$CH_2OH$) were prepared as shown below in Scheme 19:

Scheme 19

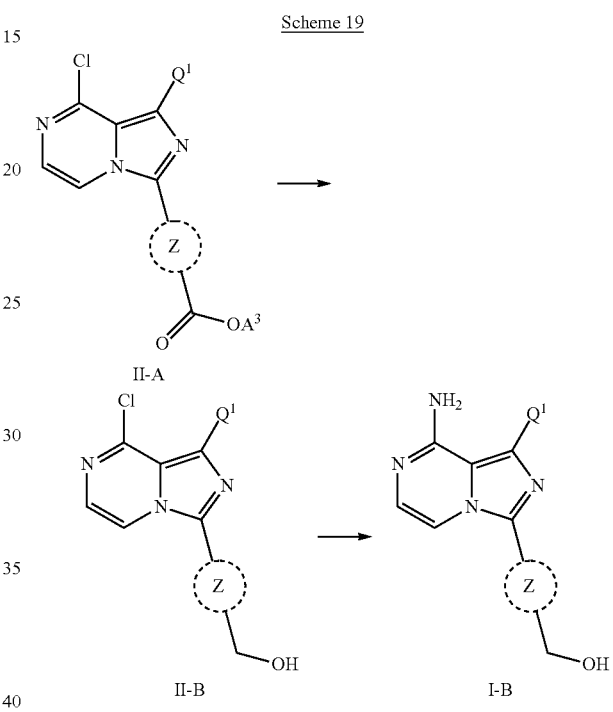

where Q¹ is as defined previously for compound of Formula I and A³=hydrogen or alkyl such as methyl or ethyl.

In a typical preparation of compound of Formula I-B, compound of Formula II-A is treated with a suitable reducing agent such as lithium aluminum hydride in a suitable solvent, such as THY to afford compound of Formula II-B. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used. The preferred solvent was THF. The above process was carried out at temperatures between about −78° C. and about 120° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Subsequent treatment of compound of Formula II-B under previously described ammonolysis conditions (ammonia in isopropanol in a sealed tube at 120° C.), afforded compound of Formula I-B.

The compounds of Formula II-C (compounds of Formula II where $R^1=Z—CH_2A^4$), II-D (compounds of Formula II where $R^1=Z—CH_2A^5(R^2)(R^3)_d$), I-B (compounds of Formula I-AA where $R^1=Z—CH_2OH$) and I-C (compounds of Formula I-AA where $R^1=Z—CH_2A^5(R^2)(R^3)_d$) were prepared as shown below in Scheme 20:

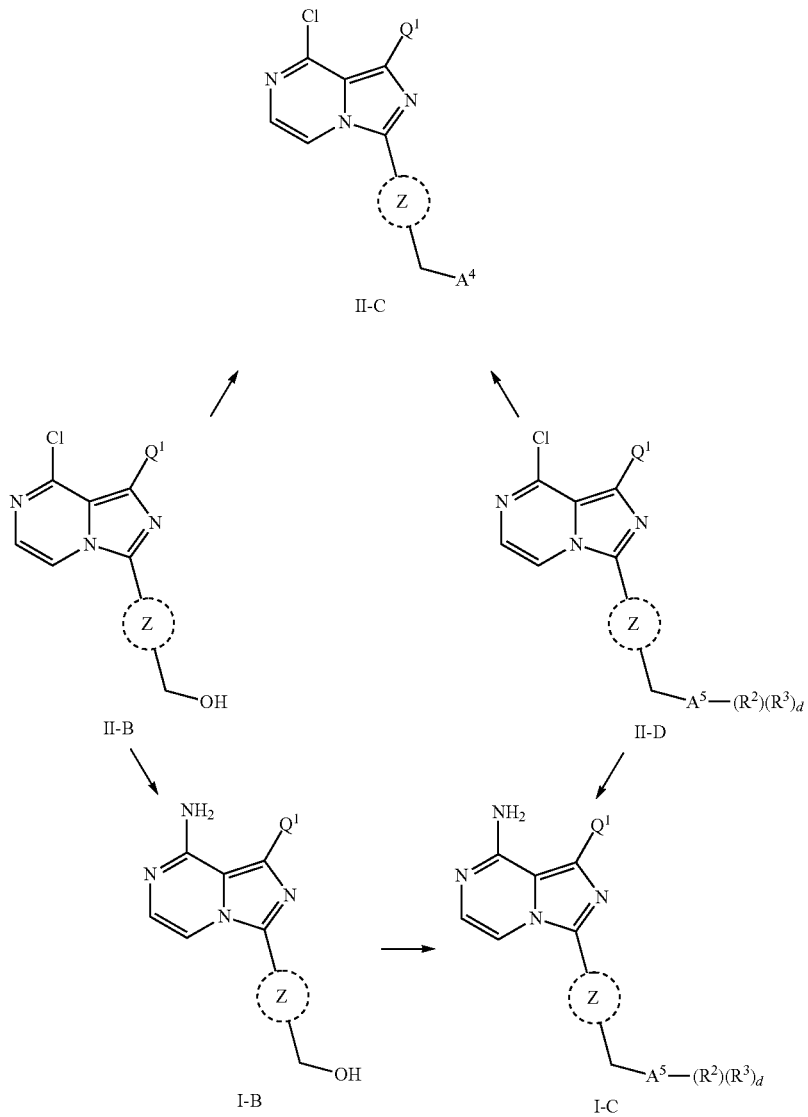

Scheme 20 where $Q^1$, $R^2$, and $R^3$ are as defined previously for compound of Formula I; $A^4$ suitable leaving group such as OTs, OMs, OTf, or halo such as chloro, bromo, or iodo; d=0 or 1; and $A^5=N$, O or S.

In a typical preparation of compound of Formula I-C, the hydroxy group of compound of Formula II-B was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C. Reaction of compound of Formula II-C with $HA^5(R^2)(R^3)_d$ afforded compound of Formula II-D. Subsequent reaction of compound of Formula II-D under previously described ammonolysis conditions afforded compound of Formula I-C. Additionally, compound of Formula II-B was converted to compound of Formula I-B as described previously in Scheme 19. Further conversion of compound of Formula I-B to compound of Formula I-C was accomplished by following the previously described conditions for the conversion of compound of Formula II-B to compound of Formula II-C and the further conversion of compound of Formula II-C to compound of Formula II-D (in the net conversion of OH to $A^5(R^2)(R^3)_d$). Furthermore, compound of Formula II-B can be directly converted to compound of Formula II-D by treating compound of Formula II-B with various alkylating agent or with phenols via the Mitsunobu reaction to afford compounds Formula II-D (compounds of Formula II where $R^1=CH_2-Z-A^5(R^2)(R^3)_d$ in which $A^5=O$, d=0, and $R^2$=alkyl or aryl).

The compounds of Formula I-C' (compounds of Formula I-AA where $R^1=Z—CH_2-A^2$), I-C'' (compounds of Formula I-AA where $R^1=Z—CH_2—NH_2$), and I-C''' (compounds of Formula I-AA where $R^1=Z—CH_2—N(R^2)(R^3)$) were prepared as shown below in Scheme 21:

Scheme 21

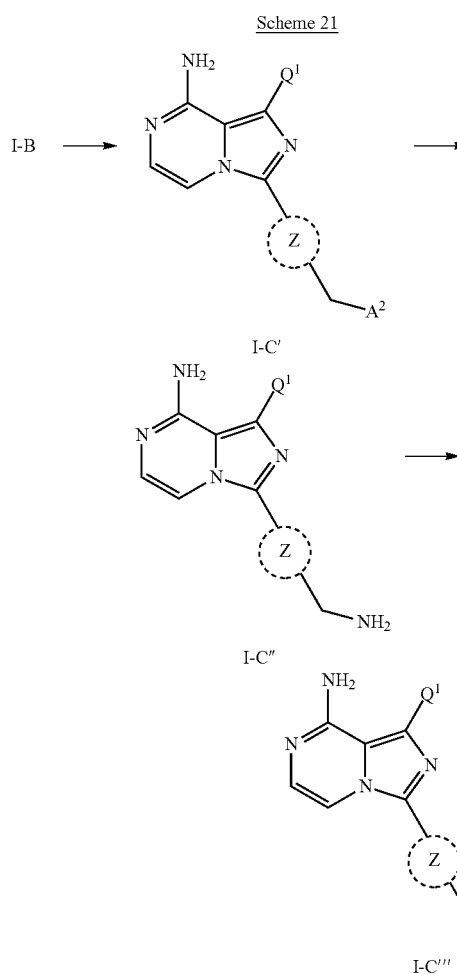

where $Q^1$, $R^2$, and $R^3$ are as defined previously for compound of Formula I and $A^2$=phthalimido or $N_3$.

In a typical preparation of compounds of Formula I-C', I-C", and I-C''', the hydroxy group of compound of Formula I-B was converted to $A^2$, following the procedures as described in Scheme 5 for the conversion of compound of Formula VII to compound of Formula VI. Reaction of compound of Formula I-C' under conditions described in Scheme 4 afforded compound of Formula I-C". Reaction of compound of Formula I-C" with, but not limited to various alkylating agents, various aldehydes/ketones under reductive amination conditions, various acylating agents such as acetic anhydride, benzoyl chlorides, or with carboxylic acids in the presence of EDC or DCC with HOBT or HOAT, or with sulphonylating agents such as $Ts_2O$ or $MeSO_2Cl$ afforded compounds of Formula I-C'''. For example, in a typical preparation of compounds of Formula I-C''', a compound of Formula I-C" is treated with a suitable acylating agent in the presence of a suitable base in a suitable solvent. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$). If desired, mixtures of these solvents were used, however, the preferred solvent was chloroform. Suitable bases for use in the above process included, but were not limited to, trialkylamines such as diisopropylethylamine, triethylamine, or resin bound trialkylamines such as PS-DIEA. The preferred base was PS-DIEA. In the case where the suitable acylating agent was acetic anhydride, the conversion of compound of Formula I-C" to compound of Formula I-C''' where $R^2$=H and $R^3$=$COCH_3$ was accomplished. The above process was carried out at temperatures between about $-78°$ C. and about $120°$ C. Preferably, the reaction was carried out between $0°$ C. and about $20°$ C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I-D (compounds of Formula I-AA where $R^1$=$(CH_2)_n$—$Z^2$—H and $Z^2$ is a heterocyclyl ring containing a nitrogen atom connected to H) and I-E (compounds of Formula I-AA where $R^1$=$(CH_2)_n$—$Z^2$—$R^2$ and $Z^2$ is a heterocyclyl ring containing a nitrogen atom connected to $R^2$) were prepared as shown below in Scheme 22:

Scheme 22

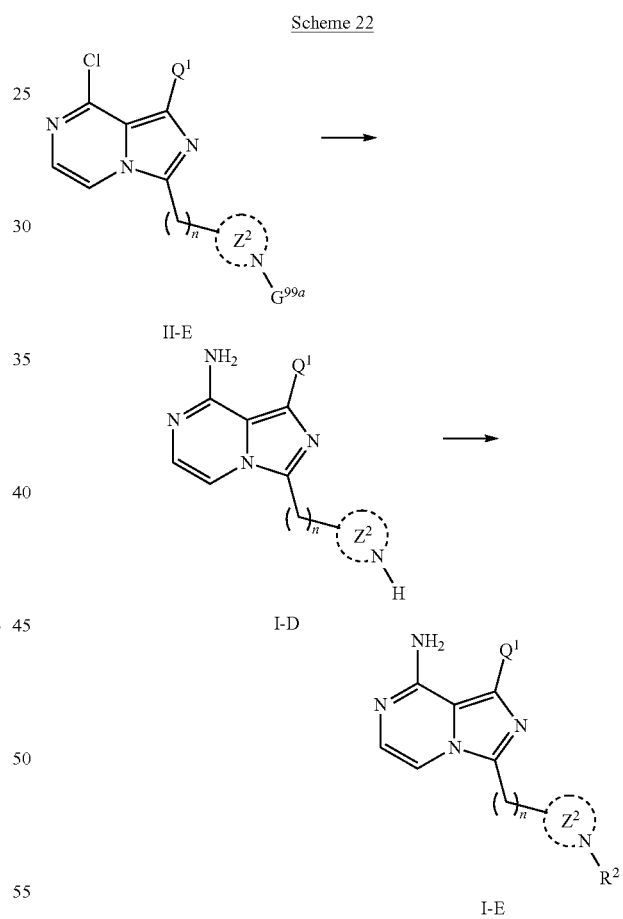

where $Q^1$ and $R^2$ are as defined previously for compound of Formula I, $G^{99a}$ is C(=O)$A^6$ or $CO_2A^6$, n=0-5, and $A^6$=alkyl, aryl, or aralkyl.

In a typical preparation of compound of Formula I-E, compound of Formula II-E is treated with suitable reagents capable of converting N-$G^{99a}$ to N-H and therefore afford compound of Formula I-D. For example, treatment of compound of Formula II-E (when $G^{99a}$ is equal to $CO_2Bn$) under previously described ammonolysis conditions followed by treatment with concentrated HCl and a suitable basic workup, affords compound of Formula I-D. Compound of Formula I-D can be subjected to various conditions including but not limited to reductive aminations, alkylations and ar(hetar)ylations, and acylations to afford amides, ureas, guanidines, carbamates, thiocarbamates, sulphonamides, and variously substituted nitrogen adducts to afford the net conversion of NH to $NR^2$.

The compounds of Formula II-G (compounds of Formula II where $R^1=Z^3$—OH), II-H (compounds of Formula II where $R^1=Z-A^5(R^2)(R^3)_d$), I-F (compounds of Formula I-AA where $R^1=Z$—OH), and I-G (compounds of Formula I-AA where $R^1=Z-A^5(R^2)(R^3)_d$) were prepared as shown below in Scheme 23:

II-H (compounds of Formula II where $R^1=Z-A^5(R^2)(R^3)_d$ where d=0, $A^5=N$, and $R^2$ and $R^3$ are as previously described for compound of Formula I) with previously described ammonolysis conditions afforded compounds of Formula I-G. Furthermore, compounds of Formula II-H from II-G and I-G from I-F can be synthesized according to the conditions described in Scheme 20 for the transformations of II-B to II-D and I-B to I-C, respectively.

The compounds of Formula I-C''' (compounds of Formula I-AA where $R^1=Z$—$CH_2$—$N(R^2)(R^3)$) were prepared as shown below in Scheme 24:

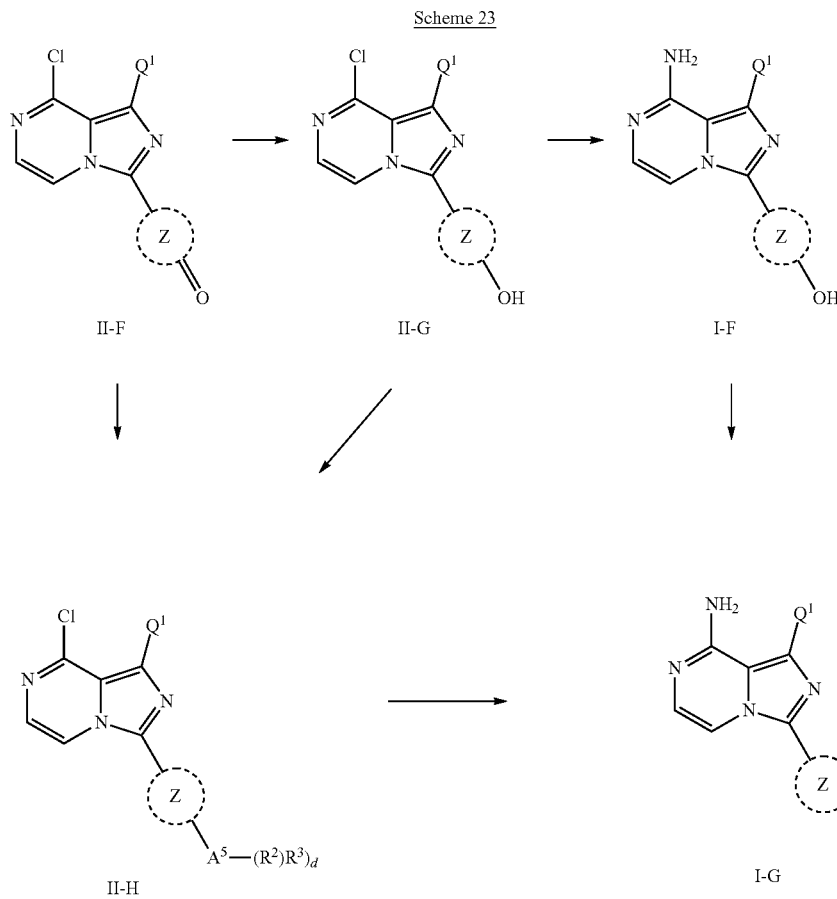

where $Q^1$, $R^2$, and $R^3$ are as defined previously for compound of Formula I; d=0 or 1; and $A^5=N$, O or S.

In a typical preparation of compound of Formula I-F and I-G, the following transformations occurred: Compound of Formula II-F was reduced with a suitable reducing agent in a suitable solvent, such as sodium borohydride in methanol to afford compound of Formula II-G. Compound of Formula II-G was subjected to previously described ammonolysis conditions to afford compound of Formula I-F. Additionally, compounds of Formula II-F can be reacted with various amines under reductive amination conditions ($NaBH_3CN$ or $NaBH(OAc)_3$ with $HA^5(R^2)(R^3)_d$ where d=0, $A^5=N$, and $R^2$ and $R^3$ are as previously described for compound of Formula I) to afford compounds of Formula II-H where d=0, $A^5=N$, and $R^2$ and $R^3$ are as previously described for compound of Formula I. Subsequent reaction of compounds of Formula

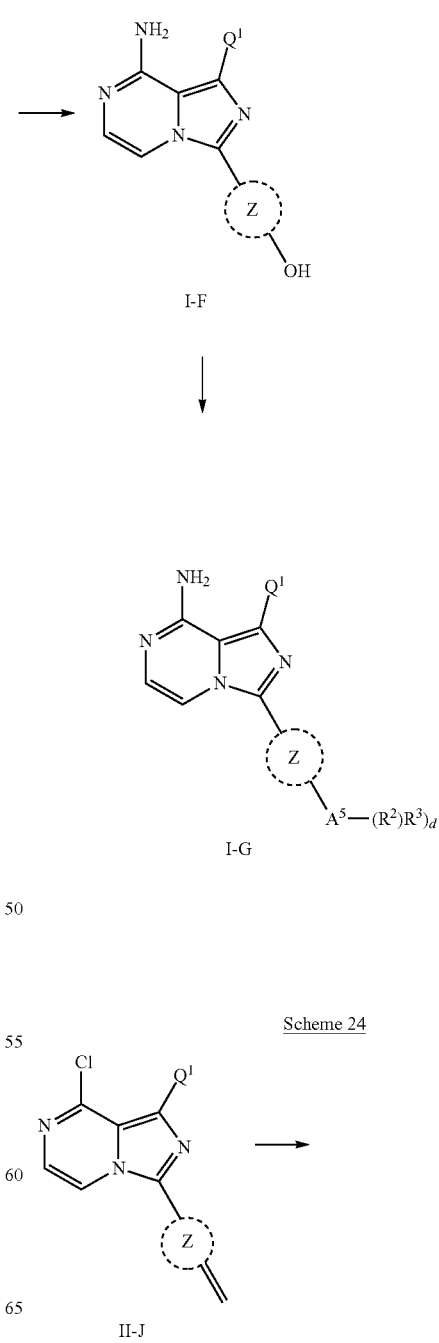

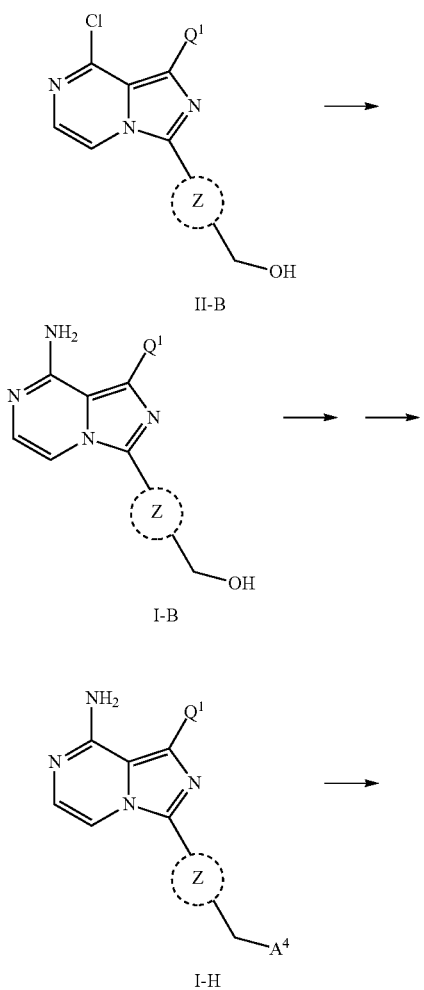

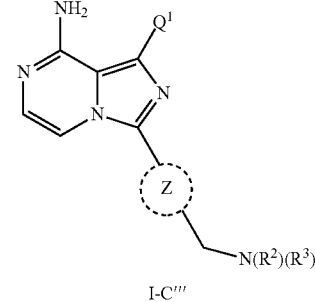

where $Q^1$, $R^2$, and $R^3$ are as defined previously for compound of Formula I and $A^4$=suitable leaving group such as Cl, OTs, OMs or OTf.

In a typical preparation of compound of Formula I-C''' (compounds of Formula I-AA where $R^1$=Z—$CH_2$—N($R^2$)($R^3$)), the following transformations occurred: Compounds of Formula II-J (compounds of Formula II where $R^1$=Z=$CH_2$) were reacted with a suitable hydroborating agent such as diborane, 9-borabicyclo[3.3.1]nonane (9-BBN), catecholborane and the like, in a suitable solvent such as THF followed by treatment with an suitable oxidizing agent such as hydrogen peroxide in basic aqueous solution or $NaBO_3.H_2O$ to afford compounds of Formula II-B. Further reaction of compounds of Formula II-B with previously described ammonolysis conditions afforded compounds of Formula I-B. The hydroxy group of compounds of Formula I-B was then converted to a suitable leaving group, $A^4$, such OTs, OMs, or OTf, by reaction with $Ts_2O$, $Ms_2O$, or $Tf_2O$, respectively, to afford compounds of Formula I-H. Further reaction of compounds of Formula I-H with HN($R^2$)($R^3$) where $R^2$ and $R^3$ are as previously described for compounds of Formula I afforded compound of Formula I-C''' (compounds of Formula I-AA where $R^1$=Z—$CH_2$—N($R^2$)($R^3$)).

The compounds of Formula I-J (compounds of Formula I-AA where $R^1$=Z—OH($CH_2OH$)), I-K (compounds of Formula I-AA where $R^1$=Z=O), and I-L (compounds of Formula I-AA where $R^1$=Z—$NR^2R^3$) were prepared as shown below in Scheme 25:

Scheme 25

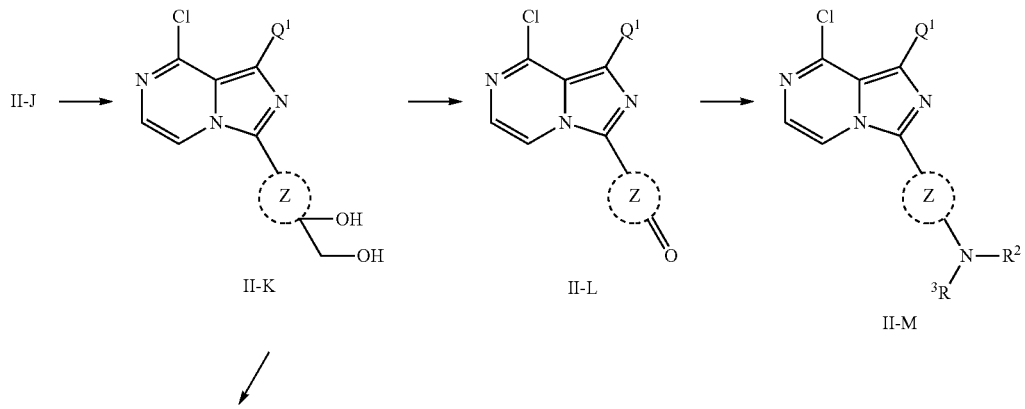

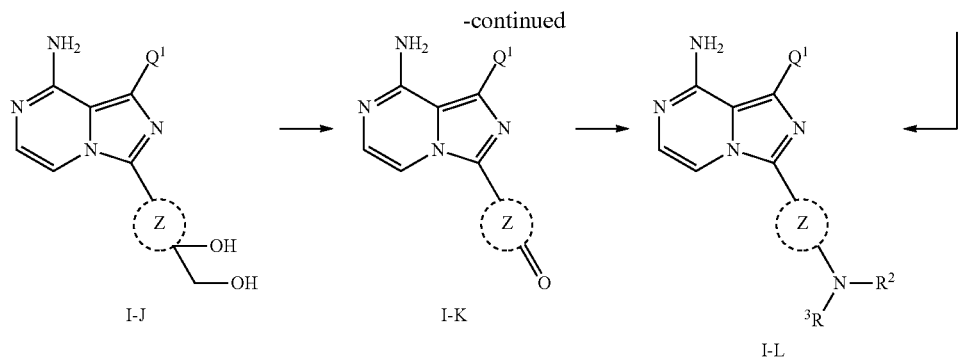

where $Q^1$, $R^2$ and $R^3$ are as defined previously for compound of Formula I.

In a typical preparation of compound of Formula I-J (compounds of Formula I-AA where $R^1$=Z—OH(CH$_2$OH)), I-K (compounds of Formula I-AA where $R^1$=Z=O), and I-L (compounds of Formula I-AA where $R^1$=Z—NR$^2$R$^3$) compound of Formula II-J was treated under (compounds of Formula II where $R^1$=Z=CH$_2$) was reacted with a suitable dihydroxylating agent such as osmium tetraoxide in the presence of NMO in a suitable solvent such as THF to afford compound of Formula II-K (compounds of Formula II where $R^1$=Z—OH(CH$_2$OH)) as a mixture of cis and trans isomers. Compounds of Formula II-K (compounds of Formula II where $R^1$=Z—OH(CH$_2$OH)) were treated with a suitable oxidizing agent, such as but not limited to, NaIO$_4$, converting the diol into a ketone moiety, affording compound of Formula II-L (compounds of Formula II where $R^1$=Z=O). Compound of Formula II-L (compounds of Formula II where $R^1$=Z=O) was then treated under typical reductive amination conditions, involving a suitable amine, HNR$^2$R$^3$ and a suitable reducing agent, such as but not limited to, NaBH(OAc)$_3$ or NaBH(CN)$_3$, affording compound of Formula II-M (compounds of Formula II where $R^1$=Z—NR$^2$R$^3$). Compound of Formula II-M (compounds of Formula II where $R^1$=Z—NR$^2$R$^3$) was treated under ammonolysis conditions, ammonia in isopropanol in a stainless steel bomb at 110° C., to afford compound of Formula I-L (compounds of Formula I-AA where $R^1$=Z—NR$^2$R$^3$). Moreover, compound of Formula II-K (compounds of Formula II where $R^1$=Z—OH(CH$_2$OH)) was treated under the ammonolysis conditions described above to afford compound of Formula I-J (compounds of Formula I-AA where $R^1$=Z—OH(CH$_2$OH)) as a mixture of isomers. Compound of Formula I-J (compounds of Formula I-AA where $R^1$=Z—OH(CH$_2$OH)) was treated with a suitable oxidizing agent, such as but not limited to, NaIO$_4$, converting the diol into a ketone moiety, affording compound of Formula I-K (compounds of Formula I-AA where $R^1$=Z=O), which was treated under the typical reductive amination conditions described above to afford compound of Formula I-L (compounds of Formula I-AA where $R^1$=Z—NR$^2$R$^3$).

The compounds of Formula I-N (compounds of Formula I-AA where $R^1$=Z—OH(CH$_2$NR$^2$R$^3$)) were prepared as shown below in Scheme 26:

where $Q^1$, $R^2$, and $R^3$ are as defined previously for compound of Formula I; $A^4$=suitable leaving group such as OTs, OMs, or OTf.

In a typical preparation of compounds of Formula I-N (compounds of Formula I-AA where $R^1$=Z—OH (CH$_2$NR$^2$R$^3$)), the primary hydroxyl group of compound of Formula I-J (compounds of Formula I-AA where $R^1$=Z—OH (CH$_2$OH)) was converted to a suitable leaving group, $A^4$, such as OTs, OMs, or OTf, by reaction with Ts$_2$O, Ms$_2$O, or Tf$_2$O in the presence of a suitable base such as diisopropylamine or pyridine and solvent such as THF or methylene chloride to afford compound of Formula I-M (compounds of Formula I-AA where R¹=Z—OH(CH₂A⁴)). Reaction of compound of Formula I-M (compounds of Formula I-AA where R¹=Z—OH(CH₂A⁴)) with HN(R²)(R³) in a suitable solvent such as THF or methylene chloride afforded compound of Formula I-N (compounds of Formula I where R¹=Z—OH(CH₂NR²R³)).

The compounds of Formula I-O (compounds of Formula I where R¹=Z³—OH(G¹¹)) were prepared as shown below in Scheme 27:

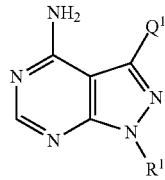

I-AB

Scheme 27

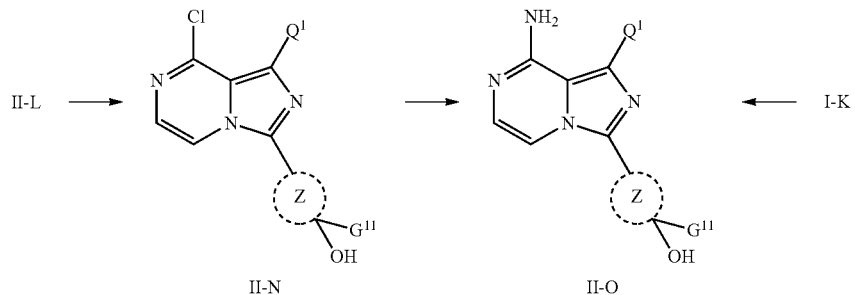

where Q¹ and G¹¹ are as defined previously for compound of Formula I.

In a typical preparation of compounds of Formula I-O (compounds of Formula I where R¹=Z—OH(G¹¹)), the ketone moiety of compound of Formula II-L (compounds of Formula II where R¹=Z=O) was reacted with a suitable nucleophilic reagent such as MeMgBr or MeLi in a suitable solvent such as THF to afford compound of Formula II-N (compounds of Formula II where R¹=Z—OH(G¹¹)). Compound of Formula II-N (compounds of Formula II where R¹=Z—OH(G¹¹)) was reacted under ammonolysis conditions, ammonia in isopropanol in a stainless steel bomb at 110° C., to afford compound of Formula I-O (compounds of Formula I where R¹=Z—OH(G¹¹)). Additionally, compound of Formula I-O (compounds of Formula I where R¹=Z—OH(G¹¹)) was prepared by reacting compound of Formula I-K (compounds of Formula I-AA where R¹=Z=O) with a suitable nucleophilic reagent such as MeMgBr or MeLi in a suitable solvent such as THF.

Compound of Formula I-AB is equal to compound of Formula I wherein X₁=CH, X₂, X₄ and X₅=N, and X₃, X₆ and X₇=C; Q¹ is as defined for a compound of Formula I; R¹ is C₁₋₁₀alkyl, cycloC₃₋₁₀alkyl, bicycloC₅₋₁₀alkyl, aryl, heteroaryl, aralkyl, heteroaralkyl, heterocyclyl, heterobicycloC₅₋₁₀alkyl, spiroalkyl, or heterospiroalkyl, any of which is optionally substituted by one or more independent G¹¹ substituents; and G¹¹ is as defined for a compound of Formula I:

Method AB was used when preparing compounds of Formula I-AB as shown below in Scheme 28:

Method AB:

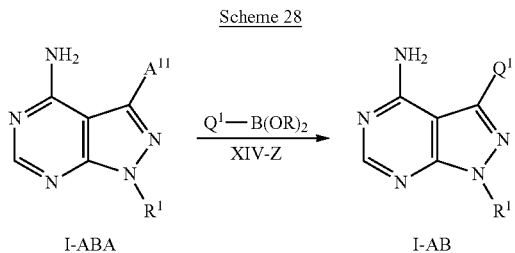

where Q¹ and R¹ are as defined previously for compound of Formula I-AB, A¹¹=halogen such as Cl, Br, or I, and Q¹-B(OR)₂=suitable boronic acid/ester.

In a typical preparation of compounds of Formula I-AB, compound of Formula I-ABA was reacted with a suitable boronic acid/ester of Formula XIV-Z (Q¹-B(OR)₂) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent systems were THF/water and DMF/water. The above process was carried out at temperatures between about 20° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AB from I-ABA. For example, compound of Formula I-ABA could be reacted with a suitable organotin reagent $Q^1$-$SnBu_3$ or the like in a suitable solvent via typical Stille coupling procedures.

The compounds of Formula I-ABA wherein $R^1$ is $C_{1-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents, of Scheme 28 were prepared as shown below in Scheme 29:

Scheme 29

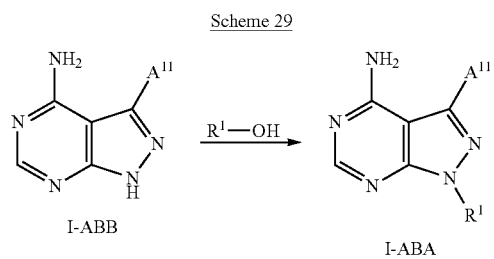

I-ABB    I-ABA where $R^1$ is $C_{1-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; $G^{11}$ is as defined previously for compound of Formula I, and $A^{11}$=halogen such as Cl, Br, or I.

In a typical preparation of a compound of Formula I-ABA, a compound of Formula I-ABB was reacted with an alcohol $R^1$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about −78° C. and about 100° C. Preferably, the reaction was carried out between about 0° C. and 25° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphosphine, DIAD, and $R^1$—OH was used per equivalent of compound of Formula I-ABB.

Alternatively, the compounds of Formula I-ABA may be prepared by alkylating compounds of Formula I-ABB with an alkylating agent $R^1$-LG, wherein LG is a leaving group including, but not limited to, chloride, bromide, iodide, tosylate, mesylate, trifluoromethanesulfonate, under typical alkylation conditions known to someone skilled in the art.

Preferably, in compounds of Formula I-ABB, $A^{11}$=Br and I. These compounds are known ($A^{11}$=I: H. B. Cottam et al., *J. Med. Chem.* 1993, 36 (22), 3424-3430; $A^{11}$=Br: T. S. Leonova et al., *Khim. Geterotsikl. Soedin.* 1982, (7), 982-984).

Compound of Formula I-AC is equal to compound of Formula I wherein $X_1$ and $X_5$=CH, $X_2$ and $X_4$=N, and $X_3$, $X_6$ and $X_7$=C; $Q^1$ is as defined for a compound of Formula I; $R^1$ is $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; and $G^{11}$ is as defined for a compound of Formula I:

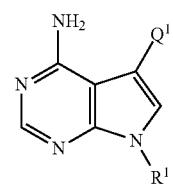

I-AC

Method AC was used when preparing compounds of Formula I-AB as shown below in Scheme 30:
Method AC:

Scheme 30

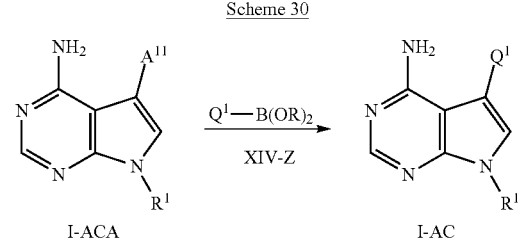

I-ACA    I-AC where $Q^1$ and $R^1$ are as defined previously for compound of Formula I-AC, $A^{11}$=halogen such as Cl, Br, or I and $Q^1$-B$(OR)_2$=suitable boronic acid/ester.

In a typical preparation of compounds of Formula I-AC, compound of Formula I-ACA was reacted with a suitable boronic acid/ester XIV-Z ($Q^1$-B$(OR)_2$) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent systems were THF/water and DMF/water. The above process was carried out at temperatures between about 20° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of formula I-AC from I-ACA. For example, compound of Formula I-ACA could be reacted with a suitable organotin reagent $Q^1$-SnBu$_3$ or the like in a suitable solvent via typical Stille coupling procedures.

The compounds of Formula I-ACA of Scheme 30 were prepared as shown below in Scheme 31:

Scheme 31

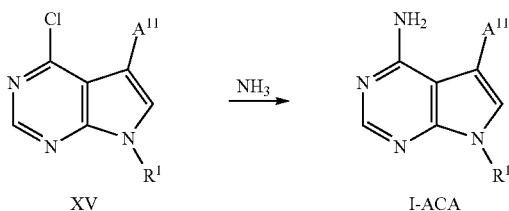

where $R^1$ is as defined previously for compound of Formula I-AC, and $A^{11}$=halogen such as Cl, Br, or I.

In a typical preparation of compounds of Formula I-ACA, compound of Formula XV was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was isopropanol. The above process was carried out at temperatures between about $-78°$ C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used.

The compounds of Formula XVA (=compounds of Formula XV of Scheme 31 wherein $R^1$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents) were prepared as shown below in Scheme 32:

Scheme 32

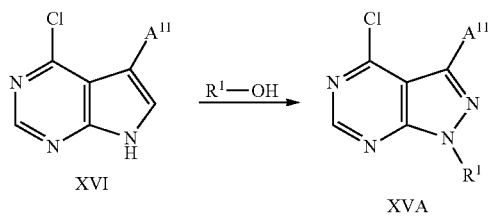

where $R^1$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents; G$^{11}$ is as defined previously for compound of Formula I; and $A^{11}$=halogen such as Cl, Br, or I.

In a typical preparation of a compound of Formula XVA, a compound of Formula XVI was reacted with an alcohol $R^1$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about $-78°$ C. and about 100° C. Preferably, the reaction was carried out between about 0° C. and 25° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphosphine, DIAD, and $R^1$—OH was used per equivalent of compound of Formula XVI.

Alternatively, the compounds of Formula XVA may be prepared by alkylating compounds of Formula XVI with an alkylating agent $R^1$-LG, wherein LG is a leaving group including, but not limited to, chloride, bromide, iodide, tosylate, mesylate, trifluoromethanesulfonate, under typical alkylation conditions known to someone skilled in the art.

The compounds of Formula XVB (=compounds of Formula XV of Scheme 31 wherein $R^1$ is aryl or heteroaryl, optionally substituted by one or more independent G$^{11}$ substituents) were prepared as shown below in Scheme 33:

Scheme 33

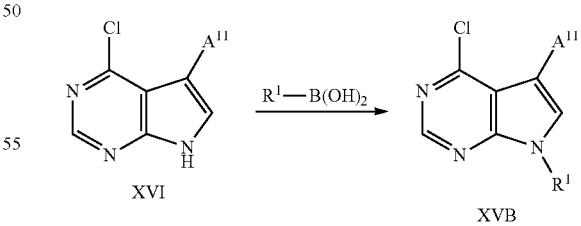

where $R^1$ is aryl or heteroaryl, optionally substituted by one or more independent G$^{11}$ substituents, G$^{11}$ is as defined previously for compound of Formula I; and $A^1$=halogen such as Cl, Br, or I.

In a typical preparation of compounds of Formula XVB, compound of Formula XVI was reacted with a suitable boronic acid of Formula $R^1\text{-B(OH)}_2$ in a suitable solvent via typical copper(II)-mediated coupling procedures. Suitable solvents for use in the above process included, but were not limited to, ethers such as tetrahydrofuran (THF), glyme, 1,4-dioxane, and the like; dimethylformamide (DMF); N-methylpyrrolidinone (NMP); chlorinated solvents such as methylene chloride ($CH_2Cl_2$). If desired, mixtures of these solvents were used, however, the preferred solvent was methylene chloride ($CH_2Cl_2$). Suitable reactants for use in the above process included, but were not limited to, copper(II) acetate ($Cu(OAc)_2$), copper(II) triflate ($Cu(OTf)_2$), and the like, and a base (pyridine, and the like). The preferred reactants were $Cu(OAc)_2$ and pyridine. The above process to produce compounds of the present invention was preferably carried out at about atmospheric pressure under air, although higher or lower pressures could be used if desired. Preferably, the reaction was carried out at about 22° C. Generally, 1.5 eq. of copper(II) acetate, 2 eq. of pyridine, and 2 eq. of boronic acid of Formula $R^1\text{-B(OH)}_2$ were used per equivalent of compound of Formula XVI.

All compounds of Formula XVI are known in the literature ($A^{11}$=I: L. B. Townsend et al., *J. Med. Chem.* 1990, 33, 1984-92; $A^{11}$=Br, Cl: L. B. Townsend et al., *J. Med. Chem.* 1988, 31, 2086-2092). Preferably, $A^{11}$=Br and I.

Both $R^1$ and $Q^1$ in the compounds described herein in some instances contain functional groups that can be further manipulated. It would be appreciated by those skilled in the art that such manipulation of functional groups can be accomplished with key intermediates or with late stage compounds. Such functional group transformations are exemplified in the following Schemes 34-35 as well as in the experimental section but are in no way meant to limit the scope of such transformations.

The compounds of Formula I-ACA' (=compounds of Formula I-ACA where $R^1$=Z—$CONR^2R^3$) were prepared from compounds of Formula XV' (=compounds of Formula XV where $R^1$=Z—$CO_2A^3$) as shown below in Scheme 34:

Scheme 34

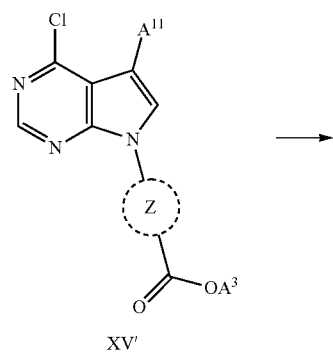

XV'

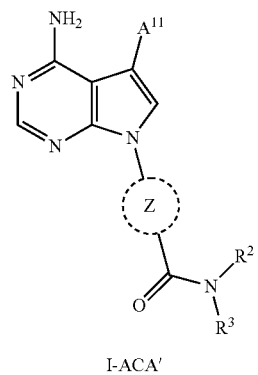

I-ACA' where $R^2$ and $R^3$ are as defined previously for compound of Formula I; $A^{11}$=halogen such as Cl, Br, or I; and $A^3$=hydrogen or alkyl such as methyl or ethyl.

In a typical preparation of compound of Formula I-ACA', when $A^3$=alkyl and $R^2$ and $R^3$ were both equal to H, reaction of compound of Formula XV' with ammonia in a suitable solvent, afforded compound of Formula I-ACA'. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about –78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used. Additionally, in a typical preparation of compound of Formula I-ACA' (compounds of Formula I-ACA where $R^1$=Z—$CONR^2R^3$), compound of Formula XV' (compounds of Formula XV' where $R^1$=Z—$CO_2A^3$) was reacted with $HNR^2R^3$ followed by ammonia in a suitable solvent. When $A^3$=H, typical coupling procedures (such as conversion of —$CO_2H$ to —COCl via treatment with $SOCl_2$ or oxalyl chloride followed by reaction with $HNR^2R^3$ or treatment of —$CO_2H$ and $HNR^2R^3$ with EDC or DCC in conjunction with DMAP, HOBT, or HOAt and the like) were employed to afford the transformation of a carboxylic acid to an amide. When $A^3$=alkyl such as methyl or ethyl, treatment of the ester with $Al(NR^2R^3)$ afforded conversion of —$CO_2A^3$ to —$CO(NR^2R^3)$. Subsequent treatment with ammonia afforded compounds of Formula I-ACA'.

The chemistry shown in Scheme 34 can also be applied to compounds with $Q^1$ in place of $A^{11}$.

The compounds of Formula XVIII (compounds of Formula XV, I-ACA, or I-AC where $R^1$=Z—$CH_2OH$), XIX (compounds of Formula XV, I-ACA, or I-AC where $R^1$=Z—$CH_2LG$), and XX (compounds of Formula XV, I-ACA, or I-AC where $R^1$=Z—$CH_2A^5(R^2)(R^3)_d$) were prepared as shown below in Scheme 35:

Scheme 35

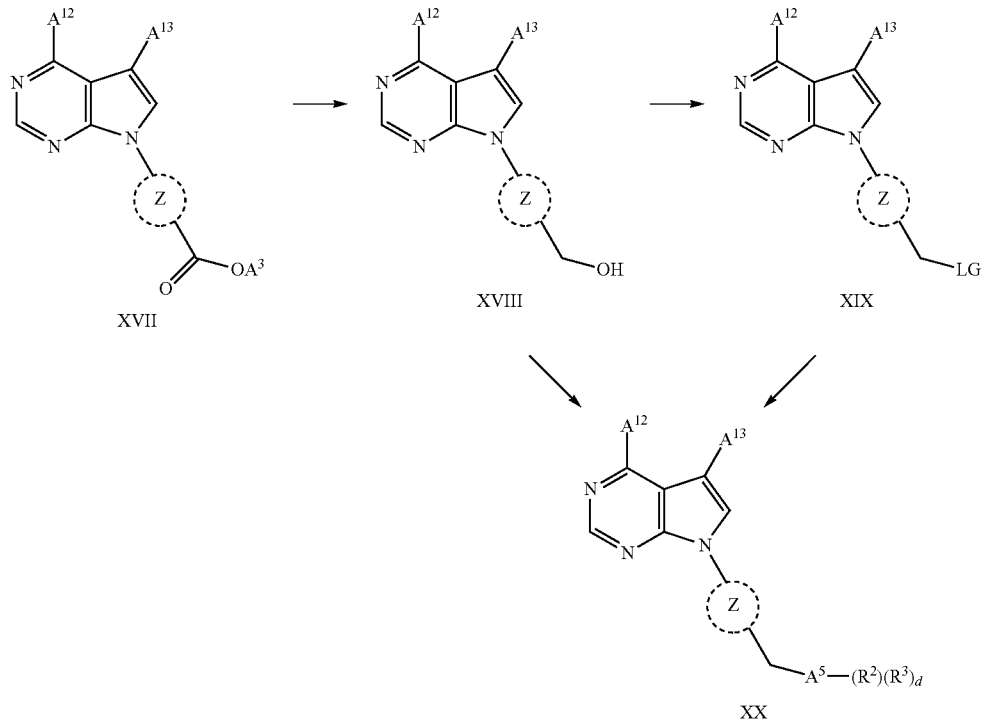

where $Q^1$, $R^2$, and $R^3$ are as defined previously for compound of Formula I; LG=suitable leaving group such as tosylate, mesylate, trifluoromethanesulfonate, or halo such as chloro, bromo, or iodo; d=0 or 1; $A^3$=hydrogen or alkyl such as methyl or ethyl; $A^{11}$=halogen such as Cl, Br, or I; $A^{12}$=Cl or $NH_2$; $A^{13}=A^{11}$ or $Q^1$; and $A^5$=N, O or S.

The following table indicates the relations between the compounds of Formulas XVII-XX, $A^{12}$, $A^{13}$, compounds of Formulas I-AC, I-ACA, and XV, and $R^1$.

| Compound of Formula... | wherein $A^{12}$ = | and $A^{13}$ = | ...is equal to Formula... | wherein $R^1$ = |
|---|---|---|---|---|
| XVII | Cl | $A^{11}$ | XV | $Z-CO_2A^3$ |
| XVII | $NH_2$ | $A^{11}$ | I-ACA | $Z-CO_2A^3$ |
| XVII | $NH_2$ | $Q^1$ | I-AC | $Z-CO_2A^3$ |
| XVIII | Cl | $A^{11}$ | XV | $Z-CH_2OH$ |
| XVIII | $NH_2$ | $A^{11}$ | I-ACA | $Z-CH_2OH$ |
| XVIII | $NH_2$ | $Q^1$ | I-AC | $Z-CH_2OH$ |
| XIX | Cl | $A^{11}$ | XV | $Z-CH_2LG$ |
| XIX | $NH_2$ | $A^{11}$ | I-ACA | $Z-CH_2LG$ |
| XIX | $NH_2$ | $Q^1$ | I-AC | $Z-CH_2LG$ |
| XX | Cl | $A^{11}$ | XV | $Z-CH_2A^5R^2(R^3)_d$ |
| XX | $NH_2$ | $A^{11}$ | I-ACA | $Z-CH_2A^5R^2(R^3)_d$ |
| XX | $NH_2$ | $Q^1$ | I-AC | $Z-CH_2A^5R^2(R^3)_d$ |

In a typical preparation of compound of Formula XVIII (compounds of Formula XV, I-ACA, or I-AC, where $R^1$=Z—$CH_2OH$), compound of Formula XVII (compounds of Formula XV, I-ACA, or I-AC, where $R^1$=Z—$CO_2A^3$) is treated with a suitable reducing agent, such as lithium aluminum hydride or diisobutylaluminum hydride, in a suitable solvent, such as THF or methylene chloride, to afford compound of Formula XVIII. In a typical preparation of compound of Formula XX (compounds of Formula XV, I-ACA, or I-AC, where $R^1$=Z—$CH_2A^5(R^2)(R^3)_d$), the hydroxy group of compound of Formula XVIII was converted to a suitable leaving group, LG, such as Cl or tosylate, mesylate, or triflate, by reaction with $SOCl_2$ or $Ts_2O$, $Ms_2O$, or $Tf_2O$ to afford compound of Formula XIX (compounds of Formula XV, I-ACA, or I-AC, where $R^1$=Z—$CH_2LG$). Reaction of compound of Formula XIX with $HA^5(R^2)(R^3)_d$ afforded compound of Formula XX. Furthermore, compound of Formula XVIII can be directly converted to compound of Formula XX by treating compound of Formula XVIII with various alkylating agents or under typical Mitsunobu reaction conditions to afford compounds of Formula XX (compounds of Formula XV, I-ACA, or I-AC, where $R^1$=Z—$CH_2A^5(R^2)(R^3)_d$) in which $A^5$=O, d=0, and $R^2$=alkyl or aryl). Someone skilled in the art will choose the most appropriate stage during the sequence shown in Scheme 35 to convert $A^{12}$=Cl to $A^{12}$=$NH_2$ as described in Scheme 31, and to convert $A^{13}=A^{11}$ to $A^{13}=Q^1$ as described in Scheme 30, if applicable.

An alternative preparation of compounds of Formula I-AC is shown in Scheme 36.

Scheme 36

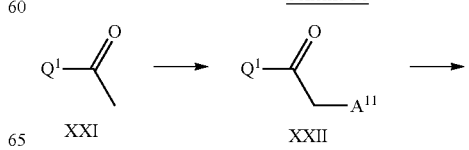

-continued

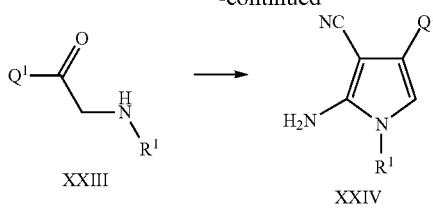

Method AQ was used when preparing compounds of Formula I-AQ as shown below in Scheme 37:

Method AQ:

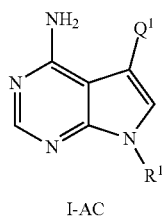

where $Q^1$ and $R^1$ are as defined previously for compound of Formula I; and $A^{11}$=halogen such as Cl, Br, or I.

The compounds of Formula XXI may be prepared from aldehydes $Q^1$-CHO (see scheme 14 for their preparation) by addition of methyllithium or a methyl Grignard reagent, followed by oxidation of the resulting alcohol to the ketone of Formula XXI. Other compounds are commercially available or can be prepared by methods well known to someone skilled in the art, see: Larock, R. C. *Comprehensive Organic Transformations*, 2$^{nd}$ ed.; Wiley and Sons: New York, 1999, 1197ff. Reaction of compounds of Formula XXI under typical halogenation conditions with typical halogenating agents including, but not limited to, Br$_2$, NBS, pyridinium perbromide, or CuBr$_2$ (for A$^{11}$=Br), or NCS or SO$_2$Cl$_2$ (for A$^{11}$=Cl) gives the compounds of Formula XXII. Their reaction with amines of Formula H$_2$N—R$^1$ gives the aminoketones of Formula XXIII that are converted to aminocyanopyrroles of Formula XXIV by reaction with malononitrile under basic conditions. Finally, reaction of compounds of Formula XXIV under typical cyclization conditions gives the compounds of Formula I-AC. Conditions for this cyclization include, but are not limited to, heating with formamide; heating with formamide and ammonia; sequential treatment with a trialkyl orthoformate, ammonia, and a base; sequential treatment with formamidine and ammonia.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Compound of Formula I-AQ is equal to compound of Formula I wherein $X_1$=CH, $X_2$, $X_3$ and $X_5$=N, and $X_4$, $X_6$, and $X_7$=C:

Scheme 37

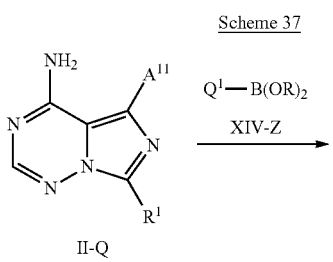 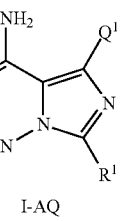

where $Q^1$ and $R^1$ are as defined previously for compound of Formula I, $A^{11}$=halogen such as Cl, Br, or I and B(OR)$_2$=suitable boronic acid/ester.

In a typical preparation of compounds of Formula I-AQ, compound of Formula II-Q was reacted with a suitable boronic acid/ester ($Q^1$-B(OR)$_2$) in a suitable solvent via typical Suzuki coupling procedures. Suitable solvents for use in the above process included, but were not limited to, water, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was glyme/water. The above process was carried out at temperatures between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AQ from II-Q. For example, compound of Formula II-Q could be reacted with a suitable organotin reagent $Q^1$-SnBu$_3$ or the like in a suitable solvent via typical Stille coupling procedures.

The compounds of Formula II-Q of Scheme 37 were prepared as shown below in Scheme 38.

Scheme 38

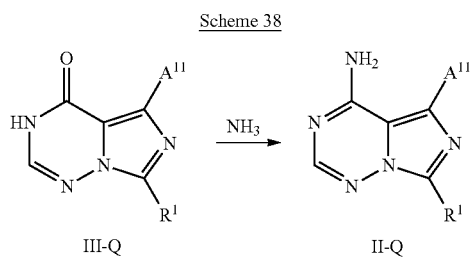

where $R^1$ is as defined previously for compound of Formula I and $A^{11}$=halogen such as Cl, Br, or I.

In a typical preparation of compounds of Formula II-Q, compound of Formula III-Q was reacted with phosphorus oxychloride (POCl$_3$) and triazole, and pyridine followed by ammonia (NH$_3$) in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was isopropanol. The above process was carried out at temperatures between about –20° C. and about 50° C. Preferably, the reaction was carried out between 0° C. and about 25° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula of Scheme 38 were prepared as shown below in Scheme 39.

Scheme 39

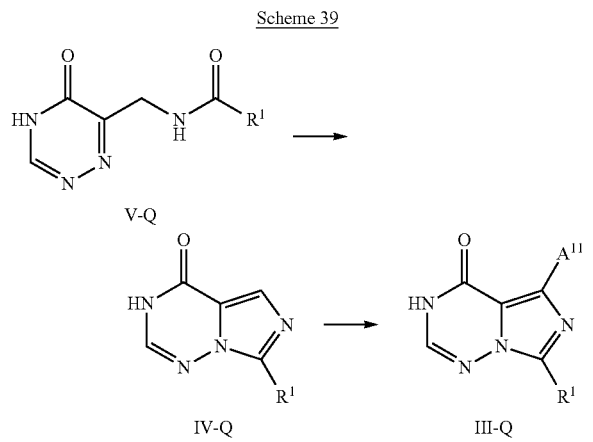

where $R^1$ is as defined previously for compound of Formula I and $A^{11}$=halogen such as Cl, Br, or I.

In a typical preparation of a compound of Formula III-Q, intermediate V-Q was converted to compound of Formula IV-Q. Intermediate of Formula V-Q was treated with phosphorus oxychloride (POCl$_3$) in a suitable solvent at a suitable reaction temperature. Suitable solvents for use in the above process included, but were not limited to, ethers such as tetrahydrofuran (THF), glyme, and the like, chlorinated solvents such as methylene chloride (CH$_2$Cl$_2$) or chloroform (CHCl$_3$), and acetonitrile. If desired, mixtures of these solvents were used. The preferred solvent was acetonitrile. The above process was carried out at temperatures between about –78° C. and about 120° C. Preferably, the reaction was carried out between 40° C. and about 95° C. The above process to produce compounds of the present invention was preferably carried out at about atmospheric pressure although higher or lower pressures were used if desired. Intermediate for Formula III-Q was prepared by reacting intermediate of Formula IV-Q with a suitable halogenating agent. Suitable halogenating agents included, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was DMF. The above process was carried out at temperatures between about –78° C. and about 120° C. Preferably, the reaction was carried out between 40° C. and about 75° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula V-Q of Scheme 39 were prepared as shown below in Scheme 40:

Scheme 40

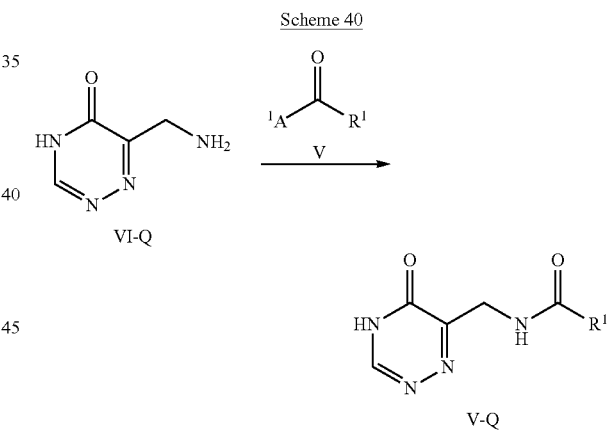

where $R^1$ is as defined previously for compound of Formula I and $A^1$=OH, alkoxy, or a leaving group such as chloro or imidazole.

In a typical preparation, of a compound of Formula V-Q, a compound of Formula VI-Q and compound of Formula V were reacted under suitable amide-coupling conditions. Suitable conditions include but are not limited to treating compounds of Formula VI-Q and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Alternatively, compounds of Formula VI-Q and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; pyridine; halogenated solvents such as chloroform or methylene chloride. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula VI-Q and V (where $A^1$=F, Cl, Br, I) and base and substoichiometric amounts of DMAP were preferably used although higher or lower amounts were used if desired. Additionally, other suitable reaction conditions for the conversion of an amine (compound of Formula VI-Q) to an amide (compound of Formula V-Q) can be found in Larock, R. C. *Comprehensive Organic Transformations*, 2$^{nd}$ ed.; Wiley and Sons: New York, 1999, pp 1941-1949.

The compounds of Formula VI-Q of Scheme 40 were prepared as shown below in Scheme 41:

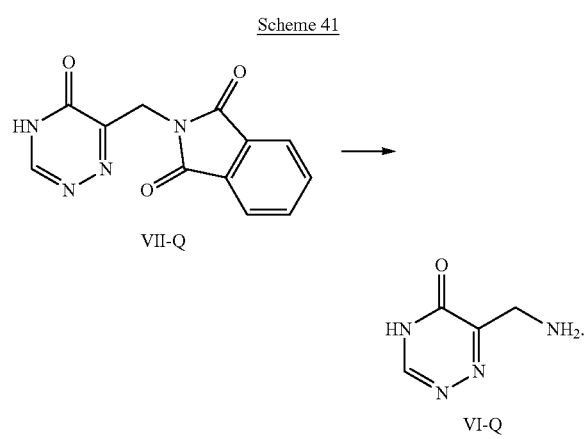

In a typical preparation, of a compound of Formula VI-Q, a compound of Formula VII-Q is reacted under suitable reaction conditions in a suitable solvent. Suitable conditions include treatment of compound of Formula VII-Q with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvents were ethanol and methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VII-Q of Scheme 41 were prepared as shown below in Scheme 42:

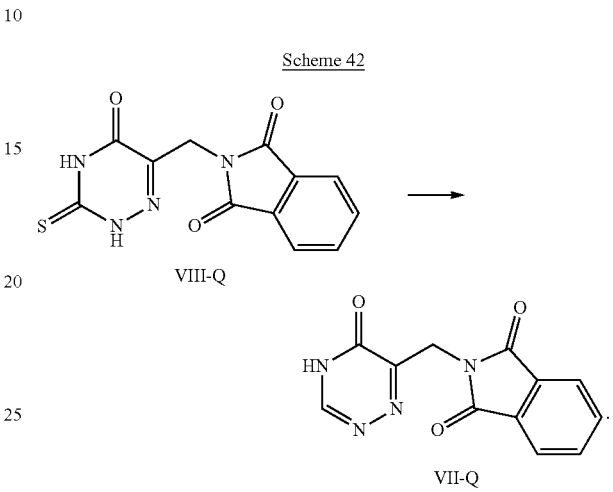

In a typical preparation of a compound of Formula VII-Q, a compound of Formula VIII-Q was reacted with Raney Nickel in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); alcohols such as methanol, ethanol, isopropanol, trifluoroethanol, and the like; chlorinated solvents such as methylene chloride (CH$_2$Cl$_2$) or chloroform (CHCl$_3$). If desired, mixtures of these solvents were used, however, the preferred solvent was ethanol. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially, equimolar amounts of reactants were preferably used although higher or lower amounts were used if desired. Additionally a compound of Formula VII-Q can be prepared by reacting a compound of Formula VIII-Q with a suitable oxidizing agent in a suitable solvent. A suitable oxidizing agent includes, but is not limited to hydrogen peroxide (H$_2$O$_2$), 3-chloro peroxybenzoic acid (mCPBA) and the like. Suitable solvents for use in the above process included, but were not limited to, ethers such as THF, glyme, and the like; DMF; DMSO; CH$_3$CN; and dimethylacetamide (DMA); chlorinated solvents such as CH$_2$Cl$_2$ or CHCl$_3$ If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VIII-Q of Scheme 42 were prepared as shown below in Scheme 43:

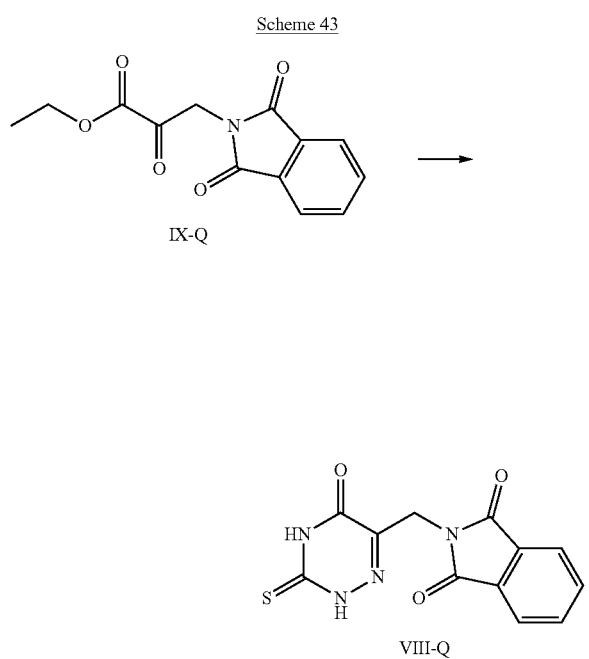

Scheme 43

IX-Q

VIII-Q

In a typical preparation of a compound of Formula VIII-Q, a compound of Formula IX-Q was reacted with thiosemicarbazide and a suitable base in a suitable solvent. Suitable bases include, but were not limited to triethylamine, ethyldiisopropylamine and the like. Suitable solvents for use in the above process included, but were not limited to, ethers such as tetrahydrofuran (THF), glyme, and the like; dimethylformamide (DMF); dimethylacetamide (DMA); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out between about 40° C. and 80° C. The above process to produce compounds of the present invention was preferably carried out at about atmospheric pressure although higher or lower pressures were used if desired. Substantially, equimolar amounts of reactants were preferably used although higher or lower amounts were used if desired. Compound of Formula IX-Q can be prepared according to literature procedures Knutsen, Lars J. S. et. al., *J. Chem. Soc. Perkin Trans 1: Organic and Bio-Organic Chemistry* (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

The following examples are intended to illustrate and not to limit the scope of the present invention.

General Experimental Information:

All melting points were determined with a MeI-Temp II apparatus and are uncorrected. Commercially available anhydrous solvents and HPLC-grade solvents were used without further purification. $^1H$ NMR and $^{13}C$ NMR spectra were recorded with Varian or Bruker instruments (400 MHz for $^1H$, 100.6 MHz for $^{13}C$) at ambient temperature with TMS or the residual solvent peak as internal standards. The line positions or multiplets are given in ppm (δ) and the coupling constants (J) are given as absolute values in Hertz, while the multiplicities in $^1H$ NMR spectra are abbreviated as follows: s (singlet), d (doublet), t (triplet), q (quartet), quint (quintet), m (multiplet), $m_c$ (centered multiplet), br (broadened), AA'BB'. The signal multiplicities in $^{13}C$ NMR spectra were determined using the DEPT135 pulse sequence and are abbreviated as follows: +(CH or $CH_3$), -($CH_2$), $C_{quart}$ (C). LC/MS analysis was performed using a Gilson 215 autosampler and Gilson 819 autoinjector attached to a Hewlett Packard HP 1100 and a MicromassZQ mass spectrometer (also referred to as "OpenLynx"), or a Hewlett Packard HP1050 and a Micromass Platform II mass spectrometer. Both setups used XTERRA MS C18 5µ 4.6×50 mm columns with detection at 254 nm and electrospray ionization in positive mode. For mass-directed purification (MDP), a Waters/Micromass system was used.

The tables below list the mobile phase gradients (solvent A: acetonitrile; solvent B: 0.01% formic acid in HPLC water) and flow rates for the analytical HPLC programs.

| Polar_5 min | | | | |
| --- | --- | --- | --- | --- |
| Time | A % | B % | Flow Rate (mL/min) MicromassZQ | Flow Rate (mL/min) Platform II |
| 0.00 | 5 | 95 | 1.3 | 1.3 |
| 3.00 | 90 | 10 | 1.3 | 1.3 |
| 3.50 | 90 | 10 | 1.3 | 1.3 |
| 4.00 | 5 | 95 | 1.3 | 1.3 |
| 5.00 | 5 | 95 | 1.3 | 1.3 |

| Nonpolar_5 min | | | | |
| --- | --- | --- | --- | --- |
| Time | A % | B % | Flow Rate (mL/min) MicromassZQ | Flow Rate (mL/min) Platform H |
| 0.00 | 25 | 75 | 1.3 | 1.3 |
| 3.00 | 99 | 1 | 1.3 | 1.3 |
| 3.50 | 99 | 1 | 1.3 | 1.3 |
| 4.00 | 25 | 75 | 1.3 | 1.3 |
| 5.00 | 25 | 75 | 1.3 | 1.3 |

Example 1

3-Cyclobutyl-1-(2-phenylquinolin-7-yl)-2H-imidazo[1,5-a]pyrazin-8-ylamine

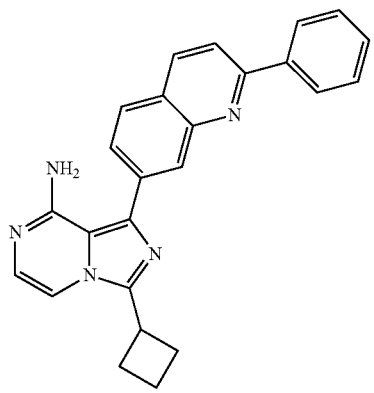 [SMILES: Nc1nccn2c(C3CCC3)nc(-c3ccc4ccc(-c5ccccc5)nc4c3)c12]

Gaseous NH₃ is condensed into a cooled (dry ice/acetone) solution of 7-(8-chloro-3-cyclobutylimidazo[1,5-a]pyrazin-1-yl)-quinoline (160.0 mg, 0.389 mmol) in 2M NH₃/iPrOH (4 mL) in a pressure tube until the volume is doubled, then the tube is sealed and heated to 110° C. (bath temp.) for 15 h. The solvents are evaporated, and the crude material is chromatographed on silica gel [Jones Flashmaster, 10 g/70 mL cartridge, eluting with CH₂Cl₂ (1-7)→1% MeOH in CH₂Cl₂ (8-23)→2% MeOH in CH₂Cl₂ (24-46)] to obtain the title compound as yellow solid; $^1$H NMR (CDCl₃, 400 MHz) δ 2.01-2.12 (m, 1H), 2.13-2.27 (m, 1H), 2.47-2.58 (m, 2H), 2.62-2.73 (m, 2H), 3.85 (quint, J=8.0 Hz, 1H), 6.00 (brs, 2H), 7.04 (d, J=5.4 Hz, 1H), 7.15 (d, J=5.4 Hz, 1H), 7.46-7.51 (m, 1H), 7.52-7.58 (m, 2H), 7.91 (dd, J=1.6, 8.4 Hz, 1H), 7.94 (d, J=8.4 Hz, 1H), 7.97 (d, J=8.0 Hz, 1H), 8.18-8.22 (m, 2H), 8.28 (d, J=8.4 Hz, 1H), 8.42 (d, J=0.8 Hz, 1H). $^{13}$C NMR (CDCl₃, 100.6 MHz, DEPT135): δ=18.89 (−), 26.92 (2C, +), 31.50 (+), 106.62 (+), 114.32 ($C_{quart}$), 119.26 (+), 126.55 ($C_{quart}$), 127.56 (3C, +), 128.06 (+), 128.15 (+), 128.83 (2C, +), 129.44 (+), 129.67 (+), 134.56 ($C_{quart}$), 136.42 ($C_{quart}$), 136.53 (+), 139.44 ($C_{quart}$), 144.40 ($C_{quart}$), 148.18 ($C_{quart}$), 151.62 ($C_{quart}$), 157.94 ($C_{quart}$). MS (ES+): m/z 392.0 (100) [MH⁺]. HPLC: $t_R$=1.7 min (MicromassZQ, nonpolar_5 min).

7-(8-Chloro-3-cyclobutyl-2H-imidazo[1,5-a]pyrazin-1-yl)-2-phenyl-quinoline

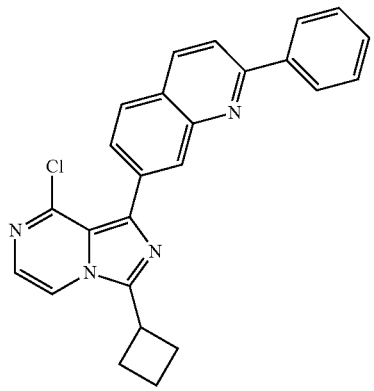 [SMILES: Clc1nccn2c(C3CCC3)nc(-c3ccc4ccc(-c5ccccc5)nc4c3)c12]

A mixture of POCl₃ (5 mL, 8 g, 55 mmol) and cyclobutanecarboxylic acid [(3-chloropyrazin-2-yl)-(2-phenylquinolin-7-yl)methyl]-amide [275 mg, 0.583 mmol] is heated to 70° C. for 21.5 h. POCl₃ is evaporated, a cold solution of NH₃ in iPrOH (2M, 11 mL, 22 mmol) is added, the suspension is sonicated, the solid is filtered off and washed with iPrOH. The solid is suspended in CHCl₃ and filtered, and the filtrate is concentrated to obtain the title compound as yellow solid. $^1$H NMR (CDCl₃, 400 MHz) δ 2.04-2.15 (m, 1H), 2.15-2.28 (m, 1H), 2.50-2.60 (m, 2H), 2.64-2.76 (m, 2H), 3.89 (quint, J=8.4 Hz, 1H), 7.35 (d, J=4.8 Hz, 1H), 7.44-7.50 (m, 1H), 7.51-7.57 (m, 3H), 7.89-7.93 (m, 3H), 8.17-8.22 (m, 2H), 8.27 (dd, J=0.8, 8.8 Hz, 1H), 8.53 (d, J=0.8 Hz, 1H). MS (ES+): m/z 410.9/412.9 (100/39) [MH⁺]. HPLC: $t_R$=3.7 min (MicromassZQ, nonpolar_5 min).

Cyclobutanecarboxylic acid [(3-chloro-pyrazin-2-yl)-(2-phenyl-quinolin-7-yl)-methyl]-amide

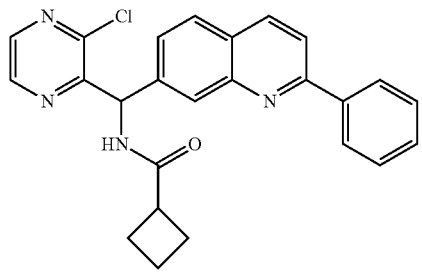 [SMILES: O=C(NC(c1ccc2ccc(-c3ccccc3)nc2c1)c1nccnc1Cl)C1CCC1]

To a solution of NEt(iPr)₂ (150 μL, 111 mg, 0.861 mmol), DMAP (5 mg, 0.04 mmol), and C-(3-chloropyrazin-2-yl)-C-(2-phenylquinolin-7-yl)-methylamine (202 mg, 0.583 mmol) in dry CH₂Cl₂ (5 mL), cooled by ice/water, is added cyclobutanecarbonyl chloride (75 μL, 78 mg, 0.66 mmol), then the cooling bath is removed, and the reaction mixture is stirred at rt for 3 h. Water is added, the layers are separated, and the aqueous layer is extracted with CH₂Cl₂ (3×15 mL). The combined CH₂Cl₂ layers are washed with water, saturated NaHCO₃ solution, and brine, dried over MgSO₄, filtered and concentrated to give crude material as yellow foam, which is used for the next step without purification. $^1$H NMR (CDCl₃, 400 MHz) δ 1.81-1.90 (m, 1H), 1.90-2.02 (m, 1H), 2.11-2.23 (m, 2H), 2.23-2.35 (m, 2H), 3.12 (quint, J=8.4 Hz, 1H), 6.80 (d, J=8.0 Hz, 1H), 7.22 (d, J=8.0 Hz, 1H), 7.43-7.48 (m, 1H), 7.48-7.54 (m, 2H), 7.73 (dd, J=2.0, 8.4 Hz, 1H), 7.82 (d, J=8.0 Hz, 1H), 7.85 (d, J=8.8 Hz, 1H), 7.90 (d, J=0.8 Hz, 1H), 8.07-8.12 (m, 2H), 8.19 (d, J=8.4 Hz, 1H), 8.38 (d, J=2.4 Hz, 1H), 8.58 (d, J=2.4 Hz, 1H). MS (ES+): m/z 429.0/431.0 (38/13) [MH⁺], 469.8/471.8 (6/2) [MH⁺+MeCN]. HPLC: $t_R$=3.6 min (MicromassZQ, polar_5 min).

C-(3-Chloro-pyrazin-2-yl)-C-(2-phenyl-quinolin-7-yl)-methylamine

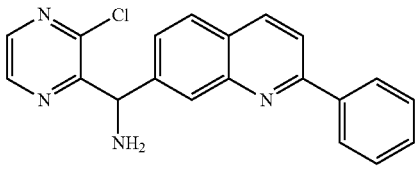 [SMILES: NC(c1ccc2ccc(-c3ccccc3)nc2c1)c1nccnc1Cl]

A solution of 2-[(3-chloropyrazin-2-yl)-(2-phenylquinolin-7-yl)-methyl]-isoindole-1,3-dione (1.536 g, 3.22 mmol) and anhydrous hydrazine (335 µL, 342 mg, 10.7 mmol) in EtOH (2 mL)/CH$_2$Cl$_2$ (12 mL) is stirred at it overnight. The white precipitate formed (phthalic hydrazide) is filtered off and washed with CH$_2$Cl$_2$. The combined filtrate and washings are concentrated in vacuo, the residue is suspended in CDCl$_3$ and filtered (0.45 µM pore size), and the filtrate is concentrated in vacuo to obtain the title compound as yellow foam, which is used for the next step without further purification. $^1$H NMR (CDCl$_3$, 400 MHz) δ 2.4 (brs, 2H), 5.79 (s, 1H), 7.43-7.55 (m, 3H), 7.61 (dd, J=1.8, 8.6 Hz, 1H), 7.81 (d, J=8.4 Hz, 1H), 7.86 (d, J=8.4 Hz, 1H), 8.06 (d, J=1.2 Hz, 1H), 8.10-8.15 (m, 2H), 8.19 (d, J=8.8 Hz, 1H), 8.31 (d, J=2.4 Hz, 1H), 8.60 (d, J=2.4 Hz, 1H). MS (ES+): m/z 347.0/349.0 (30/10) [MH$^+$], 330.0/332.0 (18/6) [MH$^+$-NH$_3$]. HPLC: t$_R$=2.1 min (MicromassZQ, polar_5 min).

2-[(3-Chloro-pyrazin-2-yl)-(2-phenyl-quinolin-7-yl)-methyl]-isoindole-1,3-dione

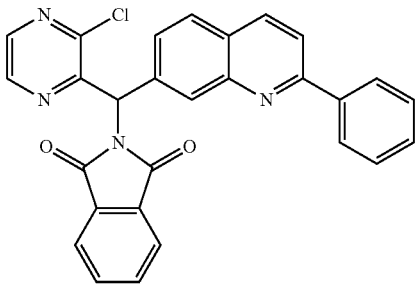 [SMILES: O=C1c2ccccc2C(=O)N1C(c1ccc2ccc(-c3ccccc3)nc2c1)c1nccnc1Cl]

To a suspension of (3-chloropyrazin-2-yl)-(2-phenylquinolin-7-yl)-methanol (1.215 g, 3.49 mmol), phthalimide (566 mg, 3.85 mmol), and PS-PPh$_3$ (loading 2.12 mmol/g; 3.29 g, 6.97 mmol) in dry THF (40 mL), cooled by ice/water, is added DIAD (830 µL, 852 mg, 4.22 mmol). The cooling bath is removed and the flask is vortexed at it for 1 d. More phthalimide (50 mg, 0.34 mmol), PS-PPh$_3$ (300 mg, 0.636 mmol), and DIAD (80 µL, 82 mg, 0.41 mmol) are added, and vortexing is continued for 2 d. The resin is filtered off on a glass frit (porosity M) and washed with CH$_2$Cl$_2$. The combined filtrates and washings are concentrated in vacuo and chromatographed on silica gel [Jones Flashmaster, 50 g/150 mL cartridge, eluting with CH$_2$Cl$_2$ (1-22)→2% EtOAc in CH$_2$Cl$_2$ (23-38)→5% (39-61)], mixed fractions are combined and chromatographed again [50 g/150 mL cartridge, eluting with CH$_2$Cl$_2$ (1-22)→>2% EtOAc in CH$_2$Cl$_2$ (23-33)→3% (34-55)→5% (56-68)] to obtain the title compound as white foam. $^1$H NMR (CDCl$_3$, 400 MHz) δ 7.14 (s, 1H), 7.43-7.55 (m, 3H), 7.72-7.79 (m, 3H), 7.82-7.90 (m, 4H), 8.09 (s, 1H), 8.09-8.14 (m, 2H), 8.22 (d, J=8.8 Hz, 1H), 8.40 (d, J=2.4 Hz, 1H), 8.51 (d, J=2.4 Hz, 1H). MS (ES+): m/z 476.9/478.9 (100/38) [MH$^+$]. HPLC: t$_R$=3.5 min (MicromassZQ, nonpolar_5 min).

(3-Chloropyrazin-2-yl)-(2-phenylquinolin-7-yl)-methanol

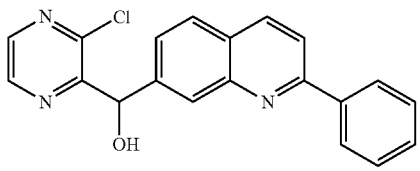 [SMILES: OC(c1ccc2ccc(-c3ccccc3)nc2c1)c1nccnc1Cl]

To a solution of 2,2,6,6-tetramethylpiperidine (0.820 mL, 0.686 g, 4.86 mmol) in dry THF (15 mL), cooled by CO$_2$(s)/acetone, is added nBuLi (2.5M in hexanes; 1.95 mL, 4.88 mmol). The cooling bath is replaced with an ice/water bath for 15 min, and then the solution is re-cooled to −78° C. After 5 min, a solution of 2-chloropyrazine (0.370 mL, 0.475 g, 4.14 mmol) in THF (0.5 mL) is added. 25 min later, a solution of 2-phenylquinoline-7-carbaldehyde (890 mg, 3.82 mmol) in dry THF (7 mL) is added slowly over 5 min from a syringe which is then rinsed with THF (1 mL), and the mixture is stirred at −78° C. for 2 h and then warmed up to 0° C. for 0.5 h. The reaction is quenched by adding citric acid (0.25M aqueous solution). The mixture is extracted with EtOAc (4×30 mL), and the combined EtOAc extracts are washed with water, sodium bicarb solution, and brine and dried over MgSO$_4$. The crude material is chromatographed on silica gel [Jones Flashmaster, 50 g/150 mL cartridge, eluting with CH$_2$Cl$_2$ (4×50 mL, then 1-16)→>2% EtOAc in CH$_2$Cl$_2$ (17-30)→5% (31-59)→7% (60-85)→10% (86-110)] to obtain the title compound as an off-white foam. $^1$H NMR (CDCl$_3$, 400 MHz) δ 4.80 (d, J=7.6 Hz, 1H), 6.25 (d, J=7.6 Hz, 1H), 7.43-7.56 (m, 3H), 7.58 (dd, J=1.8, 8.2 Hz, 1H), 7.83 (d, J=8.4 Hz, 1H), 7.87 (d, J=8.4 Hz, 1H), 8.06 (brs, 1H), 8.10-8.15 (m, 2H), 8.20 (d, J=8.4 Hz, 1H), 8.41 (d, J=2.4 Hz, 1H), 8.62 (d, J=2.4 Hz, 1H). MS (ES+): m/z 348.0/350.0 (100/37) [MH$^+$]. HPLC: t$_R$=3.3 min (MicromassZQ, polar_5 min).

2-Phenylquinoline-7-carbaldehyde

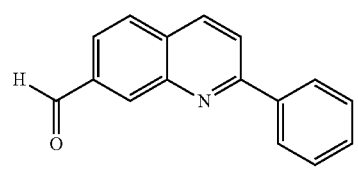 [SMILES: O=Cc1ccc2ccc(-c3ccccc3)nc2c1]

A mixture of 7-methyl-2-phenylquinoline (2.49 g, 11.4 mmol) and selenium dioxide (1.92 g, 17.3 mmol, 1.5 eq.) is heated to 160° C. (bath temp.) for 22 h. The cooled melt is suspended in CH$_2$Cl$_2$ with the aid of sonication and filtered through Celite and then through a plug of silica gel. This effectively removes the red color and the major lower spots. The material thus obtained is crystallized from hexanes/CHCl$_3$, yielding a pale beige solid, mp. 108° C. The mother liquor is concentrated and chromatographed on silica gel [Jones Flashmaster, 50 g/150 mL cartridge, eluting with hexanes:CH$_2$Cl$_2$ 1:1 (1-25)→1:3 (26-53)→CH$_2$Cl$_2$ (54-73)

→3% EtOAc in CH$_2$Cl$_2$ (74-85)] to obtain as pale yellow solid, mp. 109° C. $^1$H NMR (CDCl$_3$, 400 MHz) δ 7.48-7.60 (m, 3H), 7.94 (d, 0.1=8.8 Hz, 1H), 8.01-8.05 (m, 2H), 8.18-8.23 (m, 2H), 8.29 (d, J=8.8 Hz, 1H), 8.64 (s, 1H), 10.26 (s, 1H). MS (ES+): m/z 234.2 (100) [MH$^+$]. HPLC: t$_R$=3.0 min (MicromassZQ, nonpolar__5 min); $^{13}$C NMR (CDCl$_3$, 100.6 MHz, DEPT135) δ 121.22 (+), 122.80 (+), 127.51 (2C, +), 128.65 (+), 128.94 (2C, +), 129.83 (+), 130.69 (C$_{quart}$), 135.84 (+), 136.68 (+), 137.21 (C$_{quart}$), 138.79 (C$_{quart}$), 147.91 (C$_{quart}$), 158.48 (C$_{quart}$), 192.14 (+); IR (film): ν=3059 cm$^{-1}$, 3034, 2824, 2717, 1954, 1812, 1684, 1601, 1554, 1510, 1491, 1448, 1420, 1392, 1320, 1280, 1168, 1145, 1120, 1075, 1052, 1025, 971, 926, 897, 850, 812, 787, 757, 692, 673, 627.

7-Methyl-2-phenylquinoline

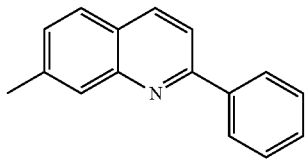 [SMILES: Cc1ccc2ccc(-c3ccccc3)nc2c1]

To a solution of 7-methylquinoline (1.63 g, 11.4 mmol) in dry THF (10 mL), cooled by ice/water, is added phenyllithium (1.9M in cyclohexane/ether 70/30, 6.0 mL, 11.4 mmol) dropwise over 5 min. After 15 min, the cooling bath is removed, and the solution is stirred at it for 5 h. The reaction is quenched by adding MeOH, and stirring is continued overnight. Water is added, the mixture is extracted with EtOAc (3×35 mL), and the combined extracts are dried over MgSO$_4$. The drying agent is filtered off, and air is bubbled into the solution for 7 d. The solvent is evaporated; the residue is dissolved in warm (≈50° C.) EtOAc/hexanes and filtered warm. The filtrate is concentrated and dried in vacuo to obtain the crude title compound that is used directly for the next step. Further purification is possible by chromatography on silica gel (Jones Flashmaster, eluting with hexanes:EtOAc 3:1-+2:1→1:1). $^1$H NMR (CDCl$_3$, 400 MHz) δ 2.58 (s, 3H), 7.31 (d, J=3.7 Hz, 1H), 7.36-7.49 (m, 1H), 7.52 (t, J=8.0 Hz, 2H), 7.72 (d, J=8.2 Hz, 1H), 7.82 (d, J=8.2 Hz, 1H), 7.96 (s, 1H), 8.16 (t, J=8.0 Hz, 2H). MS (ES+): m/z 220.3 (100) [MH$^+$]. HPLC: t$_R$=2.7 min (Platform II, nonpolar__5 min).

Additionally, 2-phenylquinoline-7-carbaldehyde could be prepared as follows: To a solution of (2-phenylquinolin-7-yl)methanol (75 mg, 0.319 mmol) in chloroform (1 mL) was added MnO$_2$ (277 mg, 3.19 mmol). The mixture was stirred at it for 20 h and filtered through a Celite pad. The filtrate was concentrated under reduced pressure and the residue was purified by silica gel chromatography. (1% MeOH in dichloromethane) to afford the title compound. $^1$H-NMR (CDCl$_3$, 400 MHz) δ 7.50-7.59 (m, 3H), 7.95 (d, J=8.8 Hz, 1H), 8.04 (dd, J=2.4, 8.8 Hz, 2H), 8.19-8.22 (m, 2H), 8.31 (d, J=8.8 Hz, 1H), 8.69 (s, 1H), 10.26 (s, 1H). MS (ES+): m/z 234 [MH$^+$]. HPLC: t$_R$=3.59 min (OpenLynx, polar__5 min).

(2-Phenylquinolin-7-yl)methanol

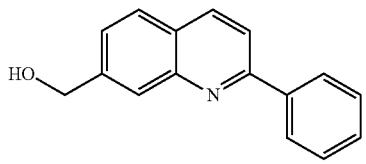 [SMILES: OCc1ccc2ccc(-c3ccccc3)nc2c1]

Under N$_2$, to a solution of 2-phenylquinoline-7-carboxylic acid hydrochloride (144 mg, 0.5 mmol) in THF (5 mL) was added LiAlH$_4$ (95 mg, 2.5 mmol) in two portions. The mixture was stirred at it for 15 h, quenched with water (1 mL), and filtered through a Celite pad, which was washed with EtOAc (30 mL). The combined filtrates were dried over MgSO$_4$, filtered, concentrated, and purified by silica gel chromatography (5% MeOH in dichloromethane) to afford the desired product. $^1$H-NMR (CDCl$_3$, 400 MHz) δ 4.93 (s, 2H), 7.46-7.57 (m, 4H), 7.84 (d, J=8.4 Hz, 1H), 7.88 (d, J=8.8 Hz, 1H), 8.14-8.18 (m, 3H), 8.23 (d, J=8.4 Hz, 1H). MS (ES+): m/z 236 [MH$^+$]. HPLC: t$_R$=2.72 min (OpenLynx, polar__5 min).

2-Phenylquinoline-7-carboxylic acid hydrochloride

Iron powder (21.05 g, 377 mmol), water (8 mL), and concentrated hydrochloric acid (0.63 mL, ~7.5 mmol) were added consecutively to a solution of methyl 4-formyl-3-nitrobenzoate (8.04 g, 38.4 mmol) in EtOH (100 mL). The mixture was stirred at 95° C. for 1.5 h. Acetophenone (4.4 mL, 37.7 mmol) and solid KOH (6.344 g, 113 mmol) were then added with caution. This mixture was stirred at 95° C. for another 5 h. The inorganic solids were filtered off when still warm and the filtrate was acidified to pH=~1.0 with 4 N HCl(aq). The solvents were removed and water (10 mL) was added. The product was extracted into THF (100 mL×3), dried over MgSO$_4$, filtered, concentrated to afford the desired product as HCl salt; $^1$H-NMR (CD$_3$OD, 400 MHz) δ 7.73-7.80 (m, 3H), 8.17-8.20 (m, 2H), 8.40-8.48 (m, 3H), 9.02 (d, J=0.8 Hz, 1H), 9.17 (d, J=8.8 Hz, 1H). MS (ES+): m/z 250 [MH⁺]. HPLC: $t_R$=3.18 min (OpenLynx, polar_5 min).

Example 2 trans-4-[8-Amino-1-(2-phenylquinolin-7-yl)-imidazo[1,5-a]pyrazin-3-yl]-cyclohexanecarboxylic acid amide

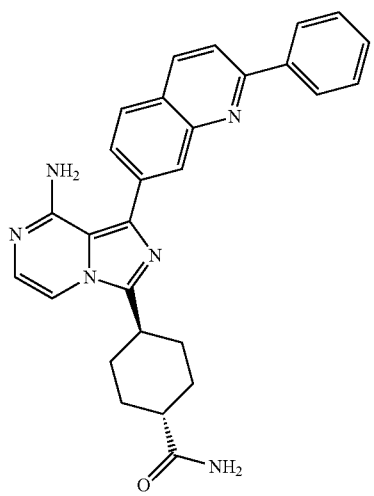

An isopropanol solution (20 mL) of trans-4-[8-chloro-1-(2-phenylquinolin-7-yl)-imidazo[1,5-a]pyrazin-3-yl]-cyclohexanecarboxylic acid methyl ester (2.0 g, 4.0 mmol) in a sealed tube was cooled to −78° C. Ammonia was bubbled into the solution for 5 min; the tube was capped and heated to 110° C. for 1 d. The reaction mixture was concentrated in vacuo and partitioned b/w CHCl₃ and water. The aqueous layer was extracted with CHCl₃ (5×) and the combined organic layers were dried over Na₂SO₄, filtered, charged with silica gel, and concentrated to yellow solids. The crude material was purified by silica gel column chromatography [Jones Flashmaster, 20 g/70 mL cartridge, eluting with 5% ~7 N NH₃ in MeOH, 5% MeOH/CHCl₃]. The purified material was recrystallized from MeOH/CHCl₃/diethyl ether to afford the desired product as a light yellow solid; ¹H NMR (DMSO-d₆, 400 MHz) δ 1.56-1.73 (m, 4H), 1.85-1.91 (m, 2H), 2.01-2.06 (m, 2H), 2.17-2.25 (m, 1H), 3.12-3.20 (m, 1H), 6.35 (s, 2H), 6.70 (s, 1H), 7.09 (d, 1H, J=4.8 Hz), 7.26 (s, 1H), 7.51-7.59 (m, 3H), 7.73 (d, 1H, J=4.8 Hz), 7.90 (dd, 1H, J=2.0 Hz, 8.4 Hz), 8.09 (d, 1H, J=8.4 Hz), 8.18 (d, 1H, J=8.8 Hz), 8.23 (s, 1H), 8.30 (d, 2H, J=7.6 Hz), 8.51 (d, 1H, J=8.4 Hz). MS (ES+): m/z 463.0 [MH⁺]; HPLC: $t_R$=2.1 min (Micromass Platform II, polar_5 min).

trans-4-[8-Chloro-1-(2-phenylquinolin-7-yl)-imidazo[1,5-a]pyrazin-3-yl]-cyclohexanecarboxylic acid methyl ester

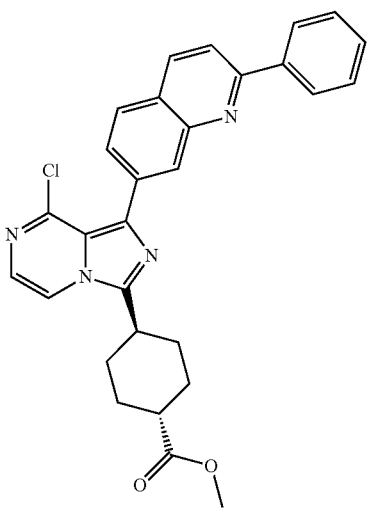 [SMILES: COC(=O)[C@H]1CC[C@H](c2nc(-c3ccc4ccc(-c5ccccc5)nc4c3)c3c(Cl)nccn32)CC1]

A CH₂Cl₂ solution (2 mL) of trans-4-{[(3-chloropyrazin-2-yl)-(2-phenyl-quinolin-7-yl)-methyl]-carbamoyl}-cyclohexanecarboxylic acid methyl ester (2.3 g, 4.5 mmol) in a round bottom flask equipped with a condenser was charged with POCl₃ (15 mL) and stirred at 80° C. for 72 h. The reaction mixture was concentrated in vacuo to a foam, cooled to 0° C., and charged with cold 2M NH₃ in isopropanol to basic pH. The mixture was concentrated in vacuo to solids and partitioned between EtOAc and water. The organic layer was washed with water (1×), brine (1×), dried over Na₂SO₄, filtered, and concentrated to a brown oil. The resulting residue was purified by silica gel chromatography (CH₂Cl₂ to 1% ~7N NH₃ in MeOH/CH₂Cl₂) to provide the desired product as a yellow solid; NMR (CDCl₃, 400 MHz) δ 1.62-1.73 (m, 2H), 1.92-2.02 (m, 2H), 2.15-2.27 (m, 4H), 2.44-2.60 (m, 1H), 2.99-3.08 (m, 1H), 3.72 (s, 3H), 7.39 (d, 1H, J=5.2 Hz), 7.45-7.50 (m, 1H), 7.51-7.57 (m, 2H), 7.61 (d, 1H, J=5.2 Hz), 7.85-7.93 (m, 3H), 8.19 (d, 2H, J=7.6 Hz), 8.27 (d, 1H, J=8.4 Hz), 8.50 (s, 1H); MS (ES+): m/z 496.9 [MH⁺]; HPLC: $t_R$=3.6 min (Micromass Platform II, nonpolar_5 min).

trans-4-{[(3-Chloropyrazin-2-yl)-(2-phenylquinolin-7-yl)-methyl]-carbamoyl}-cyclohexanecarboxylic acid methyl ester

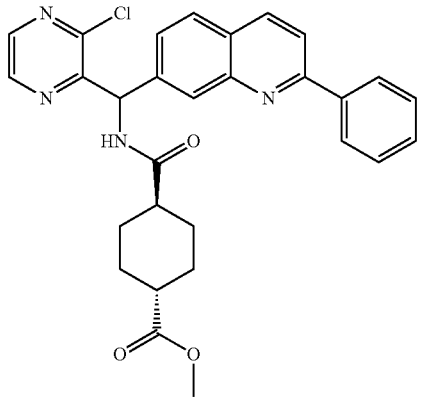 [SMILES: COC(=O)[C@H]1CC[C@H](C(=O)NC(c2ccc3ccc(-c4ccccc4)nc3c2)c2nccnc2Cl)CC1]

A THF solution (15 mL) of CDI (1.2 g, 7.3 mmol) and trans-4-carbomethoxycyclohexane-1-carboxylic acid (1.2 g, 6.6 mmol) was stirred at 60° C. for 16 h. The reaction mixture was charged with C-(3-chloropyrazin-2-yl)-C-(2-phenylquinolin-7-yl)-methylamine (compound of Formula IV where $Q^1$=2-phenylquinolin-7-yl) (2.3 g, 6.6 mmol) and stirred at 60° C. for 20 h. The reaction mixture was concentrated in vacuo, taken up in EtOAc, and washed with water (2×) and brine (1×). The organic layer was dried over $Na_2SO_4$, filtered, and concentrated in vacuo. The resulting residue was purified by silica gel chromatography (20% EtOAc/Hexanes to 100% EtOAc) the desired product as an orange foam; $^1$H NMR (CDCl$_3$, 400 MHz) δ 1.48-1.55 (m, 4H), 1.95-2.06 (m, 4H), 2.17-2.24 (m, 1H), 2.26-2.33 (m, 1H), 3.66 (s, 3H), 6.77 (d, 1H, J=7.6 Hz), 7.36-7.41 (m, 1H), 7.45-7.55 (m, 3H), 7.72-7.77 (m, 1H), 7.81-7.89 (m, 2H), 8.11 (d, 2H, J=7.2 Hz), 8.20-8.25 (m, 1H), 8.39 (d, 1H, J=2.4 Hz), 8.60 (d, 1H, J=2.8 Hz); MS (ES+): m/z 515.0 [MH$^+$]; HPLC: $t_R$=3.1 mM (Micromass Platform II, nonpolar_5 min).

Example 3 trans-4-[8-Amino-1-(2-phenylquinolin-7-yl)-imidazo[1,5-a]pyrazin-3-yl]-cyclohexanecarboxylic acid methyl ester

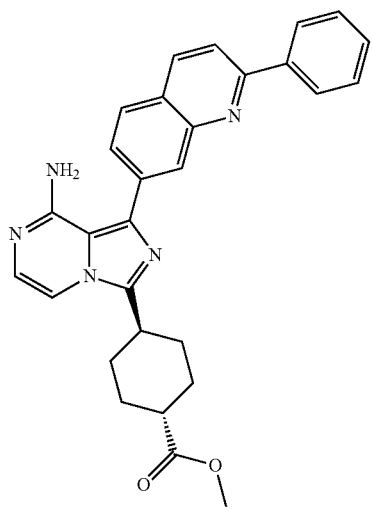 [SMILES: COC(=O)[C@H]1CC[C@H](c2nc(-c3ccc4ccc(-c5ccccc5)nc4c3)c3c(N)nccn32)CC1]

An isopropanol solution (20 mL) of trans-4-[8-chloro-1-(2-phenylquinolin-7-yl)-imidazo[1,5-a]pyrazin-3-yl]-cyclohexanecarboxylic acid methyl ester (2.0 g, 4.0 mmol) in a sealed tube was cooled to −78° C. Ammonia was bubbled into the solution for 5 min; the tube was capped and heated to 110° C. for 1 d. The reaction mixture was concentrated in vacuo and partitioned between CHCl$_3$ and water. The aqueous layer was extracted with CHCl$_3$ (5×) and the combined organic layers were dried over $Na_2SO_4$, filtered, charged with silica gel, and concentrated to yellow solids. The crude material was purified by silica gel column chromatography [Jones Flashmaster, 20 g/70 mL cartridge, eluting with 2% ~7 N NH$_3$ in MeOH/CH$_2$Cl$_2$] to afford the desired product as a yellow solid; $^1$H NMR (CDCl$_3$, 400 MHz) δ 1.62-1.73 (m, 2H), 1.92-2.02 (m, 2H), 2.15-2.27 (m, 4H), 2.44-2.60 (m, 1H), 2.99-3.08 (m, 1H), 3.72 (s, 3H), 5.25 (s, 2H), 7.13 (d, 1H, J=4.8 Hz), 7.27-7.28 (m, 1H), 7.46-7.50 (m, 1H), 7.52-7.57 (m, 2H), 7.89-7.96 (m, 3H), 8.18-8.21 (m, 2H), 8.27 (d, 1H, J=8.8 Hz), 8.40-8.42 (m, 1H); MS (ES+): m/z 478.0 [MH$^+$]; HPLC: $t_R$=2.5 min (Micromass Platform II, polar_5 min).

Example 4 trans-4-[8-Amino-1-(2-phenylquinolin-7-yl)-imidazo[1,5-a]pyrazin-3-yl]-cyclohexanecarboxylic acid

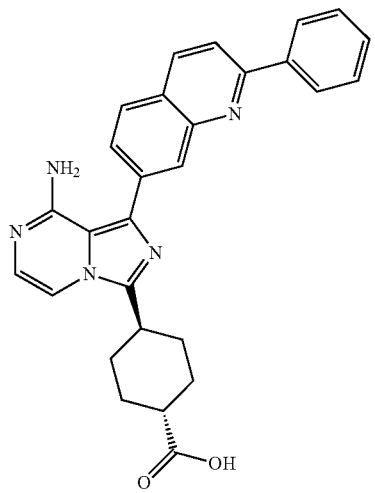 [SMILES: Nc1nccn2c1c(-c1ccc3ccc(-c4ccccc4)nc3c1)nc2[C@H]1CC[C@H](C(=O)O)CC1]

A THF solution (2 mL) of trans-4-[8-amino-1-(2-phenylquinolin-7-yl)-imidazo[1,5-a]pyrazin-3-yl]-cyclohexanecarboxylic acid methyl ester was charged with 10M NaOH (0.31 mL, 3.1 mmol); a minimal amount of methanol was added to homogenize the reaction mixture. The reaction stirred at rt for 2 h. The reaction mixture was concentrated to solids and acidified to pH 5 with 2M HCl. The aqueous layer was extracted with CHCl$_3$ (5×) and combined organic layers were dried over Na$_2$SO$_4$, filtered, and concentrated to the desired compound as a orange solid; $^1$H NMR (CDCl$_3$, 400 MHz) δ 1.62-1.73 (m, 2H), 1.92-2.02 (m, 2H), 2.15-2.27 (m, 4H), 2.44-2.60 (m, 1H), 2.99-3.08 (m, 1H), 3.72 (s, 3H), 5.25 (s, 2H), 6.91 (d, 1H, J=6.0 Hz), 7.29-7.33 (m, 1H), 7.51-7.59 (m, 3H), 7.81 (dd, 1H, J=2.0 Hz, 8.4 Hz), 8.00-8.05 (m, 2H), 8.21-8.23 (m, 2H), 8.32 (d, 1H, J=9.2 Hz), 8.41-8.42 (m, 1H); MS (ES+): m/z 464.0 [MH$^+$]; HPLC: t$_R$=2.3 min (Micromass Platform II, polar__5 min).

Example 5 trans-4-[8-Amino-1-(2-phenylquinolin-7-yl)-imidazo[1,5-a]pyrazin-3-yl]-cyclohexanecarboxylic acid methylamide

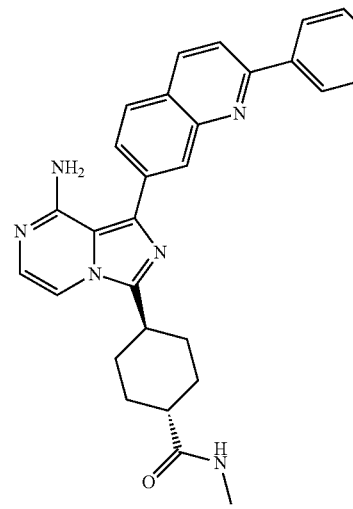

A DMF solution (3 mL) of trans-4-[8-amino-1-(2-phenylquinolin-7-yl)-imidazo[1,5-a]pyrazin-3-yl]-cyclohexanecarboxylic acid (260 mg, 0.56 mmol) and methylamine hydrochloride (379 mg, 5.6 mmol) in a sealed tube was charged with DIEA (0.98 mL, 5.6 mmol), 0.6M HOAt in DMF (0.93 mL, 0.56 mmol), and then EDC (161 mg, 0.84 mmol). The reaction mixture stirred at it for 16 h. The reaction mixture was concentrated to solids, taken up in CH$_2$Cl$_2$, charged with silica, and concentrated to brown solids. The crude material was purified by silica gel column chromatography [Jones Flashmaster, 5 g/25 mL cartridge, eluting with 2% ~7N NH$_3$ in MeOH/CH$_2$Cl$_2$]. The purified material was recrystallized from MeOH/CH$_2$Cl$_2$/diethyl ether to the desired product as a light yellow solid; $^1$H NMR (DMSO-d$_6$, 400 MHz) δ 1.56-1.73 (m, 4H), 1.85-1.91 (m, 2H), 2.01-2.06 (m, 2H), 2.17-2.25 (m, 1H), 2.52 (d, 3H, J=4.4 Hz), 3.12-3.20 (m, 1H), 6.17 (s, 2H), 7.09 (d, 1H, J=4.8 Hz), 7.51-7.59 (m, 4H), 7.73 (d, 1H, J=4.8 Hz), 7.90 (dd, 1H, J=2.0 Hz, 8.4 Hz), 8.09 (d, 1H, J=8.4 Hz), 8.18 (d, 1H, J=8.8 Hz), 8.23 (s, 1H), 8.30 (d, 2H, J=7.6 Hz), 8.51 (d, 1H, J=8.4 Hz); MS (ES+): m/z 477.0 [MH$^+$]; HPLC: t$_R$=2.1 min (Micromass Platform II, polar__5 min).

Example 6 trans-{4-[8-Amino-1-(2-phenylquinolin-7-yl)-imidazo[1,5-a]pyrazin-3-yl]-cyclohexyl}-methanol

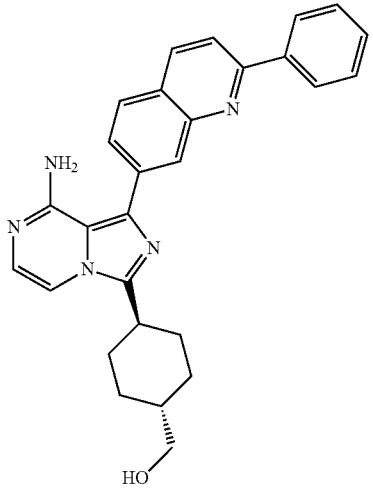 [SMILES: Nc1nccn2c1c(-c1ccc3ccc(-c4ccccc4)nc3c1)nc2[C@H]1CC[C@H](CO)CC1]

A THF solution (8 mL) of trans-4-[8-amino-1-(2-phenylquinolin-7-yl)-imidazo[1,5-a]pyrazin-3-yl]-cyclohexanecarboxylic acid methyl ester was cooled to −78° C. and charged with 1M LiAlH$_4$ in THF (1.5 mL, 1.5 mmol) dropwise; the reaction vessel was removed from the −78° C. cooling bath and stirred at rt for 4 h. The reaction mixture was charged with EtOAc, Na$_2$SO$_4$.10H$_2$O, and silica gel and concentrated in vacuo to yellow solids. The crude material was purified by silica gel column chromatography [Jones Flashmaster, 10 g/70 mL cartridge, eluting with 1% ~7N NH$_3$ in MeOH/CH$_2$Cl$_2$] to afford the desired product as a yellow solid; $^1$H NMR (CDCl$_3$, 400 MHz) δ 1.17-1.29 (m, 2H), 1.63-1.73 (m, 2H), 1.87-2.07 (m, 4H), 2.12-2.23 (m, 2H), 2.92-3.02 (m, 1H), 3.56 (d, 2H, J=6.0 Hz), 5.25 (s, 2H), 7.13 (d, 1H, J=4.8 Hz), 7.27-7.28 (m, 1H), 7.46-7.50 (m, 1H), 7.52-7.57 (m, 2H), 7.89-7.96 (m, 3H), 8.18-8.21 (m, 2H), 8.27 (d, 1H, J=8.8 Hz), 8.40-8.42 (m, 1H); MS (ES+): m/z 450.0 [MH+]; HPLC: $t_R$=2.4 min (Micromass Platform II, polar_5 min).

Example 7 trans-2-{4-[8-Amino-1-(2-phenylquinolin-7-yl)-imidazo[1,5-a]pyrazin-3-yl]-cyclohexylmethyl}-isoindole-1,3-dione

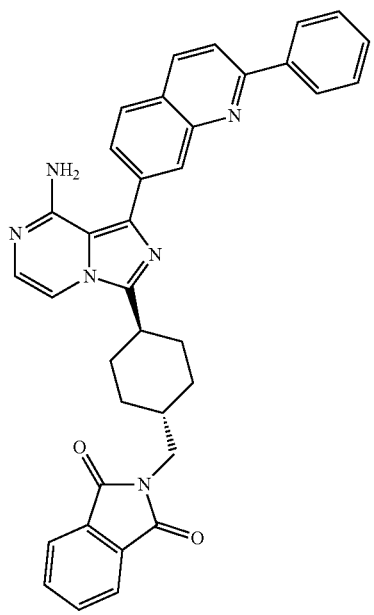 [SMILES: Nc1nccn2c1c(-c1ccc3ccc(-c4ccccc4)nc3c1)nc2[C@H]1CC[C@H](CN2C(=O)c3ccccc3C2=O)CC1]

trans-{-4-[8-Amino-1-(2-phenylquinolin-7-yl)-imidazo[1,5-a]pyrazin-3-yl]-cyclohexyl}-methanol (290 mg, 0.47 mmol), phthalimide (82 mg, 0.56 mmol), and resin-bound triphenylphosphine (PS-Ph$_3$P [Argonaut, 2.16 mmol/g]) (324 mg) were dissolved in 2.5 mL of THF, evacuated, placed under nitrogen atmosphere and charged with DIAD (0.11 mL, 0.56 mmol). After stirring for 16 h, the resin was filtered, washed with CH$_2$Cl$_2$ (5×) and concentrated to an orange-colored oil. The crude material was purified by silica gel column chromatography [Jones Flashmaster, 10 g/70 mL cartridge, eluting with 1% MeOH/CH$_2$Cl$_2$ to 2% ~7N NH$_3$ in MeOH/CH$_2$Cl$_2$] to afford the desired product as a yellow solid; $^1$H NMR (CDCl$_3$, 400 MHz) δ 1.17-1.29 (m, 2H), 1.60-1.61 (m, 1H), 1.87-2.07 (m, 4H), 2.12-2.23 (m, 2H), 2.92-3.02 (m, 1H), 3.64 (d, 2H, J=6.8 Hz), 5.25 (s, 2H), 7.11 (d, 1H, J=5.6 Hz), 7.24-7.26 (m, 1H), 7.45-7.49 (m, 1H), 7.52-7.56 (m, 2H), 7.72-7.75 (m, 2H), 7.86-7.95 (m, 5H), 8.17-8.20 (m, 2H), 8.25 (d, 1H, J=8.8 Hz), 8.38-8.39 (m, 1H); MS (ES+): m/z 579.0 [MH+]; HPLC: $t_R$=2.9 min (Micromass Platform II, nonpolar_5 min).

Example 8 trans-3-(4-Aminomethylcyclohexyl)-1-(2-phenylquinolin-7-yl)-imidazo[1,5-a]pyrazin-8-ylamine

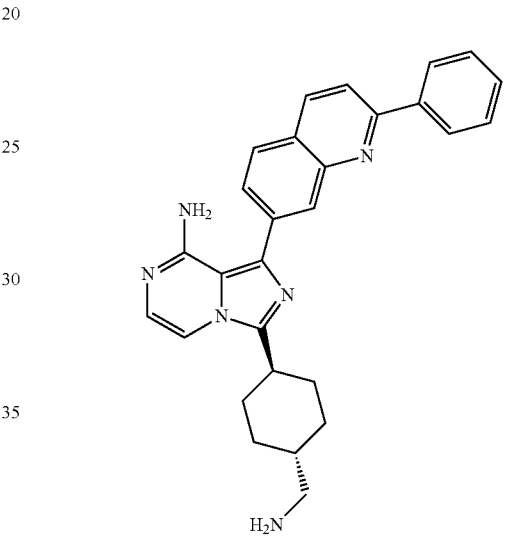

An ethanolic solution of trans-2-{-4-[8-Amino-1-(2-phenylquinolin-7-yl)-imidazo[1,5-a]pyrazin-3-yl]-cyclohexylmethyl}-isoindole-1,3-dione (265 mg, 0.46 mmol) was charged with an excess of hydrazine (0.14 mL, 4.6 mmol) and allowed to stir at rt for 16 h. The solution was filtered through a fritted glass funnel and the solids were washed with EtOH (4×). The filtrate was concentrated and the crude material was purified by silica gel column chromatography [Jones Flashmaster, 5 g/25 mL cartridge, eluting with 2% ~7 N NH$_3$ in MeOH/CH$_2$Cl$_2$ to 4% ~7N NH$_3$ in MeOH/CH$_2$Cl$_2$]. The purified material was recrystallized from CH$_2$Cl$_2$/hexanes to afford the desired product as a yellow solid; $^1$H NMR (CDCl$_3$, 400 MHz) δ 1.16-1.26 (m, 2H), 1.58-1.65 (m, 1H), 1.87-1.99 (m, 2H), 2.02-2.09 (m, 2H), 2.13-2.22 (m, 2H), 2.72 (d, 2H, J=6.4 Hz), 2.92-3.01 (m, 1H), 7.10 (d, 1H, J=5.2 Hz), 7.25-7.28 (m, 1H), 7.42-7.55 (m, 3H), 7.89-7.94 (m, 3H), 8.18-8.20 (m, 2H), 8.24 (d, 1H, J=8.8 Hz), 8.39-8.41 (m, 1H); MS (ES+): m/z 449.0 [MH+]; HPLC: $t_R$=2.0 min (Micromass Platform II, nonpolar_5 min).

Example 9

3-Methyl-1-(2-phenyl-quinolin-7-yl)-imidazo[1,5-a]pyrazin-8-ylamine

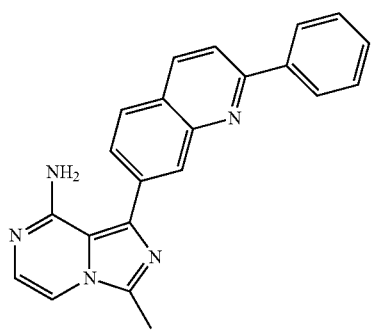

7-(8-Chloro-3-methyl-imidazo[1,5-a]pyrazin-1-yl)-2-phenyl-quinoline was dissolved in 10.0 mL of 2.0M NH$_3$ in IPA and 5.0 mL of CH$_2$Cl$_2$. The reaction was heated to 110° C. for 64 h. The salts were filtered off and washed with CH$_2$Cl$_2$. Purified with silica gel column chromatography [Jones Flashmaster, 10 g cartridge, eluting with 1% MeOH: EtOAc] to yield a dark yellow solid; $^1$H NMR (400 MHz, CDCl$_3$) δ 2.71 (s, 3H), 5.61 (brs, 2H), 7.13 (d, 1H, J=5.1 Hz), 7.2 (d, 1H, J=5.1 Hz), 7.48-7.56 (m, 3H), 7.89-7.97 (m, 3H), 8.18-8.21 (m, 2H), 8.27 (d, 1H, J=8.6 Hz), 8.39 (s, 1H); MS (ES+): 352.06 (M+1), 353.07 (M+2), 354.09 (M+3).

7-(8-Chloro-3-methyl-imidazo[1,5-a]pyrazin-1-yl)-2-phenyl-quinoline

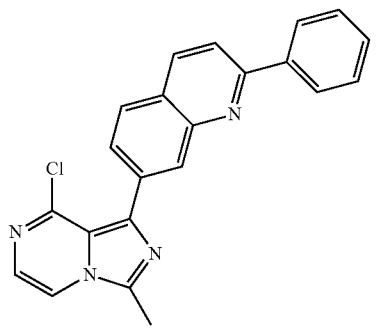 [SMILES: Cc1nc(-c2ccc3ccc(-c4ccccc4)nc3c2)c2c(Cl)nccn12]

N-[(3-Chloro-pyrazin-2-yl)-(2-phenyl-quinolin-7-yl)-methyl]-acetamide (273.0 mg, 0.702 mmol) was dissolved in 20 mL of POCl$_3$. The reaction was heated to 80° C. for 24 h. The excess POCl$_3$ was removed in vacuo. The residue was worked up by basifying with cold 2.0 M NH$_3$ in IPA followed by the addition of CH$_2$Cl$_2$ and water. The aqueous layer was washed with CH$_2$Cl$_2$ (2×). The organic layers where combined, dried over sodium sulfate, filtered and concentrated in vacuo to yield a light brown oil; $^1$H NMR (400 MHz, CDCl$_3$) δ 2.77 (s, 3H), 7.41-7.59 (m, 4H), 7.70-7.72 (m, 1H), 7.88-7.93 (m, 3H), 8.19-8.28 (brm, 3H), 8.55 (brs, 1H); MS (ES+): 370.96 (M+1), 372.97 (M+3), 373.98 (M+4).

N-[(3-Chloro-pyrazin-2-yl)-(2-phenyl-quinolin-7-yl)-methyl]-acetamide

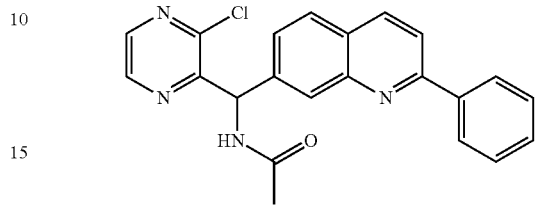

C-(3-Chloro-pyrazin-2-yl)-C-(2-phenyl-quinolin-7-yl)-methylamine (250 mg, 0.72 mmol) was dissolved in 4.0 mL of CH$_2$Cl$_2$ and DIPEA (139.8 mg, 1.08 mmol) and DMAP (8.8 mg, 0.07 mmol) were added. The reaction was cooled to 0° C. and acetyl chloride (68 mg, 0.87 mmol) was added to the homogenous reaction mixture. After 3 h the reaction was complete. Water was added and the organic layer was washed with NaHCO$_3$ sat. aq. sol (1×), H$_2$O and Brine. The organic layers where combined, dried over sodium sulfate, filtered and concentrated in vacuo. The crude product was purified with silica gel column chromatography [Jones Flashmaster, 10 g cartridge, eluting with 2% MeOH: CH$_2$Cl$_2$] to yield a dark oil; $^1$H NMR (400 MHz, CDCl$_3$) δ 2.08 (s, 3H), 6.80 (d, 1H, J=7.9 Hz), 7.26-7.23 (m, 4H), 7.70-7.92 (m, 4H), 8.09-8.11 (m, 2H), 8.17 (d, 1H, J=8.60 Hz), 8.37 (d, 1H, J=2.40 Hz), 8.57 (d, 1H, J=2.49 Hz); MS (ES+): 430.84 (M+1), 432.83 (M+3), 433.92 (M+4).

Example 10

3-Isopropyl-1-(2-phenyl-quinolin-7-yl)-imidazo[1,5-a]pyrazin-8-ylamine

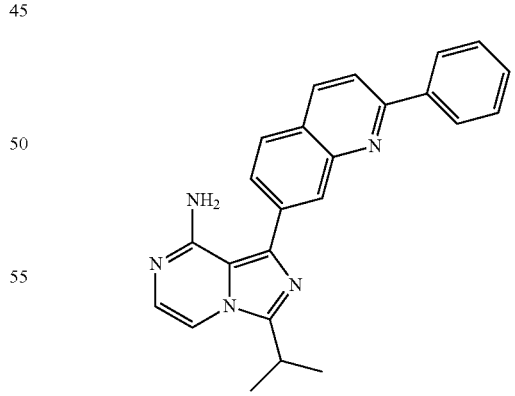

3-Isopropyl-1-(2-phenyl-quinolin-7-yl)-imidazo[1,5-a]pyrazin-8-ylamine was prepared utilizing the same procedures as those used for Example 9 except isobutyryl chloride was used in place of acetyl chloride; $^1$H NMR (400 MHz, CDCl$_3$) δ 1.24 (d, 6H, J=7.04 Hz), 2.47-2.53 (m, 1H), 6.80 (d, 1H, J=7.83 Hz), 7.26-7.23 (m, 4H), 7.70-7.92 (m, 4H), 8.09-

8.11 (m, 2H), 8.17 (d, 1H, J=8.60 Hz), 8.37 (d, 1H, J=2.50 Hz), 8.57 (d, 1H, J=2.49 Hz); MS (ES+): 486.91 (M+1), 488.86 (M+3), 489.94 (M+4).

Example 11

1-(6-Chloro-2-phenyl-quinolin-7-yl)-3-cyclobutyl-imidazo[1,5-a]pyrazin-8-ylamine

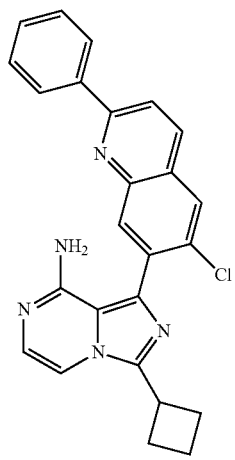 [SMILES: Nc1nccn2c(C3CCC3)nc(-c3cc4nc(-c5ccccc5)ccc4cc3Cl)c12]

1-(6-Chloro-2-phenyl-quinolin-7-yl)-3-cyclobutyl-imidazo[1,5-a]pyrazin-8-ylamine and its intermediates herein were prepared according to the procedures described for Example 1, except 6-chloro-2-phenyl-quinoline-7-carbaldehyde was used in place of 2-phenyl-quinoline-7-carbaldehyde: $^1$H NMR (CDCl$_3$, 400 MHz) δ 2.02-2.24 (m, 2H), 2.48-2.70 (m, 4H), 3.87 (quintet, 1H, J=8.6 Hz), 4.80 (brs, 2H), 7.09 (d, 1H, J=5.2 Hz), 7.19 (d, 1H, J=4.8 Hz), 7.46-7.56 (m, 3H), 7.98 (d, 1H, J=8.8 Hz), 8.02 (s, 1H), 8.16-8.22 (m, 3H), 8.35 (s, 1H); MS (ES+): 426.0/427.9 (M/M+2).

6-Chloro-7-(8-chloro-3-cyclobutyl-imidazo[1,5-a]pyrazin-1-yl)-2-phenyl-quinoline

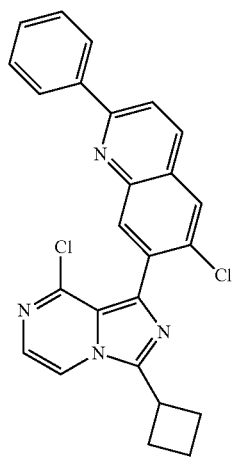 [SMILES: Clc1cc2ccc(-c3ccccc3)nc2cc1-c1nc(C2CCC2)n2ccnc(Cl)c12]

$^1$H NMR (CDCl$_3$, 400 MHz) δ 2.01-2.22 (m, 2H), 2.48-2.70 (m, 4H), 3.91 (quintet, 1H, J=8.6 Hz), 7.36 (d, 1H, J=4.8 Hz), 7.45-7.58 (m, 4H), 7.93-7.97 (m, 2H), 8.15-8.22 (m, 3H), 8.33 (s, 1H); MS (ES+): 444.9/446.9 (M/M+2).

Cyclobutanecarboxylic acid [(6-chloro-2-phenyl-quinolin-7-yl)-(3-chloro-pyrazin-2-yl)-methyl]-amide

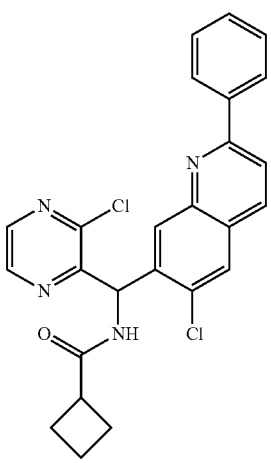 [SMILES: O=C(NC(c1cc2nc(-c3ccccc3)ccc2cc1Cl)c1nccnc1Cl)C1CCC1]

$^1$H NMR (CDCl$_3$, 400 MHz) δ 1.85-1.98 (m, 2H), 2.15-2.38 (m, 4H), 3.13 (quintet, 1H, J=8.4 Hz), 6.63 (d, 1H, J=8.0 Hz), 7.15 (d, 1H, J=8.0 Hz), 7.46-7.53 (m, 3H), 7.82 (s, 1H), 7.90 (d, 1H, J=8.8 Hz), 7.93 (s, 1H), 8.06-8.08 (m, 2H), 8.15 (d, 1H, J=8.8 Hz), 8.38 (d, 1H, J=2.4 Hz), 8.58 (d, 1H, J=2.4 Hz); MS (ES+): 462.8/464.8 (M/M+2.

C-(6-Chloro-2-phenyl-quinolin-7-yl)-C-(3-chloro-pyrazin-2-yl)-methylamine

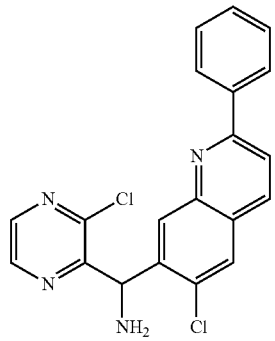 [SMILES: NC(c1cc2nc(-c3ccccc3)ccc2cc1Cl)c1nccnc1Cl]

$^1$H NMR (CDCl$_3$, 400 MHz) δ 6.11 (s, 1H), 7.44-7.53 (m, 3H), 7.80 (s, 1H), 7.89 (d, 1H, J=8.8 Hz), 7.91 (s, 1H), 8.06-8.09 (m, 2H), 8.15 (d, 1H, J=8.8 Hz), 8.37 (d, 1H, J=2.4 Hz), 8.60 (d, 1H, J=2.4 Hz); MS (ES+): 380.9/383.0 (M/M+2).

2-[(6-Chloro-2-phenyl-quinolin-7-yl)-(3-chloro-pyrazin-2-yl)-methyl]-isoindole-1,3-dione

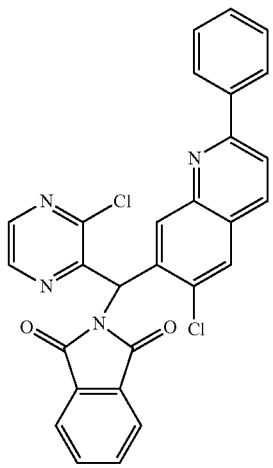 [SMILES: O=C1c2ccccc2C(=O)N1C(c1cc2nc(-c3ccccc3)ccc2cc1Cl)c1nccnc1Cl]

¹H NMR (CDCl₃, 400 MHz) δ 7.36 (s, 1H), 7.43-7.55 (m, 3H), 7.76-7.78 (m, 2H), 7.82-7.94 (m, 5H), 8.05-8.07 (m, 2H), 8.18 (d, 1H, J=5.6 Hz), 8.41 (d, 1H, J=2.4 Hz), 8.55 (d, 1H, J=2.0 Hz); MS (ES): 510.8/512.7 (M/M+2).

(6-Chloro-2-phenyl-quinolin-7-yl)-(3-chloro-pyrazin-2-yl)-methanol

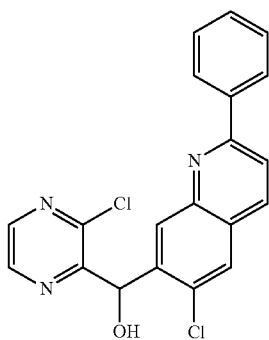 [SMILES: OC(c1cc2nc(-c3ccccc3)ccc2cc1Cl)c1nccnc1Cl]

¹H NMR (CDCl₃, 400 MHz) δ 4.67 (d, 1H, J=7.2 Hz), 6.64 (d, 1H, J=7.2 Hz), 7.46-7.53 (m, 3H), 7.70 (s, 1H), 7.90 (d, 1H, J=8.8 Hz), 7.95 (s, 1H), 8.05-8.07 (m, 2H), 8.16 (d, 1H, J=8.4 Hz), 8.47 (d, 1H, J=2.4 Hz), 8.65 (d, 1H, J=2.4 Hz); MS (ES): 381.9/383.9 (M/M+2).

6-Chloro-2-phenyl-quinoline-7-carbaldehyde

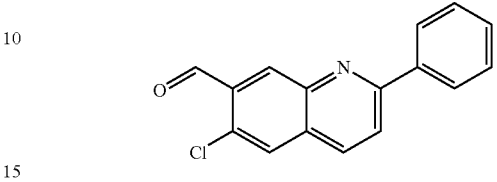

The CCl₄ (45 ml) solution of 6-chloro-7-methyl-2-phenylquinoline (753.3 mg, 2.969 mmol), AIBN (48.8 mg, 0.1 eq.) and NBS (898.4 mg, 1.7 eq.) was heated at 80° C. under N₂ for 8 h. After that time, the reaction mixture was concentrated in vacuo and the residue was dissolved in EtOAc (60 ml), washed successively with H₂O (30 mL), saturated NaS₂O₃ (30 mL), H₂O (30 mL), and brine (30 mL). The organic extract was then dried (MgSO₄), filtered and concentrated in vacuo. The residue was dissolved in DMSO (105 mL), and then NaHCO₃ (2495 mg, 10 eq.) was added. The reaction mixture was stirred at 90° C. for 3 h. Water (140 mL) was added and the mixture was extracted with EtOAc (3×200 mL). The combined organic extracts were washed with H₂O (4×60 mL) and brine (60 mL), and dried (MgSO₄), filtered, and concentrated in vacuo. The residue was recrystallized from CHCl₃/hexane (20:80, 10 mL) to give 6-chloro-2-phenylquinoline-7-carbaldehyde as pale-yellow solid; ¹H NMR (CDCl₃, 400 MHz) δ 7.51-7.58 (m, 3H), 7.93 (s, 1H), 8.03 (d, 1H, J=8.8 Hz), 8.18-8.20 (m, 3H), 8.75 (s, 1H), 10.63 (s, 1H); MS (ES+): 268.1/270.0 (M/M+2).

6-Chloro-7-methyl-2-phenyl-quinoline

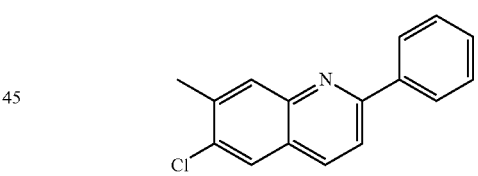

Into a solution of 6-chloro-7-methylquinoline (1000 mg, 5.644 mmol) in THF (5 mL), which was cooled in ice/water bath under N₂, was added PhLi (1.9 M in THF, 2.971 mL) dropwise over 5 min. After stirring at 0° C. for 15 min, the ice/water bath was removed and the reaction mixture was stirred at rt. After 4 h, MeOH (5 mL) was added to quench the reaction and the reaction mixture was stirred at rt overnight. After that time, the mixture was poured into water (20 mL) and extracted with EtOAc (3×30 mL). The organic extracts were dried over MgSO₄, filtered, and concentrated in vacuo. The residue was dissolved in acetonitrile (30 mL) and DDQ (1282 mg) was added and the solution was stirred under N₂ at rt for 24 h. After that time, the reaction mixture was poured into aqueous NaOH (3 N, 50 mL) and extracted with EtOAc (2×75 mL). The extracts were washed with aqueous NaOH (3N, 2×50 mL), water (2×50 mL) and brine (50 mL), dried over MgSO₄, filtered, and concentrated in vacuo to afford the title compounds; ¹H NMR (CDCl₃, 400 MHz) δ 2.60 (s, 3H), 7.47-7.55 (m, 3H), 7.83-7.86 (m, 2H), 8.04 (s, 1H), 8.10-8.16 (m, 3H); MS (ES): 254.1/256.1 (M/M+2).

Example 12

3-tert-Butyl-1-(2-phenylquinolin-7-yl)-imidazo[1,5-a]pyrazin-8-ylamine

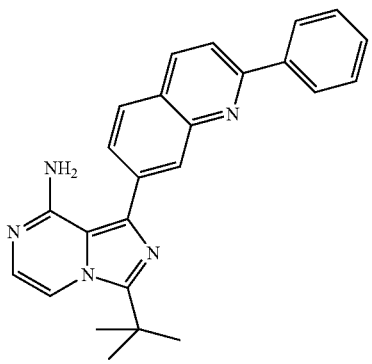 [SMILES: CC(C)(C)c1nc(-c2ccc3ccc(-c4ccccc4)nc3c2)c2c(N)nccn12]

Gaseous NH$_3$ was condensed into a cooled (−78° C.) solution of 7-(3-tert-butyl-8-chloroimidazo[1,5-a]pyrazin-1-yl)-2-phenylquinoline (92.5 mg, 0.224 mmol) in NH$_3$/i-PrOH (2M, 5 mL) in a pressure tube until the volume had doubled. The tube was sealed and heated to 110° C. for 21 h. After excess NH$_3$ and i-PrOH were removed in vacuo, the residue was suspended between CH$_2$Cl$_2$ and water, the layers were separated, and the aqueous layer was extracted with CH$_2$Cl$_2$ (3×15 mL). The combined organic layers were washed with brine (3×25 mL), dried over MgSO$_4$, filtered, and concentrated in vacuo. The crude material was purified by chromatography on silica gel [Jones Flashmaster, 5 g/25 mL cartridge, eluting with MeOH (7N NH$_3$):CH$_2$Cl$_2$ 1%→2%], affording the title compound, as a fine yellow solid. $^1$H NMR (CDCl$_3$, 400 MHz) δ 1.25 (s, 9H), 5.18 (s, —NH$_2$), 7.08 (d, J=4.8 Hz, 1H), 7.45-7.51 (m, 1H), 7.51-7.57 (m, 3H), 7.90-7.97 (m, 3H), 8.17-8.22 (m, 2H), 8.27 (d, J=8.4 Hz, 1H), 8.42-8.44 (m, 1H); MS (ES+): m/z 394.1 (25) [MH$^+$]; HPLC: t$_R$=2.5 min (OpenLynx, polar_5 min).

7-(3-tert-Butyl-8-chloroimidazo[1,5-a]pyrazin-1-yl)-2-phenylquinoline

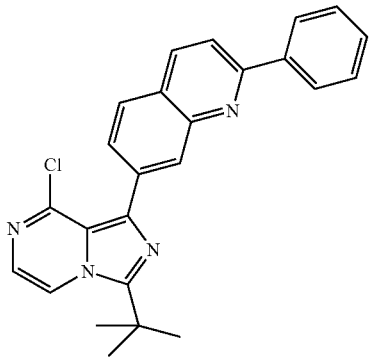 [SMILES: CC(C)(C)c1nc(-c2ccc3ccc(-c4ccccc4)nc3c2)c2c(Cl)nccn12]

To a solution of N-[(3-chloropyrazin-2-yl)-(2-phenylquinolin-7-yl)-methyl]-2,2-dimethylpropionamide (264 mg, 0.612 mmol) in THF (3 mL), cooled to 0° C., KOtBu (800 μL, 1 M, 0.796 mmol) was added, the cooling bath was removed, and the reaction mixture stirred at ambient temperature for 30 min, under N$_2$. THF was removed in vacuo, POCl$_3$ (25 mL, 42 g, 0.273 mol) was added to the residue, and the reaction mixture was vortexed at 70° C., under N$_2$, for 5 d. POCl$_3$ was evaporated (min. 2 h on high-vacuum), a cold solution of NH$_3$/i-PrOH (2M, 10 mL) was added, the suspension was filtered, and the solid was washed several times with i-PrOH. The filtrate was concentrated, extracted with CH$_2$Cl$_2$ (3×30 mL), washed with brine (50 mL), dried over MgSO$_4$, filtered, and concentrated in vacuo. The crude material was dissolved in CH$_2$Cl$_2$, adsorbed onto Hydromatrix, and purified by chromatography on silica gel [Jones Flashmaster, 5 g/25 mL cartridge, eluting with EtOAc:CH$_2$Cl$_2$ 2%→5%], yielding the title compound, as a yellow solid; $^1$H NMR (CDCl$_3$, 400 MHz) δ 1.26 (s, 9H), 7.33 (d, J=4.8 Hz, 1H), 7.44-7.50 (m, 1H), 7.50-7.58 (m, 2H), 7.87-7.94 (m, 4H), 8.17-8.22 (m, 2H), 8.24-8.30 (m, 1H), 8.51 (s, 1H); MS (ES+): m/z 412.9/414.9 (100/38) [MH$^+$]; HPLC: t$_R$=4.3 min (OpenLynx, polar_5 min).

N-[(3-Chloropyrazin-2-yl)-(2-phenylquinolin-7-yl)-methyl]-2,2-dimethylpropion-amide

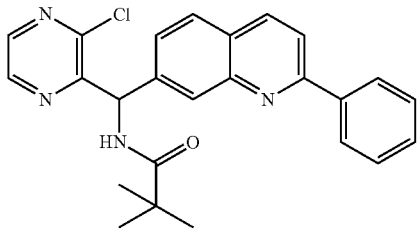 [SMILES: CC(C)(C)C(=O)NC(c1ccc2ccc(-c3ccccc3)nc2c1)c1nccnc1Cl]

To a solution of C-(3-chloropyrazin-2-yl)-C-(2-phenylquinolin-7-yl)-methylamine (231.4 mg, 0.6672 mmol), DMAP (4 mg, 0.033 mmol), and (iPr)$_2$EtN (174 μL, 129 mg, 1 mmol) in dry CH$_2$Cl$_2$ (5 mL), cooled to 0° C., pivaloyl chloride (90 μL, 89 mg, 0.734 mmol) was added under N$_2$ atmosphere, the cooling bath was removed, and the reaction mixture was allowed to stir at ambient temperature for 16 h. The reaction was quenched with H$_2$O and extracted with CH$_2$Cl$_2$ (3×20 mL). The combined CH$_2$Cl$_2$ layers were washed with (1×30 mL each) 0.25M citric acid (pH 2-3), H$_2$O, NaHCO$_3$ sat. aq. sol., and brine, dried over anhydrous MgSO$_4$, and filtered. Sample was purified by filtration through a plug of silica gel, eluting with EtOAc:CH$_2$Cl$_2$ 10:1→5:1 (300 mL). Filtrate was concentrated in vacuo, yielding the title compound, as a yellow solid, containing approximately 10% of bis-acetylated material; $^1$H NMR (CDCl$_3$, 400 MHz) δ 1.23 (s, 9H), 6.75 (d, J=7.6 Hz, 1H), 7.43-7.48 (m, 1H), 7.49-7.55 (m, 2H), 7.60 (d, br, J=7.6 Hz, —NH), 7.72-7.77 (m, 1H), 7.81-7.89 (m, 2H), 7.90 (s, 1H), 8.07-8.14 (m, 2H), 8.20 (d, J=8.8 Hz, 1H), 8.38 (d, J=2.8 Hz, 1H), 8.59 (d, J=2.0 Hz, 1H); MS (ES+): m/z 430.9/432.9 (100/37) [MH+]; HPLC: t_R=3.5 min (OpenLynx, polar_5 min).

Example 13

3-Cyclobutyl-1-(2-thiophen-2-yl-quinolin-7-yl)-imidazo[1,5-a]pyrazin-8-ylamine

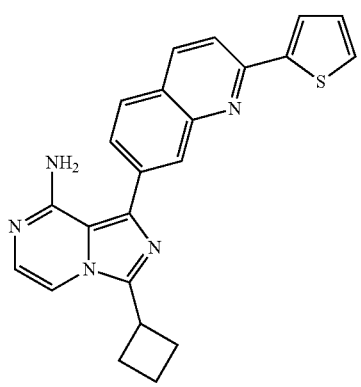 [SMILES: Nc1nccn2c(C3CCC3)nc(-c3ccc4ccc(-c5cccs5)nc4c3)c12]

To a cooled (ice/water) solution of 3-cyclobutyl-1-quinolin-7-ylimidazo[1,5-a]pyrazin-8-ylamine (52.7 mg, 0.167 mmol) in THF (5 mL) was added 2-thienyllithium (1 M in THF; 0.6 mL, 0.6 mmol), then the cooling bath was removed, and the solution was stirred overnight at ambient temperature. After 1 d and 2 d, more 2-thienyllithium (0.2 mL, 0.2 mmol) was added, and stirring was continued. The reaction was quenched by adding water and sat. NH$_4$Cl solution, the mixture was extracted with CH$_2$Cl$_2$ (3×20 mL), and the combined organic extracts were washed with brine and dried over MgSO$_4$. Air was bubbled into the solution for 8 h. The crude material was adsorbed onto Hydromatrix and chromatographed on silica gel [Jones Flashmaster, 5 g/25 mL cartridge, eluting with CH$_2$Cl$_2$ (1-6)→1% MeOH in CH$_2$Cl$_2$ (7-21)→2% MeOH in CH$_2$Cl$_2$ (22-43)], yielding a yellow film. Further purification by preparative TLC (20×20 cm silica gel plates, 500 μM thickness, eluting with 3% MeOH in CH$_2$Cl$_2$ four times) yielded the title compound as a yellow solid; $^1$H NMR (CDCl$_3$, 400 MHz) δ 2.01-2.12 (m, 1H), 2.13-2.27 (m, 1H), 2.47-2.58 (m, 2H), 2.62-2.73 (m, 2H), 3.85 (quint, J=8.0 Hz, 1H), 5.40 (brs, 2H), 7.08 (brd, J=4.8 Hz, 1H), 7.14 (d, J=4.8 Hz, 1H), 7.17 (dd, J=3.6, 5.2 Hz, 1H), 7.48 (dd, J=1.2, 5.2 Hz, 1H), 7.76 (dd, J=1.2, 3.6 Hz, 1H), 7.83 (d, J=8.8 Hz, 1H), 7.88-7.91 (m, 2H), 8.28 (dd, J=8.8, 0.8 Hz, 1H), 8.34 (d, J=0.8 Hz, 1H); MS (ES+): m/z 398.0 (60) [MH+].

3-Cyclobutyl-1-quinolin-7-yl-imidazo[1,5-a]pyrazin-8-ylamine

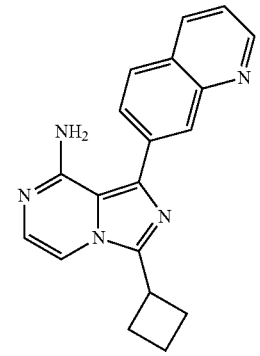 [SMILES: Nc1nccn2c(C3CCC3)nc(-c3ccc4cccnc4c3)c12]

Gaseous NH$_3$ was condensed into a cooled (dry ice/acetone) solution of 7-(8-chloro-3-cyclobutylimidazo[1,5-a]pyrazin-1-yl)-quinoline (203.2 mg, 0.607 mmol) in 2M NH$_3$/iPrOH (6 mL) in a pressure tube until the volume was doubled, then the tube was sealed and heated to 110° C. (bath temp.) for 19 h. The ammonia was evaporated, the crude material was adsorbed onto Hydromatrix and chromatographed on silica gel [Jones Flashmaster, 10 g/70 mL cartridge, eluting with CH$_2$Cl$_2$ 1:1 (1-6)→2% MeOH in CH$_2$Cl$_2$ (7-27)→4% MeOH in CH$_2$Cl$_2$ (28-37)→5% MeOH in CH$_2$Cl$_2$ (38-53)→7% MeOH in CH$_2$Cl$_2$ (54-67)], yielding the title compound as a yellow solid, >98% pure by HPLC, mp. 94-96° C.; NMR (CDCl$_3$, 400 MHz) δ 2.00-2.10 (m, 1H), 2.12-2.25 (m, 1H), 2.47-2.57 (m, 2H), 2.61-2.73 (m, 2H), 3.85 (quint, J=8.4 Hz, 1H), 5.23 (brs, 2H), 7.10 (d, J=4.4 Hz, 1H), 7.16 (d, J=4.4 Hz, 1H), 7.44 (dd, J=4.2, 8.2 Hz, 1H), 7.95 (d, J=8.4 Hz, 1H), 8.00 (d, J=8.4 Hz, 1H), 8.22 (d, J=8.2 Hz, 1H), 8.36 (s, 1H), 8.95-9.00 (m, 1H); MS (ES+): m/z 316.2 (30) [MH+].

7-(8-Chloro-3-cyclobutyl-imidazo[1,5-a]pyrazin-1-yl)-quinoline

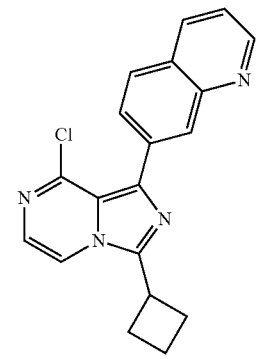 [SMILES: Clc1nccn2c(C3CCC3)nc(-c3ccc4cccnc4c3)c12]

A mixture of POCl$_3$ (8 mL, 13 g, 87 mmol) and cyclobutanecarboxylic acid [(3-chloropyrazin-2-yl)-quinolin-7-ylmethyl]-amide (566 mg, 1.60 mmol) was heated to 55° C. for 21.5 h and to 70° C. for 6 h. POCl$_3$ was evaporated, a cold solution of NH₃ in iPrOH (2 M, 10 mL) was added, the suspension was filtered, and the solid was washed with iPrOH. The crude material contained in the combined filtrate and washings was adsorbed onto Hydromatrix and chromatographed on silica gel [Jones Flashmaster, 20 g/70 mL cartridge, eluting with hexanes:EtOAc 1:1 (1-13)→1:3 (14-38)], yielding the title compound as a yellow foam; ¹H NMR (CDCl₃, 400 MHz) δ 2.05-2.14 (m, 1H), 2.16-2.28 (m, 1H), 2.50-2.60 (m, 2H), 2.63-2.75 (m, 2H), 3.89 (quint, J=8.4 Hz, 1H), 7.35 (d, J=4.4 Hz, 1H), 7.44 (dd, J=4.2, 8.2 Hz, 1H), 7.55 (d, J=5.2 Hz, 1H), 7.90 (d, J=8.4 Hz, 1H), 8.13 (dd, J=1.6, 8.4 Hz, 1H), 8.22 (d, J=8.2 Hz, 1H), 8.46 (s, 1H), 8.98 (dd, J=1.6, 4.2 Hz, 1H); MS (ES+): m/z 335.1/337.1 (100/44) [MH⁺].

Cyclobutanecarboxylic acid [(3-chloro-pyrazin-2-yl)-quinolin-7-yl-methyl]-amide

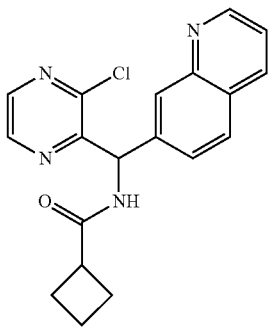 [SMILES: O=C(NC(c1ccc2cccnc2c1)c1nccnc1Cl)C1CCC1]

To a solution of NEt(iPr)₂ (520 μL, 386 mg, 2.99 mmol), DMAP (12 mg, 0.098 mmol), and C-(3-chloropyrazin-2-yl)-C-quinolin-7-ylmethylamine (compound of Formula IV where Q¹=quinolin-7-yl) (608 mg, 1.97 mmol) in dry CH₂Cl₂ (10 mL), cooled by ice/water, was added cyclobutanecarbonyl chloride (250 μL, 260 mg, 2.19 mmol), then the cooling bath was removed, and the reaction mixture was stirred at ambient temperature for 2.5 h. Water was added, the layers were separated, and the aqueous layer was extracted with CH₂Cl₂ (3×20 mL). The combined CH₂Cl₂ layers were washed with dilute HCl (pH 2), water, saturated NaHCO₃ solution, and brine and dried over MgSO₄. The crude material is chromatographed on silica gel [Jones Flashmaster, 20 g/70 mL cartridge, eluting with hexanes:EtOAc 1:1 (1-21)→1:3 (22-44)→EtOAc (45-56)], yielding the title compound as an orange foam; ¹H NMR (CDCl₃, 400 MHz) δ 1.81-1.91 (m, 1H), 1.91-2.03 (m, 1H), 2.11-2.23 (m, 2H), 2.23-2.35 (m, 2H), 3.12 (quint, J=8.6 Hz, 1H), 6.80 (d, J=8.0 Hz, 1H), 7.22 (d, J=8.0 Hz, 1H), 7.39 (dd, J=4.0, 8.0 Hz, 1H), 7.77 (d, J=8.6 Hz, 1H), 7.82 (d, J=8.6 Hz, 1H), 7.83 (s, 1H), 8.13 (d, J=8.4 Hz, 1H), 8.37 (d, J=2.2 Hz, 1H), 8.56 (d, J=2.2 Hz, 1H), 8.87 (dd, J=1.6, 4.0 Hz, 1H); MS (ES+): m/z 353.1/355.0 (100/39) [MH⁺].

C-(3-Chloro-pyrazin-2-yl)-C-quinolin-7-yl-methylamine

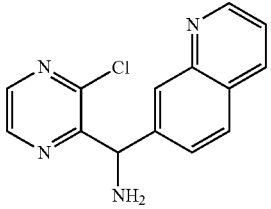 [SMILES: NC(c1ccc2cccnc2c1)c1nccnc1Cl]

A solution of 2-[(3-chloropyrazin-2-yl)-quinolin-7-ylmethyl]-isoindole-1,3-dione (789 mg, 1.97 mmol) and anhydrous hydrazine (63 μL, 64 mg, 2.0 mmol) in EtOH (4 mL)/CH₂Cl₂ (2 mL) was stirred at ambient temperature for 1 d. More hydrazine (93 μL, 95 mg, 3.0 mmol) was added, and stirring was continued for 2 d. The solid formed (phthalic hydrazide) was filtered off and washed with EtOH, and the combined filtrate and washings were dried to yield a red, sticky solid. This solid was suspended in CH₂Cl₂ and filtered, and the filtrate was concentrated to give the title compound as an orange gum; ¹H NMR (CDCl₃, 400 MHz) δ 2.4 (brs, 2H), 5.79 (s, 1H), 7.39 (dd, J=4.2, 8.2 Hz, 1H), 7.64 (dd, J=1.8, 8.6 Hz, 1H), 7.81 (d, J=8.4 Hz, 1H), 8.01 (d, J=0.8 Hz, 1H), 8.13 (dd, J=0.8, 8.0 Hz, 1H), 8.31 (d, J=2.4 Hz, 1H), 8.59 (d, J=2.4 Hz, 1H), 8.90 (dd, J=1.6, 4.4 Hz, 1H); MS (ES+): m/z 271.0/273.0 (30/10) [MH⁺], 254.1/256.1 (30/10) [MH⁺—NH₃].

2-[(3-Chloro-pyrazin-2-yl)-quinolin-7-yl-methyl]-isoindole-1,3-dione

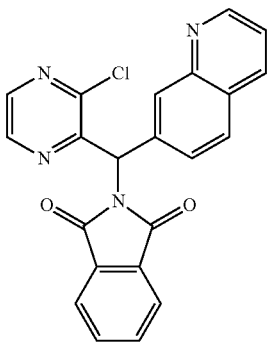 [SMILES: O=C1c2ccccc2C(=O)N1C(c1ccc2cccnc2c1)c1nccnc1Cl]

To a suspension of (3-chloropyrazin-2-yl)-quinolin-7-yl-methanol (600 mg, 2.21 mmol), phthalimide (356 mg, 2.42 mmol), and PS-PPh₃ (loading 2.12 mmol/g; 1.56 g, 3.31 mmol) in dry THF (20 mL), cooled by ice/water, was added DIAD (480 μL, 493 mg, 2.44 mmol), then the cooling bath was removed and the flask was vortexed at ambient temperature for 21.5 h. More PS-PPh₃ (520 mg, 1.10 mmol) and DIAD (160 μL, 164 mg, 0.81 mmol) were added, and vortexing was continued for 6.5 h. The resin was filtered and washed with THF and CH₂Cl₂. The crude material was chromatographed on silica gel [Jones Flashmaster, 20 g/70 mL cartridge, eluting with hexanes:EtOAc 3:1 (1-14)→2:1 (15-29)

→1:1 (30-65)→1:2 (66-80)], yielding the title compound as pale yellow solid; $^1$H NMR (CDCl$_3$, 400 MHz) δ 7.12 (s, 1H), 7.41 (dd, J=4.4, 8.0 Hz, 1H), 7.54 (dd, J=2.0, 8.4 Hz, 1H), 7.72-7.78 (m, 2H), 7.81-7.89 (m, 3H), 8.01 (d, J=0.8 Hz, 1H), 8.16 (dd, J=0.8, 8.4 Hz, 1H), 8.39 (d, J=2.4 Hz, 1H), 8.50 (d, J=2.4 Hz, 1H), 8.90 (dd, J=1.6, 4.2 Hz, 1H); MS (ES+): m/z 401.0/402.9 (100/38) [MH$^+$].

(3-chloropyrazin-2-yl)-quinolin-7-ylmethanol

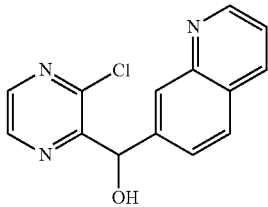 [SMILES: OC(c1ccc2cccnc2c1)c1nccnc1Cl]

To a solution of 2,2,6,6-tetramethylpiperidine (0.64 mL, 0.54 g, 3.8 mmol) in dry THF (10 mL), cooled by CO$_2$(s)/acetone, was added nBuLi (2.5 M in hexanes; 1.6 mL, 4.0 mmol). The cooling bath was replaced with an ice/water bath for 15 min, and then the solution was re-cooled to −78° C. After 10 min, 2-chloropyrazine (0.29 mL, 0.37 g, 3.2 mmol) was added. A solution of quinoline-7-carbaldehyde (500 mg, 3.18 mmol) in dry THF (5 mL), cooled by CO$_2$(s)/acetone, was transferred into the lithiochloropyrazine solution by cannula 30 min later, and the mixture was stirred at −78° C. for 2.5 h and at 0° C. for 0.5 h. The reaction was quenched by adding aq. HCl (2 mL of a 2 M solution) followed by aq. NH$_4$Cl solution. The mixture was extracted with EtOAc (4×30 mL), combined EtOAc extracts were washed with water and brine and dried over MgSO$_4$. The crude material was chromatographed on silica gel [Jones Flashmaster, 20 g/70 mL cartridge, eluting with hexanes:EtOAc 2:1 (1-21) →1:1 (22-32)→1:4 (33-62)→EtOAc (63-66)], yielding the title compound as an orange foam; $^1$H NMR (CDCl$_3$, 400 MHz) δ 4.87 (d, J=7.6 Hz, 1H), 6.26 (d, J=7.6 Hz, 1H), 7.41 (dd, J=4.4, 8.4 Hz, 1H), 7.60 (dd, J=1.6, 8.4 Hz, 1H), 7.82 (d, J=8.4 Hz, 1H), 8.02 (d, J=0.8 Hz, 1H), 8.14 (dd, J=0.8, 8.4 Hz, 1H), 8.41 (d, J=2.4 Hz, 1H), 8.60 (d, J=2.4 Hz, 1H), 8.91 (dd, J=1.6, 4.4 Hz, 1H). MS (ES+): m/z 272.1/274.1 (100/38) [MH$^+$].

Example 14 cis-3-[8-Amino-1-(2-phenyl-quinolin-7-yl)-imidazo[1,5-a]pyrazin-3-yl]-cyclobutanecarboxylic acid amide

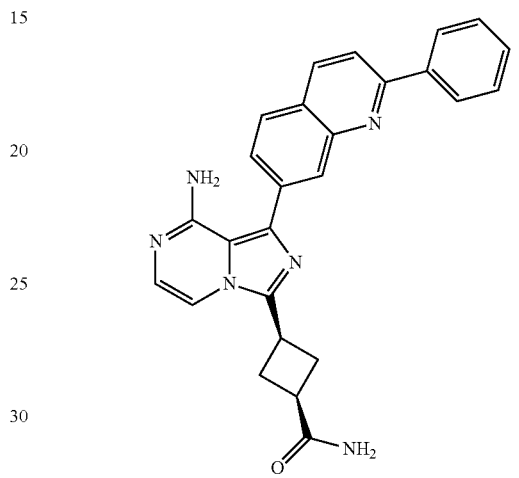

Through a suspension of cis-methyl-3-(8-chloro-1-(2-phenylquinolin-7-ylimidazo[1,5-a]pyrazin-3-yl)cyclobutanecarboxylate (153 mg, 0.32 mmol) in isopropanol (15 mL) in a Parr vessel at −70° C. was bubbled ammonia for 2 minutes. The vessel was sealed and the temperature was raised to 110° C. and the reaction was left to stir for 20 h. The reaction mixture was then cooled in a dry ice bath and transferred to a round-bottomed flask and concentrated in vacuo. The crude product was purified via MDP, to afford the title compound as a yellow solid; MS (ES+): m/z 435.29 (80) [MH$^+$]; NMR (400 MHz, DMSO-d$_6$) δ 2.54-2.59 (m, 4H) 3.04-3.12 (m, 1H) 3.84-3.92 (m, 1H) 6.23 (bs, 1H) 6.82 (bs, 1H) 7.10 (d, J=4.8 Hz, 1H) 7.52-7.59 (m, 4H) 7.94 (dd, 0.7=6.8, 1.6 Hz, 1H) 8.10 (d, 0.7=8.4 Hz, 1H) 8.18 (d, J=9.2 Hz, 1H) 8.24-8.25 (m, 1H) 8.30-8.32 (m, 21-1) 8.51 (d, 0.7=8 Hz, 1H).

cis-3-[8-Chloro-1-(2-phenyl-quinolin-7-yl)-imidazo[1,5-a]pyrazin-3-yl]-cyclobutanecarboxylic acid methyl ester and trans-3-[8-chloro-1-(2-phenyl-quinolin-7-yl)-imidazo[1,5-a]pyrazin-3-yl]-cyclobutanecarboxylic acid methyl ester To a solution of 3-(8-chloro-1-(2-phenylquinolin-7-ylimidazo[1,5-a]pyrazin-3-yl)cyclobutanecarbaldehyde (3.274 g, crude, 7.43 mmol) in MeOH (125 mL) was added MS (10 g, 44.55 mmol) and potassium carbonate (6.2 g, 44.55 mmol). The reaction flask was wrapped in aluminum foil and the reaction stirred at rt in the dark for 20 h. The mixture was then quenched with water (100 mL), diluted with DCM, and subsequently washed with sodium thiosulfate, brine, and concentrated in vacuo. The product was purified via silica gel chromatography (1:1 EtOAc:Hex) to afford the individual cis and trans products as yellow solids.

trans-3-[8-Chloro-1-(2-phenyl-quinolin-7-yl)-imidazo[1,5-a]pyrazin-3-yl]-cyclobutanecarboxylic acid methyl ester

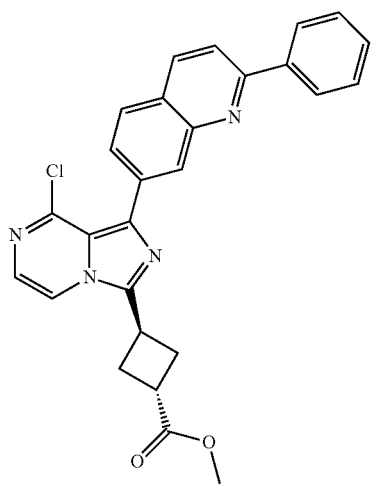 [SMILES: COC(=O)[C@H]1C[C@H](c2nc(-c3ccc4ccc(-c5ccccc5)nc4c3)c3c(Cl)nccn32)C1]

MS (ES+): m/z 469.2 (100) [MH+]; ¹H NMR (400 MHz, CDCl₃) δ 2.76-2.84 (m, 2H) 2.94-3.01 (m, 2H) 3.27-3.40 (m, 1H) 3.72 (s, 3H) 3.79-3.87 (m, 1H) 7.38 (d, J=5.2 Hz, 1H) 7.45-7.49 (m, 1H) 7.52-7.56 (m, 2H) 7.63 (d, J=4.8 Hz, 1H) 7.89-7.93 (m, 3H) 8.18-8.20 (m, 2H) 8.27 (d, J=8.0 Hz, 1H) 8.51 (s, 1H).

cis-3-[8-Chloro-1-(2-phenyl-quinolin-7-yl)-imidazo[1,5-a]pyrazin-3-yl]-cyclobutanecarboxylic acid methyl ester

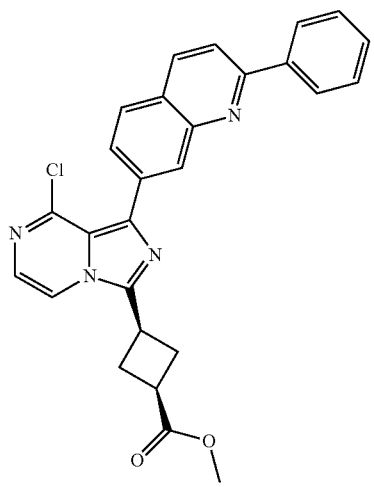 [SMILES: COC(=O)[C@H]1C[C@@H](c2nc(-c3ccc4ccc(-c5ccccc5)nc4c3)c3c(Cl)nccn32)C1]

MS (ES+): m/z 469.2 (100) [MH+]; ¹H NMR (400 MHz, CDCl₃) δ 2.81-2.86 (m, 2H) 2.92-2.99 (m, 2H) 3.33-3.41 (m, 1H) 3.77 (s, 3H) 4.04-4.10 (m, 1H) 7.38 (d, J=5.2 Hz, 1H) 7.45-7.49 (m, 1H) 7.52-7.56 (m, 2H) 7.63 (d, J=4.8 Hz, 1H) 7.89-7.93 (m, 3H) 8.18-8.20 (m, 2H) 8.27 (d, J=8.0 Hz, 1H) 8.51 (s, 1H).

3-[8-Chloro-1-(2-phenyl-quinolin-7-yl)-imidazo[1,5-a]pyrazin-3-yl]-cyclobutanecarbaldehyde

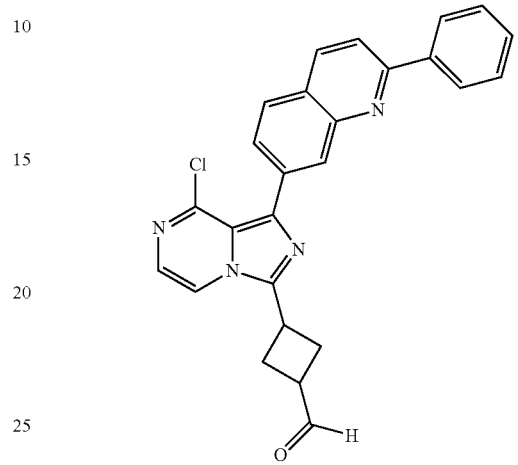

To a solution of oxalyl chloride (1.87 mL, 21.4 mmol) in anhydrous DCM (17.3 mL) was added a solution of DMSO (3.1 mL, 42.9 mmol) in DCM (8.58 mL) at −72° C. The reaction stirred for 30 minutes prior to the addition of [3-(8-chloro-1-(2-phenylquinolin-7-ylimidazo[1,5-a]pyrazin-3-yl)cyclobutyl]methanol (1.9 g, 4.29 mmol) in DCM (20 mL) at the same temperature. After 30 minutes, the reaction was quenched with triethylamine (15 mL, 107.2 mmol) and was slowly warmed to rt. The mixture was diluted with DCM (50 mL), washed with water, NaHCO₃ (sat), brine, dried over Na₂SO₄ and concentrated in vacuo, to afford a mixture of isomers; MS (ES+): ink 441.1 (80) [MH+].

Example 15 trans-3-[8-Amino-1-(2-phenyl-quinolin-7-yl)-imidazo[1,5-a]pyrazin-3-yl]-cyclobutanecarboxylic acid amide

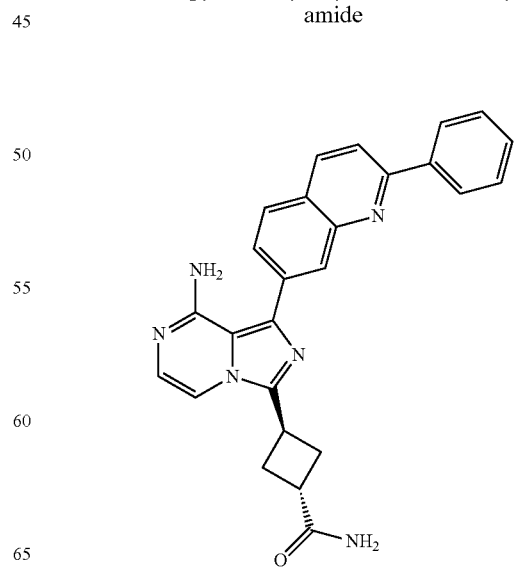

This compound was prepared utilizing the same procedures as those used for Example 14 except trans-methyl-3-(8-chloro-1-(2-phenylquinolin-7-ylimidazo[1,5-a]pyrazin-3-yl)cyclobutanecarboxylate was used in place of cis-methyl-3-(8-chloro-1-(2-phenylquinolin-7-ylimidazo[1,5-a]pyrazin-3-yl)cyclobutanecarboxylate; MS (ES+): m/z 435.29 (40) [MH$^+$]; $^1$H NMR (400 MHz, DMSO-d$_6$) δ 2.53-2.70 (m, 4H) 3.16-3.20 (m, 1H) 3.90-3.97 (m, 1H) 6.24 (bs, 2H) 6.84 (bs, 1H) 7.09 (d, J=5.1 Hz, 1H) 7.31 (bs, 1H) 7.45 (d, J=4.0 Hz, 1H) 7.50-7.60 (m, 3H) 7.96 (dd, J=6.6, 1.8 Hz, 1H) 8.11 (d, J=8.3 Hz, 1H) 8.19 (d, J=8.6 Hz, 1H) 8.28 (s, 1H) 8.30-8.33 (m, 2H) 8.52 (d, J=9.1 Hz, 1H).

Example 16 cis-3-[8-Amino-1-(2-phenyl-quinolin-7-yl)-imidazo[1,5-a]pyrazin-3-yl]-cyclobutanecarboxylic acid

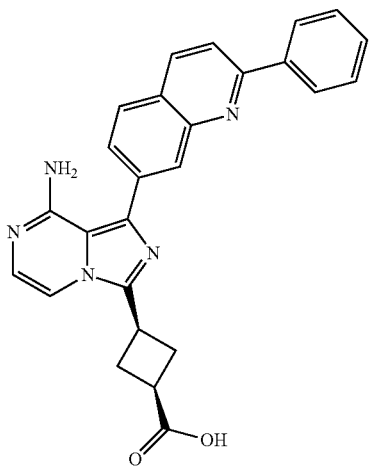 [SMILES: Nc1nccn2c1c(-c1ccc3ccc(-c4ccccc4)nc3c1)nc2[C@H]1C[C@@H](C(=O)O)C1]

This compound was prepared utilizing the same procedures as those used for the synthesis of cis-3-[8-amino-1-(2-phenyl-quinolin-7-yl)-imidazo[1,5-a]pyrazin-3-yl]-cyclobutanecarboxylic acid amide except the reaction was monitored at short intervals to minimize the amide formation. The reaction generated a mixture of ester and amide (2:1), which was treated with NaOH (0.15 mL) in THF (0.95 mL) and MeOH (1 mL). The reaction was left to stir at rt for 3 h. The mixture was concentrated in vacuo, diluted with DCM and washed with water. The product was purified by MDP, to afford the title compound as a yellow solid; MS (ES+): m/z 436.27 (40) [MH$^+$]; $^1$H NMR (400 MHz, DMSO-d$_6$) δ 2.62-2.67 (m, 5H) 3.16 (s, 1H) 3.90-3.91 (m, 1H) 6.21 (s, 1H) 7.10 (d, J=5.2 Hz, 1H) 7.50-7.59 (m, 4H) 7.93 (dd, J=6.8, 1.6 Hz, 1H) 8.10 (d, J=8.4 Hz, 1H) 8.18 (d, J=8.8 Hz, 1H) 8.25 (s, 1H) 8.30-8.33 (m, 2H) 8.51 (d, J=8.4 Hz, 1H).

Example 17

1-(2-Phenyl-quinolin-7-yl)-3-piperidin-4-yl-imidazo[1,5-a]pyrazin-8-ylamine

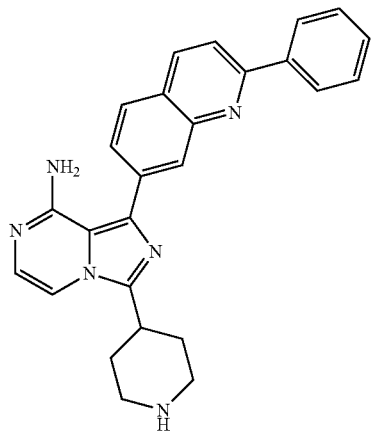 [SMILES: Nc1nccn2c(C3CCNCC3)nc(-c3ccc4ccc(-c5ccccc5)nc4c3)c12]

4-[8-Chloro-1-(2-phenyl-quinolin-7-yl)-imidazo[1,5-a]pyrazin-3-yl]-piperidine-1-carboxylic acid benzyl ester (1.6 g, 2.8 mmol) was suspended in a solution of 2M NH$_3$ in isopropanol (200 mL) in a 300 mL Parr vessel and cooled to −78° C. Ammonia gas was bubbled into the solution for 6 min and then the vessel was sealed and heated to 115° C. for 24 h. The solution was cooled to rt and transferred to a round bottom flask. Hydromatrix was added, the mixture was concentrated in vacuo, and the resulting residue was purified by silica gel chromatography (Jones Flashmaster, 25 g/150 mL cartridge, eluting with 5% 7N NH$_3$ in methanol/CH$_2$Cl$_2$) to afford a mixture of 4-[8-Amino-1-(2-phenylquinolin-7-yl)-imidazo[1,5-a]pyrazin-3-yl]-piperidine-1-carboxylic acid benzyl ester and 1-(2-Phenylquinolin-7-yl)-3-piperidin-4-yl-imidazo[1,5-a]pyrazin-8-ylamine as a yellow solid. Dissolved mixture in 37% HCl (45.0 mL) and heated to 60° C. for 2 min. Cooled to rt and diluted solution with water and washed with ether (2×) and CH$_2$Cl$_2$ (1×). Added 5N NaOH to aqueous solution until basic and filtered off 1-(2-Phenylquinolin-7-yl)-3-piperidin-4-yl-imidazo[1,5-a]pyrazin-8-ylamine as a yellow solid, which was purified by silica gel chromatography (Jones Flashmaster, 2 g/12 mL cartridge, eluting with 5% 7N NH$_3$ in methanol/CH$_2$Cl$_2$) to afford the title compound as a yellow solid; $^1$H NMR (DMSO-d$_6$, 400 MHz): δ 1.72-1.88 (m, 4H), 2.65-2.71 (m, 2H), 3.05 (d, 2H, J=12.0 Hz), 3.22-3.33 (m, 2H), 6.21 (bs, 2H), 7.09 (d, 1H, J=4.8 Hz), 7.50-7.59 (m, 3H), 7.70 (d, 1H, J=5.2 Hz), 7.92 (dd, 1H, J=8.4, 1.6 Hz), 8.09 (d, 1H, J=8.0 Hz), 8.17 (d, 1H, J=8.8 Hz), 8.24 (bs, 1H), 8.31 (dd, 2H, J=8.8, 1.6 Hz), 8.51 (d, 1H, J=8.4 Hz); MS (ES+): m/z 421 (10) [MH$^+$]; HPLC: t$_R$=1.7 min (OpenLynx, polar_5 min).

4-[8-Chloro-1-(2-phenyl-quinolin-7-yl)-imidazo[1,5-a]pyrazin-3-yl]-piperidine-1-carboxylic acid benzyl ester

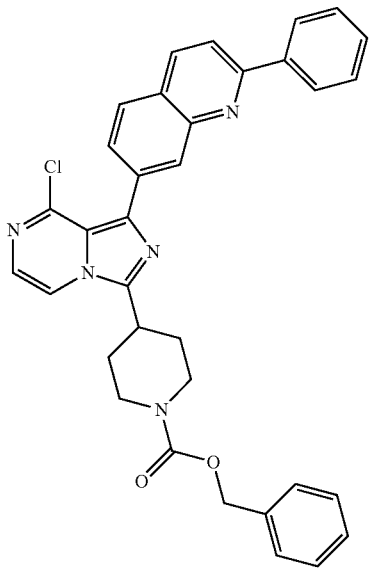 [SMILES: O=C(OCc1ccccc1)N1CCC(c2nc(-c3ccc4ccc(-c5ccccc5)nc4c3)c3c(Cl)nccn23)CC1]

4-{[(3-Chloro-pyrazin-2-yl)-(2-phenyl-quinolin-7-yl)-methyl]-carbamoyl}-piperidine-1-carboxylic acid benzyl ester (2.1 g, 3.6 mmol) was dissolved in CH$_3$CN (126.0 mL) and DMF (0.4 mL) in a round bottom flask equipped with a condenser. The reaction was charged with POCl$_3$ (1.7 mL, 17.9 mmol) and stirred at 55° C. for 3 h. The reaction mixture was concentrated in vacuo, redissolved in DCM, cooled to 0° C., and charged with 2M NH$_3$ in isopropanol to basic pH. Hydromatrix was added, the mixture was concentrated in vacuo, and the resulting residue was purified by silica gel chromatography (Jones Flashmaster, 20 g/70 mL cartridge, eluting with 100% CH$_2$Cl$_2$ to 2% CH$_3$CN/CH$_2$Cl$_2$) to afford 4-[8-chloro-1-(2-phenyl-quinolin-7-yl)-imidazo[1,5-a]pyrazin-3-yl]-piperidine-1-carboxylic acid benzyl ester as a yellow solid; MS (ES+): m/z 574 (100) [MH$^+$]; HPLC: t$_R$=4.2 min (OpenLynx, polar_5 min).

4-{[(3-Chloro-pyrazin-2-yl)-(2-phenyl-quinolin-7-yl)-methyl]-carbamoyl}-piperidine-1-carboxylic acid benzyl ester

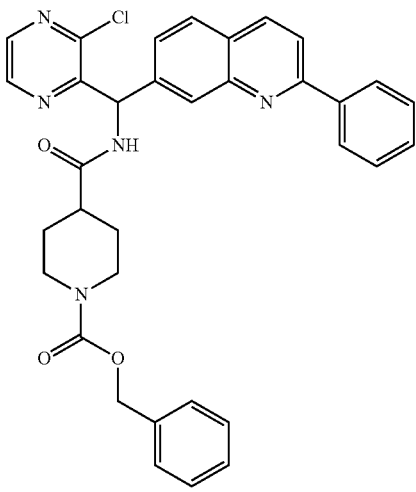 [SMILES: O=C(NC(c1ccc2ccc(-c3ccccc3)nc2c1)c1nccnc1Cl)C1CCN(C(=O)OCc2ccccc2)CC1]

A CH$_2$Cl$_2$ solution (111.0 mL) of C-(3-chloro-pyrazin-2-yl)-C-(2-phenyl-quinolin-7-yl)-methylamine (1.9 g, 5.5 mmol) and PS-DIPEA (2.8 g, 11.1 mmol) in a round bottom flask under N$_2$ atmosphere was charged with 4-chlorocarbonyl-piperidine-1-carboxylic acid benzyl ester (1.4 g, 5.0 mmol) and stirred at it for 1.5 h. The reaction mixture was filtered and concentrated in vacuo. The resulting residue was purified by silica gel chromatography (Jones Flashmaster, 20 g/70 mL cartridge, eluting with 100% CH$_2$Cl$_2$ to 10% CH$_3$CN/CH$_2$Cl$_2$) to afford 4-{[(3-chloro-pyrazin-2-yl)-(2-phenyl-quinolin-7-yl)-methyl]-carbamoyl}-piperidine-1-carboxylic acid benzyl ester as a pale yellow solid; MS (ES+): m/z 592/594 (100/50) [MH$^+$]; HPLC: t$_R$=3.7 min (OpenLynx, polar_5 min).

Example 18

1-{4-[8-Amino-1-(2-phenylquinolin-7-yl)imidazo[1,5-a]pyrazin-3-yl]piperidin-1-yl}ethanone

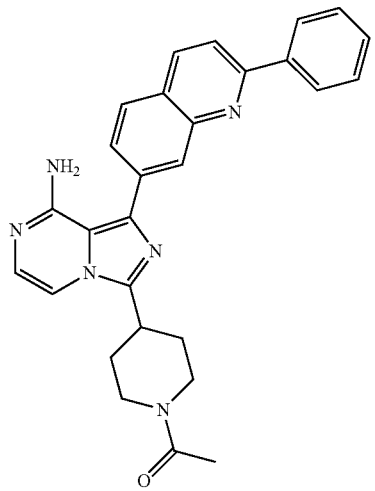 [SMILES: CC(=O)N1CCC(c2nc(-c3ccc4ccc(-c5ccccc5)nc4c3)c3c(N)nccn23)CC1]

1-(2-Phenyl-quinolin-7-yl)-3-piperidin-4-yl-imidazo[1,5-a]pyrazin-8-ylamine-tris HCl salt (59.0 mg, 0.1 mmol) was dissolved in triethylamine (1.0 mL) and DMF (0.5 mL). Acetic anhydride (12.0 μL, 0.1 mmol) was added and the reaction was stirred for 1 h. The reaction was concentrated in vacuo and purified by silica gel chromatography (Jones Flashmaster, 2 g/12 mL cartridge, eluting with 2% 7N NH$_3$ in methanol/CH$_2$Cl$_2$). The sample was further purified using MDPS to yield 1-{4-[8-amino-1-(2-phenylquinolin-7-yl)imidazo[1,5-a]pyrazin-3-yl]piperidin-1-yl}ethanone as a pale yellow solid; $^1$H NMR (CDCl$_3$, 400 MHz) δ 1.95 (ddd, 1H, J=22.4, 11.2, 4.0 Hz), 2.03-2.23 (m, 6H), 2.90 (ddd, 1H, J=13.6, 13.6, 2.8 Hz), 3.19-3.32 (m, 2H), 4.01 (bd, 1H, J=13.6 Hz), 4.64 (bd, 1H, J=13.2 Hz), 5.44 (bs, 2H), 7.11 (d, 1H, J=4.8 Hz), 7.24 (d, 1H, J=5.6 Hz), 7.46 (ddd, 1H, J=6.0, 2.4, 0.8 Hz), 7.50-7.54 (m, 2H), 7.86-7.94 (m, 3H), 8.16 (ddd, 2H, J=7.2, 3.6, 1.6 Hz), 8.24 (d, 1H, J=8.4 Hz), 8.38 (s, 1H); MS (ES+): m/z 463 (10) [MH$^+$]; HPLC: t$_R$=2.1 min (OpenLynx, polar_5 min).

Example 19

4-(8-Amino-1-(2-phenylquinolin-7-yl)imidazo[1,5-a]pyrazin-3-yl)-N-ethylpiperidine-1-carboxamide

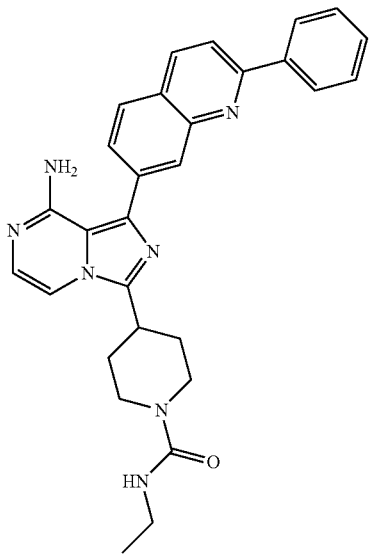 [SMILES: CCNC(=O)N1CCC(c2nc(-c3ccc4ccc(-c5ccccc5)nc4c3)c3c(N)nccn23)CC1]

4-(8-Amino-1-(2-phenylquinolin-7-yl)imidazo[1,5-a]pyrazin-3-yl)-N-ethylpiperidine-1-carboxamide was synthesized using the same procedure as 1-{4-[8-amino-1-(2-phenylquinolin-7-yl)imidazo[1,5-a]pyrazin-3-yl]piperidin-1-yl}ethanone except ethylisocyanate was used instead of acetic anhydride; yellow powder; MS (ES+): m/z 492.10 (70) [MH$^+$], 493.11 (45) [MH$^{+2}$], 211.41 (100) [MH-280]; HPLC: $t_R$=2.08 min (polar-5 min/openlynx).

Example 20

3-{1-[(Dimethylamino)acetyl]piperidin-4-yl}-1-(2-phenylquinolin-7-yl)imidazo[1,5-a]pyrazin-8-amine

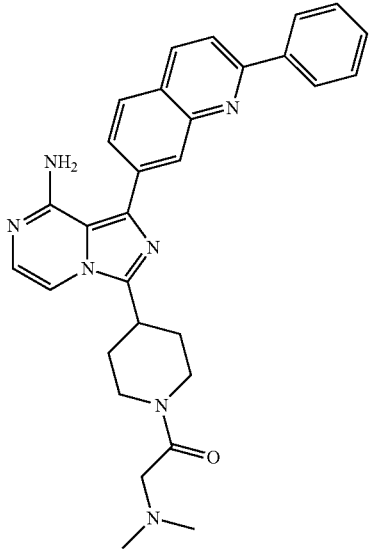 [SMILES: CN(C)CC(=O)N1CCC(c2nc(-c3ccc4ccc(-c5ccccc5)nc4c3)c3c(N)nccn23)CC1]

To a solution of 3-piperidin-4-yl-1-(2-phenylquinolin-7-yl)imidazo[1,5-a]pyrazin-8-amine in CH$_2$Cl$_2$ (2 mL), chloroacetyl chloride (73 mg, 0.64 mmol, 51 µL) and PS-DIEA (384 mg, 1.43 mmol) were added. The reaction was allowed to shake at it for 1 h. The reaction mixture was absorbed onto silica gel, and purified by silica gel column chromatography [Jones Flashmaster, 25 g/150 mL cartridge, eluting with 100% CH$_2$Cl$_2$ to 5% 7N [NH$_3$/CH$_3$OH]/CH$_2$Cl$_2$] to obtain the desired chloroketone intermediate, which was transferred to a glass pressure reaction vessel and dissolved in 2M dimethylamine solution in THF (9 mL). The reaction was heated at 80° C. for 18 h. The reaction was absorbed onto silica gel and purified [Jones Flashmaster, 10 g/70 mL cartridge, eluting with 100% CH$_2$Cl$_2$ to 5% 7N [NH$_3$/CH$_3$OH]/CH$_2$Cl$_2$] to obtain the desired product. The product was further purified by trituration with 10% DMSO in 1:1 THF/CH$_3$OH to afford the desired product as a light yellow powder; $^1$H NMR (CDCl$_3$, 400 MHz) δ 8.42 (dd, J=1.0, 1.0 Hz, 1H), 8.28 (d, J=8.0 Hz, 1H), 8.20 (m, 2H), 7.96 (d, J=8.0 Hz, 1H), 7.94 (d, J=8.8 Hz, 1H), 7.90 (dd, J=8.4, 2.0 Hz, 1H), 7.57 (m, 2H), 7.29 (d, J=4.8 Hz, 1H), 7.16 (d, J=5.2 Hz, 1H), 5.30 (br d, J=4.0 Hz, 1H), 4.66 (m, 1H), 4.30 (m, 1H), 3.76 (m, 2H), 3.33-3.22 (m, 4H), 2.97 (m, 1H), 2.38 (s, 6H), 2.30-1.90 (m, 5H), 1.86 (m, 1H); MS (ES+): m/z 56.12 (20) [MH$^+$], 507.09 (10) [MH$^{+2}$], 421.13 (50) [M-85], 253.85 (100) [MH-252]; HPLC $t_R$=1.73 min (polar-5 min/openlynx).

Example 21

(4-[8-Amino-1-(2-phenyl-quinolin-7-yl)-imidazo[1,5-a]pyrazin-3-ylmethyl]-piperidine-1-carboxylic acid benzyl ester)

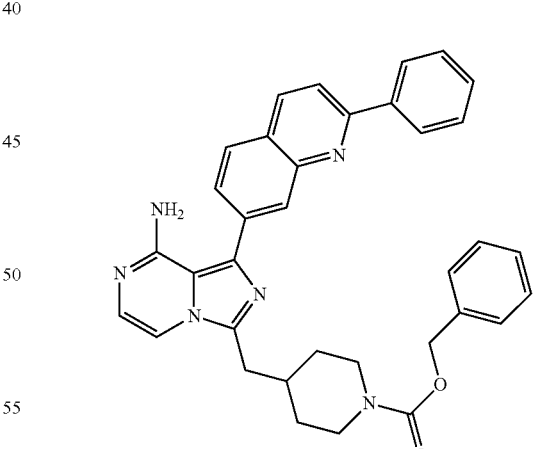

Benzyl 4-[8-Chloro-1-(2-phenyl-quinolin-7-yl)-imidazo[1,5-a]pyrazin-3-ylmethyl]-piperidine-1-carboxylic acid benzyl ester (1.50 g, 2.55 mmol) was dissolved in anhydrous 2-propanol (70.0 mL, 916 mmol) in a Parr bombs. The solution was cooled to −78° C. and ammonia was bubbled into the solution for 4 min. The bomb was sealed, stirred and heated to 110° C. for 3 days. The solvent was evaporated in vacuo. The residue was purified by a 25 g Jones silica gel (eluted with 5% MeOH/EtOAc), which afforded the desired product; $^1$H NMR (400 MHz, CHLOROFORM-d) δ 8.41 (1H, d, J=8.4), 8.30 (1H, d, J=8.64 Hz), 8.21 (2H, dd, J=1.58 Hz, J=1.18), 8.00 (2H, m), 7.84 (1H, dd, J=1.74, J=1.74), 7.54 (3H, m), 7.37 (5H, s), 7.24 (1H, d, J=5.54), 7.00 (1H, d, J=5.53), 5.13 (2H, s), 4.23 (2 H, m), 2.96 (2H, d, J=7.08), 2.82 (2H, m), 2.04 (1H, m), 1.80 (2H, m), 1.31 (2H, m); MS (ES+): m/z 569.17/570.16 (100/65) [MH$^+$]; HPLC: $t_R$=2.56 min (OpenLynx, polar_5 min).

(4-[8-Chloro-1-(2-phenyl-quinolin-7-yl)-imidazo[1,5-a]pyrazin-3-ylmethyl]-piperidine-1-carboxylic acid benzyl ester)

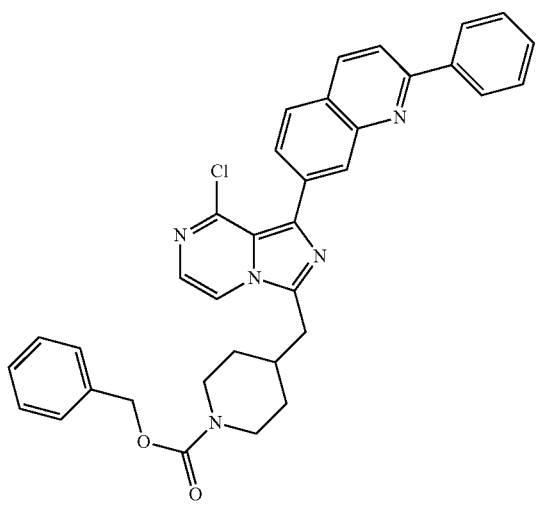 [SMILES: O=C(OCc1ccccc1)N1CCC(Cc2nc(-c3ccc4ccc(-c5ccccc5)nc4c3)c3c(Cl)nccn23)CC1]

A solution of 4-({[(3-chloro-pyrazin-2-yl)-(2-phenyl-quinolin-7-yl)-methyl]-carbamoyl}-methyl)-piperidine-1-carboxylic acid benzyl ester in anhydrous acetonitrile (165 mL) was charged with POCl$_3$ (2.03 mL, 21.84 mmol) and DMF (2.15 mL) and heated to 55° C. under N$_2$ condition. After 2 h, LC/MS and TLC analysis showed the reaction to be completed. The reaction mixture was concentrated in vacuo, diluted with CH$_2$Cl$_2$, and quenched with 2N (7N NH$_3$) in 2-propanol to pH 9. 2-Propanol was removed in vacuo. The crude product was purified by silica gel flash chromatography (loaded with 40% EtOAc/Hexanes, and run 50% EtOAc/Hexanes→80% EtOAc/Hexanes), which afforded the desired product; NMR (400 MHz, DMSO-d) δ ppm 8.53 (1H, d, J=8.52), 8.45 (1H, d, J=5.00), 8.31 (3H, m), 8.21 (1H, d, J=8.66), 8.08 (1H, d, J=8.47), 7.56 (3H, m), 7.49 (1 H, d, J=5.00), 7.34 (5H, m), 5.07 (2H, s), 4.02 (2H, d, J=12.8), 3.32 (2H, s), 3.11 (2H, d, J=6.92), 2.82 (1H, m), 2.13 (1H, m), 1.73 (2H, d, J=12.26), 1.21 (2H, m); MS (ES+): m/z 589.97 (5) [MH$^+$]; HPLC: $t_R$=3.72 min (OpenLynx, polar_5 min).

(4-({[(3-Chloro-pyrazin-2-yl)-(2-phenyl-quinolin-7-yl)-methyl]-carbamoyl}-methyl)-piperidine-1-carboxylic acid benzyl ester)

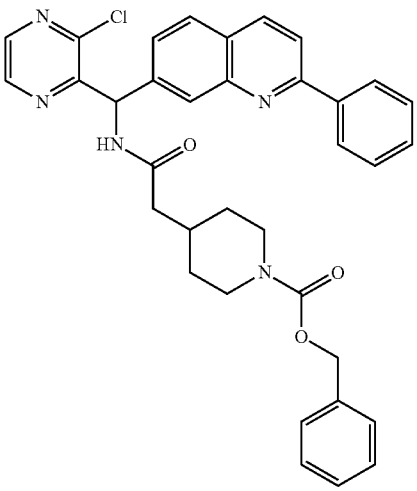 [SMILES: O=C(CC1CCN(C(=O)OCc2ccccc2)CC1)NC(c1ccc2ccc(-c3ccccc3)nc2c1)c1nccnc1Cl]

(3-Chloropyrazin-2-yl)(2-phenylquinolin-7-yl)-methanamine (120.00 mg, 0.35 mmol), EDC (100.64 mg, 0.53 mmol) and HOBt (47.29 mg, 0.35 mmol) were suspended in CH$_2$Cl$_2$ (2 mL) and charge with DIEA (122.00 μL, 0.70 mmol) followed by the addition of 1-N-Cbz-4-piperidineacetic acid (127.56 mg, 0.46 mmol). The reaction mixture was stirred at rt for 16 h. The reaction mixture was diluted with CH$_2$Cl$_2$ (10 mL) and washed with saturated NaHCO$_3$ (2×20 mL) and brine (2×20 mL). The organic layer was dried over Na$_2$SO$_4$ and concentrated in vacuo. The crude product was purified by a 10 g Jones silica gel (wetted with 50% EtOAc/Hexane, dried loaded onto silica, and run with 60% EtOAc/Hexanes→70% EtOAc/Hexanes) affording the desired product; $^1$H NMR (400 MHz, CHLOROFORM-d) δ 8.56 (1H, d, J=2.47), 8.39 (1H, d, J=2.50), 8.23 (1H, d, J=4.77), 8.11 (2H, d, J=7.06), 7.85 (3H, dd, J=8.60, J=8.38), 7.74 (1H, s), 7.50 (3H, m), 7.32 (6H, m), 6.78 (1H, d, J=7.76), 5.10 (2H, s), 4.11 (2H, m), 2.75 (2H, m), 2.21 (2H, d, J=7.00), 2.01 (1H, m), 1.67 (2H, m), 1.15 (2H, d, J=8.921); MS (ES+): m/z 605.96/606.98/608.93 (100/40/15) [MH$^+$]; HPLC: $t_R$=3.33 min. (OpenLynx, nonpolar_5 min.).

Example 22

(1-(2-Phenyl-quinolin-7-yl)-3-piperidin-4-ylmethyl-imidazo[1,5-a]pyrazin-8-ylamine)

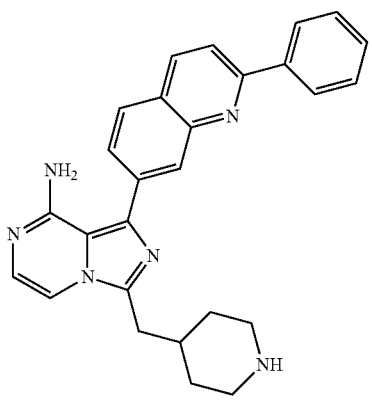 [SMILES: Nc1nccn2c(CC3CCNCC3)nc(-c3ccc4ccc(-c5ccccc5)nc4c3)c12]

4-[8-Amino-1-(2-phenyl-quinolin-7-yl)-imidazo[1,5-a]pyrazin-3-ylmethyl]-piperidine-1-carboxylic acid benzyl ester (1.94 g, 3.41 mmol) was mixed with 37% HCl (90.00 mL, 3.96 mol), heated to 60° C. and continued to stir for 5 mins. It was then cooled to rt, washed with ether (2×90 mL) and then with $CH_2Cl_2$ (2×90 mL). The aqueous layer was gradually basified with 5N NaOH and extracted with $CH_2Cl_2$ (3×50 mL). The combined organic layer was dried with $Na_2SO_4$, filtered and concentrated in vacuo. The crude product was purified by a 25 g Jones silica gel (eluted with 10% (7N $NH_3$) in MeOH/EtOAc), affording the desired product; $^1$H NMR (400 MHz, METHANOL-d) δ 8.38 (1H, d, J=8.68), 8.24 (1H, d, J=0.74 Hz), 8.08 (2H, dd, J=1.55 Hz, J=1.19), 8.00 (2H, m), 7.80 (1H, dd, J=1.68, J=1.70), 7.51 (1H, d, J=5.14), 7.44 (3H, m), 6.99 (1H, d, J=5.10), 2.99 (2H, d, J=12.60), 2.94 (2H, d, J=7.20), 2.55 (2H, t), 2.01 (1H, m), 1.66 (2H, d, J=12.72), 1.29 (2H, m); MS (ES+): m/z 435.12/436.10 (15/5) [MH$^+$]; HPLC: $t_R$=1.71 min (OpenLynx, polar 5 min).

Example 23

(3-(1-Ethyl-piperidin-4-ylmethyl)-1-(2-phenyl-quinolin-7-yl)-imidazo[1,5-a]pyrazin-8-ylamine)

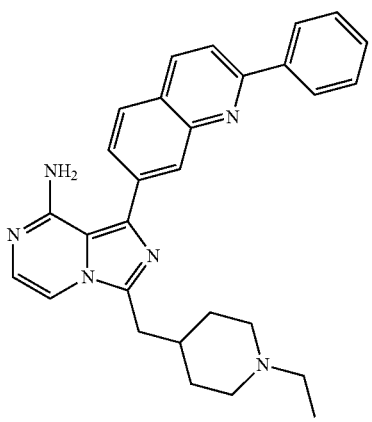 [SMILES: CCN1CCC(Cc2nc(-c3ccc4ccc(-c5ccccc5)nc4c3)c3c(N)nccn23)CC1]

Acetaldehyde (6.76 mg, 0.15 mmol) in dichloroethane (5 mL, 2 equiv) was added to 1-(2-Phenyl-quinolin-7-yl)-3-piperidin-4-ylmethyl-imidazo[1,5-a]pyrazin-8-ylamine (100.00 mg, 0.23 mmol) and sodium triacetoxyborohydride (65.0 mg, 306.8 mmol). The reaction mixture was stirred at rt overnight. The crude product was purified by a 5 g Jones silica gel (dry loaded with silica, wetted with 100% $CH_2Cl_2$, eluted with 100% $CH_2Cl_2$-+3% (7N $NH_3$) in MeOH/$CH_2Cl_2$ 6% (7N $NH_3$) in MeOH/$CH_2Cl_2$) and afforded the desired product. $^1$H NMR (400 MHz, METHANOL-d) δ 8.38 (1H, d, J=8.66), 8.25 (1H, s), 8.08 (2 H, dd, J=1.64 Hz, J=1.08), 8.00 (2H, m), 7.79 (1H, dd, J=2.06, J=1.70), 7.51 (1H, d, J=5.15), 7.44 (3H, m), 7.00 (1H, d, J=5.12), 3.06 (2H, d, J=10.88), 2.97 (2H, d, J=7.08), 2.54 (2H, d, J=5.80), 2.18 (2H, m), 1.98 (1H, m), 1.75 (2H, d, J=13.12), 1.43 (2H, m), 1.07 (3H, t); MS (ES+): m/z 435.12/436.10 (15/5) [MH$^+$]; HPLC: $t_R$=1.71 min (OpenLynx, polar_5 min).

Example 24

(1-{4-[8-Amino-1-(2-phenyl-quinolin-7-yl)-imidazo[1,5-a]pyrazin-3-ylmethyl]-piperidin-1-yl}-ethanone)

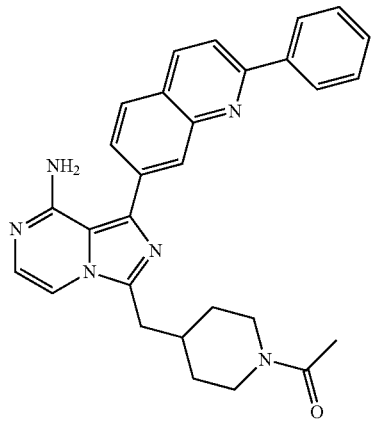 [SMILES: CC(=O)N1CCC(Cc2nc(-c3ccc4ccc(-c5ccccc5)nc4c3)c3c(N)nccn23)CC1]

1-(2-Phenyl-quinolin-7-yl)-3-piperidin-4-ylmethyl-imidazo[1,5-a]pyrazin-8-ylamine (100.00 mg, 0.23 mmol) in a dried 10 mL round-bottom flask was dissolved in 1.7 mL of methylene chloride and was charged with PS-DIEA (117.95 mg, 0.46 mmol). Acetic anhydride (Ac$_2$O) (11 μL, 0.51 equiv) was added in one portion. After 15 min., another 5.5 μL of Ac$_2$O (0.25 equiv) was added. After another 15 min., another 2.64 μL of Ac$_2$O (0.12 equiv) was added. After another 15 min., another 11 μL of Ac$_2$O (0.51 equiv) was added. The reaction was filtered through a fritted funnel, and the resins were rinsed multiple times with methylene chloride. The crude product was purified by silica gel flash chromatography (wetted with 100% EtOAc, eluted with 5% (7N NH$_3$) in MeOH/EtOAc) and afforded the desired product; $^1$H NMR (400 MHz, CHLOROFORM-d) δ 8.41 (1H, d, J=1.68), 8.28 (1H, d, J=8.20), 8.19 (2H, dd, J=1.51 Hz, J=1.18), 7.93 (3H, m), 7.53 (3H, m), 7.23 (1H, d, J=5.10), 7.12 (1H, d, J=5.76), 5.55 (2H, m), 4.67 (1H, d, J=13.28), 3.83 (1H, d, J=12.26), 3.06 (1H, m), 2.96 (2H, m), 2.56 (1H, m), 2.27 (1H, m), 2.10 (3H, s), 1.85 (2H, t), 1.31 (2H, m); MS (ES+): m/z 477.11/478.08 (40/20) [MH+]; HPLC: $t_R$=2.11 min (OpenLynx, polar_5 min).

Example 25

(1-{4-[8-Amino-1-(2-phenyl-quinolin-7-yl)-imidazo[1,5-a]pyrazin-3-ylmethyl]-piperidin-1-yl}-2-methoxy-ethanone)

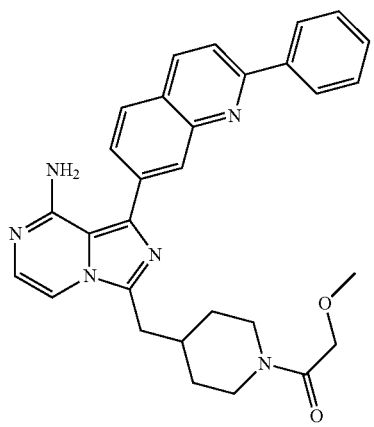 [SMILES: COCC(=O)N1CCC(Cc2nc(-c3ccc4ccc(-c5ccccc5)nc4c3)c3c(N)nccn23)CC1]

1-(2-Phenyl-quinolin-7-yl)-3-piperidin-4-ylmethyl-imidazo[1,5-a]pyrazin-8-ylamine (110.00 mg, 0.25 mmol) in a dried 15 mL round-bottom flask was dissolved in 2.00 mL of CH$_2$Cl$_2$ and charged with PS-DIEA (150 mg, 0.46 mmol). Methoxyacetyl (10 μL, 0.44 equiv) was added in one portion. After 10 min., another 10 μL of methoxyacetyl (0.44 equiv) was added. After another 10 min., another 5 μL of methoxylacetyl (0.22 equiv) was added. The reaction was filtered through a flitted funnel, and the resins were rinsed multiple times with CH$_2$Cl$_2$. The crude product was purified by a 5 g Jones silica gel (wetted with 100% ethyl acetate, eluted with 5% (7N NH$_3$) in MeOH/EtOAc) and afforded the desired product; $^1$H NMR (400 MHz, CHLOROFORM-d) δ 8.41 (1H, d, J=0.80), 8.35 (1H, d, 4 J=43.15), 8.23 (2H, m), 7.97 (2H, m), 7.88 (1H, dd, J=1.47, 1.73), 7.53 (3H, m), 7.23 (1H, d, J=5.19), 7.11 (1H, d, J=5.20), 5.77 (2H, m), 4.64 (1H, d, J=13.8), 3.90 (1H, d, 15.80), 3.49 (2H, s), 3.50 (3H, s), 3.04 (1H, d, J=13.08), 2.97 (2H, dd, J=2.44, J=2.72), 2.62 (1H, t), 2.29 (1H, m), 1.97 (2H, d, J=65.04), 1.37 (2H, m); MS (ES+): m/z 507.08/508.09 (50/30) [MH+]; HPLC: $t_R$=2.07 min (OpenLynx, polar_5 min).

Example 26

(3-(1-Methanesulfonyl-piperidin-4-ylmethyl)-1-(2-phenyl-quinolin-7-yl)-imidazo[1,5-a]pyrazin-8-ylamine)

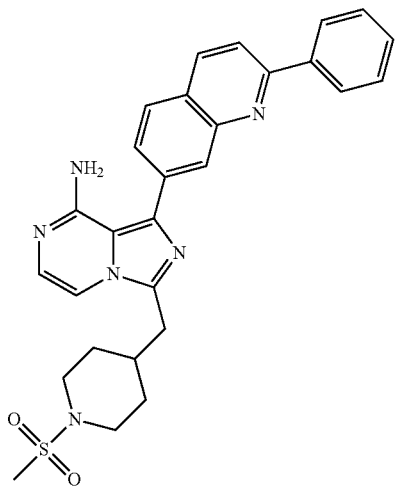 [SMILES: CS(=O)(=O)N1CCC(Cc2nc(-c3ccc4ccc(-c5ccccc5)nc4c3)c3c(N)nccn23)CC1]

1-(2-phenylquinolin-7-yl)-3-(piperidin-4-ylmethyl)-imidazo-[1,5-a]-pyrazin-8-amine (110.00 mg, 0.25 mmol) in a dried 15 mL round-bottom flask was dissolved in 2.00 mL of CH$_2$Cl$_2$ and charged with PS-DIEA (150.00 mg, 0.46 mmol). Methanesulfonyl chloride (10 μL, 0.47 equiv) was added in one portion. After 10 min., another 5 μL of methanesulfonyl chloride (0.24 equiv) was added. After another 10 min., another 2.1 μL of methanesulfonyl chloride (0.1 equiv) was added. The reaction was filtered through a fritted funnel, and the resins were rinsed multiple times with CH$_2$Cl$_2$. The crude product was purified by 5 g Jones silica gel (wetted with 100% CH$_2$Cl$_2$, dry loaded with silica, and eluted with 2% (7N NH$_3$) in MeOH/CH$_2$Cl$_2$→5% (7N NH$_3$) in MeOH/CH$_2$Cl$_2$) and afforded the desired product; $^1$H NMR (400 MHz, CHLOROFORM-d) δ 8.41 (1H, d, J=0.85), 8.29 (1H, d, J=8.86), 8.20 (2H, dd, J=1.51, J=1.12), 7.97 (2H, m), 7.86 (1H, dd, J=1.72, J=1.72), 7.53 (4H, m), 7.24 (1H, d, J=5.26), 7.08 (1H, d, J=6.75), 3.85 (2H, d, J=11.88), 2.98 (2H, d, J=7.08), 2.68 (2H, t), 2.20 (1H, m), 1.94 (2H, d, J=10.92), 1.50 (2H, m); MS (ES+): m/z 513.02/514.03 (80/70) [MH+]; HPLC: $t_R$=2.17 min (OpenLynx, polar_5 min).

Example 27

(1-{4-[8-Amino-1-(2-phenyl-quinolin-7-yl)-imidazo[1,5-a]pyrazin-3-ylmethyl]-piperidin-1-yl}-2-chloro-ethanone)

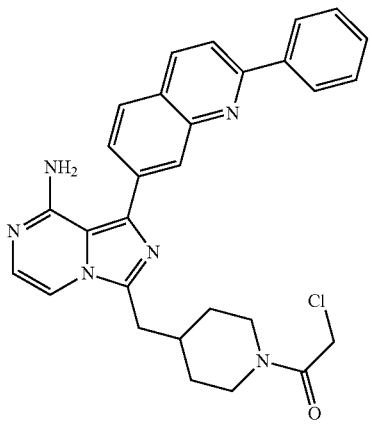 [SMILES: Nc1nccn2c(CC3CCN(C(=O)CCl)CC3)nc(-c3ccc4ccc(-c5ccccc5)nc4c3)c12]

1-(2-phenylquinolin-7-yl)-3-(piperidin-4-ylmethyl)-imidazo-[1,5a]-pyrazin-8-amine (110.00 mg, 0.25 mmol) in a dried 15 mL round bottom flask was dissolved in 2.00 mL of methylene chloride and was charged with PS-DIEA (150 mg, 0.46 mmol). Chloroacetyl chloride (10 µL, 0.42 equiv) was added in one portion. After 10 min., another 5 µL of chloroacetyl chloride (0.21 equiv) was added. After another 10 min., another 2.5 µL of methoxylacetyl (0.11 equiv) was added. The reaction was filtered through a flitted funnel, and the resins were rinsed multiple times with methylene chloride. The crude product was purified by a 5 g Jones silica gel (dry loaded with silica, wetted with 100% ethyl acetate and eluted with 5% $NH_3$ in MeOH/Ethyl Acetate) and afforded the desired product; $^1$H NMR (400 MHz, CHLOROFORM-d) δ 8.74 (1H, s), 8.30 (1H, d, J=8.68), 8.21 (2H, d, J=7.01), 7.98 (2H, m), 7.86 (1H, dd, J=1.70, J=1.70), 7.53 (3H, m), 7.24 (1H, d, J=5.34), 7.08 (1H, d, J=5.31), 4.63 (1H, d, J=13.24), 3.90 (1H, d, J=13.2), 3.15 (1H, t), 2.97 (2H, d, J=5.64), 2.70 (1H, t), 2.34 (1H, m), 2.05 (2H, s), 1.92 (2H, t), 1.42 (2H, m); MS (ES+): m/z 511.06/513.02 (50/25) [MH$^+$]; HPLC: $t_R$=2.20 min (OpenLynx, polar_5 min).

Example 28

(1-{-4-[8-Amino-1-(2-phenyl-quinolin-7-yl)-imidazo[1,5-a]pyrazin-3-ylmethyl]-piperidin-1-yl}-2-dimethylamino-ethanone)

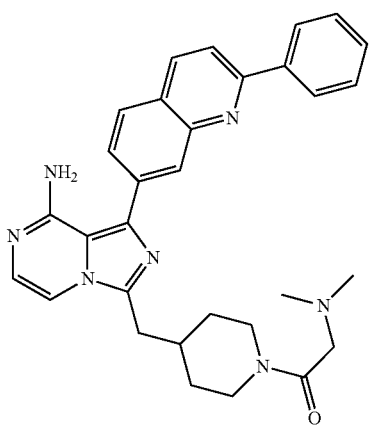 [SMILES: CN(C)CC(=O)N1CCC(Cc2nc(-c3ccc4ccc(-c5ccccc5)nc4c3)c3c(N)nccn23)CC1]

1-{4-[8-Amino-1-(2-phenyl-quinolin-7-yl)-imidazo[1,5-a]pyrazin-3-ylmethyl]-piperidin-1-yl}-2-chloro-ethanone (77.00 mg, 0.15 mmol) was transferred to a pressure reaction vessel and dissolved in 3.15 mL of 2M dimethylamine solution in THF. The reaction was heated at 80° C. overnight. The crude product was then condensed and purified by a 5 g Jones silica gel (dry loaded with silica gel; eluted with 100% $CH_2Cl_2$→2% (7N $NH_3$) in MeOH/$CH_2Cl_2$ 5% (7N $NH_3$) in MeOH/$CH_2Cl_2$) and afforded the desired product; $^1$H NMR (400 MHz, CHLOROFORM-d) δ 8.41 (1H, d, J=0.80), 8.28 (1H, d, J=8.23), 8.19 (2H, dd, J=2.04, J=1.55), 7.93 (3H, m), 7.53 (3H, dd, J=1.70, J=1.70), 7.53 (3H, m), 7.23 (1H, d, J=5.08), 7.15 (1H, d, 5.06), 5.52 (2H, m), 4.63 (1H, d, J=14.08), 4.04 (1H, d, J=11.88), 2.43 (2H, q), 2.97 (4H, d, J=6.08), 2.60 (1H, t), 2.43 (6H, s), 2.29 (1H, m), 1.86 (2H, d, J=12.96), 1.30 (2H, m); MS (ES+): m/z 520.11 (5) [MH$^+$]; HPLC: $t_R$=1.73 min (OpenLynx, polar_5 min).

Example 29

(4-[8-Amino-1-(2-phenyl-quinolin-7-yl)-imidazo[1,5-a]pyrazin-3-ylmethyl]-piperidine-1-carboxylic acid ethylamide)

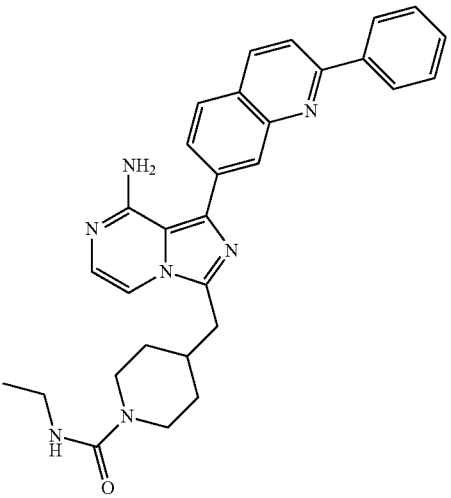 [SMILES: CCNC(=O)N1CCC(Cc2nc(-c3ccc4ccc(-c5ccccc5)nc4c3)c3c(N)nccn23)CC1]

1-(2-Phenylquinolin-7-yl)-3-(piperidin-4-ylmethyl)-imidazo-[1,5-a]-pyrazin-8-amine (110.00 mg, 0.25 mmol) in a dried 15 mL round-bottom flask was dissolved in 2.00 mL of $CH_2Cl_2$. At four 15 min. increments, 10 µl (0.47 equiv), 5 pt (0.24 equiv), 2.1 µL (0.1 equiv) and 2.1 µL (0.1 equiv) of ethyisocyanate were added dropwise, respectfully. The crude product was purified by 5 g Jones silica gel (wetted with 100% $CH_2Cl_2$; dry loaded with silica gel, eluted with 2% (7N $NH_3$) in MeOH/$CH_2Cl_2$→5% (7N $NH_3$) in MeOH/$CH_2Cl_2$) and afforded the desired product; $^1$H NMR (400 MHz, CHLOROFORM-d) δ 8.41 (1 H, d, J=1.64), 8.29 (1H, d, J=8.38), 8.20 (2H, dd, J=1.52, J=1.10), 7.97 (2H, m), 7.87 (1H, dd, J=1.71, J=1.71), 7.53 (4H, m), 7.24 (1H, d, J=5.26), 7.08 (1H, d, J=5.23), 4.38 (1H, t), 3.97 (2H, d, J=13.44), 3.28 (2H, m), 2.96 (2H, d, J=7.12), 2.79 (2H, t), 2.20 (1H, m), 1.80 (2H, d, J=10.60), 1.36 (2H, m); MS (ES+): m/z 506.07/507.08 (50/25) [MH$^+$]; HPLC: $t_R$=2.17 min (OpenLynx, polar_5 min).

Example 30 cis-3-[8-Amino-1-(2-phenyl-quinolin-7-yl)-imidazo[1,5-a]pyrazin-3-yl]-cyclobutanol

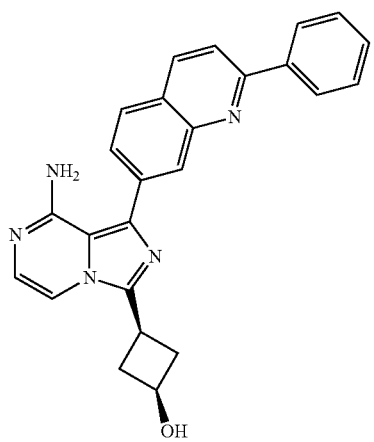 [SMILES: Nc1nccn2c1c(-c1ccc3ccc(-c4ccccc4)nc3c1)nc2[C@H]1C[C@@H](O)C1]

This compound was prepared utilizing the same procedures as those used for Example 1 except 3-[8-Chloro-1-(2-phenyl-quinolin-7-yl)-imidazo[1,5-a]pyrazin-3-yl]-cyclobutanol was used in place of 7-(8-chloro-3-cyclobutylimidazo[1,5-a]pyrazin-1-yl)-quinoline. NMR (400 MHz, CDCl$_3$) δ 8.42 (s, 1H), 8.28 (d, J=8.8 Hz, 1H), 8.19 (d, J=8.0 Hz, 2), 7.96-7.92 (m, 3H), 7.58-7.46 (m, 3H), 7.19 (d, J=5.2 Hz, 1H), 7.12 (d, J=5.2 Hz, 1H), 5.27 (b, 2H), 4.42 (p, J=7.2 Hz, 1H), 3.36 (p, J=8.0 Hz, 1H), 3.02-2.95 (m, 2H), 2.57-2.50 (m, 2H); MS (ES+): m/z 408 (100) [MH$^+$].

cis-3-[8-Chloro-1-(2-phenyl-quinolin-7-yl)-imidazo[1,5-a]pyrazin-3-yl]-cyclobutanol

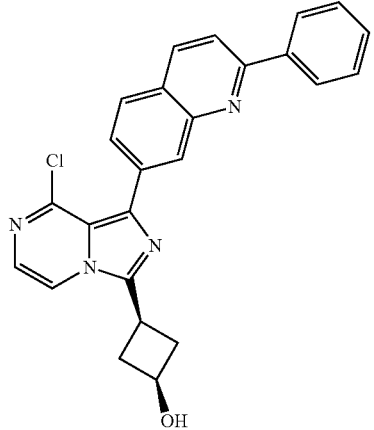 [SMILES: O[C@H]1C[C@@H](c2nc(-c3ccc4ccc(-c5ccccc5)nc4c3)c3c(Cl)nccn32)C1]

An ethanolic suspension (20 mL) of 3-[8-chloro-1-(2-phenylquinolin-7-yl)imidazo[1,5-a]pyrazin-3-yl]cyclobutanone: (2.5 mmol) was charged with NaBH$_4$(2.5 mmol) at rt. The reaction mixture was stirred at rt for 30 min until the reaction solution turned clear. The reaction mixture was quenched by an addition of Na$_2$SO$_4$·10H$_2$O and concentrated under reduced pressure. The crude mixture was dissolved in DCM, washed with water (3×15 mL), dried over Na$_2$SO$_4$, filtered and concentrated in vacuo to afford the title compound as a yellow solid. $^1$H NMR (400 MHz, CDCl$_3$) δ 8.52 (s, 1H), 8.28 (d, J=8.0 Hz, 1H), 8.19 (d, J=8.0 Hz, 2H), 7.93-7.87 (m, 3H), 7.58-7.52 (m, 3H), 7.47-7.45 (m, 1H), 7.37 (d, J=5.2 Hz, 1H), 4.44 (b, 1H), 3.37 (p, J=8.0 Hz, 1H), 3.03-2.96 (m, 2H), 2.60-2.53 (m, 2H); MS (ES+): m/z 427 (100) [MH$^+$].

Example 31 cis-3-[8-Amino-1-(2-phenyl-quinolin-7-yl)-imidazo[1,5-a]pyrazin-3-yl]-1-methyl-cyclobutanol was prepared as follows This compound was prepared utilizing the same procedures as those used for Example 1 except 3-[8-chloro-1-(2-phenyl-quinolin-7-yl)-imidazo[1,5-a]pyrazin-3-yl]-1-methyl-cyclobutanol was used in place of 7-(8-chloro-3-cyclobutylimidazo[1,5-a]pyrazin-1-yl)-quinoline. $^1$H NMR (400 MHz, CDCl$_3$) δ 8.40 (s, 1H), 8.24 (d, J=8.0 Hz, 1H), 8.19-8.17 (m, 2H), 7.92-7.88 (m, 3H), 7.56-7.45 (m, 3H), 7.17 (d, J=4.8 Hz, 1H), 7.11 (d, J=5.2 Hz, 1H), 5.29 (b, 2H), 3.46-3.49 (m, 1H), 2.72-2.61 (m, 4H), 1.50 (s, 3H); MS (ES+): 422 (M+1).

Additionally, cis-3-[8-amino-1-(2-phenyl-quinolin-7-yl)-imidazo[1,5-a]pyrazin-3-yl]-1-methyl-cyclobutanol was prepared as follows: A solution of 3-[8-amino-1-(2-phenylquinolin-7-yl)-imidazo[1,5-a]pyrazin-3-yl]-cyclobutanone (148 mg, 0.36 mmol) in THF (3 mL) at 10° C. was charged with methyl lithium and stirred at 10° C. for 10 min. The reaction was quenched with saturated ammonium chloride and extracted with DCM (3×25 mL). The combined DCM layer was washed with brine, dried over anhydrous sodium sulfate, filtered and evaporated under reduced pressure. The crude product was purified by preparative TLC using 5% ethyl acetate in hexanes as eluent to afford the title compound as a yellow solid; MS (ES+): m/z 422.33 [MH$^+$]; HPLC: t$_R$=2.09 min (OpenLynx, polar_5 min).

Example 32 trans-3-[8-Amino-1-(2-phenylquinolin-7-yl)-imidazo[1,5-a]pyrazin-3-yl]-1-methylcyclo butanol

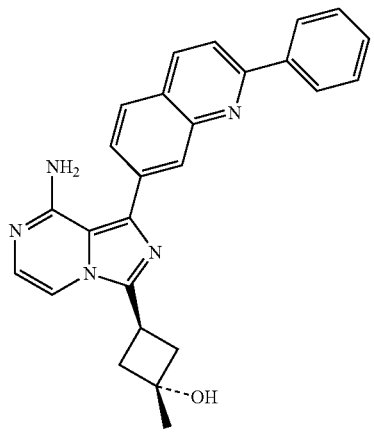 [SMILES: C[C@]1(O)C[C@H](c2nc(-c3ccc4ccc(-c5ccccc5)nc4c3)c3c(N)nccn32)C1]

To a solution of toluene-4-sulfonic acid 3-[8-amino-1-(2-phenylquinolin-7-yl)-imidazo-[1,5-a]pyrazin-3-yl]-1-hydroxycyclobutyl methyl ester (98 mg, 0.165 mmol) in THF (4 mL) at −78° C. was added LAH in THF (0.66 mL, 1 M solution) and the mixture was allowed to warm to 0° C. The reaction was quenched with saturated ammonium chloride solution (1 mL), diluted with DCM (20 mL) and filtered through a pad of celite. The filtrate was dried over anhydrous sodium sulfate and evaporated under reduced pressure. The crude product was purified by preparative TLC using 5% methanol in DCM as eluent to afford the title compound as a yellow solid; $^1$H NMR (400 MHz, CDCl$_3$) δ 8.42 (t, J=0.6 Hz, 1H), 8.26 (d, J=8.4 Hz, 1H), 8.16-8.19 (m, 2H), 7.90-7.96 (m, 3H), 7.45-7.55 (m, 3H), 7.10 (dd, J=6.6, 5.0 Hz, 2H), 5.25 (bs, 2H), 3.88-3.92 (m, 1H), 2.60-2.74 (m, 4H), 1.47 (s, 3H); MS (ES+): m/z 422.35 (100) [MH$^+$]; HPLC: t$_R$=2.13 min (OpenLynx, polar_5 min).

cis-3-[8-Chloro-1-(2-phenyl-quinolin-7-yl)-imidazo[1,5-a]pyrazin-3-yl]-1-methyl-cyclobutanol was prepared as follows

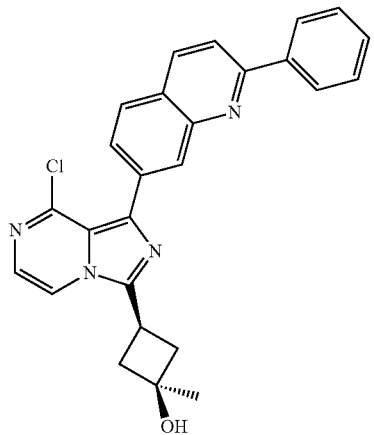 [SMILES: C[C@]1(O)C[C@@H](c2nc(-c3ccc4ccc(-c5ccccc5)nc4c3)c3c(Cl)nccn32)C1]

3-[8-Chloro-1-(2-phenylquinolin-7-yl)imidazo[1,5-a]pyrazin-3-yl]cyclobutanone was dissolved in dry THF (4.0 mL) under N$_2$ and cooled to −78° C. A solution of CH$_3$Li (1 M in Et$_2$O, 270 μL, 0.268 mmol) in Et$_2$O was added slowly to the cooled solution. The reaction mixture was stirred at −78° C. for 30 min and then allowed to warm to rt over 30 min. The reaction mixture was cooled to 0° C. and quenched by an addition of sat. aq. NH$_4$Cl solution and the aqueous layer was washed with DCM (3×). The organic layers were combined, dried (Na$_2$SO$_4$), filtered and concentrated under reduced pressure. The crude oil was purified by preparative TLC (silica gel, 1000 μm), developed with EtOAc:hexanes (6:4) and EtOAc:hexanes (7:3), yielding the title compounds as a yellow solid; $^1$H NMR (400 MHz, CDCl$_3$) δ 8.50 (d, J=1.2 Hz, 1H), 8.25 (dd, J=0.8 Hz, 8.0 Hz, 1H), 8.19 (td, J=0.8 Hz, 8.0 Hz, 2H), 7.90 (d, J=8.0 Hz, 1H), 7.87 (s, 2H), 7.56-7.44 (m, 4H), 7.34 (d, J=4.8 Hz, 1H), 3.64 (b, 1H), 3.41 (q, J=8.0 Hz, 1H), 2.72-2.63 (m, 4H), 1.50 (s, 3H); MS (ES+): 441 (M+1); HPLC: t$_R$=3.37 min (Openlynx LC-MS, polar_5 min).

Cis & trans-3-[8-Chloro-1-(2-phenylquinolin-7-yl)-imidazo[1,5-a]pyrazin-3-yl]-1-methylcyclobutanol To a solution of 7-[8-chloro-3-(3-methylenecyclobutyl)-imidazo[1,5-a]pyrazin-1-yl]-2-phenylquinoline (75 mg, 0.177 mmol) in THF (3 mL) was added mercuric acetate (59 mg, 0.185 mmol) and water (3 mL) and the mixture was stirred for 15 min. Sodium hydroxide (2 mL, 3N solution) was added followed by 0.5 N NaBH$_4$ in 3N NaOH (2 mL) and the mixture was diluted with DCM. The aqueous layer was removed and the DCM layer was filtered through a pad of celite and evaporated under reduced pressure. The crude product was purified by preparative TLC using 5% methanol in DCM as eluent to afford cis- and trans-3-[8-chloro-1-(2-phenylquinolin-7-yl)-imidazo[1,5-a]pyrazin-3-yl]-1-methyl cyclobutanol:

Trans-3-[8-Chloro-1-(2-phenylquinolin-7-yl)-imidazo[1,5-a]pyrazin-3-yl]-1-methyl cyclobutanol

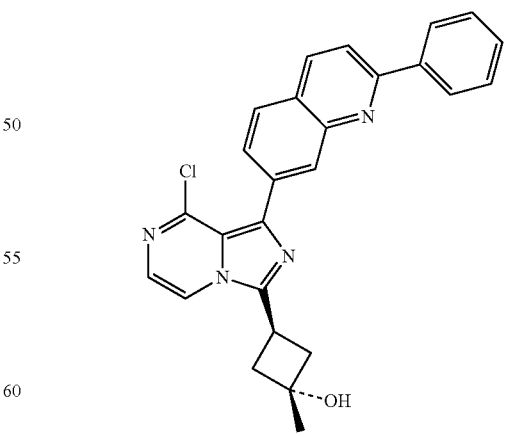

$^1$H NMR (400 MHz, CDCl$_3$) δ 8.52-8.53 (m, 1H), 8.26 (dd, J=8.5, 0.7 Hz, 1H), 8.16-8.19 (m, 2H), 7.89 (d, J=11.6 Hz, 1H), 7.88 (bs, 2H), 7.44-7.55 (m, 4H), 7.33 (d, J=4.9 Hz, 1H), 3.88-3.94 (m, 1H), 2.61-2.74 (m, 4H), 2.08 (s, 1H), 1.46 (s, cis-Toluene-4-sulfonic acid 3-[8-chloro-1-(2-phenylquinolin-7-yl)-imidazo[1,5-a]pyrazin-3-yl]-1-hydroxycyclobutylmethyl ester

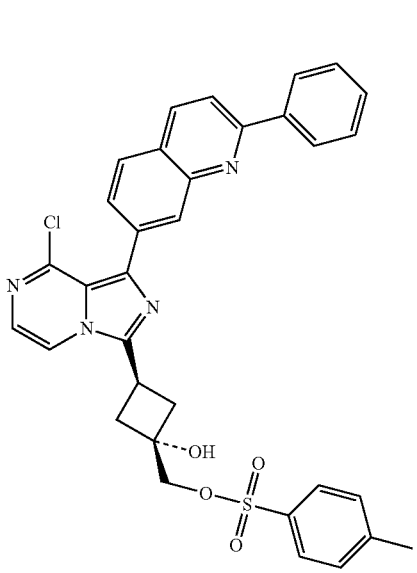 [SMILES: Cc1ccc(S(=O)(=O)OC[C@]2(O)C[C@H](c3nc(-c4ccc5ccc(-c6ccccc6)nc5c4)c4c(Cl)nccn43)C2)cc1]

A solution of 3-[8-chloro-1-(2-phenylquinolin-7-yl)-imidazo[1,5-a]pyrazin-3-yl]-1-hydroxymethyl-cyclobutanol (114 mg, 0.25 mmol) in DCM (4 mL) at −30° C. was charged with Et$_3$N (101 mg, 1 mmol) and tosyl chloride (52 mg, 0.275 mmol) and allowed to stir at RT overnight. Water was added to the reaction mixture and extracted with DCM (3×25 mL). The combined DCM layer was washed with brine, dried over anhydrous sodium sulfate and evaporated under reduced pressure. The crude product was purified by preparative TLC using 5% ethyl acetate in hexanes as eluent to afford the title compound as a yellow solid; $^1$H NMR (400 MHz, CDCl$_3$) δ 8.49 (s, 1H), 8.28 (d, J=8.5 Hz, 1H), 8.18-8.21 (m, 2H), 7.85-7.94 (m, 3H), 7.70 (d, J=8.2 Hz, 2H), 7.45-7.55 (m, 4H), 7.33 (d, J=4.9 Hz, 1H), 7.17 (d, J=8.0 Hz, 2H), 4.21 (s, 2H), 3.90-3.95 (m, 1H), 2.62-2.71 (m, 4H), 2.27 (s, 3H); MS (ES+): m/z 611.2 (100) [M$^+$]; HPLC: t$_R$=3.85 min (OpenLynx, polar_5 min).

Cis & trans methanesulfonic acid 3-[8-chloro-1-(2-phenylquinolin-7-yl)-imidazo[1,5-a]pyrazin-3-yl]-1-hydroxycyclobutylmethyl ester A solution of 3-[8-chloro-1-(2-phenylquinolin-7-yl)-imidazo[1,5-a]pyrazin-3-yl]-1-hydroxymethyl-cyclobutanol (229 mg, 0.50 mmol) in DCM (3 mL) at −30° C. was charged with Et$_3$N (101 mg, 1 mmol) and mesyl chloride (69 mg, 0.6 mmol) and allowed to warm to RT and stir overnight. Water was added to the reaction mixture and extracted with DCM (3×25 mL). The combined DCM layer was washed with brine, dried over anhydrous sodium sulfate and evaporated under reduced pressure. The crude product was purified by preparative TLC using 5% ethyl acetate in hexanes as eluent to afford the respective cis- and trans-isomers as yellow solids:

cis-Methanesulfonic acid 3-[8-chloro-1-(2-phenylquinolin-7-yl)-imidazo[1,5-a]pyrazin-3-yl]-1-hydroxycyclobutylmethyl ester

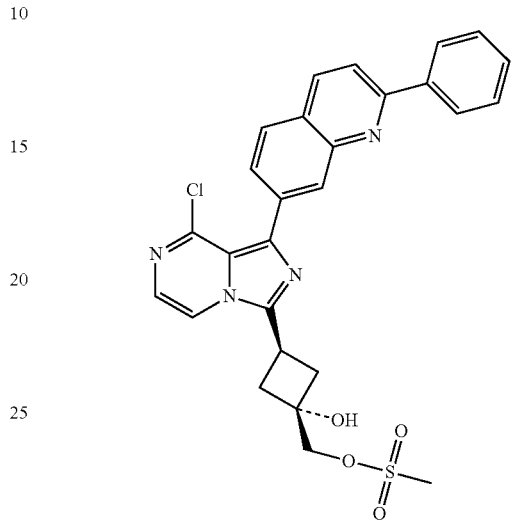

$^1$H NMR (400 MHz, CDCl$_3$) δ 8.42 (bs, 1H), 8.21 (d, J=8.6 Hz, 1H), 8.09-8.12 (m, 2H), 7.79-7.86 (m, 3H), 7.38-7.49 (m, 4H), 7.31 (d, J=4.9 Hz, 1H), 4.40 (s, 2H), 3.91-3.95 (m, 1H), 2.99-3.04 (m, 1H), 2.99 (s, 3H), 2.64-2.77 (m, 4H); MS (ES+): m/z 535.19 (100) [M$^+$]; HPLC: t$_R$=3.37 min (OpenLynx, polar_5 min).

trans-Methanesulfonic acid 3-[8-chloro-1-(2-phenylquinolin-7-yl)-imidazo[1,5-a]pyrazin-3-yl]-1-hydroxycyclobutylmethyl ester

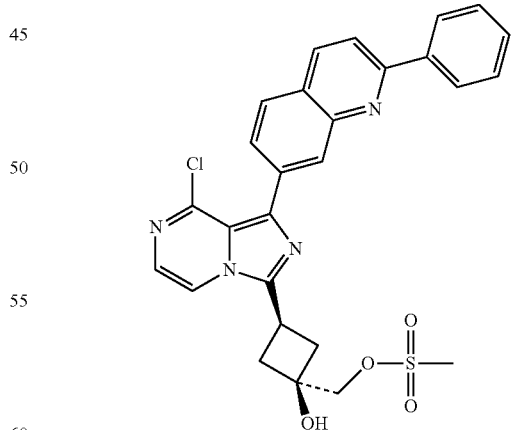

$^1$H NMR (400 MHz, CDCl$_3$) δ 8.43 (bs, 1H), 8.21 (d, J=8.8 Hz, 1H), 8.09-8.12 (m, 2H), 7.78-7.87 (m, 3H), 7.41-7.49 (m, 4H), 7.34 (d, J=4.9 Hz, 1H), 4.29 (s, 2H), 3.41-3.53 (m, 1H), 3.06 (s, 3H), 2.85-2.90 (m, 2H), 2.60-2.65 (m, 2H); MS (ES+): m/z 535.19 (100) [M$^+$]; HPLC: t$_R$=3.40 min (OpenLynx, polar_5 min).

Example 33

3-(3-Methylenecyclobutyl)-1-(2-phenylquinolin-7-yl)-imidazo[1,5-a]pyrazin-8-ylamine

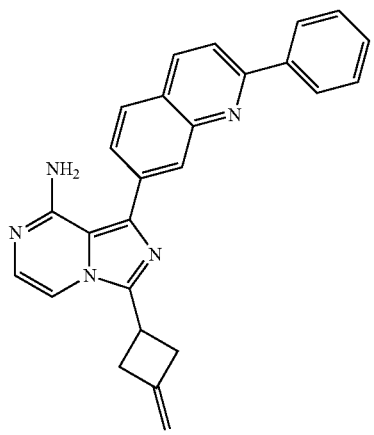 [SMILES: C=C1CC(c2nc(-c3ccc4ccc(-c5ccccc5)nc4c3)c3c(N)nccn23)C1]

Ammonia gas was bubbled in to IPA (5 mL, containing 2N NH$_3$) at −78° C., till the volume was doubled (10 mL), and this solution was added to a slurry of 7-[8-chloro-3-(3-methylenecyclobutyl)-imidazo[1,5-a]pyrazin-1-yl]-2-phenylquinoline (500 mg) in IPA (2 mL, containing 2N NH$_3$) at −78° C. The reaction mixture was heated in a high pressure bomb at 120° C. for 24 h. The reaction mixture was cooled −78° C. then allowed to warm to rt, diluted with DCM (50 mL), washed with saturated sodium bicarbonate, dried over anhydrous sodium sulfate, filtered and evaporated under reduced pressure to afford the title compound as a yellow solid; MS (ES+): m/z 404.34 (100) [MH$^+$]; HPLC: t$_R$=2.49 min (OpenLynx, polar_5 min).

Example 34 cis-3-[3-(Azidomethyl)cyclobutyl]-1-(2-phenylquinolin-7-yl)imidazo[1,5-a]pyrazin-8-amine

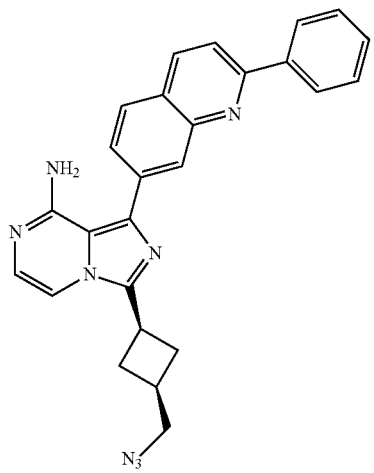 [SMILES: [N-]=[N+]=NC[C@H]1C[C@@H](c2nc(-c3ccc4ccc(-c5ccccc5)nc4c3)c3c(N)nccn32)C1]

A solution of {3-[8-amino-1-1-(2-phenylquinolin-7-yl)imidazo[1,5-a]pyrazin-3-yl]cyclobutyl}methyl 4-methylbenzenesulfonate (500 mg, 0.87 mmol) in DMF (10 mL) was charged with sodium azide (169 mg, 2.6 mmol), the reaction mixture was stirred at 50° C. overnight. The reaction mixture was diluted with water (10 mL), extracted with ethyl acetate (3×30 mL), and the combined organic phases were washed with water (2×30 mL) and brine (30 mL), and dried (Na$_2$SO$_4$). The filtrate was concentrated under reduced pressure, and the residue was purified by silica gel column chromatography (Jones Flashmaster, 10 g/70 mL cartridge) (eluting with 100% ethyl acetate), yielding the title compound as an off-white solid; $^1$H NMR (400 MHz, CDCl$_3$) δ 8.42-8.41 (m, 1H), 8.26 (dd, J=8.0 Hz, 0.8 Hz, 1H), 8.21-8.18 (m, 2H), 7.97-7.92 (m, 3H), 7.57-7.48 (m, 3H), 7.17 (d, J=4.0 Hz, 1H), 7.12 (d, J=4.0 Hz, 1H), 5.20 (b, 2H), 3.79-3.71 (m, 1H), 3.40 (d, J=2.8 Hz, 1H), 2.92 (dd, J=2.8 Hz, 0.4 Hz, 1H), 2.74-2.69 (m, 3H), 2.46-2.43 (m, 2H); MS (ES+): m/z 447.14 (60) [MH$^+$]; HPLC: t$_R$=2.48 min (OpenLynx, polar_5 min).

Example 35 cis-3-[3-(Aminomethyl)cyclobutyl]-1-(2-phenylquinolin-7-yl)imidazo[1,5-a]pyrazin-8-amine

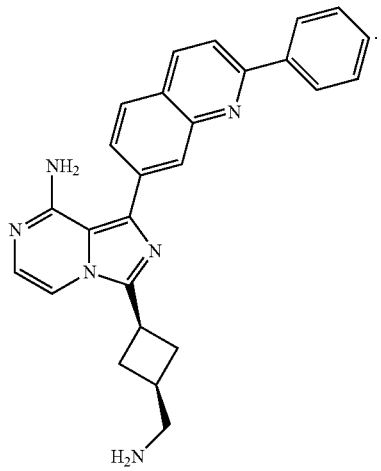 [SMILES: NC[C@H]1C[C@@H](c2nc(-c3ccc4ccc(-c5ccccc5)nc4c3)c3c(N)nccn32)C1]

3-[3-(Azidomethyl)cyclobutyl]-1-(2-phenylquinolin-7-yl)imidazo[1,5-a]pyrazin-8-amine (0.81 mmol, 360 mg) was dissolved in hot ethanol (15 mL) and charged with Lindlar catalyst (0.14 mmol, 362 mg). The reaction mixture was purged with N$_2$, evacuated and filled with H$_2$. The reaction mixture was stirred under H$_2$ for 16 h. The suspension was filtered through celite and the solvent was removed under reduced pressure. Part of the crude material (200 mg out of 300 mg) was purified by silica gel flush chromatography (Jones Flashmaster, 5 g/70 mL cartridge) eluting with 3% MeOH (7 N NH$_3$) in DCM. The final compound was recrystallized from EtOAc and hexane to generate the desired product as a light yellow solid; $^1$H NMR (400 MHz, CDCl$_3$) δ 8.42-8.41 (m, 1H), 8.27 (dd, J=8.0 Hz, 0.4 Hz, 1H), 8.21-8.19 (m, 2H), 7.95-7.92 (m, 3H), 7.57-7.48 (m, 3H), 7.19 (d, J=4.0 Hz, 1H), 7.11 (d, J=4.0 Hz, 1H), 5.20 (b, 2H), 3.73-3.69 (m, 1H), 2.81 (d, J=7.2 Hz, 2H), 2.66-2.62 (m, 2H), 2.58-2.48 (m, 1H), 2.36-2.30 (m, 2H); MS (ES+): m/z 421.13 (40) [MH+]; HPLC: t$_R$=1.69 min (OpenLynx, polar 5 min).

Example 36 cis-N-{[3-(8-Amino-1-(2-phenylquinolin-7-yl)imidazo[1,5-a]pyrazin-3-yl)cyclobutyl]methyl}acetamide

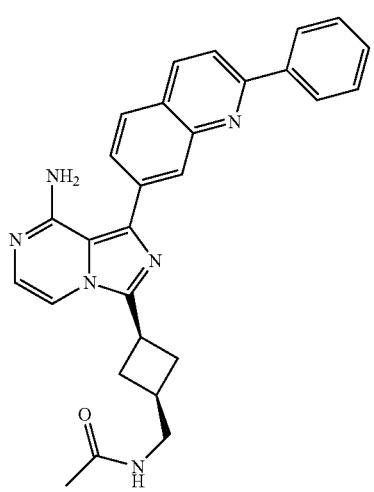 [SMILES: CC(=O)NC[C@H]1C[C@@H](c2nc(-c3ccc4ccc(-c5ccccc5)nc4c3)c3c(N)nccn32)C1]

A suspension of 3-[3-(aminomethyl)cyclobutyl]-1-(2-phenylquinolin-7-yl)imidazo[1,5-a]pyrazin-8-amine (0.237 mmol, 100 mg) in DCM (6 mL) was charged with DIEA (0.475 mmol, 83 µL) and Ac$_2$O (0.237 mmol, 22.43 µL) at −40° C. The reaction solution was warmed to rt slowly and stirred under N$_2$ for 1.5 h. The reaction was quenched with water (3 mL), diluted with methylene chloride (20 mL), washed with water (30 mL) and brine (30 mL), and dried (Na$_2$SO$_4$). The filtrate was concentrated under reduced pressure, and the crude material was purified by silica gel flush column chromatography (Jones Flashmaster, 10 g/70 mL cartridge), eluting with 3% MeOH (7 N NH$_3$) in DCM, yielding the title compound as a light yellow solid. The sample was recrystallized from DCM (minimal amount) and EtOAc. The final product was obtained as an off-white solid; $^1$H NMR (400 MHz, CDCl$_3$) δ 8.43-8.42 (m, 1H), 8.28 (dd, J=8.0 Hz, 0.4 Hz, 1H), 8.20-8.18 (m, 2H), 7.97-7.92 (m, 3H), 7.57-7.48 (m, 3H), 7.15 (d, J=4.8 Hz, 1H), 7.12 (d, J=5.2 Hz, 1H), 5.19 (b, 2H), 3.78-3.70 (m, 1H), 3.38 (t, J=5.6 Hz, 2H), 2.77-2.66 (m, 3H), 2.42-2.34 (m, 2H), 1.87 (s, 3H); MS (ES+): m/z 463 (100) [MH+]; HPLC: t$_R$=2.06 min (OpenLynx, polar 5 min).

Example 37 cis-N-([3-(8-Amino-1-(2-phenylquinolin-7-yl)imidazo[1,5-a]pyrazin-3-yl)cyclobutyl]methyl)methanesulfonamide

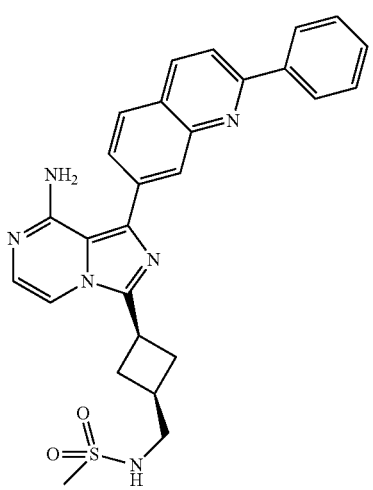 [SMILES: CS(=O)(=O)NC[C@H]1C[C@@H](c2nc(-c3ccc4ccc(-c5ccccc5)nc4c3)c3c(N)nccn32)C1]

3-[3-(Aminomethyl)cyclobutyl]-1-(2-phenylquinolin-7-yl)imidazo[1,5-a]pyrazin-8-amine (0.17 mmol, 70 mg) was dissolved in DCM (4 mL), treated with DIEA (1 mmol, 0.742 mL) and then charged with methane sulfonic acid anhydride (0.2 mmol, 34.7 mg) portionwise. The reaction mixture was stirred at rt for 16 h. The reaction was quenched with water (5 mL), diluted with methylene chloride (30 mL), washed with saturated sodium bicarbonate (40 mL) and brine (40 mL), and dried (Na$_2$SO$_4$). The crude product was purified by MDP (acidic conditions). The purified product was dissolved in DCM and washed with saturated aq NaHCO$_3$ and brine. The organic layer was dried (Na$_2$SO$_4$) and concentrated under reduced pressure, yielding the title compound as a light yellow solid; $^1$H NMR (400 MHz, CDCl$_3$) δ 8.42-8.41 (m, 1H), 8.26 (d, J=8.0 Hz, 1H), 8.20-8.18 (m, 2H), 7.96-7.91 (m, 3H), 7.56-7.48 (m, 3H), 7.11-7.08 (m, 2H), 5.35 (b, 2H), 3.71-3.67 (m, 1H), 3.25 (d, J=6.4 Hz, 1H), 2.94 (s, 3H), 2.75-2.63 (m, 3H), 2.39-2.33 (m, 3H); MS (ES+): m/z 499 [MH+]; HPLC: $t_R$=2.11 min (OpenLynx, polar_5 min).

Example 38 cis-3-(4-Methoxy-cyclohexyl)-1-(2-phenyl-quinolin-7-yl)-imidazo[1,5-a]pyrazin-8-ylamine

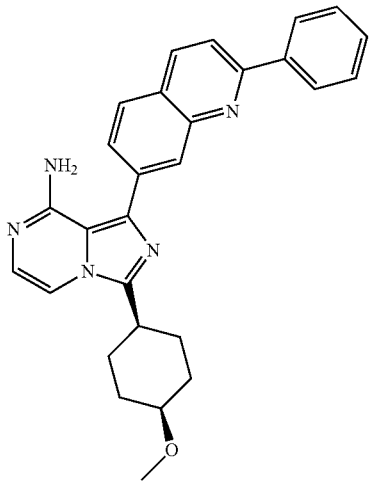 [SMILES: CO[C@H]1CC[C@@H](c2nc(-c3ccc4ccc(-c5ccccc5)nc4c3)c3c(N)nccn32)CC1]

A 2-propanol solution (40 mL) of cis-8-chloro-3-(4-methoxycyclohexyl)-1-(2-phenylquinolin-7-yl)imidazo[1,5-a]pyrazin (200 mg, 0.43 mmol) in a parr bomb was cooled to −78° C. Ammonia gas was bubbled into this solution for 3 min. The bomb was sealed and heated to 110° C. for 2 days. After cooled to rt, 2-propanol was removed and the crude product was purified by silica gel chromatography (70%→100% EtOAc in hexanes) to give the desired product as a yellow solid; $^1$H NMR (CDCl$_3$, 400 MHz) δ 1.58-1.66 (m, 2H), 1.83-1.87 (m, 2H), 2.12-2.28 (m, 4H), 3.03-3.11 (m, 1H), 3.36 (s, 3H), 3.55-3.57 (m, 1H), 7.08 (d, J=5.2 Hz, 1H), 7.30 (d, J=5.2 Hz, 1H), 7.46-7.56 (m, 3H), 7.90-7.56 (m, 3H), 8.18-8.21 (m, 2H), 8.27 (d, J=8.4 Hz, 1H), 8.41 (s, 1H); MS (ES+): m/z 450 [MH+]; HPLC: $t_R$=2.37 min (OpenLynx, polar 5 min).

Example 39 trans-3-(4-Methoxy-cyclohexyl)-1-(2-phenyl-quinolin-7-yl)-imidazo[1,5-a]pyrazin-8-ylamine

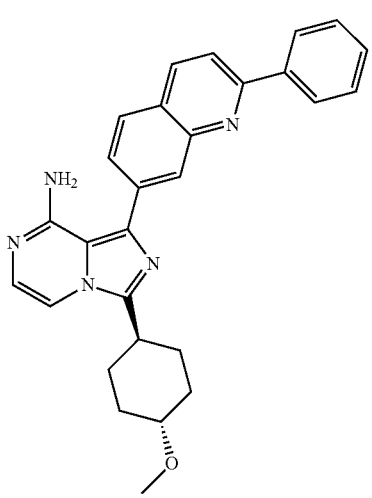 [SMILES: CO[C@H]1CC[C@H](c2nc(-c3ccc4ccc(-c5ccccc5)nc4c3)c3c(N)nccn32)CC1]

Prepared according to the procedures described for the synthesis of cis-3-(4-methoxy-cyclohexyl)-1-(2-phenyl-quinolin-7-yl)-imidazo[1,5-a]pyrazin-8-ylamine; $^1$H NMR (CDCl$_3$, 400 MHz) δ 1.37-1.47 (m, 2H), 1.91-1.98 (m, 2H), 2.15-2.19 (m, 2H), 2.27-2.31 (m, 2H), 2.94-3.00 (m, 1H), 3.27-3.35 (m, 1H), 3.48 (s, 3H), 7.10 (d, J=4.8 Hz, 1H), 7.28 (d, J=4.8 Hz, 1H), 7.46-7.56 (m, 3H), 7.87-7.97 (m, 3H), 8.18-8.20 (m, 2H), 8.27 (d, J=8.4 Hz, 1H), 8.41 (s, 1H); MS (ES+): m/z 450 [MH+]; HPLC: $t_R$=2.35 min (OpenLynx, polar_5 min).

7-[8-Chloro-3-(4-methoxy-cyclohexyl)-imidazo[1,5-a]pyrazin-1-yl]-2-phenyl-quinoline A round bottom flask, charged with carbonyldiimidazole (252.2 mg, 1.55 mmol) and 4-methoxy-cyclohexanecarboxylic acid (mixture of cis/trans isomers) (242.9 mg, 1.54 mmol) was evacuated and filled with nitrogen. THF (15 mL) was added and the reaction mixture was stirred at 60° C. for 16 h. (3-Chloropyrazin-2-yl)(2-phenylquinolin-7-yl)methylamine hydrochloride salt (500 mg, 1.10 mmol) was then added and stirring was continued at 60° C. for another 20 h. After cooled to rt, the reaction mixture was diluted with 20 mL of EtOAc and washed with sat. NaHCO$_3$ (3×30 mL) followed by brine (3×30 mL). The organic phase was dried over Na$_2$SO$_4$, filtered, concentrated under reduced pressure, and purified by silica gel chromatography (60% EtOAc in hexane→100% EtOAc). N-[(3-Chloropyrazin-2-yl)(2-phenyl-quinolin-7-yl)-methyl]-4-methoxycyclohexanecarboxamide was obtained as a yellow solid. To a solution of N-[(3-chloropyrazin-2-yl)(2-phenyl-quinolin-7-yl)-methyl]-4-methoxycyclohexanecarboxamide (440 mg, 0.91 mmol) in acetonitrile (20 mL) was added POCl$_3$ (0.17 mL, 1.69 mmol) and DMF (0.3 mL). This mixture was heated to 55° C. under N$_2$ for 2 h, concentrated under reduced pressure, and quenched with 2N NH$_3$ in 2-propanol to pH 9. 2-Propanol was removed under reduced pressure and the residue was dissolved in dichloromethane (50 mL) and water (30 mL). Layers were separated and the organic phase was washed with brine and dried over Na$_2$SO$_4$, filtered, concentrated under reduced pressure, and purified by silica gel chromatography (2%→6% CH$_3$CN in dichloromethane) to afford the individual cis-isomer and trans-isomers:

cis-7-[8-Chloro-3-(4-methoxy-cyclohexyl)-imidazo[1,5-a]pyrazin-1-yl]-2-phenyl-quinoline

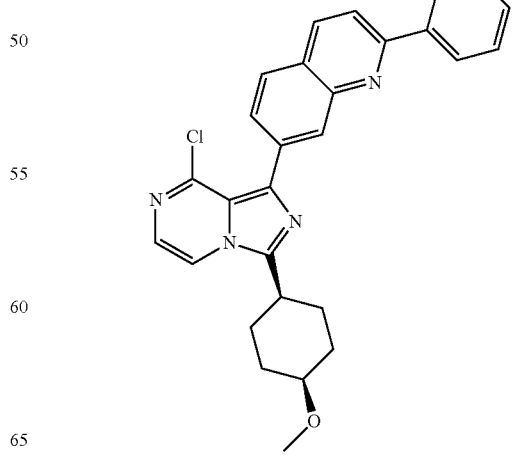

$^1$H NMR (CDCl$_3$, 400 MHz) δ 1.59-1.66 (m, 2H), 1.82-1.87 (m, 2H), 2.13-2.27 (m, 4H), 3.08-3.16 (m, 1H), 3.35 (s, 3H), 3.56-3.57 (m, 1H), 7.35 (d, J=5.2 Hz, 1H), 7.46-7.56 (m, 3H), 7.69 (d, J=5.2, 1H), 7.88-7.91 (m, 3H), 7.18-8.20 (m, 2H), 8.26 (dd, J=0.8 Hz, J=8.8 Hz, 1H), 8.51 (d, J=1.2 Hz, 1H); MS (ES+): m/z 469 [MH$^+$]; HPLC: t$_R$=4.07 min (OpenLynx, polar_5 min).

trans-7-[8-Chloro-3-(4-methoxy-cyclohexyl)-imidazo[1,5-a]pyrazin-1-yl]-2-phenyl-quinoline

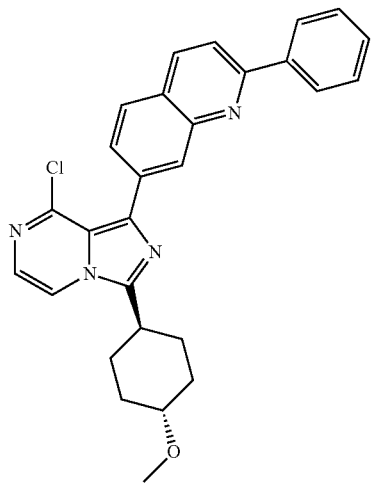 [SMILES: CO[C@H]1CC[C@H](c2nc(-c3ccc4ccc(-c5ccccc5)nc4c3)c3c(Cl)nccn32)CC1]

$^1$H NMR (CDCl$_3$, 400 MHz) δ 1.25-1.47 (m, 2H), 1.90-2.01 (m, 2H), 2.14-2.17 (m, 2H), 2.27-2.31 (m, 2H), 2.96-3.04 (m, 1H), 3.26-3.35 (m, 1H), 3.41 (s, 3H), 7.37 (d, J=4.8 Hz, 1H), 7.44-7.55 (m, 3H), 7.67 (d, J=5.2 Hz, 1H), 7.85-7.91 (m, 3H), 8.16-8.19 (m, 2H), 8.26 (d, J=8.8 Hz, 1H), 8.50 (s, 1H); MS (ES+): m/z 469 [MH$^+$]; HPLC: t$_R$=4.00 min (OpenLynx, polar_5 min).

Example 40

3-Cyclobutyl-1-(1-oxy-2-phenylquinolin-7-yl)-imidazo[1,5-a]pyrazin-8-ylamine

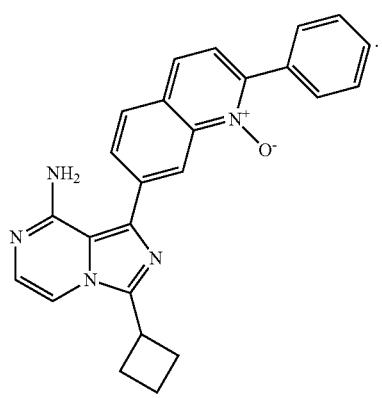 [SMILES: Nc1nccn2c(C3CCC3)nc(-c3ccc4ccc(-c5ccccc5)[n+]([O-])c4c3)c12]

To a cooled (ice-H$_2$O) solution of 7-(8-chloro-3-cyclobutylimidazo[1,5-a]pyrazin-1-yl)-2-phenylquinoline (197 mg, 0.48 mmol) in ClCH$_2$CH$_2$Cl (20 mL) was added mCPBA (97 mg, max 0.43 mmol, max. 77% Aldrich) in one portion. The solution was stirred at the temperature for 30 min and then allowed to warm to rt by removing the cooling bath and stirred at rt (2 h). The reaction mixture was again cooled (ice-H$_2$O) and treated with another portion of mCPBA (107 mg, max 0.48 mmol), stirred for 30 min at the temperature and then overnight at rt (15 h). After that time the crude mixture was filtered through hydromatrix (25 mL) pretreated with 2 M aq NaOH (10 mL). The hydromatrix column was washed with DCM (~100 mL) and the filtrate was concentrated under reduced pressure. The resultant yellow residue was purified by flash chromatography on silica gel (70 g cartridge, 0→0.75→4% MeOH in DCM) to yield 7-(8-chloro-3-cyclobutylimidazo[1,5-a]pyrazin-1-yl)-2-phenylquinoline 1-oxide as a yellow gum. A cooled (−10° C.) i-PrOH (15 mL) solution of 7-(8-chloro-3-cyclobutylimidazo[1,5-a]pyrazin-1-yl)-2-phenylquinoline 1-oxide (50 mg) in a Parr bomb was saturated with NH$_3$(g) for 3 min. The vessel was sealed and heated at 100-110° C. (bath temperature) for 2 d. The reaction mixture was then cooled to rt, concentrated under reduced pressure and purified by flash chromatography on silica gel (0-4% MeOH+2% ~6 M NH$_3$ in MeOH. A trituration with hexanes (3×) provided the title material as a bright yellow solid; $^1$H NMR (400 MHz, CDCl$_3$) δ 9.12 (s, 1H), 8.16 (dd, J=8.2 Hz, 1.8 Hz, 1H), 8.04-7.96 (m, 3H), 7.79 (d, J=8.8 Hz, 1H), 7.57-7.43 (m, 4H), 7.16 (d, J=5.2 Hz, 1H), 7.13 (d, J=4.8 Hz, 1H), 5.30 (s, 2H), 3.85 (quintet, J=8.2 Hz, 1H), 2.69-2.60 (m, 2H), 2.55-2.50 (m, 2H), 2.30-2.15 (m, 1H), 2.15-2.00 (m, 1H); MS (ES+): m/z 408.13 (100) [MH$^+$]; HPLC: t$_R$=2.14 min (OpenLynx, polar_5 min).

Example 41

7-Cyclobutyl-5-(2-phenyl-quinolin-7-yl)-imidazo[5,1-f][1,2,4]triazin-4-ylamine

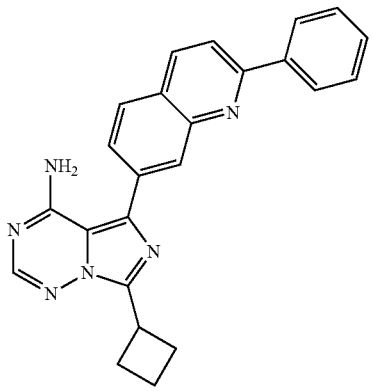 [SMILES: Nc1ncnn2c(C3CCC3)nc(-c3ccc4ccc(-c5ccccc5)nc4c3)c12]

A flask was charged with 7-cyclobutyl-5-iodo-imidazo[5,1-f][1,2,4]triazin-4-ylamine (30 mg, 0.095 mmol), 2-phenyl-7-(4,4,5,5-tetramethyl-[1,3,2]dioxaborolan-2-yl)-quinoline (38 mg, 0.110 mmol), and sodium carbonate (Na$_2$CO$_3$) (30 mg, 0.286 mmol) was evacuated and charged with nitrogen (N$_2$) (3×). To this mixture was quickly added tetrakis(triphenylphosphine)palladium(0) and evacuated and charged with N$_2$ (2×). This mixture was charged with a previously degassed solvent DME/H$_2$O (5:1) (2 mL) and heated overnight at 75° C. The reaction mixture was filtered through an autovial (0.45 μM frit) and washed with MeOH (3×). The filtrate was concentrated in vacuo and purified by mass directed purification (MDP) resulting in the title compound as a pale yellow solid;

¹H NMR (CDCl₃, 400 MHz) δ 1.96-2.10 (m, 1H), 2.10-2.25 (m, 1H); 2.40-2.56 (m, 2H); 2.60-2.78 (m, 2H); 4.12-4.29 (m, 1H); 5.99 (brs, 2H); 7.42-7.58 (m, 3H); 7.84-8.05 (m, 4H); 8.18 (d, J=7.2 Hz, 2H); 8.28 (d, J=8.4 Hz, 1H); 8.39 (s, 1H); MS (ES+): m/z 393.14 (100) [MH⁺], HPLC: t_R=3.51 min (MicromassZQ, polar_5 min).

Example 42

7-Cyclobutyl-5-(2-pyridin-2-yl-quinolin-7-yl)-imidazo[5,1-f][1,2,4]triazin-4-ylamine

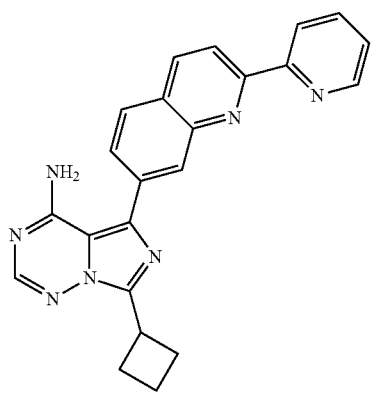

7-Cyclobutyl-5-(2-pyridin-2-yl-quinolin-7-yl)-imidazo[5,1-f][1,2,4]triazin-4-ylamine was prepared using the same procedures described as described for 7-Cyclobutyl-5-(2-phenyl-quinolin-7-yl)-imidazo[5,1-f][1,2,4]triazin-4-ylamine, except 2-pyridin-2-yl-7-(4,4,5,5-tetramethyl-[1,3,2]dioxaborolan-2-yl)-quinoline was used in place of 2-phenyl-7-(4,4,5,5-tetramethyl-[1,3,2]dioxaborolan-2-yl)-quinoline; ¹H NMR (DMSO-d₆, 400 MHz) δ 1.88-2.00 (m, 1H), 2.02-2.16 (m, 1H); 2.32-2.44 (m, 2H); 2.44-2.58 (m, 2H); 4.00-4.16 (m, 1H); 6.76 (brs, 2H); 7.45-7.59 (m, 1H); 7.94 (s, 1H); 7.94-8.05 (m, 2H); 8.13 (d, J=8.4 Hz, 1H); 8.24-8.32 (m, 1H); 8.51-8.68 (m, 3H); 8.72-8.80 (m, 1H); MS (ES+): m/z 394.08 (100) [MH⁺], HPLC: t_R=3.14 min (MicromassZQ, polar_5 min).

Example 43

7-Cyclobutyl-5-(4-methyl-2-phenyl-quinolin-7-yl)-imidazo[5,1-f][1,2,4]triazin-4-ylamine

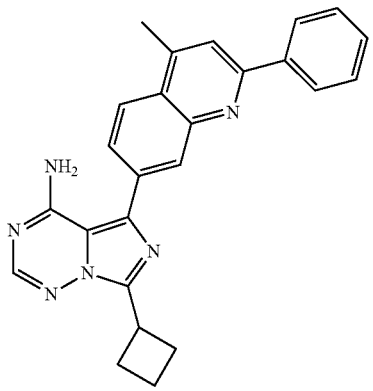

7-Cyclobutyl-5-(4-methyl-2-phenyl-quinolin-7-yl)-imidazo[5,1-f][1,2,4]triazin-4-ylamine was prepared using the same procedures described for 7-cyclobutyl-5-(2-phenyl-quinolin-7-yl)-imidazo[5,1-f][1,2,4]triazin-4-ylamine, except 4-methyl-2-phenyl-7-(4,4,5,5-tetramethyl-[1,3,2]dioxaborolan-2-yl)-quinoline was used in place of 2-phenyl-7-(4,4,5,5-tetramethyl-[1,3,2]dioxaborolan-2-yl)-quinoline and 2 equivalents of cesium carbonate was used in place of 3 equivalents of sodium carbonate; ¹H NMR (CDCl₃, 400 MHz) δ 2.06 (m, 1H), 2.17 (m, 1H); 2.47-2.52 (m, 2H); 2.67-2.72 (m, 2H); 2.82 (d, J=0.8 Hz, 3H); 4.14-4.25 (m, 1H); 5.78 (brs, 2H); 7.46-7.56 (m, 3H); 7.77 (d, J=0.8 Hz, 1H); 7.92 (s, 1H); 7.98 (dd, J=8.6, 1.8 Hz, 1H); 8.15-8.18 (m, 3H); 8.39 (d, J=1.6 Hz, 1H); MS (ES+): m/z 407.03 (100) [MH⁺], HPLC: t_R=3.54 min (MicromassZQ, polar_5 min).

Example 44

7-Cyclobutyl-5-(8-fluoro-2-phenyl-quinolin-7-yl)-imidazo[5,1f][1,2,4]-triazin-4-ylamine

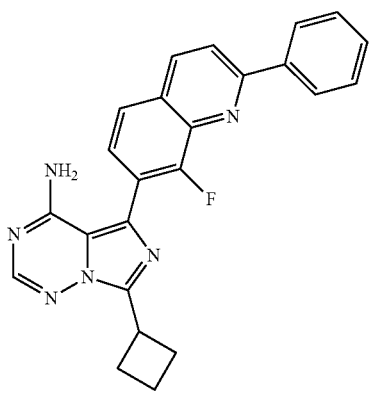 [SMILES: Nc1ncnn2c(C3CCC3)nc(-c3ccc4ccc(-c5ccccc5)nc4c3F)c12]

A stirred solution of 7-cyclobutyl-5-iodo-imidazo[5,1-f][1,2,4]triazin-4-ylamine (40 mg, 0.1 mmol), 8-fluoro-2-phenyl-7-(4,4,5,5-tetramethyl-[1,3,2]dioxaborolan-2-yl)quinoline (52 mg, 0.15 mmol) and cesium carbonate (50 mg, 0.15 mmol) in dimethoxyethane (DME) (1.67 mL) and H$_2$O (0.33 mL) was degassed for 10 minutes using N$_2$. Tetrakis(triphenylphosphine)palladium(0) (7 mg, 0.006 mmol) was added, and the reaction was heated to 75° C. and maintained at this temperature for 16 hours. After cooling, the reaction mixture was poured into saturated sodium bicarbonate (NaHCO$_3$) solution (50 ml) and extracted with EtOAc (3×50 ml). The combined organics were washed with brine (2×50 ml), dried over magnesium sulfate (MgSO$_4$), filtered and concentrated. The material was purified by chromatography on silica gel [eluting with 100% DCM→0.4% MeOH in DCM] resulting in the title compound as a white solid; $^1$H NMR (CDCl$_3$, 400 MHz) δ 2.06-1.99 (m, 1H), 2.10-2.20 (m, 1H), 2.42-2.52 (m, 2H), 2.62-2.71 (m, 2H), 4.14-4.21 (m, 1H), 7.45-7.56 (m, 3H), 7.74 (d, J=8.6 Hz, 1H), 7.79 (dd, J=6.3 Hz, 6.3 Hz, 1H), 7.87 (s, 1H), 7.99 (d, J=8.8 Hz, 1H), 8.21 (d, J=6.8 Hz, 2H), 8.27 (d, J=7.6 Hz, 1H); MS (ES+): m/z 411.00 (100) [MH$^+$], HPLC: t$_R$=3.53 min (MicromassZQ, polar_5 min).

7-Cyclobutyl-5-iodo-imidazo[5,1-f][1,2,4]triazin-4-ylamine

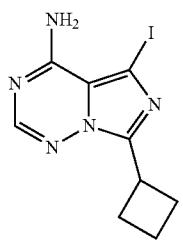 [SMILES: Nc1ncnn2c(C3CCC3)nc(I)c12]

To a solution of 1,2,4-triazole (1.28 g, 18.59 mmol) in anhydrous pyridine (10 mL) was added phosphorus oxychloride (POCl$_3$) (0.578 mL, 6.20 mmol) and stirred at rt for 15 min. This mixture was dropwise charged (3.5 min) with a solution of 7-cyclobutyl-5-iodo-3H imidazo[5,1f][1,2,4]triazin-4-one (0.653 mg, 2.07 mmol) in anhydrous pyridine (14 mL) and stirred for 1.5 h. The reaction mixture was cooled to 0° C. quenched with 2M NH$_3$ in isopropanol (IPA) until basic then allowed to reach it and stirred for an additional 2 h. The reaction mixture was filtered through a fritted Buchner funnel and washed with DCM. The filtrate was concentrated in vacuo and purified by chromatography on silica gel [eluting with 30% EtOAc in DCM] resulting in the title compound as an off-white solid; $^1$H NMR (CDCl$_3$, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH$^+$], HPLC: t$_R$=2.59 min (MicromassZQ, polar_5 min).

7-Cyclobutyl-5-iodo-3H-imidazo[5,1-f][1,2,4]triazin-4-one

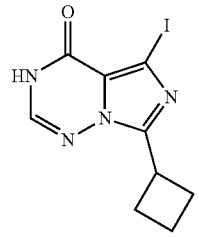 [SMILES: O=c1[nH]cnn2c(C3CCC3)nc(I)c12]

A solution of 7-cyclobutyl-3H-imidazo[5,1-f][1,2,4]triazin-4-one (789 mg, 4.15 mmol) and N-iodosuccinimide (933 mg, 4.15 mmol) in anhydrous DMF (40 mL) was stirred overnight at rt. An additional 4 equiv of NIS was added and reaction was heated to 55° C. for 6 h. The reaction mixture was concentrated in vacuo and partitioned between DCM and H$_2$O and separated. The aqueous layer was washed with DCM (3×) and the combined organic fractions were washed with 1M sodium thiosulfate (Na$_2$S$_2$O$_3$) (1×), brine (1×), dried over sodium sulfate (Na$_2$SO$_4$), filtered, and concentrated in vacuo. The solid was triturated with 20% EtOAc in DCM and filtered through a fitted Buchner funnel resulting in the title compound as an off-white solid; $^1$H NMR (DMSO-d$_6$, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH$^+$], HPLC: t$_R$=2.62 min (MicromassZQ, polar_5 min).

7-Cyclobutyl-3H-imidazo[5,1-f][1,2,4]triazin-4-one

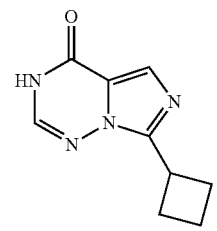 [SMILES: O=c1[nH]cnn2c(C3CCC3)ncc12]

A crude solution of cyclobutanecarboxylic acid (5-oxo-4,5-dihydro-[1,2,4]triazin-6-ylmethyl)-amide (1.33 g, 6.39 mmol) in phosphorus oxychloride (POCl$_3$) (10 mL) was heated to 55° C. The reaction was heated for 2 h then concentrated in vacuo and the crude oil was cooled to 0° C. in an ice-bath and quenched with 2 M NH$_3$ in isopropanol (IPA) until slightly basic. This crude reaction mixture was concentrated in vacuo and was partitioned between DCM and H$_2$O and separated. The aqueous layer was extracted with DCM (3×) and the combined organic fractions were dried over sodium sulfate (Na$_2$SO$_4$), filtered and concentrated in vacuo. The crude material was purified by chromatography on silica gel [eluting with 5% MeOH in DCM], resulting in the title compound as an off-white solid; $^1$H NMR (DMSO-d$_6$, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H);

11.7 (brs, 1H); MS (ES+): m/z 191.27 (100) [MH+], HPLC: $t_R$=2.06 min (MicromassZQ, polar_5 min).

Cyclobutanecarboxylic acid (5-oxo-4,5-dihydro-[1,2,4]triazin-6-ylmethyl)-amide

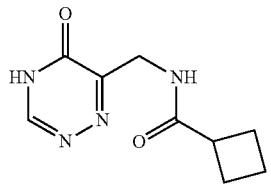 [SMILES: O=C(NCc1nnc[nH]c1=O)C1CCC1]

To a solution of 6-aminomethyl-4H-[1,2,4]triazin-5-one (500 mg, 3.96 mmol) and N,N-diisopropylethylamine (DIEA) (0.829 mL, 4.76 mmol) in anhydrous N,N-dimethylforamide (DMF) (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H$_2$O (2 mL) and concentrated in vacuo and was purified by chromatography on silica gel [eluting with 5% MeOH in DCM (200 mL)→10% MeOH in DCM (800 mL)], affording the title compound; $^1$H NMR (DMSO-d$_6$, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (brt, J=5.6 Hz, 1H); 8.67 (s, 1H); MS (ES+): m/z 209.25 (100) [MH+], HPLC: $t_R$=1.56 min (MicromassZQ, polar_5 min).

6-Aminomethyl-4H-[1,2,4]triazin-5-one

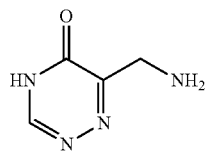

A slurry of 2-(5-oxo-4,5-dihydro-[1,2,4]triazin-6-ylmethyl)-isoindole-1,3-dione (4 g, 15.6 mmol) in DCM/EtOH (1:1) (150 mL) was charged with anhydrous hydrazine (1.23 mL, 39.0 mmol) and stirred at it for 18 h. The reaction mixture was concentrated in vacuo and the off-white solid was triturated with warm CHCl$_3$ and filtered through a fritted funnel. The solid was then triturated with hot boiling methanol (MeOH) and filtered through a flitted funnel resulting in an off-white solid. The material was triturated a second time as before and dried overnight resulting in the title compound as a white solid, which was taken on to the next step without further purification; $^1$H NMR (DMSO-d$_6$, 400 MHz) δ 3.88 (s, 2H), 8.31 (2, 1H); MS (ES+): m/z 127.07 (100) [MH+], HPLC: $t_R$=0.34 min (MicromassZQ, polar_5 min).

2-(5-Oxo-4,5-dihydro-[1,2,4]triazin-6-ylmethyl)-isoindole-1,3-dione

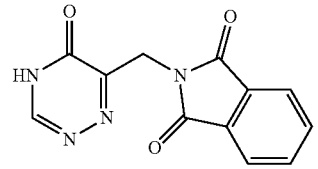 [SMILES: O=C1c2ccccc2C(=O)N1Cc1nnc[nH]c1=O]

A slurry of 2-(5-oxo-3-thioxo-2,3,4,5-tetrahydro-[1,2,4]triazin-6-ylmethyl)-isoindole-1,3-dione (1.0 g, 3.47 mmol) in EtOH (40 mL) was charged with excess Raney Ni (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; $^1$H NMR (DMSO-d$_6$, 400 MHz) δ 4.75 (s, 2H), 7.84-7.98 (m, 4H), 8.66 (s, 1H); MS (ES+): m/z 257.22 (100) [MH+], HPLC: $t_R$=2.08 min (MicromassZQ, polar_5 min).

2-(5-Oxo-3-thioxo-2,3,4,5-tetrahydro-[1,2,4]triazin-6-ylmethyl)-indan-1,3-dione

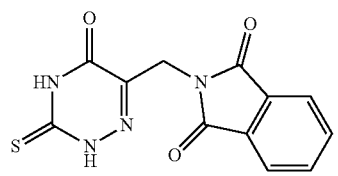 [SMILES: O=C1c2ccccc2C(=O)N1Cc1n[nH]c(=S)[nH]c1=O]

A slurry of 3-(1,3-dioxo-1,3-dihydro-isoindol-2-yl)-2-oxo-propionic acid ethyl ester (20 g, 76.6 mmol) in anhydrous EtOH (300 mL) was charged with thiosemicarbazide (6.98 g, 76.6 mmol) in one portion and heated to 80° C. for 2 hr. The reaction mixture was charged with N,N-diisopropylethylamine (DIEA) (26.7 mL, 76.56 mmol) and heated to 40° C. for 6 h then stirred at rt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; $^1$H NMR (DMSO-d$_6$, 400 MHz) δ 4.68 (s, 2H), 7.85-7.95 (m, 4H); MS (ES+): m/z 289.2 (100) [MH$^+$], HPLC: t$_R$=2.50 min (MicromassZQ, polar_5 min).

Example 45

7-Cyclobutyl-5-(2-phenylquinazolin-7-yl)-7H-pyrrolo[2,3-d]pyrimidin-4-amine

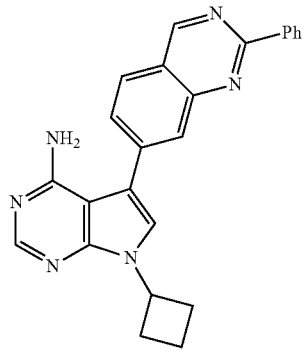 [SMILES: Nc1ncnc2c1c(-c1ccc3cnc(-c4ccccc4)nc3c1)cn2C1CCC1]

A flask equipped with a reflux condenser was charged with 2-phenyl-7-(4,4,5,5-tetramethyl-1,3,2-dioxaborolan-2-yl)quinazoline (67 mg, 0.20 mmol), 7-cyclobutyl-5-iodo-7H-pyrrolo[2,3-d]pyrimidin-4-amine (64 mg, 0.20 mmol) and Na$_2$CO$_3$ (56 mg, 0.51 mmol). The reaction setup was evacuated and refilled with Ar (3×). Pd(PPh$_3$)$_4$ (24 mg, 0.021 mmol) was added swiftly minimizing exposure to air and the system was evacuated and refilled with Ar (3×) again. Degassed solvent mixture H$_2$O-DMF (1:5 v/v, 5 mL) was added and the reaction mixture was heated at 80° C. for 42 h. The resulting orange-light brown solution was partitioned between DCM (~80 mL) and H$_2$O (10 mL). The aqueous layer was extracted with DCM (3×). Combined organics were washed with brine, dried (Na$_2$SO$_4$) and concentrated under reduced pressure (125 mg). Purification by flash chromatography (silica gel, 25 g, 0-2% MeOH in DCM) provided the title compound as a pale yellow solid; The material was also later triturated (hexane 2×, Et$_2$O 1×); $^1$H NMR (400 MHz, CDCl$_3$) δ 9.46 (d, J=0.8 Hz, 1H), 8.65-8.58 (m, 2H), 8.35 (s, 1H), 8.16 (s, 1H), 8.00 (d, J=8.4 Hz, 1H), 7.75 (dd, J=2.0 Hz, 8.4 Hz, 1H), 7.56-7.46 (m, 3H), 7.39 (s, 1H), 5.44 (br, 2H), 5.33 (quintet, J=8.2 Hz, 1H), 2.67-2.40 (m, 4H), 2.17-1.89 (m, 2H). MS (ES+): m/z 393.1 (100) [MH$^+$]; HPLC: t$_R$=2.91 min (OpenLynx, polar_5 min).

Example 46

3-Cyclobutyl-1-(4-methoxy-2-phenylquinazolin-7-yl)imidazo[1,5-a]pyrazin-8-amine

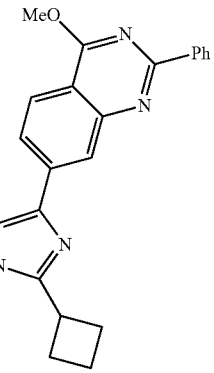

Synthesized as 7-cyclobutyl-5-(2-phenylquinazolin-7-yl)-7H-pyrrolo[2,3-d]pyrimidin-4-amine from (78 mg, 0.25 mmol) of 3-cyclobutyl-1-iodoimidazo[1,5-a]pyrazin-8-amine. The crude material was purified flash chromatography on silica gel (70 g cartridge, 0-2% MeOH in DCM) followed by recrystallization (EtOAc-hexanes) and trituration (Et$_2$O). Purification of the mother liquor by HPLC provided more of the title compound (a light orange solid); $^1$H NMR (400 MHz, CDCl$_3$) δ 8.65-8.60 (m, 2H), 8.31-8.25 (m, 2H), 7.94 (dd, J=1.6 Hz, 8.0 Hz, 1H), 7.57-7.48 (m, 3H), 7.18 (d, J=5.2 Hz, 1H), 7.13 (d, J=4.8 Hz, 1H), 5.18 (br, 2H), 4.34 (s, 3H), 3.86 (quintet, J=8.6 Hz, 1H), 2.75-2.60 (m, 2H), 2.58-2.47 (m, 2H), 2.26-2.12 (m, 1H), 2.11-2.00 (m, 1H). MS (ES+): m/z 423.0 (100) [MH$^+$]; HPLC: t$_R$=2.62 min (OpenLynx, polar_5 min).

Example 47

3-Cyclobutyl-1-(4-methyl-2-phenyl-quinazolin-7-yl)-imidazo[1,5-a]pyrazin-8-ylamine

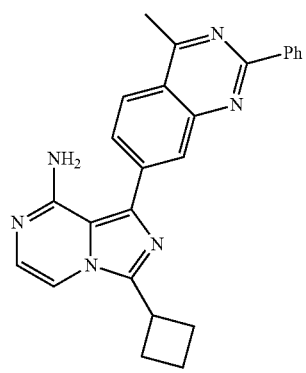 [SMILES: Cc1nc(-c2ccccc2)nc2cc(-c3nc(C4CCC4)n4ccnc(N)c34)ccc12]

Synthesized as 7-cyclobutyl-5-(2-phenylquinazolin-7-yl)-7H-pyrrolo[2,3-d]pyrimidin-4-amine from of 1-bromo-3-cyclobutylimidazo[1,5-a]pyrazin-8-amine (16 mg, 0.06 mmol). Crude material was purified by preparative TLC (silica gel, 5% MeOH in DCM) followed by a recrystallization (EtOAc) and trituration (hexanes) to afford the title compound as a light yellow solid; MS (ES+): m/z 407.1 (100); HPLC: $t_R$ (min) 2.44 (OpenLynx, polar 5 min).

Example 48

3-Cyclobutyl-1-(3-phenylquinoxalin-6-yl)imidazo[1,5-a]pyrazin-8-amine

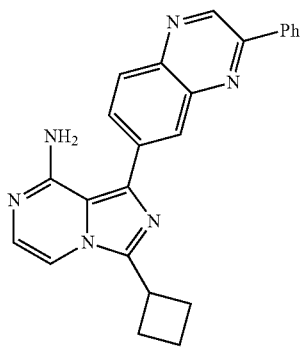 [SMILES: Nc1nccn2c(C3CCC3)nc(-c3ccc4ncc(-c5ccccc5)nc4c3)c12]

DCM solution of 7-(8-chloro-3-cyclobutyl-7,8-dihydroimidazo[1,5-a]pyrazin-1-yl)-2-phenylquinoxaline (61 mg, 0.15 mmol) was evaporated to dryness by passing a stream of $N_2$. The residue was suspended in anh. i-PrOH (4 mL) and the suspension was saturated with gaseous $NH_3$ at 0° C. (2 min). The reaction vessel was sealed and heated to 100° C. (external temperature) for 63 h. Then the reaction was cooled to rt, concentrated under reduced pressure and purified by flash chromatography (silica gel, 0-5% MeOH in DCM) and then preparative TLC (4% MeOH in $CH_3CN$) to afford the title compound as a light yellow solid; $^1$H NMR (400 MHz, $CDCl_3$) δ 9.36 (d, J=4 Hz, 1H), 8.43 (s, 1H), 8.30-8.25 (m, 4H), 7.65-7.50 (m, 3H), 7.15 (m, 2H), 5.26 (br, 2H), 3.86 (quintet, J=8 Hz, 1H), 2.75-2.60 (m, 2H), 2.60-2.45 (m, 2H), 2.20 (q, J=8 Hz, 1H), 2.07 (br, 1H). MS (ES+): m/z 393.1 (100) [MH$^+$]; HPLC: $t_R$=2.30 min (OpenLynx, polar_5 min).

7-(8-Chloro-3-cyclobutyl-7,8-dihydroimidazo[1,5-a]pyrazin-1-yl)-2-phenylquinoxaline

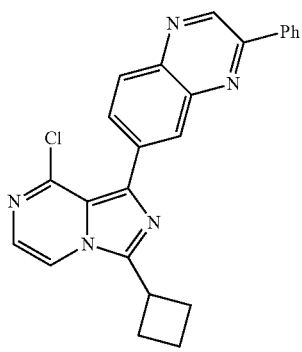 [SMILES: Clc1nccn2c(C3CCC3)nc(-c3ccc4ncc(-c5ccccc5)nc4c3)c12]

N-[(3-chloropyrazin-2-yl)(3-phenylquinoxalin-6-yl)methyl]-cyclobutanecarboxamide (56 mg, 0.13 mmol) was heated in $POCl_3$ (5 mL) under Ar at 70° C. for 26 h. Later the reaction was cooled to rt, evaporated under reduced pressure and then high vacuum. A solution of $NH_3$ in i-PrOH (2 M, 10 mL was added to the crude material cooled in an ice-$H_2O$ bath under Ar. The mixture was stirred, sonicated and filtered. The solids and the reaction flask were washed with i-PrOH multiple times. The filtrate was concentrated under reduced pressure. The light yellow residue was partitioned between DCM (60 mL) and $H_2O$ (20 mL). The aq. layer was extracted with DCM (2×). Combined organic phase was washed with brine and dried ($Na_2SO_4$) to afford the title compound as a light yellow solid; NMR (400 MHz, $CD_3CN$) δ 9.40 (s, 1H), 8.36 (s, 1H), 8.32-8.25 (m, 2H), 8.13-8.11 (m, 2H), 7.77 (d, J=4.8 Hz, 1H), 7.63-7.51 (m, 3H), 7.32 (d, J=4.8 Hz, 1H), 3.97 (qund, J=1.2 Hz, 8.4 Hz, 1H), 2.60-2.45 (m, 4H), 2.05-1.95 (m, 2H). MS (ES+): m/z 412.0 (40) [MH$^+$]; HPLC: $t_R$=4.10 min (OpenLynx, polar_5 min).

N-[(3-Chloropyrazin-2-yl)(3-phenylquinoxalin-6-yl)methyl]cyclobutanecarboxamide

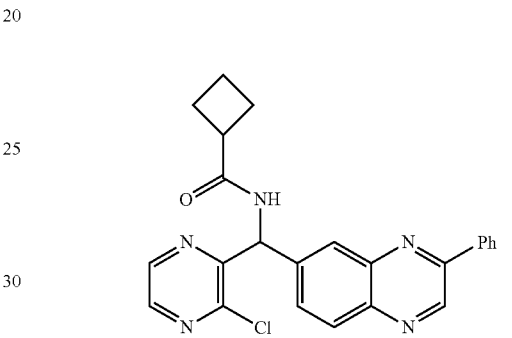

(3-Chloropyrazin-2-yl)(3-phenylquinoxalin-6-yl)methylamine (106 mg, 0.30 mmol) and cyclobutanecarboxylic acid (51 mg, 0.46 mmol) were dissolved in DCM (10 mL). EDC (93 mg, 0.49 mmol) and HOBt hydrate (62 mg, 0.46 mmol) were added in sequence followed by N,N-diisopropylethylamine (0.15 mL, 0.83 mmol). The reaction was stirred at rt under Ar for 24 h then evaporated to dryness and purified by flash chromatography (0-1.5% MeOH in DCM) to afford a reddish oil. The material was dissolved in DCM (50 mL), washed with satd $NaHCO_3$ (2×), $H_2O$ (1×), brine (1×), dried ($MgSO_4$) and concentrated under reduced pressure (light yellow oil). Purification by flash chromatography (silica gel, 33% to 65% EtOAc in hexanes) afforded the title compound as a white solid; $^1$H NMR (400 MHz, $CD_3CN$) δ 9.40 (s, 1H), 8.60 (d, J=2.8 Hz, 1H), 8.39 (d, J=2.4 Hz, 1H), 8.30-8.25 (m, 2H), 8.06 (d, J=8.4 Hz, 1H), 8.02 (s, 1H), 7.80 (dd, J=2.0 Hz, 8.8 Hz, 1H), 7.85-7.75 (m, 3H), 7.51 (d, J=7.8 Hz, 1H), 6.77 (d, J=8.0 Hz, 1H), 3.20 (quintet, J=8.4 Hz, 1H), 2.25-2.05 (m, 4H), 1.85-1.75 (m, 2H).). MS (ES+): m/z 430.0 (100) [MH$^+$]; HPLC: $t_R$=3.40 min (OpenLynx, polar_5 min).

(3-Chloropyrazin-2-yl)(3-phenylquinoxalin-6-yl)methylamine

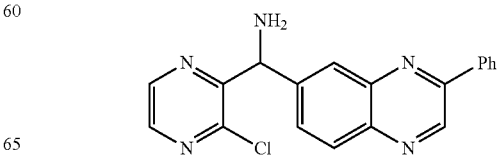

A flask containing crude (3-chloropyrazin-2-yl)(3-phenylquinoxalin-6-yl)methanol (153 mg, ~0.44 mmol) was flashed with Ar and charged with phthalimide (71 mg, 0.48 mmol) and triphenylphosphine (130 mg, 0.48 mmol) and anh. THF (10 mL). DIAD (0.1 mL, 0.48 mmol) was added slowly dropwise at rt and then the reaction was stirred at rt for 16 h. The reaction was concentrated under reduced pressure and purified by flash chromatography (silica gel, 5% EtOAc in DCM to 10%) affording 2-[(3-chloropyrazin-2-yl)(3-phenylquinoxalin-6-yl)methyl]-1H-isoindole-1,3(2H)-dione compound as a creamy solid. To stirred solution of the crude 2-[(3-chloropyrazin-2-yl)(3-phenylquinoxalin-6-yl)methyl]-1H-isoindole-1,3(2H)-dione (147 mg, 0.31 mmol) in anh. EtOH (12 mL) and anh. DCM (2 mL) under Ar was added anh. hydrazine (0.03 mL, 0.9 mmol). The reaction mixture was stirred at rt for 22 h. The 1:1 mixture of the product and a partially cleaved phthalimide was concentrated under reduced pressure at rt and dried under high vacuum overnight. The light yellow, solid residue was dissolved in anh. i-PrOH (6 mL) and anh. CHCl$_3$ (3 mL) and heated under Ar at 50° C. for 16 h. Later the reaction was cooled to rt, evaporated to dryness and triturated with DCM. The DCM aliquots were filtered through a pad of Celite affording the title compound as a light yellow solid; $^1$H NMR (400 MHz, CD$_3$OD/CDCl$_3$) δ 9.37 (s, 1H), 8.71 (d, J=2.4 Hz, 1H), 8.39 (d, J=2.4 Hz, 1H), 8.23 (d, J=6.8 Hz, 2H), 8.12 (s, 1H), 8.06 (d, J=8.4 Hz, 1H), 7.88 (dd, J=0.8 Hz, 8.8 Hz, 1H), 7.62-7.52 (m, 3H), 5.81 (s, 1H). MS (ES+): m/z 348.0 (40) [MH$^+$]; HPLC: t$_R$=2.08 min (OpenLynx, polar_5 min).

3-Chloropyrazin-2-yl)(3-phenylquinoxalin-6-yl)methanol

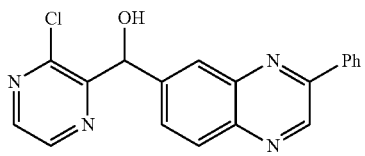 [SMILES: OC(c1ccc2ncc(-c3ccccc3)nc2c1)c1nccnc1Cl]

To a stirred, THF (3.5 mL) solution of TMP (0.11 mL, 0.62 mm) at −8° C. was added n-BuLi (1.6 M in hexanes, 0.36 mL, 0.58 mmol) dropwise. After stirring at −15 to −8° C. (external temperatures) for 10 min the mixture was cooled to −78° C. and chloropyrazine (64 mg, 0.58 mmol) was added dropwise as a solution in THF (0.2 mL) over 8 min. The flask containing the reagent was rinsed with more THF (0.1 mL) and the rinse was added to the reaction over 5 min. The resultant orange-brown mixture was stirred for 20 min and later was treated with 3-phenylquinoxaline-6-carbaldehyde (112 mg, 0.48 mmol) in THF (1.5 mL) (dropwise addition over 20 min). The reaction mixture was stirred at −75° C. (external temperature) for 2 h. Later, 0.25 M aq citric acid (10 mL) was added in one portion and the reaction was allowed to warm to rt after an immediate removal of the cooling bath. The reaction was shaken intermittently to improve stirring. Extraction with EtOAc (3×), washing (satd NaHCO$_3$, brine) and drying (Na$_2$SO$_4$) provided crude material which was purified by flash chromatography (SiO$_2$, 0-100% EtOAc in DCM) to afford the title compound. MS (ES+): m/z 349.0 (100) [MH$^+$]; HPLC: t$_R$=3.10 min (OpenLynx, polar_5 min).

3-Phenylquinoxaline-6-carbaldehyde

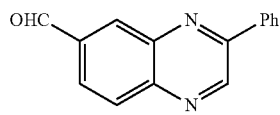 [SMILES: O=Cc1ccc2ncc(-c3ccccc3)nc2c1]

DIBAL (1.0 M in THF, 2.0 mL, 2.0 mmol was added to a THF (5 mL) solution of N-methoxy-N-methyl-3-phenylquinoxaline-6-carboxamide (198 mg, 0.67 mmol) under N$_2$ over 10 min at −78° C. The reaction was stirred for 2.5 h at the temperature, then satd solution of potassium sodium tartrate (Rochelle salt), was added. The cooling bath was removed immediately after the addition. The reaction was stirred for 30 min turning into a clear orange solution. The crude mixture was extracted with DCM (3×), washed (satd Rochelle salt, brine), dried, concentrated and purified by flash chromatography (SiO$_2$, 0-1.5% MeOH in DCM) to afford the title compound as a white solid; $^1$H NMR (400 MHz, CDCl$_3$) δ 10.27 (s, 1H), 9.43 (s, 1H), 8.63 (s, 1H), 8.26-8.20 (m, 4H), 7.65-7.52 (m, 3H). MS (ES+): m/z 235.1 (100) [MH$^+$]; HPLC: t$_R$=3.38 min (OpenLynx, polar_5 min).

N-Methoxy-N-methyl-3-phenylquinoxaline-6-carboxamide

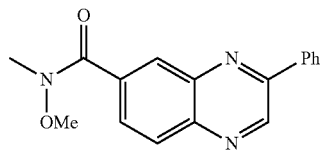 [SMILES: CON(C)C(=O)c1ccc2ncc(-c3ccccc3)nc2c1]

A suspension of the 3-nitro-4-[(2-oxo-2-phenylethyl)amino]benzoic acid (889 mg, 3.0 mmol), Pd—C (10% in Pd, 50% in H$_2$O, 315 mg, 0.15 mmol) in DMF (25 mL) and MeOH (5 mL) was shaken at rt under H$_2$ (3.3 atm) for 22 h. The reaction mixture was filtered through Celite. The Celite layer was washed with MeOH multiple times. The filtrate was evaporated to dryness and the resultant solid was triturated with hot MeOH to afford the title compound as a grey solid. The rest of the material was recrystallized from EtOH affording more of 3-phenylquinoxaline-6-carboxylic acid. To a stirred solution 3-phenylquinoxaline-6-carboxylic acid (4736-68, 217 mg, 0.87 mmol) in anh. THF (18 mL) was added CDI (212 mg, 1.3 mmol) in one portion at it. The reaction was heated at 55° C. for 2 h then cooled to it and treated in sequence with N,N-diisopropylethylamine (0.47 mL, 2.6 mmol) and Me(MeO)NH*HCl (248 mg, 2.6 mmol). The reaction was stirred at rt for 20 h. THF was removed by evaporation under reduced pressure. The resultant residue was dissolved in DCM, washed (H$_2$O (2×), brine), dried (Na$_2$SO$_4$) and concentrated under reduced pressure to afford the title material as an off-white solid; $^1$H NMR (400 MHz, CDCl$_3$) δ 9.35 (s, 1H), 8.46 (d, J=2.0 Hz, 1H), 8.22-8.15 (m, 2H), 8.12 (d, J=8.8 Hz, 1H), 7.98 (dd, J=1.6 Hz, 8.4 Hz, 1H), 7.60-7.50 (m, 3H), 3.57 (s, 3H), 3.42 (s, 3H). MS (ES+): m/z 294.1 (100) [MH+]; HPLC: $t_R$=3.03 min (OpenLynx, polar_5 min).

3-Nitro-4-[(2-oxo-2-phenylethyl)amino]benzoic acid

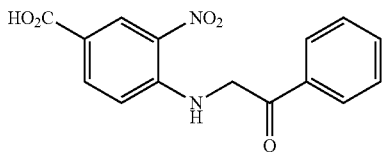 [SMILES: O=C(O)c1ccc(NCC(=O)c2ccccc2)c([N+](=O)[O-])c1]

A DCM (50 mL) suspension of 4-[(2-hydroxy-2-phenylethyl)amino]-3-nitrobenzoic acid (1.0 g, 3.3 mmol) was treated with Dess-Martin periodinane reagent (1.5 g, 3.5 mmol) at rt in one lot. The reaction mixture was stirred at rt for 2 h. The solid was filtered off and washed with DCM to afford the title compound as a yellow solid; $^1$H NMR (400 MHz, DMSO-$d_6$) δ 12.97 (br, 1H), 9.08 (t, J=4.4 Hz, 1H), 8.67 (d, J=2.0 Hz, 1H), 8.14 (d, J=8.0 Hz, 2H), 8.01 (dd, J=1.6 Hz, 8.8 Hz, 1H), 7.72 (t, J=7.6 Hz, 1H), 7.61 (t, J=7.6 Hz, 2H), 7.23 (d, J=8.8 Hz, 1H), 5.14 (d, J=4.8 Hz, 2H). MS (ES+): m/z 301.1 (40) [MH+]; HPLC: $t_R$=3.10 min (OpenLynx, polar_5 min).

4-[(2-hydroxy-2-phenylethyl)amino]-3-nitrobenzoic acid

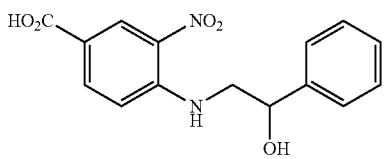 [SMILES: O=C(O)c1ccc(NCC(O)c2ccccc2)c([N+](=O)[O-])c1]

A flask, containing 4-fluoro-3-nitrobenzoic acid (8.00 g, 43.2 mmol) and 2-amino-1-phenylethanol (8.89 g, 64.8 mmol) dissolved in EtOH (80 mL), was purged with $N_2$. Anh. N,N-diisopropylethylamine (19 mL, 108 mmol) was added and the reaction mixture was heated at reflux for 24 h. Later the reaction was cooled to rt and concentrated under reduced pressure. The solid residue was dissolved in EtOAc, washed (1 M aq HCl (3×), $H_2O$ (2×), brine), dried ($Na_2SO_4$) and evaporated to dryness to afford the title compound as a bright yellow solid; $^1$H NMR (400 MHz, DMSO-$d_6$) δ 12.80 (s, 1H), 8.67 (t, J=5.2 Hz, 1H), 8.61 (d, J=2.0 Hz, 1H), 7.92 (ddd, J=0.4 Hz, 2.0 Hz, 9.2 Hz, 1H), 7.46 (d, J=8.4 Hz, 2H), 7.36 (t, 7.2 Hz, 2H), 7.28 (tt, J=1.2 Hz, 6.8 Hz, 1H), 7.18 (d, J=9.2 Hz, 1H), 5.89 (d, J=4.4 Hz, 1H), 4.91 (q, J=3.6 Hz, 1H), 3.72-3.63 (m, 1H), 3.53-3.45 (m, 1H). MS (ES+): m/z 285.1 (100) [MH+-18]; HPLC: $t_R$=2.80 min (OpenLynx, polar_5 min).

Example 49

3-[3-(4-Methyl-piperazin-1-yl)-cyclobutyl]-1-(2-phenyl-4-trifluoromethyl-quinolin-7-yl)-imidazo[1,5-a]pyrazin-8-ylamine

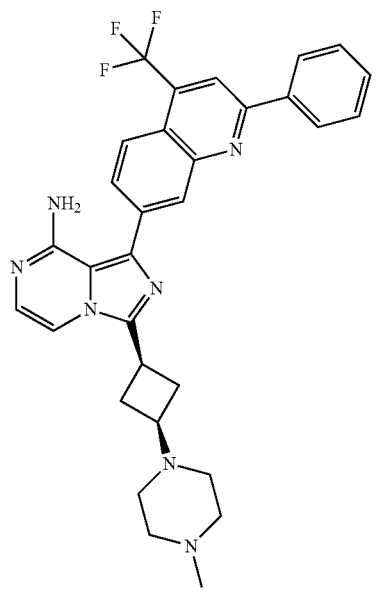 [SMILES: CN1CCN([C@H]2C[C@@H](c3nc(-c4ccc5c(C(F)(F)F)cc(-c6ccccc6)nc5c4)c4c(N)nccn43)C2)CC1]

1-Iodo-3-[3-(4-methyl-piperazin-1-yl)-cyclobutyl]-imidazo[1,5-a]pyrazin-8-ylamine (120 mg, 0.00029 mole), 2-phenyl-7-(4,4,5,5-tetramethyl-[1,3,2]dioxaborolan-2-yl)-4-trifluoromethyl-quinoline (230 mg, 0.00058 mole), cesium carbonate (330 mg, 0.0010 mole), 1,2-dimethoxyethane (6 mL, 0.06 mole) and water (1 mL) were combined in a 25 ml round bottom flask with a magnetic stir bar. The flask was subjected to three vacuum, argon cycles and charged with tetrakis(triphenylphosphine)palladium(0) (35 mg, 0.000030 mole). The flask was subjected to three vacuum, argon cycles again. The reaction was stirred under argon at 75° C. (external temperature) overnight. The product mixture was concentrated in vacuo, then allowed to stand under vacuum for 1 h. The product mixture was then chromatographed on silica gel with methylene chloride, methanol, concentrated ammonium hydroxide (140:10:1). Only the purest fractions were combined and concentration in vacuo, and placement under high vacuum for 30 minutes afforded the title compound as a yellow solid. The solid was re-crystallized from hexanes/ether to afford the title compound as a yellow solid; $^1$H NMR (CD$_3$OD, 400 MHz) δ 2.14-2.62 (m, 15H), 2.78-2.82 (Q, 1H, J=7.9 Hz), 3.62-3.67 (Q, 1H, J=7.9H), 6.32 (bs, 2H), 7.12-7.14 (d, 1H, J=4.8 Hz), 7.58-7.64 (m, 4H), 8.16-8.22 (m, 2H), 8.39-8.42 (m, 3H), 8.48 (s, 1H); $^{19}$F NMR (DMSO, 400

MHz) δ −60.15; MS (ES+): 557.98 (10) [MH⁺]; HPLC T_R 3.408 min. (100%) (polar_15 min).

Example 50

3-Cyclobutyl-1-(2-pyridin-4-ylquinolin-7-yl)imidazo[1,5-a]pyrazin-8-ylamine

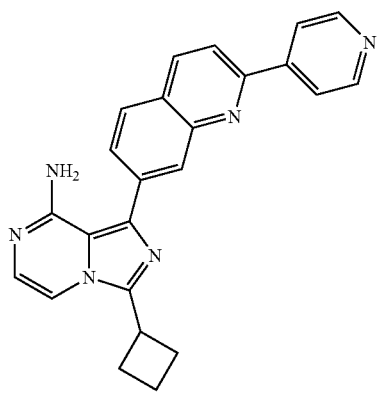 [SMILES: Nc1nccn2c(C3CCC3)nc(-c3ccc4ccc(-c5ccncc5)nc4c3)c12]

N₂ was bubbled into a stirred mixture of 1-bromo-3-cyclobutylimidazo[1,5-a]pyrazin-8-ylamine (48 mg, 0.18 mmol), 2-pyridin-4-yl-7-(4,4,5,5-tatramethyl-[1,3,2]dioxaborolan-2-yl)quinoline (90 mg, 0.27 mmol), Pd(PPh₃)₄ (12.5 mg, 0.0108 mmol), and Na₂CO₃ (48 mg, 0.45 mmol) in DMF/H₂O (5/1, 6 mL) for 5 min. This mixture was then stirred at 80° C. under N₂ for 40 h. The solvents were removed; the residue was dissolved in MeOH and submitted to the mass-directed purification system and provided the desired product; ¹H-NMR (CDCl₃, 400 MHz) δ 2.02-2.10 (m, 1H), 2.17-2.24 (m, 1H), 2.50-2.57 (m, 2H), 2.62-2.70 (m, 2H), 3.84-3.89 (m, 1H), 5.45 (s, br, 2H), 7.10 (d, J=4.4 Hz, 1H), 7.17 (d, J=5.2 Hz, 1H), 7.96 (d, J=8.8 Hz, 1H), 8.00-8.01 (m, 2H), 8.10 (d, J=6.0 Hz, 2H), 8.35 (d, J=8.4 Hz, 1H), 8.45 (s, 1H), 8.80 (d, J=4.8 Hz, 2H); MS (ES+): m/z 393 [MH⁺]; HPLC: t_R=1.94 min (OpenLynx, polar 5 min).

Example 51

3-Cyclobutyl-1-(2-pyridin-2-ylquinolin-7-yl)-imidazo[1,5-a]pyrazin-8-ylamine

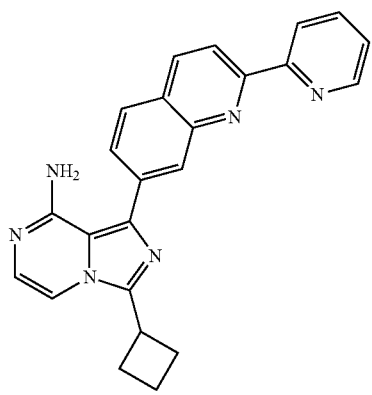 [SMILES: Nc1nccn2c(C3CCC3)nc(-c3ccc4ccc(-c5ccccn5)nc4c3)c12]

The mixture of 3-cyclobutyl-1-iodoimidazo[1,5-a]pyrazin-8-ylamine (62.8 mg 0.200 mmol), 2-pyridin-2-yl-7-(4,4,5,5-tetramethyl-[1,3,2]dioxaborolan-2-yl)-quinoline (79.1 mg, 1.2 eq.), Pd(PPh₃)₄ (14.0 mg, 6% eq.) and Na₂CO₃ (53.0 mg, 2.5 eq.) in DMF (5 ml)/H₂O (1 ml) was flushed with N₂ for 30 min at rt and heated at 80° C. for 16 h under N₂. After that time, the reaction mixture was treated with H₂O (20 ml), and was then extracted with CH₂Cl₂ (2×25 ml). The extracts were washed with H₂O (2×20 ml), and dried over MgSO₄. After the solid was filtered off and the solvent was removed in vacuo, the crude yellow oil (105 mg) was purified by MS directed purification system to obtain a yellow solid of 3-cyclobutyl-1-(2-pyridin-2-ylquinolin-7-yl)-imidazo[1,5-a]pyrazin-8-ylamine; ¹H NMR (CDCl₃, 400 MHz) δ 2.05-2.09 (m, 1H), 2.15-2.22 (m, 1H), 2.48-2.56 (m, 2H), 2.62-2.72 (m, 2H), 3.85 (quintet, 1H, J=8.4 Hz), 5.27 (s, 2H), 7.09-7.10 (d, 1H, J=4.8 Hz), 7.15-7.16 (d, 1H, J=4.8 Hz), 7.36-7.39 (m, 1H), 7.86-7.90 (m, 1H), 7.97 (m, 2H), 8.31-8.33 (d, 1H, J=8.8 Hz), 8.43 (s, 1H), 8.59-8.61 (d, 1H, J=8.8 Hz), 8.67-8.69 (d, 1H, J=7.6 Hz), 8.75-8.76 (d, 1H, J=4.0 Hz); MS (ES+): 393.4 (M+1), t_R(polar-5 min)=2.2 min.

Example 52

3-Cyclobutyl-1-(2-pyridin-3-ylquinolin-7-yl)-imidazo[1,5-a]pyrazin-8-ylamine

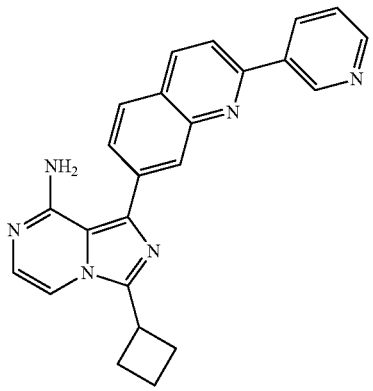 [SMILES: Nc1nccn2c(C3CCC3)nc(-c3ccc4ccc(-c5cccnc5)nc4c3)c12]

Prepared according to the procedures above for 3-cyclobutyl-1-(2-pyridin-2-ylquinolin-7-yl)-imidazo[1,5-a]pyrazin-8-ylamine; ¹H NMR (CDCl₃, 400 MHz) δ 2.03-2.11 (m, 1H), 2.14-2.23 (m, 1H), 2.49-2.56 (m, 2H), 2.57-2.72 (m, 2H), 3.82-3.91 (quintet, 1H, J=8.4 Hz), 5.18 (s, 2H), 7.11-7.12 (d, 1H, J=4.8 Hz), 7.17-7.18 (d, 1H, J=4.8 Hz), 7.46-7.49 (m, 1H), 7.92-7.94 (d, 1H, J=8.4 Hz), 7.98-7.99 (m, 2H), 8.31-8.33 (dd, 1H, J=0.4 & 8.4 Hz), 8.44 (t, 1H, J=0.8 Hz), 8.54-

8.57 (m, 1H), 8.71-8.73 (dd, 1H, J=1.6 & 4.8 Hz), 9.38 (dd, 1H, J=0.8 & 2.4 Hz); MS (ES+): 393.3 (M+1); $t_R$(polar-5 min)=2.0 min.

Example 53

Cyclobutyl-1-(4-methyl-2-phenylquinolin-7-yl)imidazo[1,5-a]pyrazin-8-ylamine

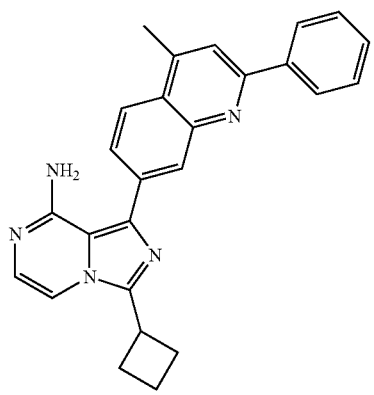 [SMILES: Cc1cc(-c2ccccc2)nc2cc(-c3nc(C4CCC4)n4ccnc(N)c34)ccc12]

To a mixture of 3-cyclobutyl-1-iodo-imidazo[1,5-a]pyrazin-8-ylamine (80 mg, 0.23 mmol), 4-methyl-2-phenyl-7-(4,4,5,5-tetramethyl-1,3,2-dioxaborolan-2-yl)quinoline (100 mg, 0.30 mmol) and base ($Na_2CO_3$ (74 mg, 0.70 mmol) under Ar was added Pd(PPh$_3$)$_4$ (14 mg, 0.013 mmol) with minimum exposure to air. The flask was then evacuated and refilled with Ar before the degassed DME (2.2 mL) and H$_2$O (0.5 mL) were added. The reaction was heated at 80° C. for 27 h, concentrated under reduced pressure and purified by SPE (MP-TsOH, 500 mg 6 mL, Argonaut lot 31562735HA) loading as a DCM suspension and eluting with 2 M NH$_3$ in MeOH to afford crude material which was purified by preparative HPLC to afford the title compound as a light yellow solid; $^1$H NMR (400 MHz, CDCl$_3$) δ 8.43 (d, J=2.0 Hz, 1H), 8.21-8.15 (m, 2H), 8.13 (d, J=8.4 Hz, 1H), 7.96 (dd, J=8.4 Hz, 2.0 Hz, 1H), 7.76 (d, J=-0.8 Hz, 1H), 7.57-7.45 (m, 3H), 7.17 (d, J=4.8 Hz, 1H), 7.10 (d, J=4.8 Hz, 1H), 5.19 (s, 2H), 3.88 (quintet, J=8.4 Hz, 1H), 2.81 (s, 3H), 2.72-2.61 (m, 2H), 2.57-2.48 (m, 2H), 2.26-2.12 (m, 1H), 2.11-2.02 (m, 1H); MS (ES+): m/z 406.2 (75) [MH$^+$]; HPLC: $t_R$=2.38 min (OpenLynx, polar_5 min).

Cis- and trans-toluene-4-sulfonic acid 3-[8-amino-1-(2-phenylquinolin-7-yl)-imidazo[1,5-a]pyrazin-3-yl]-cyclobutylmethyl ester were prepared as follows: A suspension of {3-[8-amino-1-(2-phenylquinolin-7-yl)-imidazo[1,5-a]pyrazin-3-yl]-cyclobutyl}-methanol (125 mg, 0.3 mmol) in dry methylene chloride (5 mL) and pyridine (2 mL) was charged with a solution of Ts$_2$O (108 mg, 0.33 mmol) in methylene chloride (1 mL) at −40° C. under N$_2$ atmosphere. The mixture was slowly warmed to rt overnight. The reaction was quenched with water (1 mL), diluted with methylene chloride (40 mL), washed with sat. aq. NaHCO$_3$ (2×10 mL) and brine (2×10 mL), and dried over anhydrous sodium sulfate. The filtrate was concentrated under reduced pressure, and the crude material was purified by silica gel column chromatography (eluting with 100% ethyl acetate→EtOAc:MeOH=98:2→3 96:4) to obtain the individual title compounds as a light yellow solid.

Example 54 cis-toluene-4-sulfonic acid 3-[8-amino-1-(2-phenylquinolin-7-yl)-imidazo[1,5-a]pyrazin-3-yl]-cyclobutylmethyl ester

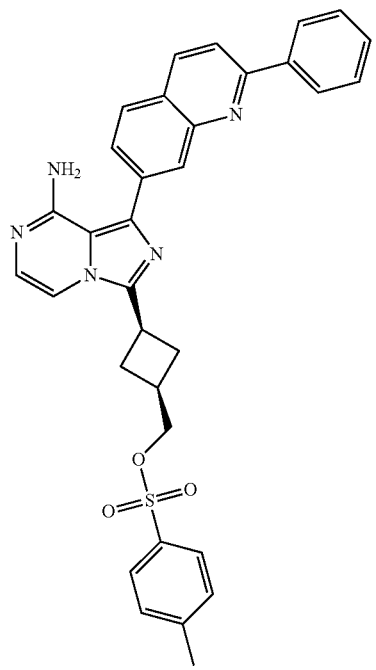 [SMILES: Cc1ccc(S(=O)(=O)OC[C@H]2C[C@@H](c3nc(-c4ccc5ccc(-c6ccccc6)nc5c4)c4c(N)nccn43)C2)cc1]

MS (ES+): m/z 576 [MH$^+$]; $^1$H NMR (CDCl$_3$, 400 MHz) δ 2.31-2.37 (m, 2H), 2.40 (s, 3H), 2.58-2.66 (m, 2H), 2.82 (m, 1H), 3.73 (m, 1H), 4.10 (d, J=6.7 Hz, 2H), 5.23 (br s, 2H, NH$_2$), 7.08-7.13 (m, 2H), 8.31 (d, J=8.1 Hz, 2H), 7.46-7.56 (m, 3H), 7.79 (d, J=8.3 Hz, 2H), 7.90-7.97 (m, 3H), 8.19-8.21 (m, 2H), 8.28 (d, J=8.5 Hz, 1H), 8.40 (s, 1H).

Example 55 trans-toluene-4-sulfonic acid 3-[8-amino-1-(2-phenylquinolin-7-yl)-imidazo[1,5-a]pyrazin-3-yl]-cyclobutylmethyl ester

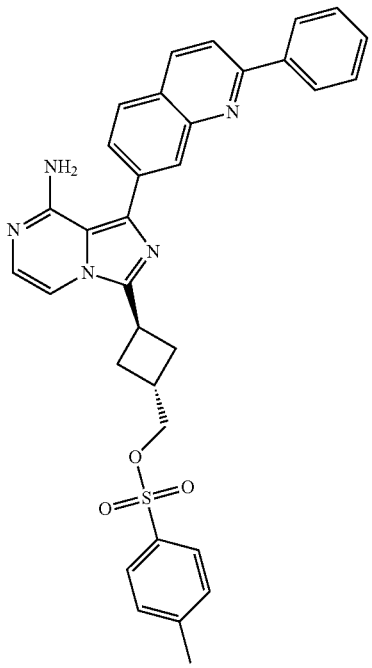 [SMILES: Cc1ccc(S(=O)(=O)OC[C@H]2C[C@H](c3nc(-c4ccc5ccc(-c6ccccc6)nc5c4)c4c(N)nccn43)C2)cc1]

$^1$H NMR (400 MHz, CDCl$_3$) δ 8.41 (t, J=0.8 Hz, 1H), 8.26 (d, J=8.8 Hz, 1H), 8.20-8.17 (m, 2H), 7.94-7.91 (m, 3H), 7.84 (d, J=8.0 Hz, 2H), 7.54-7.47 (m, 3H), 7.37 (d, J=8.0 Hz, 2H), 7.10 (d, J=5.2 Hz, 1H), 7.06 (d, 0.1=4.8 Hz, 1H), 5.27 (b, 2H), 4.20 (d, J=6.0 Hz, 2H), 3.80 (p, J=4 Hz, 1H), 2.88-2.81 (m, 1H), 2.77-2.70 (m, 2H), 2.46 (s, 3H), 2.43-2.30 (m, 2H); MS (ES+): m/z 576 (100) [MH$^+$].

Example 56

(3-[8-Amino-1-(2-phenylquinolin-7-yl)-imidazo[1,5-a]pyrazin-3-yl]-cyclobutyl)-methanol

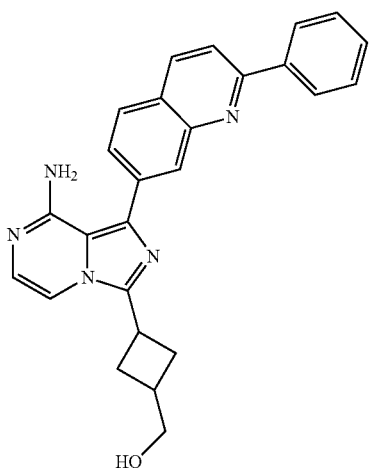 [SMILES: Nc1nccn2c(C3CC(CO)C3)nc(-c3ccc4ccc(-c5ccccc5)nc4c3)c12]

A solution of {3-[8-chloro-1-(2-phenyl-quinolin-7-yl)-imidazo[1,5-a]pyrazin-3-yl]-cyclobutyl}-methanol (compound of Formula II-B where Z=cyclobutyl and Q$^1$=2-phenylquinolin-7-yl) (265 mg, 0.6 mmol) in 5 mL of $^i$PrOH was cooled to −78° C. and charged with NH$_3$ gas for 1 min. This sealed tube was equipped with a teflon O-ring, sealed and heated at 110° C. for 3 days. The mixture was cooled to −78° C. and the cap was removed. The salt was filtered off and the filtrate was concentrated under reduced pressure. The crude material was purified by silica gel column chromatography (eluting with 100% ethyl acetate→EtOAc:MeOH=90:10) to obtain the title compound as a light yellow solid, a mixture of cis and trans isomers in the ratio of 5:1; MS (ES+): m/z 422 [MH$^+$]; $^1$H NMR (CDCl$_3$, 400 MHz): δ=2.42-2.48 (m, 2H), 2.66-2.74 (m, 3H), 3.71-3.85 (m, 3H), 5.25 (br s, 2H), 7.10-7.19 (m, 2H), 7.46-7.57 (m, 3H), 7.91-7.97 (m, 3H), 8.18-8.21 (m, 2H), 8.27 (d, J=8.6 Hz, 1H), 8.42, 8.44 (2×s, 1H, 5:1 ratio).

Example 57 cis-{3-[8-Amino-1-(2-phenylquinolin-7-yl)imidazo[1,5-a]pyrazin-3-yl]-cyclobutyl}-methanol

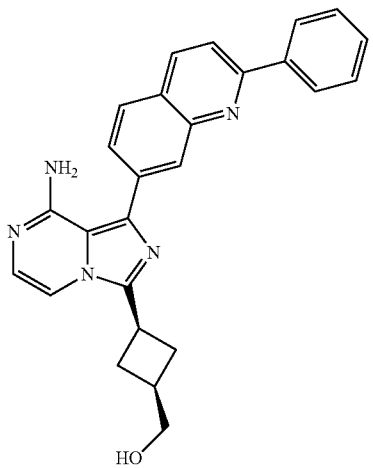 [SMILES: Nc1nccn2c1c(-c1ccc3ccc(-c4ccccc4)nc3c1)nc2[C@H]1C[C@@H](CO)C1]

A 2-propanol solution (200 mL) of cis-3-[8-chloro-1-(2-phenylquinolin-7-yl)imidazo[1,5-a]pyrazin-3-yl]cyclobutylmethyl 4-nitrobenzoate (20 g, 33.9 mmol) in a parr bomb was cooled to −78° C. Ammonia gas was bubbled into this solution for 8 min. The bomb was sealed and heated at 110° C. for 5 days. After cooled to rt, solid precipitates were collected by filtration and washed with water multiple times. The solid was dried in a vacuum oven overnight, affording the desired product. The filtrate was concentrated and the crude product was purified by silica gel chromatography (100% EtOAc→5% MeOH in EtOAc 10% MeOH in EtOAc) to afford another batch of the title compound; ¹H NMR (DMSO-d₆, 400 MHz) δ 2.15-2.25 (m, 2H), 2.43-2.50 (m, 2H, overlap with signal of DMSO), 3.43 (s, 2H), 3.78-3.86 (m, 1H), 4.54 (t, J=5.2 Hz, 1H), 6.28 (br s, 2H), 7.09 (d, J=4.8 Hz, 1H), 7.48-7.59 (m, 4H), 7.93 (dd, J=1.2 Hz, 8.0 Hz, 1H), 8.10 (d, J=8.4 Hz, 1H), 8.18 (d, J=8.8 Hz, 1H), 8.25 (s, 1H), 8.31 (d, J=7.2 Hz, 2H), 8.51 (d, J=8.4 Hz, 1H); MS (ES+): m/z 422 [MH⁺]; HPLC: t_R=2.02 min (OpenLynx, polar_5 min).

cis-3-[8-Chloro-1-(2-phenylquinolin-7-yl)imidazo[1,5-a]pyrazin-3-yl]cyclobutylmethyl 4-nitrobenzoate

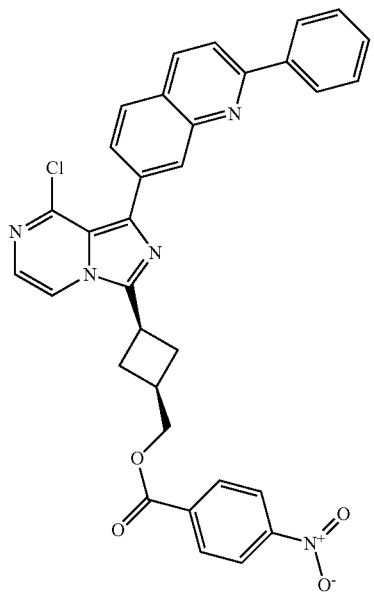 [SMILES: O=C(OC[C@H]1C[C@@H](c2nc(-c3ccc4ccc(-c5ccccc5)nc4c3)c3c(Cl)nccn32)C1)c1ccc([N+](=O)[O-])cc1]

To a solution of {3-[8-chloro-1-(2-phenylquinolin-7-yl)imidazo[1,5-a]pyrazin-3-yl]cyclobutyl}methanol (46.52 g, 105.5 mmol) and 4-nitrobenzoyl chloride (23.55 g, 126.9 mmol) in methylene chloride (260 mL) was added N,N-diisopropylethyl amine (55.17 mL, 316.7 mmol). The mixture was stirred at rt for 15 h. Yellow precipitates were collected by filtration, washed with ethyl acetate, and dried to afford the title compound; ¹H NMR (CDCl₃, 400 MHz) δ 2.70-2.78 (m, 4H), 2.96-3.02 (m, 1H), 3.81-3.86 (m, 1H), 4.41 (d, J=4.8 Hz, 2H), 7.37 (d, J=5.2 Hz, 1H), 7.44-7.48 (m, 1H), 7.51-7.55 (m, 2H), 7.58 (d, J=5.2 Hz, 1H), 7.88-7.96 (m, 5H), 8.16-8.19 (m, 2H), 8.26-8.29 (m, 2H), 8.33 (d, J=8.8 Hz, 1H), 8.54 (s, 1H); MS (ES+): m/z 590 [MH⁺]; HPLC: t_R=4.37 min (OpenLynx, polar_5 min).

{3-[8-Chloro-1-(2-phenylquinolin-7-yl)-imidazo[1,5-a]pyrazin-3-yl]-cyclobutyl}-methanol

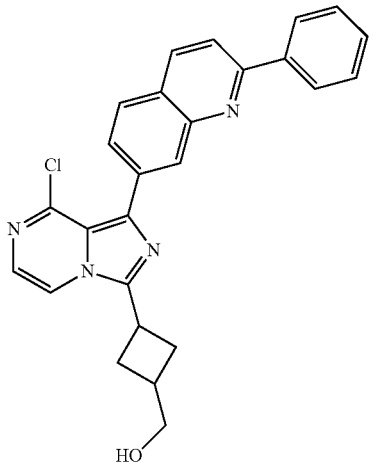 [SMILES: OCC1CC(c2nc(-c3ccc4ccc(-c5ccccc5)nc4c3)c3c(Cl)nccn23)C1]

To a solution of 7-[8-chloro-3-(3-methylenecyclobutyl)-imidazo[1,5-a]pyrazin-1-yl]-2-phenylquinoline (338 mg, 0.8 mmol) in dry THF (5 mL) was added 9-BBN (2.4 mL, 1.2 mmol, 0.5M in THF) dropwise at 0° C. under nitrogen atmosphere. The temperature was slowly warmed to it overnight. The mixture was cooled to 0° C., and 3 mL 1N aq. NaOH and 0.6 mL 30% aq. H₂O₂ were added, the resulting mixture was stirred at 0° C. for 10 min, then it for 30 min. The mixture was diluted with methylene chloride (30 mL), washed with brine (2×20 mL), and dried over anhydrous sodium sulfate. The filtrate was concentrated under reduced pressure, and the crude material was purified by silica gel column chromatography (eluting with hexanes:EtOAc=50:50→100% ethyl acetate), to obtain the title compound as a yellow solid, a mixture of cis and trans isomers in the ratio of 5:1; MS (ES+): m/z 441/443 (3/1) [MH⁺]; ¹H NMR (CDCl₃, 400 MHz) δ 2.44-2.64 (m, 6H), 3.65-3.76 (m, 3H), 7.31, 7.33 (2×d, J=5.0 Hz, 1H, 1:5 ratio), 7.39-7.57 (m, 4H), 7.86-7.98 (m, 3H), 8.18 (m, 2H), 8.26 (d, J=8.6 Hz, 1H), 8.51, 8.53 (2×s, 1H, 5:1 ratio).

7-[8-Chloro-3-(3-methylenecyclobutyl)-imidazo[1,5-a]pyrazin-1-yl]-2-phenylquinoline

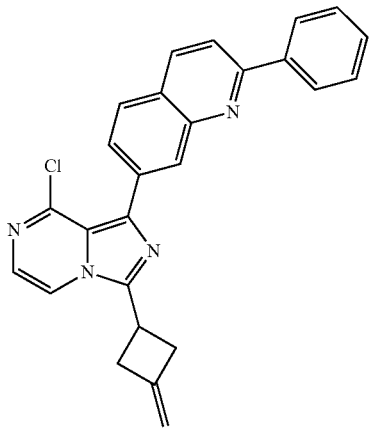 [SMILES: C=C1CC(c2nc(-c3ccc4ccc(-c5ccccc5)nc4c3)c3c(Cl)nccn23)C1]

N-[(3-Chloropyrazin-2-yl)(2-phenylquinolin-7-yl)methyl]-3-methylenecyclobutanecarboxamide (0.02 mmol, 10 g) was dissolved in 150 mL $POCl_3$ in a 250 mL rbf, charged with 0.1 mL DMF and heated to 55° C. under a consistent $N_2$ flow for 1 h (the reaction was vented with a needle). The excess $POCl_3$ was removed under reduced pressure and the residue was quenched with 2 N $NH_3$ in isopropanol (250 mL) at 0° C. and water. The aqueous layer was washed with DCM (100 mL×2) and the combined organic layer was dried over sodium sulfate, filtered and concentrated under reduced pressure. The crude product was purified by silica gel column chromatography (flash column) eluting with 20-50% EtOAc in hexane. Concentration in vacuo of the product-rich fractions afforded the desired product as yellow solid; MS (ES, Pos.): m/z 423 (100) [$MH^+$]; $^1H$ NMR ($CDCl_3$, 400 MHz) δ 3.28-3.31 (m, 2H), 3.39-3.42 (m, 2H), 3.85-3.93 (m, 1H), 4.94 (p, J=2.4 Hz, 2H), 7.38 (d, J=4.9 Hz, 1H), 7.42-7.57 (m, 4H), 7.89-7.92 (m, 3H), 8.18-8.21 (m, 2H), 8.27 (dd, J=8.6 Hz, 0.8 Hz, 1H), 8.53 (s, 1H).

3-Methylenecyclobutanecarboxylic acid [(3-chloro-pyrazin-2-yl)-(2-phenyl-quinolin-7-yl)-methyl]-amide

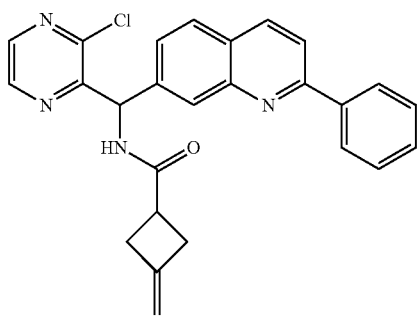 [SMILES: C=C1CC(C(=O)NC(c2ccc3ccc(-c4ccccc4)nc3c2)c2nccnc2Cl)C1]

C-(3-Chloro-pyrazin-2-yl)-C-(2-phenylquinolin-7-yl)-methylamine (690 mg, 1.99 mmol) was dissolved in 6.0 mL of $CH_2Cl_2$ followed by the addition of EDC (600 mg, 2.98 mmol) and HOBT (300 mg, 1.99 mmol). 3-Methylenecyclobutanecarboxylic acid (300 mg, 2.59 mmol) was dissolved in 1.0 mL of $CH_2Cl_2$ and added to the homogenous reaction mixture. After 24 h the reaction was concentrated in vacuo and dissolved in EtOAc and the organic layer was washed with sat. $NaHCO_3$. The organic layer was washed with $H_2O$ and brine. The organic layers where combined, dried over sodium sulfate, filtered and concentrated in vacuo. The crude product was purified by silica gel column chromatography [Jones Flashmaster, 10 g cartridge, eluting with 50% EtOAc: Hex] to obtain the desired product as a white fluffy solid; $^1H$ NMR (400 MHz, $CDCl_3$): δ=2.82-2.92 (m, 2H), 2.99-3.06 (m, 2H), 4.77-4.80 (m, 2H), 6.81 (d, 1H, J=7.8 Hz), 7.45-7.54 (m, 3H), 7.83-7.88 (m, 3H), 8.10 (d, 2H, J=7.1 Hz), 8.22-8.23 (brm, 1H), 8.39 (d, 1H, J=1.79 Hz), 8.59 (d, 1H, J=2.5 Hz); MS (ES+): 440.93 (M+1), 442.91 (M+3).

Method X7: General procedure for the synthesis of compounds of Formula I-C'''.3 (compound of Formula I-C''' where $Q^1$=2-phenyl-quinolin-7-yl and Z=cis-1,3-cyclobutyl) from compounds of Formula I-H.2 (Compound of Formula I-H where $Q^1$=2-phenyl-quinolin-7-yl and Z=cis-1,3-cyclobutyl): A sealed tube containing a solution of cis-toluene-4-sulfonic acid 3-[8-amino-1-(2-phenyl-quinolin-7-yl)-imidazo[1,5-a]pyrazin-3-yl]-cyclobutylmethyl ester (85 mg, 0.15 mmol) in THF (3 mL) was charged with $HNR^2R^3$ (3.6 mmol), sealed, and heated at 50° C. overnight. The mixture was concentrated and the residue was purified by mass-directed purification to afford the desired product.

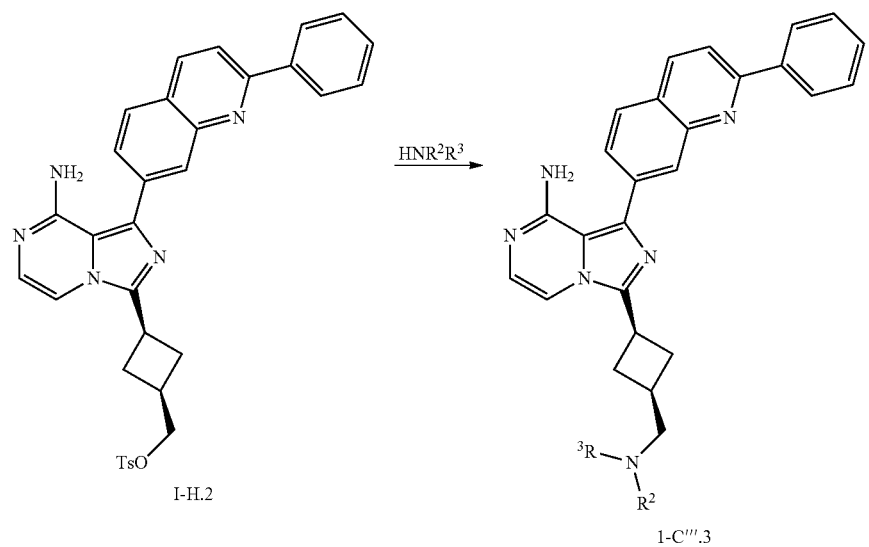

-continued

| Example | Structure | Name | HNR²R³ | MS | 1HNMR |
|---|---|---|---|---|---|
| 58 | 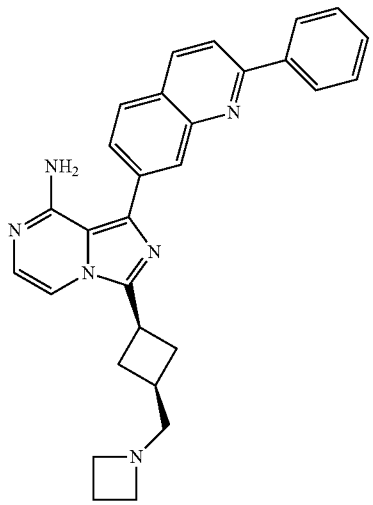 [SMILES: Nc1nccn2c1c(-c1ccc3ccc(-c4ccccc4)nc3c1)nc2[C@H]1C[C@@H](CN2CCC2)C1] | cis-3-(3-Azetidin-1-ylmethyl-cyclobutyl)-1-(2-phenyl-quinolin-7-yl)-imidazo[1,5-a]pyrazin-8-ylamine | | m/z 461 [MH⁺]. | (CDCl₃, 400 MHz): δ = 2.01-2.11 (m, 2H), 2.31-2.36 (m, 2H), 2.49-2.74 (m, 5H), 3.23-3.25 (m, 4H), 3.68 (m, 1H), 5.18 (br s, 2H, NH₂), 7.10 (m, 1H), 7.18 (d, J = 5.0 Hz, 1H), 7.46-7.57 (m, 3H), 7.91-7.95 (m, 3H), 8.19-8.21 (m, 2H), 8.27 (d, J = 8.5 Hz, 1H), 8.43 (s, 1H). |
| 59 | 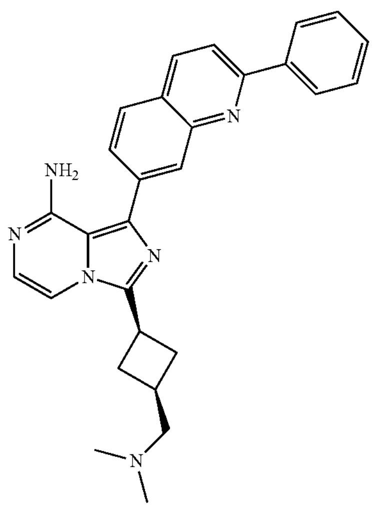 [SMILES: CN(C)C[C@H]1C[C@@H](c2nc(-c3ccc4ccc(-c5ccccc5)nc4c3)c3c(N)nccn32)C1] | cis-3-{3-[(Dimethylamino)methyl]cyclobutyl}-1-(2-phenylquinolin-7-yl)imidazo[1,5-a]pyrazin-8-ylamine | | m/z 449.34 (100) [MH⁺]. HPLC: t_R = 1.75 min (OpenLynx, polar_5min) | |
| 60 | 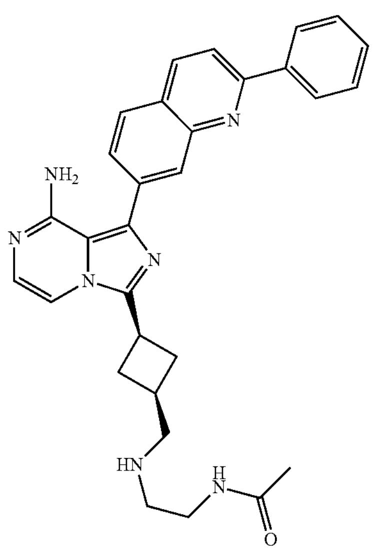 [SMILES: CC(=O)NCCNC[C@H]1C[C@@H](c2nc(-c3ccc4ccc(-c5ccccc5)nc4c3)c3c(N)nccn32)C1] | cis-N-[2-({[3-(8-Amino-1-(2-phenylquinolin-7-yl)imidazo[1,5-a]pyrazin-3-yl)cyclobutyl]methyl}amino)ethyl]acetamide. | | m/z 506.39 (100) [MH⁺]. HPLC: t_R = 1.73 min (OpenLynx, polar_5min) | |

| | | | | |
|---|---|---|---|---|
| 61 | 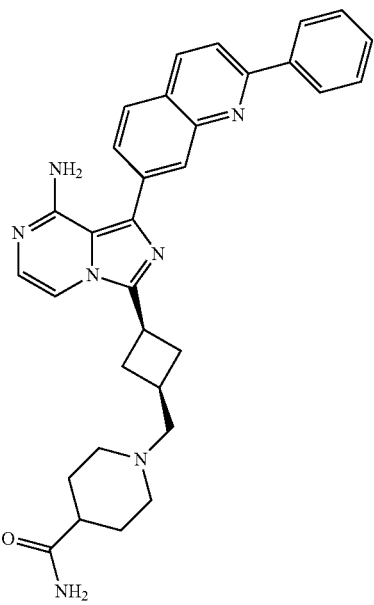 [SMILES: NC(=O)C1CCN(C[C@H]2C[C@@H](c3nc(-c4ccc5ccc(-c6ccccc6)nc5c4)c4c(N)nccn43)C2)CC1] | cis-1-{[3-(8-Amino-1-(2-phenylquinolin-7-yl)imidazo[1,5-a]pyrazin-3-yl)cyclobutyl]methyl}piperidine-4-carboxamide |  | m/z 532.40 (100) [MH$^+$]. HPLC: t$_R$ = 1.72 min (OpenLynx, polar_5min) |
| 62 | 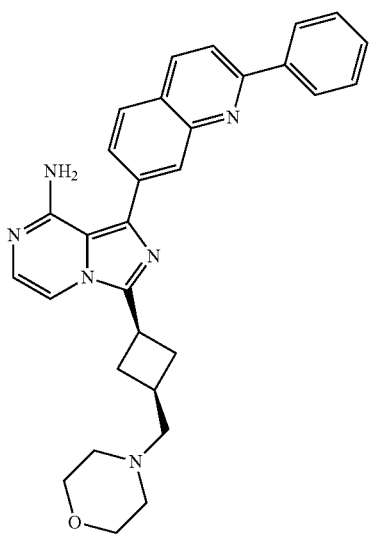 [SMILES: Nc1nccn2c1c(-c1ccc3ccc(-c4ccccc4)nc3c1)nc2[C@H]1C[C@@H](CN2CCOCC2)C1] | cis-3-[3-(Morpholin-4-ylmethyl)cyclobutyl]-1-(2-phenylquinolin-7-yl)imidazo[1,5-a]pyrazin-8-ylamine |  | m/z 491.33 (100) [MH$^+$]. HPLC: t$_R$ = 1.75 min (OpenLynx, polar_5min) |
| 63 | 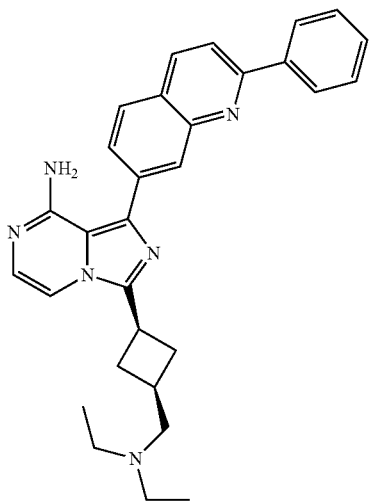 [SMILES: CCN(CC)C[C@H]1C[C@@H](c2nc(-c3ccc4ccc(-c5ccccc5)nc4c3)c3c(N)nccn32)C1] | cis-3-{3-[(Diethylamino)methyl]cyclobutyl}-1-(2-phenylquinolin-7-yl)imidazo[1,5-a]pyrazin-8-ylamine | 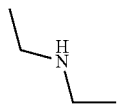 | MS (ES+): m/z 477.12 (100) [MH$^+$]. HPLC: t$_R$ = 1.86 min (OpenLynx, polar_5min) |

| | | | | |
|---|---|---|---|---|
| 64 | 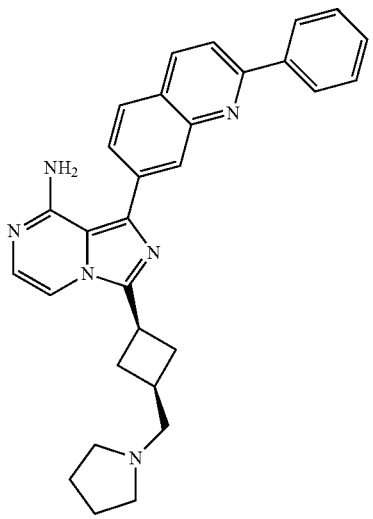 [SMILES: Nc1nccn2c1c(-c1ccc3ccc(-c4ccccc4)nc3c1)nc2[C@H]1C[C@@H](CN2CCCC2)C1] | cis-3-[3-(Pyrrolidin-1-ylmethyl)cyclobutyl]-1-(2-phenylquinolin-7-yl)imidazo[1,5-a]pyrazin-8-ylamine |  | m/z 475.17 (100) [MH⁺]. HPLC: $t_R$ = 1.73 min (OpenLynx, polar_5min) |
| 65 | 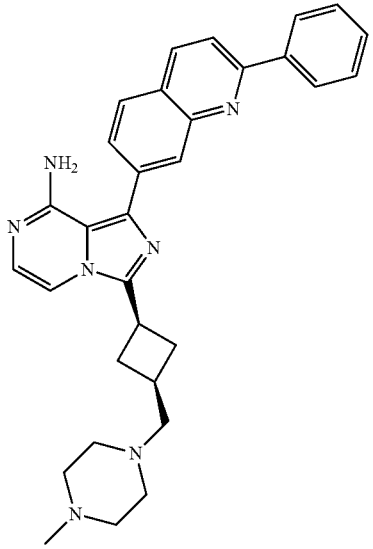 [SMILES: CN1CCN(C[C@H]2C[C@@H](c3nc(-c4ccc5ccc(-c6ccccc6)nc5c4)c4c(N)nccn43)C2)CC1] | cis-3-{3-[(4-Methylpiperazin-1-yl)methyl]cyclobutyl}-1-(2-phenylquinolin-7-yl)imidazo[1,5-a]pyrazin-8-ylamine | 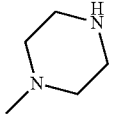 | m/z 504.18 (100) [MH⁺]. HPLC: $t_R$ = 1.65 min (OpenLynx, polar_5min) |

The compounds of Formula I-C'''.4 (compound of Formula I-C''' where Q¹=2-phenyl-quinolin-7-yl and Z=trans-1,3-cyclobutyl) were prepared from compounds of Formula I-H.3 (Compound of Formula I-H where Q¹=2-phenyl-quinolin-7-yl and Z=trans-1,3-cyclobuty: according to Method X7 except trans-toluene-4-sulfonic acid 3-[8-amino-1-(2-phenylquinolin-7-yl)-imidazo[1,5-a]pyrazin-3-yl]-cyclobutyl-methyl ester was used in place of cis-toluene-4-sulfonic acid 3-[8-amino-1-(2-phenylquinolin-7-yl)-imidazo[1,5-a]pyrazin-3-yl]-cyclobutylmethyl ester:

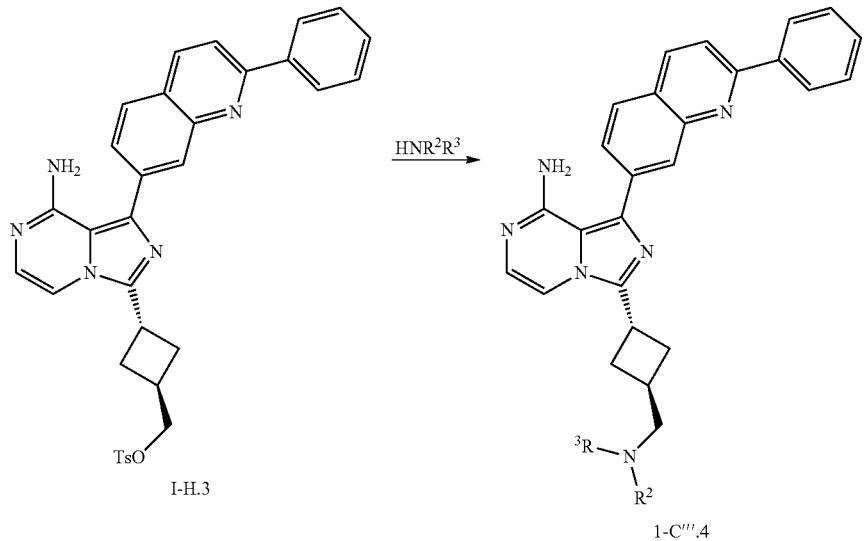
I-H.3 → 1-C'''.4
| Example | Structure | Name | HNR²R³ | MS | 1HNMR |
|---|---|---|---|---|---|
| 66 | 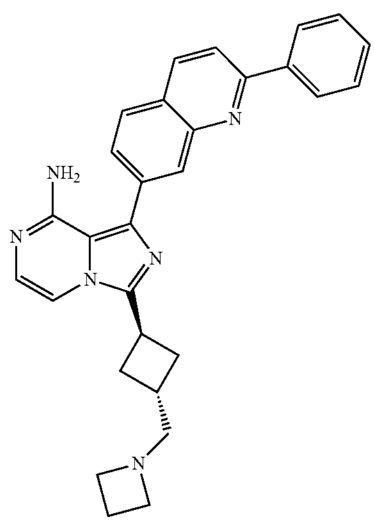 [SMILES: Nc1nccn2c1c(-c1ccc3ccc(-c4ccccc4)nc3c1)nc2[C@H]1C[C@H](CN2CCC2)C1] | trans-3-(3-Azetidin-1-ylmethyl-cyclobutyl)-1-(2-phenyl-quinolin-7-yl)-imidazo[1,5-a]pyrazin-8-ylamine | | m/z 461 [MH⁺]. | (400 MHz, CDCl₃): δ = 8.43 (d, J = 1.2 Hz, 1H), 8.26 (dd, J = 0.4, 8.0 Hz, 1H), 8.21-8.18 (m, 2H), 7.95 (d, J = 0.8 Hz, 2H), 7.92 (d, J = 8.0 Hz, 1H), 7.56-7.47 (m, 3H), 7.10 (8, 2H), 5.20 (b, 2H), 3.82 (p, J = 2.0 Hz, 1H), 3.26 (t, J = 6.8 Hz, 4H), 2.76-2.73 (m, 2H), 2.67 (d, J = 8.0 Hz, 2H), 2.68-2.65 (m, 1H), 2.31-2.29 (m, 2H), 2.13 (p, J = 7.2 Hz, 2H) |
| 67 | 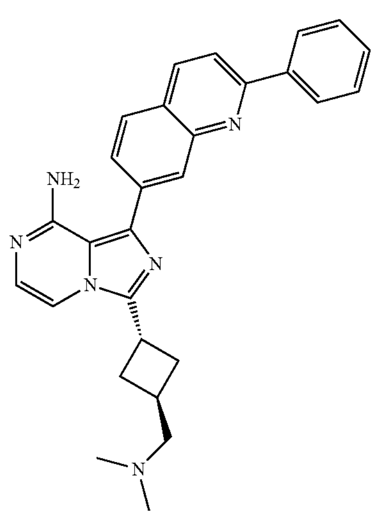 [SMILES: CN(C)C[C@H]1C[C@H](c2nc(-c3ccc4ccc(-c5ccccc5)nc4c3)c3c(N)nccn32)C1] | trans-3-{3-[(Dimethylamino)methyl]cyclobutyl}-1-(2-phenyl quinolin-7-yl)imidazo[1,5-a]pyrazin-8-ylamine | | m/z 449.37 (100) [MH⁺]. HPLC: t_R = 1.75 min (OpenLynx, polar_5min) | |

| 68 | 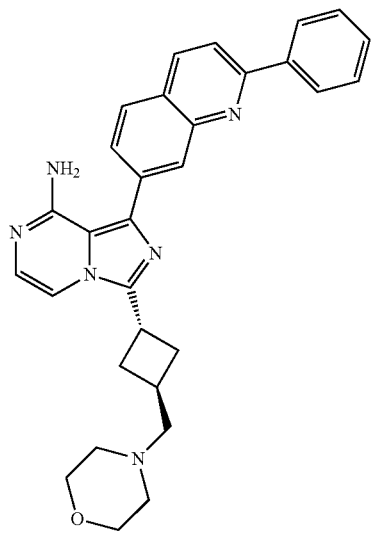 [SMILES: Nc1nccn2c1c(-c1ccc3ccc(-c4ccccc4)nc3c1)nc2[C@H]1C[C@H](CN2CCOCC2)C1] | trans-3-[3-(Morpholin-4-ylmethyl)cyclobutyl]-1-(2-phenylquinolin-7-yl)imidazo[1,5-a]pyrazin-8-ylamine | 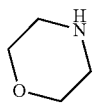 | MS (ES+): m/z 491.37 (100) [MH$^+$]. HPLC: t$_R$ = 1.78 min (OpenLynx, polar_5min) |
|---|---|---|---|---| trans- and cis-3-[8-Amino-1-(2-phenylquinolin-7-yl)imidazo[1,5-a]pyrazin-3-yl]-1-hydroxycyclobutylmethyl p-toluenesulfonate were prepared as follows: A solution of 3-[8-amino-1-(2-phenylquinolin-7-yl)imidazo[1,5-a]pyrazin-3-yl]-1-hydroxymethylcyclobutanol (500 mg, 1.14 mmol), 4 Å molecular sieve (30 mg) and pyridine (0.92 mL, 11.4 mmole) in dry methylene chloride (10 mL) was added a solution of Ts$_2$O (558 mg, 1.71 mmol) in methylene chloride (2 mL) at −40° C. under N$_2$ atmosphere through a syringe. The mixture was slowly warmed to rt overnight. The reaction was quenched with water (10 mL), diluted with methylene chloride (30 mL), washed with sat. aq. NaHCO$_3$ (3×30 mL), and dried over Na$_2$SO$_4$, concentrated under reduced pressure, and purified by silica gel column chromatography (eluting with Hexanes:EtOAc=50:50→3 30:70→100% ethyl acetate, then 2% MeOH/EtOAc) to afford the individual cis and trans-desired products:

Example 69 cis-3-[8-Amino-1-(2-phenylquinolin-7-yl)imidazo[1,5-a]pyrazin-3-yl]-1-hydroxycyclobutylmethyl p-toluenesulfonate

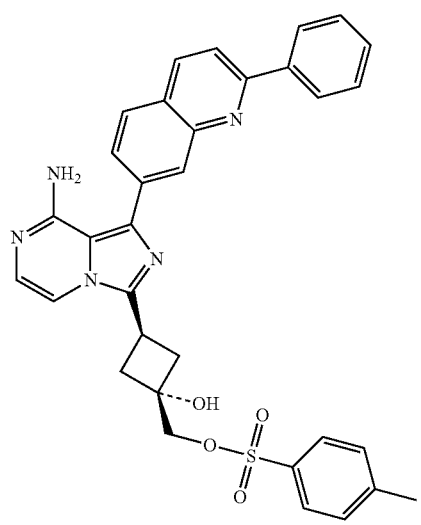 [SMILES: Cc1ccc(S(=O)(=O)OC[C@]2(O)C[C@H](c3nc(-c4ccc5ccc(-c6ccccc6)nc5c4)c4c(N)nccn43)C2)cc1]

Yellow solid; $^1$H NMR (CDCl$_3$, 400 MHz) δ 2.32 (s, 3H), 2.60-2.69 (m, 4H), 3.85-3.93 (m, 1H), 4.26 (s, 2H), 7.05 (d, J=4.8 Hz, 1H), 7.11 (d, J=5.2 Hz, 1H), 7.20 (d, J=8.4 Hz, 2H), 7.47-7.57 (m, 3H), 7.73 (d, J=8.4 Hz, 2H), 7.90-7.99 (m, 3H), 8.19-8.21 (m, 2H), 8.29 (d, J=8.4 Hz, 1H), 8.40 (s, 1H); MS (ES+): m/z 592 [MH$^+$]; HPLC: t$_R$=2.42 min (OpenLynx, polar_5 min).

Example 70 trans-3-[8-Amino-1-(2-phenylquinolin-7-yl)imidazo[1,5-a]pyrazin-3-yl]-1-hydroxycyclobutylmethyl p-toluenesulfonate

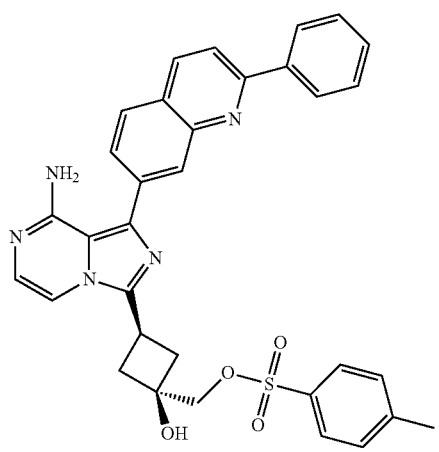 [SMILES: Cc1ccc(S(=O)(=O)OC[C@]2(O)C[C@@H](c3nc(-c4ccc5ccc(-c6ccccc6)nc5c4)c4c(N)nccn43)C2)cc1]

313

Yellow solid; ¹H NMR (CDCl₃, 400 MHz: δ 2.46 (s, 3H), 2.56-2.61 (m, 2H), 2.82-2.87 (m, 2H), 3.44-3.49 (m, 1H), 4.12 (s, 2H), 5.24 (br, NH), 7.14-7.17 (m, 2H), 7.38 (d, J=8.0 Hz, 2H), 7.48-7.56 (m, 3H), 7.84-7.95 (m, 5H), 8.17-8.20 (m, 2H), 8.26 (d, J=8.4 Hz, 1H), 8.39 (s, 1H); MS (ES+): m/z 592 [MH⁺]; HPLC: t$_R$=2.53 min (OpenLynx, polar_5 min).

Example 71

3-[8-Amino-1-(2-phenyl-quinolin-7-yl)-imidazo[1,5-a]pyrazin-3-yl]-1-hydroxymethyl-cyclobutanol

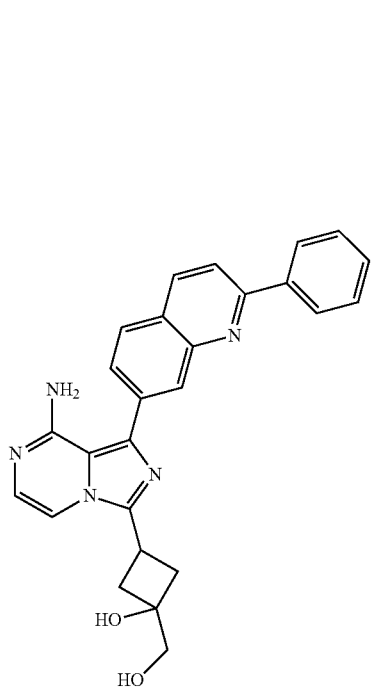 [SMILES: Nc1nccn2c(C3CC(O)(CO)C3)nc(-c3ccc4ccc(-c5ccccc5)nc4c3)c12]

Ammonia gas was bubbled in to IPA (5 mL, containing 2N NH₃) at −78° C., until the volume was doubled (10 mL), and this solution was added to a slurry of 3-[8-chloro-1-(2-phenylquinolin-7-yl)-imidazo[1,5-a]pyrazin-3-yl]-1-hydroxymethylcyclobutanol in IPA (2 mL, containing 2N NH₃) at −78° C. The reaction mixture was heated in a high pressure bomb at 120° C. for 36 h. The reaction mixture was cooled to RT and evaporated to afford the desired product as a yellow solid; MS (ES+): m/z 438.02 [MH⁺]; HPLC: t$_R$=2.52 min (OpenLynx, polar_5 min).

314

3-[8-Chloro-1-(2-phenyl-quinolin-7-yl)-imidazo[1,5-a]pyrazin-3-yl]-1-hydroxymethyl-cyclobutanol

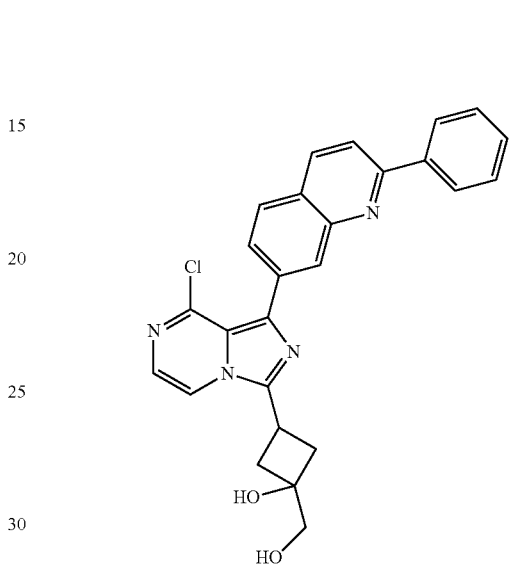

7-[8-Chloro-3-(3-methylenecyclobutyl)imidazo[1,5-a]pyrazin-1-yl]-2-phenylquinoline (0.26 mmol, 110 mg) was dissolved in 8 mL solution (THF:H₂O=3:1) and charged with NMO (0.52 mmol, 0.18 mL, 50% aq. solution) and K₂OsO₄·H₂O (0.26 mmol, 9.6 mg). The resulting mixture was stirred at rt overnight. The reaction was quenched with Na₂SO₃ (1.30 mmol, 164 mg), diluted with EtOAc (40 mL), washed with brine (30 mL), and dried over anhydrous sodium sulfate. The filtrate was concentrated under reduced pressure to give the desired product as a yellow solid; MS (ES+): m/z 457/396 (10/1) [MH⁺].

The compounds of Formula I-N.1 (compound of Formula I-N where Q¹=2-phenyl-quinolin-7-yl and Z=trans-1,3-cyclobutyl) were prepared from compounds of Formula I-M.1 (Compound of Formula I-M where Q¹=2-phenyl-quinolin-7-y, A⁴=OTs, and Z=cis-1,3-cyclobutyl) according to Method X7 except cis-3-[8-amino-1-(2-phenylquinolin-7-yl)imidazo[1,5-a]pyrazin-3-yl]-1-hydroxycyclobutylmethyl p-toluene-sulfonate was used in place of trans-toluene-4-sulfonic acid 3-[8-amino-1-(2-phenylquinolin-7-yl)-imidazo[1,5-a]pyrazin-3-yl]-cyclobutylmethyl ester:

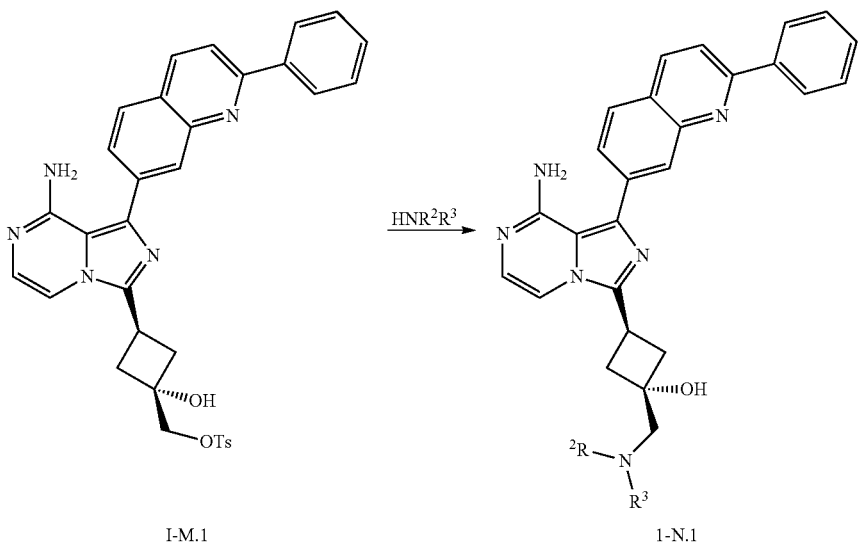

| Example | Structure | Name | HNR²R³ | Analytical data |
|---|---|---|---|---|
| 72 | 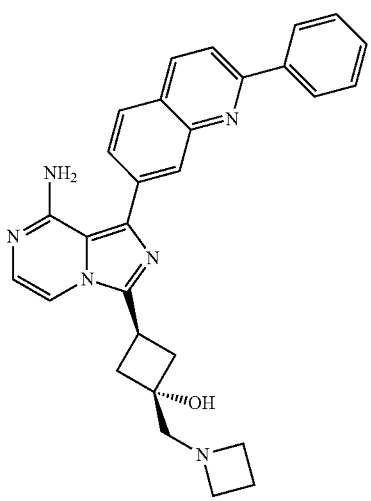 [SMILES: Nc1nccn2c1c(-c1ccc3ccc(-c4ccccc4)nc3c1)nc2[C@H]1C[C@@](O)(CN2CCC2)C1] | trans-3-[8-amino-1-(2-phenylquinolin-7-yl)imidazo[1,5-a]pyrazin-3-yl]-1-(azetidin-1-ylmethyl)cyclobutanol | | m/z 477 [MH⁺]. HPLC: $t_R$ = 1.72 min (OpenLynx, polar_5 min); ¹H NMR (CDCl₃, 400 MHz) δ 2.08-2.12 (m, 2H), 2.55-2.67 (m, 6H), 3.32 (t, J = 6.8 Hz, 4H), 3.98-4.02 (m, 1H), 5.19 (br, 2H), 7.11-7.15 (m, 2H), 7.47-7.57 (m, 3H), 7.92-7.96 (m, 3H), 8.18-8.21 (m, 2H), 8.28 (d, J = 8.4 Hz, 1H), 8.44 (s, 1H). |
| 73 | 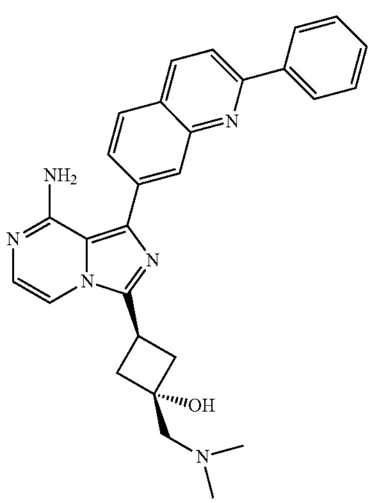 [SMILES: CN(C)C[C@]1(O)C[C@H](c2nc(-c3ccc4ccc(-c5ccccc5)nc4c3)c3c(N)nccn32)C1] | trans-3-[8-amino-1-(2-phenylquinolin-7-yl)imidazo[1,5-a]pyrazin-3-yl]-1-(dimethylamino-1-ylmethyl)cyclobutanol | | m/z 465 [MH⁺]. HPLC: $t_R$ = 1.72 min (OpenLynx, polar_5 min) |

| 74 | 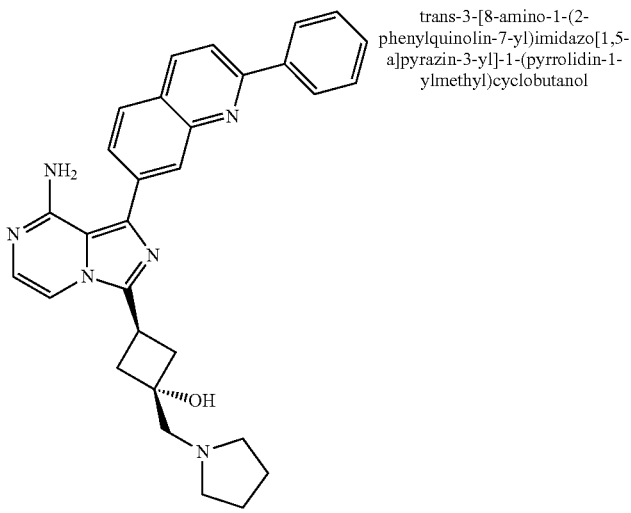 | trans-3-[8-amino-1-(2-phenylquinolin-7-yl)imidazo[1,5-a]pyrazin-3-yl]-1-(pyrrolidin-1-ylmethyl)cyclobutanol |  | m/z 491 [MH$^+$]. HPLC: $t_R$ = 1.76 min (OpenLynx, polar_5 min); $^1$H NMR (CDCl$_3$, 400 MHz) δ = 1.75-1.79 (m, 4H), 2.58-2.63 (m, 4H), 2.66-2.72 (m, 6H), 4.00-4.05 (m, 1H), 5.19 (br, 2H), 7.11 (d, J = 5.2 Hz, 1H), 7.17 (d, J = 4.8 Hz, 1H), 7.46-7.57 (m, 3H), 7.91-7.97 (m, 3H), 8.18-8.20 (m, 2H), 8.27 (d, J = 8.0 Hz, 1H), 8.43 (s, 1H). |
|---|---|---|---|---|
| 75 | 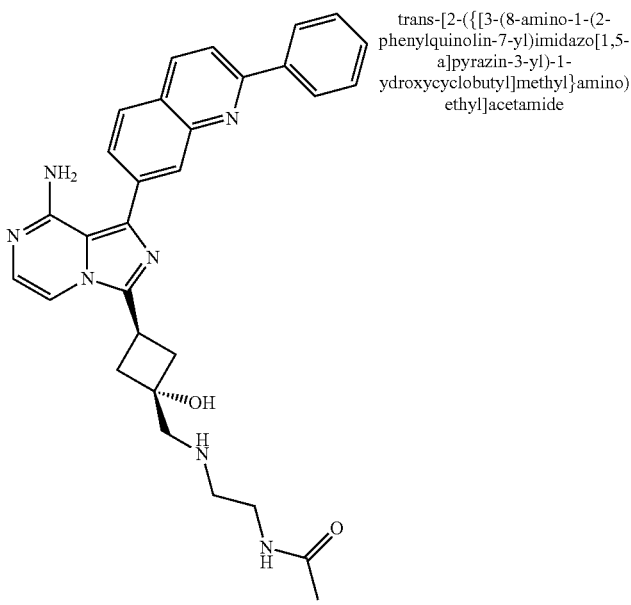 | trans-[2-({[3-(8-amino-1-(2-phenylquinolin-7-yl)imidazo[1,5-a]pyrazin-3-yl]-1-ydroxycyclobutyl]methyl}amino)ethyl]acetamide | 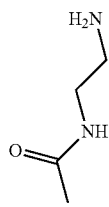 | m/z 465 [MH$^+$]. HPLC: $t_R$ = 1.72 min (OpenLynx, polar_5 min) |

The compounds of Formula I-N.2 (compound of Formula I-N where Q$^1$=2-phenyl-quinolin-7-yl and Z=cis-1,3-cyclobutyl) were prepared from compounds of Formula I-M 2 (Compound of Formula I-M where Q$^1$=2-phenyl-quinolin-7-y, A$^4$=OTs, and Z=trans-1,3-cyclobutyl) according to Method X7 except trans-3-[8-amino-1-(2-phenylquinolin-7-yl)imidazo[1,5-a]pyrazin-3-yl]-1-hydroxycyclobutylmethyl p-toluenesulfonate was used in place of cis-toluene-4-sulfonic acid 3-[8-amino-1-(2-phenylquinolin-7-yl)-imidazo[1,5-a]pyrazin-3-yl]-cyclobutylmethyl ester:

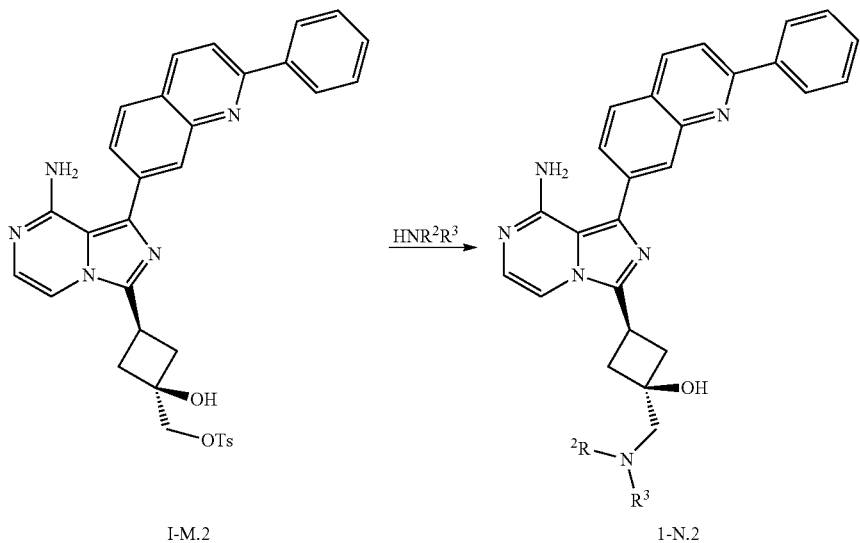

| Example | Structure | Name | HNR²R³ | Analytical data |
|---|---|---|---|---|
| 76 | 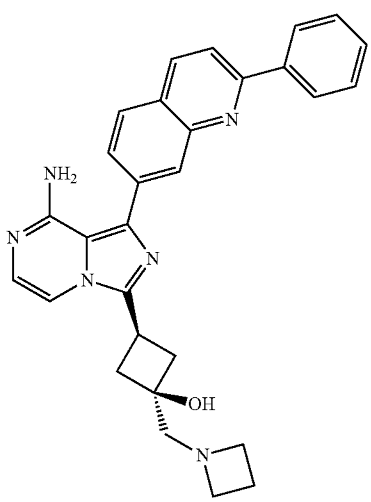 [SMILES: Nc1nccn2c1c(-c1ccc3ccc(-c4ccccc4)nc3c1)nc2[C@H]1C[C@](O)(CN2CCC2)C1] | cis-3-[8-Amino-1-(2-phenylquinolin-7-yl)imidazo[1,5-a]pyrazin-3-yl]-1-(azetidin-1-ylmethyl)cyclobutanol | | m/z 477 [MH⁺]; HPLC: $t_R$ = 1.77 min (OpenLynx, polar_5 min); 1HNMR (CDCl₃, 400 MHz) δ 2.12-2.19 (m, 2H), 2.61-2.73 (m, 4H), 2.73 (s, 2H), 3.35-3.43 (m, 5H), 5.23 (br, 2H), 7.12 (d, J = 5.2 Hz, 1H), 7.20 (d, J = 4.8 Hz, 1H), 7.46-7.56 (m, 3H), 7.91-7.95 (m, 3H), 8.18-8.20 (m, 2H), 8.27 (dd, J = 0.8 Hz, J = 8.8 Hz, 1H), 8.40 (d, J = 1.2 Hz, 1H) |
| 77 | 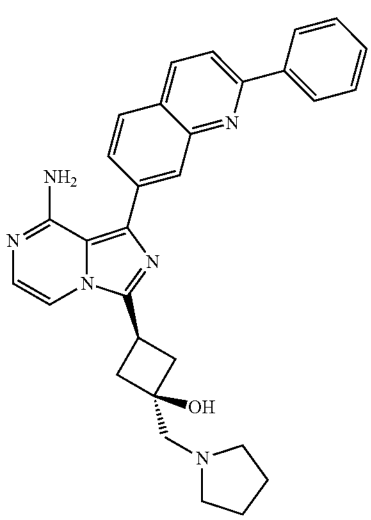 [SMILES: Nc1nccn2c1c(-c1ccc3ccc(-c4ccccc4)nc3c1)nc2[C@H]1C[C@](O)(CN2CCCC2)C1] | cis-3-[8-Amino-1-(2-phenylquinolin-7-yl)imidazo[1,5-a]pyrazin-3-yl]-1-(pyrrolidin-1-ylmethyl)cyclobutanol | | m/z 491 [MH⁺]; HPLC: $t_R$ = 1.76 min (OpenLynx, polar_5 min); 1HNMR (CDCl₃, 400 MHz): δ = 1.79-1.83 (m, 4H), 2.66-2.71 (m, 6H), 2.80-2.85 (m, 4H), 3.35-3.39 (m, 1H), 5.22 (br, 2H), 7.12 (d, J = 4.8 Hz, 1H), 7.22 (d, J = 5.2 Hz, 1H), 7.48-7.56 (m, 3H), 7.92 (d, J = 8.8 Hz, 1H), 7.95 (d, J = 1.2 Hz, 2H), 8.18-8.20 (m, 2H), 8.27 (dd, J = 0.4 Hz, J = 8.4 Hz, 1H), 8.40 (d, J = 1.2 Hz, 1H) |

Method X5: General procedure for the synthesis of compounds of Formula I-C'''.1 (compound of Formula I-C''' where Q¹=2-phenyl-quinolin-7-yl and R²=H) from compounds of Formula I-C''.1 (Compound of Formula I-C'' where Q¹=2-phenyl-quinolin-7-yl):

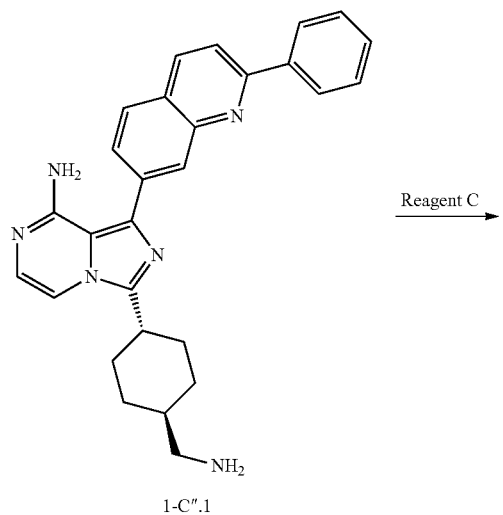

1-C''.1 → Reagent C → 1-C'''.1 trans-3-(4-Aminomethylcyclohexyl)-1-(2-phenylquinolin-7-yl)imidazo[1,5-a]pyrazin-8-ylamine (1.00 g; 2.23 mmol) was dissolved in $CH_2Cl_2$ (17 mL) and charged with PS-DIEA (1.20 g, 3.72 mmol/g loading, 4.46 mmol). Under $N_2$ atmosphere, Reagent C (1.11 mmol) was then added in one portion. After 15 min, the reaction was monitored by TLC, and additional Reagent C (0.56 mmol) was added. Over the next 30 min., additional Reagent C was added in two different portions (0.27 mmol and 0.11 mmol). When the reaction was almost complete by LC/MS, the reaction was filtered, and the resins were rinsed multiple times with $CH_2Cl_2$, chloroform, 10% $CH_3OH/CH_2Cl_2$. The filtrate was concentrated and the bright orange/yellow solid was dissolved in $CH_2Cl_2$, then loaded onto Hydromatrix. The crude product was purified by purified by silica gel column chromatography [Jones Flashmaster, 20 g/75 mL cartridge, 100% $CH_2Cl_2$, to 2% 7N ammonia in $CH_3OH/CH_2Cl_2$] to afford the desired product of >90% purity by LC/MS. The product was further purified by recrystallization from THF/diethyl ether to obtain the desired product as a yellow solid. When Reagent C was a carboxylic acid, the following procedure was used: trans-3-(4-Aminomethylcyclohexyl)-1-(2-phenylquinolin-7-yl)imidazo[1,5-a]pyrazin-8-ylamine (100 mg, 0.223 mmol) was dissolved in $CH_2Cl_2$ (1 mL) and was charged with Reagent C (0.22 mmol), EDC (64 mg, 0.33 mmol), and PS-DIEA (120 mg, 0.45 mmol, 3.9 mmol/g loading). When the reaction progress was monitored with LC/MS after 15 min., the reaction consisted of the starting amine, mono-acylated, and di-acylated products (16%, 74%, and 10% respectively). The reaction was filtered, and the resins were rinsed multiple times with $CH_2Cl_2$, chloroform, 10% $CH_3OH/CH_2Cl_2$. The bright orange/yellow solid was dissolved in methanol and purified by MDP to obtain the desired product as a yellow powder.

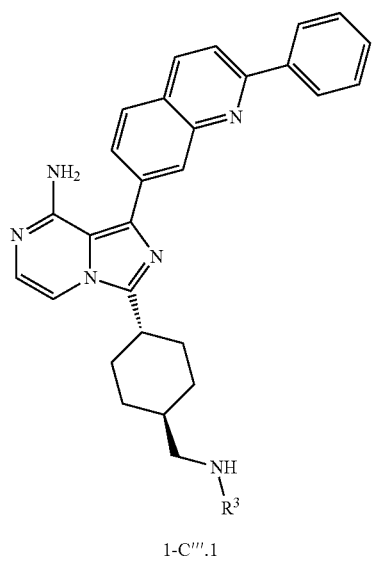

1-C'''.1

Compounds of Formula I-C''''.1 (compound of Formula I-C''' where Q¹=2-phenyl-quinolin-7-yl and R²=H) were prepared from compounds of Formula I-C''.1 (Compound of Formula I-C'' where Q¹=2-phenyl-quinolin-7-yl) by Method X5:

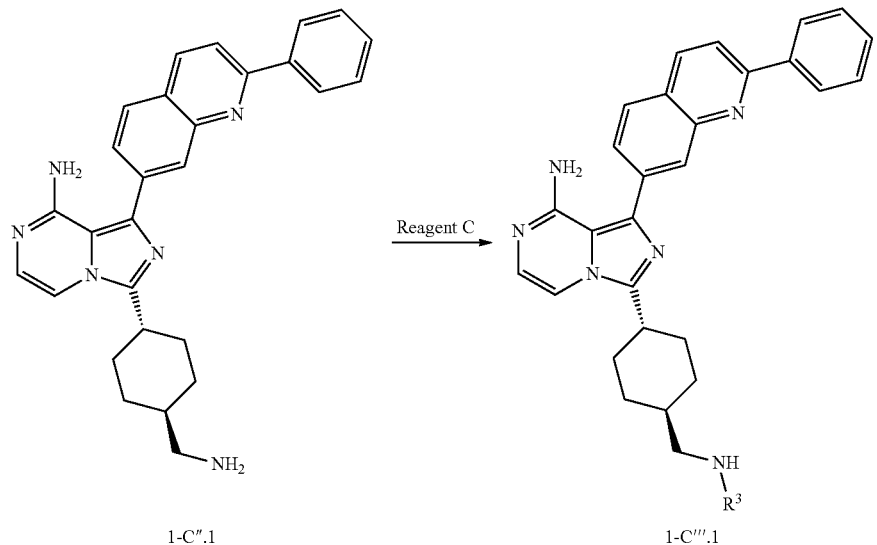

1-C''.1 → Reagent C → 1-C'''.1

| Example | Structure | Name | Reagent C | Analytical Data |
|---|---|---|---|---|
| 78 | 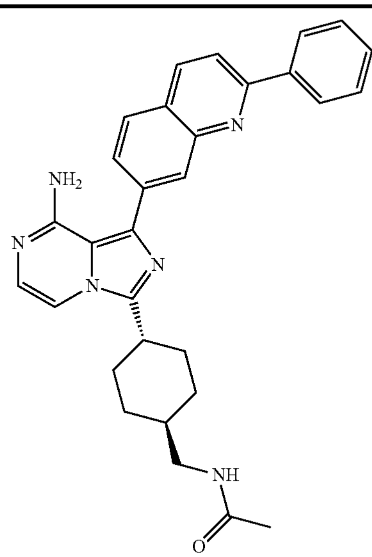 | N({trans-4-[8-Amino(2-phenylquinolin-7-yl)imidazo[1,5-a]pyrazin-3-yl]cyclohexyl}-methyl)acetamide | Ac$_2$O | m/z 491.31 (15) [MH$^+$], 246.44 (100) [MH − 244]; $^1$HNMR (CD$_3$OD, 400 MHz) δ 8.48 (d, J = 8.8 Hz, 1H), 8.33 (dd, J = 0.8, 0.8 Hz, 1H), 8.18 (m, 2H), 8.10 (d, J = 8.8 Hz, 1H), 8.07 (d, J = 8.8 Hz, 1H), 7.88 (dd, J = 8.4, 1.6 Hz, 1H), 7.62 (d, J = 5.2 Hz, 1H), 7.60-7.48 (m, 3H), 7.06 (d, J = 5.2 Hz, 1H), 3.16 (m, 1H), 3.12 (d, J = 6.8 Hz, 2H), 2.11 (m, 2H), 1.83 (ddd, J = 25.2, 12.8, 2.4 Hz, 1H), 1.65 (m, 1H), 1.26 (ddd, J = 25.2, 12.8, 2.4 Hz, 1H). |
| 79 | 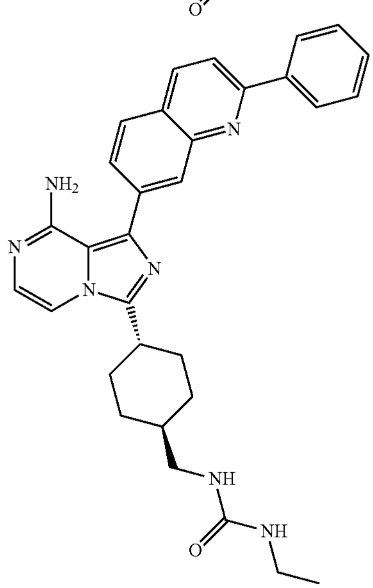 | N({trans-4-[8-Amino(2-phenylquinolin-7-yl)imidazo[1,5-a]pyrazin-3-yl]cyclohexyl}methyl)-N'-ethylurea | EtNCO | m/z 520.42 (100) [MH$^+$], 521.41 (55) [M$^{+2}$], 522.39 (15) [M$^{+3}$] |

| | | | |
|---|---|---|---|
| 80 | 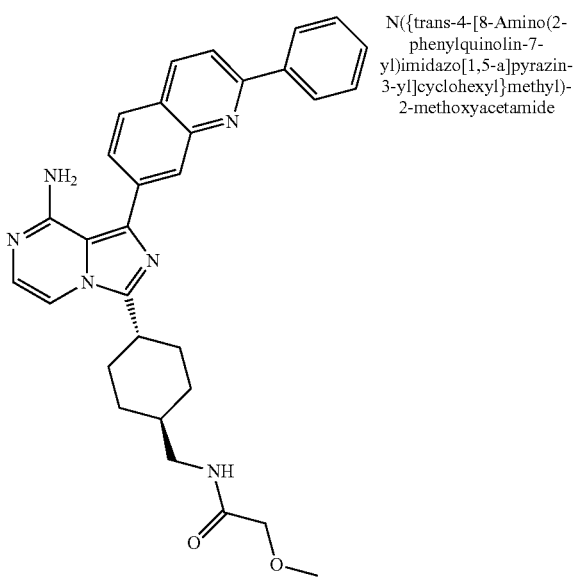 N({trans-4-[8-Amino(2-phenylquinolin-7-yl)imidazo[1,5-a]pyrazin-3-yl]cyclohexyl}methyl)-2-methoxyacetamide | 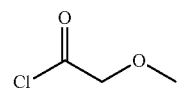 | m/z 522.13 (40) [MH+], 523.14 (20) [M+2], 524.16 (10) [M+3], 261.87 (100) [M − 259]. |
| 81 | 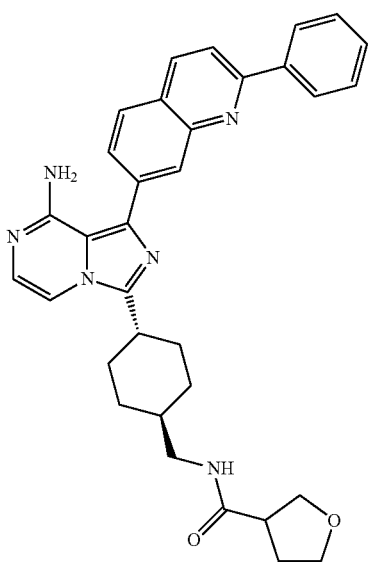 [SMILES: Nc1nccn2c1c(-c1ccc3ccc(-c4ccccc4)nc3c1)nc2[C@H]1CC[C@H](CNC(=O)C2CCOC2)CC1] N({trans-4-[8-Amino(2-phenylquinolin-7-yl)imidazo[1,5-a]pyrazin-3-yl]cyclohexyl}methyl)tetrahydrofuran-3-carboxamide | 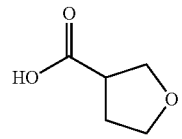 | m/z 547.10 (40) [MH+], 548.12 (70) [MH+2], 549.13 (35) [MH+3], 550.12 (10) [MH+4], 450.13 (30) [M − 97], 274.70 (100) [MH − 272]; $^1$HNMR (CDCl$_3$, 400 MHz) δ 8.41 (ddd, J = 0.8, 0.8 Hz, 1H) 8.39 (s, 1H), 8.29 (d, J = 8.8 Hz, 1H), 8.20 (m, 2H), 7.97 (d, J = 8.4 Hz, 1H), 7.83 (dd, J = 8.4, 1.6 Hz, 1H), 7.55 (m, 2H), 7.49 (m, 1H), 7.24 (d, J = 5.6 Hz, 1H), 6.94 (d, J = 5.2 Hz, 1H), 5.74 (t, J = 2.8 Hz, 1H), 3.97 (ddd, J = 8.8, 7.2, 7.2 Hz, 1H), 3.93 (quin, J = 7.2 Hz, 2H), 3.83 (ddd, J = 8.4, 7.2, 7.2 Hz, 1H), 3.22 (t, J = 6.6 Hz, 2H), 2.92 (m, 2H), 2.30-2.10 (m, 4H), 2.00-1.50 (m, 4H), 1.64 (m, 1H), 1.22 (m, 2H). |

| 82 | 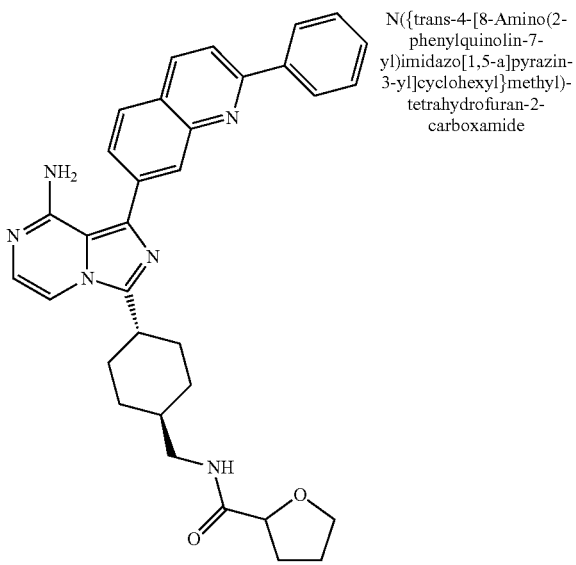 | N({trans-4-[8-Amino(2-phenylquinolin-7-yl)imidazo[1,5-a]pyrazin-3-yl]cyclohexyl}methyl)-tetrahydrofuran-2-carboxamide | 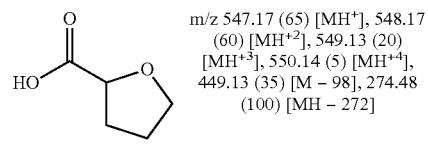 | m/z 547.17 (65) [MH+], 548.17 (60) [MH+2], 549.13 (20) [MH+3], 550.14 (5) [MH+4], 449.13 (35) [M − 98], 274.48 (100) [MH − 272] |
|---|---|---|---|---|

Method X6: General procedure for the synthesis of compounds of Formula I-C'''0.2 (compound of Formula I-C''' where $Q^1$=2-phenyl-quinolin-7-yl) from compounds of Formula I-H.1 (Compound of Formula I-H where $Q^1$=2-phenyl-quinolin-7-yl):

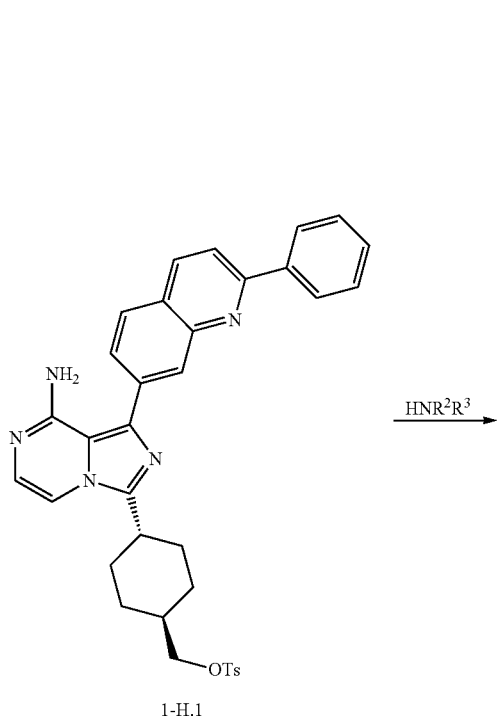

1-H.1

HNR²R³ →

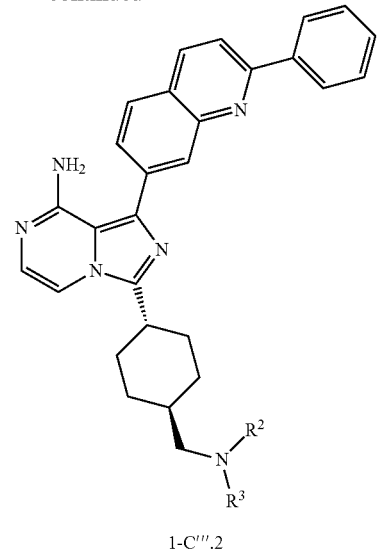

1-C'''.2

To an anhydrous THF solution (1.5 mL) of trans-toluene-4-sulfonic acid 4-[8-amino-1-(3-benzyloxy-phenyl)imidazo[1,5-a]pyrazin-3-yl]-cyclohexylmethyl ester (100 mg, 0.17 mmol) in a sealed tube, HNR²R³ (8.28 mmol) was added and stirred at 60° C. for 72 h. The reaction mixture was concentrated in vacuo and partitioned between EtOAc and sat. NaHCO₃. The organic layer was washed with sat. NaHCO₃ (2×), water, brine, dried over Na₂SO₄, filtered, and concentrated in vacuo to a yellow oil. The crude material was purified by MDPS to yield the desired product as a light yellow powder.

The compounds of Formula I-C'''.2 (compound of Formula I-C''' where $Q^1$=2-phenyl-quinolin-7-yl) were prepared from compounds of Formula I-H.1 (Compound of Formula I-H where $Q^1$=2-phenyl-quinolin-7-yl) according to Method X6:

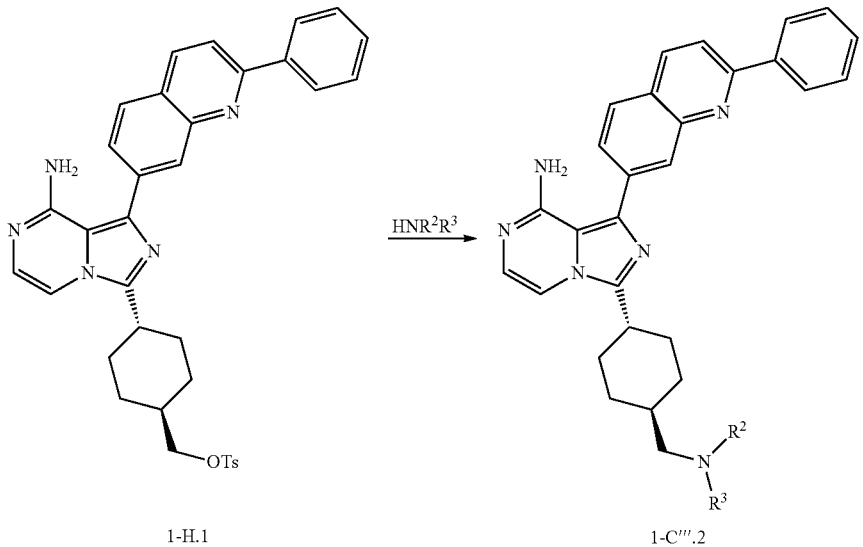
| Example | Structure | Name | HNR²R³ | Analytical data |
|---|---|---|---|---|
| 83 | 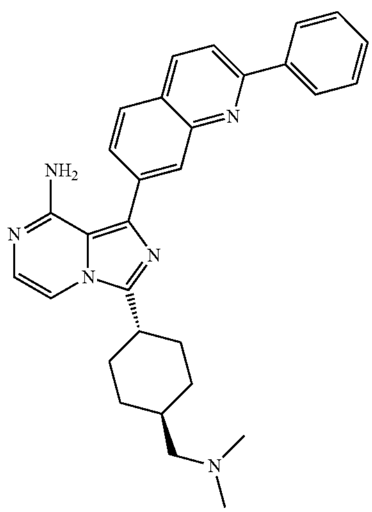 [SMILES: CN(C)C[C@H]1CC[C@H](c2nc(-c3ccc4ccc(-c5ccccc5)nc4c3)c3c(N)nccn32)CC1] | (trans-3-[4-(Dimethylamino)-methyl-cyclohexyl]-1-(2-phenylquinolin-7-yl)imidazo[1,5-a]pyrazin-8-ylamine | H–N(CH₃)₂ | m/z 477.19 (25) [MH⁺], 478.20 (10) [MH⁺²], 239.51 (100) [MH − 237]; ¹HNMR (CDCl₃, 400 MHz) δ 8.41 (dd, J = 0.8, 0.8 Hz, 1H), 8.27 (dd, J = 8.8, 0.4 Hz, 1H), 8.19 (m, 2H), 7.97-7.85 (m, 3H), 7.54 (m, 2H), 7.48 (m, 1H), 7.29 (d, J = 5.2 Hz, 1H), 7.12 (d, J = 4.8 Hz, 1H), 5.19 (br s, 2H), 2.97 (tt, J = 12.2, 3.4 Hz, 1H), 2.40-2.10 (m, 9H), 2.15 (m, 2H), 1.95 (ddd, J = 27.2, 12.4, 3.2 Hz, 2H), 1.16 (m, 2H). |
| 84 | 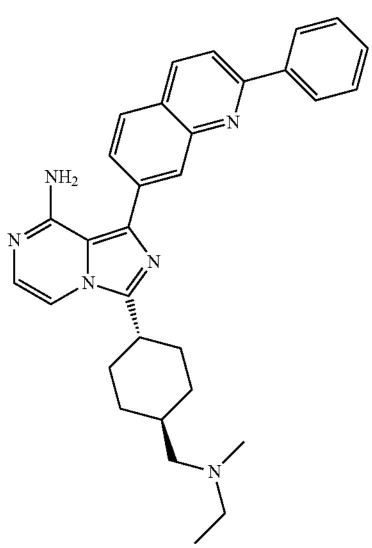 [SMILES: CCN(C)C[C@H]1CC[C@H](c2nc(-c3ccc4ccc(-c5ccccc5)nc4c3)c3c(N)nccn32)CC1] | (trans-3-{4-[ethyl(methyl)amino]methyl-cyclohexyl}-1-(2-phenylquinolin-7-yl)imidazo[1,5-a]pyrazin-8-ylamine | H–N(CH₃)(Et) | m/z 491.16 (30) [MH⁺], 492.17 (15) [MH⁺²], 246.52 (100) [MH − 244]. |

| | | | | |
|---|---|---|---|---|
| 85 | 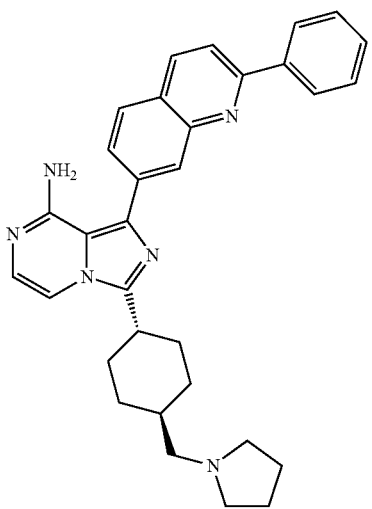 [SMILES: Nc1nccn2c1c(-c1ccc3ccc(-c4ccccc4)nc3c1)nc2[C@H]1CC[C@H](CN2CCCC2)CC1] | {trans-3-[4-(Pyrrolidinylamino)-methyl-cyclohexyl}-1-(2-phenylquinolin-7-yl)imidazo[1,5-a]pyrazin-8-ylamine |  | m/z 503.18 (20) [MH+], 504.19 (10) [MH+2], 252.52 (100) [MH − 250] |
| 86 | 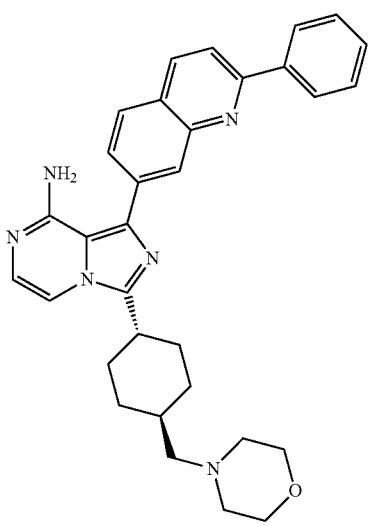 [SMILES: Nc1nccn2c1c(-c1ccc3ccc(-c4ccccc4)nc3c1)nc2[C@H]1CC[C@H](CN2CCOCC2)CC1] | {trans-3-[4-(Morpholinylamino)-methyl-cyclohexyl}-1-(2-phenylquinolin-7-yl)imidazo[1,5-a]pyrazin-8-ylamine | 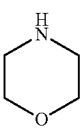 | m/z 519.16 (20) [MH+], 520.17 (10) [MH+2], 260.47 (100) [MH − 258] |
| 87 | 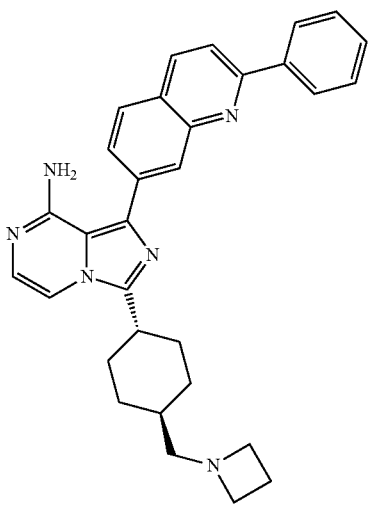 [SMILES: Nc1nccn2c1c(-c1ccc3ccc(-c4ccccc4)nc3c1)nc2[C@H]1CC[C@H](CN2CCC2)CC1] | {trans-3-[4-(Azetidinylamino)-methyl-cyclohexyl}-1-(2-phenylquinolin-7-yl)imidazo[1,5-a]pyrazin-8-ylamine |  | m/z 489.13 (30) [MH+], 490.14 (10) [MH+2], 245.50 (100) [MH − 243] |

| | | | | |
|---|---|---|---|---|
| 88 | 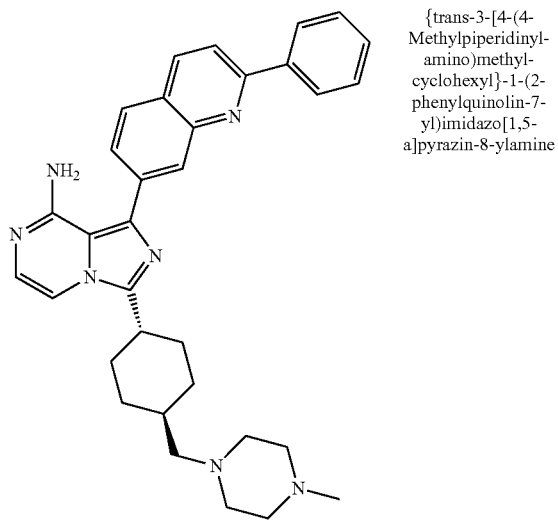 | {trans-3-[4-(4-Methylpiperidinyl-amino)methyl-cyclohexyl}-1-(2-phenylquinolin-7-yl)imidazo[1,5-a]pyrazin-8-ylamine | 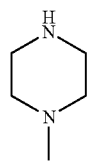 | m/z 532.19 (20) [MH$^+$], 533.20 (10) [MH$^{+2}$], 267.00 (100) [MH − 245] |
| 89 | 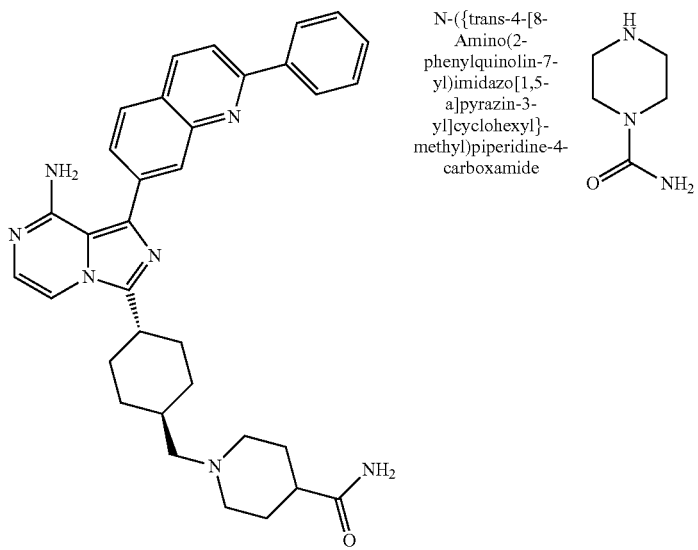 | N-({trans-4-[8-Amino(2-phenylquinolin-7-yl)imidazo[1,5-a]pyrazin-3-yl]cyclohexyl}-methyl)piperidine-4-carboxamide | 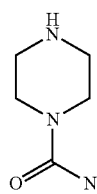 | m/z 560.20 (10) [MH$^+$], 561.21 (5) [MH$^{+2}$], 280.90 (100) [MH − 279] |

Example 90

(trans-3-[4-(Dimethylamino)methyl-cyclohexyl]-1-(4-methyl-2-phenylquinolin-7-yl)imidazo[1,5-a]pyrazin-8-ylamine

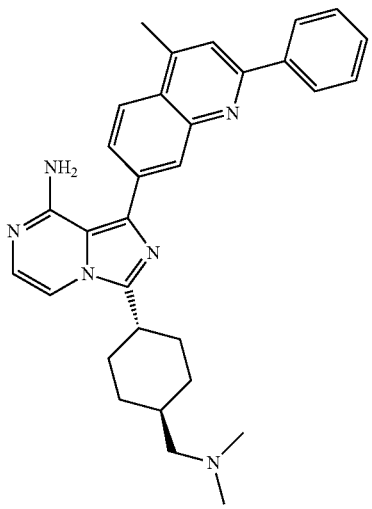 [SMILES: Cc1cc(-c2ccccc2)nc2cc(-c3nc([C@H]4CC[C@H](CN(C)C)CC4)n4ccnc(N)c34)ccc12]

Prepared according to Method X6 where HNR²R³ is dimethylamine; ¹H NMR (d₆-DMSO, 400 MHz) δ 8.35-8.25 (m, 2H), 8.23 (d, J=1.6 Hz, 1H), 8.20 (d, J=8.4 Hz, 1H), 8.06 (s, 1H), 7.91 (dd, J=8.6, 1.8 Hz, 1H), 7.68 (d, J=5.2 Hz, 1H), 7.60-7.45 (m, 3H), 7.09 (d, J=5.2 Hz, 1H), 6.19 (br s, 2H), 3.13 (tt, J=11.8, 3.2, 1H), 2.81 (s, 3H), 2.13 (s, 6H), 2.07 (d, J=7.2 Hz, 2H), 2.01 (m, 2H), 1.90 (m, 2H), 1.71 (ddd, J=25.4, 12.6, 2.4 Hz, 2H), 1.56 (m, 1H), 1.10 (m, 2H); m/z 491.02 (5) [MH⁺], 246.29 (100) [MH-244]; $t_R$(polar-5 min/openlynx)= 1.85 min.

Example 91

(trans-3-{4-[Ethyl(methyl)amino]methyl-cyclohexyl}-1-(4-methyl-2-phenylquinolin-7-yl)imidazo[1,5-a]pyrazin-8-ylamine

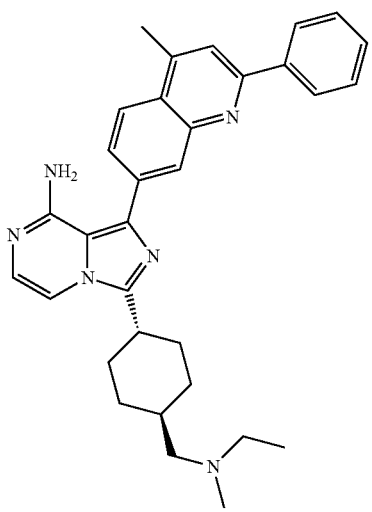 [SMILES: CCN(C)C[C@H]1CC[C@H](c2nc(-c3ccc4c(C)cc(-c5ccccc5)nc4c3)c3c(N)nccn32)CC1]

Prepared according to Method X6 where HNR²R³ is methylethylamine; ¹H NMR (d₆-DMSO, 400 MHz) δ 8.30 (d, J=7.6 Hz, 2H), 8.23 (s, 1H), 8.20 (d, J=8.4 Hz, 1H), 8.06 (s, 1H), 7.91 (d, J=8.0 Hz, 1H), 7.68 (d, J=4.8 Hz, 1H), 7.56 (dd, J=7.2, 7.2 Hz, 2H), 7.50 (dd, J=7.0 Hz, 1H), 7.09 (d, J=5.2 Hz, 1H), 6.18 (br s, 2H), 3.12 (m, 1H), 2.81 (s, 3H), 2.34 (m, 2H), 2.20-2.05 (m, 5H), 2.01 (d, J=12.0 Hz, 2H), 1.91 (d, J=11.6 Hz, 2H), 1.70 (dd, J=24.0, 11.6 Hz, 2H), 1.58 (m, 1H), 1.29 (m, 2H), 1.10 (m, 2H), 0.98 (t, J=7.0 Hz, 3H); m/z 505.06 (10) [MH⁺], 253.36 (100) [MH-251]; $t_R$(polar-5 min/openlynx)= 1.88 min.

Example 92

{trans-3-[4-(Pyrrolidinylamino)methyl-cyclohexyl}-1-(4-methyl-2-phenylquinolin-7-yl)imidazo[1,5-a]pyrazin-8-ylamine

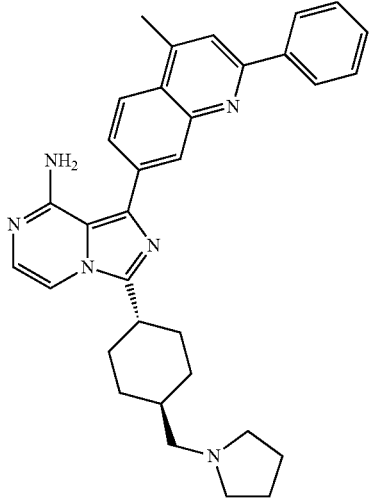

Prepared according to Method X6 where HNR²R³ is pyrrolidine; ¹H NMR (d₆-DMSO, 400 MHz) δ 8.35-8.26 (m, 2H), 8.23 (d, J=1.2 Hz, 1H), 9.20 (d, J=8.8 Hz, 1H), 8.06 (s, 1H), 7.91 (dd, J=8.6, 1.8 Hz, 1H), 7.68 (d, J=4.8 Hz, 1H), 7.56 (dd, J=7.2, 7.2 Hz, 2H), 7.51 (dd, J=7.4, 7.4 Hz, 1H), 7.09 (d, J=5.2 Hz, 1H), 6.19 (br s, 2H), 3.13 (m, 1H), 2.80 (s, 3H), 2.41 (m, 4H), 2.27 (d, J=7.2 Hz, 2H), 2.01 (m, 2H), 1.93 (m, 2H), 1.80-1.62 (m, 6H), 1.55 (m, 1H), 1.12 (m, 2H); m/z 517.01 (10) [MH⁺], 259.33 (100) [MH-257]; $t_R$(polar-5 min/openlynx)=1.89 min.

Example 93 trans-{4-[8-Amino-1-(4-methyl-2-phenylquinolin-7-yl)imidazo[1,5-a]pyrazin-3-yl]cyclohexyl} methanol/methyl 4-methylbenzenesulfonate

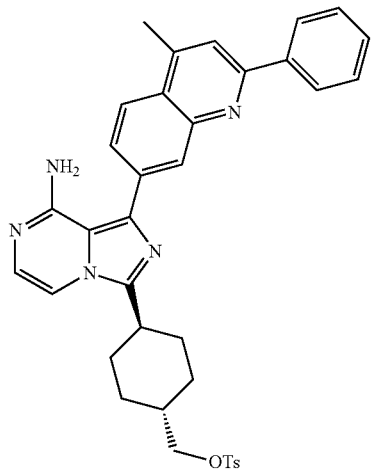 [SMILES: Cc1ccc(S(=O)(=O)OC[C@H]2CC[C@H](c3nc(-c4ccc5c(C)cc(-c6ccccc6)nc5c4)c4c(N)nccn43)CC2)cc1]

trans-{-4-[8-Amino-(4-methyl-2-phenylquinolin-7-yl) imidazo[1,5-a]pyrazin-3-yl]cyclohexyl}methanol (200 mg, 0.43 mmol) and toluene-4-sulfonic anhydride (150 mg, 0.47 mmol) were dissolved in anhydrous pyridine (8.7 mL) under nitrogen and allowed to sit at −10° C. for 24 h. Saturated aqueous sodium bicarbonate solution (10 mL) was added to the reaction mixture, then, stirred for 10 min. The reaction mixture was concentrated in vacuo, then, partitioned between saturated aqueous sodium bicarbonate solution and dichloromethane. The organic extract was separated, washed once again with sodium bicarbonate (aq) and brine, dried over anhydrous sodium sulfate, then concentrated in vacuo. The crude mixture was purified by a silica gel column chromatography [Jones Flashmaster; 10 g column, dry-loaded with silica gel; eluted with 100% DCM to 1:1 EtOAc/DCM to 10% (7N ammonia/MeOH)/chloroform] to obtain the desired mono-tosylated product as a yellow solid; $^1$H NMR (d$_6$-DMSO, 400 Hz) δ 8.29 (dd, J=8.4, 1.2 Hz, 2H), 8.22 (d, J=1.2 Hz, 1H), 8.19 (d, J=8.8 Hz, 1H), 8.06 (s, 1H), 7.90 (dd, J=8.4, 1.2 Hz, 1H), 7.82 (m, 2H), 7.69 (d, J=5.2 Hz, 1H), 7.563 (m, 2H), 7.50 (m, 3H), 7.08 (d, J=4.8 Hz, 1H), 6.19 (br s, 2H), 3.92 (d, J=5.6 Hz, 2H), 3.10 (m, 1H), 2.08 (s, 3H), 2.44 (s, 3H), 2.00 (m, 2H), 1.77 (m, 2H), 1.66 (m, 2H), 1.20 (m, 2H); MS (ES+): m/z 618.32 (40) [MH$^+$], 426.21 (60) [M-191], 412.52 (100) [M-205]; t$_R$(polar-5 min/MDPS) 3.03 min.

Example 94 trans-{-4-[8-Amino-(4-methyl-2-phenylquinolin-7-yl)imidazo[1,5-a]pyrazin-3-yl]cyclohexyl}methanol

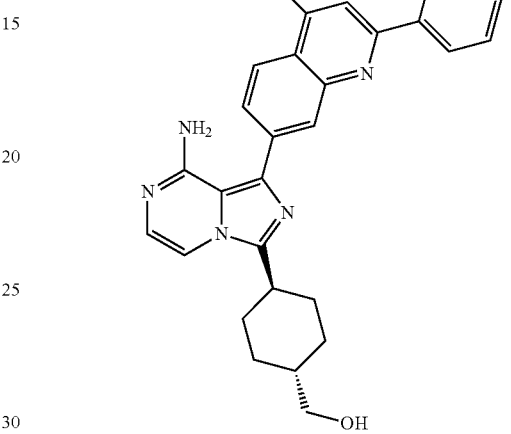

A mixture of [4-(8-amino-1-iodoimidazo[1,5-a]pyrazin-3-yl)cyclohexyl]methanol (500 mg, 1.34 mmol), 4-methyl-2-phenyl-7-(4,4,5,5-tetramethyl-[1,3,2]dioxaborolan-2-yl)quinoline (510.2 mg, 1.48 mmol), and cesium carbonate (875 mg, 2.69 mmol) were dissolved in a 1:1 mixture of 1,2-dimethoxyethane and water (10 mL). The reaction was degassed with nitrogen, then charged with tetrakis(triphenylphosphine)palladium(0) (155 mg, 0.13 mmol). The reaction was degassed once again, then the mixture was heated at 75° C. for 18 h. The mixture was cooled to rt, was diluted with dichloromethane and washed with brine. The organic extract was dried over sodium sulfate, filtered and concentrated in vacuo. The yellow residue was purified by a silica gel chromatography [Jones Flashmaster; 20 g column; eluted with 100% chloroform to 4% MeOH/chloroform to 4% (7N ammonia/MeOH)/chloroform] to give the desired product as a yellow solid. The product was contaminated with PPh$_3$ (0.053 equiv by $^1$H NMR) and pinacol (0.549 equiv by $^1$H NMR). The product was further purified by an acid-base aqueous work-up. The yellow solid was taken up in dichloromethane (30 mL), then, the desired product was taken up in an aqueous layer with 1N aqueous HCl (30 mL). The acidic aqueous layer was washed with dichloromethane, then basified with solid sodium bicarbonate until ~pH 9 to 10. The basic aqueous layer was extracted with dichloromethane, then twice with chloroform. The organic extracts were combined, dried over sodium sulfate, filtered, concentrated in vacuo and dried in an oven for 18 h to give the desired product as a yellow solid; $^1$H NMR (d$_6$-DMSO, 400 Hz) δ 8.30 (m, 2H), 8.23 (d, J=1.6 Hz, 1H), 8.20 (d, J=8.8 Hz, 1H), 8.07 (s, 1H), 7.92 (dd, J=8.8, 2.0 Hz, 1H), 7.70 (d, J=5.2 Hz, 1H), 7.57 (m, 2H), 7.51 (m, 1H), 7.09 (d, J=5.6 Hz, 1H), 6.19 (br s, 2H), 3.31 (s, 3H), 3.12 (m, 1H), 2.81 (s, 3H), 2.03 (m, 2H), 1.88 (m, 2H), 1.67 (m, 2H), 1.49 (m, 1H), 1.16 (m, 2H); MS (ES+): m/z 464.03 (30) [MH⁺], 465.02 (10) [MH⁺2], 232.90 (100) [M-231]; t_R(polar-5 min/openlynx) 2.20 min.

trans-[4-(8-Amino-1-iodoimidazo[1,5-a]pyrazin-3-yl)cyclohexyl]methanol

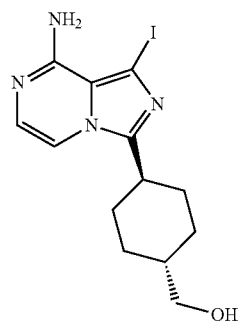

trans-[4-(8-chloro-1-iodoimidazo[1,5-a]pyrazin-3-yl)cyclohexyl]methanol (26.50 g, 67.66 mmol) was charged in a 400 mL steel bomb and was dissolved in 2M NH₃ in isopropanol (300 mL) and anhydrous THF (10 mL). The reaction mixture was cooled to −78° C. Ammonia gas was bubbled vigorously into the solution for 8 min; then the bomb was tightly sealed and heated to 120° C. for 20 h. The crude reaction mixture was concentrated in vacuo, then the reaction residue was taken up with MeOH/CHCl₃, loaded onto silica gel. The mixture was purified by a silica gel glass column chromatography [eluted with 1:1 CH₂Cl₂/EtOAc to 10% ~7 N NH₃ in MeOH/CHCl₃] to afford the desired product as a beige cream white solid; MS (ES+): m/z 373.01 (100) [MH⁺], 373.98 (50) [MH⁺2]; t_R(polar-5 min/openlynx) 1.57 min.

trans-[4-(8-Chloro-1-iodoimidazo[1,5-a]pyrazin-3-yl)cyclohexyl]methanol

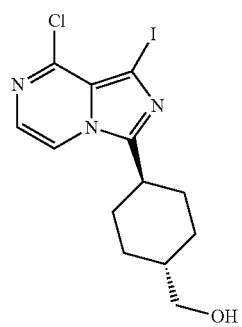 [SMILES: OC[C@H]1CC[C@H](c2nc(I)c3c(Cl)nccn32)CC1]

trans-[4-(8-Chloroimidazo[1,5-a]pyrazin-3-yl)cyclohexyl]methanol (18.00 g, 67.74 mmol) and N-iodosuccinimide (19.81 g, 88.06 mmol) in anhydrous DMF (360 mL) were stirred at 60° C. under N₂ for 6 h. The reaction was diluted with DCM (~600 mL), washed with water and brine, dried over anhydrous Na₂SO₄ and then concentrated in vacuo. The crude material was purified by a silica gel flash chromatography (eluted with 1:2 EtOAc/DCM to 1:1 EtOAc/DCM) to obtain the desired product as a pale yellow solid; By ¹H NMR analysis, the product was contaminated with 0.35 equiv of NIS-impurity. The product was carried onto the next reaction without further purification; MS (ES+): m/z 391.92 (100) [MH⁺], 393.88 (50) [MH⁺2], 394.89 (10) [MH⁺3]; t_R(polar-5 min/openlynx) 2.79 min.

trans-[4-(8-Chloroimidazo[1,5-a]pyrazin-3-yl)cyclohexyl]methanol

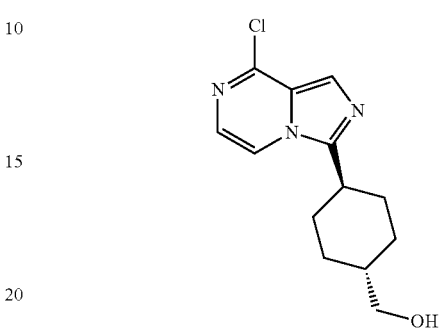

A THF solution (1.00 L) of trans-methyl 4-(8-chloroimidazo[1,5-a]pyrazin-3-yl)cyclohexanecarboxylate (29.70 g, 101.1 mmol) was cooled to −78° C. and was charged with LAH (1M in THF, 25.3 mmol, 25.3 mL) dropwise. After 30 min., the reaction mixture was charged with additional LAH (25.3 mmol) at −78° C. and then, allowed to stir at −78° C. for 1.5 h. The reaction was slowly warmed up to r.t. and stirred for additional 30 min. Ethyl acetate, Na₂SO₄·10H₂O, and silica gel were added to the reaction mixture and concentrated in vacuo to give an orange solid. The crude mixture was purified by a silica gel glass column chromatography (eluted with 2:3 EtOAc/DCM to 100% EtOAc) to obtain the title compound as a slightly yellow-tinted white solid; ¹H NMR (CDCl₃, 400 MHz) δ 1.14-1.30 (m, 2H), 1.61-1.75 (m_c, 1H), 1.84 (ddd, J=13.2, 13.2, 13.2, 3.2 Hz, 2H), 1.98-2.13 (m, 4H), 2.19 (s, br, —OH), 2.94 (tt, J=11.6, 3.2 Hz, 1H), 3.56 (d, J=6.0 Hz, 2H), 7.31 (d, J=5.2 Hz, 1H), 7.64 (dd, J=5.2, 1.2 Hz, 1H), 7.79 (d, J=0.8 Hz, 1H); MS (ES+): m/z 266.21/268.17 (100/89) [MH⁺]. HPLC: t_R=2.38 min (OpenLynx, polar_5 min). MS (ES+): m/z 266.21 (100) [MH⁺], 268.17 (80) [MH⁺2], 289.18 (20) [MH⁺3]; t_R(polar-5 min/openlynx) 2.36 min.

trans-Methyl 4-(8-Chloroimidazo[1,5-a]pyrazin-3-yl)cyclohexanecarboxylate

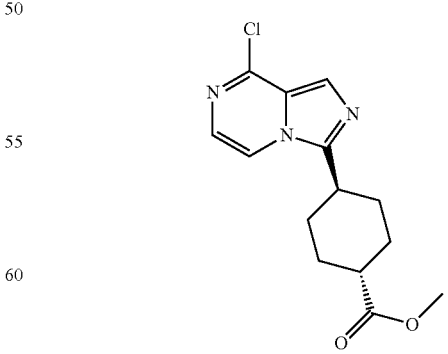

trans-Methyl 4-({[(3-chloropyrazin-2-yl)methyl]amino}carbonyl)-cyclohexanecarboxylate (29.00 g, 93.02 mmol) was dissolved in anhydrous acetonitrile (930 mL) and anhydrous DMF (9 mL) and heated at 55° C. under nitrogen for 3 h. The reaction mixture was concentrated in vacuo, then, the solid residue was taken up in DCM, then, basified to pH 10 with 2M ammonia in isopropanol. The mixture was concentrated in vacuo, re-dissolved in DCM, then, loaded onto TEA-basified silica gel. The crude product was purified by a silica gel column chromatography (eluted with 2:3 EtOAc/DCM) to obtain the title compound as a yellow powder; $^1$H NMR (CDCl$_3$, 400 MHz) δ 1.63 (ddd, J=13.2, 13.2, 13.2, 3.2 Hz, 2H), 1.85 (ddd, J=13.2, 13.2, 13.2, 2.8 Hz, 2H), 2.10 (dd, J=14.4, 3.2 Hz, 2H), 2.19 (dd, J=14.0, 3.2 Hz, 2H), 2.46 (tt, J=12.4, 3.6 Hz, 1H), 2.96 (tt, J=11.6, 3.2 Hz, 1H), 3.70 (s, 3H), 7.33 (dd, J=5.2, 1.2 Hz, 1H), 7.61 (d, J=4.8 Hz, 1H), 7.79 (s, 1H). MS (ES+): m/z 294.17/296.14 (100/86) [MH$^+$]. HPLC: t$_R$=2.85 min (OpenLynx, polar_5 min).

trans-Methyl 4-({[(3-chloropyrazin-2-yl)methyl]amino}carbonyl)cyclohexanecarboxylate

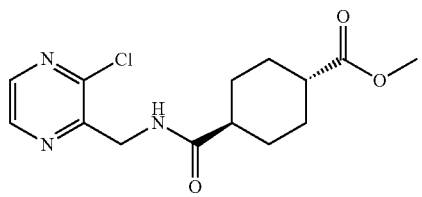 [SMILES: COC(=O)[C@H]1CC[C@H](C(=O)NCc2nccnc2Cl)CC1]

A THF (370 mL) solution of 4-(methoxycarbonyl)cyclohexanecarboxylic acid (15.14 g, 81.30 mmol) and CDI (13.18 g, 81.30 mmol) was placed under a nitrogen atmosphere and stirred at 60° C. for 4 h. The reaction mixture was cooled to r.t., then, (3-chloropyrazin-2-yl)methylamine bis-hydrochloride salt (16.00 g, 73.91 mmol) and DIPEA (31.52 g, 244.00 mmol, 42.5 mL) was added. After stirring at 60° C. for 20 h, the reaction was concentrated in vacuo. The crude reaction mixture was purified by a silica gel glass column chromatography (eluted with 3:2 DCM/EtOAc) to obtain the pure desired product as a slightly yellowish creamy white powder; NMR (CDCl$_3$, 400 MHz) δ 1.43-1.65 (m, 4H), 2.01-2.14 (m, 4H), 2.25 (tt, J=12.0, 3.6 Hz, 1H), 2.34 (tt, J=11.6, 3.2 Hz, 1H), 3.68 (s, 3H), 4.70 (d, J=4.4 Hz, 2H), 6.81 (s, br, —NH), 8.32-8.36 (m, 1H), 8.46 (d, J=2.4 Hz, 1H); MS (ES+): m/z 312.17/314.12 (84/32) [MH$^+$]; HPLC: t$_R$=2.44 min (OpenLynx, polar_5 min).

Example 95

7-(trans-3-Azetidin-1-ylmethylcyclobutyl)-5-(2-phenylquinolin-7-yl)-7H-pyrrolo[2,3-d]pyrimidin-4-ylamine

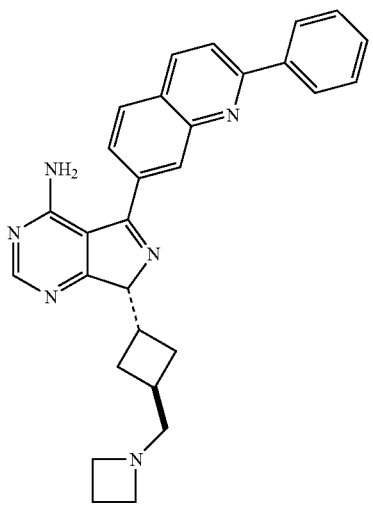

A solution of toluene-4-sulfonic acid trans-3-[4-amino-5-(2-phenylquinolin-7-yl)pyrrolo[2,3-d]pyrimidin-7-yl]-cyclobutylmethyl ester and azetidine (0.30 mL, 254 mg, 4.5 mmol) in THF (4 mL) was heated in a sealed tube to 50° C. overnight. More azetidine (0.30 mL, 254 mg, 4.5 mmol) was added, and heating was continued overnight. THF was evaporated, water and saturated NaHCO$_3$ solution were added, the mixture was extracted with CH$_2$Cl$_2$ (5×20 mL), and the combined CH$_2$Cl$_2$ extracts were washed with water and brine and dried over MgSO$_4$. The crude material was purified by chromatography on silica gel [Jones Flashmaster, 5 g/25 mL cartridge, eluting with CH$_2$Cl$_2$ (1-9)→5% MeOH in CH$_2$Cl$_2$ (10-31)→6.6% MeOH in CH$_2$Cl$_2$ (32-55)→6.6% MeOH in CH$_2$Cl$_2$+NH$_3$ (0.05 M) (56-86)], yielding the title compound as a highly viscous yellow oil. This oil was dissolved in CDCl$_3$ (0.7 mL), tBuOMe was added, and the off-white precipitate was filtered off and dried in vacuo yielding the desired product. $^1$H NMR (CDCl$_3$, 400 MHz) δ 2.15 (quint, J=7.2 Hz, 2H), 2.33-2.54 (m, 4H), 2.57-2.70 (m, 3H), 2.73 (d, J=7.4 Hz, 2H), 3.33 (t, J=7.2 Hz, 4H), 5.26 (brs, 2H), 5.44 (quint, J=8.1 Hz, 1H), 7.37 (s, 1H), 7.46-7.52 (m, 1H), 7.52-7.58 (m, 2H), 7.70 (dd, J=1.7, 8.3 Hz, 1H), 7.91 (d, J=8.5 Hz, 1H), 7.93 (d, J=7.2 Hz, 1H), 8.17-8.22 (m, 2H), 8.26 (d, J=8.6 Hz, 1H), 8.28-8.31 (m, 1H), 8.35 (s, 1H). $^{13}$C NMR (CDCl$_3$, 100.6 MHz, DEPT135) δ 17.73 (−), 27.06 (+), 33.60 (2C, −), 46.72 (+), 55.51 (2C, −), 63.99 (−), 101.05 (C$_{quart}$), 116.12 (C$_{quart}$), 118.85 (+), 120.57 (+), 125.86 (C$_{quart}$), 127.29 (+), 127.45 (2C, +), 128.18 (+), 128.34 (+), 128.76 (2C, +), 129.41 (+), 136.31 (C$_{quart}$), 136.46 (+), 139.30 (C$_{quart}$), 148.38 (C$_{quart}$), 150.73 (C$_{quart}$), 151.83 (+), 157.07 (C$_{quart}$), 157.95 (C$_{quart}$).

MS (ES+): m/z 461.2 (11) [MH+], 338.2 (14) [MH+—C4H5CH2azetidine]. HPLC: t_R=2.0 min (OpenLynx, polar 5 min).

Example 96

Toluene-4-sulfonic acid trans-3-[4-amino-5-(2-phenylquinolin-7-yl)pyrrolo[2,3-d]pyrimidin-7-yl]-cyclobutylmethyl ester

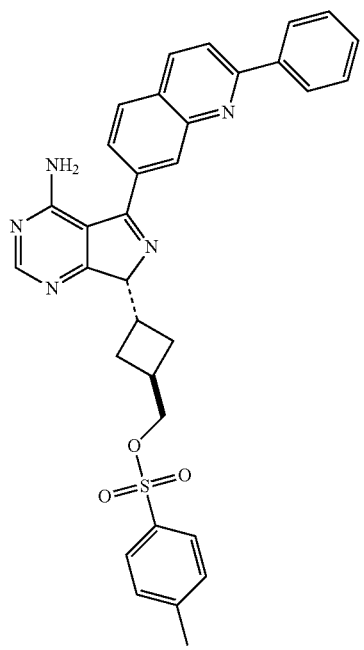

To a suspension of trans-{3-[4-amino-5-(2-phenylquinolin-7-yl)-pyrrolo[2,3-d]pyrimidin-7-yl]-cyclobutyl}-methanol (105.7 mg, 0.251 mmol) in CH2Cl2 (5 mL) and pyridine (1 mL), cooled in a dry ice/acetone bath, was added a solution of Ts2O (92 mg, 0.28 mmol) in CH2Cl2 (2 mL) over 5 min, then the reaction mixture was warmed up to ambient temperature and stirred for 16 h. More Ts2O (70 mg, 0.21 mmol) was added, and stirring at ambient temperature was continued for 4.5 h. The reaction solution was diluted with CH2Cl2 (25 mL), water and saturated NaHCO3 sol. were added, the layers were separated, the aqueous layer was extracted with CH2Cl2 (3×25 mL), and the combined CH2Cl2 extracts were washed with water and brine and dried over MgSO4. Filtration and concentration after adding toluene (10 mL; to remove remaining pyridine as azeotrop) gave the desired product. No purification before the next step. $^1$H NMR (CDCl3, 400 MHz) δ 2.43-2.51 (m, 2H), 2.47 (s, 2H), 2.67-2.86 (m, 3H), 4.22 (d, J=6.6 Hz, 2H), 5.19 (brs, 2H), 5.36 (quint, J=8.0 Hz, 1H), 7.29 (s, 1H), 7.37-7.41 (m, 2H), 7.46-7.51 (m, 1H), 7.52-7.58 (m, 2H), 7.68 (dd, J=1.8, 8.4 Hz, 1H), 7.83-7.87 (m, 2H), 7.92 (d, J=8.6 Hz, 1H), 7.93 (d, J=8.4 Hz, 1H), 8.17-8.22 (m, 2H), 8.25-8.29 (m, 2H), 8.33 (s, 1H). MS (ES+): m/z 576.1 (54) [MH+], 338.2 (10) [MH+-cyclobutene-CH2OTs]. HPLC: t_R=2.8 min (OpenLynx, nonpolar_5 min).

General procedure for the Suzuki coupling with 2-Phenyl-7-(4,4,5,5-tetramethyl-[1,3,2]dioxaborolan-2-yl)-quinoline Nitrogen is bubbled through a mixture of a 5-iodo-7H-pyrrolo[2,3-d]pyrimidin-4-ylamine (0.10 mmol), 2-phenyl-7-(4,4,5,5-tetramethyl-[1,3,2]dioxaborolan-2-yl)-quinoline (34 mg, 0.10 mmol; 1 equiv.), Na2CO3 (26 mg, 0.25 mmol; 2.5 equiv.), and Pd(PPh3)4 (7 mg, 0.006 mmol; 6 mol %) in DMF (2.5 mL)/water (0.5 mL) for 2-5 min at ambient temperature, then the mixture is heated to 80° C. overnight under nitrogen, after which time the reaction is typically complete. The solvents are evaporated, and water and CH2Cl2 are added. If necessary, the mixture is filtered through diatomaceous earth to remove a precipitate of palladium black. The layers are separated, the aqueous layer is extracted with CH2Cl2 (2×), and the combined organic extracts are washed with brine, dried over MgSO4, filtered and concentrated. If deemed necessary, a preliminary purification on an SCX column effects removal of non-basic impurities. The crude material is purified by chromatography on silica gel or HPLC.

Example 97 trans-{3-[4-Amino-5-(2-phenylquinolin-7-yl)-pyrrolo[2,3-d]pyrimidin-7-yl]-cyclobutyl}methanol

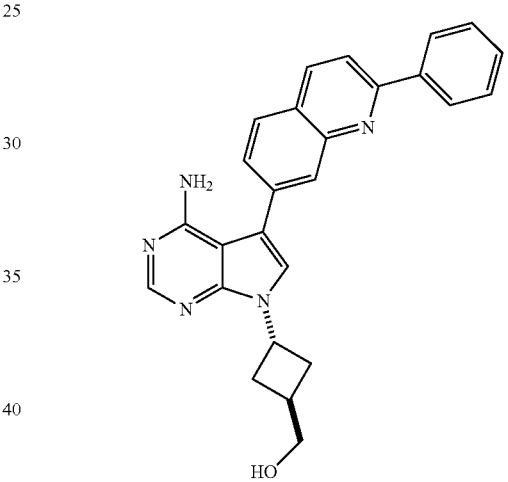

Following the general procedure for the Suzuki coupling, trans-[3-(4-amino-5-iodopyrrolo[2,3-d]pyrimidin-7-A-cyclobutyl]-methanol (139.2 mg, 0.4045 mmol) was reacted with 2-phenyl-7-(4,4,5,5-tetramethyl-[1,3,2]dioxaborolan-2-yl)-quinoline (141 mg, 0.426 mmol), Na2CO3 (107 mg, 1.01 mmol) and Pd(PPh3)4 (30 mg, 0.026 mmol) in DMF (10 mL)/water (2 mL). The crude material was purified by column chromatography on silica gel [Jones Flashmaster, 10 g/70 mL cartridge, eluting with CH2Cl2 (1-7)→2% MeOH in CH2Cl2 (8-22)→5% MeOH in CH2Cl2 (23-41)→7% MeOH in CH2Cl2 (42-51)], yielding the title compound. $^1$H NMR (CDCl3, 400 MHz) δ 2.42-2.60 (m, 3H), 2.60-2.73 (m, 3H), 3.88 (d, J=6.4 Hz, 2H), 5.19 (brs, 214), 5.44-5.53 (m_c, 1H), 7.39 (s, 1H), 7.46-7.52 (m, 1H), 7.52-7.58 (m, 2H), 7.71 (dd, J=1.7, 8.3 Hz, 1H), 7.92 (d, J=8.5 Hz, 1H), 7.94 (d, J=7.7 Hz, 1H), 8.17-8.22 (m, 2H), 8.27 (d, J=8.5 Hz, 1H), 8.29-8.32 (m, 1H), 8.36 (s, 1H). $^{13}$C NMR (CDCl3, 100.6 MHz, DEPT135) δ 30.62 (+), 32.16 (2C, −), 46.70 (+), 65.12 (−), 101.04 (C_{quart}), 116.13 (C_{quart}), 118.88 (+), 120.64 (+), 125.82 (C_{quart}), 127.27 (+), 127.45 (2C, +), 128.17 (+), 128.21 (+), 128.71 (2C, +), 129.40 (+), 136.23 (C_{quart}), 136.49 (C_{quart}), 139.23 (C_{quart}), 148.28 (C_{quart}), 150.47 (C_{quart}), 151.57 (+), 157.09 (C_{quart}), 157.97 (C_{quart}). MS (ES+): m/z 422.1 (51)

[MH+], 338.2 (39) [MH+-cyclobutene-CH2OH]. HPLC: $t_R$=2.4 min (OpenLynx, polar_5 min).

trans-[3-(4-Amino-5-iodopyrrolo[2,3-d]pyrimidin-7-yl)cyclobutyl]methanol

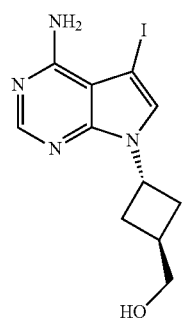 [SMILES: Nc1ncnc2c1c(I)cn2[C@H]1C[C@H](CO)C1]

Gaseous ammonia (from a lecture bottle) was condensed into a suspension of trans-[3-(4-chloro-5-iodopyrrolo[2,3-d]pyrimidin-7-yl)-cyclobutyl]-methanol (172.6 mg, 0.475 mmol) in dioxane (3 mL) and iPrOH (3 mL) in a sealable glass tube, cooled by dry ice/acetone, until the volume increased by mL, then the tube was sealed and heated to 90° C. overnight. The solvents were evaporated, water was added to the residue, and the pale yellow solid was filtered off and dried in vacuo to give the title compound as a pale yellow solid. The compound was used in the next step without further purification. $^1$H NMR (CDCl$_3$, 400 MHz) δ 2.41-2.52 (m, 2H), 2.52-2.64 (m, 3H), 3.83 (d, 0.1=6.3 Hz, 2H), 5.30-5.40 (m$_c$, 1H), 5.60 (brs, 2H), 7.29 (s, 1H), 8.26 (s, 1H). MS (ES+): m/z 345.1 (100) [MH+]. HPLC: $t_R$=1.9 min (OpenLynx, polar_5 min).

trans-[3-(4-Chloro-5-iodopyrrolo[2,3-d]pyrimidin-7-yl)-cyclobutyl]-methanol

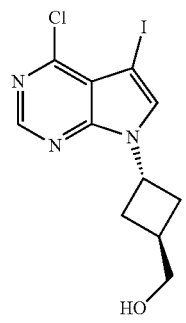 [SMILES: OC[C@H]1C[C@H](n2cc(I)c3c(Cl)ncnc32)C1]

To a solution of trans-3-(4-chloro-5-iodopyrrolo[2,3-d]pyrimidin-7-yl)-cyclobutanecarboxylic acid methyl ester (trans/cis=5:1) (116.5 mg, 0.297 mmol) in CH$_2$Cl$_2$ (5 mL), cooled by dry ice/acetone, was added DIBAL (1M in toluene, 0.65 mL, 0.65 mmol). After 40 min, the dry ice/acetone bath was replaced with and ice/water bath. The reaction was quenched 2 h later by adding potassium sodium tartrate solution, the mixture was extracted with CH$_2$Cl$_2$ (3×20 mL), the combined extracts were washed with NaHCO$_3$ solution and brine, dried over MgSO$_4$, filtered, and concentrated to give the target compound as 5:1 trans/cis mixture. This material was chromatographed on silica gel [Jones Flashmaster, 5 g/25 mL cartridge, eluting with CH$_2$Cl$_2$ (1-8)→CH$_2$Cl$_2$:EtOAc 9:1 (9-19)→CH$_2$Cl$_2$:EtOAc 5:1 (20-47)→CH$_2$Cl$_2$:EtOAc 3:1 (48-60)] to give the title compound with trans/cis=25:1. A forerunning fraction enriched with the cis isomer was also isolated. $^1$H NMR (CDCl$_3$, 400 MHz) δ 2.42-2.57 (m, 2H), 2.58-2.72 (m, 3H), 3.85 (brs, 2H), 5.36-5.48 (m$_c$, 1H), 7.61 (s, 1H), 8.60 (s, 1H). MS (ES+): m/z 363.9/365.9 (100/36) [MH+]. HPLC: $t_R$=3.0 min (OpenLynx, polar_5 min).

trans-3-(4-Chloro-5-iodopyrrolo[2,3-d]pyrimidin-7-yl)-cyclobutanecarboxylic acid methyl ester

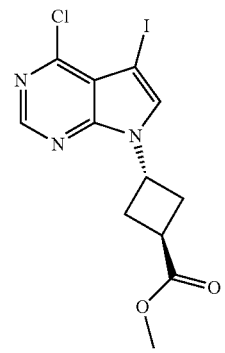 [SMILES: COC(=O)[C@H]1C[C@H](n2cc(I)c3c(Cl)ncnc32)C1]

To a mixture of 4-chloro-5-iodo-7H-pyrrolo[2,3-d]pyrimidine (prepared according to: L. B. Townsend et al., *J. Med. Chem.* 1990, 33 (7), 1984-92) (280 mg, 1.00 mmol), cis-3-hydroxycyclobutanecarboxylic acid methyl ester (trans/cis=1:5) (180 mg, 1.38 mmol), and PS-PPh$_3$ (loading 2.02 mmol/g; 951 mg, 2.02 mmol) in dry THF (10 mL), cooled by ice/water, was added DIAD (295 μL, 303 mg, 1.50 mmol), then the cooling bath was removed, and the mixture was vortexed (220 rpm) for 2 d. The resin was filtered off and washed thoroughly with THF (7480 mL), the filtrate and washings were combined, concentrated, and chromatographed on silica gel [Jones Flashmaster, 20 g/70 mL cartridge, eluting with CH$_2$Cl$_2$ (1-14)→5% EtOAc in CH$_2$Cl$_2$ (15-30)], fractions containing product were combined and chromatographed again under the same conditions. This material was suspended in iPrOH (≈1.5 mL), heated to 75° C. for 10 min and cooled to −20° C. for 2 h. The solid was filtered off, washed with cold (−20° C.) iPrOH, and dried in vacuo, giving the title compound as white solid, trans/cis=5:1. $^1$H NMR (CDCl$_3$, 400 MHz) δ 2.83-2.97 (m, 4H), 3.23-3.32 (m, 1H), 3.79 (s, 3H), 5.50 (quint, J=8.7 Hz, 1H), 7.51 (s, 1H), 8.61 (s, 1H). MS (ES+): m/z 391.9/393.9 (100/35) [MH⁺]. HPLC: t_R=3.5 min (OpenLynx, polar_5 min).

Example 98 cis-7-(3-Dimethylaminomethylcyclobutyl)-5-(2-phenylquinolin-7-yl)-7H-pyrrolo[2,3-d]pyrimidin-4-ylamine

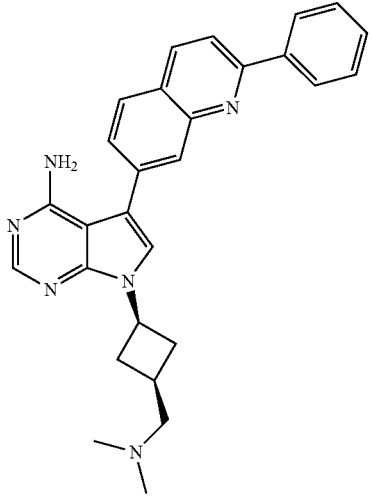 [SMILES: CN(C)C[C@H]1C[C@@H](n2cc(-c3ccc4ccc(-c5ccccc5)nc4c3)c3c(N)ncnc32)C1]

Nitrogen was bubbled into a mixture of 7-(3-dimethylaminomethylcyclobutyl)-5-iodo-7H-pyrrolo[2,3-d]pyrimidin-4-ylamine (891.5 mg, 2.401 mmol), 2-phenyl-7-(4,4,5,5-tetramethyl[1,3,2]dioxaborolan-2-yl)-quinoline (795 mg, 2.40 mmol), Na$_2$CO$_3$ (634 mg, 5.98 mmol), and Pd(PPh$_3$)$_4$ (171 mg, 0.148 mmol; 6 mol %) in DMF (40 mL)/water (8 mL) for 5 min at ambient temperature, then the mixture was heated to 80° C. (bath temp.) for 4.5 h. The solvents were evaporated, water was added, the mixture was extracted with CH$_2$Cl$_2$ (4×30 mL), and the combined extracts were washed with brine and dried over MgSO$_4$. The crude material (yellow oil) was chromatographed on silica gel [Jones Flashmaster, 50 g/150 mL cartridge, eluting with CH$_2$Cl$_2$ (1-28)→5% MeOH in CH$_2$Cl$_2$ (29-56)→10% MeOH in CH$_2$Cl$_2$ (57-80)→10% MeOH in CH$_2$Cl$_2$ with 0.07M NH$_3$ (81-130)]. Mixed fractions were chromatographed again [5 g/25 mL cartridge, eluting with CH$_2$Cl$_2$ (1-5)→5% MeOH in CH$_2$Cl$_2$ (6-24) 10% MeOH in CH$_2$Cl$_2$ with 0.07M NH$_3$ (25-40)]. One obtained the target compound as beige solid. $^1$H NMR (CDCl$_3$, 400 MHz): δ=2.10-2.23 (m$_c$, 2H), 2.27 (s, 6H), 2.35-2.46 (m$_c$, 1H), 2.49 (d, J=6.8 Hz, 2H), 2.77-2.86 (m$_c$, 2H), 5.17 (brs, 2H), 5.20-5.30 (m$_c$, 1H), 7.31 (s, 1H), 7.46-7.52 (m, 1H), 7.52-7.58 (m, 2H), 7.70 (dd, J=1.6, 8.4 Hz, 1H), 7.92 (d, J=8.7 Hz, 1H), 7.94 (d, J=8.1 Hz, 1H), 8.17-8.22 (m, 2H), 8.27 (d, J=8.5 Hz, 1H), 8.30 (brs, 1H), 8.36 (s, 1H). $^{13}$C NMR (CDCl$_3$, 100.6 MHz, DEPT135): δ=27.13 (+), 36.50 (2C, -), 45.26 (+), 45.73 (2C, +), 66.10 (-), 101.20 (C$_{quart}$), 116.07 (C$_{quart}$), 119.00 (+), 120.74 (+), 125.98 (C$_{quart}$), 127.38 (+), 127.55 (2C, +), 128.28 (+), 128.47 (+), 128.86 (2C, +), 129.52 (+), 136.45 (C$_{quart}$), 136.55 (+), 139.41 (C$_{quart}$), 148.51 (C$_{quart}$), 150.92 (C$_{quart}$), 152.04 (+), 156.99 (C$_{quart}$), 158.13 (C$_{quart}$). MS (ES+): m/z 449.2 (23) [MH⁺], 404.1 (4) [MH⁺—HN(CH$_3$)$_2$], 338.2 (4) [MH⁺—C$_4$H$_5$CH$_2$N(CH$_3$)$_2$]. HPLC: t_R=2.0 min (OpenLynx, polar_5 min).

7-(3-Dimethylaminomethylcyclobutyl)-5-iodo-7H-pyrrolo[2,3-d]pyrimidin-4-ylamine

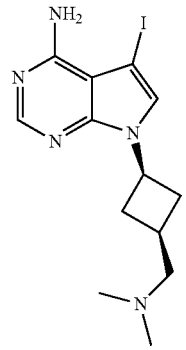 [SMILES: CN(C)C[C@H]1C[C@@H](n2cc(I)c3c(N)ncnc32)C1]

A mixture of cis-toluene-4-sulfonic acid 3-(4-amino-5-iodopyrrolo[2,3-d]pyrimidin-7-yl)-cyclobutylmethyl ester (1.50 g, 3.01 mmol) and a 2M solution of dimethylamine in THF (30 mL, 60 mmol) was heated to 55° C. for 23 h in a glass pressure tube. The solvent was evaporated, water was added, the mixture was extracted with CH$_2$Cl$_2$ (4×40 mL), and the extracts were washed with brine and dried over MgSO$_4$. The crude material was chromatographed on silica gel [Jones Flashmaster, 10 g/70 mL cartridge, eluting with CH$_2$Cl$_2$ (1-8)→5% MeOH in CH$_2$Cl$_2$ (9-24)→10% MeOH in CH$_2$Cl$_2$ (25-35)→10% MeOH in CH$_2$Cl$_2$ with 0.07M NH$_3$ (36-48)], fractions containing product were combined and dried in vacuo. One obtained the title compound as brown solid. $^1$H NMR (CDCl$_3$, 400 MHz): δ=2.01-2.11 (m$_c$, 2H), 2.26 (s, 6H), 2.30-2.43 (m$_c$, 1H), 2.46 (d, J=6.8 Hz, 2H), 2.69-2.77 (m$_c$, 2H), 5.05-5.15 (m$_c$, 1H), 5.59 (brs, 2H), 7.20 (s, 1H), 8.26 (s, 1H). MS (ES+): m/z 372.1 (20) [MH⁺]. HPLC: t_R=1.3 min (OpenLynx, polar_5 min).

cis-Toluene-4-sulfonic acid 3-(4-amino-5-iodopyrrolo[2,3-d]pyrimidin-7-yl)-cyclobutylmethyl ester

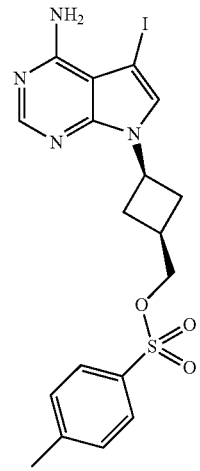

Into the suspension of cis-[3-(4-amino-5-iodopyrrolo[2,3-d]pyrimidin-7-yl)-cyclobutyl]-methanol (1322 mg, 3.842 mmol) in CH$_2$Cl$_2$ (55 mL) was added dropwise pyridine (6749 μL, 21.7 eq.) at −78° C. under N$_2$ over 10 min followed by the addition of a solution of Ts$_2$O (1568 mg, 1.25 eq.) in CH$_2$Cl$_2$ (35 mL) over 20 min. After stirring at rt for 3 h, the reaction mixture was treated with saturated NaHCO$_3$, and the organic phase was separated. The aqueous phase was extracted with CH$_2$Cl$_2$ (50 mL). The combined organic phases were washed with H$_2$O (2×100 mL) and brine (100 mL), and dried over MgSO$_4$. After removing the solvent, a brown paste (2050 mg) was obtained. The brown paste was purified by chromatography on silica gel (50 g pre-packed column) and eluted with CH$_2$Cl$_2$ (600 mL), 2% MeOH/CH$_2$Cl$_2$ (600 mL), and 4% MeOH/CH$_2$Cl$_2$ (600 mL) to obtain the title compound as a light-brown foam. $^1$H NMR (CDCl$_3$, 400 MHz): δ=2.20-2.28 (m, 2 H), 2.47 (s, 3H), 2.47-2.52 (m, 1H), 2.57-2.64 (m, 2H), 4.12-4.13 (d, 2H, J=5.2 Hz), 5.07-5.11 (m, 1H), 5.63 (brs, 2H), 7.14 (s, 1H), 7.37-7.39 (d, 2H, J=7.6 Hz), 7.81-7.84 (m, 2H), 8.22 (s, 1H). MS (ES+): m/z 498.9 (100) [MH$^+$]. HPLC: t$_R$=3.0 min (OpenLynx, polar_5 min).

cis-[3-(4-Amino-5-iodopyrrolo[2,3-d]pyrimidin-7-yl)-cyclobutyl]-methanol

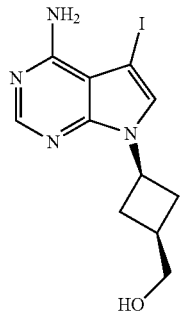 [SMILES: Nc1ncnc2c1c(I)cn2[C@H]1C[C@@H](CO)C1]

Gaseous ammonia (from a lecture bottle) was bubbled into a suspension of cis-[3-(4-chloro-5-iodopyrrolo[2,3-d]pyrimidin-7-yl)-cyclobutyl]-methanol (406.8 mg, 1.12 mmol) in dioxane (10 mL) and iPrOH (10 mL) in a Parr bomb, cooled by dry ice/acetone, for 5 min, then the vessel was sealed and heated to 90° C. overnight. LC/MS after 17 h indicated incomplete conversion. More ammonia was bubbled into the mixture, and heating to 90° C. was continued. After 1 d, conversion was complete. The solvents were evaporated, water was added to the residue, and the pale yellow solid was filtered off and dried in vacuo to give the title compound as a pale yellow solid. The compound was used in the next step without further purification. The aqueous filtrate was extracted with CH$_2$Cl$_2$ (3×20 mL), the combined extracts were dried over MgSO$_4$, filtered and concentrated to give a yellow oil that slowly solidified. Purification by HPLC gave analytically pure material. $^1$H NMR (CDCl$_3$, 400 MHz): δ=2.40-2.57 (m, 4H), 2.57-2.66 (m, 2H), 3.73 (d, J=4.4 Hz, 2H), 5.03 (quint, J=8.4 Hz, 1H), 5.62 (brs, 2H), 7.21 (s, 1H), 8.26 (s, 1H). $^{13}$C NMR (DMSO-d$_6$, 100.6 MHz, DEPT135): b=29.96 (+), 32.70 (2C, −), 44.42 (+), 50.25 (C$_{quart}$), 64.16 (−), 102.98 (C$_{quart}$), 126.94 (+), 149.41 (C$_{quart}$), 151.72 (+), 157.13 (C$_{quart}$). MS (ES+): m/z 345.0 (100) [MH$^+$]. HPLC: t$_R$=1.7 min (OpenLynx, polar_5 min). C$_{11}$H$_{13}$IN$_4$O·⅔H$_2$O: C: calc. 37.10, found 36.92; H: calc. 4.06, found 3.88; N: calc. 15.73, found 16.07.

cis-[3-(4-Chloro-5-iodopyrrolo[2,3-d]pyrimidin-7-yl)-cyclobutyl]-methanol

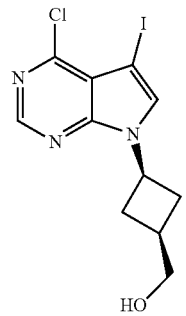 [SMILES: OC[C@H]1C[C@@H](n2cc(I)c3c(Cl)ncnc32)C1]

To a solution of cis-3-(4-chloro-5-iodopyrrolo[2,3-d]pyrimidin-7-yl)-cyclobutanecarboxylic acid methyl ester (2.15 g, 5.49 mmol) in CH$_2$Cl$_2$ (85 mL), cooled by dry ice/acetone, was added DIBAL (1M in toluene, 12.4 mL, 12.4 mmol) over 5 min. Note that the ester started precipitating at the low temperature; but upon adding the DIBAL solution, a clear, pale yellow solution formed. After 50 min, the dry ice/acetone bath was replaced with and ice/water bath. The reaction was quenched 2.5 h later by adding Na$_2$SO$_4$·10H$_2$O. A very slow gas evolution occurred, even with vigorous stirring or sonication. MeOH (2 mL) was added at ambient temperature, and a precipitate slowly formed, which was filtered off and washed with 150 mL of 10% MeOH in CH$_2$Cl$_2$. The combined filtrate and washings were concentrated, the resulting solid was suspended in 80 mL of 10% MeOH/CH$_2$Cl$_2$, heated briefly to 45° C., and cooled to −20° C. overnight. The white solid was filtered off and dried in vacuo, yielding the title compound. The aluminum-containing precipitate was suspended in potassium sodium tartrate solution and extracted with CH$_2$Cl$_2$ (3×100 mL), the combined extracts were dried over MgSO$_4$, filtered, and combined with the mother liquor of the white solid. This material was adsorbed onto Hydromatrix and chromatographed on silica gel [Jones Flashmaster, 10 g/70 mL cartridge, eluting with CH$_2$Cl$_2$ (1-7)→CH$_2$Cl$_2$: EtOAc 5:1 (8-32)→CH$_2$Cl$_2$:EtOAc 4:1 (33-43)] to give a second crop of the title compound. $^1$H NMR (CDCl$_3$, 400 MHz): δ=1.79 (brs, 1H), 2.40-2.53 (m, 3H), 2.59-2.71 (m, 2H), 3.74 (brs, 2H), 5.13-5.23 (m$_c$, 1H), 7.60 (s, 1H), 8.60 (s, 1H). MS (ES+): m/z 364.0/366.0 (100/40) [MH⁺]. HPLC: $t_R$=2.9 min (OpenLynx, polar_5 min).

cis-3-(4-Chloro-5-iodopyrrolo[2,3-d]pyrimidin-7-yl)-cyclobutanecarboxylic acid methyl ester

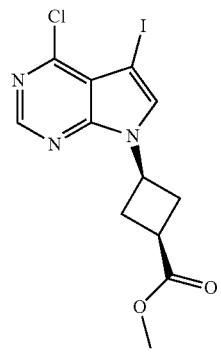 [SMILES: COC(=O)[C@H]1C[C@@H](n2cc(I)c3c(Cl)ncnc32)C1]

To a mixture of 4-chloro-5-iodo-7H-pyrrolo[2,3-d]pyrimidine (prepared according to: L. B. Townsend et al., *J. Med. Chem.* 1990, 33 (7), 1984-92) (2.10 g, 7.51 mmol), trans-3-hydroxycyclobutanecarboxylic acid methyl ester (trans/cis=5:1) (1.11 g, 8.53 mmol), and PS-PPh₃ (loading 2.21 mmol/g; 6.80 g, 15.0 mmol) in dry THF (80 mL), cooled by ice/water, was added DIAD (2.20 mL, 2.26 g, 11.2 mmol), then the cooling bath was removed, and the mixture was vortexed (150 rpm) overnight. The resin was filtered off and washed thoroughly with THF mL), the filtrate and washings were combined, concentrated, and chromatographed on silica gel [Jones Flashmaster, 50 g/150 mL cartridge, eluting with $CH_2Cl_2$ (1-16)→5% EtOAc in $CH_2Cl_2$ (17-40)]. Fractions 3-32 were combined, concentrated, and suspended in iPrOH (10 mL). The suspension was heated to 85° C. for 20 min and cooled to −20° C. for 2 h, the solid was filtered off, washed with cold (−20° C.) iPrOH, and dried in vacuo. One obtained the title compound as white solid. Analytically pure material with cis/trans=50:1 had a melting point of 168-169° C. ¹H NMR (CDCl₃, 400 MHz): δ=2.66-2.78 (m, 2H), 2.81-2.93 (m, 2H), 3.06 (quint, J=8.7 Hz, 1H), 3.76 (s, 3H), 5.32 (quint, J=8.7 Hz, 1H), 7.68 (s, 1H), 8.60 (s, 1H). ¹³C NMR (CDCl₃, 100.6 MHz, DEPT135): S=30.93 (+), 34.09 (2C, −), 44.65 (+), 51.58 ($C_{quart}$), 52.19 (+), 117.07 ($C_{quart}$), 131.87 (+), 150.48 ($C_{quart}$), 150.72 (+), 152.69 ($C_{quart}$), 174.31 ($C_{quart}$). MS (ES+): m/z 391.9/393.9 (100/38) [MH⁺]. HPLC: $t_R$=3.5 min (OpenLynx, polar_5 min). $C_{12}H_{11}ClIN_3O_2$ (391.60): C: calc. 36.81, found 36.88/36.78; H: calc. 2.83, found 2.81/2.76; N: calc. 10.73, found 10.59/10.50.

trans-3-Hydroxycyclobutanecarboxylic acid methyl ester

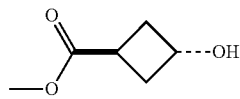

To a solution of trans-3-acetoxycyclobutanecarboxylic acid methyl ester (trans/cis=5:1) (4.70 g, 27.3 mmol) in dry methanol (45 mL) was added sodium methoxide (25 wt % solution in MeOH, 0.62 mL, 2.7 mmol), and the solution was stirred at ambient temperature. More NaOMe solution (0.31 mL, 2.4 mmol) was added after 1 h and 2 h, and stirring was continued overnight. Most of the methanol was evaporated, water was added (≈100 mL), and the mixture was extracted with $CH_2Cl_2$ (6×60 mL). The combined organic layers were washed with NaHCO₃ solution and brine, dried over MgSO₄, filtered and concentrated (vacuum down to mbar) to give the title compound as brown oil, trans/cis=5:1 based on ¹H NMR. The material thus obtained was used without further purification. ¹H NMR (CDCl₃, 400 MHz) δ 2.17-2.27 (m, 2H), 2.54-2.64 (m, 2H), 3.00-3.09 ($m_c$, 1H), 3.70 (s, 3H), 4.53-4.62 ($m_c$, 1H).

trans-3-Acetoxycyclobutanecarboxylic acid methyl ester

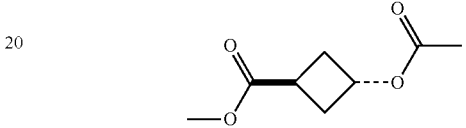

A mixture of potassium acetate (16.9 g, 172 mmol) and cis-3-(toluene-4-sulfonyloxy)-cyclobutanecarboxylic acid methyl ester (9.8 g, 34 mmol; trans/cis=1:5) in dry DMF (50 mL) was heated to 120° C. for 21 h. DMF was partially distilled off (≈30 mL), water was added, and the mixture was extracted with EtOAc (6×50 mL). The combined organic layers were washed with water (2×), brine, dried over MgSO₄, filtered and concentrated to give the title compound as brown oil, trans/cis=5:1 based on ¹H NMR. The material thus obtained was used without further purification.

trans-3-Acetoxycyclobutanecarboxylic acid methyl ester: ¹H NMR (CDCl₃, 400 MHz) δ 2.044 (s, 3H), 2.31-2.41 (m, 2H), 2.62-2.71 (m, 2H), 3.09-3.17 ($m_c$, 1H), 3.71 (s, 3H), 5.15-5.23 ($m_c$, 1H).

cis-3-Acetoxycyclobutanecarboxylic acid methyl ester: ¹H NMR (CDCl₃, 400 MHz) δ 2.035 (s, 3H), 2.31-2.41 (m, 2H), 2.62-2.71 (m, 2H), 2.71-2.80 ($m_c$, 1H), 3.70 (s, 3H), 4.88-4.96 ($m_c$, 1H).

cis-3-(Toluene-4-sulfonyloxy)-cyclobutanecarboxylic acid methyl ester

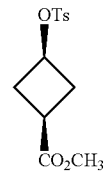 [SMILES: COC(=O)[C@H]1C[C@@H](OS(=O)(=O)c2ccc(C)cc2)C1]

An ice bath cooled methylene chloride (80.0 mL) solution of cis-3-hydroxy-cyclobutanecarboxylic acid methyl ester (4.00 g, 31.0 mmol; predominantly cis) was charged with pyridine (3.00 mL, 37.0 mmol) and Ts₂O (11.1 g, 34.0 mmol). After 45 min, TLC analysis (EtOAc) revealed no starting material (KMnO₄ stain for alcohol sm). The reaction mixture was concentrated in vacuo, resuspended in ether (50.0 mL) and washed with 0.5 N HCl (2×25 mL), saturated bicarbonate (2×25 mL), water (2×25 mL), brine (1×25 mL), and then dried over Na₂SO₄, filtered and concentrated to yield the title compound as colorless oil, predominantly cis. ¹H NMR (400

MHz, CDCl₃): δ=2.44-2.55 (m, 7H), 2.56-2.65 (m, 1H), 3.65 (s, 3H), 4.59-4.77 (m, 1H), 7.33 (d, 2H, J=8.0 Hz), 7.77 (d, 2H, J=8.0 Hz).

cis-3-Hydroxycyclobutanecarboxylic acid methyl ester

A methanolic solution (210 mL) of 3-oxocyclobutanecarboxylic acid, cooled in an ice bath, was charged portionwise with sodium borohydride (4.66 g, 123 mmol). After stirring for 2 h, the reaction was deemed complete by TLC analysis (10% MeOH/CH₂Cl₂, KMnO₄ stain). The reaction was charged with 2N HCl in ether until the pH of the solution became acidic (pH=2). The reaction mixture was diluted with 400 mL of methanol and heated to 75° C. for 16 h. The reaction was concentrated in vacuo, resuspended in CH₂Cl₂ (100 mL), washed with water (2×50 mL), saturated bicarbonate (1×50 mL), water (1×50 mL), and brine (1×50 mL), then dried over Na₂SO₄, filtered and concentrated to afford the desired product as an oil (predominantly cis). IR (film) 3406, 2989, 2949, 1727, 1720 cm⁻¹. ¹H NMR (400 MHz, CDCl₃) δ 1.97 (d, 1H, J=7.2 Hz), 2.13-2.21 (m, 2H), 2.56-2.64 (m, 3H), 3.67-3.70 (m, 3H), 4.17-4.20 (m, 1H).

3-Oxo-cyclobutanecarboxylic acid

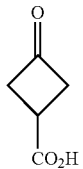

3,3-Dimethoxy-cyclobutane-1,1-dicarboxylic acid diisopropyl ester (0.1 mmol, 30 g) was refluxed in 20% HCl aqueous solution for 60 h. Part of the HCl aqueous solution was evaporated under high vacuum and light brown color oil remained. The oil was dissolved by EtOAc and washed by brine. The organic layer was dried by NaSO₄, filtered, and evaporated under vacuum. The title compound was obtained as an off-white solid after recrystallization from chloroform.

3,3-Dimethoxy-cyclobutane-1,1-dicarboxylic acid diisopropyl ester

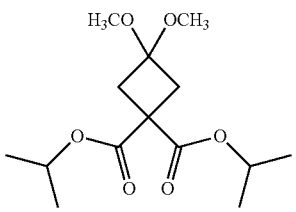 [SMILES: COC1(OC)CC(C(=O)OC(C)C)(C(=O)OC(C)C)C1]

A 1 L, two-necked flask containing 95% NaH (5.04 g, 210 mmol) was charged with 75 mL of DMF, evacuated, placed under a nitrogen atm, and cooled in an ice bath. Diisopropyl malonate (34.0 mL, 191 mmol) was carefully added dropwise via addition funnel under a positive flow of nitrogen (reaction vented through a needle placed in a septum on the second neck of the flask). After the addition of the malonate, the solution became very thick and yellow in color. After stirring for 1 h, the reaction was charged with 1,3-dibromo-2,2-dimethoxypropane (25.0 g, 95.4 mmol) in one portion and the reaction was heated to 140° C. for 24 h, upon which time the reaction became thick and orange in color. Saturated ammonium chloride (300 mL) was added and the mixture was extracted with hexanes (3×, 500 mL). The organic layers were combined, washed with water (2×, 500 mL), saturated bicarbonate (2×, 500 mL), water (2×, 500 mL), and brine (1×, 500 mL), then dried over Na₂SO₄, filtered and concentrated to an oil. Short path distillation (4-5 torr, oil bath temperature at 60° C. to 143° C.) afforded the title compound as a clear oil; ¹H NMR (400 MHz, CDCl₃) δ 1.24 (d, 12H, J=6.0 Hz), 2.70 (s, 4H), 3.15 (s, 6H), 5.06 (m, 2H).

Example 99

7-Cyclopropylmethyl-5-(2-phenylquinolin-7-yl)-7H-pyrrolo[2,3-d]pyrimidin-4-ylamine

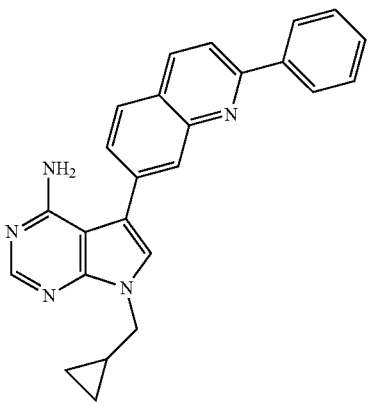 [SMILES: Nc1ncnc2c1c(-c1ccc3ccc(-c4ccccc4)nc3c1)cn2CC1CC1]

Following the general procedure for the Suzuki coupling, 7-cyclopropylmethyl-5-iodo-7H-pyrrolo[2,3-d]pyrimidin-4-ylamine (94.0 mg, 0.299 mmol) was reacted with 2-phenyl-7-(4,4,5,5-tetramethyl-[1,3,2]dioxaborolan-2-yl)-quinoline (104 mg, 0.314 mmol), Na₂CO₃ (79.0 mg, 0.745 mmol) and Pd(PPh₃)₄ (21 mg, 0.018 mmol) in DMF (7.5 mL)/water (1.5 mL). The crude material was purified by an SCX column (2 g/6 mL barrel) followed by column chromatography on silica gel [Jones Flashmaster, 10 g/70 mL cartridge, eluting with CH₂Cl₂ (1-14)→1% MeOH in CH₂Cl₂ (15-34)→2% MeOH in CH₂Cl₂ (35-56)], yielding the title compound as an off-white yellow solid. ¹H NMR (CDCl₃, 400 MHz): δ=0.44-0.50 (m, 2H), 0.63-0.71 (m, 2H), 1.29-1.39 (m, 1H), 4.15 (d, J=7.2 Hz, 2H), 5.20 (brs, 2H), 7.29 (s, 1H), 7.46-7.52 (m, 1H), 7.52-7.58 (m, 2H), 7.71 (dd, J=1.8, 8.2 Hz, 1H), 7.91 (d, J=8.8 Hz, 1H), 7.93 (d, J=8.4 Hz, 1H), 8.17-8.22 (m, 2H), 8.27 (d, J=8.8 Hz, 1H), 8.29-8.32 (m, 1H), 8.36 (s, 1H). ¹³C NMR (CDCl₃, 100.6 MHz, DEPT135): S=4.05 (2C, −), 11.31 (+), 48.99 (−), 100.98 ($C_{quart}$), 115.67 ($C_{quart}$), 118.96 (+), 123.30 (+), 125.94 ($C_{quart}$), 127.46 (+), 127.55 (2C, +), 128.23 (+), 128.47 (+), 128.87 (2C, +), 129.50 (+), 136.50 ($C_{quart}$), 136.55 (+), 139.45 ($C_{quart}$), 148.52 ($C_{quart}$), 150.97 ($C_{quart}$), 152.04 (+), 156.99 ($C_{quart}$), 158.12 ($C_{quart}$). MS (ES+): m/z 392.1 (100) [MH⁺], 338.2 (22) [MH⁺—C₄H₆]. HPLC: $t_R$=2.9 min (OpenLynx, polar_5 min).

7-Cyclopropylmethyl-5-iodo-7H-pyrrolo[2,3-d]pyrimidin-4-ylamine

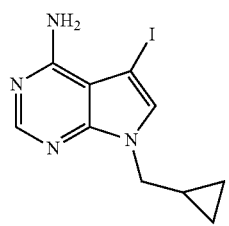 [SMILES: Nc1ncnc2c1c(I)cn2CC1CC1]

Gaseous ammonia (from a lecture bottle) was condensed into a suspension of 4-chloro-7-cyclopropylmethyl-5-iodo-7H-pyrrolo[2,3-d]pyrimidine (394.8 mg, 1.184 mmol) in dioxane (3 mL) and iPrOH (2 mL) in a sealable glass tube, cooled by dry ice/acetone, until the volume increased by ≈1 mL, then the tube was sealed and heated to 100° C. overnight. The solvents were evaporated, water was added, the mixture was extracted with CH₂Cl₂ (3×20 mL), and the combined CH₂Cl₂ extracts were washed with brine, dried over MgSO₄, filtered and concentrated to give the title compound as a white solid. ¹H NMR (CDCl₃, 400 MHz): δ=0.36-0.43 (m, 2H), 0.58-0.66 (m, 2H), 1.19-1.29 (m, 1H), 4.03 (d, J=6.8 Hz, 2H), 5.63 (brs, 2H), 7.19 (s, 1H), 8.27 (s, 1H). ¹³C NMR (CDCl₃, 100.6 MHz, DEPT135): δ=4.02 (2C, −), 11.28 (+), 48.46 ($C_{quart}$), 49.19 (−), 103.96 ($C_{quart}$), 128.70 (+), 150.03 ($C_{quart}$), 152.05 (+), 156.88 ($C_{quart}$). MS (ES+): m/z 315.1 (100) [MH⁺]. HPLC: $t_R$=2.3 min (OpenLynx, polar_5 min).

4-Chloro-7-cyclopropylmethyl-5-iodo-7H-pyrrolo[2,3-d]pyrimidine

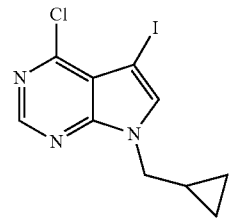 [SMILES: Clc1ncnc2c1c(I)cn2CC1CC1]

To a mixture of 4-chloro-5-iodo-7H-pyrrolo[2,3-d]pyrimidine (prepared according to: L. B. Townsend et al., *J. Med. Chem.* 1990, 33 (7), 1984-92) (419 mg, 1.50 mmol), cyclopropylmethanol (165 μL, 147 mg, 2.04 mmol), and PS-PPh₃ (2.12 mmol/g; 1.41 g, 2.99 mmol) in dry THF (10 mL), cooled by ice/water, was added DIAD (440 μL, 452 mg, 2.23 mmol; 1.5 equiv.), then the cooling bath was removed and the mixture was vortexed overnight. The resin was filtered off and washed thoroughly with THF, and the filtrate and washings were combined and concentrated. Chromatography of the crude material thus obtained on silica gel (Jones Flashmaster, 2 columns, 10 g/70 mL cartridge each, eluting with CH₂Cl₂) gave the title compound as an off-white solid. ¹H NMR (CDCl₃, 400 MHz): δ=0.41-0.47 (m, 2H), 0.63-0.69 (m, 2H), 1.20-1.31 (m, 1H), 4.12 (d, J=7.2 Hz, 2H), 7.52 (s, 1H), 8.61 (s, 1H). MS (ES+): m/z 333.9/335.9 (100/38) [MH⁺]. HPLC: $t_R$=3.7 min (OpenLynx, polar_5 min).

Example 100

7-Cyclobutyl-5-(2-phenylquinolin-7-yl)-7H-pyrrolo[2,3-d]pyrimidin-4-ylamine

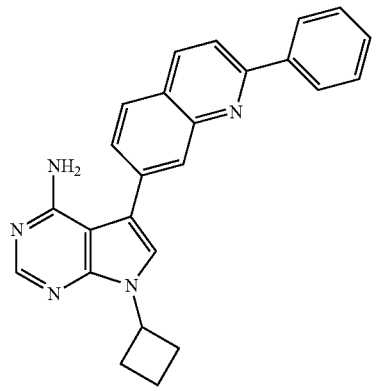 [SMILES: Nc1ncnc2c1c(-c1ccc3ccc(-c4ccccc4)nc3c1)cn2C1CCC1]

Following the general procedure for the Suzuki coupling, 7-cyclobutyl-5-iodo-7H-pyrrolo[2,3-d]pyrimidin-4-ylamine (142.5 mg, 0.4536 mmol) was reacted with 2-phenyl-7-(4,4,5,5-tetramethyl-[1,3,2]dioxaborolan-2-yl)-quinoline (150.2 mg, 0.4533 mmol), Na₂CO₃ (120 mg, 1.13 mmol) and Pd(PPh₃)₄ (32 mg, 0.028 mmol) in DMF (10 mL)/water (2 mL). The crude material was purified by column chromatography on silica gel [Jones Flashmaster, 10 g/70 mL cartridge, eluting with CH$_2$Cl$_2$ (1-12)→1% MeOH in CH$_2$Cl$_2$ (13-37) →2% MeOH in CH$_2$Cl$_2$ (38-61)], yielding the title compound as a pale yellow solid. $^1$H NMR (CDCl$_3$, 400 MHz): δ=1.88-2.00 (m, 2H), 2.44-2.56 (m, 2H), 2.56-2.65 (m, 2H), 5.27 (brs, 2H), 5.35 (quint, J=8.6 Hz, 1H), 7.35 (s, 1H), 7.46-7.51 (m, 1H), 7.52-7.58 (m, 2H), 7.70 (dd, J=1.8, 8.2 Hz, 1H), 7.91 (d, J=8.4 Hz, 1H), 7.93 (d, J=8.0 Hz, 1H), 8.17-8.22 (m, 2H), 8.26 (d, J=8.4 Hz, 1H), 8.28-8.31 (m, 1H), 8.36 (s, 1H). $^{13}$C NMR (CDCl$_3$, 100.6 MHz, DEPT135): δ=15.03 (−), 31.11 (2C, +), 48.26 (+), 101.15 (C$_{quart}$), 115.99 (C$_{quart}$), 118.99 (+), 120.86 (+), 125.97 (C$_{quart}$), 127.42 (+), 127.55 (2C, +), 128.26 (+), 128.48 (+), 128.87 (2C, +), 129.52 (+), 136.49 (C$_{quart}$), 136.55 (+), 139.43 (C$_{quart}$), 148.52 (C$_{quart}$), 150.79 (C$_{quart}$), 151.97 (+), 156.97 (C$_{quart}$), 158.12 (C$_{quart}$). MS (ES+): m/z 392.1 (17) [MH$^+$], 338.2 (22) [MH$^+$-cyclobutene]. HPLC: t$_R$=3.0 min (OpenLynx, polar_5 min).

7-Cyclobutyl-5-iodo-7H-pyrrolo[2,3-d]pyrimidin-4-ylamine

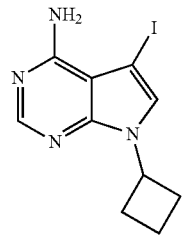 [SMILES: Nc1ncnc2c1c(I)cn2C1CCC1]

Gaseous ammonia (from a lecture bottle) was condensed into a suspension of 4-chloro-7-cyclobutyl-5-iodo-7H-pyrrolo[2,3-d]pyrimidine (70.7 mg, 0.8115 mmol) in dioxane (2 mL) and iPrOH (2 mL) in a sealable glass tube, cooled by dry ice/acetone, until the volume increased by ≈2 mL, then the tube was sealed and heated to 100° C. overnight. The solvents were evaporated, water was added, the mixture was extracted with CH$_2$Cl$_2$ (3×30 mL), and the combined CH$_2$Cl$_2$ extracts were washed with brine, dried over MgSO$_4$, filtered and concentrated to give the title compound as a white solid. $^1$H NMR (CDCl$_3$, 400 MHz): S=1.83-1.95 (m, 2H), 2.34-2.47 (m, 2H), 2.48-2.58 (m, 2H), 5.22 (quint, J=8.7 Hz, 1H), 5.63 (brs, 2H), 7.26 (s, 1H), 8.26 (s, 1H). $^{13}$C NMR (CDCl$_3$, 100.6 MHz, DEPT135): δ=14.92 (−), 31.05 (2C, −), 48.50 (+), 48.82 (C$_{quart}$), 104.11 (C$_{quart}$), 126.39 (+), 149.82 (C$_{quart}$), 152.00 (+), 156.94 (C$_{quart}$). MS (ES+): m/z 315.0 (100) [MH$^+$]. HPLC: t$_R$=2.4 min (OpenLynx, polar_5 min).

4-Chloro-7-cyclobutyl-5-iodo-7H-pyrrolo[2,3-d]pyrimidine

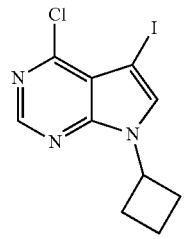 [SMILES: Clc1ncnc2c1c(I)cn2C1CCC1]

To a mixture of 4-chloro-5-iodo-7H-pyrrolo[2,3-d]pyrimidine (prepared according to: L. B. Townsend et al., *J. Med. Chem.* 1990, 33 (7), 1984-92) (419 mg, 1.50 mmol), cyclobutanol (160 µL, 147 mg, 2.04 mmol), and PS-PPh$_3$ (2.12 mmol/g; 1.41 g, 2.99 mmol) in dry THF (10 mL), cooled by ice/water, was added DIAD (440 µL, 452 mg, 2.23 mmol; 1.5 equiv.), then the cooling bath was removed and the mixture was vortexed overnight. The resin was filtered off and washed thoroughly with THF, and the filtrate and washings were combined and concentrated. The crude material thus obtained was chromatographed on silica gel (Jones Flashmaster, 2 columns, 10 g/70 mL cartridge each, eluting with CH$_2$Cl$_2$) to give a 10:1 mixture of the title compound and 4-chloro-7-cyclopropylmethyl-5-iodo-7H-pyrrolo[2,3-d]pyrimidine (vide supra for a separate synthesis) as an off-white solid. $^1$H NMR (CDCl$_3$, 400 MHz): δ=1.88-2.01 (m, 2H), 2.41-2.65 (m, 4H), 5.28 (quint, J=8.6 Hz, 1H), 7.58 (s, 1H), 8.60 (s, 1H). MS (ES+): m/z 333.9/335.9 (100/38) [MH$^+$]. HPLC: t$_R$=3.8 min (OpenLynx, polar_5 min).

Example 101 cis-7-(3-Azetidin-1-ylmethylcyclobutyl)-5-(2-phenylquinolin-7-yl)-7H-pyrrolo[2,3-d]pyrimidin-4-ylamine

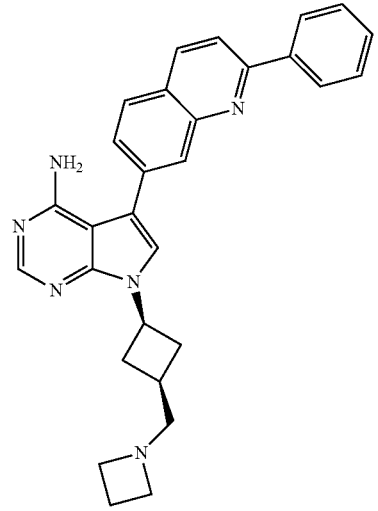 [SMILES: Nc1ncnc2c1c(-c1ccc3ccc(-c4ccccc4)nc3c1)cn2[C@H]1C[C@@H](CN2CCC2)C1]

To the DMF solution from the preparation of cis-7-(3-azetidin-1-ylmethylcyclobutyl)-5-iodo-7H-pyrrolo[2,3-d]pyrimidin-4-ylamine were added 2-phenyl-7-(4,4,5,5-tetramethyl-[1,3,2]dioxaborolan-2-yl)-quinoline (40 mg, 0.12 mmol), Na$_2$CO$_3$ (27 mg, 0.25 mmol), Pd(PPh$_3$)$_4$ (7 mg, 0.006 mmol), and water (0.6 mL). The solution was purged with nitrogen for 10 min and heated to 80° C. for 16 h. To the cooled reaction solution was added sat. Na$_2$CO$_3$ solution (10 mL), the mixture was extracted with EtOAc (3×20 mL), the combined organic layers were washed with water (3×15 mL) and brine, dried over MgSO$_4$, filtered, and concentrated to give a brown oil. Purification by HPLC gave the title compound as brown oil. $^1$H NMR (CDCl$_3$, 400 MHz): δ=2.06-2.26 (m, 5H), 2.56-2.57 (d, 2H, J=6.2), 2.71-2.77 (m, 2H), 3.21-3.24 (m, 4H), 5.17 (brs, 2H), 5.19-5.26 (m, 1H), 7.31 (s, 1H), 7.46-7.56 (m, 3H), 7.69-7.71 (dd, 1H, J=1.6 & 8.4 Hz), 7.90-7.94 (m, 2H), 8.18-8.20 (m, 2H), 8.26-8.29 (m, 2H), 8.35 (s, 1H). MS (ES+): 461.2 [MH$^+$]. HPLC: $t_R$=2.0 min (polar_5 min).

cis-7-(3-Azetidin-1-ylmethylcyclobutyl)-5-iodo-7H-pyrrolo[2,3-d]pyrimidin-4-ylamine

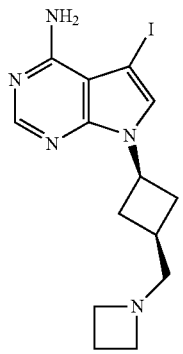 [SMILES: Nc1ncnc2c1c(I)cn2[C@H]1C[C@@H](CN2CCC2)C1]

The DMF (3 mL) solution of cis-toluene-4-sulfonic acid 3-(4-amino-5-iodopyrrolo[2,3-d]pyrimidin-7-yl)-cyclobutylmethyl ester (see above for its preparation) (63 mg, 80% purity, 0.10 mmol) and azetidine (12 mg, 2 eq.) was stirred at 50° C. overnight in a sealed tube. The reaction mixture was used directly for further reaction. MS (ES+): 384.1 [MH$^+$]. HPLC: $t_R$=1.4 min (polar_5 min). For $^1$H NMR analysis, a small sample was taken out for HPLC purification. $^1$H NMR (DMSO-d$_6$, 400 MHz): δ=1.99-2.06 (quintet, 2H, J=6.9 Hz), 2.08-2.22 (m, 3H), 2.49-2.53 (m, 2H), 2.54-2.56 (d, 2H, J=6.4 Hz), 3.15-3.19 (d, 4H, J=7.2 Hz), 5.01-5.10 (quintet, 2H, J=8.7 Hz), 6.69 (brs, 2H), 7.80 (s, 1H), 8.16 (s, 1H).

Example 102 trans-3-[4-Amino-5-(2-phenylquinolin-7-yl)-pyrrolo[2,3-d]pyrimidin-7-yl]cyclobutanecarboxylic acid amide

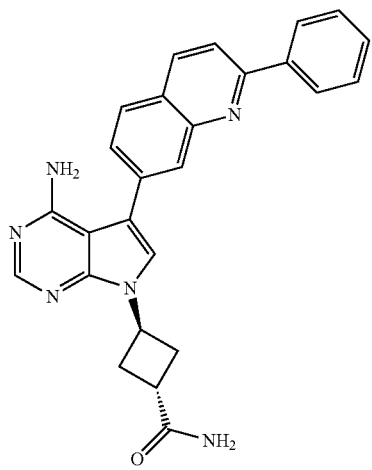 [SMILES: Nc1ncnc2c1c(-c1ccc3ccc(-c4ccccc4)nc3c1)cn2[C@H]1C[C@H](C(N)=O)C1]

A mixture of trans-3-(4-amino-5-iodopyrrolo[2,3-d]pyrimidin-7-yl)-cyclobutanecarboxylic acid amide (119 mg, 0.333 mmol), 2-phenyl-7-(4,4,5,5-tetramethyl-[1,3,2]dioxaborolan-2-yl)-quinoline (133 mg, 0.402 mmol), Na$_2$CO$_3$ (88.3 mg, 0.833 mmol), Pd(PPh$_3$)$_4$ (23.1 mg, 0.0200 mmol), DMF (5 mL), and water (1 mL) was purged with nitrogen for 30 min and heated to 80° C. for 22 h. To the cooled reaction solution was added water (10 mL), the mixture was extracted with EtOAc (3×15 mL), the combined organic layers were washed with water (2×10 mL) and brine, dried over MgSO$_4$, filtered, and concentrated. The residue was triturated with MeOH to give the title compound as light yellow solid. Chromatography of the mother liquor on silica gel (8 g, eluting with 2%→4%→6%→8%→10% MeOH in CH$_2$Cl$_2$) gave an additional batch. Both batches contained a small amount of the corresponding cis isomer (see below for its independent synthesis). $^1$H NMR (CDCl$_3$, 400 MHz): δ=2.70-2.78 (m, 2H), 2.97-3.08 (m, 2H), 3.21-3.26 (m, 1H), 5.66-5.72 (quintet, 1H, J=8.4 Hz), 6.54 (brs, 2H), 7.08 (s, 1H), 7.59 (s, 1H), 7.68-7.78 (m, 3H), 7.94-7.98 (m, 1H), 8.12 (s, 1H), 8.26-8.28 (d, 1H, J=8.4 Hz), 8.32-8.37 (m, 3H), 8.48-8.53 (m, 2H), 8.66-8.68 (d, 1H, J=8.8 Hz). MS (ES+): 435.2 [MH$^+$]. HPLC: $t_R$=2.3 min (polar_5 min).

trans-3-(4-Amino-5-iodopyrrolo[2,3-d]pyrimidin-7-yl)-cyclobutanecarboxylic acid amide

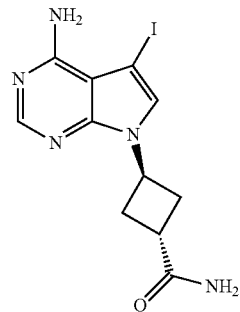 [SMILES: Nc1ncnc2c1c(I)cn2[C@H]1C[C@H](C(N)=O)C1]

Gaseous ammonia (from a lecture bottle) was condensed into a solution of cis-3-(4-chloro-5-iodopyrrolo[2,3-d]pyrimidin-7-yl)-cyclobutanecarboxylic acid methyl ester (see above for its preparation) (134.7 mg, 0.344 mmol) in CH$_2$Cl$_2$ (2 mL) and 2M NH$_3$ in iPrOH (4 mL) in a stainless steel Parr reactor, cooled by dry ice/acetone, until the volume approximately doubled, then the reactor was sealed, warmed to ambient temperature overnight, and heated to 110° C. for 8 h. After cooling, the solvents were evaporated; the residue was washed with water and CH$_2$Cl$_2$ and dried in vacuo, yielding the title compound as beige solid. The aqueous filtrate was concentrated, dissolved in EtOAc, washed with water and brine, dried over MgSO$_4$, filtered and concentrated to give a second batch of the title compound as beige solid. Both batches were combined for the next step. $^1$H NMR (DMSO-d$_6$, 400 MHz): δ=2.50 (m, 2H), 2.66-2.74 (m, 2H), 2.97-3.02 (m, 1H), 5.33-5.39 (quintet, 1H, J=8.4 Hz), 6.60 (brs, 2H), 6.89 (s, 1H), 7.39 (s, 1H), 7.78 (s, 1H), 8.09 (s, 1H). MS (ES+): 357.9 [MH$^+$]. HPLC: $t_R$=2.1 min (polar_5 min).

Example 103 cis-3-[4-Amino-5-(2-phenylquinolin-7-yl)-pyrrolo[2,3-d]pyrimidin-7-yl]cyclobutanecarboxylic acid amide

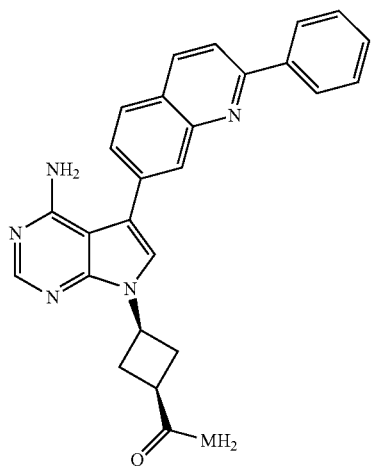

A mixture of cis-3-(4-amino-5-iodopyrrolo[2,3-d]pyrimidin-7-yl)-cyclobutanecarboxylic acid amide (131 mg, 0.367 mmol), 2-phenyl-7-(4,4,5,5-tetramethyl-[1,3,2]dioxaborolan-2-yl)-quinoline (146 mg, 0.441 mmol), Na$_2$CO$_3$ (97.2 mg, 0.917 mmol), Pd(PPh$_3$)$_4$ (25.5 mg, 0.0221 mmol), DMF (5 mL), and water (1 mL) was purged with nitrogen for 30 min and heated to 80° C. for 18 h. To the cooled reaction solution was added water (15 mL), the mixture was extracted with EtOAc (3×20 mL), the combined organic layers were washed with water (2×15 mL) and brine, dried over MgSO$_4$, filtered, and concentrated. The residue was triturated with MeOH to give the title compound as yellow solid. $^1$H NMR (CDCl$_3$, 400 MHz): δ=2.60-2.70 (m, 4H), 2.84-2.90 (m, 1H), 5.14-5.23 (quintet, 1H, J=8.7 Hz), 6.31 (brs, 2H), 6.92 (s, 1H), 7.40 (s, 1H), 7.50-7.62 (m, 3H), 7.78-7.82 (m, 2H), 8.08-8.10 (d, 1H, J=8.4 Hz), 8.15-8.23 (m, 3H), 8.30-8.37 (m, 2H), 8.49-8.51 (d, 1H, J=8.4 Hz). MS (ES+): 435.0 [MH$^+$]. HPLC: t$_R$=2.4 min (polar_5 min).

cis-3-(4-Amino-5-iodopyrrolo[2,3-d]pyrimidin-7-yl)-cyclobutanecarboxylic acid amide

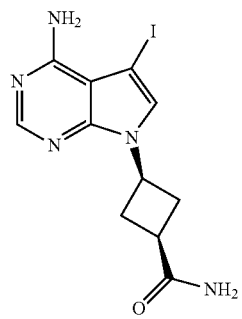 [SMILES: Nc1ncnc2c1c(I)cn2[C@H]1C[C@@H](C(N)=O)C1]

Gaseous ammonia (from a lecture bottle) was condensed into a solution of cis-3-(4-chloro-5-iodopyrrolo[2,3-d]pyrimidin-7-yl)-cyclobutanecarboxylic acid methyl ester (see above for its preparation) (200 mg, 0.511 mmol) in CH$_2$Cl$_2$ (3 mL) and 2M NH$_3$ in iPrOH (3 mL) in a stainless steel Parr reactor, cooled by dry ice/acetone, until the volume approximately doubled, then the reactor was sealed, warmed to ambient temperature overnight, and heated to 115° C. for 8 h. After cooling, the solvents were evaporated; the residue was washed with water and CH$_2$Cl$_2$ and dried in vacuo, yielding the title compound as off-white solid. The aqueous filtrate was extracted with EtOAc (2×60 mL), and the combined EtOAc extracts were dried over MgSO$_4$, filtered and concentrated to give a second batch of the title compound as beige solid. Both batches were combined for the next step. $^1$H NMR (DMSO-d$_6$, 400 MHz): δ=2.64-2.70 (m, 4H), 2.88-2.96 (quintet, 1H, J=8.5 Hz), 5.10-5.19 (quintet, 1H, J=8.6 Hz), 6.64 (brs, 2H), 7.00 (s, 1H), 7.48 (s, 1H), 7.72 (s, 1H), 8.19 (s, 1H). MS (ES+): 358.1 [MH$^+$]. HPLC: t$_R$=1.7 min (polar_5 min).

Example 104 cis-{-4-[4-Amino-5-(2-phenylquinolin-7-yl)-pyrrolo[2,3-d]pyrimidin-7-yl]-cyclohexyl}-methanol

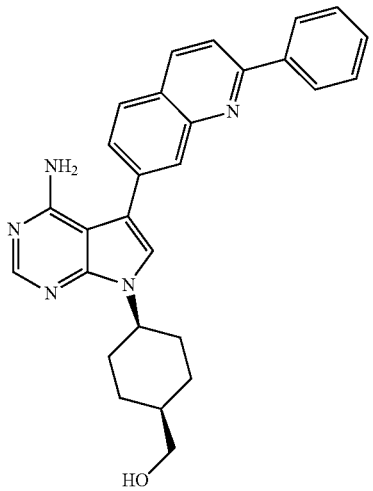 [SMILES: Nc1ncnc2c1c(-c1ccc3ccc(-c4ccccc4)nc3c1)cn2[C@H]1CC[C@@H](CO)CC1]

Into the THF (1 mL) solution of cis-4-[4-amino-5-(2-phenylquinolin-7-yl)-pyrrolo[2,3-d]pyrimidin-7-yl]-cyclohexanecarboxylic acid ethyl ester (13.3 mg, 0.0271 mmol) was added dropwise LiAlH$_4$ (1 M in THF, 203 μL, 0.75 eq.) at 0° C. under N$_2$. After stirring at rt for 2 h, the reaction mixture was treated with saturated potassium sodium tartarate solution (5 mL) and extracted with EtOAc (2×10 mL). The extracts were washed with H$_2$O (10 mL) and brine (10 mL), and dried over MgSO$_4$. The drying agent was filtered off, and the filtrate was concentrated in vacuo. The crude material thus obtained was purified by preparative TLC (silica gel, eluting with 7% MeOH/CH$_2$Cl$_2$) to yield the title compound as beige powder. $^1$H NMR (CDCl$_3$, 400 MHz): δ=1.77-2.02 (m, 9H), 3.77-3.78 (d, 2H, J=7.2 Hz), 4.77-4.82 (m, 1H), 5.30 (brs, 2H), 7.24 (s, 1H), 7.46-7.57 (m, 3H), 7.67-7.70 (dd, 1H, J=1.6

& 8.4 Hz), 7.89-7.93 (m, 2H), 8.18-8.20 (m, 2H), 8.25-8.28 (m, 2H), 8.36 (s, 1 H). MS (ES+): 450.2 [MH+]. HPLC: $t_R$=2.5 min (polar_5 min).

Example 105 cis-4-[4-amino-5-(2-phenylquinolin-7-yl)-pyrrolo[2,3-d]pyrimidin-7-yl]-cyclohexanecarboxylic acid ethyl ester

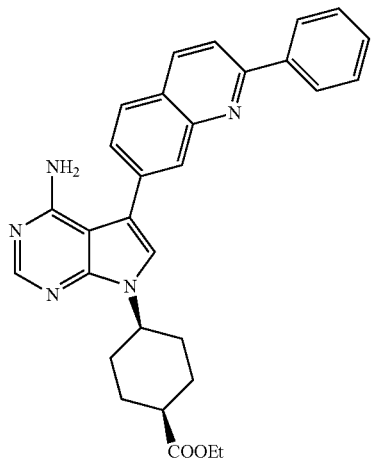 [SMILES: CCOC(=O)[C@H]1CC[C@@H](n2cc(-c3ccc4ccc(-c5ccccc5)nc4c3)c3c(N)ncnc32)CC1]

A solution of cis-4-(4-amino-5-iodopyrrolo[2,3-d]pyrimidin-7-yl)-cyclohexanecarboxylic acid ethyl ester (16.2 mg 0.0391 mmol), 2-phenyl-7-(4,4,5,5-tetramethyl-[1,3,2]dioxaborolan-2-yl)-quinoline (15.6 mg, 1.2 eq.), Pd(PPh$_3$)$_4$ (2.7 mg, 0.06 eq.) and Na$_2$CO$_3$ (10.4 mg, 2.5 eq.) in DMF (2.5 mL)/H$_2$O (0.5 mL) was flushed with N$_2$ for 30 min at rt and heated at 80° C. for 16 h under nitrogen. After that time, the reaction mixture was treated with H$_2$O and extracted with EtOAc (3×10 mL). The combined extracts were washed with H$_2$O (2×5 mL) and brine (5 mL), and dried over MgSO$_4$. The drying agent was filtered off, the filtrate was concentrated in vacuo, and the crude yellow oil was purified by HPLC to obtain the title compound as yellow oil. $^1$H NMR (CDCl$_3$, 400 MHz): δ=1.29-1.36 (t, 3H, J=7.2 Hz), 1.74-2.09 (m, 6H), 2.34-2.41 (m, 2H), 2.75 (m, 1H), 4.19-4.25 (q, 2H, J=7.2 Hz), 4.77-4.85 (m, 1H), 5.22 (brs, 2H), 7.22 (s, 1H), 7.46-7.57 (m, 3H), 7.68-7.70 (dd, 1H, J=1.6 & 8.0 Hz), 7.89-7.93 (m, 2H), 8.18-8.20 (dd, 2H, J=0.8 & 8.0 Hz), 8.25-8.27 (m, 2H), 8.37 (s, 1H). MS (ES+): 492.1 [MH+]. HPLC: $t_R$=3.1 min (polar_5 min).

cis-4-(4-Amino-5-iodopyrrolo[2,3-d]pyrimidin-7-yl)-cyclohexanecarboxylic acid ethyl ester

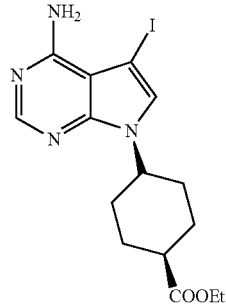

Gaseous ammonia was bubbled into an $^i$PrOH (1 mL) solution of cis-4-(4-chloro-5-iodo-pyrrolo[2,3-d]pyrimidin-7-yl)-cyclohexanecarboxylic acid ethyl ester (30 mg, 70% pure by HPLC peak area, 0.048 mmol) in a glass pressure tube, cooled to −78° C. in a dry ice/acetone bath, for 15 min. The tube was equipped with a Teflon washer, sealed and heated to 110° C. for 7 h. After that time, the excess NH$_3$ and the solvent were evaporated. The residue was used for the next reaction without purification. A portion of above crude material were purified by HPLC to give the title compound as pale yellow oil. $^1$H NMR (CDCl$_3$, 400 MHz): δ=1.31 (t, 3H, J=7.6 Hz), 1.63-1.98 (m, 6H), 2.29-2.35 (m, 2H), 2.73 (m, 1H), 4.22 (q, 2H, J=7.6 Hz), 4.64-4.71 (m, 1H), 5.58 (brs, 2H), 7.11 (s, 1H), 8.26 (s, 1H). MS (ES+): 415.0 [MH+]. $t_R$=2.7 min (polar_5 min).

cis-4-(4-Chloro-5-iodopyrrolo[2,3-d]pyrimidin-7-yl)-cyclohexanecarboxylic acid ethyl ester

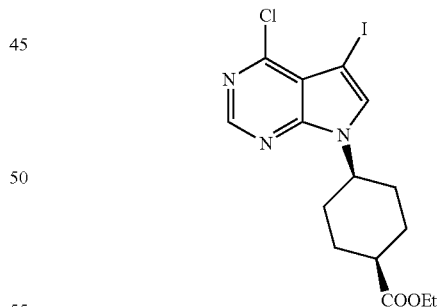

Into the THF (5 mL) solution of 4-chloro-5-iodo-7H-pyrrolo[2,3-d]pyrimidine (prepared according to: L. B. Townsend et al., *J. Med. Chem.* 1990, 33 (7), 1984-92) (140 mg, 0.500 mmol), 4-hydroxycyclohexanecarboxylic acid ethyl ester (104 mg, 0.600 mmol; Aldrich, cis/trans mixture), and PPh$_3$ (263 mg, 1.00 mmol) was added DIAD (203 mg, 1.00 mmol) dropwise at 0° C. under N$_2$ over 5 min. The reaction was then stirred at rt for 2 days. After that time, the solvent was evaporated, and the residue was purified by chromatography on silica gel, eluting with 200 mL of 5%, 10%, 20% and 30% EtOAc/hexane to obtain cis-4-(4-chloro-5- iodopyrrolo[2,3-d]pyrimidin-7-yl)-cyclohexanecarboxylic acid ethyl ester as a white solid, which was further purified by HPLC. $^1$H NMR (CDCl$_3$, 400 MHz): δ=1.32 (t, 3H, J=7.2 Hz), 1.74-1.78 (m, 2H), 1.88-1.98 (m, 4H), 2.33-2.36 (m, 2H), 2.75-2.77 (m, 1H), 4.23 (q, 2H, J=7.2 Hz), 4.73-4.81 (m, 1H), 7.45 (s, 1H), 8.60 (s, 1 H). MS (ES+): 433.9/435.9 [MH$^+$]. HPLC: $t_R$=4.0 min (polar_5 min).

Example 106

7-Phenyl-5-(2-phenylquinolin-7-yl)-7H-pyrrolo[2,3-d]pyrimidin-4-ylamine

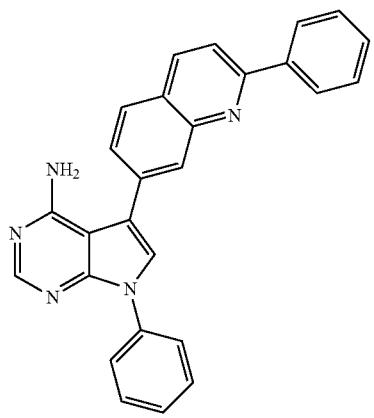 [SMILES: Nc1ncnc2c1c(-c1ccc3ccc(-c4ccccc4)nc3c1)cn2-c1ccccc1]

Following the general procedure for the Suzuki coupling, 5-iodo-7-phenyl-7H-pyrrolo[2,3-d]pyrimidin-4-ylamine (27 mg, 0.080 mmol) was reacted with 2-phenyl-7-(4,4,5,5-tetramethyl-[1,3,2]dioxaborolan-2-yl)-quinoline (26.5 mg, 0.080 mmol), Na$_2$CO$_3$ (22 mg, 0.21 mmol) and Pd(PPh$_3$)$_4$ (6 mg, 0.005 mmol) in DMF (2.5 mL)/water (0.5 mL). The crude material was purified by chromatography on an SCX column (1 g/6 mL barrel) followed by column chromatography on silica gel [Jones Flashmaster, 5 g/25 mL cartridge, eluting with CH$_2$Cl$_2$ (1-12) 1% MeOH in CH$_2$Cl$_2$ (13-33)→2% MeOH in CH$_2$Cl$_2$ (34-40)], yielding the title compound as an off-white solid. $^1$H NMR (CDCl$_3$, 400 MHz): δ=5.31 (brs, 2H), 7.38-7.42 (m, 1H), 7.43 (s, 1H), 7.47-7.52 (m, 1H), 7.53-7.59 (m, 4H), 7.75 (dd, J=2.0, 8.4 Hz, 1H), 7.75-7.79 (m, 2H), 7.94 (d, J=8.4 Hz, 1H), 7.97 (d, J=8.0 Hz, 1H), 8.18-8.22 (m, 2H), 8.26 (d, J=8.4 Hz, 1H), 8.35-8.37 (m, 1H), 8.44 (s, 1H). MS (ES+): m/z 414.0 (25) [MH$^+$]. HPLC: $t_R$=3.4 min (OpenLynx, polar_5 min).

5-Iodo-7-phenyl-7H-pyrrolo[2,3-d]pyrimidin-4-ylamine

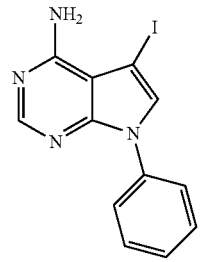 [SMILES: Nc1ncnc2c1c(I)cn2-c1ccccc1]

Gaseous ammonia (from a lecture bottle) was condensed into a suspension of 4-chloro-5-iodo-7-phenyl-7H-pyrrolo[2,3-d]pyrimidine (30 mg, 0.084 mmol) in dioxane (2 mL) and iPrOH (2 mL) in a sealable glass tube, cooled by dry ice/acetone, until the volume increased by ≈2 mL, then the tube was sealed and heated to 100° C. overnight. The solvents were evaporated, water was added, the mixture was extracted with CH$_2$Cl$_2$ (3×30 mL), and the combined CH$_2$Cl$_2$ extracts were washed with brine, dried over MgSO$_4$, filtered and concentrated to give the title compound as a white solid. $^1$H NMR (CDCl$_3$, 400 MHz): δ=5.69 (brs, 2H), 7.36 (s, 1H), 7.36-7.41 (m, 1H), 7.49-7.55 (m, 2H), 7.60-7.64 (m, 2H), 8.33 (s, 1H). MS (ES+): m/z 337.0 (100) [MH$^+$]. HPLC: $t_R$=2.8 min (OpenLynx, polar_5 min).

4-Chloro-5-iodo-7-phenyl-7H-pyrrolo[2,3-d]pyrimidine

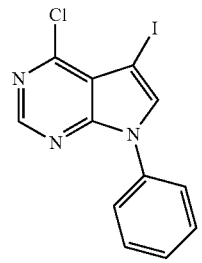 [SMILES: Clc1ncnc2c1c(I)cn2-c1ccccc1]

A mixture of 4-chloro-5-iodo-7H-pyrrolo[2,3-d]pyrimidine (prepared according to: L. B. Townsend et al., J. Med. Chem. 1990, 33 (7), 1984-92) (280 mg, 1.00 mmol), phenylboronic acid (244 mg, 2.00 mmol), pyridine (165 μL, 161 mg, 2.04 mmol), and Cu(OAc)$_2$ (272 mg, 1.50 mmol) in CH$_2$Cl$_2$ (5 mL) was stirred under air at ambient temperature for 12 d. Aqueous ammonia (1 M) and CH$_2$Cl$_2$ were added, the solids were filtered off, the layers of the filtrate were separated, the aqueous layer was extracted with CH$_2$Cl$_2$ (2×30 mL), the combined CH$_2$Cl$_2$ layers were washed with 1 M aqueous ammonia (2×), 2 M NaOH (2×), and brine and dried over MgSO$_4$. The crude material was adsorbed onto Hydromatrix and chromatographed on silica gel [Jones Flashmaster, 20 g/70 mL cartridge, eluting with CH$_2$Cl$_2$], yielding the title compound as off-white solid. $^1$H NMR (CDCl$_3$, 400 MHz): δ=7.43-7.48 (m, 1H), 7.54-7.60 (m, 2H), 7.61-7.65 (m, 2H), 7.69 (s, 1H), 8.68 (s, 1H). MS (ES+): m/z 355.9/357.9 (100/35) [MH+]. HPLC: $t_R$=3.8 min (OpenLynx, polar_5 min).

Example 107

1-Cyclobutyl-3-(2-phenylquinolin-7-yl)-1H-pyrazolo[3,4-d]pyrimidin-4-ylamine

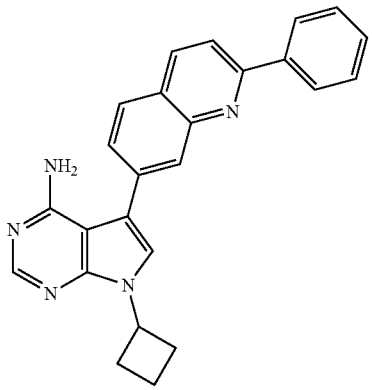 [SMILES: Nc1ncnc2c1c(-c1ccc3ccc(-c4ccccc4)nc3c1)cn2C1CCC1]

Nitrogen was bubbled into a mixture of 1-cyclobutyl-3-iodo-1H-pyrazolo[3,4-d]pyrimidin-4-ylamine (60.0 mg, 0.190 mmol), 2-phenyl-7-(4,4,5,5-tetramethyl-[1,3,2]dioxaborolan-2-yl)-quinoline (64.4 mg, 0.194 mmol), $Na_2CO_3$ (50.5 mg, 0.476 mmol), and $Pd(PPh_3)_4$ (13.7 mg, 0.0119 mmol) in DMF (4 mL)/water (1 mL) for 5 min, then the mixture was heated under nitrogen to 80° C. (bath temp.) for 17 h. The solvents were evaporated, water was added, the mixture was extracted with $CH_2Cl_2$ (3×20 mL), and the combined extracts were washed with brine and dried over $MgSO_4$. $MgSO_4$ was filtered off, and the filtrate was concentrated and chromatographed on an SCX column (1 g/6 mL barrel). The amine-containing fraction was adsorbed onto Hydromatrix and chromatographed on silica gel [Jones Flashmaster, 5 g/25 mL cartridge, eluting with $CH_2Cl_2$ (1-11)→1% MeOH in $CH_2Cl_2$ (12-28)→2% MeOH in $CH_2Cl_2$ (29-46)], yielding the title compound as off-white solid. $^1$H NMR (CDCl$_3$, 400 MHz): δ=1.87-2.04 (m, 2H), 2.48-2.58 (m$_c$, 2H), 2.86-2.98 (m$_c$, 2H), 5.50 (quint, J=8.0 Hz, 1H), 5.57 (brs, 2H), 7.47-7.52 (m, 1H), 7.53-7.58 (m, 2H), 7.96 (dd, J=1.6, 8.3 Hz, 1H), 7.97 (d, J=8.6 Hz, 1H), 8.02 (d, J=8.0 Hz, 1H), 8.19-8.23 (m, 2H), 8.31 (d, J=8.6 Hz, 1H), 8.42 (s, 1H), 8.49-8.52 (m, 1H). $^{13}$C NMR (CDCl$_3$, 100.6 MHz, DEPT135): S=14.99 (−), 29.91 (2C, −), 50.61 (+), 98.68 ($C_{quart}$), 119.59 (+), 126.53 (+), 126.97 ($C_{quart}$), 127.56 (2C, +), 128.66 (+), 128.79 (2C, +), 129.00 (+), 129.53 (+), 134.83 ($C_{quart}$), 136.53 (+), 139.14 ($C_{quart}$), 143.40 ($C_{quart}$), 148.22 ($C_{quart}$), 154.00 ($C_{quart}$), 155.53 (+), 157.92 ($C_{quart}$), 158.18 ($C_{quart}$). MS (ES+): m/z 393.1 (53) [MH+]. HPLC: $t_R$=3.1 min (OpenLynx, nonpolar_5 min), 3.6 min (OpenLynx, polar_5 min).

1-Cyclobutyl-3-iodo-1H-pyrazolo[3,4-d]pyrimidin-4-ylamine

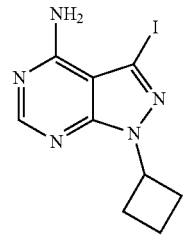 [SMILES: Nc1ncnc2c1c(I)nn2C1CCC1]

DIAD (440 μL, 452 mg, 2.23 mmol) was added to a cooled (ice/water) mixture of 3-iodo-1H-pyrazolo[3,4-d]pyrimidin-4-ylamine (472 mg, 1.81 mmol, purchased from CNH Technologies, Inc.), PS-PPh$_3$ (Argonaut, loading 2.21 mmol/g; 1.37 g, 3.03 mmol), and cyclobutanol (160 μL, 147 mg, 2.04 mmol) in dry THF (15 mL), then the cooling bath was removed, and the mixture was vortexed at ambient temp. for 16 d. More PS-PPh$_3$ (330 mg, 0.729 mmol), DIAD (110 μL, 113 mg, 0.56 mmol), cyclobutanol (40 μL, 37 mg, 0.51 mmol), and THF (5 mL) were added, and vortexing was continued for 4 d. The resin was filtered off, washed thoroughly with THF, and the combined filtrate and washings were concentrated. The crude material was adsorbed onto Hydromatrix and chromatographed on silica gel [Jones Flashmaster, 10 g/70 mL cartridge, eluting with $CH_2Cl_2$ (1-10)→2% MeOH in $CH_2Cl_2$ (11-24)→2.5% MeOH (25-30)→3% MeOH (31-44)]. Fr. 15-27 were combined and dried overnight in vacuo. One obtained the title compound as a white solid. This material was used in the next step without further purification. $^1$H NMR (CDCl$_3$, 400 MHz): δ=1.81-2.00 (m, 2H), 2.40-2.50 (m$_c$, 2H), 2.72-2.84 (m$_c$, 2H), 5.28-5.38 (m$_c$, 1H), 5.89 (brs, 2H), 8.32 (s, 1H). MS (ES+): m/z 316.0 (100) [MH+]. HPLC: $t_R$=1.9 min (OpenLynx, nonpolar_5 min), 2.7 min (OpenLynx, polar_5 min).

3-[8-chloro-1-(2-phenylquinolin-7-yl)imidazo[1,5-a]pyrazin-3-yl]-1-(hydroxymethyl)cyclobutanol

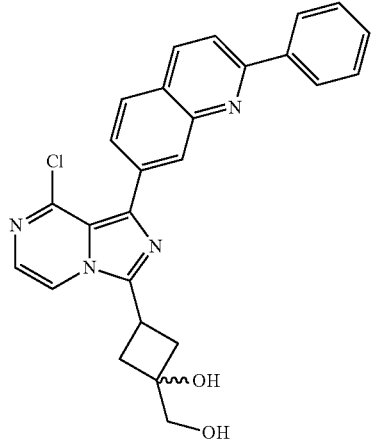 [SMILES: OCC1(O)CC(c2nc(-c3ccc4ccc(-c5ccccc5)nc4c3)c3c(Cl)nccn23)C1]

To a solution of 7-[8-chloro-3-(3-methylenecyclobutyl)imidazo[1,5-a]pyrazin-1-yl]-2-phenylquinoline (3.2 g, 7.6 mmol) in THF-water mixture (100 mL, 3:1) were added NMO (1.94 g, 8.3 mmol) and potassium osmate dihydrate (0.14 g, 0.4 mmol). The reaction mixture was stirred at rt. After 20 h the reaction was quenched with Na$_2$SO$_3$ (4.8 g, 38 mmol). The reaction mixture was diluted with EtOAc (250 mL) and washed with brine (2×100 mL). Part of the solvent was removed and the organic phase was passed through celite, dried over anhydrous Na$_2$SO$_4$ and concentrated in vacuo. The material was carried on to the subsequent oxidation without further purification.

3-[8-chloro-1-(2-phenylquinolin-7-yl)imidazo[1,5-a]pyrazin-3-yl]cyclobutanone

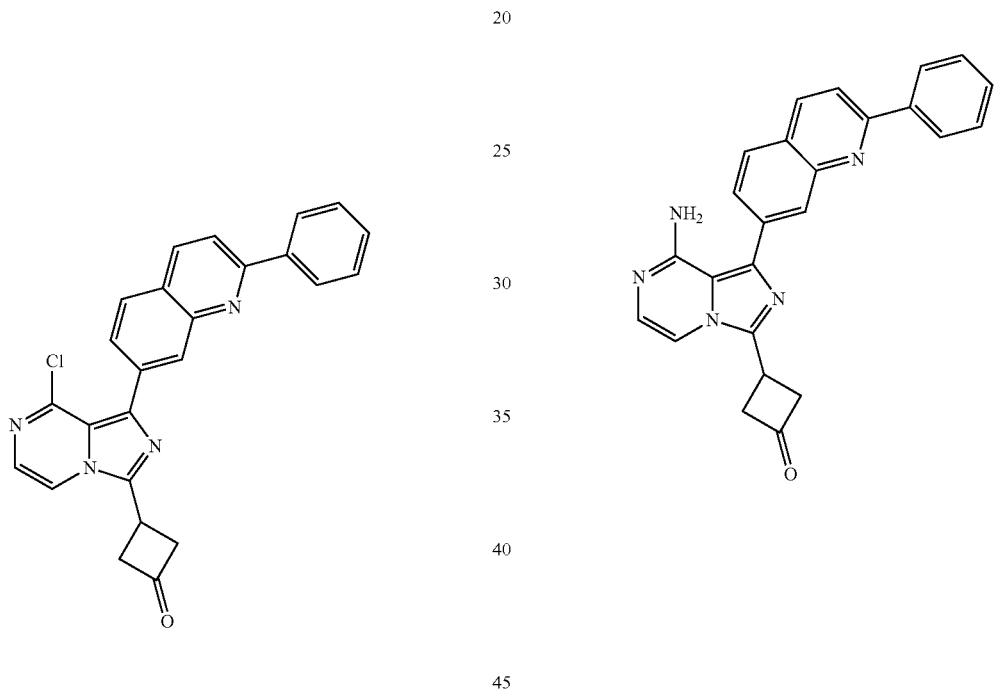

To a solution of 3-[8-chloro-1-(2-phenylquinolin-7-yl)imidazo[1,5-a]pyrazin-3-yl]-1-(hydroxymethyl)cyclobutanol (7.6 mmol) in a THF-water mixture (200 mL, 3:1) was added NaIO$_4$ (1.95 g, 9.2 mmol) at 0° C. The reaction mixture was slowly warmed to rt and stirred for 4 h. The reaction mixture was diluted with EtOAc (200 mL) and washed with brine (2×75 mL). The organic phase was dried over anhydrous Na$_2$SO$_4$ and concentrated in vacuo. The resulting residue was purified by silica gel chromatography (Jones Flashmaster, 70 g/150 mL cartridge), eluting with 1:9 EtOAc/Hex→1:1 EtOAc/Hex to afford the desired product as a yellow solid. $^1$H NMR (400 MHz, CDCl$_3$) δ 3.70-3.62 (m, 2H), 3.94-3.85 (m, 3H), 7.56-7.45 (m, 4H), 7.64 (d, J=5.2, 1H), 7.94-7.89 (m, 3H), 8.20-8.18 (m, 2H), 8.28 (dd, J=0.4 Hz, 8.4 Hz, 1H), 8.52 (t, J=0.8 Hz, 1H). MS (ES+): m/z 425/427 (3/1) [MH$^+$]. HPLC: t$_R$=3.7 min (Mass Directed purification system polar 5 min method).

Example 108

3-[8-Amino-1-(2-phenyl-quinolin-7-yl)-imidazo[1,5-a]pyrazin-3-yl]-cyclobutanone

To a solution of 3-[8-amino-1-(2-phenylquinolin-7-yl)-imidazo[1,5-a]pyrazin-3-yl]-1-hydroxymethyl-cyclobutanol (7.282 g, 17.69 mmol) in THF-water mixture (200 mL, 3:1) was added NaIO$_4$ (4.542 g, 21.23 mmol) and the reaction was stirred at rt overnight. The reaction mixture was diluted with DCM (500 mL) and the DCM layer was separated, washed with brine, dried over anhydrous Na$_2$SO$_4$ and evaporated in vacuo. The crude product was purified by chromatography on silica gel using DCM: MeOH as eluent (0%→2%) yielded the desired compound as a yellow solid. MS (ES+): m/z 406.15 [MH$^+$]. HPLC: t$_R$=2.23 min (OpenLynx, polar_5 min). $^1$H NMR (400 MHz, CDCl$_3$) δ 3.60-3.36 (m, 2H), 3.82-3.92 (m, 3H), 5.31 (br, 2H), 7.21 (dd, J=12.8, 4.8 Hz, 2H), 7.48-7.56 (m, 3H), 7.91-7.98 (m, 3H), 8.18-8.20 (m, 2H), 8.28 (d, J=8.0 Hz, 1H), 8.42 (s, 1H).

Method X1: General procedure for the synthesis of compounds of Formula II-M1 (compound of Formula II-M where Q$^1$=2-phenyl-quinolin-7-yl) from compounds of Formula II-L1 (Compound of Formula II-L where Q$^1$=2-phenyl-quinolin-7-yl):

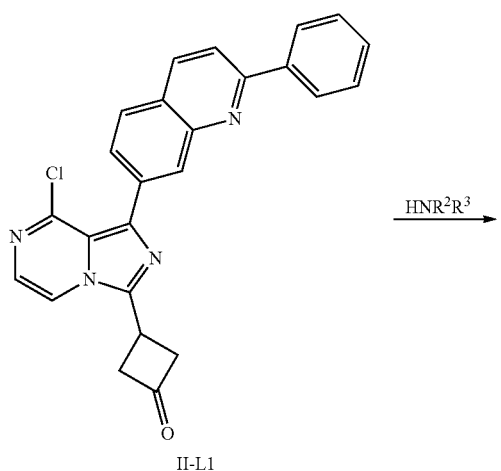

II-L1

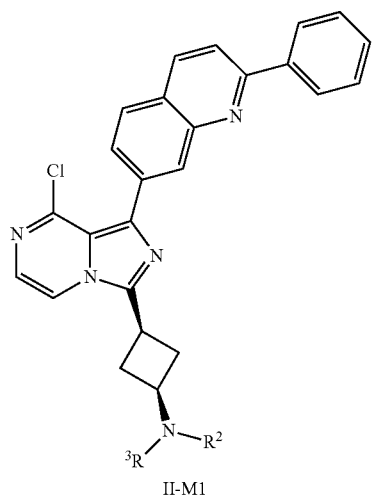

II-M1

To a solution of 3-{(8-chloroimidazo)-2-phenylquinolin[1,5-a]pyrazin-3-yl}cyclobutanone (2.2 mmol, 953 mg) in DCE (0.2 M), HNR²R³ (3.4 mmol) and sodium triacetoxyborohydride (4.4 mmol, 930 mg) were added. The resulting mixture was stirred at rt overnight. The reaction mixture was diluted with DCM (50 mL) and washed with saturated NaHCO₃ (2×45 mL) and brine (45 mL). The solvent was dried over anhydrous Na₂SO₄ and concentrated in vacuo. The resulting residue was purified by silica gel chromatography, eluting with 0%→1% 2M NH₃ in MeOH/DCM to afford the desired product as a yellow solid.

To a solution of 3-{(8-chloroimidazo)-2-phenylquinolin[1,5-a]pyrazin-3-yl}cyclobutanone (60 mg, 0.1 mmol) in DCE (0.2M) were added HNR²R³ (0.2 mmol) and a catalytic amount of AcOH (10 μL). The mixture was stirred at rt for 30 min then charged with resin-bound triacetoxyborohydride (0.2 mmol, 100 mg). Reaction mixture was stirred at it. After 16 h the solution was filtered through a Buchner funnel to remove the resin. The filtrate was concentrated and the residue was dissolved in DCM (15 mL), washed with saturated NaHCO₃ (2×15 mL) and brine (15 mL). The solvent was dried over anhydrous Na₂SO₄ and concentrated in vacuo. The resulting residue was purified by silica gel chromatography, eluting with 0%→1% 2M NH₃ in MeOH/DCM to afford the desired product as a yellow solid.

Compounds of Formula II-M1 (compound of Formula II-M where Q¹=2-phenyl-quinolin-7-yl) synthesized according to Method X1:

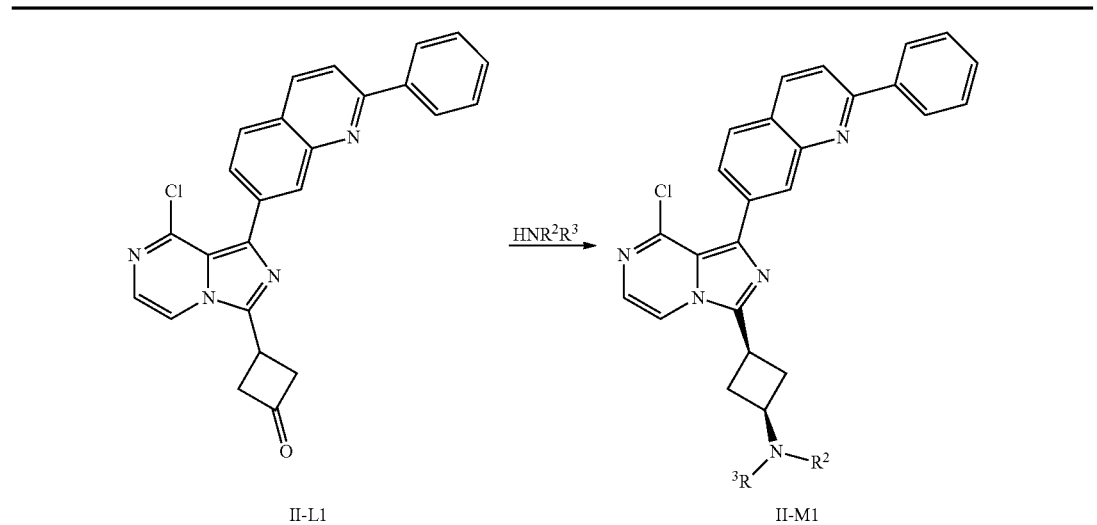

| Compound | Structure | Name | HNR²R³ | Analytical data |
|---|---|---|---|---|
| II-M1.1 | 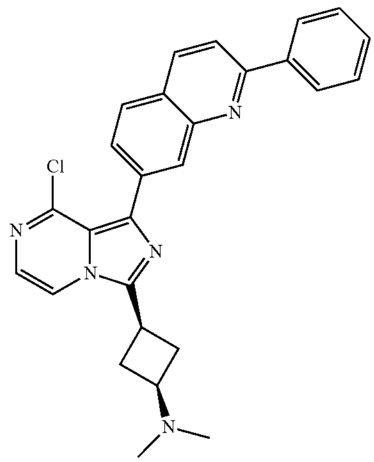 [SMILES: CN(C)[C@H]1C[C@@H](c2nc(-c3ccc4ccc(-c5ccccc5)nc4c3)c3c(Cl)nccn32)C1] | [3-(8-Chloro-2-phenylquinolin imidazo[1,5-a]pyrazin-3-yl)-cyclobutyl]-dimethyl-amine | H-N(CH₃)₂ | MS (ES+): m/z 454/456 (3/1) [MH⁺]; (CDCl₃, 400 MHz) δ 2.20 (s, 6H), 2.53 (m, 2H), 2.69 (m, 2H), 2.88 (m, 1H), 3.49 (m, 1H), 5.27 (br, 2H), 7.35 (d, J = 5.2 Hz, 1H), 7.47 (m, 1H), 7.53 (m, 1H), 7.61 (d, J = 5.2 Hz, 1H), 7.88 (m, 2H), 7.9 (d, J = 8.4 Hz, 1H), 8.19 (m, 2H), 8.25 (d, J = 9.2 Hz, 1H), 8.49 (s, 1H). |
| II-M1.2 | 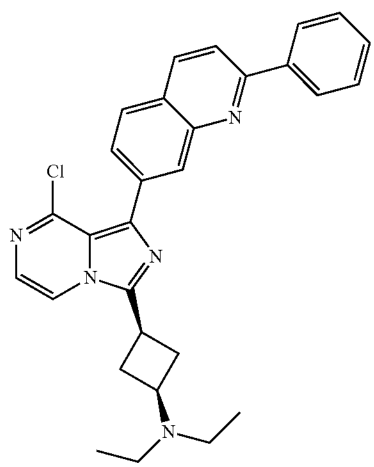 [SMILES: CCN(CC)[C@H]1C[C@@H](c2nc(-c3ccc4ccc(-c5ccccc5)nc4c3)c3c(Cl)nccn32)C1] | [3-(8-Chloro-2-phenylquinolin imidazo[1,5-a]pyrazin-3-yl)-cyclobutyl]-diethyl-amine | H-N(Et)₂ | MS (ES+): m/z 482/484 (3/1) [MH⁺]. |
| II-M1.3 | 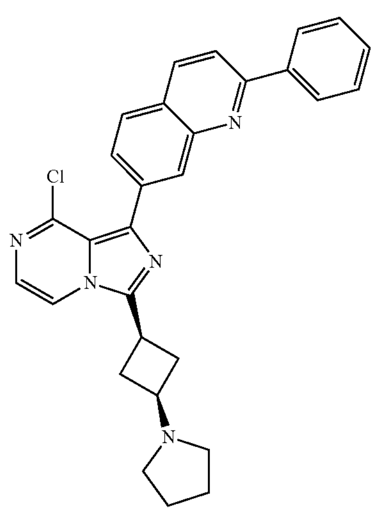 [SMILES: Clc1nccn2c1c(-c1ccc3ccc(-c4ccccc4)nc3c1)nc2[C@H]1C[C@@H](N2CCCC2)C1] | 7-[8-Chloro-3(3-pyrrolidin-1-yl-cyclobutyl)-imidazo[1,5-a]pyrazin-1-yl]-2-phenyl-quinoline | H-N(pyrrolidine) | MS (ES+): m/z 482/484 (3/1) [MH⁺]. |

| | | | |
|---|---|---|---|
| II-M1.4 | 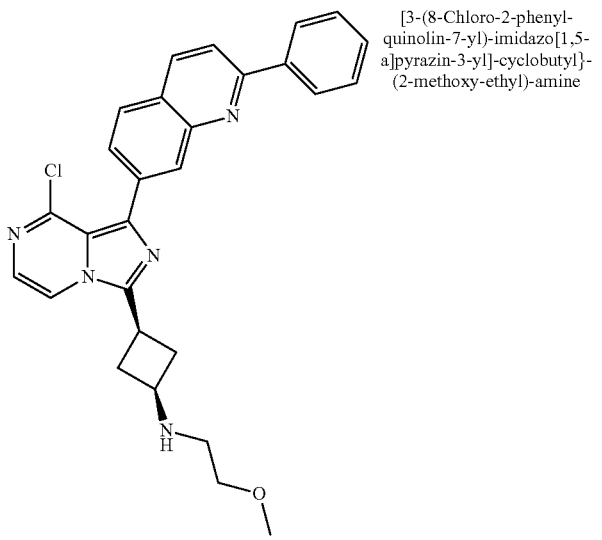 [3-(8-Chloro-2-phenyl-quinolin-7-yl)-imidazo[1,5-a]pyrazin-3-yl]-cyclobutyl}-(2-methoxy-ethyl)-amine | H‑NH‑CH₂CH₂‑OCH₃ | MS (ES+): m/z 484/486 (3/1) [MH⁺]. |
| II-M1.5 | 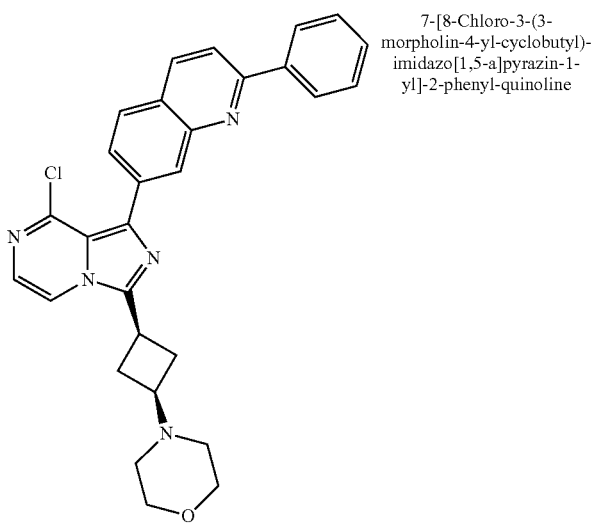 7-[8-Chloro-3-(3-morpholin-4-yl-cyclobutyl)-imidazo[1,5-a]pyrazin-1-yl]-2-phenyl-quinoline | morpholine | MS (ES+): m/z 496/498 (3/1) [MH⁺]. |
| II-M1.6 | 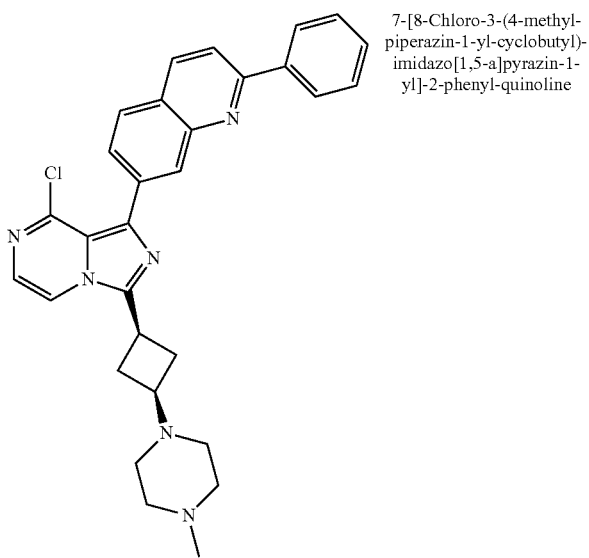 7-[8-Chloro-3-(4-methyl-piperazin-1-yl-cyclobutyl)-imidazo[1,5-a]pyrazin-1-yl]-2-phenyl-quinoline | 4-methylpiperazine | MS (ES+): m/z 509/511 (3/1) [MH⁺]; (CDCl₃, 400 MHz) δ 2.30(s, 3H), 2.38-2.73 (m, 12H), 2.96-3.00 (m, 1H), 3.48-3.54 (m, 1H), 7.35 (d, J = 5.2 Hz, 1H), 7.47-7.48 (m, 1H), 7.52-7.55 (m, 2H), 7.60 (d, J = 5.2, 1H), 7.88-7.92 (m, 3H), 8.18-8.20 (m, 2H), 8.26 (d, J = 8.8 Hz, 1H), 8.50 (s, 1H). |

| | | | |
|---|---|---|---|
| II-M1.7 | 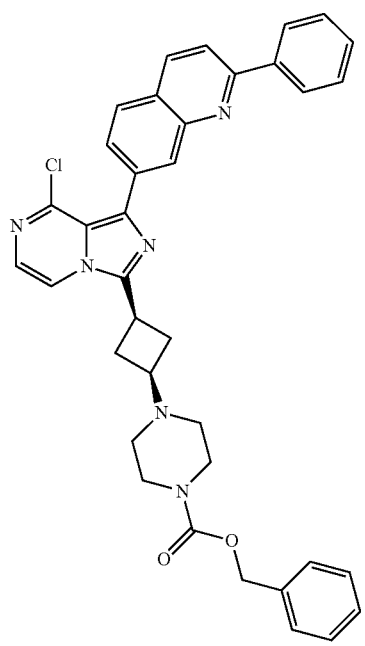 [SMILES: O=C(OCc1ccccc1)N1CCN([C@H]2C[C@@H](c3nc(-c4ccc5ccc(-c6ccccc6)nc5c4)c4c(Cl)nccn43)C2)CC1] | 4-(3-[8-Chloro-1-(2-phenyl-quinolin-7-yl)-imidazo[1,5-a]pyrazin-3-yl]-cyclobutyl)-piperazine-1-carboxcylic acid benzyl ester | 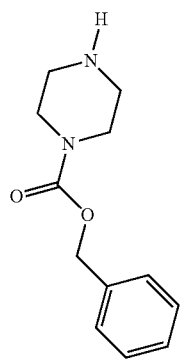 [SMILES: O=C(OCc1ccccc1)N1CCNCC1] MS (ES+): m/z 629/631 (3/1) [MH$^+$]. |
| II-M1.8 | 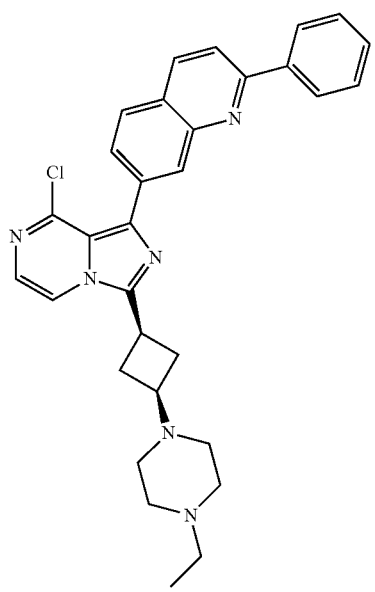 [SMILES: CCN1CCN([C@H]2C[C@@H](c3nc(-c4ccc5ccc(-c6ccccc6)nc5c4)c4c(Cl)nccn43)C2)CC1] | 7-[8-Chloro-3-(4-ethyl-piperazin-1-yl-cyclobutyl)-imidazo[1,5-a]pyrazin-1-yl]-2-phenyl-quinoline | 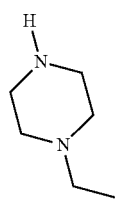 MS (ES+): m/z 523/525 (3/1) [MH$^+$]. |

-continued
| | | | | |
|---|---|---|---|---|
| II-M1.9 | 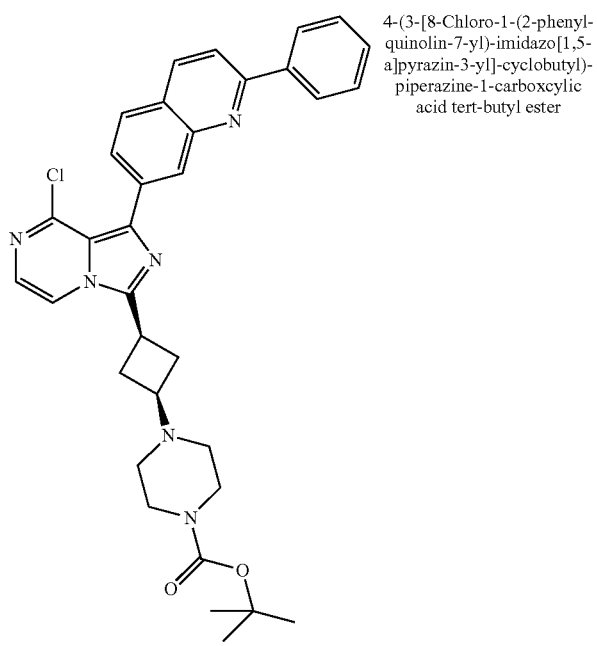 | 4-(3-[8-Chloro-1-(2-phenyl-quinolin-7-yl)-imidazo[1,5-a]pyrazin-3-yl]-cyclobutyl)-piperazine-1-carboxcylic acid tert-butyl ester | 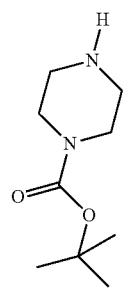 | MS (ES+): m/z 595/597 (3/1) [MH+]. |
| II-M1.10 | 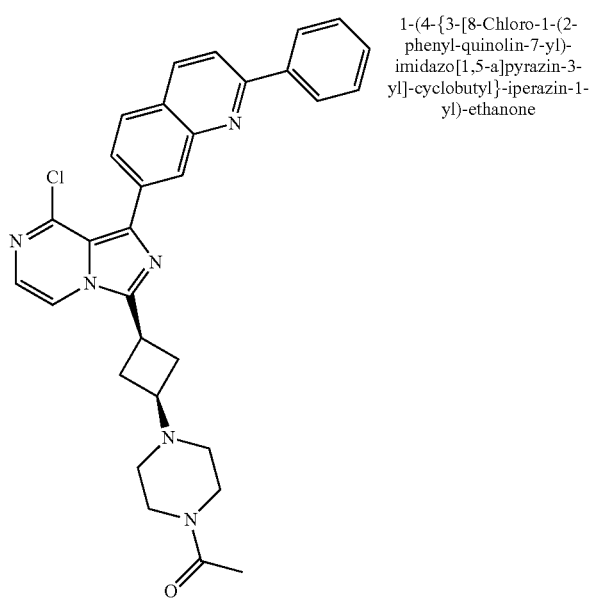 | 1-(4-{3-[8-Chloro-1-(2-phenyl-quinolin-7-yl)-imidazo[1,5-a]pyrazin-3-yl]-cyclobutyl}-iperazin-1-yl)-ethanone | 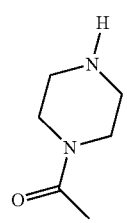 | MS (ES+): m/z 536/538 (3/1) [MH+]; (CDCl₃, 400 MHz) δ 2.09 (s, 3H), 2.35-2.41 (m, 4H), 2.52-2.59 (m, 2H), 2.67-2.74 (m, 2H), 2.92-2.99 (m, 1H), 3.46-3.64 (m, 5H), 7.37 (d, J = 5.2 Hz, 1H), 7.45-7.56 (m, 3H), 7.59 (d, J = 4.8 Hz, 1H), 7.89-7.92 (m, 3H), 8.18-8.20 (m, 2H), 8.27 (d, J = 8.8 Hz, 1H), 8.51 (s, 1H). |

Method X2: General procedure for the synthesis of compounds of Formula I-L1 (compound of Formula I-L where Q¹=2-phenyl-quinolin-7-yl) from compounds of Formula II-M1 (Compound of Formula II-M where Q¹=2-phenyl-quinolin-7-yl):

Q¹=2-phenyl-quinolin-7-yl) from compounds of Formula I-K1 (Compound of Formula I-K where Q¹=2-phenyl-quinolin-7-yl):

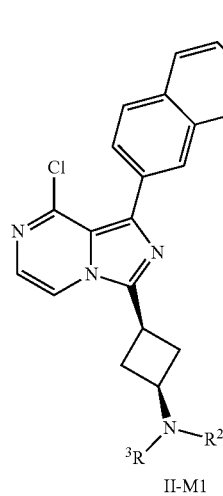

II-M1

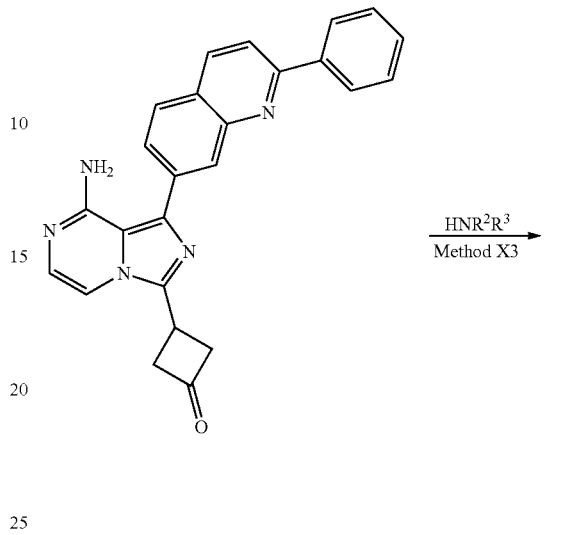

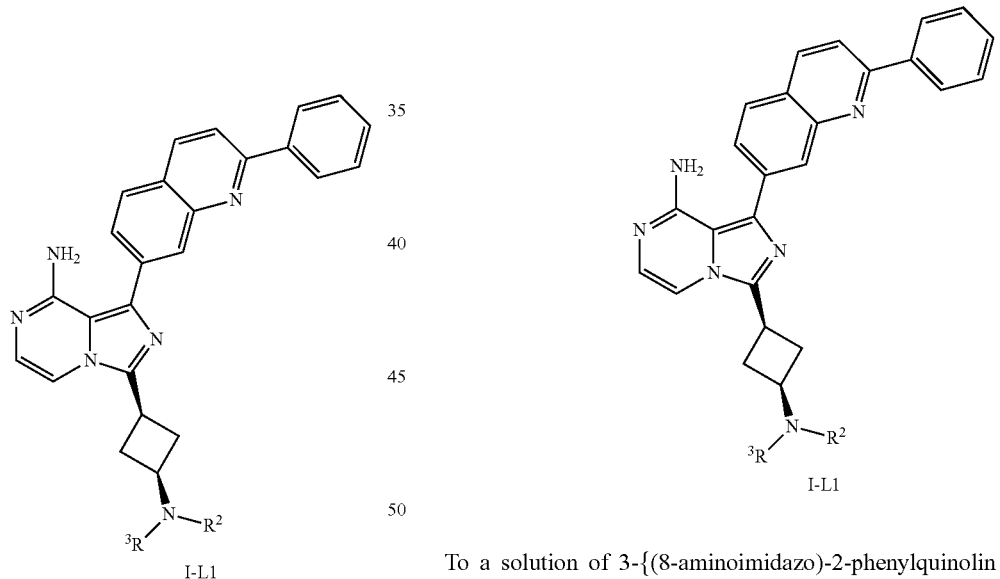

I-L1

Into a Parr pressure reactor a suspension of compound of Formula II-M1 (0.105 g, 0.22 mmol) in i-PrOH and Tetrahydrofuran (10:1, 30 mL) was cooled to −78° C. and was charged with liquid $NH_3$ for 3-6 min. The resulting solution was heated at 110° C. for 18-48 h. The Parr vessel was cooled to −78° C. and the reaction slurry was transferred to a round bottom flask and the solvent was removed in vacuo. The resulting mixture was re-suspended in DCM and was filtered through a glass-fitted funnel to remove $NH_4Cl$. The reaction was chromatographed on $SiO_2$ eluting with 1%→2%→3% 2M $NH_3$ in MeOH/DCM resulting in the desired yellow solid.

Method X3: General procedure for the synthesis of compounds of Formula I-L1 (compound of Formula I-L where To a solution of 3-{(8-aminoimidazo)-2-phenylquinolin[1,5-a]pyrazin-3-yl}cyclobutanone (2.2 mmol, 953 mg) in DCE (0.2M), $HNR^2R^3$ (3.4 mmol) and sodium triacetoxyborohydride (4.4 mmol, 930 mg) were added. The resulting mixture was stirred at it overnight. The reaction mixture was diluted with DCM (50 mL) and washed with saturated $NaHCO_3$ (2×45 mL) and brine (45 mL). The solvent was dried over anhydrous $Na_2SO_4$ and concentrated in vacuo. The resulting residue was purified by silica gel chromatography, eluting with 1%→2%→3% 2M $NH_3$ in MeOH/DCM to afford the desired product as a yellow solid, further purification via re-crystallization when necessary.

The following compounds of Formula I-L1 (compound of Formula I-L where Q¹=2-phenyl-quinolin-7-yl) were synthesized according to either Method X2 or X3:

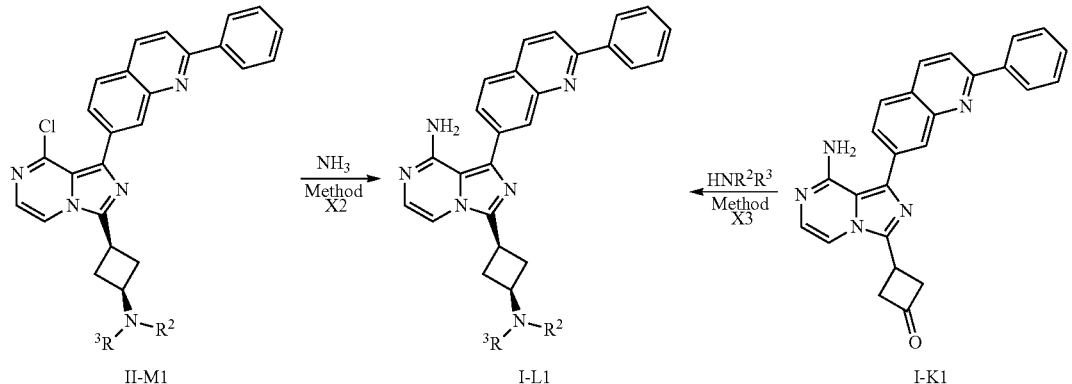

| Example | Structure | Name | HNR²R³ | Analytical data | Method |
|---|---|---|---|---|---|
| 109 | 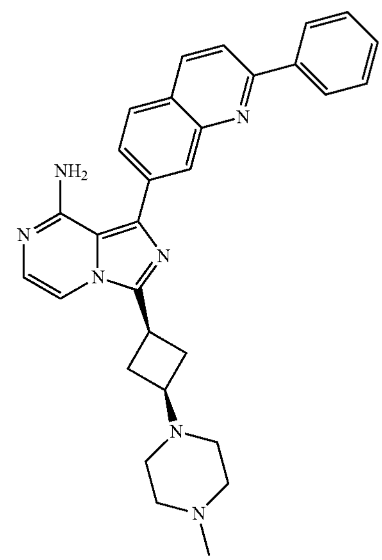 [SMILES: CN1CCN([C@H]2C[C@@H](c3nc(-c4ccc5ccc(-c6ccccc6)nc5c4)c4c(N)nccn43)C2)CC1] | 3-[3-(4-Methyl-piperazin-1-yl)-cyclobutyl]-1-(2-phenyl-quinolin-7-yl)-imidazo[1,5-a]pyrazin-8-ylamine | H-N(piperazine)-N-CH₃ | (ES+): m/z 490 [MH⁺]; (400 MHz, $(CD_3)_2SO$) δ 0.96 (t, J = 3.2 HZ, 3H), 2.16-2.44 (m, 10H), 2.52-2.59 (m, 2H), 2.74-2.80 (m, 1H), 3.29 (m, 2H), 3.59-3.64 (m, 1H), 6.19 (br, 2H), 7.08 (d, J = 4.8 Hz, 1H), 7.48-7.58 (m, 4H), 7.92 (d, J = 6.4 Hz, 1H), 8.08 (d, J = 8.4 Hz, 1H), 8.17 (d, J = 8.4 Hz, 1H), 8.23 (s, 1H), 8.29-8.31 (m, 2H), 8.50 (d, J = 8.8 Hz, 1H). | X2 |
| 110 | 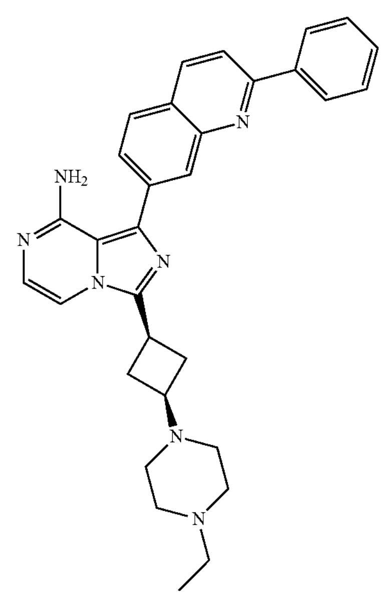 [SMILES: CCN1CCN([C@H]2C[C@@H](c3nc(-c4ccc5ccc(-c6ccccc6)nc5c4)c4c(N)nccn43)C2)CC1] | 3-[3-(4-Ethyl-piperazin-1-yl)-cyclobutyl]-1-(2-phenyl-quinolin-7-yl)-imidazo[1,5-a]pyrazin-8-ylamine | H-N(piperazine)-N-CH₂CH₃ | (ES+): m/z 504 [MH⁺]; (400 MHz, $CDCl_3$) δ 1.10 (t, J = 6.8 Hz, 3H) 1.63 (m, 4H), 2.48-2.58 (m, 6H), 2.96 (m, 1H), 3.49 (m, 3H), 5.19 (br, 2H), 7.11 (d, J = 4.8 Hz, 1H), 7.19 (d, J = 5.2 Hz, 1H), 7.48-7.56 (m, 3H), 7.91-7.94 (m, 3H), 8.18-8.21 (m, 2H), 8.27 (d, J = 8 Hz, 1H), 8.39 (s, 1H). | X2 |

| 111 | 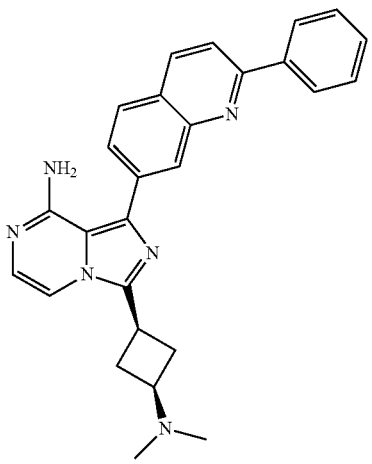 [SMILES: CN(C)[C@H]1C[C@@H](c2nc(-c3ccc4ccc(-c5ccccc5)nc4c3)c3c(N)nccn32)C1] | 3-[3-(dimethylamino)cyclobutyl]-1-(2-phenyl-quinolin-7-yl)imidazol[1,5-a]pyrazin-8-ylamine |  | (ES+): m/z 435 [MH+]; (400 MHz, CDCl$_3$) δ 2.23 (s, 6H), 2.54 (m, 2H), 2.69 (m, 2H), 2.90 (m, 1H), 3.45 (m, 1H), 5.27 (br, 2H), 7.11 (d, J = 4.8 Hz, 1H), 7.21 (d, J = 4.8 Hz, 1H), 7.47-7.56 (m, 3H), 7.91-7.94 (m, 3H), 8.18-8.20 (m, 2H), 8.27 (d, J = 8.8 Hz, 1H), 8.39 (s, 1H). | X2 |
|---|---|---|---|---|---|
| 112 | 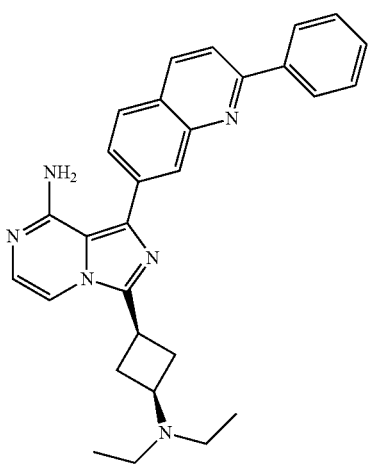 [SMILES: CCN(CC)[C@H]1C[C@@H](c2nc(-c3ccc4ccc(-c5ccccc5)nc4c3)c3c(N)nccn32)C1] | 3-[3-(diethylamino)cyclobutyl]-1-(2-phenyl-quinolin-7-yl)imidazol[1,5-a]pyrazin-8-ylamine | 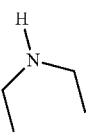 | (ES+): m/z 463 [MH+]; (400 MHz, CDCl$_3$) δ 1.02 (t, J = 7.2 Hz, 6H), 2.52-2.69 (m, 8H), 3.29 (m, 1H), 3.43 (m, 1H), 5.29 (br, 2H), 7.09 (d, J = 4.0 Hz, 1H), 7.18 (d, J = 4.8, 1H), 7.47-7.55 (m, 3H), 7.89-7.93 (m, 3H), 8.18 (m, 2H), 8.25 (d, J = 8.0 Hz, 1H), 8.39 (s, 1H). | X2 |
| 113 | 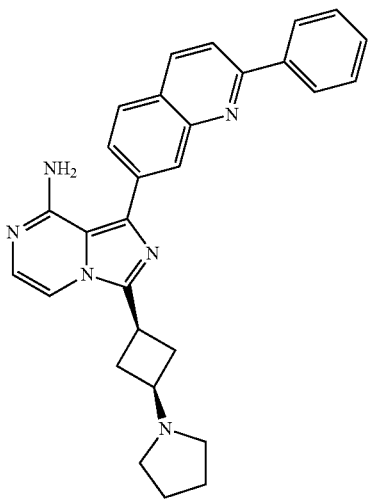 [SMILES: Nc1nccn2c1c(-c1ccc3ccc(-c4ccccc4)nc3c1)nc2[C@H]1C[C@@H](N2CCCC2)C1] | 1-(2-Phenyl-quinolin-7-yl)-3-(3-pyrrolidin-1-yl-cyclobutyl)-imidazo[1,5-a]pyrazin-8-ylamine | 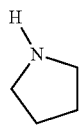 | (ES+): m/z 461 [MH+]; (400 MHz, CDCl$_3$) δ 1.80 (m, 4H), 2.54-2.69 (m, 8H), 3.15 (m, 1H), 3.5 (m, 1H), 5.23 (br, 2H), 7.10 (d, J = 4.4 Hz, 1H), 7.19 (d, J = 4.8, 1H), 7.47-7.55 (m, 3H), 7.90-7.94 (m, 3H), 8.19 (m, 2H), 8.26 (d, J = 8.0 Hz, 1H), 8.39 (s, 1H). | X2 |

| | | | | |
|---|---|---|---|---|
| 114 | 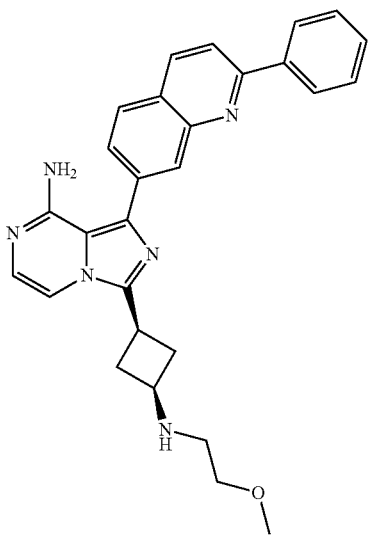 [SMILES: COCCN[C@H]1C[C@@H](c2nc(-c3ccc4ccc(-c5ccccc5)nc4c3)c3c(N)nccn32)C1] | 3-[3-(2-Methoxy-ethylamino)-cyclobutyl]-1-(2-phenyl-quinolin-7-yl)imidazo[1,5-a]pyrazin-8-ylamine | 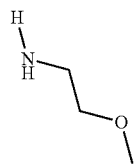 | (ES+): m/z 465 [MH$^+$]; (400 MHz, CDCl$_3$) δ 2.39-2.46 (m, 2H), 2.84-2.95 (m, 5H), 3.28 (s, 3H), 3.47-3.54 (m, 3H), 7.10 (d, J = 5.2 Hz, 1H), 7.17 (d, J = 4.8, 1H), 7.47-7.55 (m, 3H), 7.90-7.96 (m, 3H), 8.18-8.20 (m, 2H), 8.26 (d, J = 8.4 Hz, 1H), 8.40 (s, 1H). | X2 |
| 115 | 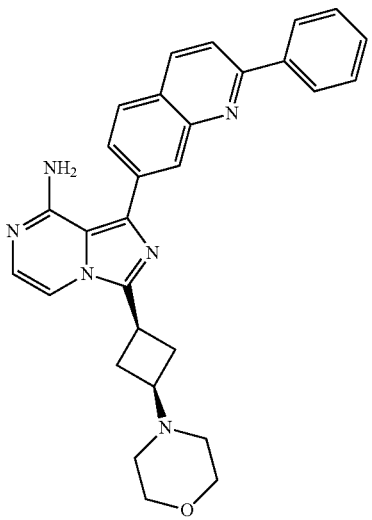 | 3-(3-morpholin-4-ylcyclobutyl)-1-(2-phenyl-quinolin-7-yl)imidazol[1,5-a]pyrazin-8-ylamine | 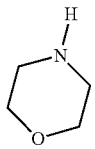 | (ES+): m/z 477 [MH$^+$]; (400 MHz, CDCl$_3$) δ 2.43 (m, 4H), 2.51-2.54 (m, 2H), 2.66-2.70 (m, 2H), 2.96 (m, 1H), 3.51 (m, 1H), 3.72-3.74 (m, 4H), 5.23 (br, 2H), 7.12 (d, J = 4.8 Hz, 1H), 7.20 (d, J = 4.8, 1H), 7.48-7.56 (m, 3H), 7.91-7.95 (m, 3H), 8.18-8.20 (m, 2H), 8.27 (d, J = 8.4 Hz, 1H), 8.40 (s, 1H). | X2 |

-continued
| | | | | | |
|---|---|---|---|---|---|
| 116 | 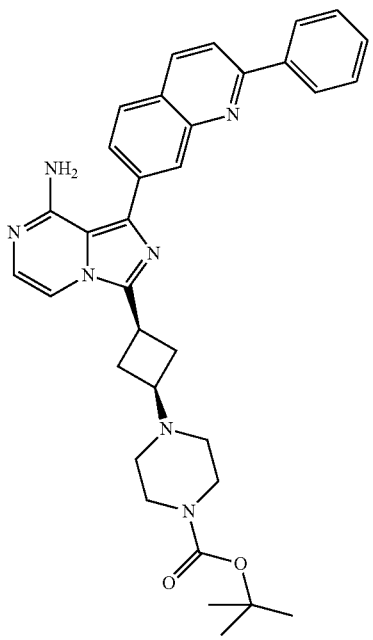 | 3-[(3-(4-tert butyl carboxylate piperazin-1-yl)cyclobutyl]-1-(2-phenyl-quinolin-7-yl)imidazol[1,5-a]pyrazin-8-ylamine | H 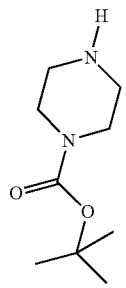 | (ES+): m/z 576 [MH⁺]; (400 MHz, CDCl₃) δ 1.46 (s, 9H), 2.34-2.37 (m, 4H), 2.51-2.54 (m, 2H), 2.68-2.70 (m, 2H), 2.94 (m, 1H), 3.44-3.49 (m, 5H), 5.29 (br, 2H), 7.11 (d, J = 5.2 Hz, 1H), 7.20 (d, J = 5.2 Hz, 1H), 7.48-7.55 (m, 3H), 7.92-7.95 (m, 3H), 8.18-8.21 (m, 2H), 8.27 (d, J = 8 Hz, 1H), 8.40 (s, 1H). | X2 |
| 117 | 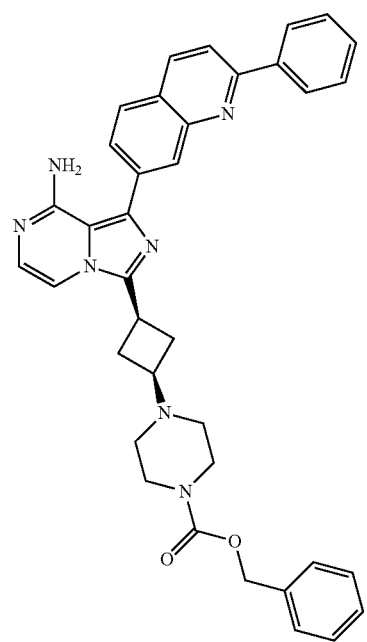 [SMILES: Nc1nccn2c1c(-c1ccc3ccc(-c4ccccc4)nc3c1)nc2[C@H]1C[C@@H](N2CCN(C(=O)OCc3ccccc3)CC2)C1] | 3-[(3-(4-benzyl carboxylate piperazin-1-yl)cyclobutyl]-1-(2-phenyl-quinolin-7-yl)imidazol[1,5-a]pyrazin-8-ylamine | H 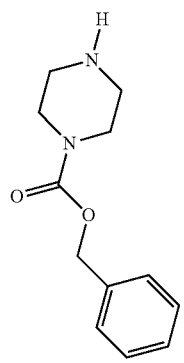 | (ES+): m/z 610 [MH⁺]; (400 MHz, CDCl₃) δ 2.35-2.38 (m, 4H), 2.51-2.56 (m, 2H), 2.66-2.72 (m, 2H), 2.93 (m, 1H), 3.47-3.55 (m, 5H), 5.13 (s, 2H), 5.34 (br, 2H), 7.10 (d, J = 5.2 Hz, 1H), 7.19 (d, J = 5.2 Hz, 1H), 7.33-7.37 (m, 5H), 7.48-7.55 (m, 3H), 7.93 (m, 3H), 8.19-8.21 (m, 2H), 8.27 (d, J = 8.4 Hz, 1H), 8.40 (s, 1H). | X2 |

| | | | | | |
|---|---|---|---|---|---|
| 118 | 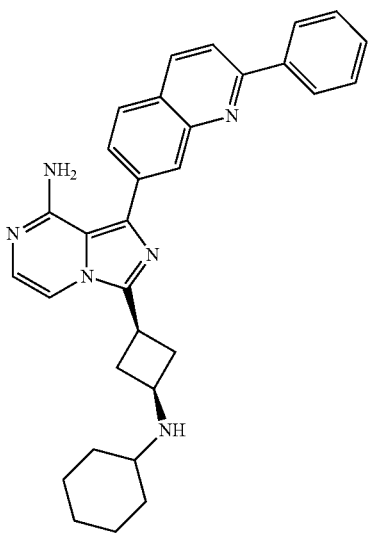 [SMILES: Nc1nccn2c1c(-c1ccc3ccc(-c4ccccc4)nc3c1)nc2[C@H]1C[C@@H](NC2CCCCC2)C1] | 3-[(3-Cyclohexylamino-cyclobutyl)-1-(2-phenyl-quinolin-7-yl)imidazol[1,5-a]pyrazin-8-ylamine | 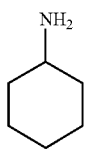 | (ES+): m/z 489 [MH+]; (400 MHz, CDCl$_3$) δ 1.11-1.25 (m, 6H), 1.71 (m, 1H), 1.74 (m, 2H), 1.86 (m, 2H), 2.33-2.36 (m, 2H), 2.55 (m, 1H), 2.88-2.91 (m, 2H), 3.43 (m, 1H), 3.55 (m, 1H), 5.29 (br, 2H), 7.10 (d, J = 4.8 Hz, 1H), 7.18 (d, J = 5.2 Hz, 1H), 7.47-7.55 (m, 3H), 7.90-7.96 (m, 3H), 8.17-8.19 (m, 2H), 8.26 (d, J = 8.8 Hz, 1H), 8.40 (s, 1H). | X3 |
| 119 | 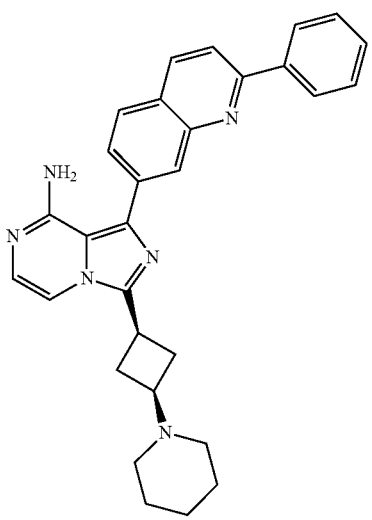 [SMILES: Nc1nccn2c1c(-c1ccc3ccc(-c4ccccc4)nc3c1)nc2[C@H]1C[C@@H](N2CCCCC2)C1] | 1-(2-Phenyl-quinolin-7-yl)-3-(3-piperidin-1-yl-cyclobutyl)-1-imidazo[1,5-a]pyrazin-8-ylamine | 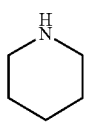 | (ES+): m/z 475 [MH+]; (400 MHz, CDCl$_3$) δ 1.45-1.46 (m, 2H), 1.57-1.62 (m, 4H), 2.31-2.39 (m, 4H), 2.50-2.55 (m, 2H), 2.65-2.72 (m, 2H), 2.88 (m, 1H), 3.47 (m, 1H), 5.22 (br, 2H), 7.10 (d, J = 4.8 Hz, 1H), 7.20 (d, J = 5.2 Hz, 1H), 7.47-7.56 (m, 3H), 7.91-7.94 (m, 3H), 8.18-8.21 (m, 2H), 8.26 (d, J = 8.4 Hz, 1H), 8.38 (s, 1H). | X3 |
| 120 | 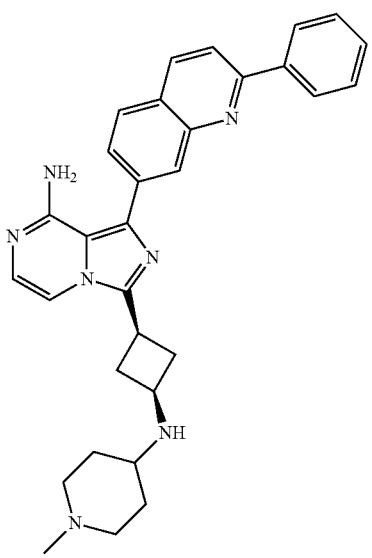 [SMILES: CN1CCC(N[C@H]2C[C@@H](c3nc(-c4ccc5ccc(-c6ccccc6)nc5c4)c4c(N)nccn43)C2)CC1] | 3-[3-(1-Methyl-piperidin-4-ylamino)-cyclobutyl]-1-(2-phenyl-quinolin-7-yl)imidazol[1,5-a]pyrazin-8-ylamine | 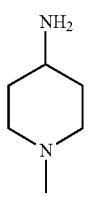 | (ES+): m/z 504 [MH+]; (400 MHz, CDCl$_3$) δ 1.25-1.28 (m, 3H), 1.84 (m, 2H), 2.00 (m, 2H), 2.28-2.37 (m, 5H), 2.56 (br, 1H), 2.85-2.92 (m, 4H), 3.40-3.52 (m, 1H), 5.18 (br, 2H), 7.12 (d, J = 5.2 Hz, 1H), 7.18 (d, J = 5.2 Hz, 1H), 7.48-7.56 (m, 3H), 7.91-7.95 (m, 3H), 8.18-8.20 (m, 2H), 8.27 (d, J = 8.4 Hz, 1H), 8.41 (s, 1H). | X3 |

| | | | | | |
|---|---|---|---|---|---|
| 121 | 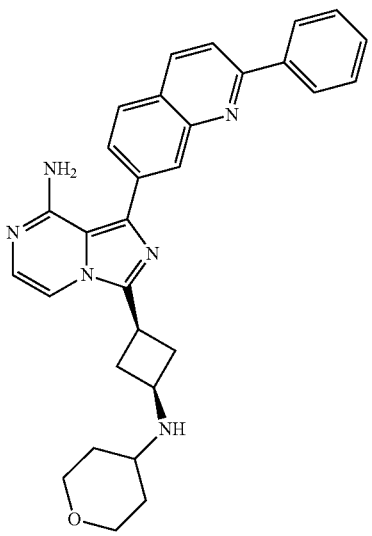 | 1-(2-Phenyl-quinolin-7-yl)-3-[3-(tetrahydro-pyran-4-ylamino)-cyclobutyl]-imidazo[1,5-a]pyrazin-8-ylamine | 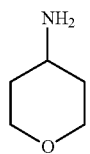 | (ES+): m/z 491 [MH+]; (400 MHz, CDCl$_3$) δ 1.26 (m, 2H), 1.40-1.49 (m, 2H), 1.78-1.82 (m, 2H), 2.30-2.38 (m, 2H), 2.77-2.79 (m, 1H), 2.86-2.92 (m, 2H), 3.38-3.54 (m, 3H), 3.96-3.99 (m, 2H), 5.25 (br, 2H), 7.11 (d, J = 4.8 Hz, 1H), 7.18 (d, J = 4.8 Hz, 1H), 7.48-7.56 (m, 3H), 7.91-7.96 (m, 3H), 8.19 (m, 2H), 8.27 (d, J = 8.8 Hz, 1H), 8.41 (s, 1H). | X3 |
| 122 | 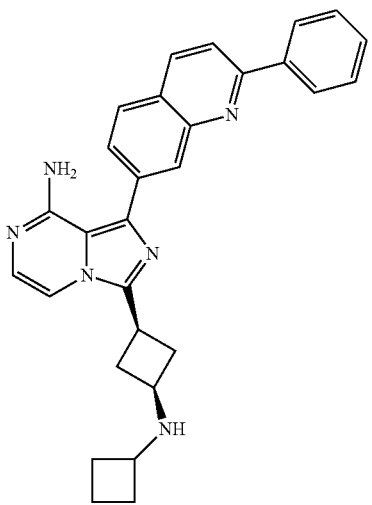 [SMILES: Nc1nccn2c1c(-c1ccc3ccc(-c4ccccc4)nc3c1)nc2[C@H]1C[C@@H](NC2CCC2)C1] | 3-(3-cyclobutylamino-cyclobutyl)-1-(2-phenyl-quinolin-7-yl)imidazol[1,5-a]pyrazin-8-ylamine |  | (ES+): m/z 461 [MH+]; (400 MHz, CDCl$_3$) δ 1.65-1.78 (m, 4H), 2.17-2.21 (m, 2H), 2.34-2.37 (m, 2H), 2.38-2.86 (m, 2H), 3.33-3.42 (m, 3H), 5.29 (br, 2H), 7.11 (d, J = 4.8 Hz, 1H), 7.18 (d, J = 5.2 Hz, 1H), 7.47-7.56 (m, 3H), 7.90-7.96 (m, 3H), 8.18-8.20 (m, 2H), 8.26 (d, J = 8.8 Hz, 1H), 8.41 (s, 1H). | X3 |
| 123 | 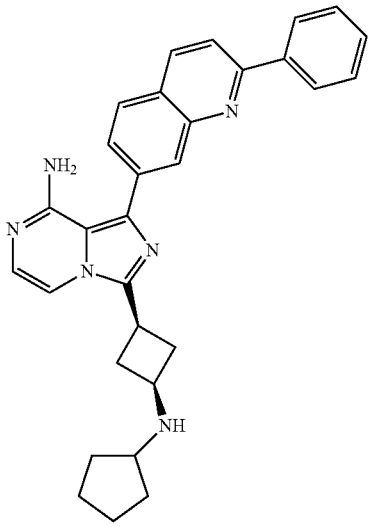 [SMILES: Nc1nccn2c1c(-c1ccc3ccc(-c4ccccc4)nc3c1)nc2[C@H]1C[C@@H](NC2CCCC2)C1] | 3-(3-cyclopentylamino-cyclobutyl)-1-(2-phenyl-quinolin-7-yl)imidazol[1,5-a]pyrazin-8-ylamine | 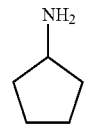 | (ES+): m/z 475 [MH+]; (400 MHz, CDCl$_3$) δ 1.41-1.45 (m, 2H), 1.52-1.56 (m, 2H), 1.70-1.75 (m, 2H), 1.84-1.90 (m, 2H), 2.36-2.45 (m, 3H), 2.90-2.97 (m, 2H), 3.17-3.21 (m, 1H), 3.46-3.54 (m, 1H), 5.57 (br, 2H), 7.08 (d, J = 5.2 Hz, 1H), 7.19 (d, J = 4.8 Hz, 1H), 7.48-7.57 (m, 3H), 7.90-7.97 (m, 3H), 8.18-8.21 (m, 2H), 8.28 (d, J = 8.8 Hz, 1H), 8.40 (s, 1H). | X3 |

| | | | | | |
|---|---|---|---|---|---|
| 124 | 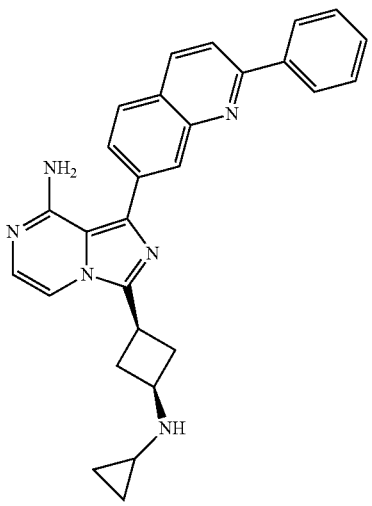 [SMILES: Nc1nccn2c1c(-c1ccc3ccc(-c4ccccc4)nc3c1)nc2[C@H]1C[C@@H](NC2CC2)C1] | 3-(3-cyclopropylamino-cyclobutyl)-1-(2-phenyl-quinolin-7-yl)imidazol[1,5-a]pyrazin-8-ylamine |  | (ES+): m/z 447 [MH+]; (400 MHz, CDCl$_3$) δ 0.38-0.41 (m, 2H), 0.44-0.47 (m, 2H), 2.17-2.20 (m, 1H), 2.36-2.41 (m, 2H), 2.88-2.94 (m, 2H), 3.43-3.55 (m, 2H), 5.30 (br, 2H), 7.12 (d, J = 5.2 Hz, 1H), 7.19 (d, J = 5.2 Hz, 1H), 7.48-7.56 (m, 3H), 7.92-7.95 (m, 3H), 8.18-8.21 (m, 2H), 8.27 (d, J = 8.8 Hz, 1H), 8.42 (s, 1H). | X3 |
| 125 | 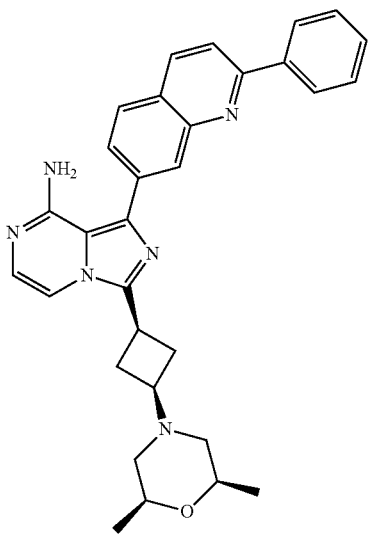 [SMILES: C[C@@H]1CN([C@H]2C[C@@H](c3nc(-c4ccc5ccc(-c6ccccc6)nc5c4)c4c(N)nccn43)C2)C[C@H](C)O1] | 3-[3-((2R,6S)-2,6-Dimethyl-morpholin-4-yl)-cyclobutyl]-1-(2-phenyl-quinolin-7-yl)imidazol[1,5-a]pyrazin-8-ylamine | 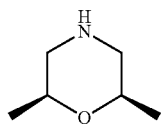 | (ES+): m/z 505 [MH+]; (400 MHz, CDCl$_3$) δ 1.17 (s, 3H), 1.18 (s, 3H), 2.50-2.55 (m, 2H), 2.66-2.68 (m, 2H), 2.74-2.77 (mm 2H), 2.91 (m, 1H), 3.49 (m, 1H), 3.65-3.70 (m, 2H), 5.24 (br, 2H), 7.11 (d, J = 5.2 Hz, 1H), 7.20 (d, J = 5.2 Hz, 1H), 7.45-7.57 (m, 3H), 7.91-7.94 (m, 3H), 8.18-8.20 (m, 2H), 8.27 (d, J = 8.4 Hz, 1H), 8.40 (s, 1H). | X3 |
| 126 | 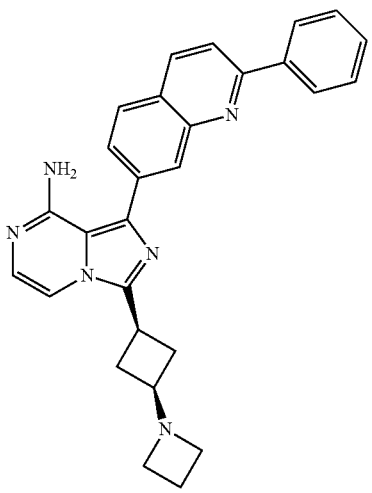 [SMILES: Nc1nccn2c1c(-c1ccc3ccc(-c4ccccc4)nc3c1)nc2[C@H]1C[C@@H](N2CCC2)C1] | 3-(3-Azetidin-1-yl)-cyclobutyl)-1-(2-phenyl-quinolin-7-yl)imidazol[1,5-a]pyrazin-8-ylamine |  | (ES+): m/z 447 [MH+]; (400 MHz, CDCl$_3$) δ 2.05-2.09 (m, 2H), 2.50-2.60 (m, 4H), 3.25-3.29 (m, 6H), 5.20 (br, 2H), 7.11 (d, J = 5.2 Hz, 1H), 7.19 (d, J = 5.2 Hz, 1H), 7.48-7.57 (m, 3H), 7.91-7.95 (m, 3H), 8.18-8.20 (m, 2H), 8.27 (d, J = 8.4 Hz, 1H), 8.41 (s, 1H). | X3 |

| | | | | |
|---|---|---|---|---|
| 127 | 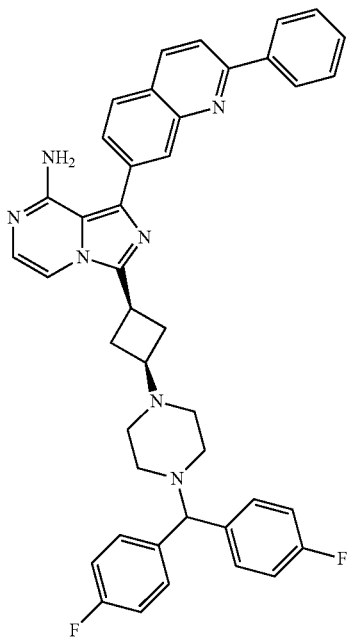 [SMILES: Nc1nccn2c1c(-c1ccc3ccc(-c4ccccc4)nc3c1)nc2[C@H]1C[C@@H](N2CCN(C(c3ccc(F)cc3)c3ccc(F)cc3)CC2)C1] | 3-(3-{4-[Bis-(4-fluoro-phenyl)-methyl]-piperazine-1-yl)-cyclobutyl)-1-(2-phenyl-quinolin-7-yl)imidazol[1,5-a]pyrazin-8-ylamine | 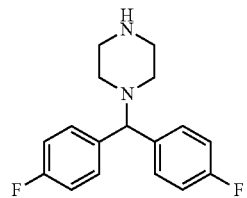 [SMILES: Fc1ccc(C(c2ccc(F)cc2)N2CCNCC2)cc1] | (ES+): m/z 678 [MH+]; (400 MHz, CDCl$_3$) δ 2.29-2.54 (m, 10H), 2.64-2.70 (m, 2H), 2.96-2.30 (m, 1H), 3.45-3.50 (m, 1H), 4.22 (s, 1H), 5.20 (br, 2H), 6.94-6.98 (m, 4H), 7.10 (d, J = 5.2 Hz, 1H), 7.18 (d, J = 5.2 Hz, 1H), 7.32-7.35 (m, 4H), 7.48-7.54 (m, 3H), 7.91-7.93 (m, 3H), 8.18-8.20 (m, 2H), 8.26 (d, J = 8.4 Hz, 1H), 8.38 (s, 1H). | X3 |
| 128 | 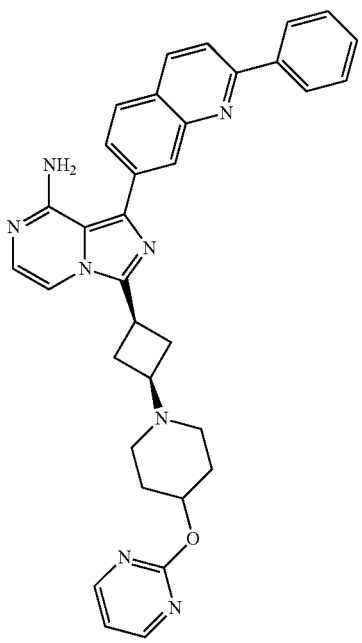 [SMILES: Nc1nccn2c1c(-c1ccc3ccc(-c4ccccc4)nc3c1)nc2[C@H]1C[C@@H](N2CCC(Oc3ncccn3)CC2)C1] | 1-(2-Phenyl-quinolin-7-yl)-3-{3-[4-(prrimidin-2-yloxy)-piperidin-1-yl]-cyclobutyl}-imidazo[1,5-a]pyrazin-8-ylamine | 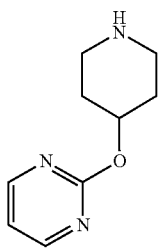 | (ES+): m/z 569 [MH+]; (400 MHz, CDCl$_3$) δ 1.91-1.96 (m, 2H), 2.01-2.10 (m, 2H), 2.29-2.32 (m, 2H), 2.53-2.58 (m, 2H), 2.68-2.75 (m, 4H), 2.96-2.98 (m, 1H), 3.46-3.50 (m, 1H), 5.08-5.10 (m, 1H), 5.22 (br, 2H), 6.89-6.91 (m, 1H), 7.11 (d, J = 5.2 Hz, 1H), 7.20 (d, J = 5.2 Hz, 1H), 7.46-7.56 (m, 3H), 7.91-7.95 (m, 3H), 8.18-8.21 (m, 2H), 8.27 (d, J = 8.8 Hz, 1H), 8.39 (s, 1H). | X3 |

-continued

| | | | | | |
|---|---|---|---|---|---|
| 129 | 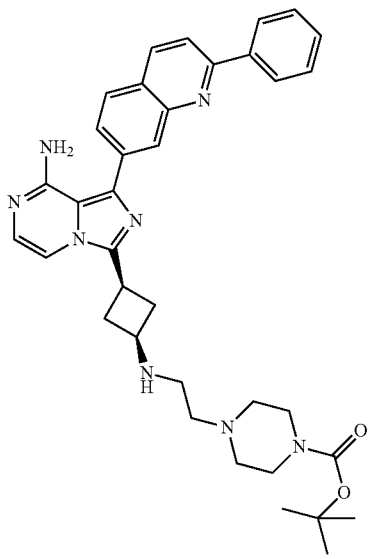 [SMILES: CC(C)(C)OC(=O)N1CCN(CCN[C@H]2C[C@@H](c3nc(-c4ccc5ccc(-c6ccccc6)nc5c4)c4c(N)nccn43)C2)CC1] | 4-(2-{3-[8-Amino-1-(2-phenyl-quinolin-7-yl)-imidazo[1,5-a]pyrazin-3-yl]-yclobutylamino}-ethyl)-piperazine-1-carboxylic acid tert-butyl ester | 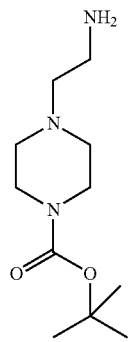 | (ES+): m/z 619 [MH+]; (400 MHz, CDCl3) δ 1.44 (s, 9H), 2.32-2.41 (m, 6H), 2.48-2.51 (m, 2H), 2.72-2.75 (m, 2H), 2.88-2.91 (m, 2H), 3.40-3.49 (m, 6H), 5.20 (br, 2H), 7.12 (d, J = 5.2 Hz, 1H), 7.20 (d, J = 5.2, 1H), 7.48-7.56 (m, 3H), 7.92-7.97 (m, 3H), 8.18-8.21 (m, 2H), 8.28 (d, J = 8.8 Hz, 1H), 8.41 (s, 1H). | X3 |
| 130 | 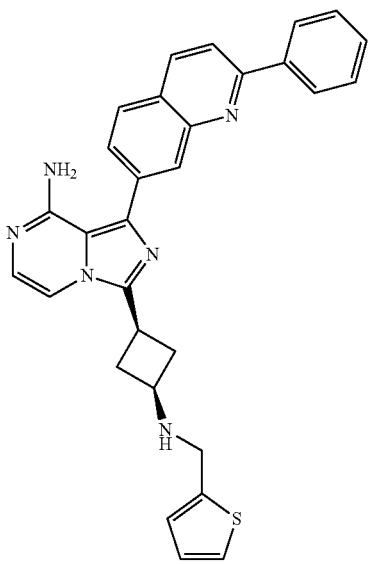 [SMILES: Nc1nccn2c1c(-c1ccc3ccc(-c4ccccc4)nc3c1)nc2[C@H]1C[C@@H](NCc2cccs2)C1] | 1-(2-Phenyl-quinolin-7-yl)-3-{3-[(thiophen-2-ylmethyl)-amino]-cyclobutyl}-midazo[1,5-a]pyrazin-8-ylamine | 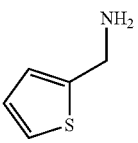 | (ES+): m/z 503 [MH+]; (400 MHz, CDCl3) δ 2.35-2.38 (m, 2H), 2.86-2.89 (m, 2H), 3.42-3.51 (m, 2H), 4.01 (s, 2H), 5.23 (br, 2H), 6.94-6.95 (m, 2H), 7.12 (m, 1H), 7.18-7.22 (m, 2H), 7.48-7.56 (m, 4H), 7.92-7.95 (m, 3H), 8.18-8.21 (m, 2H), 8.27 (d, J = 8.4 Hz, 1H), 8.41 (s, 1H). | X3 |
| 131 | 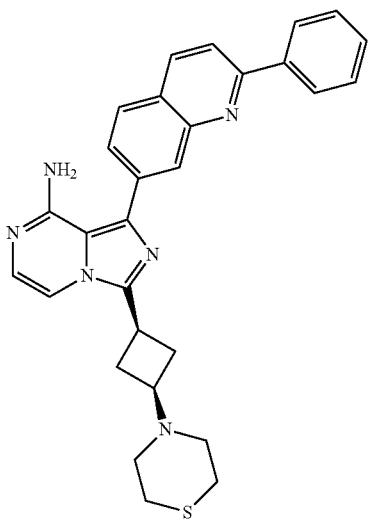 [SMILES: Nc1nccn2c1c(-c1ccc3ccc(-c4ccccc4)nc3c1)nc2[C@H]1C[C@@H](N2CCSCC2)C1] | 1-(2-Phenyl-quinolin-7-yl)-3-(3-thiomorpholin-4-yl-cyclobutyl)-imidazo[1,5-a]pyrazin-8-ylamine | 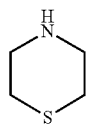 | (ES+): m/z 493 [MH+]; (400 MHz, CDCl3) δ 2.43-2.51 (m, 2H), 2.64-2.73 (m, 10H), 2.94-2.98 (m, 1H), 3.45-3.50 (m, 1H), 5.24 (br, 2H), 7.11 (d, J = 5.2 Hz, 1H), 7.19 (d, J = 5.2, 1H), 7.46-7.57 (m, 3H), 7.91-7.97 (m, 3H), 8.18-8.21 (m, 2H), 8.27 (d, J = 8.8 Hz, 1H), 8.40 (s, 1H). | X3 |

| 132 | 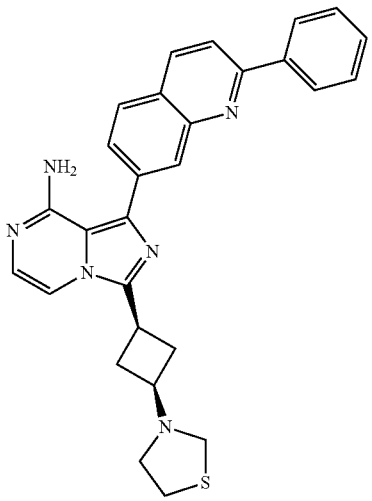 | 1-(2-Phenyl-quinolin-7-yl)-3-(3-thiazolidin-3-yl-cyclobutyl)-imidazo[1,5-a]pyrazin-8-ylamine |  | (ES+): m/z 479 [MH+]; (400 MHz, CDCl3) δ 2.55-2.62 (m, 2H), 2.69-2.73 (m, 2H), 2.89-2.92 (m, 2H), 3.09-3.12 (m, 2H), 3.27-3.31 (m, 1H), 3.45-3.50 (m, 1H), 4.08 (s, 2H), 5.24 (br, 2H), 7.12 (d, J = 5.2 Hz, 1H), 7.19 (d, J = 4.8, 1H), 7.46-7.57 (m, 3H), 7.92-7.96 (m, 3H), 8.18-8.21 (m, 2H), 8.27 (d, J = 8.8 Hz, 1H), 8.41 (s, 1H). | X3 |
|---|---|---|---|---|---|
| 133 | 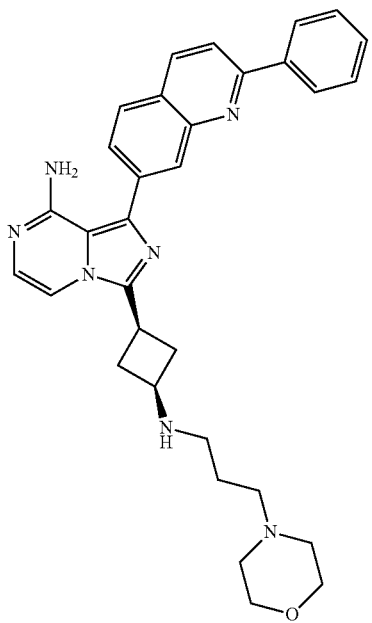 [SMILES: Nc1nccn2c1c(-c1ccc3ccc(-c4ccccc4)nc3c1)nc2[C@H]1C[C@@H](NCCCN2CCOCC2)C1] | 3-[3-(3-Morpholin-4-yl-propylamino)-cyclobutyl)-1-(2-phenyl-quinolin-7-yl)-imidazo[1,5-a]pyrazin-8-ylamine | 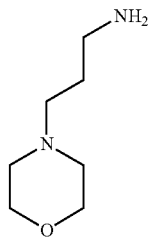 | (ES+): m/z 534 [MH+]. (400 MHz, CDCl3) δ 2.31-2.43 (m, 10H), 2.65-2.69 (m, 2H), 2.86-2.91 (m, 2H), 3.42-3.49 (m, 2H), 3.69-3.71 (m, 4H), 5.19 (br, 2H), 7.12 (d, J = 4.8 Hz, 1H), 7.20 (d, J = 5.2 Hz, 1H), 7.48-7.57 (m, 3H), 7.91-7.97 (m, 3H), 8.18-8.20 (m, 2H), 8.27 (d, J = 8.4 Hz, 1H), 8.41 (s, 1H). | X3 |

| | | | | | |
|---|---|---|---|---|---|
| 134 | 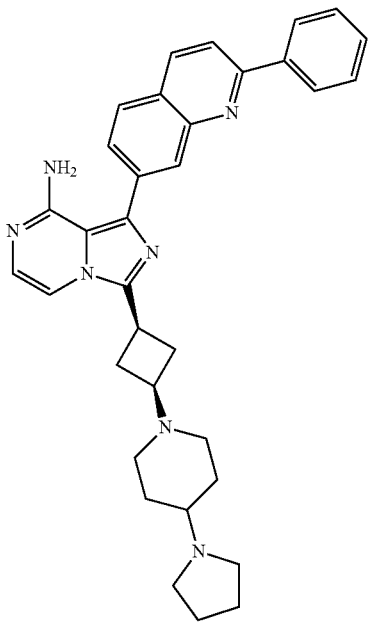 [SMILES: Nc1nccn2c1c(-c1ccc3ccc(-c4ccccc4)nc3c1)nc2[C@H]1C[C@@H](N2CCC(N3CCCC3)CC2)C1] | 1-(2-Phenyl-quinolin-7-yl)-3-[3-(4-pyrrolidin-1-yl-piperidin-1-yl)-cyclobutyl]-imidazo[1,5-a]pyrazin-8-ylamine | 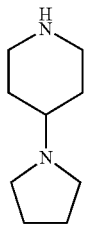 | (ES+): m/z 544 [MH$^+$]. (400 MHz, CDCl3) δ 1.64-1.70 (m, 6H), 1.80-1.94 (m, 6H), 2.50-2.55 (m, 3H), 2.64-2.70 (m, 4H), 2.92-2.96 (m, 3H), 3.46-3.49 (m, 1H), 5.19 (br, 2H), 7.11 (d, J = 4.8 Hz, 1H), 7.22 (d, J = 5.2, 1H), 7.48-7.54 (m, 3H), 7.91-7.94 (m, 3H), 8.18-8.20 (m, 2H), 8.27 (d, J = 8.4 Hz, 1H), 8.39 (s, 1H). | X3 |
| 135 | 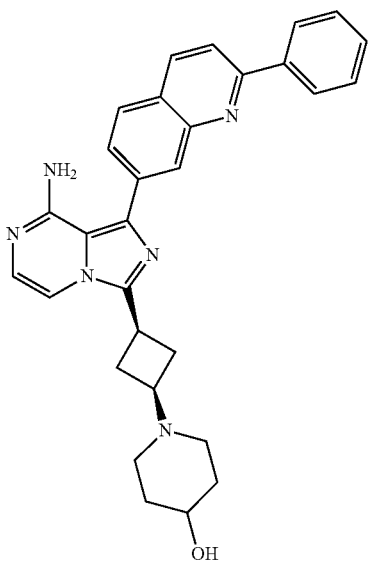 [SMILES: Nc1nccn2c1c(-c1ccc3ccc(-c4ccccc4)nc3c1)nc2[C@H]1C[C@@H](N2CCC(O)CC2)C1] | 1-{3-[8-Amino-1-(2-phenyl-quinolin-7-yl)-imidazo[1,5-a]pyrazin-3-yl]-cyclobutyl}-piperidin-4-ol | 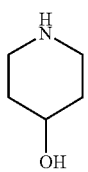 | (ES+): m/z 491 [MH$^+$]. (400 MHz, CDCl$_3$) δ 1.55-1.64 (m, 2H), 1.90-1.94 (m, 2H), 2.01-2.09 (m, 2H), 2.51-2.56 (m, 2H), 2.66-2.77 (m, 4H), 2.91-2.93 (m, 1H), 3.45-3.49 (m, 1H), 3.72 (m, 1H), 5.22 (br, 2H), 7.11 (d, J = 5.2 Hz, 1H), 7.20 (d, J = 5.2 Hz, 1H), 7.48-7.57 (m, 3H), 7.91-7.95 (m, 3H), 8.18-8.21 (m, 2H), 8.27 (d, J = 8.8 Hz, 1H), 8.39 (s, 1H). | X3 |

| 136 | 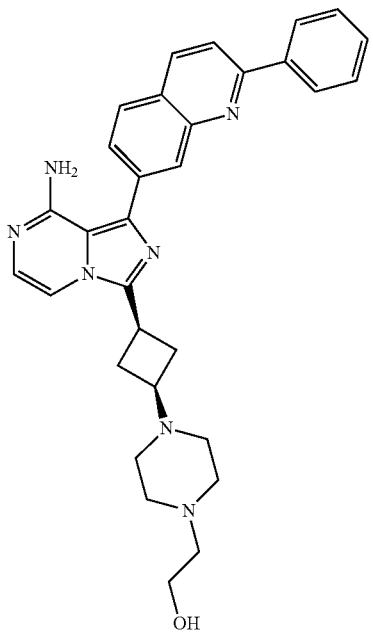 [SMILES: Nc1nccn2c1c(-c1ccc3ccc(-c4ccccc4)nc3c1)nc2[C@H]1C[C@@H](N2CCN(CCO)CC2)C1] | 2-(4-{3-[8-Amino-1-(2-phenyl-quinolin-7-yl)-imidazo[1,5-a]pyrazin-3-yl]-cyclobutyl}-piperazin-1-yl)-ethanol | 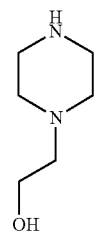 | (ES+): m/z 519 [MH+]. (400 MHz, CDCl₃) δ 2.47-2.57 (m, 11H), 2.66-2.72 (m, 3H), 2.92-2.98 (m, 1H), 3.46-3.51 (m, 1H), 3.60-3.63 (m, 2H), 5.23 (br, 2H), 7.11 (d, J = 4.8 Hz, 1H), 7.19 (d, J = 5.2 Hz, 1H), 7.48-7.56 (m, 3H), 7.91-7.94 (m, 3H), 8.18-8.21 (m, 2H), 8.27 (d, J = 8.8 Hz, 1H), 8.39 (s, 1H). | X3 |
|---|---|---|---|---|---|
| 137 | 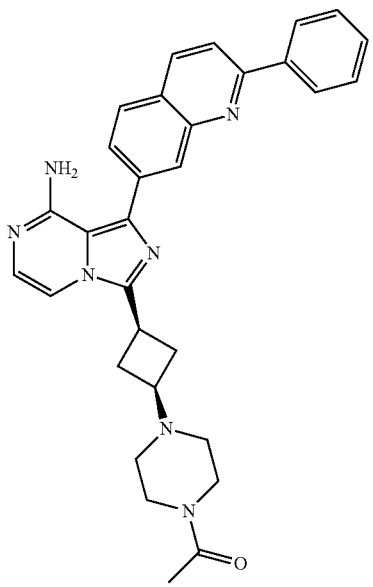 [SMILES: CC(=O)N1CCN([C@H]2C[C@@H](c3nc(-c4ccc5ccc(-c6ccccc6)nc5c4)c4c(N)nccn43)C2)CC1] | 3-{3-[4-(3H-imidazol-4-ylmethyl)-piperazin-1-yl]-cyclobutyl}-1-(2-phyenyl-quinolin-7-yl)-imidazo[1,5a]pyrazin-8-ylamine | 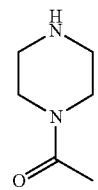 | (ES+): m/z 518 [MH+]. (400 MHz, CDCl₃) δ 2.09 (s, 3H), 2.36-2.42 (m, 4H), 2.49-2.57 (m, 2H), 2.66-2.73 (m, 2H), 2.94 (m, 1H), 3.46-3.52 (m, 3H), 3.26-3.65 (m, 2H), 5.23 (br, 2H), 7.12 (d, J = 4.8 Hz, 1H), 7.19 (d, J = 5.2, 1H), 7.48-7.56 (m, 3H), 7.92-7.95 (m, 3H), 8.19 (m, 2H), 8.27 (d, J = 8.0 Hz, 1H), 8.41 (s, 1H). | X3 |

| | | | | | |
|---|---|---|---|---|---|
| 138 | 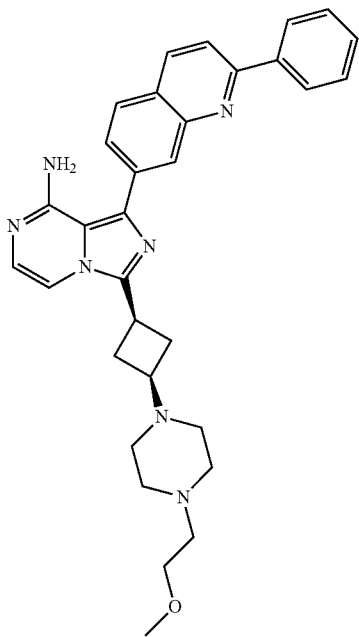 [SMILES: COCCN1CCN([C@H]2C[C@@H](c3nc(-c4ccc5ccc(-c6ccccc6)nc5c4)c4c(N)nccn43)C2)CC1] | 3-{3-[4-(2-Methoxy-ethyl)-piperazin-1-yl]-cyclobutyl}-1-(2-phenyl-quinolin-7-yl)-imidazo[1,5-a]pyrazin-8-ylamine | 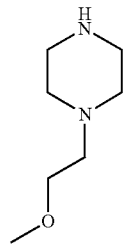 | (ES+): m/z 534 [MH+]. (400 MHz, CDCl₃) δ 2.38-2.70 (m, 14H), 2.93-2.99 (m, 1H), 3.35 (s, 3H), 3.43-3.53 (m, 3H), 5.21 (br, 2H), 7.11 (d, J = 4.8 Hz, 1H), 7.18 (d, J = 4.8 Hz, 1H), 7.47-7.56 (m, 3H), 7.91-7.94 (m, 3H), 8.18-8.20 (m, 2H), 8.27 (d, J = 8.4 Hz, 1H), 8.38 (s, 1H). | X3 |
| 139 | 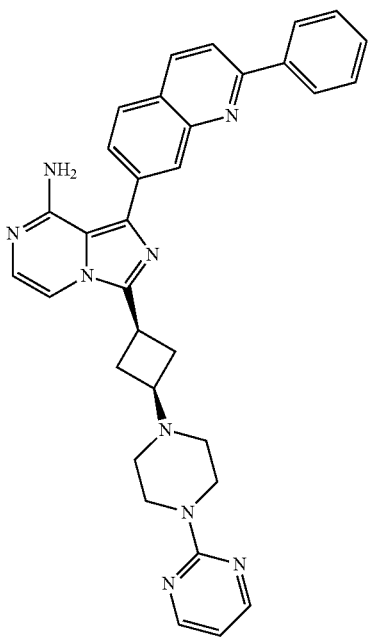 [SMILES: Nc1nccn2c1c(-c1ccc3ccc(-c4ccccc4)nc3c1)nc2[C@H]1C[C@@H](N2CCN(c3ncccn3)CC2)C1] | 1-(2-Phenyl-quinolin-7-yl)-3-[3-(4-pyrimidin-2-yl-piperidin-1-yl)-cyclobutyl]-imidazo[1,5-a]pyrazin-8-ylamine | 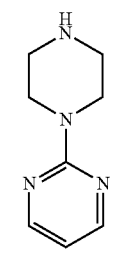 | (ES+): m/z 554 [MH+]. (400 MHz, CDCl₃) δ 2.47-2.50 (m, 4H), 2.62-2.54 (m, 2H), 2.70-2.76 (m, 2H), 2.96-3.00 (m, 1H), 3.49-3.54 (m, 1H), 3.84-3.87 (m, 4H), 5.26 (br, 2H), 6.49 (t, J = 4.8 Hz, 1H), 7.12 (d, J = 5.2 Hz, 1H), 7.22 (d, J = 4.8 Hz, 1H), 7.48-7.57 (m, 3H), 7.92-7.95 (m, 3H), 8.19-8.21 (m, 2H), 8.28 (d, J = 8.4 Hz, 1H), 8.31 (d, J = 4.8 Hz, 2H), 8.38 (s, 1H). | X3 |

| | | | | | |
|---|---|---|---|---|---|
| 140 | 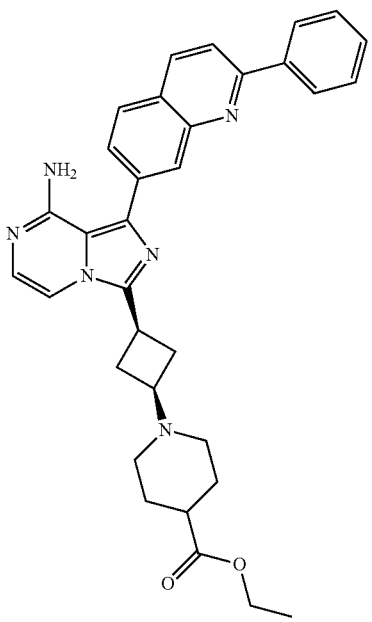 [SMILES: CCOC(=O)C1CCN([C@H]2C[C@@H](c3nc(-c4ccc5ccc(-c6ccccc6)nc5c4)c4c(N)nccn43)C2)CC1] | 1-{3-[8-Amino-1-(2-phenyl-quinolin-7-yl)-imidazo[1,5-a]pyrazin-3-yl]-cyclobutyl}-piperidine-4-carboxylic acid ethyl ester | 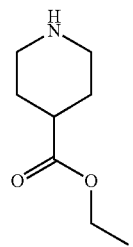 | (ES+): m/z 547 [MH+]. (400 MHz, CDCl$_3$) δ 1.25 (t, J = 7.2 Hz, 3H), 1.74-1.80 (m, 2H), 1.91-1.93 (m, 4H), 2.26-2.29 (m, 1H), 2.47-2.55 (m, 2H), 2.65-2.72 (m, 2H), 2.87-2.93 (m, 3H), 3.44-3.49 (m, 1H), 4.13 (q, J = 7.6 Hz, 2H), 5.23 (br, 2H), 7.11 (d, J = 5.2 Hz, 1H), 7.20 (d, J = 5.2 Hz, 1H), 7.45-7.56 (m, 3H), 7.91-7.96 (m, 3H), 8.18-8.20 (m, 2H), 8.27 (d, J = 8.8 Hz, 1H), 8.39 (s, 1H). | X3 |
| 141 | 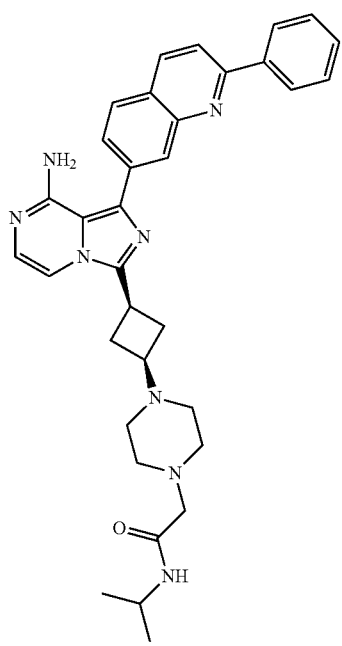 [SMILES: CC(C)NC(=O)CN1CCN([C@H]2C[C@@H](c3nc(-c4ccc5ccc(-c6ccccc6)nc5c4)c4c(N)nccn43)C2)CC1] | 2-(4-{3-[8-Amino-1-(2-phenyl-quinolin-7-yl)-imidazo[1,5-a]pyrazin-3-yl]-cyclobutyl}-piperazin-1-yl)-N-isopropyl-acetamide | 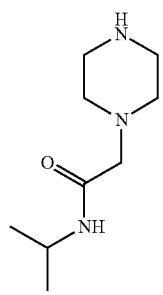 | (ES+): m/z 575 [MH+]. (400 MHz, CDCl$_3$) δ 0.88 (t, J = 6.8 Hz, 1H), 1.16 (d, J = 6.4 Hz, 6H), 2.46-2.56 (m, 9H), 2.65-2.72 (m, 2H), 2.97-3.01 (m, 3H), 3.47-3.52 (m, 1H), 4.07 (m, 1H), 5.24 (br, 2H), 6.93 (br, 1H), 7.11 (d, J = 4.4 Hz, 1H), 7.19 (d, J = 5.2 Hz, 1H), 7.46-7.56 (m, 3H), 7.91-7.94 (m, 3H), 8.17-8.20 (m, 2H), 8.27 (d, J = 8.8 Hz, 1H), 8.39 (s, 1H). | X3 |

| | | | | |
|---|---|---|---|---|
| 142 | 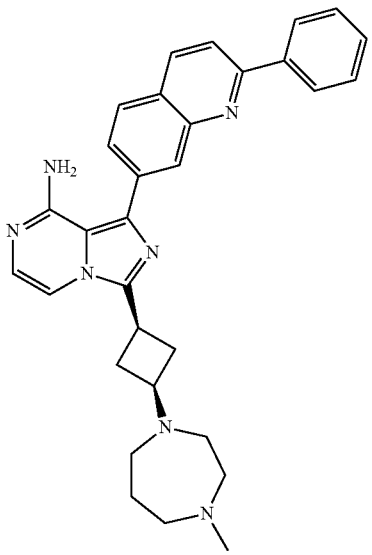 [SMILES: CN1CCCN([C@H]2C[C@@H](c3nc(-c4ccc5ccc(-c6ccccc6)nc5c4)c4c(N)nccn43)C2)CC1] | 3-[3-(4-Methyl-[1,4]diazepan-1-yl)-cyclobutyl]-1-(2-phenyl-quinolin-7-yl)-imidazo[1,5-a]pyrazin-8-ylamine | 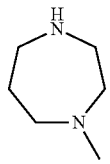 | (ES+): m/z 504 [MH+]. (400 MHz, CDCl$_3$) δ 1.86 (m, 2H), 2.40-2.51 (m, 5H), 2.64-2.72 (m, 10H), 3.12-3.18 (m, 1H), 3.38-3.44 (m, 1H), 5.21 (br, 2H), 7.11 (d, J = 5.2 Hz, 1H), 7.21 (d, J = 4.8 Hz, 1H), 7.46-7.57 (m, 3H), 7.91-7.95 (m, 3H), 8.18-8.21 (m, 2H), 8.27 (d, J = 8.8 Hz, 1H), 8.40 (s, 1H). | X3 |
| 143 | 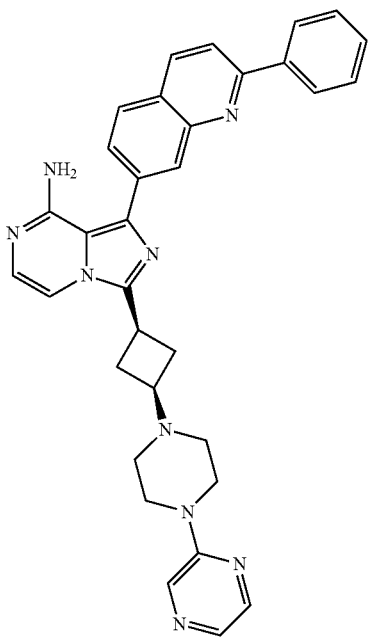 [SMILES: Nc1nccn2c1c(-c1ccc3ccc(-c4ccccc4)nc3c1)nc2[C@H]1C[C@@H](N2CCN(c3cnccn3)CC2)C1] | 1-(2-Phenyl-quinolin-7-yl)-3-[3-(2,3,5,6-tetrahydro-[1,2']bipyrazinyl-4-yl)-cyclobutyl]-imidazo[1,5-a]pyrazin-8-ylamine | 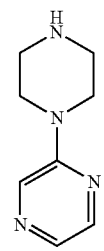 [SMILES: c1cnc(N2CCNCC2)cn1] | (ES+): m/z 554 [MH+]. (400 MHz, CDCl$_3$) δ 2.52-2.61 (m, 6H), 2.70-2.76 (m, 2H), 2.97-3.02 (m, 1H), 3.49-3.54 (m, 1H), 3.61-3.63 (m, 4H), 5.28 (br, 2H), 7.12 (d, J = 4.8 Hz, 1H), 7.21 (d, J = 5.2 Hz, 1H), 7.46-7.56 (m, 3H), 7.84 (m, 1H), 7.92-7.95 (m, 3H), 8.06 (m, 1H), 8.14 (m, 1H), 8.18-8.21 (m, 2H), 8.27 (d, J = 8.4 Hz, 1H), 8.41 (s, 1H). | X3 |

| 144 | 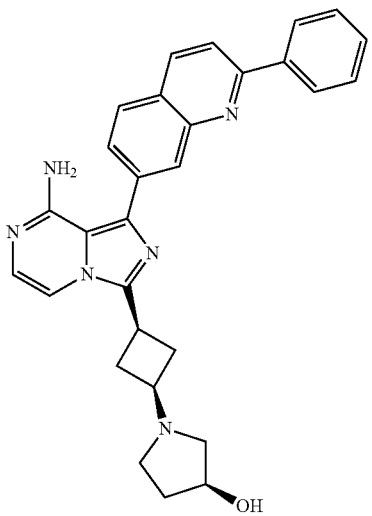 [SMILES: Nc1nccn2c1c(-c1ccc3ccc(-c4ccccc4)nc3c1)nc2[C@H]1C[C@@H](N2CC[C@H](O)C2)C1] | (S)-1-{3-[8-Amino-1-(2-phenyl-quinolin-7-yl)-imidazo[1,5-a]pyrazin-3-yl]-cyclobutyl}-pyrrolidin-3-ol | 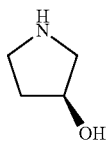 | (ES+): m/z 477 [MH$^+$]. (400 MHz, CDCl$_3$) δ 1.78 (m, 1H), 2.15-2.23 (m, 2H), 2.37-2.38 (m, 2H), 2.55-2.75 (m, 6H), 2.89-2.93 (m, 1H), 3.18-3.22 (m, 1H), 3.48-3.52 (m, 1H), 4.35-4.38 (m, 1H), 5.24 (br, 2H), 7.11 (d, J = 4.8 Hz, 1H), 7.18 (d, J = 4.8 Hz, 1H), 7.47-7.56 (m, 3H), 7.90-7.94 (m, 3H), 8.17-8.20 (m, 2H), 8.26 (d, J = 8.4 Hz, 1H), 8.40 (s, 1H). | X3 |
|---|---|---|---|---|---|
| 145 | 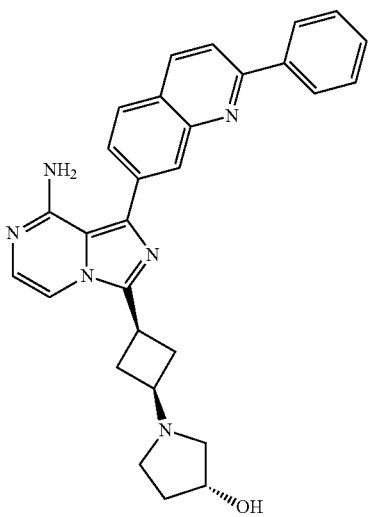 [SMILES: Nc1nccn2c1c(-c1ccc3ccc(-c4ccccc4)nc3c1)nc2[C@H]1C[C@@H](N2CC[C@@H](O)C2)C1] | (R)-1-{3-[8-Amino-1-(2-phenyl-quinolin-7-yl)-imidazo[1,5-a]pyrazin-3-yl]-cyclobutyl}-pyrrolidin-3-ol | 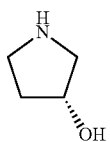 | (ES+): m/z 477 [MH$^+$]. (400 MHz, CDCl$_3$) δ 1.75-1.78 (m, 1H), 2.14-2.38 (m, 4H), 2.54-2.73 (m, 6H), 2.87-2.93 (m, 1H), 3.16-3.21 (m, 1H), 3.47-3.52 (m, 1H), 4.35-4.38 (m, 1H), 5.25 (br, 2H), 7.11 (d, J = 4.8 Hz, 1H), 7.17 (d, J = 4.8 Hz, 1H), 7.47-7.56 (m, 3H), 7.91-7.94 (m, 3H), 8.18-8.20 (m, 2H), 8.26 (d, J = 8.8 Hz, 1H), 8.40 (s, 1H). | X3 |
| 146 | 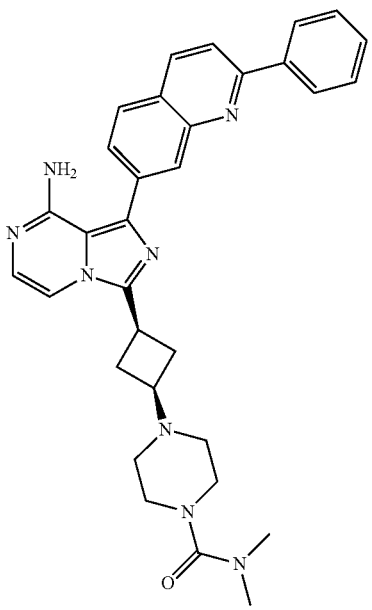 [SMILES: CN(C)C(=O)N1CCN([C@H]2C[C@@H](c3nc(-c4ccc5ccc(-c6ccccc6)nc5c4)c4c(N)nccn43)C2)CC1] | 4-{3-[8-Amino-1-(2-phenyl-quinolin-7-yl)-imidazo[1,5-a]pyrazin-3-yl]-cyclobutyl}-piperidine-4-carboxylic acid dimethylamide | 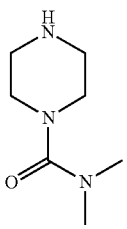 | (ES+): m/z 547 [MH$^+$]. (400 MHz, CDCl$_3$) δ 2.40-2.43 (m, 4H), 2.50-2.57 (m, 2H), 2.66-2.72 (m, 2H), 2.83 (s, 6H), 2.94-2.99 (m, 1H), 3.27-3.29 (m, 4H), 3.47-3.52 (m, 1H), 5.29 (br, 2H), 7.11 (d, J = 4.8 Hz, 1H), 7.20 (d, J = 5.2 Hz, 1H), 7.46-7.57 (m, 3H), 7.92-7.97 (m, 3H), 8.18-8.21 (m, 2H), 8.27 (d, J = 8.8 Hz, 1H), 8.40 (s, 1H). | X3 |

| 147 | 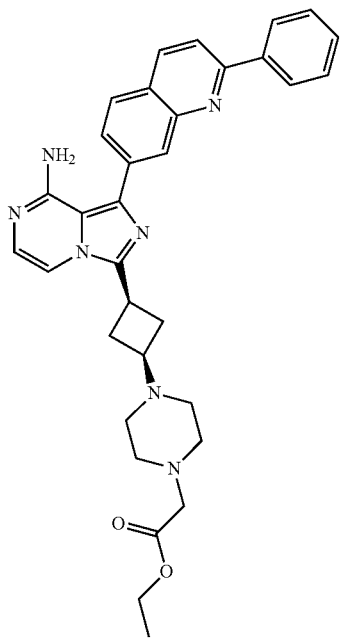 [SMILES: CCOC(=O)CN1CCN([C@H]2C[C@@H](c3nc(-c4ccc5ccc(-c6ccccc6)nc5c4)c4c(N)nccn43)C2)CC1] | (4-{3-[8-Amino-1-(2-phenyl-quinolin-7-yl)-imidazo[1,5-a]pyrazin-3-yl]-cyclobutyl}-piperazin-1-yl)-acetic acid ethyl ester | 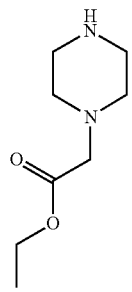 | (ES+): m/z 562 [MH$^+$]. (400 MHz, CDCl$_3$) δ 1.23-1.33 (m, 5H), 1.81-1.84 (m, 2H), 2.29-2.37 (m, 2H), 2.70-2.93 (m, 6H), 3.41-3.54 (m, 2H), 4.07-4.15 (m, 4H), 5.22 (br, 2H), 7.12 (d, J = 4.8 Hz, 1H), 7.19 (d, J = 4.8 Hz, 1H), 7.48-7.56 (m, 3H), 7.92-7.97 (m, 3H), 8.18-8.20 (m, 2H), 8.27 (d, J = 8.4 Hz, 1H), 8.41 (s, 1H). | X3 |
|---|---|---|---|---|---|
| 148 | 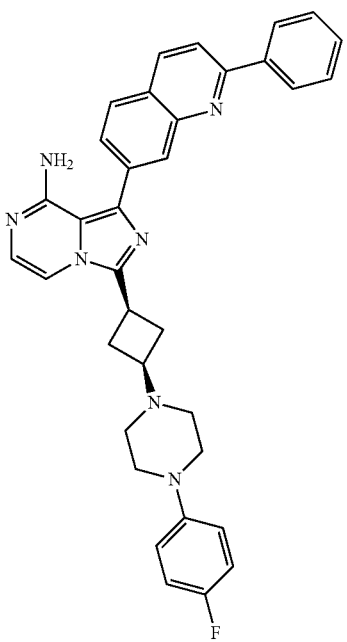 [SMILES: Nc1nccn2c1c(-c1ccc3ccc(-c4ccccc4)nc3c1)nc2[C@H]1C[C@@H](N2CCN(c3ccc(F)cc3)CC2)C1] | 3-{3-[4-(4-Fluoro-phenyl)piperazin-1-yl]-cyclobutyl}-1-(2-phenyl-quinolin-7-yl)-imidazo[1,5-a]pyrazin-8-ylamine | 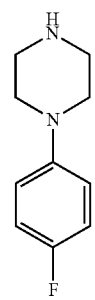 | (ES+): m/z 570 [MH$^+$]. (400 MHz, CDCl$_3$) δ 2.53-2.61 (m, 6H), 2.70-2.76 (m, 2H), 3.00-3.05 (m, 1H), 3.13-3.15 (m, 4H), 3.49-3.54 (m, 1H), 5.36 (br, 2H), 6.87-6.90 (m, 2H), 6.94-6.98 (m, 2H), 7.11 (d, J = 4.8 Hz, 1H), 7.21 (d, J = 5.2 Hz, 1H), 7.48-7.56 (m, 3H), 7.91-7.95 (m, 3H), 8.18-8.20 (m, 2H), 8.27 (d, J = 8.8 Hz, 1H), 8.40 (s, 1H). | X3 |

| 149 | 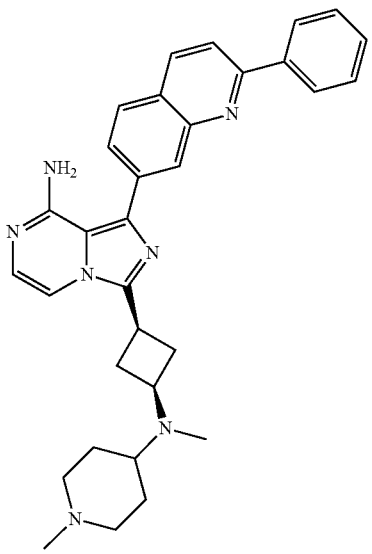 [SMILES: CN1CCC(N(C)[C@H]2C[C@@H](c3nc(-c4ccc5ccc(-c6ccccc6)nc5c4)c4c(N)nccn43)C2)CC1] | 3-{3-[Methyl-(1-methyl-piperidin-4-yl)-amino]-cyclobutyl}-1-(2-phenyl-quinolin-7-yl)-imidazo[1,5-a]pyrazin-8-ylamine | 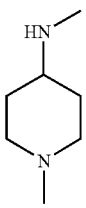 | (ES+): m/z 518 [MH+]. (400 MHz, CDCl$_3$) δ 1.70-1.75 (m, 4H), 1.96-1.02 (m, 2H), 2.21 (s, 3H), 2.31 (m, 3H), 2.50-2.57 (m, 3H), 2.63-2.70 (m, 2H), 2.96-2.98 (m, 2H), 3.33-3.49 (m, 2H), 5.21 (br, 2H), 7.11 (d, J = 5.2 Hz, 1H), 7.19 (d, J = 5.2 Hz, 1H), 7.47-7.56 (m, 3H), 7.91-7.94 (m, 3H), 8.18-8.20 (m, 2H), 8.27 (d, J = 8.4 Hz, 1H), 8.39 (s, 1H). | X3 |

Additionally, 3-[(3-(4-benzyl carboxylate piperazin-1-yl)cyclobutyl]-1-(2-phenyl-quinolin-7-yl)imidazol[1,5-a]pyrazin-8-ylamine could be prepared as follows: Prepared according to Method X1 where HNR$^2$R$^3$ is equal to Cbz-piperazine followed by Method X2. The crude material was re-crystallized (DCM/Hex), yielding a yellow solid. $^1$H NMR (400 MHz, CDCl$_3$) δ 2.35-2.38 (m, 4H), 2.51-2.56 (m, 2H), 2.66-2.72 (m, 2H), 2.93 (m, 1H), 3.47-3.55 (m, 5H), 5.13 (s, 2H), 5.34 (br, 2H), 7.10 (d, J=5.2 Hz, 1H), 7.19 (d, J=5.2, 1H), 7.33-7.37 (m, 5H), 7.48-7.55 (m, 3H), 7.93 (m, 3H), 8.19-8.21 (m, 2H), 8.27 (d, J=8.4 Hz, 1H), 8.40 (s, 1H). MS (ES+): m/z 610 [MH+]. HPLC: t$_R$=2.13 min (Open-Lynx polar 5 min).

Additionally, 3-[(3-(4-tert butyl carboxylate piperazin-1-yl)cyclobutyl]-1-(2-phenyl-quinolin-7-yl)imidazol[1,5-a]pyrazin-8-ylamine could be prepared as follows: Prepared according to Method X1 where HNR$^2$R$^3$ is equal to Cbz-piperazine followed by Method X2. The crude material was purified using Jones column (5 g, 25 mL) eluting with 1%→3%→5% of MeOH/EtOAc, to give the desired yellow solid. $^1$H NMR (400 MHz, CDCl$_3$) δ 1.46 (s, 9H), 2.34-2.37 (m, 4H), 2.51-2.54 (m, 2H), 2.68-2.70 (m, 2H), 2.94 (m, 1H), 3.44-3.49 (m, 5H), 5.29 (br, 2H), 7.11 (d, J=5.2 Hz, 1H), 7.20 (d, J=5.2 Hz, 1H), 7.48-7.55 (m, 3H), 7.92-7.95 (m, 3H), 8.18-8.21 (m, 2H), 8.27 (d, J=8 Hz, 1H), 8.40 (s, 1H). MS (ES+): m/z 576 [MH+]. HPLC: t$_R$=2.05 min (Open-Lynx polar 5 min).

Example 150

3-[(3-(piperazin-1-yl)cyclobutyl]-1-(2-phenyl-quinolin-7-yl)imidazol[1,5-a]pyrazin-8-ylamine

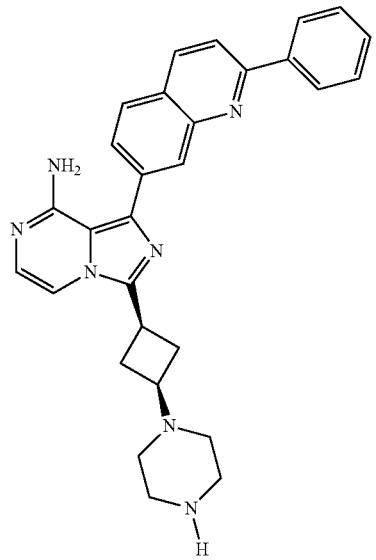 [SMILES: Nc1nccn2c1c(-c1ccc3ccc(-c4ccccc4)nc3c1)nc2[C@H]1C[C@@H](N2CCNCC2)C1]

To a solution of 3-[(3-(4-benzyl carboxylate piperazin-1-yl)cyclobutyl]-1-(2-phenyl-quinolin-7-yl)imidazol[1,5-a]pyrazin-8-ylamine (90 mg, 0.1 mmol) in DCM, 5 mL of 37% HCl was added and the resulting solution was heated for 30 min at 60° C. The reaction mixture was diluted with water (5 mL) and washed with ether (2×10 mL), DCM (10 mL), the aqueous layer was basified with 3M NaOH and the solid was collected by filtration. The solid was dissolved DCM (10 mL) and washed with brine (10 mL), the organic layer was dried over anhydrous Na₂SO₄ and concentrated under in vacuo, to afford the desired product as a yellow solid. ¹H NMR (400 MHz, CDCl₃) δ 2.39-2.53 (m, 7H), 2.68 (m, 2H), 2.90-2.94 (m, 5H), 3.49 (m, 1H), 5.19 (br, 2H), 7.11 (d, J=5.2 Hz, 1H), 7.20 (d, J=5.2 Hz, 1H), 7.47-7.54 (m, 3H), 7.91-7.95 (m, 3H), 8.18-8.21 (m, 2H), 8.27 (d, J=7.6 Hz, 1H), 8.39 (s, 1H). MS (ES+): m/z 476 [MH⁺]. HPLC: $t_R$=1.69 min (Open-Lynx polar 5 min).

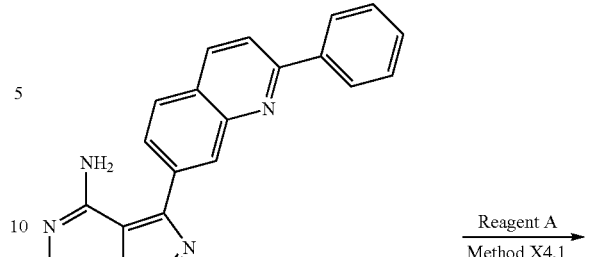

Method X4.1: General procedure for the synthesis of compounds of Formula I-L1.2 (compound of Formula I-L where Q¹=2-phenyl-quinolin-7-yl and

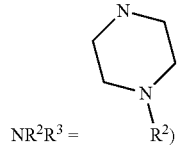

NR²R³ = (R²)

from reaction of Reagent A with compounds of Formula I-L1.1 (Compound of Formula I-L where Q1=2-phenyl-quinolin-7-yl and

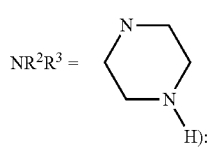

NR²R³ = H):

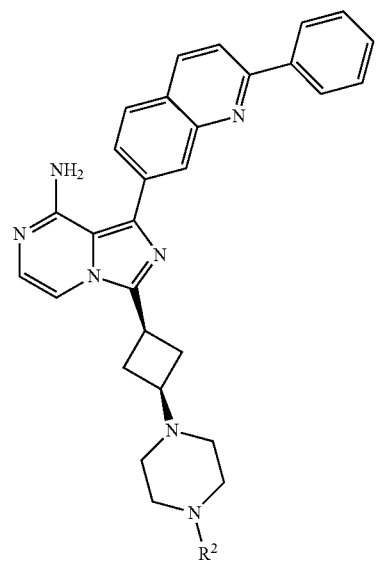

I-L1.2

To a solution of 1-(2-Phenyl-quinolin-7-yl)-3-(3-piperazin-1-yl-cyclobutyl)-imidazo [1,5-a]pyrazin-8-lamine (0.2 mmol, 100 mg) in DCE (0.1M), aldehyde (0.3 mmol) and sodium triacetoxyborohydride (0.42 mmol, 89 mg) were added. The resulting mixture was stirred at it overnight. The reaction mixture was diluted with DCM (30 mL) and washed with saturated NaHCO₃ (2×25 mL) and brine (25 mL). The solvent was dried over anhydrous Na₂SO₄ and concentrated in vacuo. The resulting residue was purified by silica gel chromatography, eluting with 0%→3% 2M NH₃ in MeOH/DCM to afford the desired product as a yellow solid.

Method X4.2: General procedure for the synthesis of compounds of Formula I-L1.2 (compound of Formula I-L where Q1=2-phenyl-quinolin-7-yl and

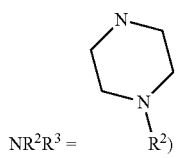

NR²R³ = (R²)

from reaction of Reagent B with compounds of Formula I-L1.1 (Compound of Formula I-L where Q1=2-phenyl-quinolin-7-yl and

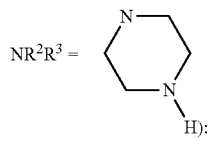

NR²R³ = (H):

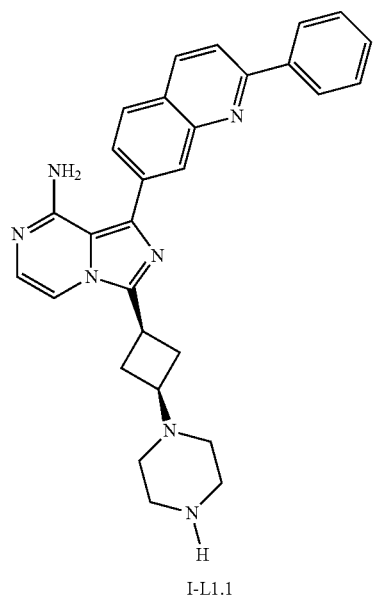

I-L1.1

Reagent B
Method X4.2
→

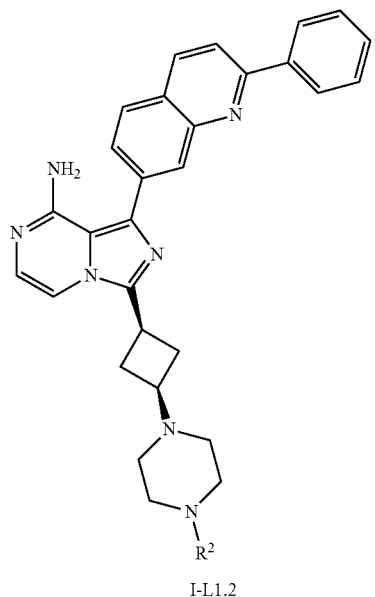

I-L1.2

To a solution of 3-[(3-(piperazin-1-yl)cyclobutyl]-1-(2-phenyl-quinolin-7-yl)imidazol[1,5-a]pyrazin-8-ylamine (50 mg, 0.11 mmol) in DCM (5 mL) were added DIPEA (0.81 mL, 0.6 mmol) and Reagent B (0.12 mmol). The resulting reaction mixture was stirred overnight at it. The mixture was diluted with DCM (10 mL) then washed with saturated NaHCO₃ (10 mL) and brine (10 mL). The organic layer was dried over anhydrous Na₂SO₄ and concentrated in vacou. The resulting residue was purified by silica gel chromatography, eluting with 0%→3% 2M NH₃ in MeOH/DCM to afford the desired product as a yellow solid.

The following compounds of Formula I-L1.2 (compound of Formula I-L where Q1=2-phenyl-quinolin-7-yl and

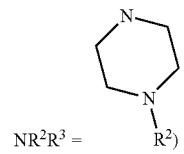

NR²R³ = (R²)

were synthesized according to Method X4.1 or X4.2:

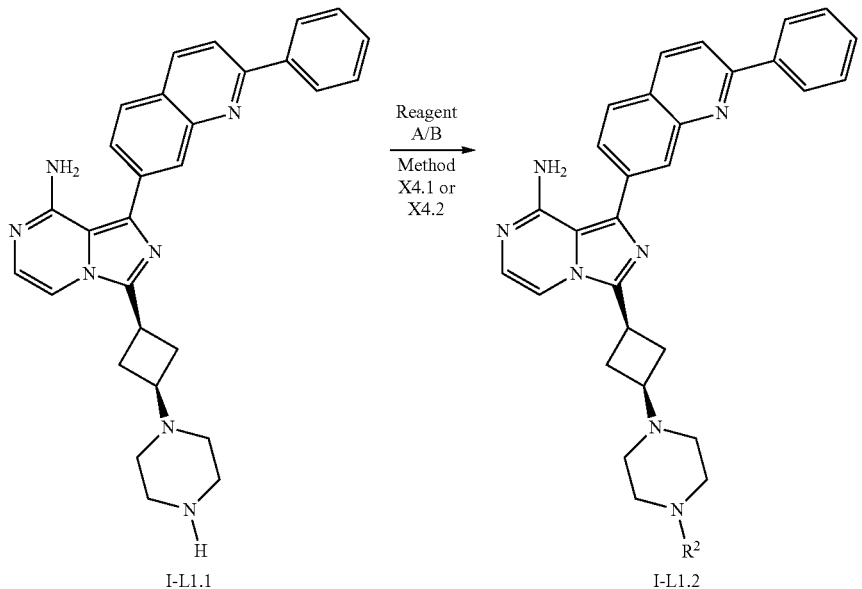
| Example | Structure | Name | Reagent/Method | MS | 1HNMR |
|---|---|---|---|---|---|
| 151 | 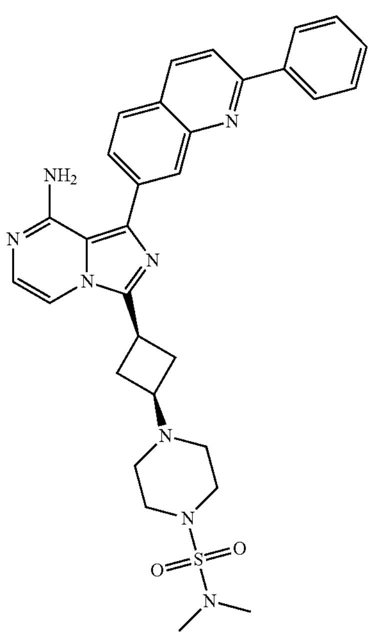 [SMILES: CN(C)S(=O)(=O)N1CCN([C@H]2C[C@@H](c3nc(-c4ccc5ccc(-c6ccccc6)nc5c4)c4c(N)nccn43)C2)CC1] | 3-(N,N-dimethylpiperazine-1-sulfonamide-4-ylcyclobutyl)-1-(2-phenyl-quinolin-7-yl)imidazol[1,5-a]pyrazin-8-ylamine | Method X4.2 | (ES+): m/z 583 [MH+]. | (400 MHz, CDCl$_3$) δ 2.45-2.43 (m, 6H), 2.68-2.70 (m, 2H), 2.83 (s, 6H), 2.98 (m, 1H), 3.29-3.31 (m, 4H), 3.49 (m, 1H), 5.26 (br, 2H), 7.12 (d, J = 4.8 Hz, 1H), 7.19 (d, J = 4.0 Hz, 1H), 7.48-7.56 (m, 3H), 7.91-7.95 (m, 3H), 8.18-8.20 (m, 2H), 8.27 (d, J = 8 Hz, 1H), 8.41 (s, 1H). |

| | | | | | |
|---|---|---|---|---|---|
| 152 | 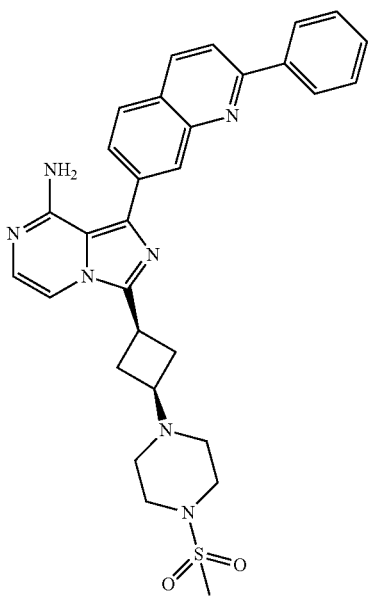 [SMILES: CS(=O)(=O)N1CCN([C@H]2C[C@@H](c3nc(-c4ccc5ccc(-c6ccccc6)nc5c4)c4c(N)nccn43)C2)CC1] | 3[3-(4-Methanesulfonyl-piperazin-1-yl)-cyclobutyl]-1-(2-phenyl-quinolin-7-yl)-imidazol[1,5-a]pyrazin-8-ylamine | 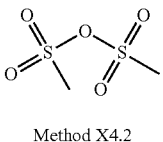  Method X4.2 | (ES+): m/z 554 [MH+]. | (400 MHz, CDCl$_3$) δ 2.47-2.55 (m, 6H), 2.68-2.74 (m, 2H), 2.77 (s, 3H), 2.99 (m, 1H), 3.25-3.27 (m, 4H), 3.51 (m, 1H), 5.37 (br, 2H), 7.11 (d, J = 4.8 Hz, 1H), 7.19 (d, J = 4.8, 1H), 7.48-7.56 (m, 3H), 7.92-7.97 (m, 3H), 8.18-8.20 (m, 2H), 8.27 (d, J = 8.8 Hz, 1H), 8.41 (s, 1H). |
| 153 | 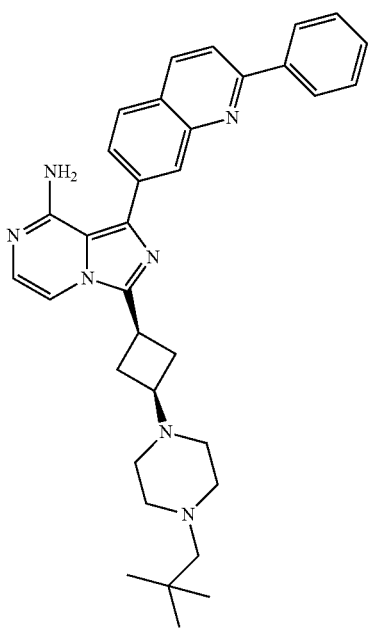 [SMILES: CC(C)(C)CN1CCN([C@H]2C[C@@H](c3nc(-c4ccc5ccc(-c6ccccc6)nc5c4)c4c(N)nccn43)C2)CC1] | 3-{3-[4-(2,2-Dimethyl-propyl)-piperazin-1-yl]-cyclobutyl}-1-{2-phyenyl-quinolin-7-yl)-imidazo[1,5a]pyrazin-8-ylamine | 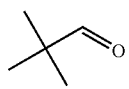  Method X4.1 | (ES+): m/z 546 [MH+]. | (400 MHz, CDCl$_3$) δ 0.86 (s, 9H), 2.01 (s, 2H), 2.42-2.56 (m, 10H), 2.66-2.69 (m, 2H), 2.95 (m, 1H), 3.48 (m, 1H), 5.23 (br, 2H), 7.10 (d, J = 4.8 Hz, 1H), 7.19 (d, J = 4.8, 1H), 7.48-7.56 (m, 3H), 7.91-7.94 (m, 3H), 8.18-8.20 (m, 2H), 8.26 (d, J = 8.4 Hz, 1H), 8.38 (s, 1H). |

| 154 | 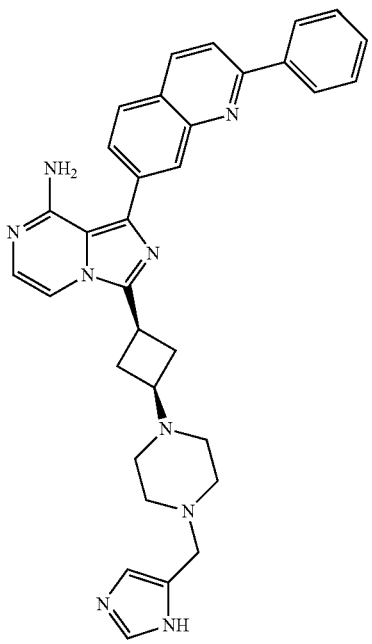 [SMILES: Nc1nccn2c1c(-c1ccc3ccc(-c4ccccc4)nc3c1)nc2[C@H]1C[C@@H](N2CCN(Cc3cnc[nH]3)CC2)C1] | 3-{3-[4-(3H-imidazol-4-ylmethyl)-piperazin-1-yl]-cyclobutyl}-1-(2-phyenyl-quinolin-7-yl)-imidazo[1,5a]pyrazin-8-ylamine | 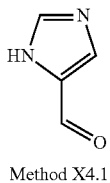<br>Method X4.1 | (ES+): m/z 556 [MH⁺]. | (400 MHz, CDCl₃) δ 2.44-2.69 (m, 12H), 2.94-2.98 (m, 1H), 3.46-3.49 (m, 1H), 3.58 (s, 2H), 5.22 (br, 2H), 6.96 (s, 1H), 7.11 (d, J = 4.8 Hz, 1H), 7.18 (d, J = 5.2, 1H), 7.48-7.59 (m, 4H), 7.91-7.93 (m, 3H), 8.19 (m, 2H), 8.27 (d, J = 8.8 Hz, 1H), 8.39 (s, 1H). |
|---|---|---|---|---|---|

Additionally, 3-[3-(4-Methyl-piperazin-1-yl)-cyclobutyl]-1-(2-phenyl-quinolin-7-yl)-imidazo[1,5-a]pyrazin-8-ylamine can be prepared as follows: A mixture of 1-iodo-3-[3-(4-methyl-piperazin-1-yl)-cyclobutyl]-imidazo[1,5-a]pyrazin-8-ylamine (206 mg, 0.5 mmol) and 2-phenyl-7-(4,4,5,5-tetramethyl-[1,3,2]dioxaborolan-2-yl)-quinoline (182 mg, 0.55 mmol) and cesium carbonate (326 mg, 1.0 mmol) in 1,2-dimethoxyethane (10 mL) and water (2 mL) was evacuated and refilled with nitrogen (3×), then tetrakis(triphenylphosphine)palladium(0) (58 mg, 0.05 mmol) was added, and the flask was again evacuated and refilled with nitrogen (3×). The mixture was heated at 75° C. overnight. LC-MS (5127-03-1) showed the reaction was complete. The mixture was concentrated under reduced pressure, the residue was dissolved in MeOH-DMSO and purified by MDPS to give a yellow solid; LC-MS (ES, Pos.): 490 [MH⁺]; ¹H NMR (CDCl₃, 400 MHz) δ 2.30 (s, 3H), 2.32-2.73 (m, 12H), 2.96 (m, 1H), 3.49 (m, 1H), 5.19 (brs, 2H), 7.12 (d, J=5.0 Hz, 1H), 7.19 (d, J=5.0 Hz, 1H), 7.46-7.56 (m, 3H), 7.91-7.97 (m, 3H), 8.19-8.21 (m, 2H), 8.27 (d, J=8.6 Hz, 1H), 8.39 (s, 1H).

Example 155

1-(4-Methyl-2-phenyl-quinolin-7-yl)-3-[3-(4-methyl-piperazin-1-yl)-cyclobutyl]-imidazo[1,5-a]pyrazin-8-ylamine

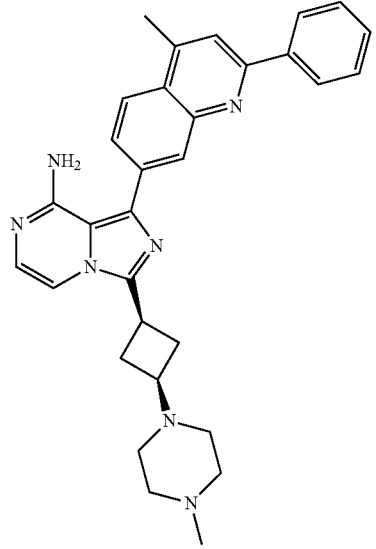 [SMILES: Cc1cc(-c2ccccc2)nc2cc(-c3nc([C@H]4C[C@@H](N5CCN(C)CC5)C4)n4ccnc(N)c34)ccc12]

A mixture of 1-iodo-3-[3-(4-methyl-piperazin-1-yl)-cyclobutyl]-imidazo[1,5-a]pyrazin-8-ylamine (206 mg, 0.500 mmol) and 4-methyl-2-phenyl-7-(4,4,5,5-tetramethyl-[1,3,2]dioxaborolan-2-yl)-quinoline (190 mg, 0.550 mmol) and cesium carbonate (326 mg, 1.00 mmol) in 1,2-dimethoxyethane (10.0 mL) and water (2.0 mL) was evacuated and refilled with nitrogen (3×), then charged with tetrakis(triphenylphosphine)palladium(0) (58 mg, 0.05 mmol), and the flask was again evacuated and refilled with nitrogen (3×). The mixture was heated at 75° C. overnight. The mixture was cooled to rt and diluted with ethyl acetate (30 mL), then washed with brine (15 mL); the organic phase was dried over anhydrous sodium sulfate, filtered, and concentrated to afforded a yellow solid, which was purified by silica gel chromatography [CH$_2$Cl$_2$→5% MeOH/CH$_2$Cl$_2$→5% (2N NH$_3$-MeOH)/CH$_2$Cl$_2$, then 10% (2N NH$_3$-MeOH)/CH$_2$Cl$_2$ to give the title compound as a yellow solid; LC-MS (ES, Pos.): 504 [MH$^+$]; $^1$H NMR (CDCl$_3$, 400 MHz) δ 2.30 (s, 3H), 2.32-2.71 (m, 12H), 2.81 (d, J=0.9 Hz, 3H), 2.95 (m, 1H), 3.49 (m, 1H), 5.19 (brs, 2H), 7.11 (d, J=5.0 Hz, 1H), 7.19 (d, J=5.0 Hz, 1H), 7.45-7.55 (m, 3H), 7.75 (d, J=0.8 Hz, 1H), 7.94 (dd, J=8.6 Hz, 1.8 Hz, 1H), 8.12 (d, J=8.6 Hz, 1H), 8.16-8.19 (m, 2H), 8.39 (d, J=1.4 Hz, 1H).

Example 156

1-(8-Fluoro-2-phenyl-quinolin-7-yl)-3-[3-(4-methyl-piperazin-1-yl)-cyclobutyl]-imidazo[1,5-a]pyrazin-8-ylamine

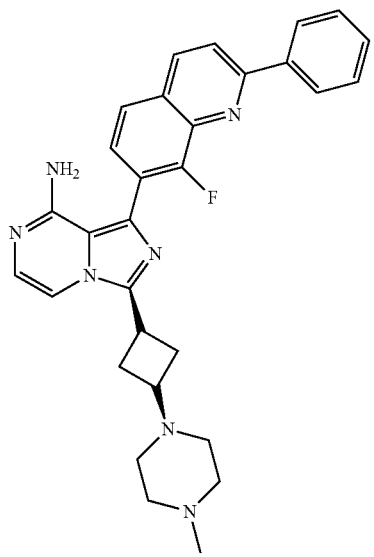

A solution of 1-iodo-3-[3-(4-methyl-piperazin-1-yl)-cyclobutyl]-imidazo[1,5-a]pyrazin-8-ylamine (93 mg, 0.22 mmol), 8-fluoro-2-phenyl-7-(4,4,5,5-tetramethyl-[1,3,2]dioxaborolan-2-yl)quinoline (87 mg, 0.25 mmol) and cesium carbonate (88 mg, 0.27 mmol) in DME (3.33 mL) and H$_2$O (0.67 mL) was degassed with N$_2$ for 10 minutes. Tetrakis(triphenylphosphine)palladium(0) (13 mg, 0.011 mmol) was added, and the reaction heated at 75° C. overnight. The reaction was allowed to cool to rt, poured into saturated NaHCO$_3$ solution (50 ml) and extracted with ethyl acetate (3×50 ml). The combined organics were washed with brine (3×50 ml), dried (MgSO$_4$), filtered and concentrated in vacuo. Flash chromatography (DCM stepping up to 5% MeOH in DCM) gave the title compound as an off-white solid; NMR (CDCl$_3$, 400 MHz) δ 8.27 (1H, d, J=8.6 Hz), 8.23 (2H, d, J=7.1 Hz), 7.99 (1H, d, J=8.8 Hz), 7.73-7.67 (2H, m), 7.55-7.48 (3H, m), 7.16 (1H, d, 5.1 Hz), 7.06 (1H, d, J=5.1 Hz), 3.46 (1H, m), 2.94 (1H, m), 2.71-2.32 (15H, m); MS (ES+): m/z 508.03 [MH$^+$]; HPLC: t$_R$=1.71 min (MicromassZQ, polar_5 min).

The following compounds in Table ZA.1 were prepared according to procedures described herein before:

| Example | Structure | Name | MS (M + H) |
|---|---|---|---|
| 157 | 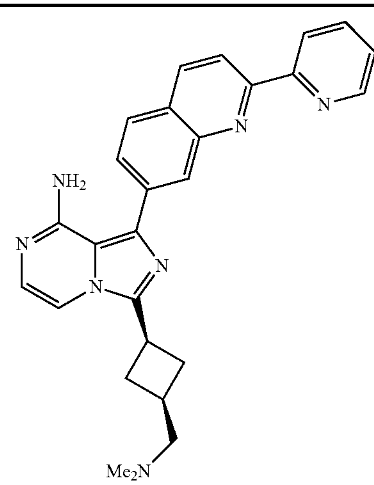 | 3-(3-Dimethylaminomethylcyclobutyl)-1-(2-pyridin-2-yl-quinolin-7-yl)imidazo[1,5-a]pyrazin-8-ylamine | 450.07 |

-continued
| 158 | 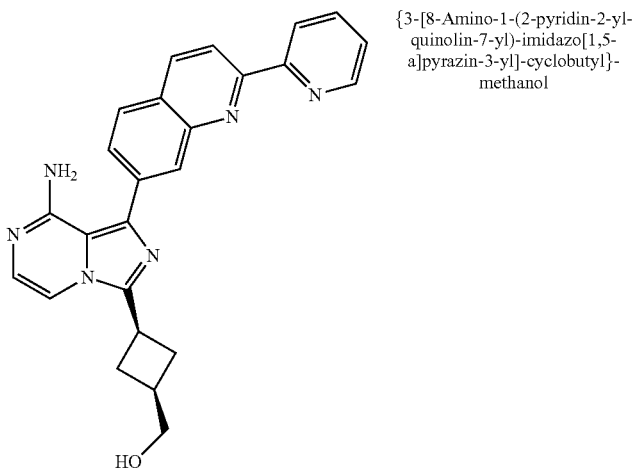 | {3-[8-Amino-1-(2-pyridin-2-yl-quinolin-7-yl)-imidazo[1,5-a]pyrazin-3-yl]-cyclobutyl}-methanol | 423.07 |
| --- | --- | --- | --- |
| 159 | 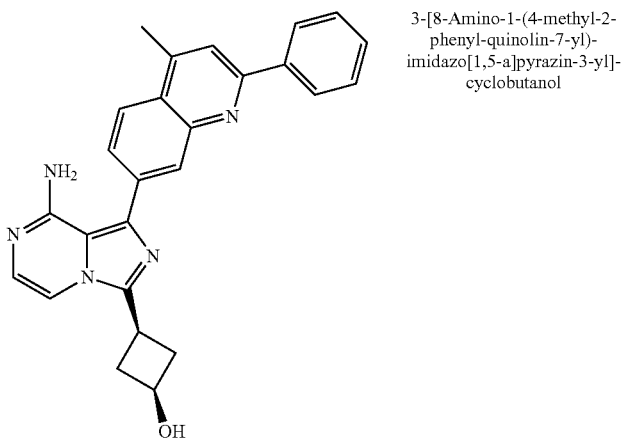 | 3-[8-Amino-1-(4-methyl-2-phenyl-quinolin-7-yl)-imidazo[1,5-a]pyrazin-3-yl]-cyclobutanol | 422.01 |
| 160 | 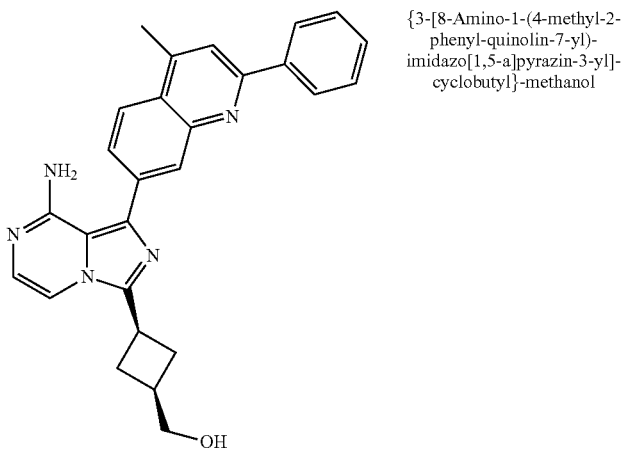 | {3-[8-Amino-1-(4-methyl-2-phenyl-quinolin-7-yl)-imidazo[1,5-a]pyrazin-3-yl]-cyclobutyl}-methanol | 436.03 |

| | | | |
|---|---|---|---|
| 161 | 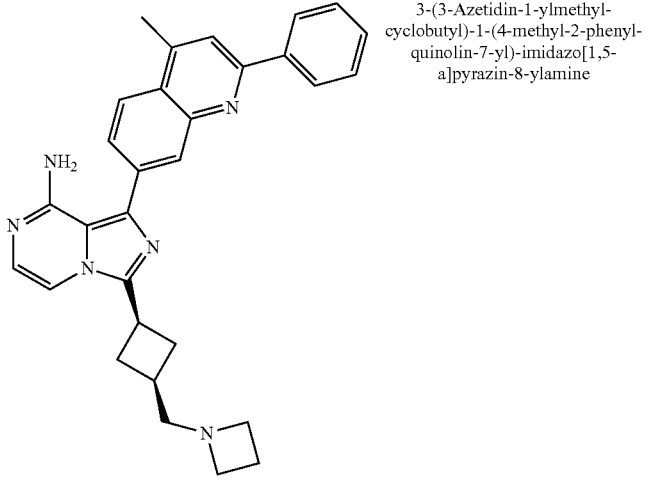 | 3-(3-Azetidin-1-ylmethyl-cyclobutyl)-1-(4-methyl-2-phenyl-quinolin-7-yl)-imidazo[1,5-a]pyrazin-8-ylamine | 474.98 |
| 162 | 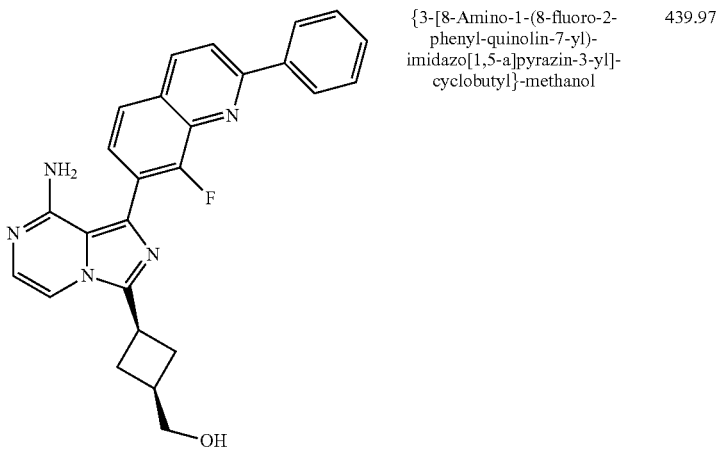 | {3-[8-Amino-1-(8-fluoro-2-phenyl-quinolin-7-yl)-imidazo[1,5-a]pyrazin-3-yl]-cyclobutyl}-methanol | 439.97 |
| 163 | 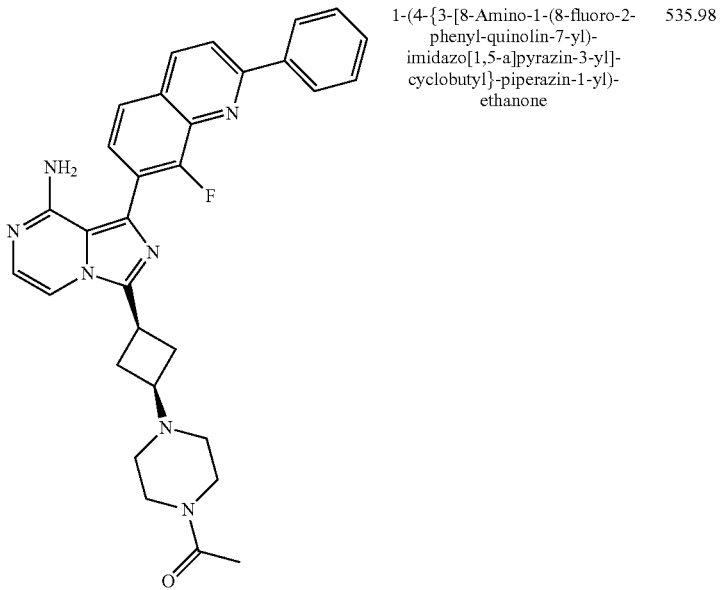 | 1-(4-{3-[8-Amino-1-(8-fluoro-2-phenyl-quinolin-7-yl)-imidazo[1,5-a]pyrazin-3-yl]-cyclobutyl}-piperazin-1-yl)-ethanone | 535.98 |

| | | | |
|---|---|---|---|
| 164 | 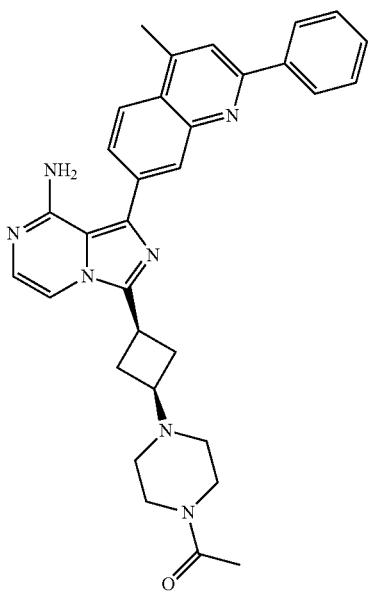 [SMILES: CC(=O)N1CCN([C@H]2C[C@@H](c3nc(-c4ccc5c(C)cc(-c6ccccc6)nc5c4)c4c(N)nccn43)C2)CC1] | 1-(4-{3-[8-Amino-1-(4-methyl-2-phenyl-quinolin-7-yl)-imidazo[1,5-a]pyrazin-3-yl]-cyclobutyl}-piperazin-1-yl)-ethanone | 532.03 |
| 165 | 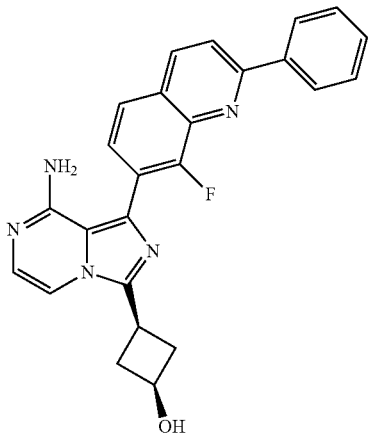 [SMILES: Nc1nccn2c1c(-c1ccc3ccc(-c4ccccc4)nc3c1F)nc2[C@H]1C[C@@H](O)C1] | 3-[8-Amino-1-(8-fluoro-2-phenyl-quinolin-7-yl)-imidazo[1,5-a]pyrazin-3-yl]-cyclobutanol | 425.94 |
| 166 | 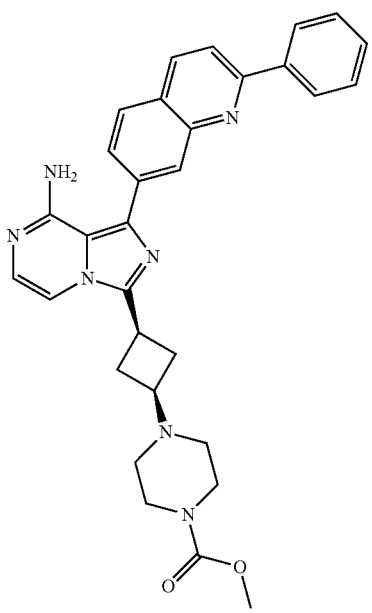 [SMILES: COC(=O)N1CCN([C@H]2C[C@@H](c3nc(-c4ccc5ccc(-c6ccccc6)nc5c4)c4c(N)nccn43)C2)CC1] | 4-{3-[8-Amino-1-(2-phenyl-quinolin-7-yl)-imidazo[1,5-a]pyrazin-3-yl]-cyclobutyl}-piperazine-1-carboxylic acid methyl ester | 534.00 |

| | | | |
|---|---|---|---|
| 167 | 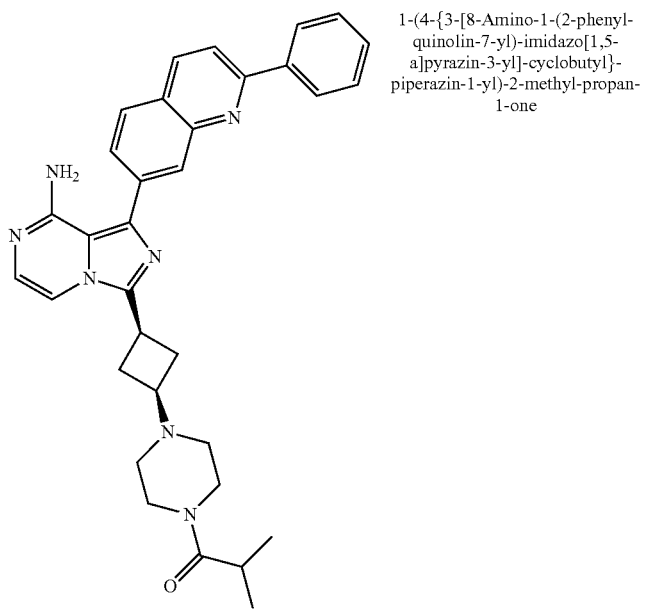 | 1-(4-{3-[8-Amino-1-(2-phenyl-quinolin-7-yl)-imidazo[1,5-a]pyrazin-3-yl]-cyclobutyl}-piperazin-1-yl)-2-methyl-propan-1-one | 546.02 |
| 168 | 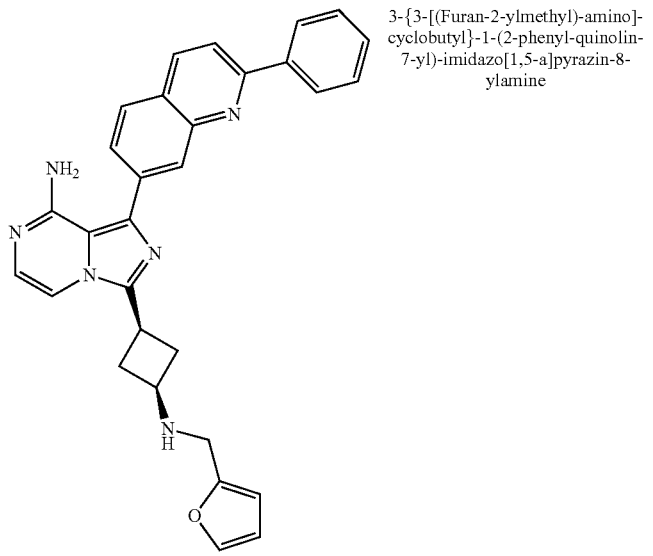 | 3-{3-[(Furan-2-ylmethyl)-amino]-cyclobutyl}-1-(2-phenyl-quinolin-7-yl)-imidazo[1,5-a]pyrazin-8-ylamine | 487.96 |

| 169 | 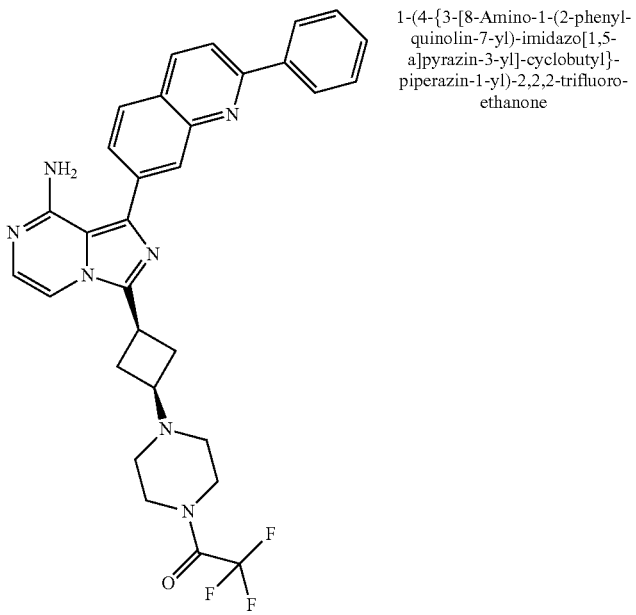 | 1-(4-{3-[8-Amino-1-(2-phenyl-quinolin-7-yl)-imidazo[1,5-a]pyrazin-3-yl]-cyclobutyl}-piperazin-1-yl)-2,2,2-trifluoro-ethanone | 571.97 |
|---|---|---|---|
| 170 | 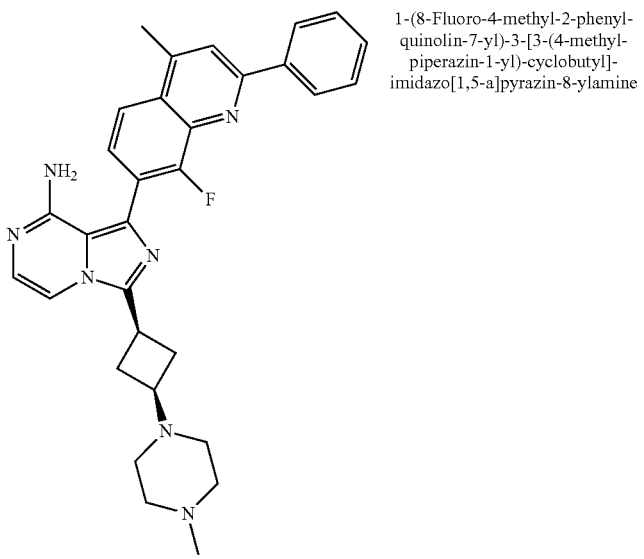 | 1-(8-Fluoro-4-methyl-2-phenyl-quinolin-7-yl)-3-[3-(4-methyl-piperazin-1-yl)-cyclobutyl]-imidazo[1,5-a]pyrazin-8-ylamine | 522.06 |
| 171 | 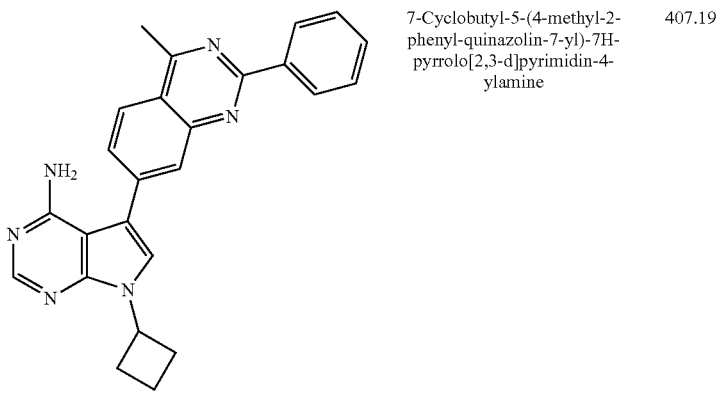 | 7-Cyclobutyl-5-(4-methyl-2-phenyl-quinazolin-7-yl)-7H-pyrrolo[2,3-d]pyrimidin-4-ylamine | 407.19 |

(1-Iodo-3-[3-(4-methyl-piperazin-1-yl)-cyclobutyl]-imidazo[1,5-a]pyrazin-8-ylamine)

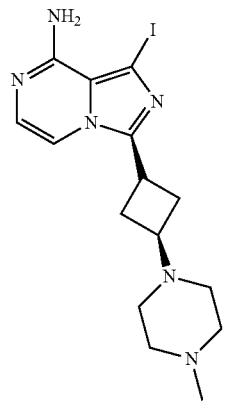

A solution of 2N ammonia in isopropyl alcohol (350 mL) and THF (30 mL, 0.4 mol) was added to 8-chloro-1-iodo-3-[3-(4-methyl-piperazin-1-yl)-cyclobutyl]-imidazo[1,5-a]pyrazine (19.91 g, 0.04612 mol) in a Parr bomb and cooled to −78° C. Ammonia was bubbled into the solution for 8-10 min. The bomb was sealed, stirred and heated to at 110° C. over 3 d. The solvent was then evaporated in vacuo and purified by flash silica gel chromatography (wetted with CHCl$_3$, dried loaded with silica, and eluted with 8% (7N NH$_3$) MeOH in CHCl$_3$), which afforded the title compound; $^1$H NMR (CDCl$_3$, 400 MHz) δ 7.31 (1H, d, J=5.01), 7.16 (1H, d, J=6.25), 5.83 (2H, s), 3.49 (1H, m), 3.06 (1H, m), 2.76 (4H, m), 2.64 (8H, m), 2.46 (3H, s); MS (ES+): m/z 412.89/413.91 (50/10) [MH$^+$]; HPLC: t$_R$=0.31 min. (OpenLynx, polar_5 min.).

(8-Chloro-1-iodo-3-[3-(4-methyl-piperazin-1-yl)-cyclobutyl]-imidazo[1,5-a]pyrazine)

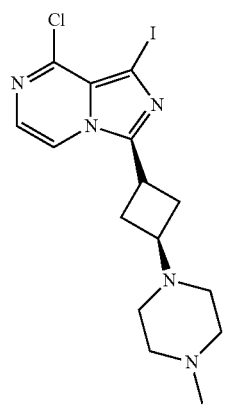

1-Methyl piperazine (5.75 mL, 0.0514 mol) in 1,2-dichloroethane (1096.7 mL, 13.892 mol) was added to 3-(8-chloro-1-iodo-imidazo[1,5-a]pyrazin-3-yl)-cyclobutanone (17.00 g, 0.04892 mol) and sodium triacetoxyborohydride (21.8 g, 0.0978 mol). The reaction stirred at it for 3 h. The reaction was concentrated, dissolved in CH$_2$Cl$_2$, and then washed with saturated NaHCO$_3$ solution and brine. The product was dried over sodium sulfate, filtered, and concentrated in vacuo. The product was flushed through a quick silica gel plug (wetted with 100% CHCl$_3$, eluted with 8% (7N NH$_3$) MeOH in CHCl$_3$), to afford the title compound; $^1$H NMR (CDCl$_3$, 400 MHz) δ 7.63 (1H, d), 7.30 (1H, d), 3.42 (1H, m), 2.94 (1H, m), 2.65 (4H, m), 2.44 (8H, m), 2.32 (3H, s); MS (ES+): m/z 431.85/433.87 (100/45) [MH$^+$]; HPLC: t$_R$=1.82 min. (OpenLynx, polar_5 min.).

1-{4-[3-(8-Amino-1-iodo-imidazo[1,5-a]pyrazin-3-yl)-cyclobutyl]-piperazin-1-yl}-ethanone 1-{4-[3-(8-Chloro-1-iodo-imidazo[1,5-a]pyrazin-3-yl)-cyclobutyl]-piperazin-1-yl}-ethanone (13.2 g, 0.029 mol) was dissolved in isopropyl alcohol (100 mL) into a Parr pressure reactor. The vessel was cooled to −78° C. and saturated with ammonia gas and sealed. The reaction was heated for 19 h at 110° C., at which point the reaction was cooled and the solvent concentrated in vacuo. The crude product was purified via silica gel chromatography eluting with 5-10% MeOH (7M NH$_3$): CH$_2$Cl$_2$ to yield the title compounds as an off white solid; MS (ES+): m/z 440.89 (100) [MH$^+$], 441.89 (20) [MH$^{++}$]; HPLC: t$_R$=0.46 min (OpenLynx, polar_5 min); $^1$H NMR (CDCl$_3$, 400 MHz) δ 2.09 (s, 3H) 2.28-2.48 (m, 6H)

2.54-2.71 (m, 2H) 2.80-2.99 (m, 1H) 3.27-3.43 (m, 1H) 3.43-3.54 (m, 2H) 3.56-3.70 (m, 2H) 7.02 (d, J=5.05 Hz, 1H) 7.16 (d, J=5.05 Hz, 2H).

1-{4-[3-(8-Chloro-1-iodo-imidazo[1,5-a]pyrazin-3-yl)-cyclobutyl]-piperazin-1-yl}-ethanone

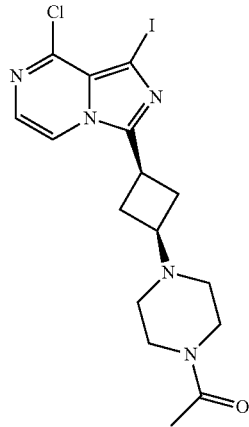 [SMILES: CC(=O)N1CCN([C@H]2C[C@@H](c3nc(I)c4c(Cl)nccn43)C2)CC1]

Into a RBF 3-(8-chloro-1-iodo-imidazo[1,5-a]pyrazin-3-yl)-cyclobutanone (1.00 g, 0.0029 mol) and sodium triacetoxyborohydride (1.30 g, 0.006 mol) were dissolved in 1,2-dichloroethane (65.0 mL) and a solution of 1-acetylpiperazine (0.39 g, 0.003 mol) in 1,2-dichloroethane was added to the reaction. The reaction mixture was stirred at room temperature for 2 h. The crude product was concentrated in vacuo and the dissolved in CH$_2$Cl$_2$ (25.0 mL) and washed with saturated NaHCO$_3$ solution (1×40 mL). The product was dried with sodium sulfate and concentrated in vacuo to yield a light yellow solid; MS (ES+): m/z 459.84 (100) [MH$^+$], 461.80 (40) [MH$^{+++}$]; HPLC: t$_R$=1.81 min (OpenLynx, polar_5 min); $^1$H NMR (CDCl$_3$, 400 MHz) δ 2.04-2.15 (m, 3H) 2.26-2.50 (m, 6H) 2.55-2.72 (m, 2 H) 2.83-2.99 (m, 1H) 3.29-3.52 (m, 3H) 3.56-3.67 (m, 2H) 7.29 (d, 1H) 7.58 (d, 1H).

(3-(8-Chloro-1-iodo-imidazo[1,5-a]pyrazin-3-yl)-cyclobutanone)

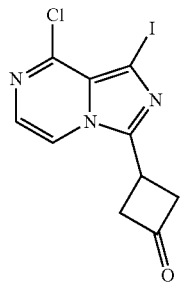 [SMILES: O=C1CC(c2nc(I)c3c(Cl)nccn23)C1]

A solution of 3-(8-chloro-1-iodo-imidazo[1,5-a]pyrazin-3-yl)-1-hydroxymethyl-cyclobutanol (4.08 g, 0.011 mol) in THF (120 mL) and water (40 mL) was charged with sodium periodate (2.8 g, 0.013 mol) at 0° C. The reaction warmed to it and stirred for 5 h. The reaction mixture was diluted with ethyl acetate and then washed with brine. The organic phase was dried over Na$_2$SO$_4$, filtered, and concentrated in vacuo to afford the title compound as a yellow solid; $^1$H NMR (CDCl$_3$, 400 MHz) δ 7.56 (1H, d, J=4.94), 7.32 (1H, d, J=4.98), 3.64 (5H, m); MS (ES+): m/z 347.82/349.85 (100/30) [MH$^1$]; HPLC: t$_R$=2.89 min. (OpenLynx, polar_5 min.).

3-(8-Chloro-1-iodo-imidazo[1,5-a]pyrazin-3-yl)-1-hydroxymethyl-cyclobutanol

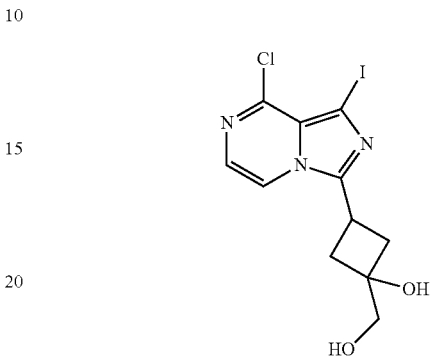

Under inert atmosphere N-iodosuccinimide (3.6 g, 0.016 mol) and 3-(8-chloro-imidazo[1,5-a]pyrazin-3-yl)-1-hydroxymethyl-cyclobutanol (3.16 g, 0.012 mol) were dissolved in N,N-dimethylformamide (30 mL) and heated at 60° C. for 3.0 hours. The reaction mixture was then concentrated in vacuo to a dark oil and purified by HPFC Jones 20 g silica gel column, eluting with 5% MeOH: CH$_2$Cl$_2$ to yield a light brown fluffy solid which was triturated with diethyl ether and hexanes to afford the title compound; MS (ES+): m/z 379.85 (100) [MH$^+$], 381.80 (30) [MH$^{+++}$]; HPLC: t$_R$=2.30 min (OpenLynx, polar_5 min).

3-(8-Chloro-imidazo[1,5-a]pyrazin-3-yl)-1-hydroxymethyl-cyclobutanol

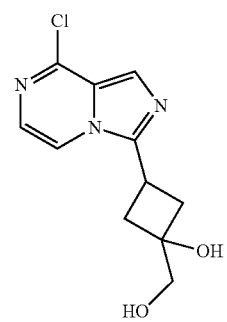 [SMILES: OCC1(O)CC(c2ncc3c(Cl)nccn23)C1]

To a THF solution (170 mL) of 8-chloro-3-(3-methylene-cyclobutyl)-imidazo[1,5-a]pyrazine (3.1 g, 14 mmol), water (18 mL), 50% N-methylmorpholine-N-oxide in water (3.2 mL) and potassium osmate, dehydrate (200 mg, 0.70 mmol) were added and the reaction was allowed to stir at rt for 4 h. Sodium sulfite (8.0 g, 70.0 mmol) was added to the reaction mixture and allowed to stir for 30 min at which point the reaction was concentrated in vacuo. The crude product was extracted from the aqueous with EtOAc. The organics were washed with brine and the combined aqueous washes were back extracted with EtOAc (5×50 mL). The combined organics were dried over sodium sulfate, filtered, and concentrated in vacuo to yield the title compounds as a sticky tan/off-white solid; MS (ES+): m/z 254.17 (100) [MH⁺], 256.19 (50) [MH⁺⁺⁺]; HPLC: $t_R$=1.95 min (OpenLynx, polar_5 min).

3-(8-Amino-1-iodo-imidazo pyrazin-3-yl)-cyclobutanol

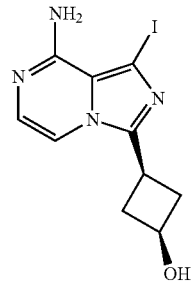 [SMILES: Nc1nccn2c1c(I)nc2[C@H]1C[C@@H](O)C1]

In a Parr pressure reactor 3-(8-chloro-1-iodo-imidazo[1,5-a]pyrazin-3-yl)-cyclobutanol (4.159 g, 0.0119 mol) was dissolved with 2.0 M ammonia in isopropyl alcohol (40 mL). The mixture was cooled to −20° C. and saturated with ammonia. The reaction was heated at 110° C. for 63 h at which point it was cooled and concentrated in vacuo. The crude product was purified using HPFC Jones 25 gram silica gel column eluting with 5-8% MeOH: CH₂Cl₂ to yield the title compounds; MS (ES+): m/z 330.88 (100) [MH⁺], 331.89 (10) [MH⁺⁺]; HPLC: $t_R$=0.48 min (OpenLynx, polar_5 min); ¹H NMR (CDCl₃, 400 MHz) δ 2.55-2.76 (m, 2H) 3.06-3.22 (m, 2H) 3.32-3.50 (m, 1H) 4.51-4.69 (m, 1H) 6.15 (br. s., 2H) 7.24 (d, J=5.05 Hz, 1H) 7.39 (d, J=5.05 Hz, 1H)

3-(8-Chloro-1-iodo-imidazo[1,5-a]pyrazin-3-yl)-cyclobutanol

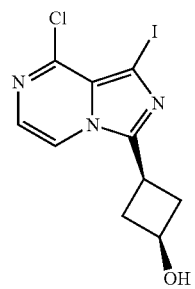 [SMILES: O[C@H]1C[C@@H](c2nc(I)c3c(Cl)nccn32)C1]

3-(8-Chloro-1-iodo-imidazo[1,5-a]pyrazin-3-yl)-cyclobutanone (5.0 g, 14 mmol) was dissolved in a 1:1 mixture of methanol (35.0 mL) and CH₂Cl₂ (35.0 mL). To the solution mixture sodium tetrahydroborate (560 mg, 14.0 mmol) was added slowly, gas evolution was observed. After 4.5 h at rt under nitrogen, the reaction was concentrated in vacuo. The crude mix was dissolved in EtOAc and washed with water. The organic layer was dried over sodium sulfate, filtered and concentrated in vacuo. The crude product was purified using HPFC Jones 50 gram silica gel column eluting with 50% EtOAc: Hex to 100% EtOAc, to yield the title compound as a light yellow solid; MS (ES+): m/z 349.81 (100) [MH⁺], 351.50 (30) [MH⁺⁺⁺]; HPLC: $t_R$=2.49 min (OpenLynx, polar_5 min); ¹H NMR (CDCl₃, 400 MHz) δ 2.41-2.54 (m, 2H) 2.78-3.05 (m, 1H) 3.12-3.32 (m, 1H) 4.08-4.75 (m, 1H) 5.30 (s, 1H) 7.31 (d, J=5.05 Hz, 1H) 7.57 (d, J=4.80 Hz, 1H)

2-Phenyl-7-(4,4,5,5-tetramethyl-[1,3,2]dioxaborolan-2-yl)-quinoline

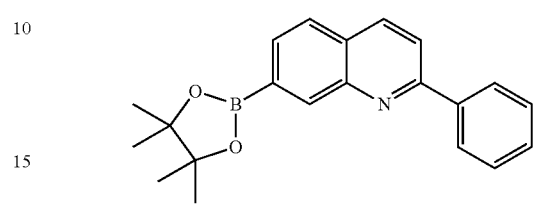

A mixture of PdCl₂dppf.CH₂Cl₂ (28 mg, 0.038 mmol), dppf (21 mg, 0.038 mmol), potassium acetate (370 mg, 3.77 mmol), bis(pinacolato)diboron (384 mg, 1.51 mmol), and trifluoromethanesulfonic acid 2-phenylquinolin-7-yl ester (444.3 mg, 1.258 mmol) in dry 1,4-dioxane (10 mL) was heated under nitrogen to 80° C. for 27 h. After cooling to RT, water was added, the mixture was extracted with EtOAc (3×35 mL), the combined extracts were washed with water and brine, dried over MgSO₄, filtered, and adsorbed onto Hydromatrix. Chromatography on silica gel [Jones Flashmaster, 10 g/70 mL cartridge, eluting with hexanes:EtOAc 19:1→9:1→5:1] gave the title compound as pale yellow solid; ¹H NMR (CDCl₃, 400 MHz) δ 1.40 (s, 12H), 7.43-7.49 (m, 1H), 7.50-7.56 (m, 2H), 7.81 (d, J=8.4 Hz, 1H), 7.88 (dd, J=8.0, 0.8 Hz, 1H), 7.92 (d, J=8.4 Hz, 1H), 8.17-8.23 (m, 2H), 8.70 (s, 1H); MS (ES+): m/z 332.1 (100) [MH⁺]; HPLC: $t_R$=4.4 min (OpenLynx, polar_5 min).

Trifluoromethanesulfonic acid 2-phenylquinolin-7-yl ester

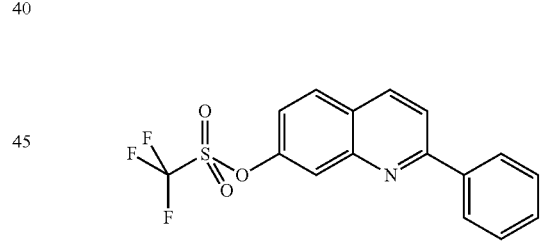

To a suspension of 2-phenylquinolin-7-ol (295.7 mg, 1.336 mmol) in dry pyridine (285 μL, 279 mg, 3.5 mmol) and dry CH₂Cl₂ (12 mL), cooled by ice/water, was added triflic anhydride (295 μL, 495 mg, 1.75 mmol) dropwise over 10 min. All material dissolved slowly; the solution, which became dark red, slowly warmed up to ambient temperature. After 3 h, TLC (eluent CH₂Cl₂) indicated complete conversion of the starting material. Water (15 mL) was added, the layers were separated, the aqueous layer was extracted with CH₂Cl₂ (3×15 mL), and the combined CH₂Cl₂ layers were washed with water (2×) and brine and dried over MgSO₄. Filtration and concentration gave a red oil that slowly solidified on standing. The material thus obtained was used without further purification in the next step; ¹H NMR (CDCl₃, 400 MHz) δ 7.46 (dd, J=2.4, 8.8 Hz, 1H), 7.48-7.59 (m, 3H), 7.93 (d, J=8.4 Hz, 1H), 7.98 (d, J=8.4 Hz, 1H), 8.10 (d, J=2.4 Hz, 1H), 8.16-8.20 (m, 2H), 8.28 (d, J=8.8 Hz, 1H); MS (ES+): m/z 354.0 (100) [MH⁺]; HPLC: $t_R$=4.2 min (OpenLynx, polar_5 min).

2-Phenylquinolin-7-ol

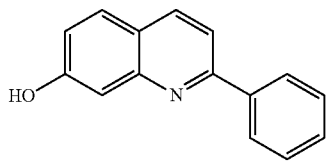 [SMILES: Oc1ccc2ccc(-c3ccccc3)nc2c1]

To a solution of 7-(tert-butyldimethylsilyloxy)quinoline (3.992 g, 15.39 mmol) in dry THF (35 mL), cooled by ice/water, was added phenyllithium (1.8 M in cyclohexane:ether 70:30, 10 mL, 18 mmol). The solution slowly warmed up to ambient temperature and was stirred overnight. More phenyllithium (1.0 mL, 1.8 mmol) was added, and stirring was continued for 4 h. The reaction was quenched by adding saturated NH₄Cl solution and water. Most of the THF was evaporated, the residue was extracted with EtOAc (4×30 mL) and the combined EtOAc layers were washed with water (2×) and brine and dried over MgSO₄. LC/MS indicated that a significant amount of the TBDMS ether had been cleaved during the workup, the ratio of quinolines to dihydroquinolines was about 1:1. Air was bubbled into the solution overnight, the MgSO₄ was filtered off, the filtrate was concentrated, dissolved in MeOH, aq. HCl (2 M, 2 mL, 4 mmol) was added, and the solution was stirred at ambient temperature overnight. Sat. NaHCO₃ solution was added, most of the MeOH was evaporated, water (≈100 mL) was added, and the dark brown precipitate was filtered off and washed with more water. The combined filtrate and washings were extracted with EtOAc (4×60 mL), the combined EtOAc extracts were washed with water and brine and dried over MgSO₄. The dark brown precipitate was dissolved in MeOH (≈100 mL), the solution was filtered, and the filtrate was adsorbed onto Hydromatrix and chromatographed on silica gel [Jones Flashmaster, 50 g/150 mL cartridge, eluting with CH₂Cl₂→5% EtOAc in CH₂Cl₂→10% EtOAc→15% EtOAc]. The mixed fractions were combined with the crude material from the EtOAc extracts and chromatographed on silica gel [Jones Flashmaster, material adsorbed onto Hydromatrix, 10 g/70 mL cartridge, eluting with CH₂Cl₂→5% EtOAc in CH₂Cl₂→7.5% EtOAc]. Combination of pure fractions of both columns gave the title compound as light beige solid; ¹H NMR (DMSO-d₆, 400 MHz) δ 7.15 (dd, J=8.8, 2.4 Hz, 1H), 7.29 (d, J=2.4 Hz, 1H), 7.45-7.51 (m, 1H), 7.51-7.57 (m, 2H), 7.83 (d, J=8.8 Hz, 1H), 7.89 (d, J=8.8 Hz, 1H), 8.20-8.25 (m, 2H), 8.29 (d, J=8.8 Hz, 1H), 10.19 (s, 1H); MS (ES+): m/z 222.1 (100) [MH⁺]; HPLC: $t_R$=2.2 min (OpenLynx, polar_5 min).

Additionally, 2-phenylquinolin-7-ol can be prepared as follows: Into a suspension of 7-hydroxyquinoline (290.3 mg, 2.0 mmol) in THF (5 mL), which was cooled in ice/H₂O bath, was added PhLi (1.8 M in n-Bu₂O, 2.05 eq., 2278 μL) dropwise under N₂ over 5 min. After stirring at 0° C. for 1 h, the ice/H₂O bath was removed and the mixture was warmed to rt and stirring was continuing for another 1-3 h. After that time, methanol (10 mL) was added followed by addition of H₂O (20 mL). The mixture was then extracted with EtOAc (4×20 mL). The extracts were washed with brine (4×20 mL). Air was bubbled through the above extracts at rt while stirring for 3-4 days. After that time, solvent was removed in vacuo and the solid was triturated with 50% EtOAc/Hexane (20 mL) to obtain the title compound as a brown powder.

7-(tert-Butyldimethylsilyloxy)quinoline

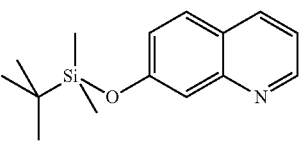 [SMILES: CC(C)(C)[Si](C)(C)Oc1ccc2cccnc2c1]

To a suspension of 7-hydroxyquinoline (2.240 g, 15.43 mmol) in dry CH₂Cl₂ (30 mL) were added (in this order) DMAP (94 mg, 0.77 mmol), triethylamine (4.3 mL, 3.1 g, 31 mmol), and TBDMSCl (2.558 g, 16.97 mmol), and the mixture was stirred overnight at ambient temperature. Water and sat. NH₄Cl sol. (10 mL each) were added, the layers were separated, and the aqueous layer was extracted with CH₂Cl₂ (2×30 mL). The combined organic layers were washed with 0.25 M citric acid (2×), water, sat. NaHCO₃ solution, and brine, and dried over MgSO₄. EtOAc (10 mL) was added to the solution, which was then filtered through a silica gel plug (60 mL glass frit filled ≈½ with silica gel) and concentrated to give the title compound as pale yellow oil. The material thus obtained was used without further purification; ¹H NMR (CDCl₃, 400 MHz) δ 0.29 (s, 6H), 1.03 (s, 9H), 7.15 (dd, J=2.8, 8.8 Hz, 1H), 7.26 (dd, J=4.0, 8.0 Hz, 1H), 7.46 (d, J=2.8 Hz, 1H), 7.70 (d, J=8.8 Hz, 1H), 8.08 (dd, J=0.8, 8.0 Hz, 1H), 8.83 (dd, J=1.6, 4.0 Hz, 1H); MS (ES+): m/z 260.2 (100) [MH⁺]; HPLC: $t_R$=3.8 min (OpenLynx, polar 5 min).

Additionally, 2-phenyl-7-(4,4,5,5-tetramethyl-[1,3,2]dioxaborolan-2-yl)-quinoline can be prepared as follows: A mixture of 7-chloro-2-phenylquinoline (14.40 g, 60 mmol), bis(pinacolato)diboron (17.1 g, 69.6 mmol), KOAc (14.7 g, 150 mmol), Pd(OAc)₂ (400 mg, 1.8 mmol) and 1,3-bis(2,6-diisopropylphenyl)imidazolium chloride (1.53 g, 3.6 mmol) in THF (300 mL) was refluxed under nitrogen overnight (14 h). LC-MS showed the reaction completed. The mixture was diluted with EtOAc (300 mL) and brine (100 mL), then filtered through celite to remove most of the black materials. Another two reactions from 60 mmol and 40 mmol of 7-chloro-2-phenylquinoline were combined with the above. All the filtrates were combined, washed with brine (300 mL), and dried over anhydrous sodium sulfate. Filtration through a pad of silica gel removed the trace amount of black materials. The filtrate was concentrated under reduced pressure to ca. 500 mL, the white precipitate was collected by filtration to afford the first batch of product. The filtrate was further concentrated to 200 mL and provided the second batch as a light-yellow solid. The filtrate was then concentrated to 100 mL and provided the third batch of the title compound as a light-yellow solid; LC-MS (ES, Pos.): 332 (MH⁺) and 250 (for the corresponding boronic acid hydrolyzed under LC-MS acid condition); ¹H NMR (CD₃COCD₃, 400 MHz) δ 1.41 (s, 12H), 7.48-7.58 (m, 3H), 7.85 (dd, J=8.0, 1.0 Hz, 1H), 7.96

(d, J=8.0 Hz, 1H), 8.16 (d, J=8.6 Hz, 1H), 8.34-8.36 (m, 2H), 8.42 (d, J=8.6 Hz, 1H), 8.55 (s, 1H).

7-Chloro-2-phenyl-quinoline

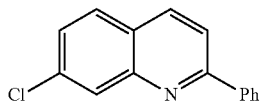 [SMILES: Clc1ccc2ccc(-c3ccccc3)nc2c1]

To a solution of 4-chloro-2-nitrobenzaldehyde (55.7 g, 300 mmol) in ethanol (600 mL) and water (60 mL) was added iron powder (167 g, 3000 mmol) and conc. HCl (5 mL, 60 mmol), the resulting mixture was stirred with a mechanical stirrer under refluxing condition. 1 h later, LC-MS showed ca. 50% conversion, there was not much change after another one hour. Conc. HCl (2 mL) was added, LC-MS showed the reduction was complete after the mixture was refluxed for an additional 30 min. Then acetophenone (35 mL, 300 mmol) and KOH (50.5 g, 900 mmol) were added, the resulting mixture was further refluxed for 1 h, LC-MS showed the reaction was complete and the desired product was formed. The mixture was cooled to 40° C. and diluted with methylene chloride (1 L), then filtered through celite and the filtrate was concentrated. The residue was dissolved in methylene chloride (1 L) and washed with brine (2×300 mL), and dried over anhydrous sodium sulfate. The solvent was concentrated to ca. 200 mL and diluted with hexanes (500 mL), the light-yellow solid was collected by filtration as the first batch of desired product. The mother liquid was concentrated and then recrystallized with acetonitrile to give the second batch of the title compound as a light-yellow solid; LC-MS (ES, Pos.): 240/242 (3/1) [MH$^+$]; $^1$H NMR (CDCl$_3$, 400 MHz) δ 7.46-7.56 (m, 4H), 7.77 (d, J=8.7 Hz, 1H), 7.89 (d, J=8.6 Hz, 1H), 8.14-8.18 (m, 3H), 8.20 (d, J=8.6 Hz, 1H).

2-Pyridin-2-yl-7-(4,4,5,5-tetramethyl-[1,3,2]dioxaborolan-2-yl)quinoline

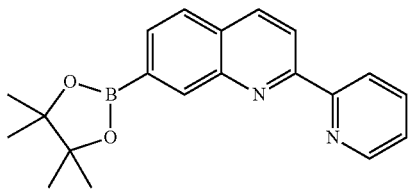 [SMILES: CC1(C)OB(c2ccc3ccc(-c4ccccn4)nc3c2)OC1(C)C]

N$_2$ was bubbled into a stirred mixture of 7-chloro-2-pyridin-2-ylquinoline (38.225 g, 158.8 mmol), diboron (46.765 g, 184.15 mmol), PdCl$_2$(d$_{PPf}$O—CH$_2$Cl$_2$ (32.413 g, 39.69 mmol), and KOAc (38.96 g, 396.9 mmol) in THF (700 mL) for 10 min. This mixture was then stirred under reflux for 72 h. After cooled to rt, EtOAc (300 mL) and water (200 mL) were added. The organic layer was collected and the aqueous phase was extracted with EtOAc (300 mL). The combined organic phases were dried over MgSO$_4$, filtered through a Celite pad, concentrated in vacuo to a volume of ~200 mL. This black-colored solution was passed through a short silica column, which was washed with EtOAc (~1800 mL). The resulting organic phase was concentrated (~200 mL) and passed through another short silica column. The above process was repeated until the color of the resulting EtOAc solution turned to light brown to orange. At this point, almost all the catalyst was removed. The EtOAc solution was concentrated under reduced pressure to ~100 mL. Products crashed out were collected by filtration. The above process was repeated several times until most of the products were fished out. Combining all batches afforded the title compound as an off-white solid product; $^1$H-NMR (Acetone-d$_6$, 400 MHz) δ 1.41 (s, 12H), 7.47-7.51 (m, 1H), 7.88 (dd, J=1.2, 8.0 Hz, 1H), 7.99-8.03 (m, 2H), 8.47 (d, J=8.8 Hz, 1H), 8.57 (s, 1H), 8.71 (d, J=8.4 Hz, 1H), 8.74-8.77 (m, 2H); MS (ES+): m/z 333.2 (M$^+$); HPLC: t$_R$=4.30 min (OpenLynx, polar_5 min).

2-Pyridin-3-yl-7-(4,4,5,5-tetramethyl-[1,3,2]dioxaborolan-2-yl)-quinoline

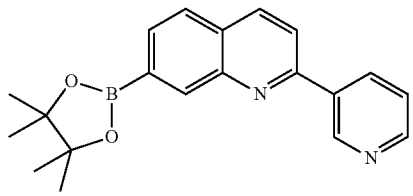 [SMILES: CC1(C)OB(c2ccc3ccc(-c4cccnc4)nc3c2)OC1(C)C]

Prepared according to the procedures for 2-pyridin-2-yl-7-(4,4,5,5-tatramethyl-[1,3,2]dioxaborolan-2-yl)quinoline; MS (ES+): 333.4 (M+1), t$_R$(polar_5 min)=3.7 min.

2-Pyridin-4-yl-7-(4,4,5,5-tatramethyl-[1,3,2]dioxaborolan-2-yl)quinoline

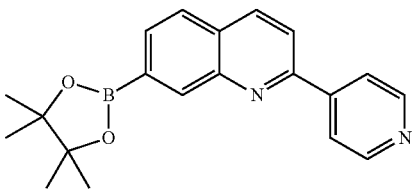 [SMILES: CC1(C)OB(c2ccc3ccc(-c4ccncc4)nc3c2)OC1(C)C]

N$_2$ was bubbled into a stirred mixture of 7-chloro-2-pyridin-4-ylquinoline (240.7 mg, 1.0 mmol), diboron (294.6 mg, 1.16 mmol), Pd(OAc)$_2$ (6.7 mg, 0.03 mmol), imidazolium ligand (25.5 mg, 0.06 mmol) and KOAc (245 mg, 2.5 mmol) in THF (20 mL) for 10 min. This mixture was then refluxed under N$_2$ overnight. Solvents were removed and the residue was purified by silica gel chromatography (10% EtOAc in hexane) to afford a mixture of the desired title compound and 2-pyridin-4-ylquinoline. This mixture was used directly in the next step; $^1$H-NMR (CDCl$_3$, 400 MHz) δ 1.41 (s, 12H), 7.58-7.62 (m, 1H), 7.84 (d, J=8.4 Hz, 1H), 7.94 (d, J=8.4 Hz, 1H), 8.07-8.10 (m, 2H), 8.28 (d, J=8.8 Hz, 1H), 8.71 (s, 1H), 8.77-8.80 (m, 2H); MS (ES+): m/z 333 (MH+).

General Procedure for Preparing Pyridinyl-Derived Quinolines

7-Chloro-2-pyridin-2-ylquinoline

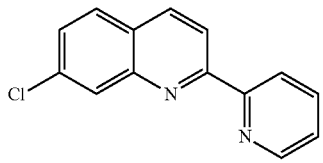 [SMILES: Clc1ccc2ccc(-c3ccccn3)nc2c1]

Iron powder (167 g, 2990 mmol), water (60 mL), and concentrated hydrochloric acid (3 mL, ~36 mmol) were added consecutively to a solution of 4-chloro-2-nitrobenzaldehyde (55.7 g, 300 mmol) in EtOH (600 mL). After stirred (mechanically) at 95° C. for 10 min, another aliquot of concentrated hydrochloric acid (2 mL, ~24 mmol) was added. Stirring was continued at 95° C. for another 80 min. 1-Pyridin-2-ylethanone (33 mL, 294.1 mmol) and solid KOH (50.5 g, 900 mmol) were then added in portions with caution. The resulting mixture was stirred at 95° C. for 4 h. After cooled to rt, the reaction was diluted with dichloromethane (500 mL) and filtered through a Celite pad. The filtrate was concentrated to approximately 100 mL. The desired precipitated product was collected by filtration; $^1$H-NMR (CDCl$_3$, 400 MHz) δ 7.37-7.40 (m, 1H), 7.51 (dd, J=2.0, 8.8 Hz, 1H), 7.79 (d, J=8.4 Hz, 1H), 7.89 (dt, J=1.6, 8.0 Hz, 1H), 8.19 (s, 1H), 8.26 (d, J=8.8 Hz, 1H), 8.57 (d, J=8.8 Hz, 1H), 8.64 (d, J=8.4 Hz, 1H), 8.74-8.75 (m, 1H); MS (ES+): m/z 241 (MH+, $^{35}$Cl), 243 (MH+, $^{37}$Cl); HPLC: t$_R$=3.95 min (OpenLynx, polar_5 min).

7-Chloro-2-pyridin-3-ylquinoline

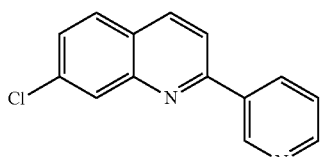

Prepared according to the general procedure for pyridinyl-derived quinolines; $^1$H-NMR (CDCl$_3$, 400 MHz) δ 7.47 (dq, J=0.8, 4.8 Hz, 1H), 7.52 (dd, J=2.0, 8.8 Hz, 1H), 7.80 (d, J=8.8 Hz, 1H), 7.90 (d, J=8.8 Hz, 1H), 8.19 (d, J=2.0 Hz, 1H), 8.26 (d, J=8.4 Hz, 1H), 8.50-8.53 (m, 1H), 8.72 (dd, J=1.6, 4.8 Hz, 1 H), 9.35 (dd, J=0.8, 2.4 Hz, 1H); MS (ES+): m/z 241 (MH+, $^{35}$Cl), 243 (MH+, $^{37}$Cl); HPLC: t$_R$=3.35 min (OpenLynx, polar_5 min).

7-Chloro-2-pyridin-4-ylquinoline

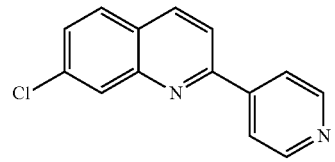 [SMILES: Clc1ccc2ccc(-c3ccncc3)nc2c1]

Prepared according to the general procedure for pyridinyl-derived quinolines; $^1$H-NMR (CDCl$_3$, 400 MHz) δ 7.55 (dd, J=2.4, 8.8 Hz, 1H), 7.81 (d, J=8.8 Hz, 1H), 7.92 (d, J=8.4 Hz, 1H), 8.05-8.06 (m, 2H), 8.21 (d, J=2.0 Hz, 1H), 8.28 (d, J=8.4 Hz, 1H), 8.79-8.81 (m, 2H); MS (ES+): m/z 241 (MH+, $^{35}$Cl), 243 (MH+, $^{37}$Cl); HPLC: t$_R$=3.22 min (OpenLynx, polar_5 min).

4-Chloro-2-nitrobenzaldehyde

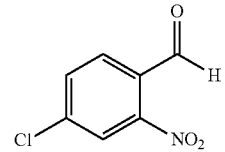

A solution of 4-chloro-2-nitrotoluene (514.8 mg, 3.000 mmol) and dimethylformamide dimethylacetal (1.200 ml, 1074 mg, 9.000 mmol) in DMF (1.2 ml) was heated at 135° C. in a sealed tube for 15 h. The reaction mixture was cooled to rt and added dropwise to a 20° C. solution of NaIO$_4$ (1926 mg, 9.000 mmol) in water (6.18 ml) and DMF (3.09 ml). After 3 h, the mixture was treated with water (20 ml) and extracted with EtOAc (3×15 ml). The extracts were washed with water (3×15 ml) and brine (15 ml), and dried over MgSO$_4$. After the solid was filtered off and the solvent was removed in vacuo, a brown solid of 4-chloro-2-nitrobenzaldehyde was obtained (*J. Org. Chem.* 2003, 68, 4104-4107). NMR (CDCl$_3$, 400 MHz) δ 7.74-7.78 (m, 1H), 7.94-7.96 (m, 1H), 8.11-8.12 (m, 1H), 10.39 (s, 1H).

4-Methyl-2-phenyl-7-(4,4,5,5-tetramethyl-1,3,2-dioxaborolan-2-yl)quinoline

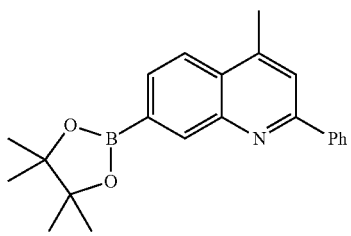 [SMILES: Cc1cc(-c2ccccc2)nc2cc(B3OC(C)(C)C(C)(C)O3)ccc12]

A mixture of 7-chloro-4-methyl-2-phenylquinoline (335 mg, 1.3 mmol), bis(pinacolato)diboron (389 mg, 1.5 mmol), Pd(OAc)$_2$ (18 mg, 0.08 mmol), 1,3-bis(2,6-di-i-propylphenyl)imidazolium chloride (67 mg, 0.16 mmol) and KOAc (130 mg, 1.3 mmol) in anh THF (18 mL) under Ar heated at reflux for 21 h. Then the reaction was charged again with Pd(OAc)$_2$ (18 mg, 0.08 mmol), 1,3-bis(2,6-di-1-propylphenyl)imidazolium chloride (67 mg, 0.16 mmol) and evacuated and refilled with Ar (4×) while being cooled in a dry ice-acetone bath. The reaction mixture was heated at reflux for 27 h. The mixture was the cooled to rt, diluted with EtOAc (100 mL), washed (brine, 2×20 mL), dried (Na$_2$SO$_4$) and concentrated under reduced pressure to yield a light brown gum. The material was taken into hexanes to provide the title compound as a yellow solid which was used in the following step without further purification; MS (ES+): m/z 346.2 (100) [MH$^+$]; HPLC: t$_R$=3.99 min (OpenLynx, nonpolar_5 min).

7-Chloro-4-methyl-2-phenylquinoline

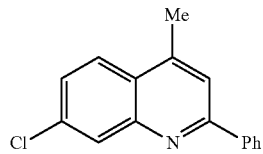 [SMILES: Cc1cc(-c2ccccc2)nc2cc(Cl)ccc12]

Acetophenone (0.66 mL, 5.69 mmol) was added to 1-(2-amino-4-chlorophenyl)ethanone (0.868 g, 5.69 mmol) and [Hbim]BF$_4$ (1.50 g, 7.08 mmol) under Ar. The reaction mixture was heated at 100° C. for 57 h then cooled to rt and partitioned between EtOAc and H$_2$O. The aq layer was extracted with EtOAc. The combined organics were dried (Na$_2$SO$_4$) and concentrated under reduced pressure. Purification by flash chromatography on SiO$_2$ (70 g, EtOAc in hexanes 0:100→1:40→1:30) afforded a lightly colored oil. The material was dissolved in DCM (100 mL) and stirred with PS-Ts-NHNH$_2$ (2.07 g, 2.87 mmol/g, 5.94 mmol) for 2.5 d at rt and then with MP-carbonate (~0.25 g, 2.74 mmol/g, 0.68 mmol) for 4 h. The resins were removed by filtration through Celite. The residue and Celite were rinsed with DCM multiple times. The filtrate was concentrated under reduced pressure to provide the title compound as a light yellow oil; $^1$H NMR (400 MHz, CDCl$_3$) δ 8.18-8.12 (m, 3H), 7.92 (d, J=8.4 Hz, 1H), 7.71 (d, J=0.8 Hz, 1H), 7.54-7.46 (m, 4H), 2.75 (s, 3H); MS (ES+): m/z 254.24 (35) [MH$^+$]; HPLC: t$_R$=3.82 min (OpenLynx, nonpolar_5 min).

1-(2-amino-4-chlorophenyl)ethanone

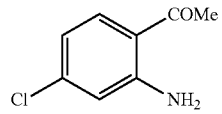

To a vigourously stirred, Et$_2$O (100 mL) solution of 2-amino-4-chlorobenzonitrile (1.00 g, 6.55 mmol) cooled in an ice-H$_2$O bath was added MeMgCl (3.0 M in THF, 6.5 mL, 19.7 mmol) dropwise over 5 min. During that time the reaction became a thick yellow suspension. Stirring was continued at the temperature for 1 h before the cooling bath was removed and the reaction stirred for 21 h at rt. The resultant light yellow suspension cooled to −60° C. and treated with aq HCl (5 M, 8 mL, 40 mmol) dropwise over ~3 min. The mixture was allowed to warm slowly to it within the cooling bath. Later more aq HCl (5 M, 6.5 mL, 33 mmol) was added. The Et$_2$O layer was separated, the aq phase was basicified (pH 4-5) by addition of solid KOH and later extracted with EtOAc (3×). The Et$_2$O and EtOAc layers were combined, dried (Na$_2$SO$_4$) and concentrated under reduced pressure to afford the title material which was used without further purification; $^1$H NMR (400 MHz, CDCl$_3$) δ 7.63 (d, J=8.4 Hz, 1H), 6.65 (d, J=2.0 Hz, 1H), 6.60 (dd, J=2.0 Hz, 8.0 Hz, 1H), 6.40 (br, 2H), 2.55 (s, 3H); MS (ES+): m/z 170.07 (100) [MH$^+$]; HPLC: t$_R$=3.12 min (OpenLynx, polar_5 min).

4-Methyl-2-phenyl-7-(4,4,5,5-tetramethyl-1,3,2-dioxaborolan-2-yl)quinazoline

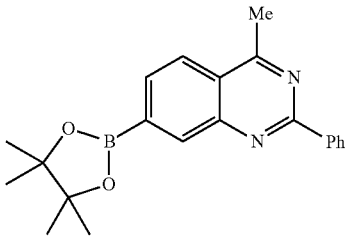 [SMILES: Cc1nc(-c2ccccc2)nc2cc(B3OC(C)(C)C(C)(C)O3)ccc12]

A flask containing dry 7-chloro-4-methyl-2-phenylquinazoline under Ar was charged with KOAc (80 mg, 0.81 mmol), bis(pinacolato)diboron (151 mg, 0.60 mmol) and Pd[P(C$_6$H$_{11}$)$_3$]$_2$ (Strem, 22 mg, 0.03 mmol) (the catalyst was added rapidly minimizing exposure to air). A reflux condenser was attached and the set-up was quickly evacuated and refilled with Ar (3×). Anh. 1,4-dioxane was added via syringe (2 mL) and the reaction mixture was stirred at rt for 30 min (brown solution) and later heated at 80° C. for 3 d. The reaction was evaporated to dryness under high vacuum at 35° C., purified by flash chromatography (silica gel, 100:0.5-10:1 hexanes:EtOAc) affording the title compound as a light yellow solid; $^1$H NMR (400 MHz, CDCl$_3$) δ 8.70-8.56 (m, 2H), 8.02 (d, J=8.4 Hz, 1H), 7.99 (dd, J=1.2 Hz, 8.0 Hz, 1H), 7.58-7.43 (m, 4H), 2.99 (s, 3H), 1.38 (s, 12H).

4-Methoxy-2-phenyl-7-(4,4,5,5-tetramethyl-1,3,2-dioxaborolan-2-yl)quinazoline

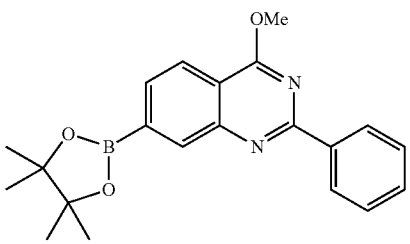 [SMILES: COc1nc(-c2ccccc2)nc2cc(B3OC(C)(C)C(C)(C)O3)ccc12]

Synthesized from of 7-chloro-4-methoxy-2-phenylquinazoline (189 mg, 0.7 mmol) as 4-methyl-2-phenyl-7-(4,4,5,5-tetramethyl-1,3,2-dioxaborolan-2-yl)quinazoline;

off-white solid. MS (ES+): m/z 347.2 (20) MS (ES+): m/z 281.2 (100) [MH⁺ −82]; HPLC: $t_R$=3.19 min (OpenLynx, polar_5 min).

4,7-Dichloro-2-phenylquinazoline

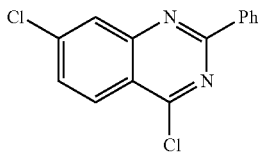 [SMILES: Clc1ccc2c(Cl)nc(-c3ccccc3)nc2c1]

7-Chloro-2-phenylquinazolin-4(3H)-one (3.11 g, 12.1 mmol) in POCl₃ (40 mL) was heated with stirring at 90° C. under N₂ for 2 d. The reaction was cooled to rt and evaporated to dryness under high vacuum. The residue was stirred for 30 min at 0° C. under Ar as a suspension in NH₃/i-PrOH (2 M, 45 mL). Later DCM (~100 mL) was added and stirring was continued for 1 h at it Aq NH₄OH (conc, 50 mL) was added and layers were separated. The aqueous layer was extracted with DCM (2×). The organic phase was washed (satd NaHCO₃, H₂O, brine), dried (Na₂SO₄) and concentrated under reduced pressure to provide the title compound as a light yellow solid; ¹H NMR (400 MHz, CD₂Cl₂) δ 8.56-8.46 (m, 2H), 8.14 (d, J=9.2 Hz, 1H), 8.02 (d, J=2.4 Hz, 1H), 7.56 (dd, J=2.4 Hz, 9.2 Hz, 1H), 7.52-7.45 (m, 3H).

7-Chloro-4-methyl-2-phenylquinazoline

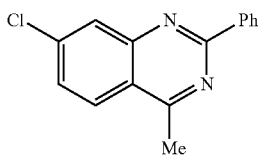 [SMILES: Cc1nc(-c2ccccc2)nc2cc(Cl)ccc12]

MeMgCl (3.0 M in THF, 0.36 mL, 1.1 mmol) was added dropwise to a red solution of 4,7-dichlorquinazoline (297 mg, 1.1 mmol) and Fe(acac)₃ (38 mg, 0.11 mmol) in THF (10 mL) at rt under Ar. On addition the reaction became black. Stirring was continued for 3 h at rt. Satd aq NH₄Cl (5 mL) was added and the reaction was left standing overnight. The aqueous layer was extracted with DCM (3×). The combined organics were washed (0.13 M aq citric acid (2×), brine), dried (Na₂SO₄) and concentrated under reduced pressure. The crude material was purified by flash chromatography (SiO₂, 50 g, 0-3% EtOAc in hexanes) affording the title compound as a light yellow solid; ¹H NMR (400 MHz, CDCl₃) δ 8.65-8.56 (m, 2H), 8.08 (d, J=2.0 Hz, 1H), 8.00 (d, J=8.8 Hz, 1H), 7.58-7.46 (m, 4H), 2.98 (s, 3H).

7-Chloro-4-methoxy-2-phenylquinazoline

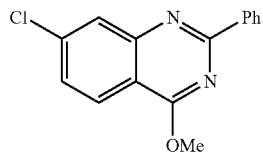 [SMILES: COc1nc(-c2ccccc2)nc2cc(Cl)ccc12]

A flask containing 4,7-dichlorquinazoline (250 mg, 0.91 mmol) equipped with a reflux condenser was evacuated and refilled with Ar several times. MeONa (2 mL, 25% wt in MeOH, 8.7 mmol) and anh. MeOH (20 mL) were added and the reaction mixture was heated to reflux under Ar for 5 h. The reaction was cooled to rt and stored at rt overnight then partitioned between DCM (80 mL) and H₂O (10 mL). The aqueous layer was extracted with DCM (1×). The combined organics were washed (brine), dried (Na₂SO₄) and concentrated under reduced pressure to provide the title compound as an off-white solid; ¹H NMR (400 MHz, CDCl₃) δ 8.55-8.62 (m, 2H), 8.08 (d, J=9.2 Hz, 1H), 7.99 (d, J=2.0 Hz, 1H), 7.52-7.48 (m, 3H), 7.45 (dd, J=2.0 Hz, 8.8 Hz, 1H), 4.28 (s, 3H).

2-Phenyl-7-(4,4,5,5-tetramethyl-1,3,2-dioxaborolan-2-yl)quinazoline

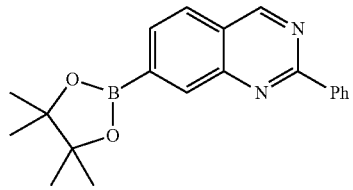 [SMILES: CC1(C)OB(c2ccc3cnc(-c4ccccc4)nc3c2)OC1(C)C]

A flask containing 7-chloro-2-phenylquinazoline (76 mg, 0.32 mmol) under Ar was charged, minimizing exposure to air, with KOAc (47 mg, 0.47 mmol)), bis(pinacolato)diboron (88 mg, 0.35 mmol) and Pd(PCy₃)₂ (13 mg, 0.019 mmol). A reflux condenser was attached and the set-up was rapidly evacuated and refilled with Ar (3×). Anh. 1,4-dioxane was added via syringe (5 mL) and the reaction mixture was stirred at rt for 30 min and later heated at 80° C. (bath temperature) for 92 h. The reaction was then evaporated to dryness and purified by flash chromatography (silica gel, 10:1 to 10:3 hexanes:EtOAc then 2:1 hexanes:EtOAc) to afford the title compound as a light yellow solid; ¹H NMR (400 MHz, CD$_2$Cl$_2$) δ 9.49 (s, 1H), 8.70-8.60 (m, 2H), 8.51 (s, 1H), 7.94 (s, 2H), 7.60-7.46 (m, 3H), 1.40 (s, 12H).

7-Chloro-2-phenylquinazoline

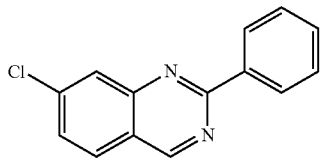 [SMILES: Clc1ccc2cnc(-c3ccccc3)nc2c1]

7-Chloro-2-phenylquinazolin-4(3H)-one (40 mg, 0.16 mmol) was suspended in POCl$_3$ (2 mL) and heated to 50° C. with stirring for 24 h. Later the reaction was heated to 90° C. for 16 h. With minimum exposure to moisture, the crude mixture was evaporated to dryness under reduced pressure and treated with 2 M NH$_3$/i-PrOH (8 mL) with cooling on ice-H$_2$O bath under Ar. The mixture was partitioned between DCM and H$_2$O and the organic layer was washed (H$_2$O, satd NaHCO$_3$ and brine), dried (Na$_2$SO$_4$) to afford crude material which was used directly in the following de-chlorination step. The crude material (31 mg, 0.113 mmol) and tosylhydrazide (63 mg, 0.34 mmol) were dissolved in anh CHCl$_3$ (10 mL) and heated at 60° C. (overnight, bath temperature) and, then refluxed for 4 h. The solvent was removed under reduced pressure and the solid residue was heated under Ar in anh. PhMe (10 mL) and anh ClCH$_2$CH$_2$Cl (5 mL) at 80° C. (bath temperature) for 63 h: The reaction was cooled to rt and a pale yellow precipitate was collected by filtration and washed with PhMe and DCM (2x). The collected solid in aq Na$_2$CO$_3$ (10%, 10 mL) was placed in a preheated bath at 90° C. After stirring at the temperature for 45 min, the reaction was cooled and left standing at it overnight. The crude reaction mixture was extracted with DCM (3x), washed (H$_2$O, brine), dried (Na$_2$SO$_4$), concentrated under reduced pressure, and purified by flash chromatography (silica gel, 100:0→10:1 EtOAc: hexanes) to afford the title compound as a light orange solid; $^1$H NMR (400 MHz, CDCl$_3$) δ 9.43 (s, 1H), 8.63-8.56 (m, 2H), 8.09 (d, J=0.8 Hz, 1H), 7.86 (d, J=8.8 Hz, 1H), 7.58-7.50 (m, 4H).

7-Chloro-2-phenylquinazolin-4(3H)-one

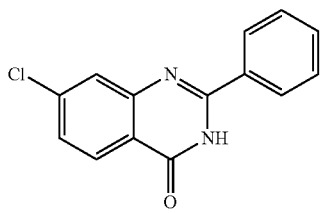 [SMILES: O=c1[nH]c(-c2ccccc2)nc2cc(Cl)ccc12]

To a suspension of N-(5-chloro-2-cyanophenyl)benzamide (150 mg, 0.58 mmol) in H$_2$O (5 mL) was added in sequence NaOH (100 mg, 2.5 mmol) and H$_2$O$_2$ (30% in H$_2$O, 0.25 mL, 2.2 mmol). The reaction was heated to 80° C. for 24 h then cooled to it and stirred at it for 1 d. Aq HCl (2 M, 6 mL) was added forming a thick precipitate that was collected by a filtration. The filter cake was washed with H$_2$O several times affording the title compound as a creamy-white solid; MS (ES+): m/z 257.1 (100) [MH$^+$]; HPLC: t$_R$=3.34 min (Open-Lynx, polar_5 min).

N-(5-Chloro-2-cyanophenyl)benzamide

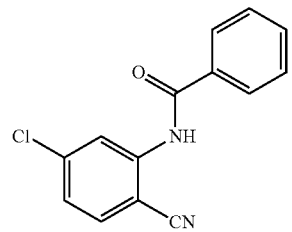 [SMILES: N#Cc1ccc(Cl)cc1NC(=O)c1ccccc1]

To a solution of 2-amino-4-chlorobenzonitrile (7.25 g, 47.5 mmol), in anh. pyridine (38 mL, 475 mmol) and DCM (300 mL) cooled in an ice-H$_2$O bath under Ar was added PhCOCl (5.8 mL, 50 mmol) dropwise. The reaction was allowed to slowly warm to rt within the cooling bath and then was stirred at rt overnight. The reaction mixture was washed (H$_2$O, 2 M aq HCl (2x), H$_2$O, brine), dried (Na$_2$SO$_4$) and concentrated under reduced pressure to afford the title compound as a white solid; MS (ES+): m/z 257.1 (100) [MH$^+$]; HPLC: t$_R$=3.27 min (OpenLynx, polar_5 min).

8-Fluoro-2-phenyl-7-(4,4,5,5-tetramethyl-[1,3,2]dioxaborolan-2-yl)-quinoline

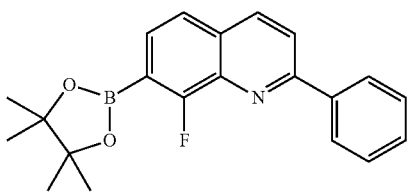 [SMILES: CC1(C)OB(c2ccc3ccc(-c4ccccc4)nc3c2F)OC1(C)C]

A stirred solution of 7-chloro-8-fluoro-2-phenylquinoline (923 mg, 3.58 mmol), 4,4,4',4',5,5,5',5'-octamethyl-2,2'-bi-1,3,2-dioxaborolane (1060 mg, 4.15 mol), 1,3-bis(2,6-diisopropylphenyl)imidazol-2-ylidene hydrochloride (90 mg, 0.2 mmol), palladium acetate (20 mg, 0.1 mmol) and potassium acetate (880 mg, 9.0 mmol) in anhydrous tetrahydrofuran (20 mL) was heated to reflux under nitrogen overnight. The reaction mixture was allowed to cool to rt, and was diluted with ethyl acetate (50 ml). The mixture was filtered through celite, washing with ethyl acetate (100 ml). The resulting organic layer was washed with brine (2x50 ml), dried (MgSO$_4$), filtered and concentrated. Trituration using dichloromethane and hexanes gave the title compound as an off-white solid; $^1$H NMR (Acetone-d$_6$, 400 MHz) δ 8.34 (1H, dd, J=12.1 Hz, 2.6

Hz), 8.23 (2H, d, J=8.9 Hz), 8.12 (1H, d, 8.6 Hz), 7.63 (2H, d, 2.5 Hz), 7.47-7.37 (3H, m), 1.27 (12H, s).

7-Chloro-8-fluoro-2-phenyl-quinoline

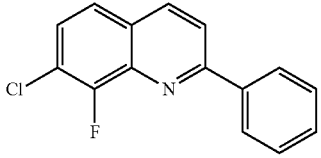 [SMILES: Fc1c(Cl)ccc2ccc(-c3ccccc3)nc12]

To a stirred solution of 3-chloro-2-fluoroaniline (2.9 g, 20 mmol) and trans-cinnamaldehyde (2.64 g, 20 mmol) in toluene (25 ml) was added 6N HCl (100 ml). The resulting suspension was heated at reflux for 40 hours. After cooling, the reaction mixture was poured into 5N NaOH solution (200 ml) and extracted with EtOAc (3×100 ml). The combined organics were washed with brine (2×100 ml), dried (MgSO$_4$), filtered and concentrated. The crude product was dissolved in MeOH and loaded onto an SCX-2 cartridge (50 g/150 ml), and the product eluted with MeOH, giving the title compound as a yellow solid. Additionally, the title compound could be prepared as follows: 4-Bromo-7-chloro-8-fluoro-2-phenyl-quinoline (6.0 g, 0.018 mole) and THF (240 mL) were combined in a 3 neck 1 L round bottom flask with a magnetic stir bar under an atmosphere of nitrogen. The reaction was stirred and cooled with a THF/liquid nitrogen bath to −100° C. 2.5 M of n-butyllithium in Hexane (7.34 mL) was then added dropwise over 3 minutes so as not to exceed −90° C. The solution turned light green, and darkened over a few minutes. Acetic acid (1.22 mL, 0.0214 mole) was added 3 minutes after the n-butyllithium addition was done. The cooling bath was removed, and the reaction was allowed to stir for 20 minutes. To work up, saturated sodium bicarbonate solution (100 mL) was added, and the mixture was transferred to a 1 L separatory funnel with 250 mL of ethyl acetate. The layers were separated, and the organic layer was washed with 2×60 mL of brine. The organic solution was suction filtered through a short pad of silica gel, rinsing with ethyl acetate. The filtrate was concentrated in vacuo, and the residue was placed under high vacuum overnight to afford the crude product. The crude product was pre-adsorbed on 55 mL of Silica gel from methylene chloride. 100 mL of Toluene was added, and the slurry was concentrated on the rotovap to afford a finely divided powder. This was applied to a silica column and chromatographed (4:3 hexanes/methylene chloride) affording the title compound as a white solid. The solid was re-chromatographed with, and then placed in the vacuum oven at 45° C. overnight to afford the very pure product as a white solid; $^1$H NMR (CDCl$_3$, 400 MHz) δ 8.24-8.21 (3H, m), 7.96 (1H, d, J=8.6 Hz), 7.58-7.48 (5H, m); MS (ES+): m/z 258.13 [MH$^+$]; HPLC: t$_R$=3.64 min (MicromassZQ, non-polar_5 min).

8-Fluoro-4-methyl-2-phenyl-7-(4,4,5,5-tetramethyl-[1,3,2] dioxaborolan-2-yl) quinoline

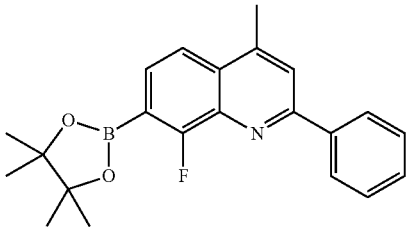 [SMILES: Cc1cc(-c2ccccc2)nc2c(F)c(B3OC(C)(C)C(C)(C)O3)ccc12]

7-Chloro-8-fluoro-4-methyl-2-phenylquinoline (390 mg, 1.4 mmol), 4,4,4',4',5,5,5',5'-octamethyl-2,2'-bi-1,3,2-dioxaborolane (423 mg, 1.66 mmol), potassium acetate (352 mg, 3.59 mol), palladium acetate (9.7 mg, 0.043 mol), 1,3-bis(2,6-diisopropylphenyl)imidazol-2-ylidene hydrochloride (37 mg, 0.086 mol), and THF (2.9 mL) were combined in a 25 mL R.B. flask fit with a reflux condensor. The reaction was stirred and subject to 3 vacuum-argon cycles, and then refluxed for 2 days. The reaction was allowed to cool, and was then filtered through a pad of silica gel eluting rinsing with THF. The solvent was evaporated in vacuo, and the residue was stirred in 15 mL of hexanes. The solid was collected, washed with hexanes and put under vacuum overnight to afford the title compound as a white crystalline solid; $^1$H NMR (CDCl$_3$, 400 MHz) δ 1.37 (s, 12H), 2.77 (s, 3H), 7.52-7.60 (m, 3H), 7.70-7.73 (dd, 1H, J=8.3 & 5.6 Hz), 7.87-7.89 (dd, 1H, J=8.3 Hz), 8.18 (d, 1H, J=0.8 Hz), 8.27-8.30 (m, 2H); MS (ES+): 349.93 (100) [MH$^+$]; HPLC t$_R$=3.94 min (OpenLynx, nonpolar_5 min).

7-Chloro-8-fluoro-4-methyl-2-phenylquinoline

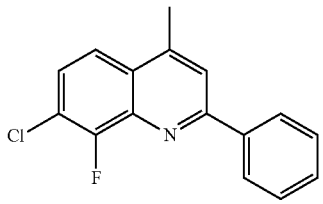 [SMILES: Cc1cc(-c2ccccc2)nc2c(F)c(Cl)ccc12]

4-Bromo-7-chloro-8-fluoro-2-phenylquinoline (1.1 g, 03.3 mmol), methane boronic acid (196 mg, 3.27 mmol), potassium carbonate (1.4 g, 9.8 mmol) and 1,4-dioxane (4 mL) were combined and stirred in a 10 mL R.B. flask. The flask was subjected to 3 vacuum-argon cycles. Tetrakis(triphenylphosphine)palladium(0) (380 mg, 0.33 mmol) was added, and the reaction was again subjected to 3 vacuum argon-cycles. The reaction was heated at 108° C. (external temperature) for 27 h, at which point the reaction was allowed to cool, and was diluted with ethyl acetate (30 mL), and water (30 mL). The layers were separated, and the aqueous layer extracted with ethyl acetate (30 mL). The organics were combined, dried over sodium carbonate, and concentrated in vacuo. The residue was chromatographed on silica gel, eluting with hexanes:methylene chloride 2:1. This afforded the title compound as a white solid; $^1$H NMR (CDCl$_3$, 400 MHz)

δ 2.75 (s, 3H), 7.47-7.55 (m, 4H), 7.69-7.72 (dd, 1H, J=8.9 & 1.6 Hz), 7.77 (s, 1H), 8.18-8.21 (m, 2H); MS (APCI+): 272.07 (100) [MH+], 274.03 (30) [(M+2)H+]; HPLC $t_R$=3.80 min (OpenLynx, nonpolar_5 min).

4-Bromo-7-chloro-8-fluoro-2-phenyl-quinoline

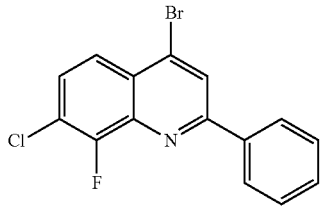 [SMILES: Fc1c(Cl)ccc2c(Br)cc(-c3ccccc3)nc12]

Phosphorus oxybromide (19 g, 0.066 mole), 7-chloro-8-fluoro-2-phenyl-1H-quinolin-4-one (6.2 g, 0.022 mole) and acetonitrile (40 mL) were combined in a 150 mL pressure bottle with a magnetic stir bar. The flask was heated at 100° C. and stirred overnight. Heat was removed, and an ice-water bath was installed. After 10 minutes, the bottle was opened, and water (60 mL) was added to the cooled stirring reaction. The quenching was exothermic to ca. 50° C. After stirring 10 minutes, a nice, filterable solid had formed, however, the reaction was extracted with 100 mL, then 3×50 mL methylene chloride. The extracts were combined, washed with saturated sodium bicarbonate solution (100 mL), and suction filtered through a small pad of silica gel, rinsing with methylene chloride. The filtrate was concentrated in vacuo, and put under high vacuum at 45° C. for 1 h to afford the crude product, which was recrystallized from 100 mL of ethanol, suction filtered to collect, and washed with ethanol. The purified product was vacuum oven dried for 1 h at 45° C. to afford the title compound as a white solid. A second crop was taken. The mother liquor was concentrated then chromatographed on silica gel with hexanes/methylene chloride 1:1 and combined with the second crop to afford additional material; $^1$H NMR (CDCl$_3$, 400 MHz) δ 7.49-7.55 (m, 4H), 7.87-7.90 (dd, 1H, J=1.7 & J=8.9 Hz), 8.15-8.18 (dd, 2H, J=1.5 Hz & J=7.9 Hz), 8.21 (s, 1H); HPLC $t_R$=4.15 min (OpenLynx, nonpolar_5 min).

7-Chloro-8-fluoro-2-phenyl-1H-quinolin-4-one

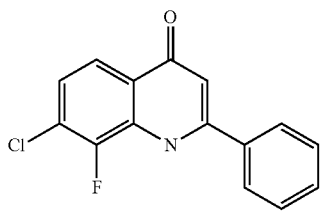 [SMILES: O=c1cc(-c2ccccc2)[nH]c2c(F)c(Cl)ccc12]

3-(3-Chloro-2-fluoro-phenylamino)-3-phenyl-acrylic acid ethyl ester (9.2 g, 0.029 mole) and polyphosphoric acid (160 mL, 3.0 mole) were combined and mechanically stirred under nitrogen at 175° C. external temperature for 40 minutes. While still hot, the reaction was poured over 800 mL of stirring ice-water rinsing with water. The mixture was a fine suspension, and was allowed to stir overnight. After stirring overnight, the mixture was filtered to collect the solid. The solid was washed with 4×150 mL water, and then with 4×150 mL of 4:1 ether/methanol. The solid was placed in the vacuum oven at 45° C. for 4 h and afforded the title compound as an off white product; $^1$H NMR (DMSO-d$_6$, 400 MHz) δ 6.58 (bs, 1H), 7.50-7.54 (d of d, 1H, J=6.6 Hz & J=8.9 Hz), 7.60-7.64 (m, 3H), 7.82-7.84 (m, 2H), 8.07-8.09 (d of d, 1H, J=1.5 Hz & J=8.7 Hz); MS (ES+): 274.03 (100) [MH$^+$], 275.99 (30) [(M+2)H+]. LCMS $t_R$=2.97 min (OpenLynx, polar_5 min).

3-(3-Chloro-2-fluoro-phenylamino)-3-phenyl-acrylic acid ethyl ester

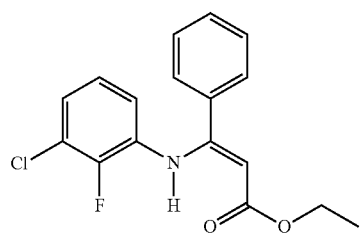 [SMILES: CCOC(=O)/C=C(\Nc1cccc(Cl)c1F)c1ccccc1]

2-Fluoro-3-chloroaniline (7.55 mL, 0.0687 mole), ethyl benzoylacetate (13.2 g, 0.0687 mole) and p-toluenesulfonic acid (1.18 g, 0.007 mole) were combined in a 250 mL round bottom flask with toluene (60 mL) and a magnetic stir-bar. The reaction was stirred at reflux with a Dean-Stark water trap. Reflux was stopped after 3 h. The product mixture was allowed to cool, and was then passed through a short pad of silica gel with methylene chloride, and concentrated in vacuo. Standing under high vacuum for 1 h afforded an oil. The oil was stirred in 100 mL of hexanes overnight, then suction filtered to remove a solid impurity. The filtrate was concentrated, and put on high vacuum to afford an oil. The oil was chromatographed with hexanes, ethyl acetate (8:1), and put under high vacuum for 1 h to afford the title compound as a yellow oil; $^1$H NMR (CDCl$_3$, 400 MHz) δ 1.30-1.34 (t, 3H, J=7.1 Hz), 4.20-4.25 (Q, 2H, J=7.1 Hz), 5.13 (s, 1H), 6.19-6.23 (t, 1H), 6.60-6.65 (t of d, 1H, J=1.7 &J=8.2), 6.88-6.92 (t of d, 1H, J=1.5 &J=6.6), 7.29-7.37 (m, 5H), 10.21 (bs, 1H); MS (ES+): 319.99 (100) [MH$^+$], 322.02 (30) [(M+2)H+].

2-Phenyl-7-(4,4,5,5-tetramethyl-[1,3,2]dioxaborolan-2-yl)-4-trifluoromethyl-quinoline

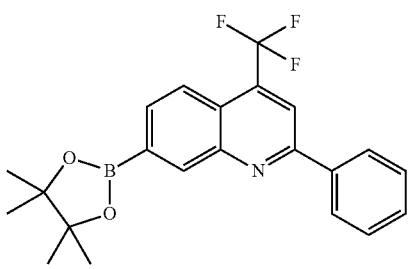 [SMILES: CC1(C)OB(c2ccc3c(C(F)(F)F)cc(-c4ccccc4)nc3c2)OC1(C)C]

7-Chloro-2-phenyl-4-trifluoromethyl-quinoline (1.0 g, 0.0033 mole), 4,4,4',4',5,5,5',5'-octamethyl-2,2'-bi-1,3,2-dioxaborolane (0.96 g, 0.0038 mole), potassium acetate (0.78 g, 0.0081 mole), palladium acetate (0.022 g, 0.0001 mole), and 1,3-bis(2,6-diisopropylphenyl)imidazol-2-ylidene hydrochloride (0.083 g, 0.0002 mol) were combined in THF (50 mL). The reaction was stirred and purged with argon for 5 minutes. The reaction was then stirred at reflux under an atmosphere of argon overnight. The reaction was allowed to cool, and was then suction filtered through a pad of silica gel. The filtrate was concentrated in vacuo and taken up in hexanes. A flocculent dark precipitate formed, and was filtered off. The filtrate was concentrated in vacou to afford a brown oil. The oil was chromatographed on Silica gel with Hexanes, THF (60:1), then flushed with THF to afford the title compound as a tan oil; $^1$H NMR (DMSO-$d_6$, 400 MHz) δ 1.38 (s, 12H), 7.58-7.64 (m, 3H), 7.97-8.00 (dd, 1H, J=2.1 & 8.5 Hz), 8.10-8.13 (dq, 1H, J=2.1 & J=8.5 Hz), 8.38-8.40 (dd, 2H, J=2.1 & 8.1 Hz), 8.52-8.54 (d, 1H, J=7.0 Hz); MS (ES+): 400.0 (100) [MH$^+$].

7-Chloro-2-phenyl-4-trifluoromethyl-quinoline

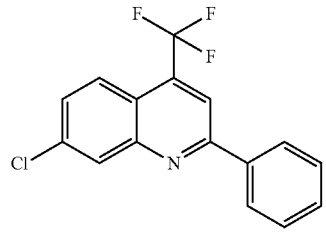 [SMILES: FC(F)(F)c1cc(-c2ccccc2)nc2cc(Cl)ccc12]

4-(3-Chloro-phenylamino)-1,1,1-trifluoro-4-phenyl-but-3-en-2-one (2.8 g, 0.0086 mole) and polyphosphoric acid (60 mL) in a 250 mL 3 neck round bottom flask was stirred mechanically under an atmosphere of Nitrogen at 165° C. internal temperature for 3 h. The reaction was poured over stirring ice water (600 ml). The product precipitated, and was collected by suction filtration, washed with water, and air dried overnight. The solids remaining in the Buchner funnel, and beaker from aqueous quench were rinsed into a flask concentrated in vacuo, then combined with the filtered sample and chromatographed on silica gel with 3:1 Hexanes/methylene chloride to afford the title compound as a white solid; $^1$H NMR (CDCl$_3$, 400 MHz) δ 7.53-7.59 (m, 3H), 7.60-7.63 (dd, 1H, J=2.2 & J=9.1 Hz), 8.06-8.09 (dq, 1H, J=1.9 & J=9.0 Hz), 8.16-8.20 (m, 3H), 8.29 (d, 1H, J=2.1 Hz); $^{19}$F NMR δ −61.48; MS (ES+): 308.0 (100) [MH+], 310.0 (30) [M+2H+].

4-(3-Chloro-phenylamino)-1,1,1-trifluoro-4-phenyl-but-3-en-2-one

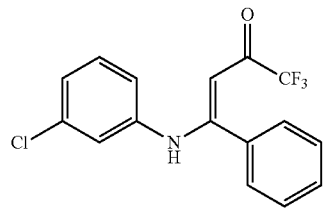 [SMILES: O=C(/C=C(/Nc1cccc(Cl)c1)c1ccccc1)C(F)(F)F]

Into a 1-Neck round-bottom flask was added 1,1,1-trifluoro-4-phenyl-but-3-yn-2-one (2.0 g, 0.01 mole), methanol (5 mL) and m-chloroaniline (0.961 mL, 0.0091 mol). The reaction was stirred. TLC (SiO$_2$, hexanes/methylene chloride 1:1) indicated near reaction completion after 1 h. After 1.5 h the product was concentrated in vacuo to afford an orange oil, which was placed on high vacuum overnight, affording a yellow gum. The crude product was chromatographed on Silica gel with hexanes, Methylene Chloride 2:1, and place on high vacuum for 2 h to afford the title compound as a yellow gum; $^1$H NMR (CDCl$_3$, 400 MHz) δ 5.74 (s, 1H), 6.67-6.69 (m, 1H), 6.85 (m, 1H), 7.08-7.10 (m, 1H), 7.31-7.39 (m, 4H), 7.43-7.47 (ft, 1H), 12.39 (bs, 1H)

1,1,1-Trifluoro-4-phenyl-but-3-yn-2-one

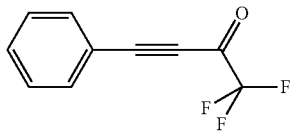 [SMILES: O=C(C#Cc1ccccc1)C(F)(F)F]

Phenylacetylene (10.8 mL, 0.098 mole) was added into a 3-Neck round bottom flask under an atmosphere of Nitrogen. THF (100 mL) was added and the reaction was stirred and cooled to 0° C. 2.5 M n-butyllithium in hexane (36 mL, 0.089 mole) was added via syringe at 0° C. over 30 min. The reaction was stirred at 0° C. for 30 minutes. Ethyl trifluoroacetate (5.31 mL, 0.045 mole) was added via syringe at −60 to −50° C. over 10 minutes. The reaction was stirred at −70° C. for 1 h. Ammonium chloride 28% w/w in water (60 mL) was added and the mixture was extracted with Ether (2×50 mL). The organic phase was dried over magnesium sulfate, filtered and concentrated in vacuo, and then allowed to stand under high vacuum for 2 h to afford an orange oil. The oil was chromatographed on silica gel with 2:1 hexanes, methylene chloride to afford the title compound as a yellow oil; $^1$H NMR (CDCl$_3$, 400 MHz) δ 7.44-7.48 (tt, 2H), 7.55-7.60 (tt, 1H), 7.67-7.70 (m, 2 H); $^{19}$F NMR (CDCl$_3$, 400 MHz) δ 77.54 (s).

1-Bromo-3-cyclobutyl-imidazo[1,5-a]pyrazin-8-ylamine

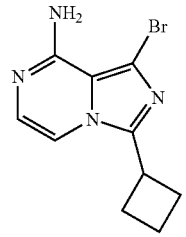 [SMILES: Nc1nccn2c(C3CCC3)nc(Br)c12]

A suspension of 1-bromo-8-chloro-3-cyclobutylimidazo [1,5-a]pyrazine (341 mg, 1.2 mmol) in IPA (3 mL) was saturated with NH$_3$(g) at 0° C. for 3 min. The tube was sealed and heated at 100° C. for 17 h. H$_2$O (10 mL) was added and the mixture was extracted with EtOAc (3×30 mL). The organic phase was washed with brine and concentrated under reduced pressure to provide the title compound as a white solid; $^1$H NMR (400 MHz, CDCl$_3$) δ 7.30 (d, J=4.8 Hz, 1H), 6.97 (d, J=5.2 Hz, 1H), 5.65 (br, 2H), 3.70 (qud, J=0.8 Hz, 8.4 Hz, 1H), 2.55-2.35 (m, 4H), 2.18-1.93 (m, 2H); MS (ES+): m/z 267.1 (100), 269.1 (100) [MH⁺]; HPLC: $t_R$=1.70 min (OpenLynx, polar_5 min).

3-Cyclobutyl-1-iodoimidazo[1,5-a]pyrazin-8-amine

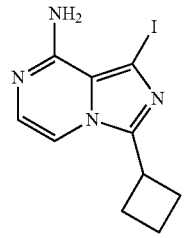 [SMILES: Nc1nccn2c(C3CCC3)nc(I)c12]

A Parr bomb containing 8-chloro-3-cyclobutyl-1-iodoimidazo[1,5-a]pyrazine (759 mg, 2.3 mmol) in IPA (100 mL) was saturated with NH₃(g) for 5 min at 0° C. then sealed and heated at 115° C. for 38 h. The reaction mixture was then concentrated under reduced pressure, partitioned between DCM (200 mL) and H₂O (50 mL) and extracted with DCM (50 mL). Combined organic fractions were washed with brine, dried (Na₂SO₄) and concentrated under reduced pressure to provide the title compound as a white solid; ¹H NMR (400 MHz, CDCl₃) δ 7.13 (d, J=4.8 Hz, 1H), 7.01 (d, J=5.2 Hz, 1H), 5.63 (br, 2H), 3.73 (quintetd, J=0.8 Hz, 8.4 Hz, 1H), 2.60-2.38 (m, 4H), 2.20-1.90 (m, 2H); MS (ES+): m/z 315.9 (100) [MH⁺]; HPLC: $t_R$=1.75 min (OpenLynx, polar_5 min).

1-Bromo-8-chloro-3-cyclobutylimidazo[1,5-a]pyrazine

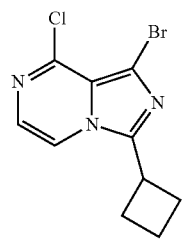 [SMILES: Clc1nccn2c(C3CCC3)nc(Br)c12]

To a clear, vigorously stirred and cooled (0° C.) solution of 8-chloro-3-cyclobutylimidazo[1,5-a]pyrazine (0.75 g, 3.6 mmol) in DCM (90 mL) was added Br₂ (0.28 mL, 5.4 mmol) in DCM (90 mL) over 34 min. The reaction became a light orange suspension towards the end of the addition. Stirring was continued at the temperature for 10 min then concentrated under reduced pressure at rt. The mixture was diluted with H₂O (~20 mL), basified with 2 M aq NaOH to ~pH 7-9 and extracted with DCM (3×80 mL). The organic layers were washed (satd aq NaHCO₃, brine), dried (Na₂SO₄), filtered, and concentrated under reduced pressure. Purification by flash chromatography on silica gel (50 g cartridge, 100% DCM) yielded the title compound as an off-white solid; ¹H NMR (400 MHz, CD₂Cl₂) δ 7.41 (d, J=5.2 Hz, 1H), 7.16 (d, J=5.2 Hz, 1H), 3.70 (qud, J=1.2 Hz, 8.4 Hz, 1H), 2.48-2.33 (m, 4H), 2.13-2.02 (m, 1H), 1.98-1.88 (m, 1H); MS (ES+): m/z 286.1 (90), 288.0 (100) [MH⁺]; HPLC: $t_R$=3.33 min (OpenLynx, polar_5 min).

8-Chloro-3-cyclobutyl-1-iodoimidazo[1,5-a]pyrazine

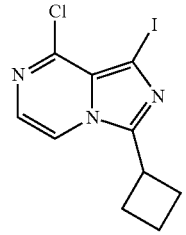 [SMILES: Clc1nccn2c(C3CCC3)nc(I)c12]

8-Chloro-3-cyclobutylimidazo[1,5-a]pyrazine (1058 mg, 5.1 mmol) and MS (1146 mg, 5.1 mmol) in anh DMF (10 mL) were stirred at 60° C. under Ar for 6 h. The reaction was diluted with DCM (~400 mL), washed (H₂O, brine), dried (Na₂SO₄) and concentrated under reduced pressure. Purification of the crude material by flash chromatography on silica gel (50 g cartridge, 10:1-8:1-7:1-6:1 hexanes:EtOAc) afforded the title compound as a pale yellow solid; ¹H NMR (400 MHz, CDCl₃) δ 7.51 (d, J=4.8 Hz, 1H), 7.26 (d, J=4.8 Hz, 1H), 3.75 (quintetd, J=1.2 Hz, 8.4 Hz, 1H), 2.62-2.42 (m, 4H), 2.32-1.98 (m, 2H); MS (ES+): m/z 334.0 (100) [MH⁺]; HPLC: $t_R$=3.38 min (OpenLynx, polar_5 min).

8-Chloro-3-cyclobutyl-imidazo[1,5-a]pyrazine

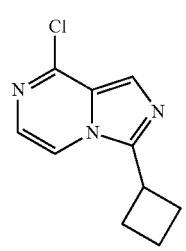 [SMILES: Clc1nccn2c(C3CCC3)ncc12]

Prepared according to the procedures described (8-Chloro-3-(3-methylene-cyclobutyl)-imidazo[1,5a]pyrazine).

Cyclobutanecarboxylic acid (3-chloro-pyrazin-2-ylmethyl)-amide

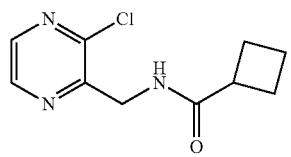 [SMILES: O=C(NCc1nccnc1Cl)C1CCC1]

Prepared according to the procedures described for 3-methylene-cyclobutanecarboxylic acid (3-chloropyrazin-2-yl-methyl)-amide.

[3-(8-Amino-1-iodoimidazo[1,5-a]pyrazin-3-yl)cyclobutyl]methanol

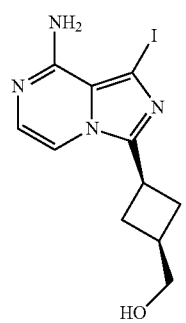 [SMILES: Nc1nccn2c1c(I)nc2[C@H]1C[C@@H](CO)C1]

To a Parr reactor was added cis-3-(8-chloro-1-iodoimidazo[1,5-a]pyrazin-3-yl)cyclobutylmethyl 4-nitrobenzoate (1.00 g, 1.95 mmol) and i-PrOH (30 mL). Ammonia gas was bubbled into this mixture for 5 min at −78° C. The reactor was sealed and heated at 110° C. for 60 h with stirring. After cooling to −78° C., the reactor was opened (after being depressurized) and the reaction mixture was transferred into a flask. The i-PrOH was removed and the residue was dissolved in 40 mL (1:1) mixture of 4 N HCl (aq) and EtOAc under heating. Layers were separated and the aqueous phase was basified cautiously with solid KOH to pH=>11 at 0° C. The crystals formed during basification were collected through filtration, washed with water (3 mL×3), dried to afford the desired compound; $^1$H-NMR (DMSO-d$_6$, 400 MHz) δ 2.02-2.09 (m, 2H), 2.34-2.46 (m, 3H), 3.31-3.37 (m, 2H), 3.64-3.73 (m, 1 H), 4.52 (t, J=5.2 Hz, 1H), 6.53 (s, br, 2H), 6.95 (d, J=5.2 Hz, 1H), 7.49 (d, J=5.6 Hz, 1H); MS (ES+): m/z 344.96; HPLC: $t_R$=1.52 min (OpenLynx, polar_5 min).

cis-3-(8-Chloroimidazo[1,5-a]pyrazin-3-yl)cyclobutylmethyl toluene-4-sulfonate and trans-3-(8-chloroimidazo[1,5-a]pyrazin-3-yl)cyclobutylmethyl toluene-4-sulfonate were prepared as follows: To a solution of [3-(8-chloroimidazo[1,5-a]pyrazin-3-yl)cyclobutyl]methanol (~5:1 mixture of cis- and trans-isomers, contaminated with unknown amount of cyclooctane-1,5-diol from the previous reaction, 118.8 mg, 0.5 mmol) and p-toluenesulfonic anhydride (244.8 mg, 0.75 mmol) in dichloromethane (2.0 mL) was added i-Pr$_2$NEt (0.26 mL, 1.5 mmol). The resulting mixture was stirred at rt for 15 h. Solvents were removed and the residue was purified by silica gel chromatography (hexanes/EtOAc: 4/1 to 1/1) to afford the respective cis- and trans-title compounds:

cis-3-(8-Chloroimidazo[1,5-a]pyrazin-3-yl)cyclobutylmethyl toluene-4-sulfonate

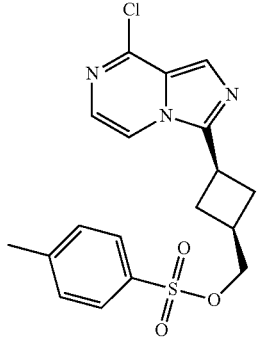 [SMILES: Cc1ccc(S(=O)(=O)OC[C@H]2C[C@@H](c3ncc4c(Cl)nccn43)C2)cc1]

$^1$H-NMR (CDCl$_3$, 400 MHz) δ 2.25-2.34 (m, 2H), 2.45 (s, 3H), 2.56-2.63 (m, 2H), 2.77-2.86 (m, 1H), 3.66-3.75 (m, 1H), 4.06 (d, J=6.4 Hz, 2H), 7.30 (d, J=4.8 Hz, 1H), 7.34 (d, J=8.8 Hz, 2H), 7.52 (dd, J=0.8, 5.2 Hz, 1H), 7.76 (s, 1H), 7.77 (d, J=8.8 Hz, 2H). MS (ES+): m/z 392.06 (MH$^+$, $^{35}$Cl), 394.01 (MH$^+$, $^{37}$Cl). HPLC: $t_R$=3.32 min (OpenLynx, polar_5 min).

trans-3-(8-Chloroimidazo[1,5-a]pyrazin-3-yl)cyclobutylmethyl toluene-4-sulfonate

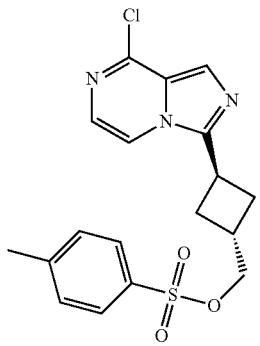 [SMILES: Cc1ccc(S(=O)(=O)OC[C@H]2C[C@H](c3ncc4c(Cl)nccn43)C2)cc1]

$^1$H-NMR (CDCl$_3$, 400 MHz) δ 2.36-2.43 (m, 2H), 2.47 (s, 3H), 2.62-2.69 (m, 2H), 2.79-2.87 (m, 1H), 3.77-3.83 (m, 1H), 4.18 (d, J=5.6 Hz, 2H), 7.32 (d, J=5.2 Hz, 1H), 7.37 (d, J=8.0 Hz, 2H), 7.45 (d, J=5.2 Hz, 1H), 7.81 (s, 1H), 7.83 (d, J=8.0 Hz, 2H). MS (ES+): m/z 392.06 (MH$^+$, $^{35}$Cl), 394.01 (MH$^+$, $^{37}$Cl). HPLC: $t_R$=3.38 min (OpenLynx, polar_5 min).

cis-3-(8-Chloroimidazo[1,5-a]pyrazin-3-yl)cyclobutylmethyl 4-nitrobenzoate and trans-3-(8-Chloroimidazo[1,5-a]pyrazin-3-yl)cyclobutylmethyl 4-nitrobenzoate were prepared according to the general procedure for the preparation for cis-3-(8-chloroimidazo[1,5-a]pyrazin-3-yl)cyclobutylmethyl toluene-4-sulfonate and trans-3-(8-chloroimidazo[1,5- a]pyrazin-3-yl)cyclobutylmethyl toluene-4-sulfonate, except 4-nitrobenzoyl chloride was used instead of p-toluenesulfonic anhydride.

cis-3-(8-Chloroimidazo[1,5-a]pyrazin-3-yl)cyclobutylmethyl 4-nitrobenzoate

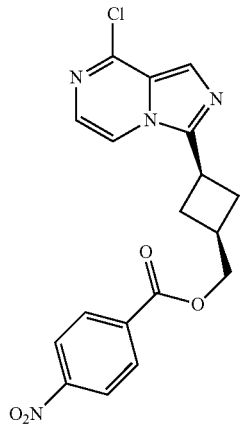 [SMILES: O=C(OC[C@H]1C[C@@H](c2ncc3c(Cl)nccn32)C1)c1ccc([N+](=O)[O-])cc1]

$^1$H-NMR (CDCl$_3$, 400 MHz) δ 2.51-2.59 (m, 2H), 2.68-2.75 (m, 2H), 2.92-3.02 (m, 1H), 3.73-3.82 (m, 1H), 4.43 (d, J=6.0 Hz, 2H), 7.32 (dd, J=0.8, 5.2 Hz, 1H), 7.52 (d, J=4.8 Hz, 1H), 7.83 (s, 1H), 8.24 (d, J=8.8 Hz, 2H), 8.29 (d, J=8.8 Hz, 2H). MS (ES+): m/z 387.00 (MH$^+$, $^{35}$Cl), 389.02 (MH$^+$, $^{37}$Cl). HPLC: t$_R$=3.42 min (OpenLynx, polar 5 min).

trans-3-(8-Chloroimidazo[1,5-a]pyrazin-3-yl)cyclobutylmethyl 4-nitrobenzoate

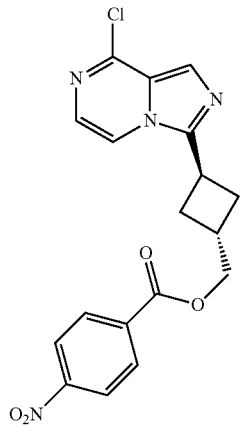 [SMILES: O=C(OC[C@H]1C[C@H](c2ncc3c(Cl)nccn32)C1)c1ccc([N+](=O)[O-])cc1]

$^1$H-NMR (CDCl$_3$, 400 MHz) δ 2.46-2.53 (m, 2H), 2.74-2.81 (m, 2H), 3.02-3.12 (m, 1H), 3.88-3.93 (m, 1H), 4.56 (d, J=7.2 Hz, 2H), 7.33 (d, J=5.2 Hz, 1H), 7.48 (dd, J=0.8, 5.2 Hz, 1H), 7.85 (d, J=0.8 Hz, 1H), 8.24 (d, J=9.2 Hz, 2H), 8.28 (d, J=9.2 Hz, 2H); MS (ES+): m/z 387.00 (MH$^+$, $^{35}$Cl), 389.02 (MH$^+$, $^{37}$Cl); HPLC: t$_R$=3.45 min (OpenLynx, polar_5 min).

cis-3-[3-(tert-Butyldimethylsilanyloxymethyl)cyclobutyl]-8-chloroimidazo[1,5-a]pyrazine and trans-3-[3-(tert-butyldimethylsilanyloxymethyl)cyclobutyl]-8-chloroimidazo[1,5-a]pyrazine were prepared according to the general procedure for the preparation for cis-3-(8-chloroimidazo[1,5-a]pyrazin-3-yl)cyclobutylmethyl toluene-4-sulfonate and trans-3-(8-chloroimidazo[1,5-a]pyrazin-3-yl)cyclobutylmethyl toluene-4-sulfonate, except tert-butylchlorodimethylsilane was used instead of p-toluenesulfonic anhydride.

cis-3-[3-(tert-Butyldimethylsilanyloxymethyl)cyclobutyl]-8-chloroimidazo[1,5-a]pyrazine

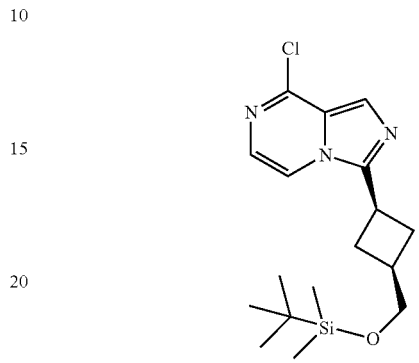

$^1$H-NMR (CDCl$_3$, 400 MHz) δ 0.05 (s, 6H), 0.88 (s, 9H), 2.30-2.39 (m, 2H), 2.49-2.57 (m, 2H), 2.61-2.67 (m, 1H), 3.63 (d, J=5.6 Hz, 2H), 3.67-3.72 (m, 1H), 7.29 (d, J=4.8 Hz, 1H), 7.60 (dd, J=0.8, 4.8 Hz, 1H), 7.79 (d, J=1.2 Hz, 1H). MS (ES+): m/z 352.14 (MH$^+$, $^{35}$Cl), 354.12 (MH$^+$, $^{37}$Cl). HPLC: t$_R$=4.34 min (OpenLynx, polar_5 min).

trans-3-[3-(tert-Butyldimethylsilanyloxymethyl)cyclobutyl]-8-chloroimidazo[1,5-a]pyrazine

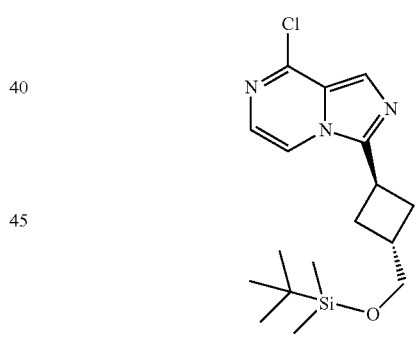

$^1$H-NMR (CDCl$_3$, 400 MHz) δ 0.09 (s, 6H), 0.94 (s, 9H), 2.17-2.43 (m, 2H), 2.59-2.71 (m, 3H), 3.75 (d, J=4.8 Hz, 2H), 3.80-3.86 (m, 1H), 7.29 (d, J=5.2 Hz, 1H), 7.45 (dd, J=1.2, 5.2 Hz, 1H), 7.82 (d, J=0.8 Hz, 1H). MS (ES+): m/z 352.14 (MH$^+$, $^{35}$Cl), 354.12 (MH$^+$, $^{37}$Cl). HPLC: t$_R$=4.41 min (OpenLynx, polar_5 min).

cis-3-(8-Chloro-1-iodoimidazo[1,5-a]pyrazin-3-yl)cyclobutylmethyl(R)-formyloxyphenylacetate and trans-3-(8-chloro-1-iodoimidazo[1,5-a]pyrazin-3-yl)cyclobutylmethyl (R)-formyloxyphenylacetate: To a solution of [3-(8-chloro-1-iodoimidazo[1,5-a]pyrazin-3-yl)cyclobutyl]methanol (~5:1 mixture of cis- and trans-isomers, 109.1 mg, 0.3 mmol) and (R)-O-formylmandeloyl chloride (71.5 mg, 0.36 mmol) in dichloromethane (1.0 mL) was added i-Pr$_2$NEt (0.16 mL, 0.9 mmol). The resulting mixture was stirred at rt for 15 h. Solvents were removed and the residue was purified by silica gel chromatography (hexanes/EtOAc: 4/1 to 1/1) to afford the respective cis- and trans-title compounds.

cis-3-(8-Chloro-1-iodoimidazo[1,5-a]pyrazin-3-yl) cyclobutylmethyl (R)-formyloxyphenylacetate

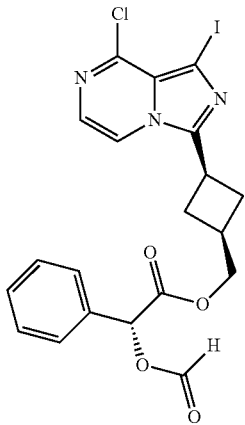 [SMILES: O=CO[C@@H](C(=O)OC[C@H]1C[C@@H](c2nc(I)c3c(Cl)nccn32)C1)c1ccccc1]

$^1$H-NMR (CDCl$_3$, 400 MHz) δ 2.18-2.26 (m, 1H), 2.31-2.38 (m, 1H), 2.40-2.53 (m, 2H), 2.67-2.76 (m, 1H), 3.53-3.60 (m, 1H), 4.18 (dd, J=4.0, 6.4 Hz, 2H), 6.04 (s, 1H), 7.28 (d, J=4.8 Hz, 1H), 7.33-7.38 (m, 3H), 7.44-7.49 (m, 2H), 7.46 (d, J=4.8 Hz, 1H), 8.20 (s, 1H). MS (ES+): m/z 525.84 (MH$^+$, $^{35}$Cl), 527.87 (MH$^+$, $^{37}$Cl). HPLC: t$_R$=3.58 min (OpenLynx, polar_5 min).

trans-3-(8-Chloro-1-iodoimidazo[1,5-a]pyrazin-3-yl) cyclobutylmethyl (R)-formyloxyphenylacetate

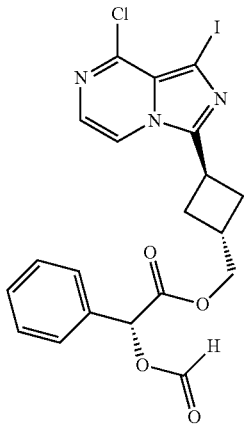 [SMILES: O=CO[C@@H](C(=O)OC[C@H]1C[C@H](c2nc(I)c3c(Cl)nccn32)C1)c1ccccc1]

$^1$H-NMR (CDCl$_3$, 400 MHz) δ 2.18-2.28 (m, 2H), 2.56-2.67 (m, 2H), 2.67-2.81 (m, 1H), 3.58-3.64 (m, 1H), 4.33 (dq, J=5.2, 10.8 Hz, 2H), 6.09 (s, 1H), 7.28 (d, J=5.2 Hz, 1H), 7.39-7.45 (m, 4H), 7.50-7.53 (m, 2H), 8.23 (s, 1H); MS (ES+): m/z 525.84 (MH$^+$, $^{35}$Cl), 527.87 (MH$^+$, $^{37}$Cl); HPLC: t$_R$=3.69 min (OpenLynx, polar_5 min).

cis-3-(8-Chloro-1-iodoimidazo[1,5-a]pyrazin-3-yl)cyclobutylmethyl 4-nitrobenzoate and trans-3-(8-Chloro-1-iodoimidazo[1,5-a]pyrazin-3-yl)cyclobutylmethyl 4-nitrobenzoate were prepared according to the general procedure for the preparation for cis-3-(8-chloroimidazo[1,5-a]pyrazin-3-yl)cyclobutylmethyl toluene-4-sulfonate and trans-3-(8-chloroimidazo[1,5-a]pyrazin-3-yl)cyclobutylmethyl toluene-4-sulfonate, except 4-nitrobenzoyl chloride was used instead of p-toluenesulfonic anhydride.

cis-3-(8-Chloro-1-iodoimidazo[1,5-a]pyrazin-3-yl) cyclobutylmethyl 4-nitrobenzoate

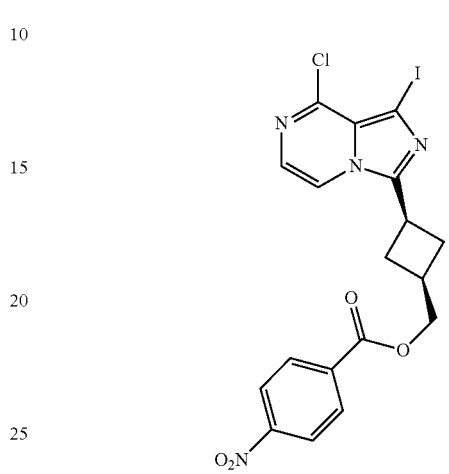

$^1$H-NMR (CDCl$_3$, 400 MHz) δ 2.56-2.70 (m, 4H), 2.92-2.99 (m, 1H), 3.67-3.74 (m, 1H), 4.40 (d, J=5.2 Hz, 2H), 7.31 (d, J=4.4 Hz, 1H), 7.55 (d, J=5.2 Hz, 1H), 8.28 (d, J=8.8 Hz, 2H), 8.36 (d, J=8.8 Hz, 2H); MS (ES+): m/z 512.85 (MH$^+$, $^{35}$Cl), 514.84 (MH$^+$, $^{37}$Cl); HPLC: t$_R$=3.81 min (OpenLynx, polar_5 min).

trans-3-(8-Chloro-1-iodoimidazo[1,5-a]pyrazin-3-yl) cyclobutylmethyl 4-nitrobenzoate

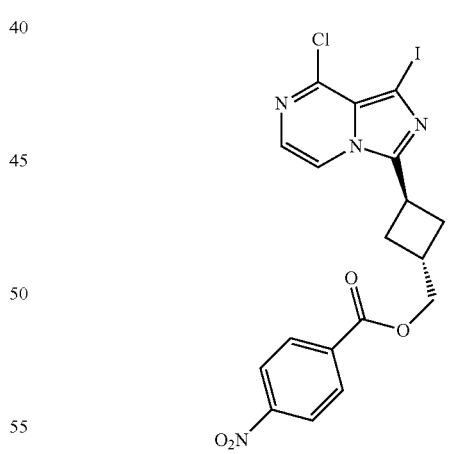

$^1$H-NMR (CDCl$_3$, 400 MHz) δ 2.43-2.50 (m, 2H), 2.74-2.81 (m, 2H), 3.00-3.08 (m, 1H), 3.81-3.88 (m, 1H), 4.54 (d, J=6.8 Hz, 2H), 7.31 (d, J=4.8 Hz, 1H), 7.50 (d, J=5.2 Hz, 1H), 8.23 (d, J=8.8 Hz, 2H), 8.31 (d, J=9.2 Hz, 2H); MS (ES+): m/z 512.84 (MH$^+$, $^{35}$Cl), 514.85 (MH$^+$, $^{37}$Cl); HPLC: t$_R$=3.84 min (OpenLynx, polar_5 min).

cis-3-[3-(tert-Butyldimethylsilanyloxymethyl)cyclobutyl]-8-chloro-1-iodoimidazo[1,5-a]pyrazine and trans-3-[3-(tert-butyldimethylsilanyloxymethyl)cyclobutyl]-8-chloro-1-iodoimidazo[1,5-a]pyrazine were prepared according to the general procedure for the preparation for cis-3-(8-chloroimidazo[1,5-a]pyrazin-3-yl)cyclobutylmethyl toluene-4-sulfonate and trans-3-(8-chloroimidazo[1,5-a]pyrazin-3-yl)cyclobutylmethyl toluene-4-sulfonate, except tert-butylchlorodimethylsilane was used instead of p-toluenesulfonic anhydride.

cis-3-[3-(tert-Butyldimethylsilanyloxymethyl)cyclobutyl]-8-chloro-1-iodoimidazo[1,5-a]pyrazine

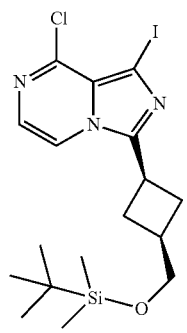 [SMILES: CC(C)(C)[Si](C)(C)OC[C@H]1C[C@@H](c2nc(I)c3c(Cl)nccn32)C1]

$^1$H-NMR (CDCl$_3$, 400 MHz) δ 0.05 (s, 6H), 0.88 (s, 9H), 2.31-2.38 (m, 2H), 2.46-2.53 (m, 2H), 2.59-2.65 (m, 1H), 3.61 (d, J=5.2 Hz, 2H), 3.60-3.66 (m, 1H), 7.27 (d, J=4.8 Hz, 1H), 7.62 (dd, J=0.8, 4.8 Hz, 1H). MS (ES+): m/z 477.96 (MH$^+$, $^{35}$Cl). HPLC: t$_R$=4.21 min (OpenLynx, polar_5 min).

trans-3-[3-(tert-Butyldimethylsilanyloxymethyl)cyclobutyl]-8-chloro-1-iodoimidazo[1,5-a]pyrazine

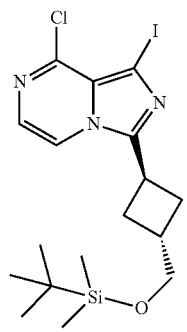 [SMILES: CC(C)(C)[Si](C)(C)OC[C@H]1C[C@H](c2nc(I)c3c(Cl)nccn32)C1]

$^1$H-NMR (CDCl$_3$, 400 MHz) δ 0.09 (s, 6H), 0.94 (s, 9H), 2.36-2.40 (m, 2H), 2.58-2.63 (m, 3H), 3.73 (d, J=4.4 Hz, 2H), 3.72-3.78 (m, 1H), 7.27 (d, J=0.8, 4.8 Hz, 1H), 7.47 (dd, J=0.8, 5.2 Hz, 1H); MS (ES+): m/z 477.93 (MH$^+$, $^{35}$Cl), 479.96 (MH$^+$, $^{37}$Cl); HPLC: t$_R$=3.77 min (OpenLynx, polar_5 min).

[3-(8-Amino-1-iodoimidazo[1,5-a]pyrazin-3-yl)-cyclobutyl]methanol

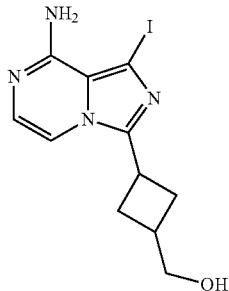 [SMILES: Nc1nccn2c(C3CC(CO)C3)nc(I)c12]

[3-(8-Chloro-1-iodoimidazo[1,5-a]pyrazin-3-yl)cyclobutyl]methanol (6.9 g) in i-PrOH (200 mL) was saturated with NH$_{3(g)}$, by passing a slow a slow stream of ammonia for 10 min at −20° C., and then heated in a Parr bomb at 110° C. for 2 d. The reaction mixture was then cooled to it, filtered through a sintered glass and the solid residue and the Parr vessel were rinsed with i-PrOH several times. The filtrate was concentrated under reduced pressure to provide an orange solid (7.9 g) still containing NH$_4$Cl. The material was taken up into refluxing MeCN (250 mL) and filtered hot. The step was repeated with another portion of hot MeCN (200 mL). The combined MeCN filtrates were concentrated under reduced pressure to provide the title compound as an orange solid; HPLC: (polar5 min) 0.53 and 1.51 min; MS (ES+): 345.1 (100, M$^+$ +1); $^1$H NMR (400 MHz, DMSO-d$_6$) δ 7.50 (d, J=5.2 Hz, 1H), 7.44 (d, J=5.2 Hz, 0.27H, minor isomer), 6.95 (d, J=5.2 Hz, 1.29H overlapped with the minor isomer) 6.63 (br, 2H), 4.61 (t, J=5.2 Hz, 0.27H, minor isomer), 4.52 (t, J=5.2 Hz, 1H), 3.69 (quintet, J=5.6 Hz, 0.32H, minor isomer), 3.54 (quintet, J=5.6 Hz, 1H), 2.52-2.25 (m, 4H), 2.10-2.00 (m, 1H).

[3-(8-Chloro-1-iodo-imidazo[1,5-a]pyrazin-3-yl)-cyclobutyl]-methanol

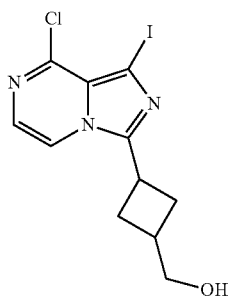 [SMILES: OCC1CC(c2nc(I)c3c(Cl)nccn23)C1]

To a solution of NIS (6.31 g, 28.0 mmol) in anh DMF (100 mL) under Ar was added dry [3-(8-chloroimidazo[1,5-a]pyrazin-3-yl)cyclobutyl]methanol (6.67 g) dissolved in anh DMF (30 mL). The flask containing [3-(8-chloroimidazo[1,5-a]pyrazin-3-yl)cyclobutyl]methanol was rinsed with another portion of anh DMF (20 mL) and the rinse was added to the reaction mixture. The reaction was heated to 60° C. (rt→60° C. ~30 min) and the stirred at this temperature for 3 h. The mixture was then cooled to rt, partitioned between 1 M aq $Na_2S_2O_3$ (60 mL), brine (60 mL) and DCM (160 mL). The aq layer was extracted with DCM (3×100 mL). The combined organics were dried ($Na_2SO_4$), concentrated under reduced pressure and purified by flash chromatography on $SiO_2$ (0-8% MeOH in DCM) to provide a material, homogenous by UV on both TLC and HPLC, still containing DMF. The material was dissolved in DCM (200 mL) and washed with water (3×40 mL), dried ($Na_2SO_4$) and concentrated under reduced pressure to provide the title compound as a pale yellow solid; HPLC (polar5 min) 2.52 min; MS (ES+): m/z (rel. int.) 364.0 (100, $M^4+1$); $^1H$ NMR (400 MHz, $CDCl_3$) δ 7.59 (d, J=4.8 Hz, 1H), 7.49 (d, J=4.8 Hz, 0.22H, minor isomer), 7.29 (d, J=4.8 Hz, 1H), 7.28 (d, J=5.2 Hz, 0.23H, minor isomer), 3.83-3.80 (m, 0.7H), 3.72-3.62 (m, 3H), 2.75-2.55 (m, 4H), 2.42-2.32 (m, 1-2H).

[3-(8-Chloro-imidazo[1,5-a]pyrazin-3-yl)-cyclobutyl]-methanol

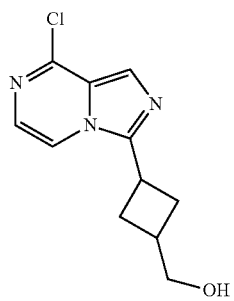 [SMILES: OCC1CC(c2ncc3c(Cl)nccn23)C1]

To a solution of 8-chloro-3-(3-methylenecyclobutyl)imidazo[1,5-a]pyrazine (4.48 g, 20.4 mmol) in anh THF (255 mL) at −78° C. under Ar, 9-BBN (61.2 mL, 0.5 M in THF, 30.6 mmol) was added dropwise over 8 min (a suspension). The cooling bath was replaced with ice-$H_2O$ and the reaction was allowed to warm slowly to rt. After being stirred for 17 h, $H_2O$ (100 mL,) was added followed by, after ~5 min, $NaBO_3.H_2O$ (12.2 g, 122.3 mmol) added in one lot. The reaction was stirred at rt for 5 h and then filtered through Celite. The Celite and residual solids were washed with DCM and EtOAc. The filtrate was concentrated under reduced pressure to yield an aq solution, which was saturated with NaCl and extracted with EtOAc (3×). The extracts were dried ($Na_2SO_4$) and concentrated under reduced pressure to yield a light yellow oil which was purified by flash chromatography on $SiO_2$ (9:1 DCM:MeOH) to afford the title compound as a light yellow oil; HPLC: $t_R$ (mass-directed HPLC, polar7 min) 2.52 min; MS (ES+): 238.0. The addition may be carried out at 0° C. Suspension quickly clears up after the exchange of cooling baths. The final product contained 1,5-cis-octanediol derived from 9-BBN. Based on $^1H$ NMR estimated roughly to be 66% target material and 33% of the byproduct. The crude product was taken onto next step crude, stereoselectivity of the product was 4-5:1 as judged by $^1H$ NMR.

(8-Chloro-3-(3-methylene-cyclobutyl)-imidazo[1,5a]pyrazine)

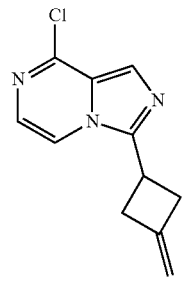

3-Methylene-cyclobutanecarboxylic acid (3-chloro-pyrazin-2-ylmethyl)-amide (52.1 g, 219.2 mmol) was dissolved in 1.0 L of anhydrous MeCN. Followed by the addition of DMF (1.0 mL) and $POCl_3$ (100 mL, 1.09 mol). The reaction was heated to 55° C. for 30 min. with a slow $N_2$ bubbling the reaction. The reaction was then concentrated in vacuo, basified with cold 2.0 M $NH_3$ in IPA with $CH_2Cl_2$. The IPA/$CH_2Cl_2$ was concentrated in vacuo and the salts were dissolved with minimal water and extracted with $CH_2Cl_2$ (4×). The organic layers where combined and washed with sat. $NaHCO_3$ (1×), dried over sodium sulfate, filtered and concentrated in vacuo. The crude product was purified via silica gel column chromatography [eluting with 2:1Hex:EtOAc] to yield the title compound as a light yellow solid; $^1H$ NMR (400 MHz, $CDCl_3$) δ 3.24-3.30 (4H, m), 3.78-3.85 (1H, m), 4.89-4.94 (2H, m), 7.33 (1H, d, J=4.99 Hz), 7.53 (1H, d, J=5.09 Hz), 7.82 (1H, s); MS (ES+): m/z 220.28/222.30 (100/80) [MH+]; HPLC: $t_R$=2.87 min (OpenLynx, polar 5 min).

3-Methylene-cyclobutanecarboxylic acid (3-chloropyrazin-2-ylmethyl)-amide

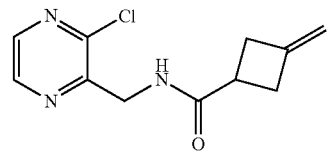 [SMILES: C=C1CC(C(=O)NCc2nccnc2Cl)C1]

C-(3-Chloropyrazin-2-yl)-methylamine bis-HCl (1.0 g, 4.62 mmol), N-ethyl-N'-(3-dimethylaminopropyl)carbodiimide (EDC) (1.31 g, 6.47 mmol, 1.4 eq.), 4-dimethylaminopyridine (DMAP) (0.141 g, 1.15 mmol, 0.25 eq.), and diisopropylethylamine (DIPEA) (2.42 mL, 1.79 g, 13.9 mmol, 3.0 eq.) were dissolved in anhydrous $CH_2Cl_2$ (25 mL). To this solution, a solution of 3-methylenecyclobutanecarboxylic acid (0.622 g, 5.54 mmol, 1.2 eq.) in anhydrous $CH_2Cl_2$ (25 mL) was added under $N_2$ and the reaction was allowed to stir overnight at rt. Reaction mixture was concentrated in vacuo and the resulting residue was dissolved in EtOAc, washed with water (2×), $NaHCO_3$ (1×), water (1×), and brine (1×), dried over $Na_2SO_4$, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid. Additionally, the title compound could be prepared by the following route: 1,1'-Carbonyldiimidazole (CDT) (0.824 g, 5.08 mmol, 1.1 eq.) and 3-methylenecyclobutanecarboxylic acid (0.570 g, 5.08 mmol, 1.1 eq.) were dissolved in anhydrous THF (12 mL) and allowed to stir at 60° C. for 2 h. A solution of C-(3-chloropyrazin-2-yl)-methylamine bis-HCl (1.0 g, 4.62 mmol) and diisopropylethylamine (DIPEA) (2.42 mL, 1.79 g, 13.9 mmol, 3.0 eq.) in anhydrous $CH_2Cl_2$ (13 mL) was added to the acid mixture and the reaction was allowed to stir at 60° C., under $N_2$, overnight. The reaction mixture was concentrated in vacuo and the resulting residue was dissolved in EtOAc, washed with $NaHCO_3$ (2×) and brine (1×), dried over $Na_2SO_4$, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid; $^1$H NMR (CDCl$_3$, 400 MHz) δ 2.86-2.96 (m, 2H), 3.03-3.19 (m, 3H), 4.72 (dd, J=4.4, 0.8 Hz, 2H), 4.79-4.84 (m, 2H), 6.78 (s, —NH), 8.32-8.34 (m, 1H), 8.46 (d, J=2.8 Hz, 1H); MS (ES+): m/z 238.19 (90) [MH$^+$]; HPLC: $t_R$=2.67 min (OpenLynx, polar 7 min).

C-(3-Chloropyrazin-2-yl)-methylamine bis-hydrochloride

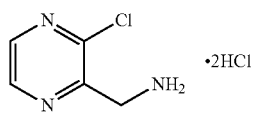

A solution of 2-(3-chloropyrazin-2-ylmethyl)-isoindole-1,3-dione (10.0 g, 36.5 mmol) in anhydrous $CH_2Cl_2$ (200 mL) was charged with hydrazine (2.87 mL, 2.93 g, 91.3 mmol, 2.5 eq.) at rt, under $N_2$ atmosphere. After 2.5 h, MeOH (300 mL) was added and the reaction was heated until the solution was homogenous. The reaction mixture was allowed to stir for 19 h. The white ppt which had formed (2,3-dihydrophthalazine-1,4-dione byproduct), was filtered off and washed several times with ether. The clear filtrate was concentrated in vacuo and the concentrate was dissolved in EtOAc and filtered again to remove white ppt. All solvent was removed, giving a yellow oil which was dissolved into EtOAc and ether and charged with HCl (g). The title compound, a pale yellow solid, instantly precipitated. The title compound was dried in a 40° C. oven for 72 h, affording the title compound, as a dark yellow solid; $^1$H NMR (400 MHz, CD$_3$OD) δ 4.55 (2H, s), 8.27 (1H, d, J=2.52 Hz), 8.54 (1H, d, J=2.56 Hz); MS (ES+): m/z 143.96/145.96 (100/60) [MH$^+$]; HPLC: $t_R$=0.41 min (OpenLynx, polar_7 min).

2-(3-Chloropyrazin-2-ylmethyl)-isoindole-1,3-dione

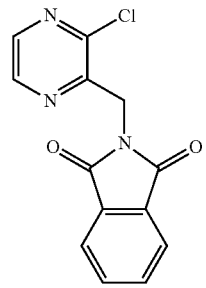 [SMILES: O=C1c2ccccc2C(=O)N1Cc1nccnc1Cl]

A solution of (3-chloropyrazin-2-yl)-methanol (47 g, 0.33 mol), isoindole-1,3-dione (58.3 g, 0.396 mol, 1.2 eq.), and triphenylphosphine (89.7 g, 0.396 mol, 1.2 eq.) in anhydrous THF (1.5 L) was charged with DIAD (80.2 g, 0.396 mol, 77.1 mL, 1.2 eq.) dropwise at rt, under $N_2$, making sure the internal temperature did not surpass 40° C. The crude material was adsorbed onto silica gel, dry loaded, and purified by chromatography on silica gel [6"×16" column, 2.75 kg silica gel, eluting with Hex:CH$_2$Cl$_2$ 1:1→neat CH$_2$Cl$_2$→MeCN:CH$_2$Cl$_2$ 2→10%.] Material was combined and concentrated in vacuo. Residue was dissolved as best as possible in hot $CH_2Cl_2$ (500 mL), after which i-PrOH was added and a white crystalline solid began to precipitate out of solution. Solid was filtered, washed with i-PrOH, and oven-dried to remove all traces of solvent, affording the title compound, as an off-white solid; $^1$H NMR (400 MHz, CDCl$_3$) δ 5.10 (s, 1H), 7.75-7.80 (m, 2H), 7.89-7.94 (m, 2H), 8.26 (1H, d, J=2.45 Hz), 8.31 (1H, d, J=2.49 Hz); MS (ES+): m/z 274.21/276.19 (100/50) [MH$^+$]; HPLC: $t_R$=3.35 min (OpenLynx, nonpolar_7 min).

(3-Chloropyrazin-2-yl)-methanol

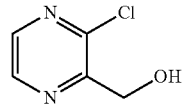

To a solution of 2,2,6,6-tetramethylpiperidine (TMP) (43.8 mL, 36.4 g, 0.258 mol, 1.18 eq.) in anhydrous THF (600 mL), cooled to −78° C., 2.5 M n-BuLi in hexanes (110.9 mL, 0.277 mol, 1.27 eq.) was added directly. The solution was allowed to warm to 0° C. for 20 min, after which the reaction was again cooled to −78° C. A solution of chloropyrazine (19.2 mL, 25.0 g, 0.218 mol) in THF (50 mL) was added dropwise over 10 min; a color change from light yellow to dark brown was observed. The reaction was allowed to react at −78° C. to −70° C. for 10 min. A solution of DMF (42.0 mL, 39.9 g, 0.546 mol, 2.5 eq.) in THF (50 mL) was added slowly over 12 min. The temperature was maintained at −78° C. to −70° C. for 2 h. The reaction was quenched with MeOH (400 mL) at −78° C. and charged with $NaBH_4$ (16.5 g, 0.437 mol, 2.0 eq.) at 0° C. for 2 h. The solvent was partially removed in vacuo and additional $CH_2Cl_2$ (200 mL) was added to the oil and the reaction mixture was quenched with 2N HCl (900 mL) to a neutral pH. The aqueous layer was extracted with $CH_2Cl_2$ (4×) and EtOAc (2×). The organic layers were combined, dried over $Na_2SO_4$, filtered, and concentrated in vacuo, giving a crude black liquid. The crude material was adsorbed onto silica gel (for dry loading) and purified by chromatography on silica gel [2 kg silica gel, eluting with MeCN:$CH_2Cl_2$ 2%→5%→10%] affording the title compound, as a dark brown oil; $^1$H NMR (400 MHz, $CDCl_3$) δ 4.86 (2H, s), 8.36 (1H, d, J=4.35 Hz), 8.51 (1H, d, J=2.56 Hz); MS (ES+): m/z 144.93 (100) [MH$^+$]; HPLC: $t_R$=1.60 min (OpenLynx, polar_7 min).

What is claimed is:
1. A compound represented by Formula I:

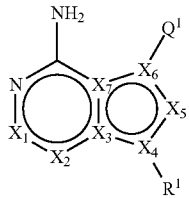

I or a pharmaceutically acceptable salt thereof, wherein:
$X_1$ is CH;
$X_2$ and $X_4$ are both N;
$X_5$ is CH or N;
$X_3$, $X_6$, and $X_7$ are all C;
$Q^1$ is

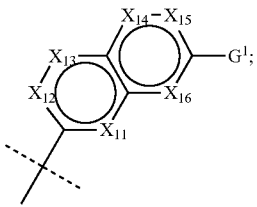

$X_{11}$ is C-$E_{11}$ wherein $E_{11}$ is H or halogen;
$X_{12}$ and $X_{13}$ are CH;
$X_{15}$ is CH or N;
$X_{14}$ is C-$E^{11}$, wherein $E^{11}$ is halogen, $C_{0-10}$alkyl, or —$OC_{0-10}$alkyl;
$X_{16}$ is N;
$R^1$ is $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents;
$G^1$ is phenyl or pyridyl, either of which is optionally substituted with one or more independent halo, —$CF_3$, —$OCF_3$, —$OR^{222}$, —$NR^{222}R^{333}(R^{222a})_{j2a}$, —C(O)$R^{222}$, —$CO_2R^{222}$, —C(=O)$NR^{222}R^{333}$, —$NO_2$, —CN, —S(O)$_{j2a}R^{222}$, —$SO_2NR^{222}R^{333}$, —$NR^{222}$C(=O)$R^{333}$, —$NR^{222}$C(=O)$OR^{333}$, —$NR^{222}$C(=O)$NR^{333}R^{222a}$, —$NR^{222}$S(O)$_{j2a}R^{333}$, —C(=S)$OR^{222}$, —C(=O)$SR^{222}$, —$NR^{222}$C(=NR$^{333}$)$NR^{222a}R^{333a}$, —$NR^{222}$C(=NR$^{333}$)$OR^{222a}$, —$NR^{222}$C(=NR$^{333}$)$SR^{222a}$, —OC(=O)$OR^{222}$, —OC(=O)$NR^{222}R^{333}$, —OC(=O)$SR^{222}$, —SC(=O)$OR^{222}$, or —SC(=O)$NR^{222}R^{333}$ substituents;

$G^{11}$ is halo, carbonyl oxygen, —$CF_3$, —$OCF_3$, —$OR^{21}$, —$NR^{21}R^{31}(R^{2a1})_{j4}$, —C(O)$R^{21}$, —$CO_2R^{21}$, —C(=O)$NR^{21}R^{31}$, —$NO_2$, —CN, —S(O)$_{j4}R^{21}$, —$SO_2NR^{21}R^{31}$, —$NR^{21}$(C=O)$R^{31}$, —$NR^{21}$C(=O)$OR^{31}$, —$NR^{21}$C(=O)$NR^{31}R^{2a1}$, —$NR^{21}$S(O)$_{j4}R^{31}$, —C(=S)$OR^{21}$, —C(=O)$SR^{21}$, —$NR^{21}$C(=NR$^{31}$)$NR^{2a1}R^{3a1}$, —$NR^{21}$C(=NR$^{31}$)$OR^{2a1}$, —$NR^{21}$C(=NR$^{31}$)$SR^{2a1}$, —OC(=O)$OR^{21}$, —OC(=O)$NR^{21}R^{31}$, —OC(=O)$SR^{21}$, —SC(=O)$OR^{21}$, —SC(=O)$NR^{21}R^{31}$, —P(O)$OR^{21}OR^{31}$, $C_{1-10}$alkylidene, $C_{0-10}$alkyl, $C_{2-10}$alkenyl, $C_{2-10}$alkynyl, $C_{1-10}$alkoxy$C_{1-10}$alkenyl, $C_{1-10}$alkoxy$C_{2-10}$alkenyl $C_{1-10}$alkoxy$C_{2-10}$alkynyl, $C_{1-10}$alkylthio$C_{1-10}$alkenyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, carbonyl oxygen, —$CF_3$, —$OCF_3$, —$OR^{2221}$, —$NR^{2221}R^{3331}(R^{222a1})_{j4a}$, C(O)$R^{2221}$, —$CO_2R^{2221}$, —C(=O)$NR^{2221}R^{3331}$, —$NO_2$, —CN, —S(O)$_{j4a}R^{2221}$, —$SO_2NR^{2221}R^{3331}$, —$NR^{2221}$C(=O)$R^{3331}$, —$NR^{2221}$C(=O)$OR^{3331}$, —$NR^{2221}$C(=O)$NR^{3331}R^{222a1}$, —$NR^{2221}$S(O)$_{j4a}R^{3331}$; —C(=S)$OR^{2221}$, —C(=O)$SR^{2221}$, —$NR^{2221}$C(=NR$^{3331}$)$NR^{222a1}R^{333a1}$, —$NR^{2221}$C(=NR$^{3331}$)$OR^{222a1}$, —$NR^{2221}$C(=NR$^{3331}$)$SR^{222a1}$, —OC(=O)$OR^{2221}$, —OC(=O)$NR^{2221}R^{3331}$, —OC(=O)$SR^{2221}$, —SC(=O)$OR^{2221}$, —P(O)$OR^{2221}OR^{3331}$, or —SC(=O)$NR^{2221}R^{3331}$ substituents;

or $G^{11}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{2221}$, —$NR^{2221}R^{3331}(R^{222a1})_{j5a}$, —C(O)$R^{2221}$, —$CO_2R^{2221}$, —C(=O)$NR^{2221}R^{3331}$, —$NO_2$, —CN, —S(O)$_{j5a}R^{2221}$, —$SO_2NR^{2221}R^{3331}$, —$NR^{2221}$C(=O)$R^{3331}$, —$NR^{2221}$C(=O)$OR^{3331}$, —$NR^{2221}$C(=O)$NR^{3331}R^{222a1}$, —$NR^{2221}$S(O)$_{j5a}R^{3331}$, —C(=S)$OR^{2221}$, —C(=O)$SR^{2221}$, —$NR^{2221}$C(=NR$^{3331}$)$NR^{222a1}R^{333a1}$, —$NR^{2221}$C(=NR$^{3331}$)$OR^{222a1}$, —$NR^{2221}$C(=NR$^{3331}$)$SR^{222a1}$, —OC(=O)$OR^{2221}$, —OC(=O)$NR^{2221}R^{3331}$, —OC(=O)$SR^{2221}$, —SC(=O)$OR^{2221}$, —P(O)$OR^{2221}OR^{3331}$, or —SC(=O)$NR^{2221}R^{3331}$ substituents;

or $G^{11}$ is C, taken together with the carbon to which it is attached forms a C=C double bond which is substituted with $R^5$ and $G^{111}$;

$R^2$, $R^{2a}$, $R^3$, $R^{3a}$, -$R^{222}$, $R^{222a}$, $R^{333}$, $R^{333a}$, $R^{21}$, $R^{2a1}$, $R^{31}$, $R^{3a1}$, $R^{2221}$, $R^{222a1}$, $R^{3331}$, and $R^{333a1}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl $C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl $C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, or aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted by one or more independent $G^{111}$ substituents;

or in the case of $-NR^{222}R^{333}(R^{222a})_{j1a}$ or $-NR^{222}R^{333}(R^{222a})_{j2a}$ or $-NR^{21}R^{31}(R^{2a1})_{j4}$ or $-NR^{2221}R^{3331}(R^{222a1})_{j4a}$ or $-NR^{2221}R^{3331}(R^{222a1})_{j5a}$, then $R^{222}$ and $R^{333}$, or $R^{2221}$ and $R^{3331}$, respectfully, are optionally taken together with the nitrogen atom to which they are attached to form a 3-10 membered saturated or unsaturated ring, wherein said ring is optionally substituted by one or more independent $G^{1111}$ substituents and wherein said ring optionally includes one or more heteroatoms other than the nitrogen to which $R^{222}$ and $R^{333}$, or $R^{2221}$ and $R^{3331}$ are attached;

$R^5$, $G^{111}$, and $G^{1111}$ are each independently $C_{0-10}$alkyl, $C_{2-10}$alkenyl, $C_{2-10}$alkynyl, $C_{1-10}$alkoxy$C_{1-10}$alkenyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, $-CF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $-NR^{77}C(=O)R^{87}$, $-NR^{77}C(=O)OR^{87}$, $-NR^{77}C(=O)NR^{78}R^{87}$, $-NR^{77}S(O)_{j5a}R^{87}$, $-C(=S)OR^{77}$, $-C(=O)SR^{77}$, $-NR^{77}C(=NR^{87})NR^{78}R^{88}$, $-NR^{77}C(=NR^{87})OR^{78}$, $-NR^{77}C(=NR^{87})SR^{78}$, $-OC(=O)OR^{77}$, $-OC(=O)NR^{77}R^{87}$, $-OC(=O)SR^{77}$, $-SC(=O)OR^{77}$, $-P(O)OR^{77}OR^{87}$, or $-SC(=O)NR^{77}R^{87}$ substituents;

$R^{77}$, $R^{78}$, $R^{87}$, $R^{88}$ are each independently $C_{0-10}$alkyl, $C_{2-10}$alkenyl, $C_{2-10}$alkynyl, $C_{1-10}$alkoxy$C_{1-10}$alkyl, $C_{1-10}$-alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, $-SO_2N(C_{0-4}$alkyl)($C_{0-4}$alkyl), or $-N(C_{0-4}$alkyl)($C_{0-4}$alkyl) substituents;

or $R^{77}$, $R^{78}$, $R^{87}$, $R^{88}$ are each independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CON(C_{0-4}$alkyl)($C_{0-10}$alkyl), $-SO_2N(C_{0-4}$alkyl)($C_{0-4}$alkyl), or $-N(C_{0-4}$alkyl)($C_{0-4}$alkyl) substituents;

j1, j1a, j2a, j4, j4a, j5a are each independently 0, 1, or 2.

2. The compound of claim 1, wherein $X_{15}$ is CH.

3. The compound of claim 1, wherein: $X_{11}$, $X_{12}$, $X_{13}$, $X_{14}$, and $X_{15}$ are each CH.

4. The compound of claim 1 wherein $R^1$ is cyclo$C_{3-10}$alkyl, bicyclo$C_{5-10}$alkyl, aryl, heteroaralkyl, heterocyclyl, heterobicyclo$C_{5-10}$alkyl, spiroalkyl, or heterospiroalkyl any of which is optionally substituted by one or more independent $G^{11}$ substituents.

5. The compound of claim 1 wherein $R^1$ is $C_{0-10}$alkyl, heteroaralkyl, or aralkyl, any of which is optionally substituted by one or more independent $G^{11}$ substituents.

6. The compound of claim 1 wherein $R^1$ is cyclo$C_{3-10}$alkyl, bicyclo$C_{5-10}$alkyl, spiroalkyl, or heterospiroalkyl any of which is optionally substituted by one or more independent $G^{11}$ substituents.

7. The compound of claim 1 wherein $R^1$ is heterocyclyl or heterobicyclo$C_{5-10}$alkyl, either of which is optionally substituted by one or more independent $G^{11}$ substituents.

8. The compound of claim 1 wherein $R^1$ is aryl or heteroaryl, either of which is optionally substituted by one or more independent $G^{11}$ substituents.

9. The compound of claim 1 wherein $R^1$ is $C_{0-10}$alkyl, cyclo$C_{3-10}$alkyl, bicyclo$C_{5-10}$alkyl, aralkyl, heteroaralkyl, heterocyclyl, heterobicyclo$C_{5-10}$alkyl, spiroalkyl, or heterospiroalkyl any of which is optionally substituted by one or more independent $G^{11}$ substituents.

10. The compound of claim 4 wherein $G^{11}$ is carbonyl oxygen, $-OR^{21}$, $-NR^{21}R^{31}(R^{2a1})_{j4}$, $-CO_2R^{21}$, $-C(=O)NR^{21}R^{31}$, $C_{0-10}$alkyl, heterocyclyl-$C_{0-10}$alkyl, any of which is optionally substituted with one or more independent halo, carbonyl oxygen, $-CF_3$, $-OCF_3$, $-OR^{2221}$, $-NR^{2221}R^{3331}(R^{222a1})_{j4a}$, $-C(O)R^{2221}$, $-CO_2R^{2221}$, $-C(=O)NR^{2221}R^{3331}$, $-NO_2$, $-CN$, $-S(O)_{j4a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{222a1}$, $-NR^{2221}S(O)_{j4a}R^{3331}$, $-C(=S)OR^{2221}$, $-C(=O)SR^{2221}$, $-NR^{2221}C(=NR^{3331})NR^{222a1}R^{333a1}$, $-NR^{2221}C(=NR^{3331})OR^{222a1}$, $-NR^{2221}C(=NR^{3331})SR^{222a1}$, $-OC(=O)OR^{2221}$, $-OC(=O)NR^{2221}R^{3331}$, $-OC(=O)SR^{2221}$, $-SC(=O)OR^{2221}$, $-P(O)OR^{2221}OR^{3331}$, or $-SC(=O)NR^{2221}R^{3331}$ substituents;

or $G^{11}$ is hetaryl-$C_{0-10}$alkyl, any of which is optionally substituted with one or more independent halo, $-CF_3$, $-OCF_3$, $-OR^{2221}$, $-NR^{2221}R^{3331}(R^{222a1})_{j5a}$, $C(O)R^{2221}$, $-CO_2R^{2221}$, $-C(=O)NR^{2221}R^{3331}$, $-NO_2$, $-CN$, $-S(O)_{j5a}R^{2221}$, $-SO_2NR^{2221}R^{3331}$, $-NR^{2221}C(=O)R^{3331}$, $-NR^{2221}C(=O)OR^{3331}$, $-NR^{2221}C(=O)NR^{3331}R^{222a1}$, $-NR^{2221}S(O)_{j5a}R^{3331}$, $-C(=S)OR^{2221}$, $-C(=O)SR^{2221}$, $-NR^{2221}C(=NR^{3331})NR^{222a1}R^{333a1}$, $-NR^{2221}C(=NR^{3331})OR^{222a1}$, $-NR^{2221}C(=NR^{3331})SR^{222a1}$, $-OC(=O)OR^{2221}$, $-OC(=O)NR^{2221}R^{3331}$, $-OC(=O)SR^{2221}$, $-SC(=O)OR^{2221}$, $-P(O)OR^{2221}OR^{3331}$, or $-SC(=O)NR^{2221}R^{3331}$ substituents.

11. The compound of claim 4 wherein $G^{11}$ is carbonyl oxygen, $-OR^{21}$, $-NR^{21}R^{31}(R^{2a1})_{j4}$, $-CO_2R^{21}$, $-C(=O)NR^{21}R^{31}$, $C_{0-10}$alkyl, heterocyclyl-$C_{0-10}$alkyl, any of which is optionally substituted with one or more independent halo, carbonyl oxygen, $-OR^{2221}$, or $-NR^{2221}R^{3331}(R^{222a1})_{j4a}$ substituents;

or $G^{11}$ is hetaryl-$C_{0-10}$alkyl, any of which is optionally substituted with one or more independent halo, $-CF_3$, $-OCF_3$, $-OR^{2221}$, $-NR^{2221}R^{3331}(R^{222a1})_{j5a}$, $-C(O)R^{2221}$, $-CO_2R^{2221}$, $-C(=O)NR^{2221}R^{3331}$, $-NO_2$, $-CN$, $-S(O)_{j5a}R^{2221}$, $-SO_2NR^{2221}R^{3331}$, $NR^{2221}C$ (=O)R³³³¹, —NR²²²¹C(=O)OR³³³¹, —NR²²²¹C(=O)NR³³³¹R²²²ᵃ¹, —NR²²²¹S(O)ⱼ₅ₐR³³³¹, —C(=S)OR²²²¹, —C(=O)SR²²²¹, —NR²²²¹C(=NR³³³¹)NR²²²ᵃ¹R³³³ᵃ¹, —NR²²²¹C(=NR³³³¹)OR²²²ᵃ¹, —NR²²²¹C(=NR³³³¹)SR²²²ᵃ¹, —OC(=O)OR²²²¹, —OC(=O)NR²²²¹R³³³¹, —OC(=O)SR²²²¹, —SC(=O)OR²²²¹, —P(O)OR²²²¹OR³³³¹, or —SC(=O)NR²²²¹R³³³¹ substituents.

12. The compound of claim 1 selected from:

7-Cyclobutyl-5-(2-phenylquinolin-7-yl)-7H-pyrrolo[2,3-d]pyrimidin-4-ylamine;
7-Cyclobutyl-5-(2-pyridin-2-ylquinolin-7-yl)-7H-pyrrolo[2,3-d]pyrimidin-4-ylamine;
7-Cyclobutyl-5-(2-thiophen-2-ylquinolin-7-yl)-7H-pyrrolo[2,3-d]pyrimidin-4-ylamine;
[7-(4-Amino-7-cyclobutyl-7H-pyrrolo[2,3-d]-pyrimidin-5-yl)-quinolin-2-yl]-phenylamine;
7-Cyclobutyl-5-(2-phenoxyquinolin-7-yl)-7H-pyrrolo[2,3-d]pyrimidin-4-ylamine;
5-(6-Chloro-2-phenylquinolin-7-yl)-7-cyclobutyl-7H-pyrrolo[2,3-d]pyrimidin-4-ylamine;
5-(6-Chloro-2-pyridin-2-ylquinolin-7-yl)-7-cyclobutyl-7H-pyrrolo[2,3-d]pyrimidin-4-ylamine;
5-(6-Chloro-2-thiophen-2-ylquinolin-7-yl)-7-cyclobutyl-7H-pyrrolo[2,3-d]pyrimidin-4-ylamine;
5-(6-Chloro-2-phenoxyquinolin-7-yl)-7-cyclobutyl-7H-pyrrolo[2,3-d]pyrimidin-4-ylamine;
[7-(4-Amino-7-cyclobutyl-7H-pyrrolo[2,3-d]pyrimidin-5-yl)-6-chloroquinolin-2-yl]-phenylamine;
3-[4-Amino-5-(2-phenylquinolin-7-yl)-pyrrolo[2,3-d]pyrimidin-7-yl]-cyclobutanol;
3-[4-Amino-5-(2-thiophen-2-ylquinolin-7-yl)-pyrrolo[2,3-d]pyrimidin-7-yl]-cyclobutanol;
3-[4-Amino-5-(2-pyridin-2-ylquinolin-7-yl)-pyrrolo[2,3-d]pyrimidin-7-yl]-cyclobutanol;
3-[4-Amino-5-(2-phenylaminoquinolin-7-yl)-pyrrolo[2,3-d]pyrimidin-7-yl]-cyclobutanol;
3-[4-Amino-5-(2-phenoxyquinolin-7-yl)-pyrrolo[2,3-d]pyrimidin-7-yl]-cyclobutanol;
3-[4-Amino-5-(6-chloro-2-pyridin-2-ylquinolin-7-yl)-pyrrolo[2,3-d]pyrimidin-7-yl]-cyclobutanol;
3-[4-Amino-5-(6-chloro-2-phenylquinolin-7-yl)-pyrrolo[2,3-d]pyrimidin-7-yl]-cyclobutanol;
3-[4-Amino-5-(6-chloro-2-thiophen-2-ylquinolin-7-yl)-pyrrolo[2,3-d]pyrimidin-7-yl]-cyclobutanol;
3-[4-Amino-5-(6-chloro-2-phenoxyquinolin-7-yl)-pyrrolo[2,3-d]pyrimidin-7-yl]-cyclobutanol;
3-[4-Amino-5-(6-chloro-2-phenylaminoquinolin-7-yl)-pyrrolo[2,3-d]pyrimidin-7-yl]-cyclobutanol;
3-[4-Amino-5-(8-fluoro-2-phenylquinolin-7-yl)-pyrrolo[2,3-d]pyrimidin-7-yl]-cyclobutanol;
3-[4-Amino-5-(8-fluoro-2-thiophen-2-ylquinolin-7-yl)-pyrrolo[2,3-d]pyrimidin-7-yl]-cyclobutanol;
3-[4-Amino-5-(8-fluoro-2-pyridin-2-ylquinolin-7-yl)-pyrrolo[2,3-d]pyrimidin-7-yl]-cyclobutanol;
3-[4-Amino-5-(8-fluoro-2-phenylaminoquinolin-7-yl)-pyrrolo[2,3-d]pyrimidin-7-yl]-cyclobutanol;
3-[4-Amino-5-(8-fluoro-2-phenoxyquinolin-7-yl)-pyrrolo[2,3-d]pyrimidin-7-yl]-cyclobutanol;
7-Cyclobutyl-5-(8-fluoro-2-phenylquinolin-7-yl)-7H-pyrrolo[2,3-d]pyrimidin-4-ylamine;
7-Cyclobutyl-5-(8-fluoro-2-pyridin-2-ylquinolin-7-yl)-7H-pyrrolo[2,3-d]pyrimidin-4-ylamine;
7-Cyclobutyl-5-(8-fluoro-2-thiophen-2-yl-quinolin-7-yl)-7H-pyrrolo[2,3-d]pyrimidin-4-ylamine;
7-Cyclobutyl-5-(8-fluoro-2-phenoxyquinolin-7-yl)-7H-pyrrolo[2,3-d]pyrimidin-4-ylamine;
[7-(4-Amino-7-cyclobutyl-7H-pyrrolo[2,3-d]pyrimidin-5-yl)-8-fluoroquinolin-2-yl]-phenylamine;
7-(3-Azetidin-1-ylmethylcyclobutyl)-5-(2-phenylquinolin-7-yl)-7H-pyrrolo[2,3-d]pyrimidin-4-ylamine;
7-(3-Azetidin-1-ylmethylcyclobutyl)-5-(2-pyridin-2-ylquinolin-7-yl)-7H-pyrrolo[2,3-d]pyrimidin-4-ylamine;
7-(3-Azetidin-1-ylmethylcyclobutyl)-5-(2-thiophen-2-ylquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-quinolin-2-yl}-phenylamine;
7-(3-Azetidin-1-ylmethylcyclobutyl)-5-(2-phenoxyquinolin-7-yl)-7H-pyrrolo[2,3-d]pyrimidin-4-ylamine;
7-(3-Azetidin-1-ylmethylcyclobutyl)-5-(6-chloro-2-pyridin-2-ylquinolin-7-yl)-7H-pyrrolo[2,3-d]pyrimidin-4-ylamine;
7-(3-Azetidin-1-ylmethylcyclobutyl)-5-(6-chloro-2-phenylquinolin-7-yl)-7H-pyrrolo[2,3-d]pyrimidin-4-ylamine;
7-(3-Azetidin-1-ylmethylcyclobutyl)-5-(6-chloro-2-thiophen-2-ylquinolin-7-yl)-7H-pyrrolo[2,3-d]pyrimidin-4-ylamine;
7-(3-Azetidin-1-ylmethylcyclobutyl)-5-(6-chloro-2-phenoxyquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-6-chloroquinolin-2-yl}-phenylamine;
7-(3-Azetidin-1-ylmethylcyclobutyl)-5-(8-fluoro-2-phenylquinolin-7-yl)-7H-pyrrolo[2,3-d]pyrimidin-4-ylamine;
7-(3-Azetidin-1-ylmethylcyclobutyl)-5-(8-fluoro-2-pyridin-2-ylquinolin-7-yl)-7H-pyrrolo[2,3-d]pyrimidin-4-ylamine;
7-(3-Azetidin-1-ylmethylcyclobutyl)-5-(8-fluoro-2-thiophen-2-ylquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-8-fluoroquinolin-2-yl}-phenyl-amine;
7-(3-Azetidin-1-ylmethylcyclobutyl)-5-(8-fluoro-2-phenoxyquinolin-7-yl)-7H-pyrrolo[2,3-d]pyrimidin-4-ylamine;
7-(3-Azetidin-1-ylmethylcyclobutyl)-5-(4-methyl-2-pyridin-2-ylquinolin-7-yl)-7H-pyrrolo[2,3-d]pyrimidin-4-ylamine;
7-(3-Azetidin-1-ylmethylcyclobutyl)-5-(4-methyl-2-phenylquinolin-7-yl)-7H-pyrrolo[2,3-d]pyrimidin-4-ylamine;
7-(3-Azetidin-1-ylmethylcyclobutyl)-5-(4-methyl-2-thiophen-2-ylquinolin-7-yl)-7H-pyrrolo[2,3-d]pyrimidin-4-ylamine;
7-(3-Azetidin-1-ylmethylcyclobutyl)-5-(4-methyl-2-phenoxyquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-4-methylquinolin-2-yl}-phenylamine;
{7-[4-Amino-7-(3-azetidin-1-ylmethylcyclobutyl)-7H-pyrrolo[2,3-d]pyrimidin-5-yl]-2-phenylquinolin-4-yl}-methylamine;
{7-[4-Amino-7-(3-azetidin-1-ylmethylcyclobutyl)-7H-pyrrolo[2,3-d]pyrimidin-5-yl]-2-pyridin-2-ylquinolin-4-yl}-methylamine;

{7-[4-Amino-7-(3-azetidin-1-ylmethylcyclobutyl)-7H-pyrrolo[2,3-d]pyrimidin-5-yl]-2-thiophen-2-ylquinolin-4-yl}-methylamine;

7-[4-Amino-7-(3-azetidin-1-ylmethylcyclobutyl)-7H-pyrrolo[2,3-d]pyrimidin-5-yl]-N$^4$-methyl-N$^2$-phenylquinoline-2,4-diamine;

{7-[4-Amino-7-(3-azetidin-1-ylmethylcyclobutyl)-7H-pyrrolo[2,3-d]pyrimidin-5-yl]-2-phenoxyquinolin-4-yl}-methylamine;

7-(3-Dimethylaminomethylcyclobutyl)-5-(2-phenylquinolin-7-yl)-7H-pyrrolo[2,3-d]pyrimidin-4-ylamine;

7-(3-Dimethylaminomethylcyclobutyl)-5-(2-pyridin-2-ylquinolin-7-yl)-7H-pyrrolo[2,3-d]pyrimidin-4-ylamine;

7-(3-Dimethylaminomethylcyclobutyl)-5-(2-thiophen-2-ylquinolin-7-yl)-7H-pyrrolo[2,3-d]pyrimidin-4-ylamine;

7-(3-Dimethylaminomethylcyclobutyl)-5-(2-phenoxyquinolin-7-yl)-7H-pyrrolo[2,3-d]pyrimidin-4-ylamine;

{7-[4-Amino-7-(3-dimethylaminomethylcyclobutyl)-7H-pyrrolo[2,3-d]pyrimidin-5-yl]-quinolin-2-yl}-phenylamine;

5-(6-Chloro-2-phenylquinolin-7-yl)-7-(3-dimethylaminomethylcyclobutyl)-7H-pyrrolo[2,3-d]pyrimidin-4-ylamine;

5-(6-Chloro-2-pyridin-2-ylquinolin-7-yl)-7-(3-dimethylaminomethylcyclobutyl)-7H-pyrrolo[2,3-d]pyrimidin-4-ylamine;

5-(6-Chloro-2-thiophen-2-ylquinolin-7-yl)-7-(3-dimethylaminomethylcyclobutyl)-7H-pyrrolo[2,3-d]pyrimidin-4-ylamine;

{7-[4-Amino-7-(3-dimethylaminomethylcyclobutyl)-7H-pyrrolo[2,3-d]pyrimidin-5-yl]-6-chloroquinolin-2-yl}-phenylamine;

5-(6-Chloro-2-phenoxyquinolin-7-yl)-7-(3-dimethylaminomethylcyclobutyl)-7H-pyrrolo[2,3-d]pyrimidin-4-ylamine;

7-(3-Dimethylaminomethylcyclobutyl)-5-(8-fluoro-2-pyridin-2-ylquinolin-7-yl)-7H-pyrrolo[2,3-d]pyrimidin-4-ylamine;

7-(3-Dimethylaminomethylcyclobutyl)-5-(8-fluoro-2-phenylquinolin-7-yl)-7H-pyrrolo[2,3-d]pyrimidin-4-ylamine;

7-(3-Dimethylaminomethylcyclobutyl)-5-(8-fluoro-2-thiophen-2-ylquinolin-7-yl)-7H-pyrrolo[2,3-d]pyrimidin-4-ylamine;

7-(3-Dimethylaminomethylcyclobutyl)-5-(8-fluoro-2-phenoxyquinolin-7-yl)-7H-pyrrolo[2,3-d]pyrimidin-4-ylamine;

7-(3-Dimethylaminomethylcyclobutyl)-5-(4-methyl-2-phenylquinolin-7-yl)-7H-pyrrolo[2,3-d]pyrimidin-4-ylamine;

7-(3-Dimethylaminomethylcyclobutyl)-5-(4-methyl-2-pyridin-2-ylquinolin-7-yl)-7H-pyrrolo[2,3-d]pyrimidin-4-ylamine;

7-(3-Dimethylaminomethylcyclobutyl)-5-(4-methyl-2-thiophen-2-ylquinolin-7-yl)-7H-pyrrolo[2,3-d]pyrimidin-4-ylamine;

7-(3-Dimethylaminomethylcyclobutyl)-5-(4-methyl-2-phenoxyquinolin-7-yl)-7H-pyrrolo[2,3-d]pyrimidin-4-ylamine;

4-[4-Amino-5-(2-phenylquinolin-7-yl)-pyrrolo[2,3-d]pyrimidin-7-yl]-cyclohexanecarboxylic acid amide;

4-[4-Amino-5-(2-pyridin-2-ylquinolin-7-yl)-pyrrolo[2,3-d]pyrimidin-7-yl]-cyclohexanecarboxylic acid amide;

4-[4-Amino-5-(2-thiophen-2-ylquinolin-7-yl)-pyrrolo[2,3-d]pyrimidin-7-yl]-cyclohexanecarboxylic acid amide;

4-[4-Amino-5-(2-phenoxyquinolin-7-yl)-pyrrolo[2,3-d]pyrimidin-7-yl]-cyclohexanecarboxylic acid amide;

4-[4-Amino-5-(2-phenylquinolin-7-yl)-pyrrolo[2,3-d]pyrimidin-7-yl]-cyclohexanecarboxylic acid methylamide;

4-[4-Amino-5-(2-thiophen-2-ylquinolin-7-yl)-pyrrolo[2,3-d]pyrimidin-7-yl]-cyclohexanecarboxylic acid methylamide;

4-[4-Amino-5-(2-phenoxyquinolin-7-yl)-pyrrolo[2,3-d]pyrimidin-7-yl]-cyclohexanecarboxylic acid methylamide;

4-[4-Amino-5-(2-pyridin-2-ylquinolin-7-yl)-pyrrolo[2,3-d]pyrimidin-7-yl]-cyclohexanecarboxylic acid methylamide;

4-[4-Amino-5-(6-chloro-2-pyridin-2-ylquinolin-7-yl)-pyrrolo[2,3-d]pyrimidin-7-yl]-cyclohexanecarboxylic acid methylamide;

4-[4-Amino-5-(6-chloro-2-phenylquinolin-7-yl)-pyrrolo[2,3-d]pyrimidin-7-yl]-cyclohexanecarboxylic acid methylamide;

4-[4-Amino-5-(6-chloro-2-thiophen-2-ylquinolin-7-yl)-pyrrolo[2,3-d]pyrimidin-7-yl]-cyclohexanecarboxylic acid methylamide;

4-[4-Amino-5-(6-chloro-2-phenoxyquinolin-7-yl)-pyrrolo[2,3-d]pyrimidin-7-yl]-cyclohexanecarboxylic acid methylamide;

4-[4-Amino-5-(6-chloro-2-pyridin-2-ylquinolin-7-yl)-pyrrolo[2,3-d]pyrimidin-7-yl]-cyclohexanecarboxylic acid amide;

4-[4-Amino-5-(6-chloro-2-phenylquinolin-7-yl)-pyrrolo[2,3-d]pyrimidin-7-yl]-cyclohexanecarboxylic acid amide;

4-[4-Amino-5-(6-chloro-2-thiophen-2-ylquinolin-7-yl)-pyrrolo[2,3-d]pyrimidin-7-yl]-cyclohexanecarboxylic acid amide;

4-[4-Amino-5-(6-chloro-2-phenoxyquinolin-7-yl)-pyrrolo[2,3-d]pyrimidin-7-yl]-cyclohexanecarboxylic acid amide;

7-(4-Aminomethylcyclohexyl)-5-(2-thiophen-2-ylquinolin-7-yl)-7H-pyrrolo[2,3-d]pyrimidin-4-ylamine;

7-(4-Aminomethylcyclohexyl)-5-(2-phenylquinolin-7-yl)-7H-pyrrolo[2,3-d]pyrimidin-4-ylamine;

7-(4-Aminomethylcyclohexyl)-5-(2-phenoxyquinolin-7-yl)-7H-pyrrolo[2,3-d]pyrimidin-4-ylamine;

7-(4-Aminomethylcyclohexyl)-5-(2-pyridin-2-ylquinolin-7-yl)-7H-pyrrolo[2,3-d]pyrimidin-4-ylamine;

7-(4-Aminomethylcyclohexyl)-5-(6-chloro-2-thiophen-2-ylquinolin-7-yl)-7H-pyrrolo[2,3-d]pyrimidin-4-ylamine;

7-(4-Aminomethylcyclohexyl)-5-(6-chloro-2-pyridin-2-ylquinolin-7-yl)-7H-pyrrolo[2,3-d]pyrimidin-4-ylamine;

7-(4-Aminomethylcyclohexyl)-5-(6-chloro-2-phenoxyquinolin-7-yl)-7H-pyrrolo[2,3-d]pyrimidin-4-ylamine;

7-(4-Aminomethylcyclohexyl)-5-(6-chloro-2-phenylquinolin-7-yl)-7H-pyrrolo[2,3-d]pyrimidin-4-ylamine;

487

7-(4-Aminomethylcyclohexyl)-5-(4-methyl-2-phenylquinolin-7-yl)-7H-pyrrolo[2,3-d]pyrimidin-4-ylamine;

7-(4-Aminomethylcyclohexyl)-5-(4-methyl-2-thiophen-2-ylquinolin-7-yl)-7H-pyrrolo[2,3-d]pyrimidin-4-ylamine;

7-(4-Aminomethylcyclohexyl)-5-(4-methyl-2-phenoxyquinolin-7-yl)-7H-pyrrolo[2,3-d]pyrimidin-4-ylamine;

7-(4-Aminomethylcyclohexyl)-5-(4-methyl-2-pyridin-2-ylquinolin-7-yl)-7H-pyrrolo[2,3-d]pyrimidin-4-ylamine;

or a pharmaceutically acceptable salt thereof.

13. The compound of claim 1 selected from

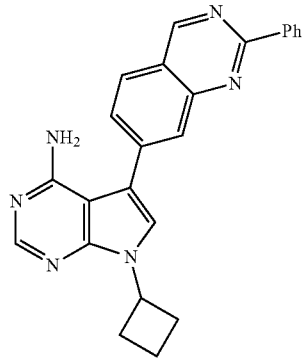

488

-continued

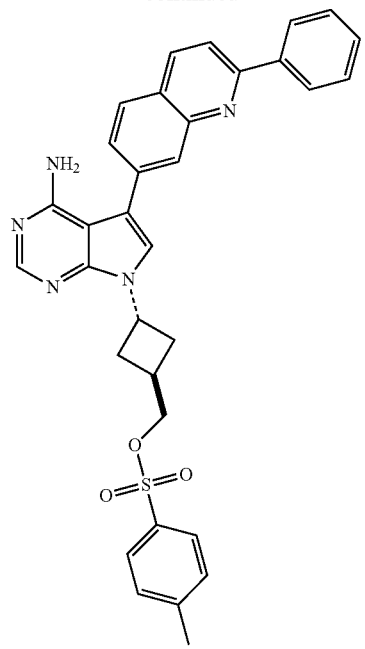

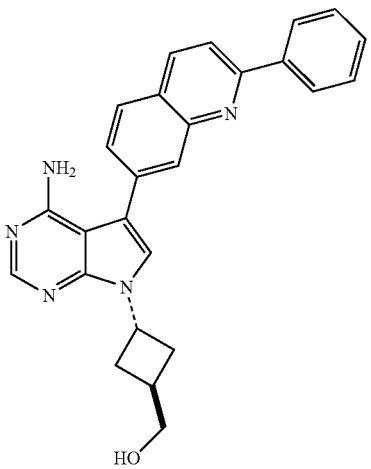

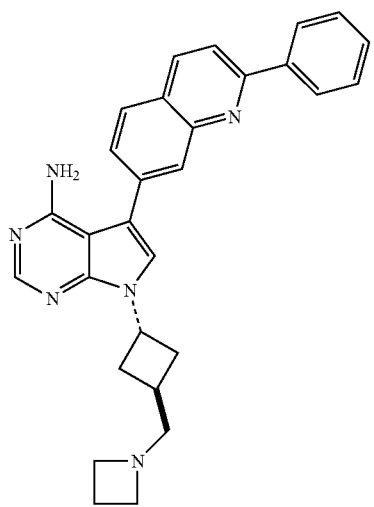

| 489 | 490 |
|---|---|
| -continued | -continued |
| 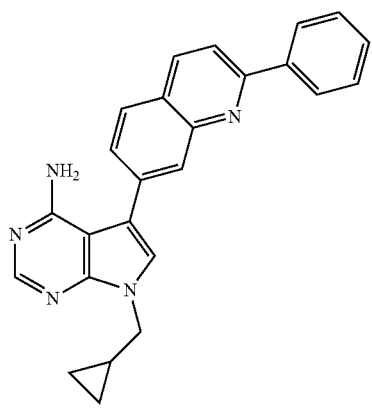 | 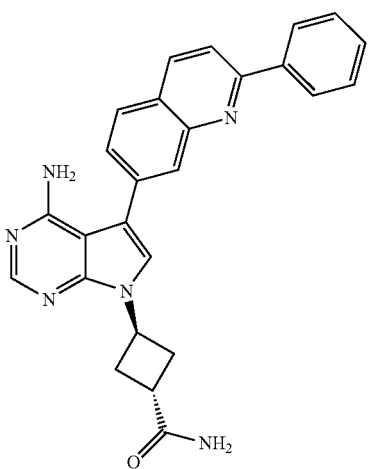 |
| 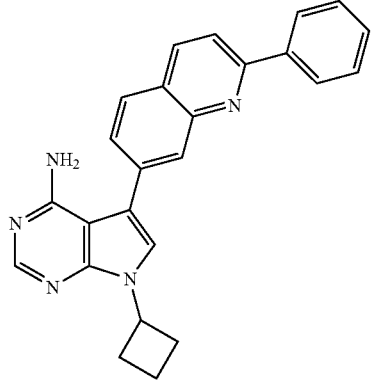 | 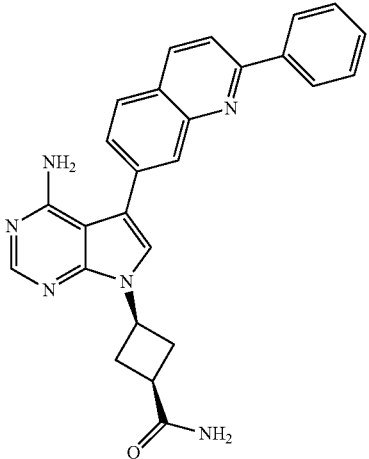 |
| 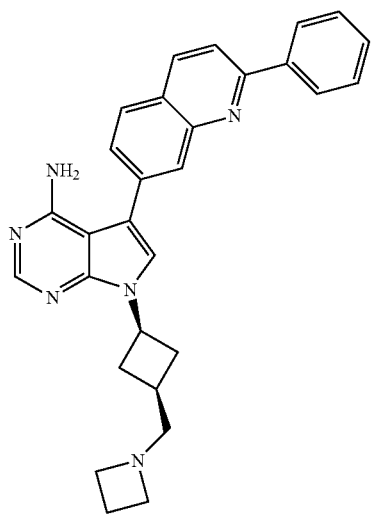 | 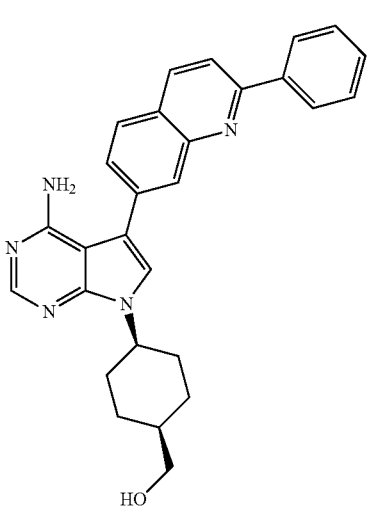 |

491
-continued
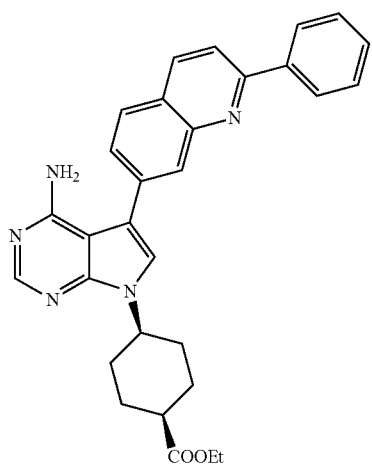
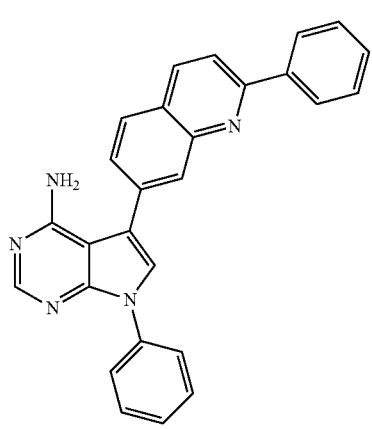
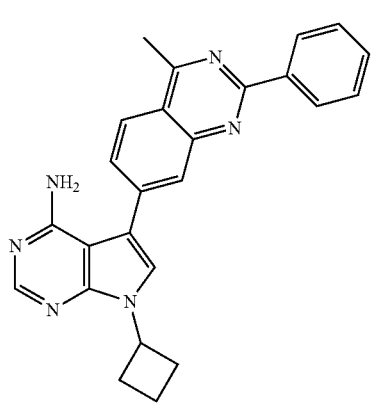
or a pharmaceutically acceptable salt thereof.
492
14. The compound of claim 1 selected from:
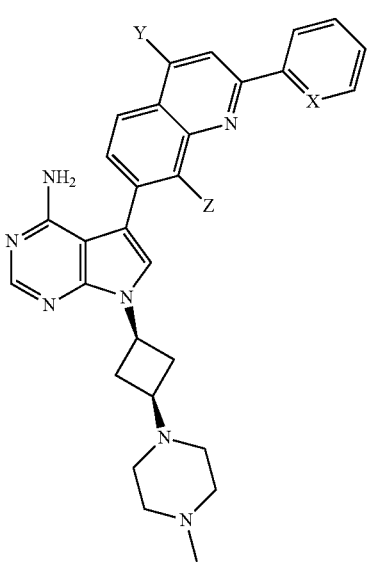
| X | Y | Z |
|----|-----|---|
| CH | H | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
| CF | CH$_3$ | H |
| CF | H | F |
| CF | CH$_3$ | F |
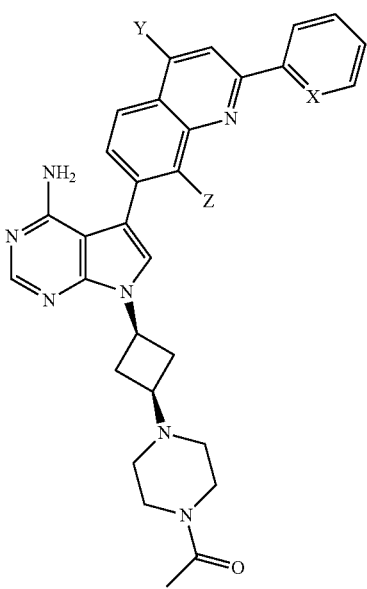

493
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
494
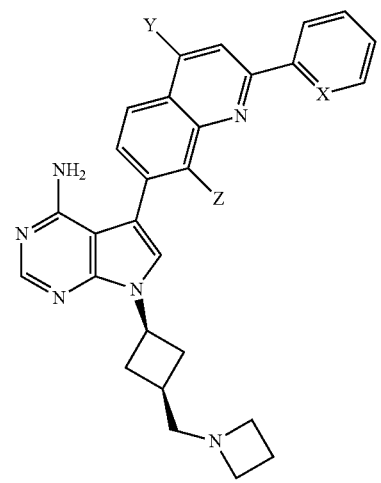
| X | Y | Z |
|---|---|---|
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
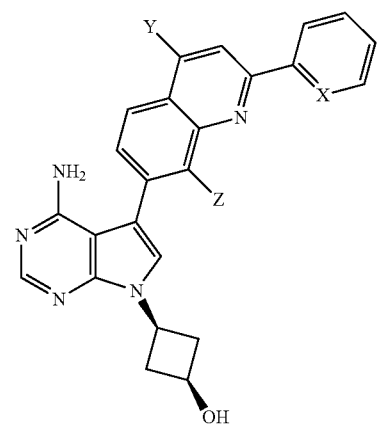
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |

495
-continued
| X  | Y   | Z |
|----|-----|---|
| CF | CH₃ | H |
| CF | H   | F |
| CF | CH₃ | F |
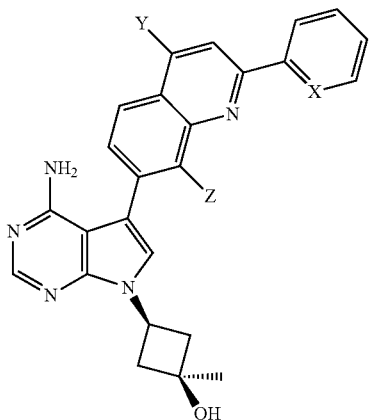
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |
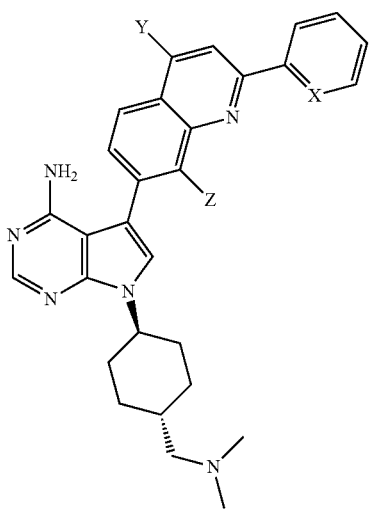
496
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |
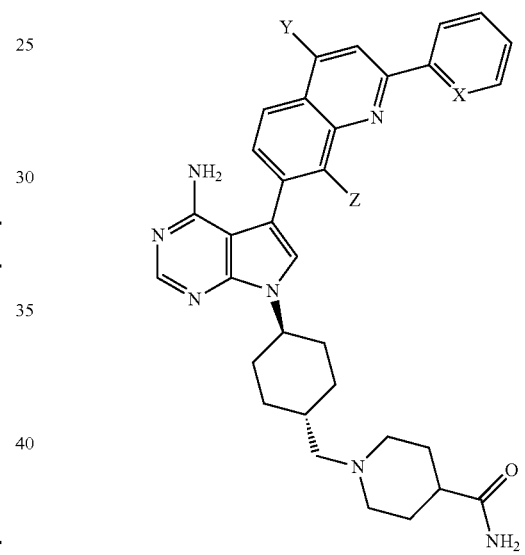
| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |

497
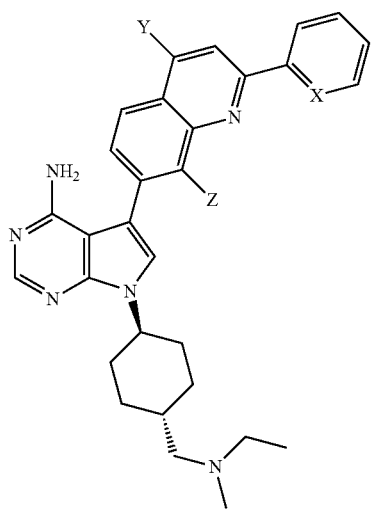
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
498
-continued
| X | Y | Z |
|---|---|---|
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
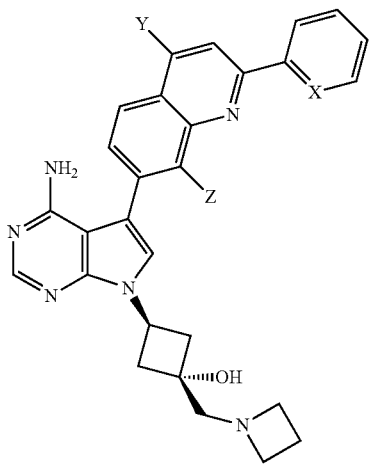
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

499
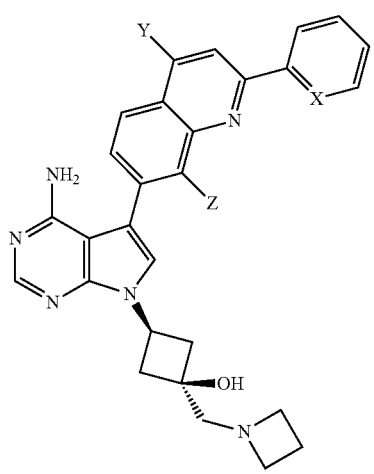
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
500
-continued
| X | Y | Z |
|---|---|---|
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

501
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
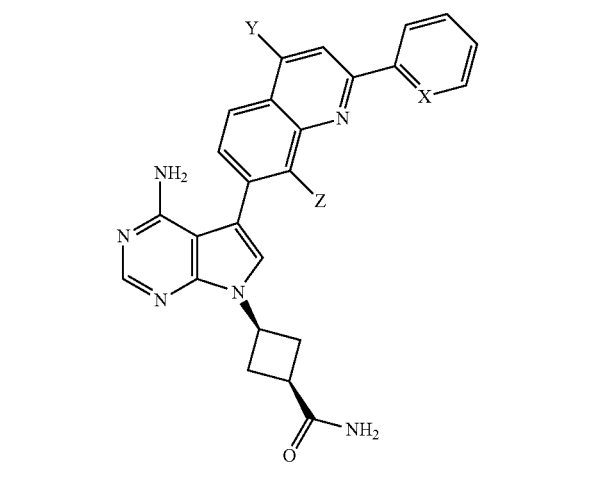
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
502
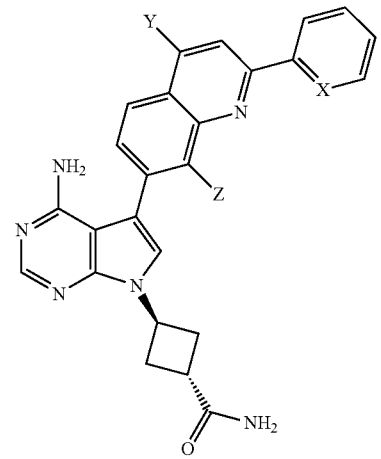
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |

503
-continued
| X | Y | Z |
|---|---|---|
| N | CH₃ | F |
| CF | H | H |
| CF | CH₃ | H |
| CF | H | F |
| CF | CH₃ | F |
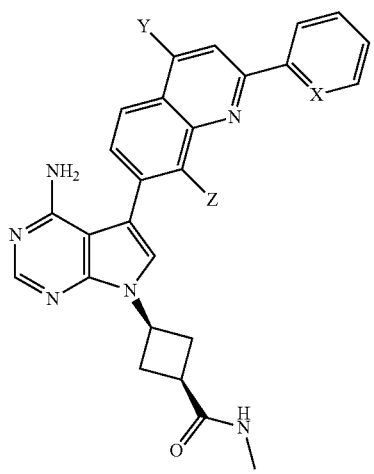
504
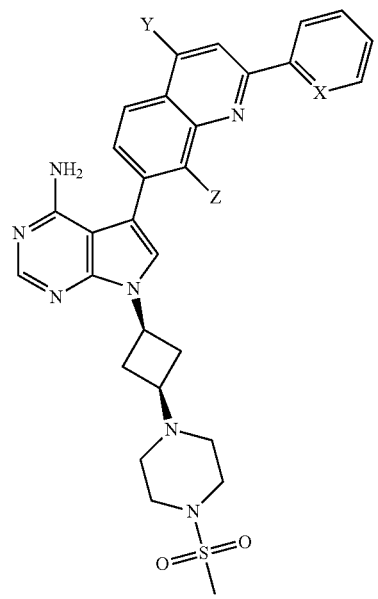
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
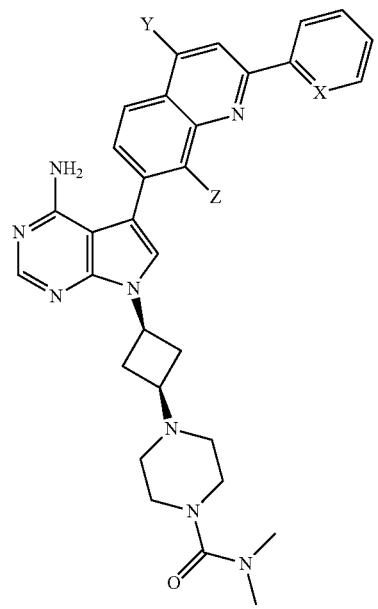

505

| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |

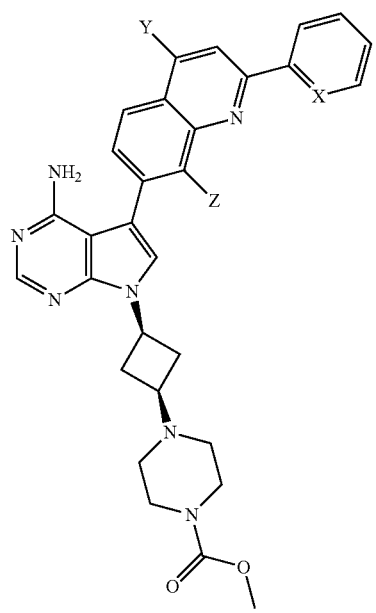

| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F |

506

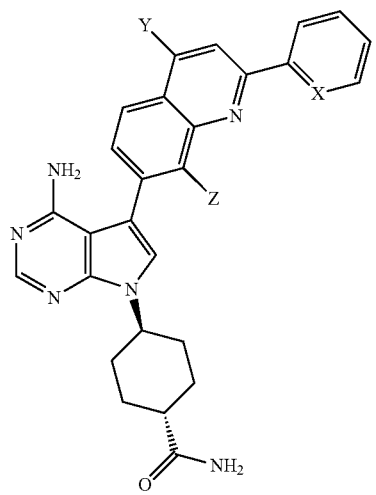

| X  | Y   | Z |
|----|-----|---|
| CH | H   | H |
| CH | CH₃ | H |
| CH | H   | F |
| CH | CH₃ | F |
| N  | H   | H |
| N  | CH₃ | H |
| N  | H   | F |
| N  | CH₃ | F |
| CF | H   | H |
| CF | CH₃ | H |
| CF | H   | F |
| CF | CH₃ | F | or a pharmaceutically acceptable salt thereof.

15. The compound of claim 1 selected from:
1-(4-Aminomethylcyclohexyl)-3-(2-thiophen-2-ylquinolin-7-yl)-1H-pyrazolo[3,4-d]pyrimidin-4-ylamine;
1-(4-Aminomethylcyclohexyl)-3-(2-pyridin-2-yl-quinolin-7-yl)-1H-pyrazolo[3,4-d]pyrimidin-4-ylamine;
1-(4-Aminomethylcyclohexyl)-3-(2-phenoxyquinolin-7-yl)-1H-pyrazolo[3,4-d]pyrimidin-4-ylamine;
1-(4-Aminomethylcyclohexyl)-3-(2-phenylquinolin-7-yl)-1H-pyrazolo[3,4-d]pyrimidin-4-ylamine;
1-(4-Aminomethylcyclohexyl)-3-(6-chloro-2-phenylquinolin-7-yl)-1H-pyrazolo[3,4-d]pyrimidin-4-ylamine;
1-(4-Aminomethylcyclohexyl)-3-(6-chloro-2-pyridin-2-ylquinolin-7-yl)-1H-pyrazolo[3,4-d]pyrimidin-4-ylamine;
1-(4-Aminomethylcyclohexyl)-3-(6-chloro-2-thiophen-2-ylquinolin-7-yl)-1H-pyrazolo[3,4-d]pyrimidin-4-ylamine;
1-(4-Aminomethylcyclohexyl)-3-(6-chloro-2-phenoxyquinolin-7-yl)-1H-pyrazolo[3,4-d]pyrimidin-4-ylamine;
1-(4-Aminomethylcyclohexyl)-3-(4-methyl-2-thiophen-2-ylquinolin-7-yl)-1H-pyrazolo[3,4-d]pyrimidin-4-ylamine;
1-(4-Aminomethylcyclohexyl)-3-(4-methyl-2-pyridin-2-ylquinolin-7-yl)-1H-pyrazolo[3,4-d]pyrimidin-4-ylamine;
1-(4-Aminomethylcyclohexyl)-3-(4-methyl-2-phenoxyquinolin-7-yl)-1H-pyrazolo[3,4-d]pyrimidin-4-ylamine;

1-(4-Aminomethylcyclohexyl)-3-(4-methyl-2-phenylquinolin-7-yl)-1H-pyrazolo[3,4-d]pyrimidin-4-ylamine;

1-(4-Aminomethylcyclohexyl)-3-(8-fluoro-2-thiophen-2-yl-quinolin-7-yl)-1H-pyrazolo[3,4-d]pyrimidin-4-ylamine;

1-(4-Aminomethylcyclohexyl)-3-(8-fluoro-2-phenylquinolin-7-yl)-1H-pyrazolo[3,4-d]pyrimidin-4-ylamine;

1-(4-Aminomethylcyclohexyl)-3-(8-fluoro-2-phenoxyquinolin-7-yl)-1H-pyrazolo[3,4-d]pyrimidin-4-ylamine;

1-(4-Aminomethylcyclohexyl)-3-(8-fluoro-2-pyridin-2-ylquinolin-7-yl)-1H-pyrazolo[3,4-d]pyrimidin-4-ylamine;

4-[4-Amino-3-(2-pyridin-2-ylquinolin-7-yl)-pyrazolo[3,4-d]pyrimidin-1-yl]-cyclohexanecarboxylic acid amide;

4-[4-Amino-3-(2-phenylquinolin-7-yl)-pyrazolo[3,4-d]pyrimidin-1-yl]-cyclohexanecarboxylic acid amide;

4-[4-Amino-3-(2-thiophen-2-ylquinolin-7-yl)-pyrazolo[3,4-d]pyrimidin-1-yl]-cyclohexanecarboxylic acid amide;

4-[4-Amino-3-(2-phenoxyquinolin-7-yl)-pyrazolo[3,4-d]pyrimidin-1-yl]-cyclohexanecarboxylic acid amide;

4-[4-Amino-3-(6-chloro-2-phenylquinolin-7-yl)-pyrazolo[3,4-d]pyrimidin-1-yl]-cyclohexanecarboxylic acid amide;

4-[4-Amino-3-(6-chloro-2-pyridin-2-ylquinolin-7-yl)-pyrazolo[3,4-d]pyrimidin-1-yl]-cyclohexanecarboxylic acid amide;

4-[4-Amino-3-(6-chloro-2-thiophen-2-ylquinolin-7-yl)-pyrazolo[3,4-d]pyrimidin-1-yl]-cyclohexanecarboxylic acid amide;

4-[4-Amino-3-(6-chloro-2-phenoxyquinolin-7-yl)-pyrazolo[3,4-d]pyrimidin-1-yl]-cyclohexanecarboxylic acid amide;

4-[4-Amino-3-(8-fluoro-2-phenylquinolin-7-yl)-pyrazolo[3,4-d]pyrimidin-1-yl]-cyclohexanecarboxylic acid amide;

4-[4-Amino-3-(6-chloro-2-thiophen-2-ylquinolin-7-yl)-pyrazolo[3,4-d]pyrimidin-1-yl]-cyclohexanecarboxylic acid methylamide;

4-[4-Amino-3-(8-fluoro-2-pyridin-2-ylquinolin-7-yl)-pyrazolo[3,4-d]pyrimidin-1-yl]-cyclohexanecarboxylic acid amide;

4-[4-Amino-3-(8-fluoro-2-phenoxyquinolin-7-yl)-pyrazolo[3,4-d]pyrimidin-1-yl]-cyclohexanecarboxylic acid amide;

4-[4-Amino-3-(4-methyl-2-phenylquinolin-7-yl)-pyrazolo[3,4-d]pyrimidin-1-yl]-cyclohexanecarboxylic acid amide;

4-[4-Amino-3-(4-methyl-2-thiophen-2-ylquinolin-7-yl)-pyrazolo[3,4-d]pyrimidin-1-yl]-cyclohexanecarboxylic acid amide;

4-[4-Amino-3-(4-methyl-2-pyridin-2-ylquinolin-7-yl)-pyrazolo[3,4-d]pyrimidin-1-yl]-cyclohexanecarboxylic acid amide;

4-[4-Amino-3-(4-methyl-2-phenoxyquinolin-7-yl)-pyrazolo[3,4-d]pyrimidin-1-yl]-cyclohexanecarboxylic acid amide;

4-[4-Amino-3-(2-pyridin-2-ylquinolin-7-yl)-pyrazolo[3,4-d]pyrimidin-1-yl]-cyclohexanecarboxylic acid methylamide;

4-[4-Amino-3-(2-phenylquinolin-7-yl)-pyrazolo[3,4-d]pyrimidin-1-yl]-cyclohexanecarboxylic acid methylamide;

4-[4-Amino-3-(2-thiophen-2-ylquinolin-7-yl)-pyrazolo[3,4-d]pyrimidin-1-yl]-cyclohexanecarboxylic acid methylamide;

4-[4-Amino-3-(2-phenoxyquinolin-7-yl)-pyrazolo[3,4-d]pyrimidin-1-yl]-cyclohexanecarboxylic acid methylamide;

4-[4-Amino-3-(6-chloro-2-phenylquinolin-7-yl)-pyrazolo[3,4-d]pyrimidin-1-yl]-cyclohexanecarboxylic acid methylamide;

4-[4-Amino-3-(6-chloro-2-pyridin-2-ylquinolin-7-yl)-pyrazolo[3,4-d]pyrimidin-1-yl]-cyclohexanecarboxylic acid methylamide;

4-[4-Amino-3-(6-chloro-2-thiophen-2-ylquinolin-7-yl)-pyrazolo[3,4-d]pyrimidin-1-yl]-cyclohexanecarboxylic acid methylamide;

4-[4-Amino-3-(6-chloro-2-phenoxyquinolin-7-yl)-pyrazolo[3,4-d]pyrimidin-1-yl]-cyclohexanecarboxylic acid methylamide;

4-[4-Amino-3-(8-fluoro-2-phenylquinolin-7-yl)-pyrazolo[3,4-d]pyrimidin-1-yl]-cyclohexanecarboxylic acid methylamide;

4-[4-Amino-3-(6-chloro-2-thiophen-2-ylquinolin-7-yl)-pyrazolo[3,4-d]pyrimidin-1-yl]-cyclohexanecarboxylic acid methylamide;

4-[4-Amino-3-(8-fluoro-2-pyridin-2-ylquinolin-7-yl)-pyrazolo[3,4-d]pyrimidin-1-yl]-cyclohexanecarboxylic acid methylamide;

4-[4-Amino-3-(8-fluoro-2-phenoxyquinolin-7-yl)-pyrazolo[3,4-d]pyrimidin-1-yl]-cyclohexanecarboxylic acid methylamide;

4-[4-Amino-3-(4-methyl-2-phenylquinolin-7-yl)-pyrazolo[3,4-d]pyrimidin-1-yl]-cyclohexanecarboxylic acid methylamide;

4-[4-Amino-3-(4-methyl-2-thiophen-2-ylquinolin-7-yl)-pyrazolo[3,4-d]pyrimidin-1-yl]-cyclohexanecarboxylic acid methylamide;

4-[4-Amino-3-(4-methyl-2-pyridin-2-ylquinolin-7-yl)-pyrazolo[3,4-d]pyrimidin-1-yl]-cyclohexanecarboxylic acid methylamide;

4-[4-Amino-3-(4-methyl-2-phenoxyquinolin-7-yl)-pyrazolo[3,4-d]pyrimidin-1-yl]-cyclohexanecarboxylic acid methylamide;

1-Cyclobutyl-3-(2-thiophen-2-ylquinolin-7-yl)-1H-pyrazolo[3,4-d]pyrimidin-4-ylamine;

1-Cyclobutyl-3-(2-phenylquinolin-7-yl)-1H-pyrazolo[3,4-d]pyrimidin-4-ylamine;

1-Cyclobutyl-3-(2-phenoxyquinolin-7-yl)-1H-pyrazolo[3,4-d]pyrimidin-4-ylamine;

1-Cyclobutyl-3-(2-pyridin-2-ylquinolin-7-yl)-1H-pyrazolo[3,4-d]pyrimidin-4-ylamine;

3-(6-Chloro-2-phenylquinolin-7-yl)-1-cyclobutyl-1H-pyrazolo[3,4-d]pyrimidin-4-ylamine;

3-(6-Chloro-2-pyridin-2-ylquinolin-7-yl)-1-cyclobutyl-1H-pyrazolo[3,4-d]pyrimidin-4-ylamine;

3-(6-Chloro-2-thiophen-2-ylquinolin-7-yl)-1-cyclobutyl-1H-pyrazolo[3,4-d]pyrimidin-4-ylamine;

3-(6-Chloro-2-phenoxyquinolin-7-yl)-1-cyclobutyl-1H-pyrazolo[3,4-d]pyrimidin-4-ylamine;

1-Cyclobutyl-3-(4-methyl-2-thiophen-2-ylquinolin-7-yl)-1H-pyrazolo[3,4-d]pyrimidin-4-ylamine;

1-Cyclobutyl-3-(4-methyl-2-pyridin-2-ylquinolin-7-yl)-1H-pyrazolo[3,4-d]pyrimidin-4-ylamine;

1-Cyclobutyl-3-(4-methyl-2-phenylquinolin-7-yl)-1H-pyrazolo[3,4-d]pyrimidin-4-ylamine;

1-Cyclobutyl-3-(4-methyl-2-phenoxyquinolin-7-yl)-1H-pyrazolo[3,4-d]pyrimidin-4-ylamine;

3-[4-Amino-3-(2-phenylquinolin-7-yl)-pyrazolo[3,4-d]pyrimidin-1-yl]-cyclobutanol;
3-[4-Amino-3-(2-pyridin-2-ylquinolin-7-yl)-pyrazolo[3,4-d]pyrimidin-1-yl]-cyclobutanol;
3-[4-Amino-3-(2-thiophen-2-ylquinolin-7-yl)-pyrazolo[3,4-d]pyrimidin-1-yl]-cyclobutanol;
3-[4-Amino-3-(2-phenoxyquinolin-7-yl)-pyrazolo[3,4-d]pyrimidin-1-yl]-cyclobutanol;
3-[4-Amino-3-(6-chloro-2-thiophen-2-ylquinolin-7-yl)-pyrazolo[3,4-d]pyrimidin-1-yl]-cyclobutanol;
3-[4-Amino-3-(6-chloro-2-pyridin-2-ylquinolin-7-yl)-pyrazolo[3,4-d]pyrimidin-1-yl]-cyclobutanol;
3-[4-Amino-3-(6-chloro-2-phenylquinolin-7-yl)-pyrazolo[3,4-d]pyrimidin-1-yl]-cyclobutanol;
3-[4-Amino-3-(6-chloro-2-phenoxyquinolin-7-yl)-pyrazolo[3,4-d]pyrimidin-1-yl]-cyclobutanol;
3-[4-Amino-3-(4-methyl-2-phenylquinolin-7-yl)-pyrazolo[3,4-d]pyrimidin-1-yl]-cyclobutanol;
3-[4-Amino-3-(4-methyl-2-pyridin-2-ylquinolin-7-yl)-pyrazolo[3,4-d]pyrimidin-1-yl]-cyclobutanol;
3-[4-Amino-3-(4-methyl-2-thiophen-2-ylquinolin-7-yl)-pyrazolo[3,4-d]pyrimidin-1-yl]-cyclobutanol;
3-[4-Amino-3-(4-methyl-2-phenoxyquinolin-7-yl)-pyrazolo[3,4-d]pyrimidin-1-yl]-cyclobutanol;
1-(3-Azetidin-1-ylmethylcyclobutyl)-3-(2-pyridin-2-ylquinolin-7-yl)-1H-pyrazolo[3,4-d]pyrimidin-4-ylamine;
1-(3-Azetidin-1-ylmethylcyclobutyl)-3-(2-phenylquinolin-7-yl)-1H-pyrazolo[3,4-d]pyrimidin-4-ylamine;
1-(3-Azetidin-1-ylmethylcyclobutyl)-3-(2-thiophen-2-ylquinolin-7-yl)-1H-pyrazolo[3,4-d]pyrimidin-4-ylamine;
1-(3-Azetidin-1-ylmethylcyclobutyl)-3-(2-phenoxyquinolin-7-yl)-1H-pyrazolo[3,4-d]pyrimidin-4-ylamine;
1-(3-Azetidin-1-ylmethylcyclobutyl)-3-(6-chloro-2-thiophen-2-ylquinolin-7-yl)-1H-pyrazolo[3,4-d]pyrimidin-4-ylamine;
1-(3-Azetidin-1-ylmethylcyclobutyl)-3-(6-chloro-2-phenylquinolin-7-yl)-1H-pyrazolo[3,4-d]pyrimidin-4-ylamine;
1-(3-Azetidin-1-ylmethylcyclobutyl)-3-(6-chloro-2-phenoxyquinolin-7-yl)-1H-pyrazolo[3,4-d]pyrimidin-4-ylamine;
1-(3-Azetidin-1-ylmethylcyclobutyl)-3-(6-chloro-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-phenylquinolin-7-yl)-1H-pyrazolo[3,4-d]pyrimidin-4-ylamine;
1-(3-Azetidin-1-ylmethylcyclobutyl)-3-(4-methyl-2-thiophen-2-ylquinolin-7-yl)-1H-pyrazolo[3,4-d]pyrimidin-4-ylamine;
1-(3-Azetidin-1-ylmethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(2-phenylquinolin-7-yl)-1H-pyrazolo[3,4-d]pyrimidin-4-ylamine;
1-(3-Dimethylaminomethylcyclobutyl)-3-(2-thiophen-2-ylquinolin-7-yl)-1H-pyrazolo[3,4-d]pyrimidin-4-ylamine;
1-(3-Dimethylaminomethylcyclobutyl)-3-(2-pyridin-2-ylquinolin-7-yl)-1H-pyrazolo[3,4-d]pyrimidin-4-ylamine;
1-(3-Dimethylaminomethylcyclobutyl)-3-(2-phenoxyquinolin-7-yl)-1H-pyrazolo[3,4-d]pyrimidin-4-ylamine;
3-(6-Chloro-2-phenylquinolin-7-yl)-1-(3-dimethylaminomethylcyclobutyl)-1H-pyrazolo[3,4-d]pyrimidin-4-ylamine;
3-(6-Chloro-2-thiophen-2-ylquinolin-7-yl)-1-(3-dimethylaminomethylcyclobutyl)-1H-pyrazolo[3,4-d]pyrimidin-4-ylamine;
3-(6-Chloro-2-phenoxyquinolin-7-yl)-1-(3-dimethylaminomethylcyclobutyl)-1H-pyrazolo[3,4-d]pyrimidin-4-ylamine;
3-(6-Chloro-2-pyridin-2-ylquinolin-7-yl)-1-(3-dimethylaminomethylcyclobutyl)-1H-pyrazolo[3,4-d]pyrimidin-4-ylamine;
1-(3-Dimethylaminomethylcyclobutyl)-3-(4-methyl-2-pyridin-2-ylquinolin-7-yl)-1H-pyrazolo[3,4-d]pyrimidin-4-ylamine;
1-(3-Dimethylaminomethylcyclobutyl)-3-(4-methyl-2-phenylquinolin-7-yl)-1H-pyrazolo[3,4-d]pyrimidin-4-ylamine;
1-(3-Dimethylaminomethylcyclobutyl)-3-(4-methyl-2-thiophen-2-ylquinolin-7-yl)-1H-pyrazolo[3,4-d]pyrimidin-4-ylamine;
1-(3-Dimethylaminomethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(8-fluoro-2-phenylquinolin-7-yl)-1H-pyrazolo[3,4-d]pyrimidin-4-ylamine;
1-(3-Dimethylaminomethylcyclobutyl)-3-(8-fluoro-2-pyridin-2-ylquinolin-7-yl)-1H-pyrazolo[3,4-d]pyrimidin-4-ylamine;
1-(3-Dimethylaminomethylcyclobutyl)-3-(8-fluoro-2-thiophen-2-ylquinolin-7-yl)-1H-pyrazolo[3,4-d]pyrimidin-4-ylamine;
1-(3-Dimethylaminomethylcyclobutyl)-3-(8-fluoro-2-phenoxyquinolin-7-yl)-1H-pyrazolo[3,4-d]pyrimidin-4-ylamine;

or a pharmaceutically acceptable salt thereof.

16. The compound of claim 1 selected from:

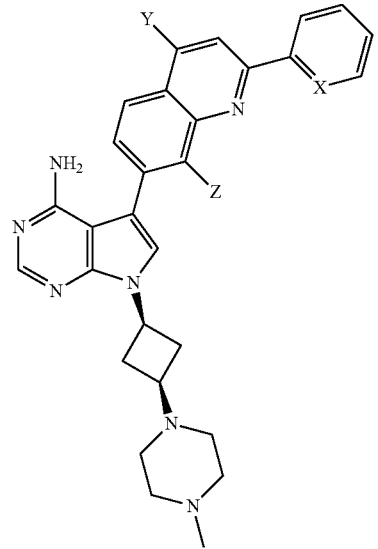

511
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
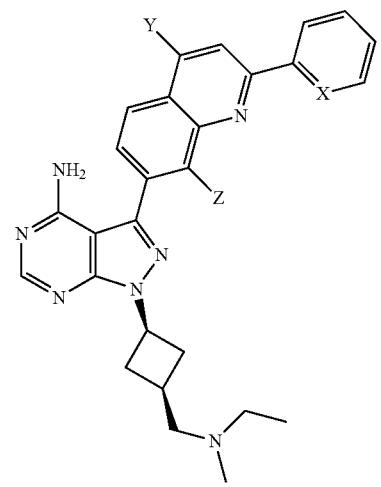
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
512
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | CH₃ | H |
| CH | H | F |
| CH | CH₃ | F |
| N | H | H |
| N | CH₃ | H |

-continued
| X | Y | Z |
|---|---|---|
| N | H | F |
| N | CH₃ | F |
| CF | H | H |
| CF | CH₃ | H |
| CF | H | F |
| CF | CH₃ | F |
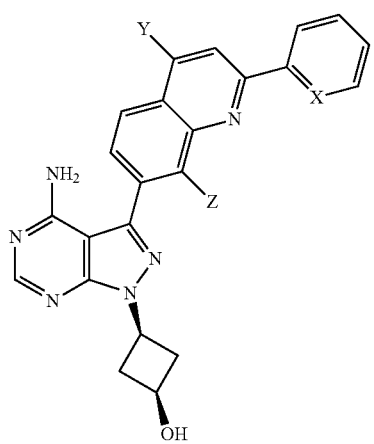
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
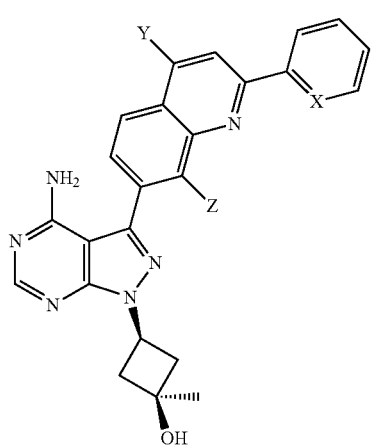
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
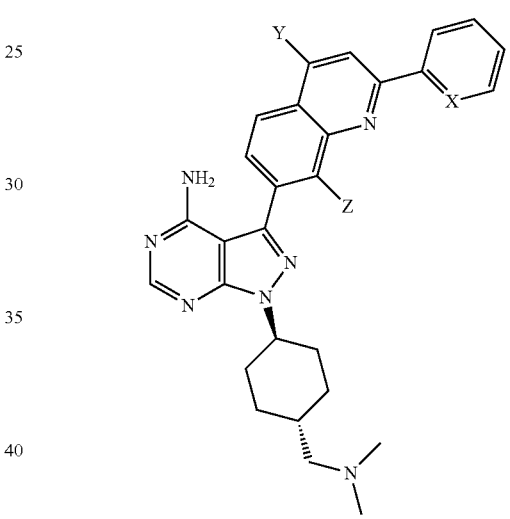
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

515
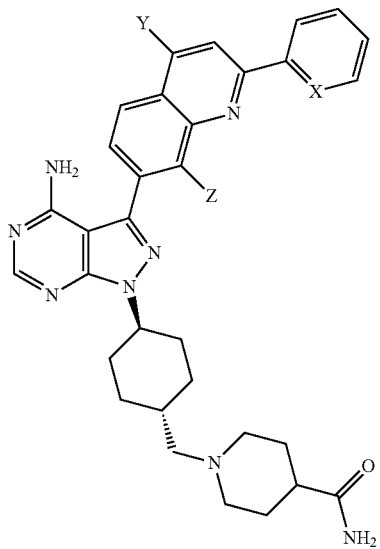
| X | Y | Z |
|---|---|---|
| CH | H | H |
| CH | CH3 | H |
| CH | H | F |
| CH | CH3 | F |
| N | H | H |
| N | CH3 | H |
| N | H | F |
| N | CH3 | F |
| CF | H | H |
| CF | CH3 | H |
| CF | H | F |
| CF | CH3 | F |
516
| X | Y | Z |
|---|---|---|
| CH | H | H |
| CH | CH3 | H |
| CH | H | F |
| CH | CH3 | F |
| N | H | H |
| N | CH3 | H |
| N | H | F |
| N | CH3 | F |
| CF | H | H |
| CF | CH3 | H |
| CF | H | F |
| CF | CH3 | F |
| X | Y | Z |
|---|---|---|
| CH | H | H |
| CH | CH3 | H |
| CH | H | F |
| CH | CH3 | F |
| N | H | H |
| N | CH3 | H |
| N | H | F |
| N | CH3 | F |
| CF | H | H |
| CF | CH3 | H |
| CF | H | F |
| CF | CH3 | F |

517
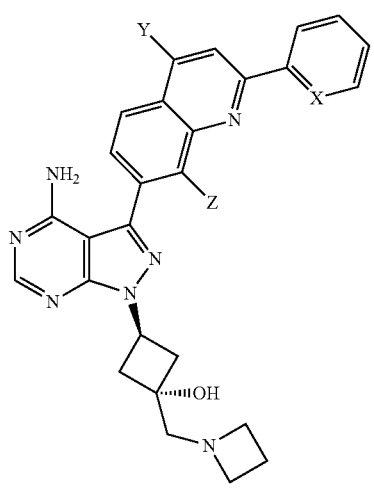
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
518
| X | Y | Z |
|---|---|---|
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |

519
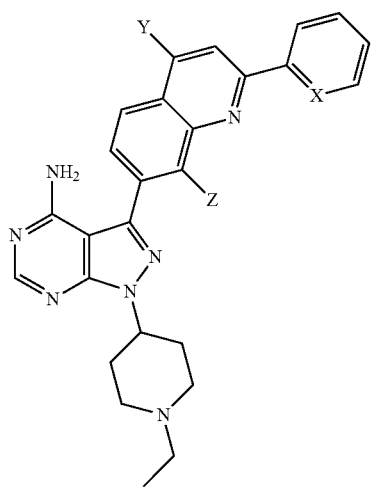
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
520
-continued
| X | Y | Z |
|---|---|---|
| N | CH₃ | F |
| CF | H | H |
| CF | CH₃ | H |
| CF | H | F |
| CF | CH₃ | F |
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

521
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
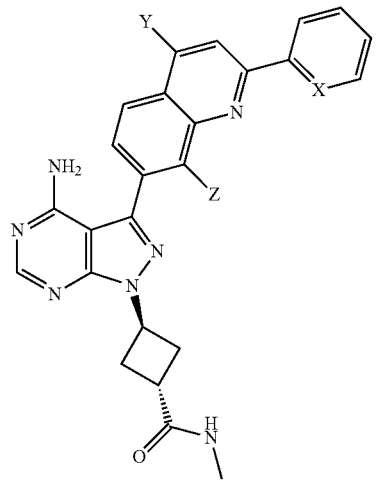
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
522
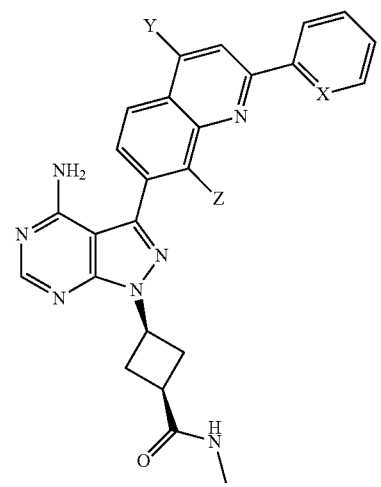
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
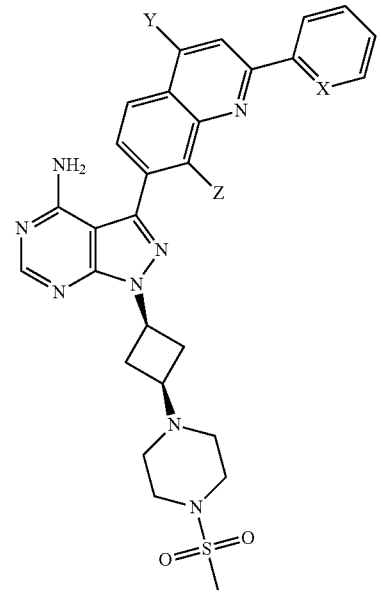

523
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
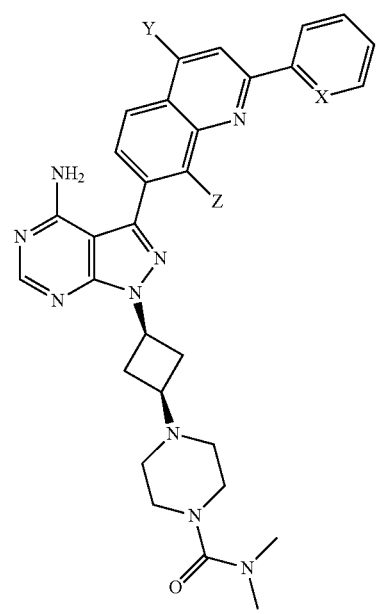
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
524
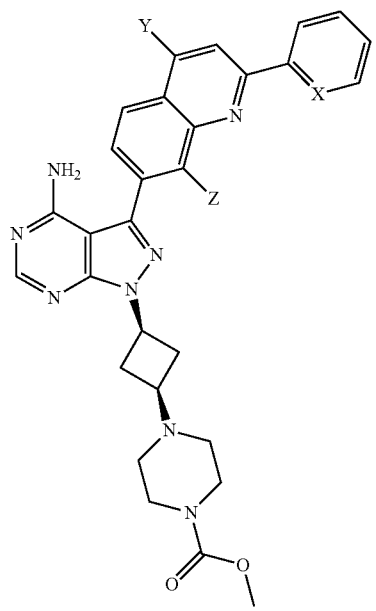
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
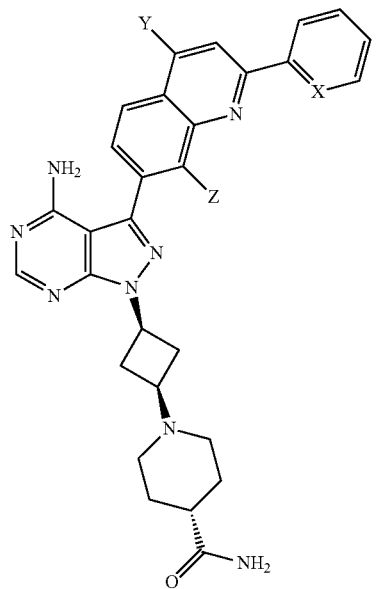

| X | Y | Z |
|---|---|---|
| CH | H | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
| CF | CH$_3$ | H |
| CF | H | F |
| CF | CH$_3$ | F | or a pharmaceutically acceptable salt thereof.

17. A pharmaceutical composition comprising a compound of claim 1, or a pharmaceutically acceptable salt thereof, and a pharmaceutically acceptable carrier.

* * * * *